US010550106B2

(12) United States Patent
Munoz et al.

(10) Patent No.: US 10,550,106 B2
(45) Date of Patent: Feb. 4, 2020

(54) COMPOUNDS, COMPOSITIONS, AND METHODS FOR MODULATING CFTR

(71) Applicant: Proteostasis Therapeutics, Inc., Cambridge, MA (US)

(72) Inventors: Benito Munoz, Newtonville, MA (US); Cecilia M. Bastos, South Grafton, MA (US); Daniel Parks, Pepperell, MA (US); David Kombo, Lexington, MA (US)

(73) Assignee: Proteostasis Therapeutics, Inc., Boston, MA (US)

( * ) Notice: Subject to any disclaimer, the term of this patent is extended or adjusted under 35 U.S.C. 154(b) by 0 days.

(21) Appl. No.: 15/766,667

(22) PCT Filed: Oct. 6, 2016

(86) PCT No.: PCT/US2016/055693
§ 371 (c)(1),
(2) Date: Apr. 6, 2018

(87) PCT Pub. No.: WO2017/062581
PCT Pub. Date: Apr. 13, 2017

(65) Prior Publication Data
US 2018/0291006 A1    Oct. 11, 2018

Related U.S. Application Data

(60) Provisional application No. 62/319,433, filed on Apr. 7, 2016, provisional application No. 62/277,600, filed on Jan. 12, 2016, provisional application No. 62/237,887, filed on Oct. 6, 2015.

(51) Int. Cl.
| *C07D 405/14* | (2006.01) |
| *C07D 405/04* | (2006.01) |
| *C07D 413/14* | (2006.01) |
| *C07D 401/04* | (2006.01) |
| *C07D 409/04* | (2006.01) |
| *C07D 409/14* | (2006.01) |
| *C07D 413/04* | (2006.01) |
| *C07D 417/04* | (2006.01) |
| *C07D 471/04* | (2006.01) |
| *C07D 487/04* | (2006.01) |
| *C07D 493/08* | (2006.01) |
| *A61P 11/00*  | (2006.01) |

(52) U.S. Cl.
CPC ............ *C07D 405/04* (2013.01); *A61P 11/00* (2018.01); *C07D 401/04* (2013.01); *C07D 405/14* (2013.01); *C07D 409/04* (2013.01); *C07D 409/14* (2013.01); *C07D 413/04* (2013.01); *C07D 413/14* (2013.01); *C07D 417/04* (2013.01); *C07D 471/04* (2013.01); *C07D 487/04* (2013.01); *C07D 493/08* (2013.01)

(58) Field of Classification Search
CPC .. C07D 405/04; C07D 405/14; C07D 413/14; C07D 413/04; C07D 409/14; C07D 417/04; A61P 11/00
See application file for complete search history.

(56) References Cited

U.S. PATENT DOCUMENTS

| 3,870,712 | A | * | 3/1975 | Holmes ................ C07D 401/04 546/168 |
| 5,523,408 | A | * | 6/1996 | Batt ..................... C07D 215/56 544/128 |
| 5,780,393 | A | | 7/1998 | Newton |
| 5,888,941 | A | | 3/1999 | Bartroli et al. |
| 7,846,951 | B2 | | 12/2010 | Miller et al. |
| 7,915,297 | B2 | | 3/2011 | Cho et al. |
| 7,981,935 | B2 | | 7/2011 | Olson et al. |
| 8,193,225 | B2 | | 6/2012 | Schneider et al. |
| 8,236,838 | B2 | | 8/2012 | Jones et al. |
| 8,623,860 | B2 | | 1/2014 | Fleck et al. |
| 8,815,924 | B2 | | 8/2014 | Dorsch et al. |
| 9,745,292 | B2 | | 8/2017 | Bastos et al. |
| 9,790,219 | B2 | | 10/2017 | Bastos et al. |
| 10,017,503 | B2 | | 7/2018 | Bastos et al. |
| 10,174,014 | B2 | | 1/2019 | Bastos et al. |
| 2006/0041006 | A1 | | 2/2006 | Ibrahim et al. |
| 2006/0100226 | A1 | | 5/2006 | Sikorski et al. |
| 2008/0090882 | A1 | | 4/2008 | Dorsch et al. |
| 2009/0069288 | A1 | | 3/2009 | Breinlinger et al. |
| 2009/0163545 | A1 | | 6/2009 | Goldfarb |
| 2009/0264486 | A1 | | 10/2009 | Jones et al. |
| 2009/0318429 | A1 | | 12/2009 | Doyle et al. |
| 2010/0234367 | A1 | | 9/2010 | Nomura et al. |
| 2011/0003784 | A1 | | 1/2011 | Garvey et al. |
| 2011/0082181 | A1 | | 4/2011 | Seiders et al. |
| 2011/0212975 | A1 | | 9/2011 | Kao et al. |

(Continued)

FOREIGN PATENT DOCUMENTS

| CA | 2736441 A1 | 10/2012 |
| EP | 0337263 A2 | 10/1989 |

(Continued)

OTHER PUBLICATIONS

Buu-Hoi, J Chem Soc, p. 173-176, Jan. 1, 1964. (Year: 1964).*
Ardashev, Kimiya Geterotsiklicheskikh Soedinenii, vol. 2, p. 202-203, 1968, abstract only CA 69:106504. (Year: 1968).*
Mehariya, Chem & Biology Interface, vol. 5(2), 128-136, 2015. (Year: 2015).*
U.S. Appl. No. 14/900,345, published as US 2016-0151335 A1 on Jun. 2, 2016, Methods of Modulating CFTR Activity, filed Dec. 21, 2015.

(Continued)

*Primary Examiner* — D Margaret M Seaman
(74) *Attorney, Agent, or Firm* — Goodwin Procter LLP

(57) ABSTRACT

The present disclosure is directed to disclosed compounds that modulate, e.g., address underlying defects in cellular processing of CFTR activity.

13 Claims, No Drawings

(56) References Cited

U.S. PATENT DOCUMENTS

| | | |
|---|---|---|
| 2012/0095002 A1 | 4/2012 | Ratcliffe et al. |
| 2012/0264738 A1 | 10/2012 | Sugimoto et al. |
| 2013/0217883 A1 | 8/2013 | Adaway |
| 2013/0237502 A1 | 9/2013 | Curtis et al. |
| 2014/0364467 A1 | 12/2014 | Schneider et al. |
| 2016/0151335 A1 | 6/2016 | Tait et al. |
| 2017/0001991 A1 | 1/2017 | Bastos et al. |
| 2017/0001993 A1 | 1/2017 | Bastos et al. |
| 2017/0233379 A1 | 8/2017 | Bastos et al. |
| 2017/0362214 A1 | 12/2017 | Bastos et al. |
| 2017/0369480 A1 | 12/2017 | Bastos et al. |
| 2017/0369482 A1 | 12/2017 | Bastos et al. |
| 2018/0127400 A1 | 5/2018 | Bastos et al. |
| 2018/0147187 A1 | 5/2018 | Bastos et al. |
| 2018/0214419 A1 | 8/2018 | Munoz et al. |
| 2018/0291006 A1 | 10/2018 | Munoz et al. |
| 2018/0327363 A1 | 11/2018 | Bastos et al. |
| 2018/0369209 A1 | 12/2018 | Miller et al. |
| 2019/0022071 A1 | 1/2019 | Lee |

FOREIGN PATENT DOCUMENTS

| | | |
|---|---|---|
| EP | 0957099 A2 | 11/1999 |
| JP | 2006176443 A | 7/2006 |
| WO | 98/57931 * | 12/1998 |
| WO | WO-9857931 A2 | 12/1998 |
| WO | WO-9857952 | 12/1998 |
| WO | WO-2002000651 A2 | 1/2002 |
| WO | WO-2003093297 A2 | 11/2003 |
| WO | WO-2005035514 A2 | 4/2005 |
| WO | WO-2005077345 A1 | 8/2005 |
| WO | WO-2005077373 A2 | 8/2005 |
| WO | WO-2006014134 A1 | 2/2006 |
| WO | WO-2006136924 A1 | 12/2006 |
| WO | WO-2007075896 A2 | 7/2007 |
| WO | WO-2007078113 A1 | 7/2007 |
| WO | WO-2007086584 A1 | 8/2007 |
| WO | WO-2007126362 A1 | 11/2007 |
| WO | WO-2008046072 A2 | 4/2008 |
| WO | WO-2008051757 A1 | 5/2008 |
| WO | WO-2008070739 A1 | 6/2008 |
| WO | WO-2009005269 A2 | 1/2009 |
| WO | WO-2009011850 A2 | 1/2009 |
| WO | WO-2009016241 A1 | 2/2009 |
| WO | WO-2010089297 A1 | 8/2010 |
| WO | WO-2010142801 A1 | 12/2010 |
| WO | WO-2011008931 A2 | 1/2011 |
| WO | WO-2012007500 A2 | 1/2012 |
| WO | WO-2013019561 A1 | 2/2013 |
| WO | WO-2013146970 A1 | 10/2013 |
| WO | WO-2014144860 A1 | 9/2014 |
| WO | WO-2014181287 A1 | 11/2014 |
| WO | WO-2014210159 A1 | 12/2014 |
| WO | WO-2015051230 A1 | 4/2015 |
| WO | WO-2015138909 A1 | 9/2015 |
| WO | WO-2015138934 A1 | 9/2015 |
| WO | WO-2015154169 A1 | 10/2015 |
| WO | WO-2015196071 A1 | 12/2015 |
| WO | WO-2016054560 A1 | 4/2016 |
| WO | WO-2016105468 A1 | 6/2016 |
| WO | WO-2016105477 A1 | 6/2016 |
| WO | WO-2016105484 A1 | 6/2016 |
| WO | WO-2016105485 A2 | 6/2016 |
| WO | WO-2016115090 A1 | 7/2016 |
| WO | WO-2017019589 A1 | 2/2017 |
| WO | WO-2017040606 A1 | 3/2017 |
| WO | WO-2017112853 A1 | 6/2017 |

OTHER PUBLICATIONS

U.S. Pat. No. 9,790,219, issued on Oct. 17, 2017, U.S. Appl. No. 15/125,827; published as US 2017-0001993 A1 on Jan. 5, 2017, Compounds, Compositions and Methods for Increasing CFTR Activity, filed Sep. 13, 2016.
U.S. Pat. No. 9,745,292, issued on Aug. 29, 2017, U.S. Appl. No. 15/125,830; published as US 2017-0001991 A1 on Jan. 5, 2017, Compounds, Compositions and Methods for Increasing CFTR Activity, filed Sep. 13, 2016.
U.S. 10,017,503, issued on Jul. 10, 2018; U.S. Appl. No. 15/653,934, published as US 2018-0127400 A1 on May 10, 2018, Compounds, Compositions and Methods for Increasing CFTR Activity, filed Jul. 19, 2017.
U.S. 10,174,014, issued on Jan. 8, 2019; U.S. Appl. No. 15/320,172, published as US 2017-0233379 Al on Aug. 17, 2017, Compounds, Compositions and Methods for Increasing CFTR Activity, filed Dec. 19, 2016.
U.S. Appl. No. 16/190,964, Compounds, Compositions and Methods for Increasing CFTR Activity, filed Nov. 14, 2018.
U.S. Appl. No. 15/539,392, published as US 2017-0369480 A1 on Dec. 28, 2017, Compounds, Compositions and Methods for Increasing CFTR Activity, filed Jun. 23, 2017.
U.S. Appl. No. 15/539,397, published as US 2017-0369482 A1 on Dec. 28, 2017, Derivatives of 5-Phenyl- or 5-Heteroarylathiazol-2-Carboxylic Amide Useful for the Treatment of Inter Alia Cystic Fibrosis, filed Jun. 23, 2017.
U.S. Appl. No. 15/539,401, published as US 2018-0327363 A1 on Nov. 15, 2018, Derivatives of 5-(Hetero)Arylpyrazol-3-Carboxylic Amide or 1-(Hetero)Aryltriazol-4-Carboxylic Amide Useful for the Treatment of Inter Alia Cystic Fibrosis, filed Jun. 23, 2017.
U.S. Appl. No. 15/539,405, published as US 2017-0362214 A1 on Dec. 21, 2017, Derivatives of 3-Heteroarylisoxazol-5-Carboxylic Amide Useful for the Treatment of Inter Alia Cystic Fibrosis, filed Jun. 23, 2017.
U.S. Appl. No. 15/542,997, published as US 2018-0147187 A1 on May 31, 2018, Compounds, Compositions, and Methods of Increasing CFTR Activity, filed Jul. 12, 2017.
U.S. Appl. No. 15/747,290, published as US 2018-0214419 A1 on Aug. 2, 2018, Compounds, Compositions, and Methods of Increasing CFTR Activity, filed Jan. 24, 2018.
U.S. Appl. No. 15/755,738, published as US 2019-0022071 A1 on Jan. 24, 2019, Methods of Treating Pulmonary Diseases and Disorders, filed Feb. 27, 2018.
U.S. Appl. No. 16/065,384, published as US 2018-0369209 A1 on Dec. 27, 2018, Methods of Treating Pulmonary Diseases and Disorders, filed Jun. 22, 2018.
"AID 775-Screen for Chemicals that Extend Yeast Lifespan," PubChem, 1-11 (Jul. 12, 2007), XP055331102.
Bai et al., "Synthesis and Structure-Activity Relationship Studies of Conformationally Flexible Tetrahydroisoquinolinyl Triazole Carboxamide and Triazole Substituted Benzamide Analogues as sigma 2 Receptor Ligands," Journal of Medicinal Chemistry, 57:10 4239-4251(2014), XP002754990.
CAS Registry No. 797781-85-2 (available Dec. 15, 2004).
Chang, X., "3-(2-chlorophenyl)-N-methylisoxazole-5-Carboxamide," ACTA Crystallographica, Section E: Structure Reports Online, vol. E63(7), pp. O3074-sup-7 (2007).
Compound Summary for CID 70741394, PUBCHEM: Create Date: Mar. 4, 2013 [retrieved on May 12, 2015].
Compound Summary for CID 70756362, PUBCHEM: Create Date: Mar. 4, 2013 [retrieved on May 12, 2015].
Compound Summary for: CID 36257620, PUBCHEM: Create Date: May 29, 2009 [retrieved on May 12, 2015].
Compound Summary for: CID 55795703, PUBCHEM: Create Date: Jan. 25, 2012 [retrieved on May. 12, 2015].
Demina et al., "5-substituted Pyridylisoxazoles as Effective Inhibitors of Platelet Aggregation," Russian Chemical Bulletin, International Edition, vol. 63(2) 2095-2113 (2014).
International Search Report and Written Opinion for International Application No. PCT/US2014/044100, dated Oct. 10, 2014, 8 pages.
International Search Report and Written Opinion for International Application No. PCT/US2015/000189, dated Mar. 18, 2016, 10 pages.
International Search Report and Written Opinion for International Application No. PCT/US2015/000202, dated Mar. 22, 2016, 8 pages.

(56) References Cited

OTHER PUBLICATIONS

International Search Report and Written Opinion for International Application No. PCT/US2015/000211, dated Mar. 29, 2016, 10 pages.
International Search Report and Written Opinion for International Application No. PCT/US2015/000212, dated Jul. 1, 2016, 22 pages.
International Search Report and Written Opinion for International Application No. PCT/US2015/020460, dated Jun. 9, 2015, 7 pages.
International Search Report and Written Opinion for International Application No. PCT/US2015/020499, dated Jun. 9, 2015, 8 pages.
International Search Report and Written Opinion for International Application No. PCT/US2015/036691, dated Aug. 20, 2015, 12 pages.
International Search Report and Written Opinion for International Application No. PCT/US2016/012982, dated Mar. 7, 2016, 12 pages.
International Search Report and Written Opinion for International Application No. PCT/US2016/043835, dated Oct. 10, 2016, 8 pages.
International Search Report and Written Opinion for International Application No. PCT/US2016/049622, dated Nov. 18, 2016, 10 pages.
International Search Report and Written Opinion for International Application No. PCT/US2016/068266, dated Feb. 27, 2017, 11 pages.
International Search Report and Written Opinion for International Application No. PCT/US2017040606, dated Nov. 30, 2016, 10 pages.
Kalid et al., "Small Molecule Correctors of F508del-CFTR Discovered by Structure-based Virtual Screening," Journal of Computer-Aided Molecular Design, vol. 24:971-991 (2010).
Lack et al., "Targeting the Binding Function 3 (BF3) Site of the Human Androgen Receptor through Virtual Screening," Journal of Medicinal Chemistry, vol. 54(24) 8563-8573 (2011).
Liedtke, W., "Role of TRPV ion Channels in Sensory Transduction of Osmotic Stimuli in Mammals," Experimental Physiology, 92:3 507-512 (2007) XP055252392.
Lukevics et al.,"Synthesis and Cytotoxicity of Silyl- and Carbonyl-substituted Isoxazoles,"Chemistry of Heterocyclic Compounds, Springer New York LLC, vol. 36(10); 1226-1231 (1995).
Munchhof et al., "Discovery of PF-04449913, a Potent and Orally Bioavailable Inhibitor of Smoothened," ACS Medicinal Chemistry Letters, vol . 3(2) 106-111 (2012).
Phuan Puay-Wah et al., "Potentiators of Defective Delta F508-CFTR Gating that do not Interfere with Corrector Action," XP002754658, Database Accession No. PREV201500722877, Database Biosis [Online] Biosciences Information Service, Philadelphia, PA, US; Oct. 1, 2015 (Oct. 1, 2015). 1 page.
Pubchem: "ST062658 | C15H12N2O3—PubChem", Jul. 9, 2005 (Jul. 9, 2005), XP055331105, Retrieved from the Internet: URL:https://pubchem.ncbi.nlm.nih.gov/compound/973870#section=Biological-Test-Results [retrieved on Dec. 22, 2016].
Qian et al., "Potent MCH-1 Receptor Antagonists from Cis-1,4-Diaminocyclohexane-derived Indane Analogs," Bioorganic & Medicinal Chemistry Letters, 23:14 4216-4220 (2013).
Stoops et al., "Identification and Optimization of Small Molecules that Restore E-cadherin Expression and Reduce Invasion in Colorectal Carcinoma Cells," ACS Chemical Biology, American Chemical Society, Washington, DC, US, vol. 6., No. 5, pp. 452-465 (2011).
Supplemental European Search Report dated Jan. 9, 2017 in European Patent No. 14816975.8 (19 pages).
U.S. Appl. No. 15/539,401, "Derivatives of 5-(Hetero) Arylpyrazol-3-Carboxylic Amide or 1-(Hetero) Aryltriazol -4-Carboxylic Amide Useful for the Treatment of Inter Alia Cystic Fibrosis," filed on Jun. 23, 2017 (74 pages).
U.S. Appl. No. 15/755,738, "Methods of Treating Pulmonary Diseases and Disorders," filed on Feb. 27, 2018 (177 pages).
U.S. Appl. No. 16/190,964, "Compounds, Compositions and Methods for Increasing CFTR Activity," filed Nov. 14, 2018 (230 pages).
International Search Report and Written Opinion for International Application No. PCT/US2016/055693, dated Dec. 14, 2016, 12 pages.
Buu-Hoi et al., "27. Oxygen Heterocycles. Part X. The Acylation of Benzofuran," Journal of the Chemical Society, pp. 173-176 (1964).

\* cited by examiner

COMPOUNDS, COMPOSITIONS, AND METHODS FOR MODULATING CFTR

CROSS-REFERENCE TO RELATED APPLICATIONS

This application is a national stage filing under 35 U.S.C. § 371 of PCT/US2016/055693, filed Oct. 6, 2016, which claims the benefit of, and priority to, U.S. provisional application Ser. No. 62/237,887, filed Oct. 6, 2015; 62/277,600, filed Jan. 12, 2016; and 62/319,433, filed Apr. 7, 2016; the contents of each of which are hereby incorporated by reference herein in their entirety.

BACKGROUND

Cells normally maintain a balance between protein synthesis, folding, trafficking, aggregation, and degradation, referred to as protein homeostasis, utilizing sensors and networks of pathways (Sitia et al., *Nature* 426: 891-894, 2003; Ron et al., *Nat Rev Mol Cell Biol* 8: 519-529, 2007). The cellular maintenance of protein homeostasis, or proteostasis, refers to controlling the conformation, binding interactions, location and concentration of individual proteins making up the proteome. Protein folding in vivo is accomplished through interactions between the folding polypeptide chain and macromolecular cellular components, including multiple classes of chaperones and folding enzymes, which minimize aggregation (Wiseman et al., *Cell* 131: 809-821, 2007). Whether a given protein folds in a certain cell type depends on the distribution, concentration, and subcellular localization of chaperones, folding enzymes, metabolites and the like (Wiseman et al.). Cystic fibrosis and other maladies of protein misfolding arise as a result of an imbalance in the capacity of the protein homeostasis (proteostasis) environment to handle the reduced energetic stability of misfolded, mutated proteins that are critical for normal physiology (Balch et al., *Science* 319, 916-9 (2008); Powers, et al., *Annu Rev Biochem* 78, 959-91 (2009); Hutt et al., *FEBS Lett* 583, 2639-46 (2009)).

Cystic Fibrosis (CF) is caused by mutations in the cystic fibrosis transmembrane conductance regulator (CFTR) gene which encodes a multi-membrane spanning epithelial chloride channel (Riordan et al., *Annu Rev Biochem* 77, 701-26 (2008)). Approximately ninety percent of patients have a deletion of phenylalanine (Phe) 508 (ΔF508) on at least one allele. This mutation results in disruption of the energetics of the protein fold leading to degradation of CFTR in the endoplasmic reticulum (ER). The ΔF508 mutation is thus associated with defective folding and trafficking, as well as enhanced degradation of the mutant CFTR protein (Qu et al., *J Biol Chem* 272, 15739-44 (1997)). The loss of a functional CFTR channel at the plasma membrane disrupts ionic homeostasis (Cl⁻, Na⁺, HCO₃⁻) and airway surface hydration leading to reduced lung function (Riordan et al.). Reduced periciliary liquid volume and increased mucus viscosity impede mucociliary clearance resulting in chronic infection and inflammation, phenotypic hallmarks of CF disease (Boucher, *J Intern Med* 261, 5-16 (2007)). In addition to respiratory dysfunction, ΔF508 CFTR also impacts the normal function of additional organs (pancreas, intestine, gall bladder), suggesting that the loss-of-function impacts multiple downstream pathways that will require correction.

In addition to cystic fibrosis, mutations in the CFTR gene and/or the activity of the CFTR channel has also been implicated in other conditions, including for example, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), dry eye disease, Sjogren's syndrome and chronic sinusitis, (Sloane et al. (2012), PLoS ONE 7(6): e39809.doi:10.1371/journal. pone.0039809; Bombieri et al. (2011), J Cyst Fibros. 2011 June; 10 Suppl 2:S86-102; (Albert et al. (2008), Clinical Respiratory Medicine, Third Ed., Mosby Inc.; Levin et al. (2005), Invest Ophthalmol Vis Sci., 46(4):1428-34; Froussard (2007), Pancreas 35(1): 94-5).

There remains a need in the art for compounds, compositions and methods of increasing CFTR activity as well as for methods of treating CF, other CFTR-related diseases, and other maladies of protein misfolding.

SUMMARY

This disclosure is directed in part to compounds having Formula I:

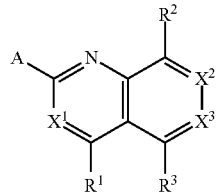

Formula I and pharmaceutically acceptable salts thereof, in which A, $X^1$, $X^2$, $X^3$, $R^1$, $R^2$, and $R^3$ are as defined herein.

Also contemplated herein are pharmaceutical compositions that include a disclosed compound such as those compounds having disclosed formulas such as Formula I and a pharmaceutically acceptable carrier or excipient. In certain embodiments, the compositions can include at least one additional CFTR modulator, for example, may include one, two, three, four, five or more additional CFTR modulators.

In certain embodiments, a method is provided comprising administering a disclosed compound to a subject (e.g., a human patient) suffering from a disease associated with decreased CFTR activity (e.g., cystic fibrosis, congenital bilateral absence of vas deferens (CBAVD), acute, recurrent, or chronic pancreatitis, disseminated bronchiectasis, asthma, allergic pulmonary aspergillosis, chronic obstructive pulmonary disease (COPD), chronic sinusitis, dry eye disease, protein C deficiency, A-β-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, Sjogren's syndrome, familial hypercholesterolemia, I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, nephrogenic DI, Charcot-Marie Tooth syndrome, Perlizaeus-Merzbacher disease, Alzheimer's disease, Parkinson's disease, amyotrophic lateral sclerosis, progressive supranuclear palsy, Pick's disease, Huntington's disease, spinocerebellar ataxia type I, spinal and bulbar muscular atrophy, dentatorubral pallidoluysian, myotonic dystrophy, hereditary Creutzfeldt-Jakob disease (due to prion protein processing defect), Fabry disease, and Straussler-Scheinker syndrome). In certain embodiments, the disease is cystic fibrosis. For example, contemplated herein is a method for treating a patient suffering from cystic fibrosis comprising administering to said patient an effective amount of a disclosed compound.

In some embodiments, disclosed methods described herein can further include administering at least one additional CFTR modulator e.g., administering at least two, three, four or five additional CFTR modulators. In certain embodiments, at least one additional CFTR modulator is a CFTR corrector (e.g., VX-809, VX-661 and VX-983) or potentiator (e.g., ivacaftor and genistein). In certain of these embodiments, one of the at least two additional therapeutic agents is a CFTR corrector (e.g., VX-809, VX-661 and VX-983) and the other is a CFTR potentiator (e.g., ivacaftor and genistein).

DETAILED DESCRIPTION

As used herein, the words "a" and "an" are meant to include one or more unless otherwise specified. For example, the term "an agent" encompasses both a single agent and a combination of two or more agents.

As discussed above, the present disclosure is directed in part to compounds as described herein having the Formula I or a pharmaceutically acceptable salt, prodrug or solvate thereof, pharmaceutical compositions, methods of increasing CFTR activity and methods of treating cystic fibrosis.

For example, provided herein are compounds having Formula I:

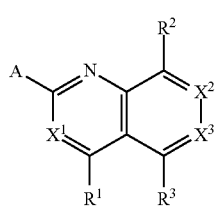

Formula I or a pharmaceutically acceptable salt, prodrug, or stereoisomer thereof, wherein:

A is a 8-10 membered bicyclic heteroaryl having 1, 2, or 3 heteroatoms each selected from the group consisting of O, N, and S; wherein the bicyclic heteroaryl may optionally be substituted by one, two or three substituents each independently selected from $R^{A1}$;

$X^1$ is selected from the group consisting of N and $C(R^{X1})$;
$X^2$ is selected from the group consisting of N and $C(R^{X2})$;
$X^3$ is selected from the group consisting of N and $C(R^{X3})$;
wherein only one of $X^1$, $X^2$ or $X^3$ can be N;

$R^1$ is selected from the group consisting of hydrogen; —C(O)OH, —C(O)OC$_{1-6}$alkyl, —C(O)—C(O)OH, —P(O)(OH)$_2$, C$_{1-6}$alkyl, and a 5-6 membered monocyclic heteroaryl having one, two, three, or four heteroatoms each selected from the group consisting of O, N, and S; wherein C$_{1-6}$ alkyl may optionally be substituted by one, two, or three substituents each selected independently from the group consisting of halogen, hydroxyl, C(O)OH, —P(O)(OH)$_2$, and —C(O)OC$_{1-6}$alkyl; and wherein said heteroaryl may optionally be substituted by one or two substituents each independently selected from the group consisting of halogen, hydroxyl, and C$_{1-4}$alkyl;

$R^2$ is selected from the group consisting of hydrogen, halogen, cyano, C$_{1-6}$alkyl, C$_{1-6}$alkoxy, and C$_{3-6}$cycloalkyl; wherein C$_{1-6}$alkyl, C$_{1-6}$alkoxy, and C$_{3-6}$cycloalkyl may optionally be substituted by one or more substituents each independently selected from the group consisting of halogen, hydroxyl, and phenyl; and wherein phenyl may optionally be substituted by one or more substituents each independently selected from $R^p$;

$R^3$ is selected from the group consisting of hydrogen, halogen, hydroxyl, C$_{1-6}$alkyl, C$_{1-6}$alkoxy, —S(O)$_w$—C$_{1-6}$alkyl (where w is 0, 1, or 2), —NR$^a$—C$_{1-6}$alkyl, C$_{3-6}$cycloalkoxy, —S(O)$_w$—C$_{3-6}$cycloalkyl (where w is 0, 1, or 2), —NR$^a$—C$_{3-6}$cycloalkyl, —O-phenyl, —S(O)$_w$-phenyl (where w is 0, 1, or 2), —NR$^a$-phenyl, C$_{8-12}$benzocycloalkoxy, —NR$^a$R$^b$, —OC(O)NR$^a$-phenyl, —NR$^a$—C(O)—O-phenyl, —NR$^a$—C(O)—C$_{1-6}$alkyl-phenyl, C$_{1-6}$alkyl NR$^a$ phenyl, —NR$^a$—C$_{1-6}$alkyl-phenyl, and a 4-10 membered monocyclic, bridged bicyclic, or spirocyclic heterocyclyloxy, heterocyclyl-NR$^a$—, or heterocyclyl-S(O)$_w$— moiety (where w is 0, 1, or 2) having one or two heteroatoms each independently selected from the group consisting of O, N, and S; wherein if said heterocyclyloxy, heterocyclyl-NR$^a$—, or heterocyclyl-S(O)$_w$— ring contains an —NH moiety, that nitrogen may optionally be substituted by a substituent selected from the group consisting of C$_{1-6}$alkyl, —C(O)—C$_{1-6}$alkyl, —C(O)—O—C$_{1-6}$alkyl, and —S(O)$_w$—C$_{1-3}$alkyl (where w is 0, 1, or 2); and wherein said heterocyclyloxy, heterocyclyl-NR$^a$—, and heterocyclyl-S(O)$_w$ may optionally be substituted by one, two, three, or four substituents each independently selected from R$^{ff}$; and wherein said phenyl moiety of —O-phenyl, —S(O)$_w$-phenyl, —NR$^a$-phenyl, —OC(O)NR$^a$-phenyl, —NR$^a$—C(O)—O-phenyl, —NR$^a$—C(O)—C$_{1-6}$alkyl-phenyl, —C$_{1-6}$alkyl-NR$^a$-phenyl and —NR$^a$—C$_{1-6}$alkyl-phenyl may optionally be substituted by one, two, or three substituents each independently selected from R$^p$; and wherein C$_{1-6}$alkoxy, —S(O)$_w$—C$_{1-6}$alkyl (where w is 0, 1, or 2), —NR$^a$—C$_{1-6}$alkyl, C$_{3-6}$cycloalkoxy, —S(O)$_w$—C$_{3-6}$cycloalkyl (where w is 0, 1, or 2), and —NR$^a$—C$_{3-6}$cycloalkyl may optionally be substituted by one, two, or three substituents each independently selected from R$^{gg}$;

R$^{ff}$ is independently selected for each occurrence from the group consisting of halogen, hydroxyl, —NR$^a$R$^b$, oxo, C$_{1-6}$alkyl and C$_{1-6}$alkoxy;

R$^{gg}$ is independently selected for each occurrence from the group consisting of halogen, hydroxyl, —NR$^a$R$^b$, C$_{1-6}$alkyl, C$_{1-6}$alkoxy, C$_{3-6}$cycloalkyl (optionally substituted by one, two or three substituents independently selected from the group consisting of halogen, hydroxyl, C$_{1-3}$alkyl and C$_{1-3}$alkoxy (optionally substituted by one, two or three fluorine atoms)), phenyl, a 5-6 membered monocyclic or 8-10 membered bicyclic heteroaryl having one, two or three heteroatoms each independently selected from the group consisting of O, N, and S, and a 4-10 membered monocyclic, bridged bycyclic, or spirocyclic heterocyclic ring having one or two heteroatoms each independently selected from the group consisting of O, N, and S; wherein if said heterocyclic ring contains an —NH moiety, that nitrogen may optionally be substituted by a substituent selected from the group consisting of C$_{1-6}$alkyl, —C(O)—C$_{1-6}$alkyl, and —S(O)$_w$—C$_{1-3}$alkyl (where w is 0, 1, or 2); and wherein phenyl may optionally be substituted by one, two or three substituents each independently selected from R$^{hh}$; and wherein said 4-10 membered monocyclic, bridged bicyclic, or spirocyclic heterocyclic ring may optionally be substituted by one, two, three, or four substituents each independently selected from $R^{ii}$;

$R^{hh}$ is independently selected for each occurrence from the group consisting of halogen, cyano, $C_{1-6}$alkyl, $C_{1-6}$alkoxy, $S(O)_w$—$C_{1-3}$alkyl, —$S(O)_w$—$NR^aR^b$, —$NR^a$—$S(O)_w$—$C_{1-3}$alkyl (where w is 0, 1, or 2), a 5-6 membered monocyclic heteroaryl having one, two or three heteroatoms each independently selected from the group consisting of O, N, and S, and a 4-7 membered heterocyclic ring having one or two heteroatoms each independently selected from the group consisting of O, N, and S; wherein $C_{1-6}$alkoxy and $S(O)_w$—$C_{1-3}$alkyl may optionally be substituted by one, two, or three halogens;

$R^{ii}$ is independently selected for each occurrence from the group consisting of halogen, hydroxyl, —$NR^aR^b$, oxo, $C_{1-6}$alkyl and $C_{1-6}$alkoxy;

$R^{A1}$ is independently for each occurrence selected from the group consisting of hydrogen, halogen, $C_{1-6}$alkyl, $C_{2-6}$alkenyl, $C_{2-6}$alkynyl, $C_{1-6}$alkoxy, $C_{3-6}$cycloalkyl, phenyl, —$NR^aR^b$, —O—C(O)—$NR^a$-phenyl, —$NR^a$—C(O)-phenyl, and —$NR^a$—$C_{1-4}$alkyl-phenyl; wherein $C_{1-6}$alkyl, $C_{2-6}$alkenyl, $C_{2-6}$alkynyl, $C_{1-6}$alkoxy, $C_{3-6}$cycloalkyl and phenyl may optionally be substituted by one or more substituents selected from the group consisting of halogen, hydroxyl, phenyl, and —$NR^aR^b$;

$R^{X1}$ is selected from the group consisting of hydrogen, —C(O)OH, and $C_{1-6}$alkyl; wherein $C_{1-6}$alkyl may optionally be substituted by one, two or three halogens;

$R^{X2}$ is selected from the group consisting of hydrogen, halogen, $C_{1-6}$alkyl, $C_{1-6}$alkoxy, and —$C_{1-6}$alkoxy-phenyl; wherein phenyl may optionally be substituted by one or more substituents selected from $R^p$;

$R^{X3}$ is selected from the group consisting of hydrogen, halogen, cyano, $C_{1-6}$alkyl, $C_{1-6}$alkoxy, —$C_{1-6}$alkoxy-phenyl, $C_{3-6}$cycloalkyl, $C_{3-6}$cycloalkoxy, and phenyl; wherein $C_{1-6}$alkyl and $C_{1-6}$alkoxy may optionally be substituted by one, two, or three substituents selected from the group consisting of hydroxyl and halogen; and wherein phenyl may optionally be substituted by one or more substituents selected from $R^p$;

$R^a$ and $R^b$ are each independently selected from the group consisting of hydrogen, $C_{1-6}$ alkyl, phenyl, —C(O)-phenyl, and —C(O)—$C_{1-6}$alkyl; or $R^a$ and $R^b$ taken together with the nitrogen to which they are attached form a heterocyclic ring; and $R'$ is independently selected for each occurrence from the group consisting of halogen, hydroxyl, cyano, $C_{1-6}$alkyl, $C_{3-6}$cycloalkyl, $C_{1-6}$alkoxy, phenyl, $C_{3-6}$cycloalkoxy, —$S(O)_w$—$C_{1-3}$alkyl (where w is 0, 1, or 2), —$S(O)_w$—$NR^aR^b$, and —$NR^aR^b$.

In some embodiments, A may be selected from the group consisting of:

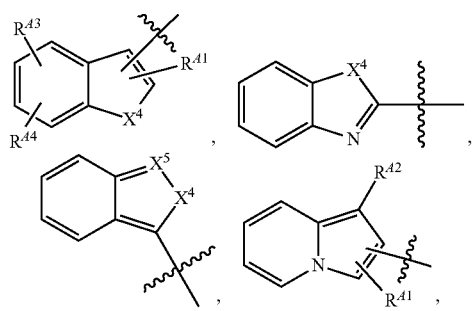

-continued

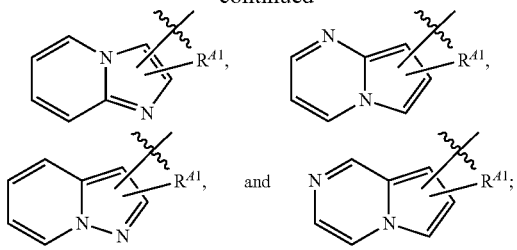

wherein:

$X^4$ may independently for each occurrence be selected from the group consisting of 0, S, and $N(R^4)$;

$X^5$ may be selected from the group consisting of N and $C(R^{X5})$;

$R^{A1}$ may independently for each occurrence be selected from the group consisting of hydrogen, halogen, $C_{1-6}$alkyl, $C_{2-6}$alkenyl, $C_{2-6}$alkynyl, $C_{1-6}$alkoxy, $C_{3-6}$cycloalkyl, phenyl, —$NR^aR^b$, —$OC(O)NR^aR^b$, —$NR^a$—C(O)-phenyl, and —O—C(O)—$NR^a$-phenyl; wherein $C_{1-6}$alkyl, $C_{2-6}$alkenyl, $C_{2-6}$alkynyl, $C_{1-6}$alkoxy, $C_{3-6}$cycloalkyl, phenyl, —OC(O)$NR_aR_b$, —$NR_a$—C(O)-phenyl, and —O—C(O)—$NR_a$-phenyl may optionally be substituted by one or more substituents selected from the group consisting of halogen, hydroxyl, phenyl, and $NR^aR^b$;

$R^{A2}$ may be selected from the group consisting of hydrogen and $C_{1-6}$alkyl;

$R^{A3}$ and $R^{A4}$ may be each independently selected from the group consisting of hydrogen, halogen, $C_{1-6}$alkyl, $C_{1-6}$alkoxy, and $NR^aR^b$, wherein $C_{1-6}$alkyl and $C_{1-6}$alkoxy may optionally be substituted by one or more substituents selected from the group consisting of halogen, hydroxyl, phenyl, and $NR^aR^b$;

$R^4$ may be selected from the group consisting of hydrogen, $C_{1-6}$alkyl, $C_{3-6}$cycloalkyl, phenyl, heterocycle, $C_{1-6}$alkyl-$S(O)_2$—, and phenyl-$S(O)_2$—; wherein $C_{1-6}$alkyl, $C_{3-6}$cycloalkyl, phenyl, and heterocycle may optionally be substituted by one or more substituents selected from the group consisting of halogen, hydroxyl, phenyl, and $NR^aR^b$;

and $R^{X5}$ may be selected from the group consisting of hydrogen, halogen, and $C_{1-6}$alkyl.

In certain embodiments, $R^1$ may be —C(O)OH.

In certain other embodiments, $R^1$ may be selected from the group consisting of:

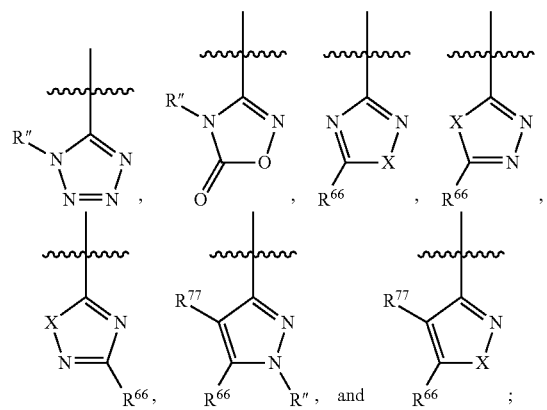

wherein X is selected from the group consisting of O and S; R" is hydrogen or $C_{1-4}$alkyl; and each $R^{66}$ and $R^{77}$ is independently from the group consisting of hydrogen, halogen, hydroxyl, and $C_{1-4}$alkyl.

For example, $R^1$ may be selected from the group consisting of:

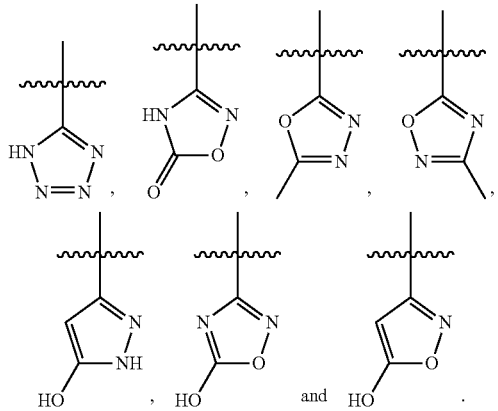

In certain embodiments, $R^2$ may be selected from the group consisting of hydrogen, $C_{1-6}$alkyl, $C_{1-6}$cycloalkyl, and halogen. For example, $R^2$ may be methyl or ethyl.

In certain embodiments, $R^3$ may be $C_{3-6}$cycloalkoxy; wherein $C_{3-6}$cycloalkoxy may be optionally substituted by one or two substituents selected from $R^{gg}$. For example, $R^{gg}$ may be selected from the group consisting of: $C_{1-6}$alkyl,

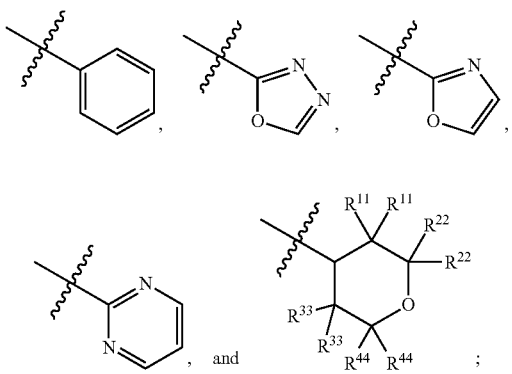

wherein $R^{11}$, $R^{22}$, $R^{33}$ and $R^{44}$ are independently selected for each occurrence from the group consisting of hydrogen and $C_{1-6}$alkyl.

For example, $R^{gg}$ may be

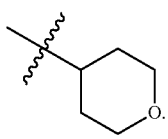 [SMILES: *C1CCOCC1]

In certain embodiments, $R^3$ may be $C_{1-6}$alkoxy, wherein $C_{1-6}$alkoxy may be optionally substituted by one, two or three substituents selected from $R^{gg}$. For example, $R^{gg}$ may be selected from the group consisting of: halogen, hydroxyl, $C_{1-6}$alkoxy, $C_{3-6}$cycloalkyl (optionally substituted by one or two substituents independently selected from the group consisting of hydroxyl, $C_{1-3}$alkyl and $C_{1-3}$alkoxy), phenyl,

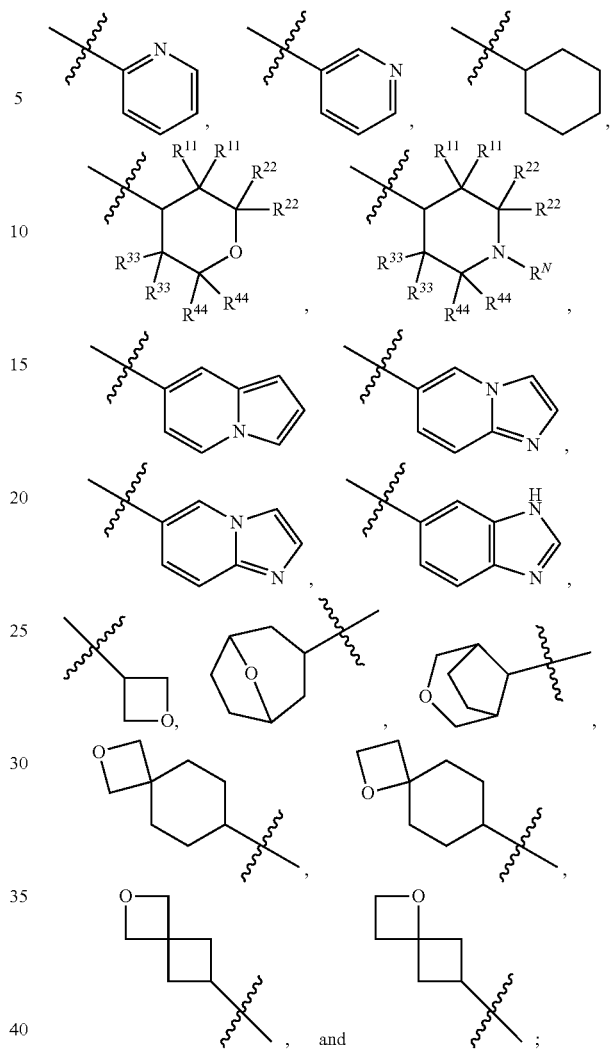

wherein $R^{11}$, $R^{22}$, $R^{33}$ and $R^{44}$ are independently selected for each occurrence from the group consisting of hydrogen, hydroxyl, $C_{1-6}$alkyl, $C_{1-3}$alkoxy and oxo; and wherein $R^N$ is selected from the group consisting of hydrogen and $-S(O)_2-C_{1-3}$alkyl; and wherein phenyl may be optionally substituted by on one two substituents selected from $R^{hh}$.

For example, $R^{gg}$ may be selected from the group consisting of:

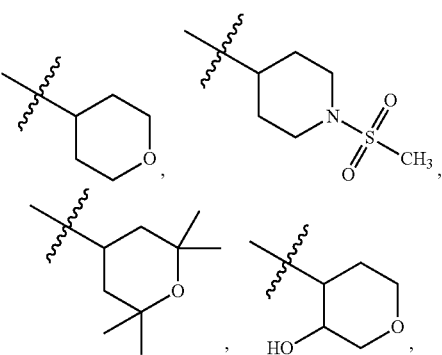

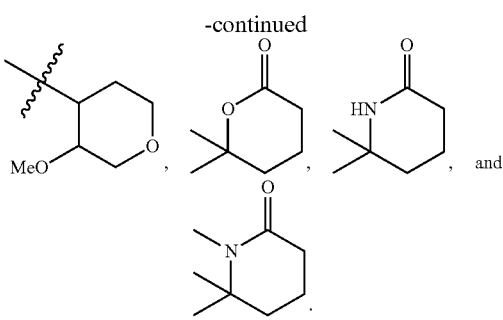

In certain embodiments, $R^{hh}$ may be selected from the group consisting of: halogen, $C_{1-3}$alkyl, $C_{1-3}$alkoxy, cyano, —S(O)$_w$—C$_{1-3}$ alkyl (where w is 0, 1, or 2), —S(O)$_w$—NR$^a$R$^b$, —NR$^a$—S(O)$_w$—C$_{1-3}$alkyl,

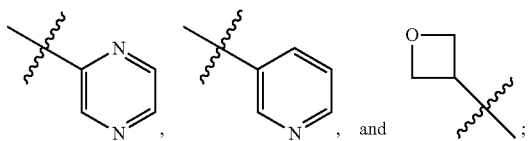

wherein $R^a$ is hydrogen or methyl; and wherein $C_{1-3}$alkoxy and S(O)$_w$—C$_{1-3}$alkyl may optionally be substituted by one, two, or three fluorine atoms.

In certain embodiments, $R^3$ may be a monocyclic, spirocyclic, or bridged bicyclic heterocyclyloxy.

For example, $R^3$ may be selected from the group consisting of:

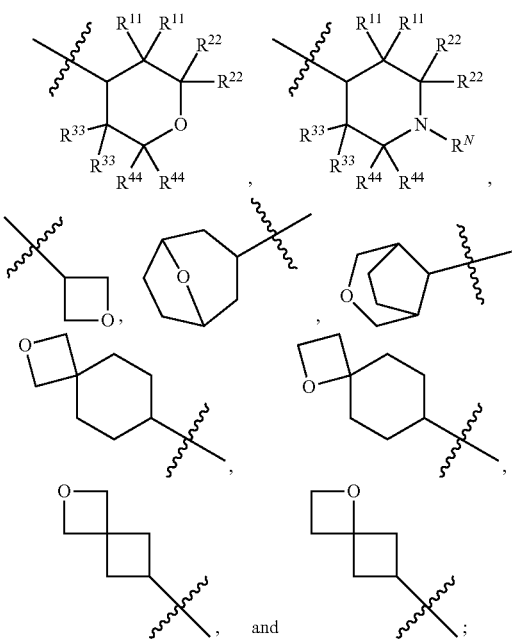

wherein $R^{11}$, $R^{22}$, $R^{33}$ and $R^{44}$ are independently selected for each occurrence from the group consisting of hydrogen, hydroxyl, $C_{1-6}$alkyl, $C_{1-3}$alkoxy and oxo; and wherein $R^N$ is selected from the group consisting of hydrogen and —S(O)$_2$—C$_{1-3}$alkyl.

For example, $R^3$ may be selected from the group consisting of:

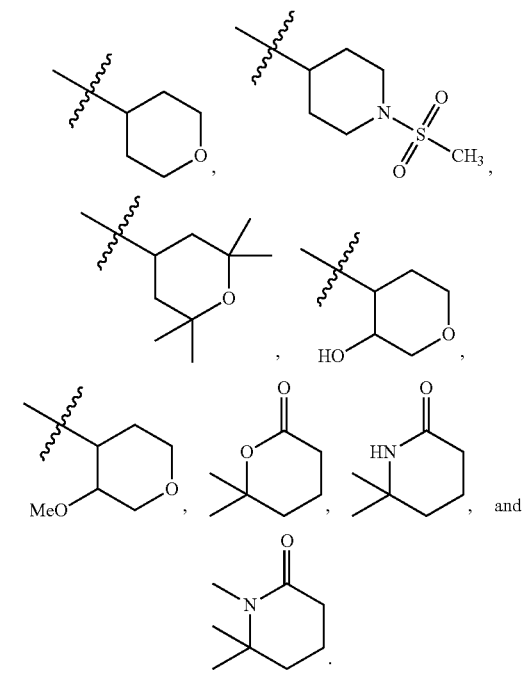

In certain embodiments, $X^1$ may be $C(R^{X1})$, $X^2$ is $C(R^{X2})$, and $X^3$ is $C(R^{X3})$.

In an embodiment, A may be selected from the group consisting of:

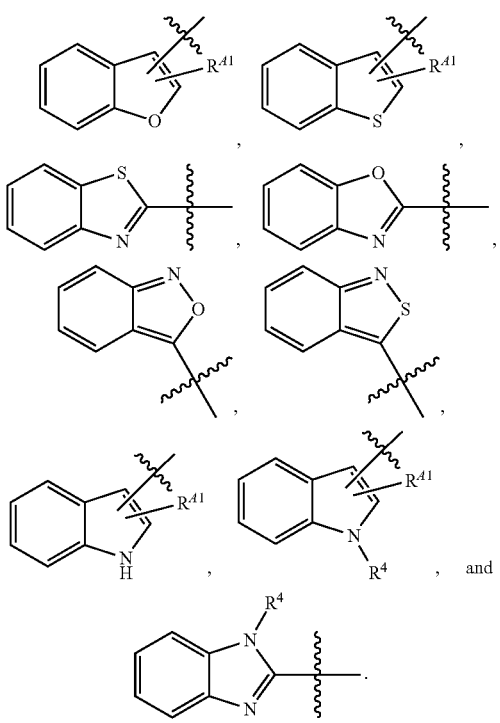

For example, A may be selected from the group consisting of:

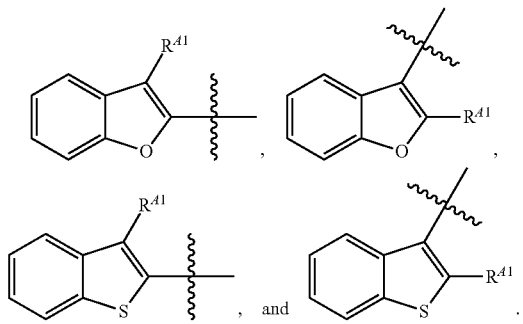

In certain embodiments, a disclosed compound of Formula I may be represented by:

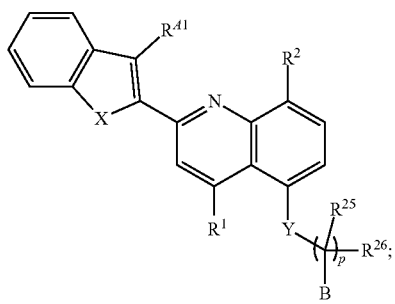

(Ia)

wherein
X is O or S;
R$^{41}$ is selected from the group consisting of hydrogen and C$_{1-6}$alkyl;
R$^1$ is selected from the group consisting of —C(O)OH and a 5-6 membered monocyclic heteroaryl having one, two, three, or four heteroatoms each selected from the group consisting of O, N, and S; wherein said heteroaryl may optionally be substituted by one or two substituents each independently selected from the group consisting of halogen, hydroxyl, and C$_{1-4}$alkyl;
R$^2$ is selected from the group consisting of hydrogen, halogen, cyano, C$_{1-6}$alkyl, C$_{1-6}$alkoxy, and C$_{3-6}$cycloalkyl;
Y is O or S(O)$_w$ (where w is 0, 1 or 2);
R$^{25}$ and R$^{26}$ are each independently selected from the group consisting of hydrogen and C$_{1-6}$alkyl;
p is 0 or 1; and
B is a 4-10 membered monocyclic, bridged bicyclic, or spirocyclic heterocyclic ring having one or two heteroatoms each independently selected from the group consisting of O, N, and S; wherein if said heterocyclic ring contains an —NH moiety, that nitrogen may optionally be substituted by a substituent selected from the group consisting of C$_{1-6}$alkyl, —C(O)—C$_{1-6}$alkyl, —C(O)—O—C$_{1-6}$alkyl, and —S(O)$_w$—C$_{1-3}$alkyl (where w is 0, 1, or 2); and wherein said heterocyclic ring may optionally be substituted by one, two, three, or four substituents each independently selected from hydroxyl, C$_{1-6}$alkyl, C$_{1-6}$alkoxy, and oxo.

In certain embodiments, X may be O. In certain other embodiments, R$^{41}$ may be methyl. In a further embodiment, R$^1$ may be —C(O)OH. In a further embodiment, p may be 1.

For example, a disclosed compound of Formula I may be represented by

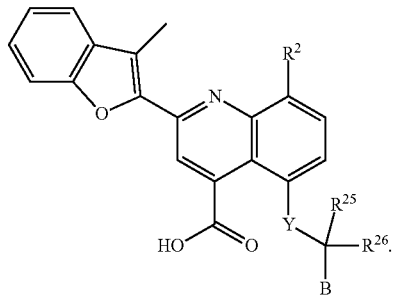

In certain embodiments, Y may be O. In certain other embodiments, R$^2$ may be C$_{1-6}$alkyl.

For example, a disclosed compound may be represented by:

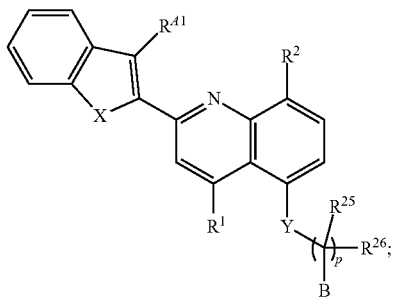

(Ia)

wherein
X is O or S;
R$^{41}$ is selected from the group consisting of hydrogen and C$_{1-6}$alkyl;
R$^1$ is selected from the group consisting of —C(O)OH and a 5-6 membered monocyclic heteroaryl having one, two, three, or four heteroatoms each selected from the group consisting of O, N, and S; wherein said heteroaryl may optionally be substituted by one or two substituents each independently selected from the group consisting of halogen, hydroxyl, and C$_{1-4}$alkyl;
R$^2$ is selected from the group consisting of hydrogen, halogen, cyano, C$_{1-6}$alkyl, C$_{1-6}$alkoxy, and C$_{3-6}$cycloalkyl;
Y is O or S(O)$_w$ (where w is 0, 1 or 2);
R$^{25}$ and R$^{26}$ are each independently selected from the group consisting of hydrogen and C$_{1-6}$alkyl;
p is 0 or 1; and

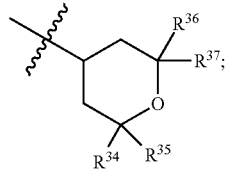

B is wherein R$^{34}$, R$^{35}$, R$^{36}$ and R$^{37}$ are each independently from the group consisting of hydrogen, hydroxyl, methyl and methoxy, or R$^{36}$ and R$^{37}$ taken together form an oxo moiety.

For example, provided herein are compounds represented by Formula II, III, IV, or V:

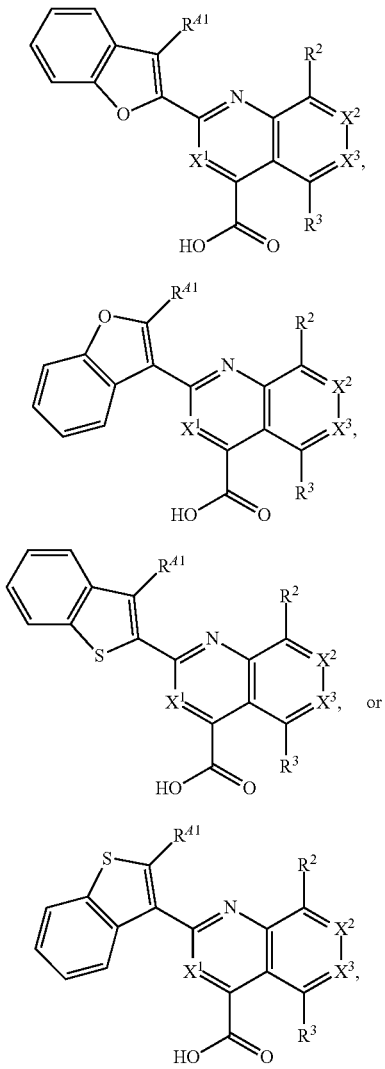

and pharmaceutically acceptable salts thereof, wherein:
$X^1$ is selected from the group consisting of N and C($R^{X1}$);
$X^2$ is selected from the group consisting of N and C($R^{X2}$);
$X^3$ is selected from the group consisting of N and C($R^{X3}$);
wherein only one of $X^1$, $X^2$ or $X^3$ can be N;
$R^2$ is selected from the group consisting of hydrogen, halogen, cyano, $C_{1-6}$alkyl, $C_{1-6}$alkoxy, and $C_{3-6}$cycloalkyl; wherein $C_{1-6}$alkyl, $C_{1-6}$alkoxy, and $C_{3-6}$cycloalkyl may optionally be substituted by one or more substituents each independently selected from the group consisting of halogen, hydroxyl, and phenyl; and wherein phenyl may optionally be substituted by one or more substituents each independently selected from $R^p$;
$R^3$ is selected from the group consisting of hydrogen, halogen, hydroxyl, $C_{1-6}$alkyl, $C_{1-6}$alkoxy, —S(O)$_w$—$C_{1-6}$alkyl (where w is 0, 1, or 2), —NR$^a$—$C_{1-6}$alkyl, $C_{3-6}$cycloalkoxy, —S(O)$_w$—$C_{3-6}$cycloalkyl (where w is 0, 1, or 2), —NR$^a$—$C_{3-6}$cycloalkyl, —O-phenyl, —S(O)$_w$-phenyl (where w is 0, 1, or 2), —NR$^a$-phenyl, $C_{8-12}$benzocycloalkoxy, —NR$^a$R$^b$, —OC(O)NR$^a$-phenyl, —NR$^a$—C(O)—O— phenyl, —NR$^a$—C(O)—$C_{1-6}$alkyl-phenyl, —$C_{1-6}$ alkyl-NR$^a$-phenyl, —NR$^a$—$C_{1-6}$alkyl-phenyl, and a 4-10 membered monocyclic, bridged bicyclic, or spirocyclic heterocyclyloxy, heterocyclyl-NR$^a$—, or heterocyclyl-S(O)$_w$— moiety (where w is 0, 1, or 2) having one or two heteroatoms each independently selected from the group consisting of O, N, and S; wherein if said heterocyclyloxy, heterocyclyl-NR$^a$—, or heterocyclyl-S(O)$_w$— ring contains an —NH moiety, that nitrogen may optionally be substituted by a substituent selected from the group consisting of $C_{1-6}$alkyl, —C(O)—$C_{1-6}$alkyl, —C(O)—O—$C_{1-6}$alkyl, and —S(O)$_w$—$C_{1-3}$alkyl (where w is 0, 1, or 2); and wherein said heterocyclyloxy, heterocyclyl-NR$^a$—, and heterocyclyl-S(O), may optionally be substituted by one, two, three, or four substituents each independently selected from R$^{ff}$; and wherein said phenyl moiety of —O-phenyl, —S(O)$_w$-phenyl, —NR$^a$-phenyl, —OC(O)NR$^a$-phenyl, —NR$^a$—C(O)—O-phenyl, —NR$^a$—C(O)—$C_{1-6}$alkyl-phenyl, —$C_{1-6}$alkyl-NR$^a$-phenyl and —NR$^a$—$C_{1-6}$alkyl-phenyl may optionally be substituted by one, two, or three substituents each independently selected from R$^p$; and wherein $C_{1-6}$alkoxy, —S(O)$_w$—$C_{1-6}$alkyl (where w is 0, 1, or 2), —NR$^a$—$C_{1-6}$alkyl, $C_{3-6}$cycloalkoxy, —S(O)$_w$—$C_{3-6}$cycloalkyl (where w is 0, 1, or 2), and —NR$^a$—$C_{3-6}$cycloalkyl may optionally be substituted by one, two, or three substituents each independently selected from R$^{gg}$;
R$^{ff}$ is independently selected for each occurrence from the group consisting of halogen, hydroxyl, —NR$^a$R$^b$, oxo, $C_{1-6}$alkyl and $C_{1-6}$alkoxy;
R$^{gg}$ is independently selected for each occurrence from the group consisting of halogen, hydroxyl, —NR$^a$R$^b$, $C_{1-6}$alkyl, $C_{1-6}$alkoxy, $C_{3-6}$cycloalkyl (optionally substituted by one, two or three substituents independently selected from the group consisting of halogen, hydroxyl, $C_{1-3}$alkyl and $C_{1-3}$alkoxy (optionally substituted by one, two or three fluorine atoms)), phenyl, a 5-6 membered monocyclic or 8-10 membered bicyclic heteroaryl having one, two or three heteroatoms each independently selected from the group consisting of O, N, and S, and a 4-10 membered monocyclic, bridged bicyclic, or spirocyclic heterocyclic ring having one or two heteroatoms each independently selected from the group consisting of O, N, and S; wherein if said heterocyclic ring contains an —NH moiety, that nitrogen may optionally be substituted by a substituent selected from the group consisting of $C_{1-6}$alkyl, —C(O)—$C_{1-6}$alkyl, and —S(O)$_w$—$C_{1-3}$alkyl (where w is 0, 1, or 2); and wherein phenyl may optionally be substituted by one, two, or three substituents each independently selected from R$^{hh}$; and wherein said 4-10 membered monocyclic, bridged bicyclic, or spirocyclic heterocyclic ring may optionally be substituted by one, two, three, or four substituents each independently selected from R$^{ii}$;
R$^{hh}$ is independently selected for each occurrence from the group consisting of halogen, cyano, $C_{1-6}$alkoxy, —S(O)$_w$—NR$^a$R$^b$, —NR$^a$—S(O)$_w$—$C_{1-3}$alkyl (where w is 0, 1, or 2), a 5-6 membered monocyclic heteroaryl having one, two or three heteroatoms each independently selected from the group consisting of O, N, and S, and a 4-7 membered heterocyclic ring having one or two heteroatoms each independently selected from the group consisting of O, N, and S; wherein $C_{1-6}$alkoxy and S(O)$_w$—$C_{1-3}$alkyl may optionally be substituted by one, two, or three halogens;
R$^{ii}$ is independently selected for each occurrence from the group consisting of halogen, hydroxyl, —NR$^a$R$^b$, oxo, $C_{1-6}$alkyl and $C_{1-6}$alkoxy;

$R^{41}$ is independently for each occurrence selected from the group consisting of hydrogen, halogen, $C_{1-6}$alkyl, $C_{2-6}$alkenyl, $C_{2-6}$alkynyl, $C_{1-6}$alkoxy, $C_{3-6}$cycloalkyl, phenyl, —$NR^aR^b$, —O—C(O)—$NR^a$-phenyl, —$NR^a$—C(O)-phenyl, and —$NR^a$—$C_{1-4}$alkyl-phenyl; wherein $C_{1-6}$alkyl, $C_{2-6}$alkenyl, $C_{2-6}$alkynyl, $C_{1-6}$alkoxy, $C_{3-6}$cycloalkyl and phenyl may optionally be substituted by one or more substituents selected from the group consisting of halogen, hydroxyl, phenyl, and —$NR^aR^b$;

$R^{X1}$ is selected from the group consisting of hydrogen, —C(O)OH, and $C_{1-6}$alkyl; wherein $C_{1-6}$alkyl may optionally be substituted by one, two or three halogens;

$R^{X2}$ is selected from the group consisting of hydrogen, halogen, $C_{1-6}$alkyl, $C_{1-6}$alkoxy, and —$C_{1-6}$alkox-phenyl; wherein phenyl may optionally be substituted by one or more substituents selected from $R^p$;

$R^{X3}$ is selected from the group consisting of hydrogen, halogen, cyano, $C_{1-6}$ alkyl, $C_{1-6}$alkoxy, —$C_{1-6}$alkoxy-phenyl, $C_{3-6}$cycloalkyl, $C_{3-6}$cycloalkoxy, and phenyl; wherein $C_{1-6}$alkyl and $C_{1-6}$alkoxy may optionally be substituted by one, two, or three substituents selected from the group consisting of hydroxyl and halogen; and wherein phenyl may optionally be substituted by one or more substituents selected from $R^p$;

$R^a$ and $R^b$ are each independently selected from the group consisting of hydrogen, $C_{1-6}$alkyl, phenyl, —C(O)-phenyl, and —C(O)—$C_{1-6}$alkyl; or $R^a$ and $R^b$ taken together with the nitrogen to which they are attached form a heterocyclic ring; and R' is independently selected, for each occurrence, from the group consisting of halogen, hydroxyl, cyano, $C_{1-6}$alkyl, $C_{3-6}$cycloalkyl, $C_{1-6}$alkoxy, phenyl, $C_{3-6}$cycloalkoxy, —$S(O)_w$—$C_{1-3}$alkyl (where w is 0, 1, or 2), —$S(O)_w$—$NR^aR^b$, and —$NR^aR^b$.

In certain embodiments, $R^2$ may be selected from the group consisting of hydrogen, $C_{1-6}$alkyl, $C_{1-6}$cycloalkyl, and halogen. For example, $R^2$ may be methyl or ethyl.

In certain embodiments, $R^3$ may be $C_{3-6}$cycloalkoxy; wherein $C_{3-6}$cycloalkoxy may be optionally substituted by one or two substituents selected from $R^{gg}$. For example, $R^{gg}$ may be selected from the group consisting of: $C_{1-6}$alkyl,

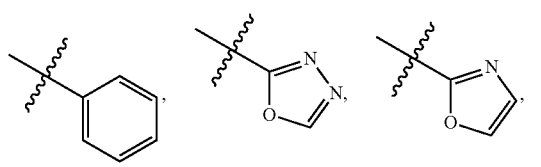

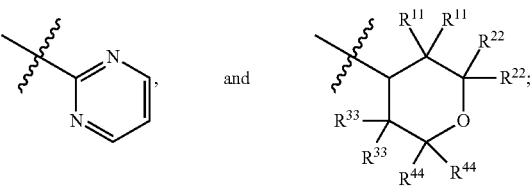

wherein $R^{11}$, $R^{22}$, $R^{33}$ and $R^{44}$ are independently selected for each occurrence from the group consisting of hydrogen and $C_{1-6}$alkyl.

For example, $R^{gg}$ may be

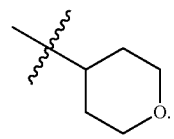

In certain embodiments, $R^3$ may be $C_{1-6}$alkoxy, wherein $C_{1-6}$alkoxy may be optionally substituted by one, two or three substituents selected from $R^{gg}$. For example, $R^{gg}$ may be selected from the group consisting of: halogen, hydroxyl, $C_{1-6}$alkoxy, $C_{3-6}$cycloalkyl (optionally substituted by one or two substituents independently selected from the group consisting of hydroxyl, $C_{1-3}$alkyl and $C_{1-3}$alkoxy), phenyl,

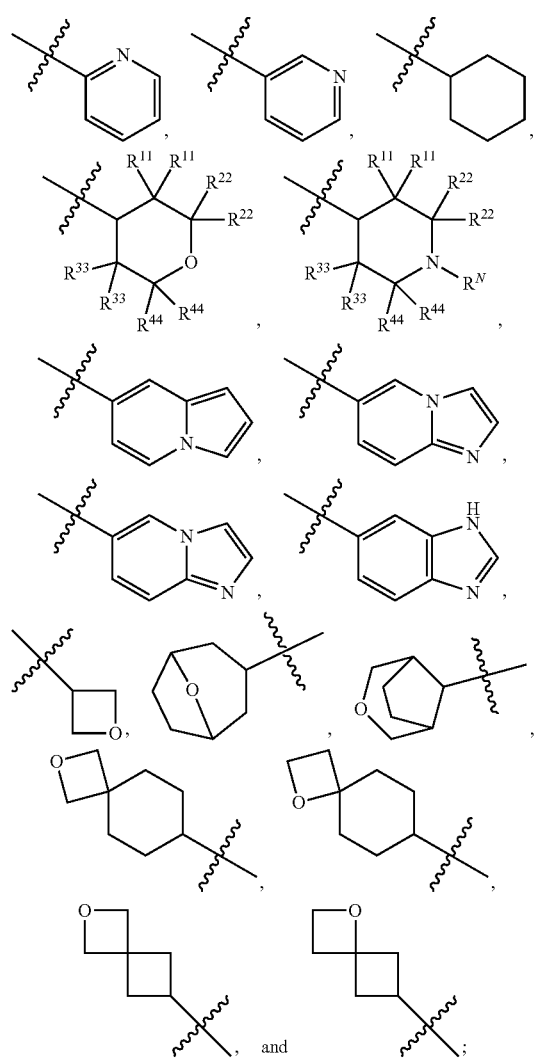

wherein $R^{11}$, $R^{22}$, $R^{33}$ and $R^{44}$ are independently selected for each occurrence from the group consisting of hydrogen, hydroxyl, $C_{1-6}$alkyl, $C_{1-3}$alkoxy and oxo; and wherein $R^N$ is selected from the group consisting of hydrogen and —$S(O)_2$—$C_{1-3}$alkyl; and wherein phenyl may be optionally substituted by on one two substituents selected from $R^{hh}$.

For example, $R^{gg}$ may be selected from the group consisting of:

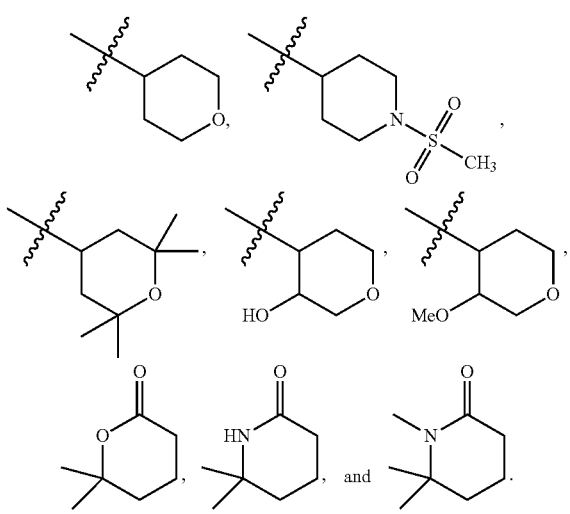

In certain embodiments, $R^{hh}$ may be selected from the group consisting of:
halogen, $C_{1-3}$alkyl, $C_{1-3}$alkoxy, cyano, $-S(O)_w-C_{1-3}$alkyl (where w is 0, 1, or 2), $-S(O)_w-NR^aR^b$, $-NR^a-S(O)_w-C_{1-3}$ alkyl,

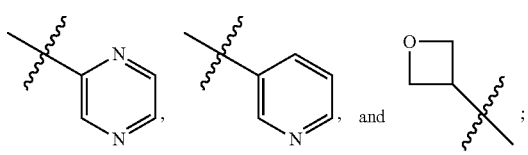

wherein $R^a$ is hydrogen or methyl; and wherein $C_{1-3}$alkoxy and $S(O)_w-C_{1-3}$alkyl may optionally be substituted by one, two, or three fluorine atoms.

In certain embodiments, $R^3$ may be a monocyclic, spirocyclic, or bridged bicyclic heterocyclyloxy.

For example, $R^3$ may be selected from the group consisting of:

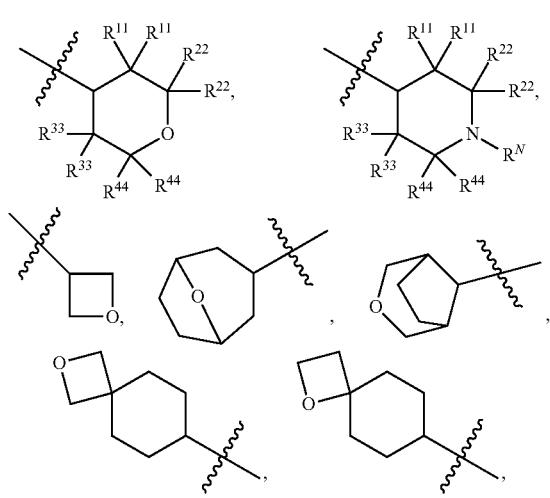

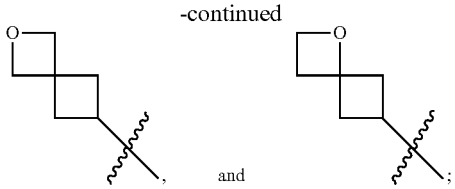

wherein $R^{11}$, $R^{22}$, $R^{33}$ and $R^{44}$ are independently selected for each occurrence from the group consisting of hydrogen, hydroxyl, $C_{1-6}$alkyl, $C_{1-3}$alkoxy and oxo; and wherein $R^N$ is selected from the group consisting of hydrogen and $-S(O)_2-C_{1-3}$alkyl.

For example, $R^3$ may be selected from the group consisting of:

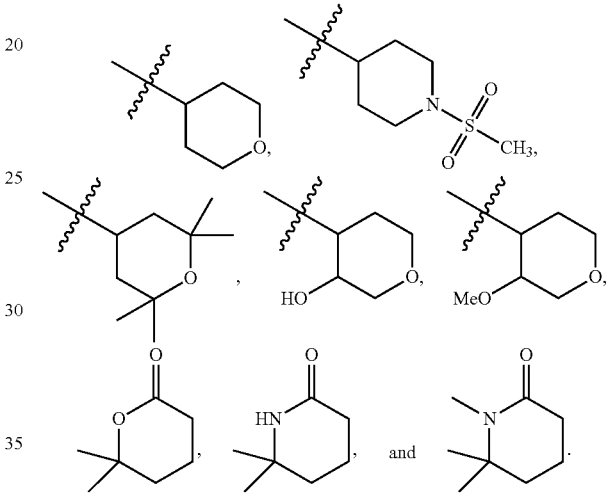

In certain embodiments, $R^{X1}$ in Formula I and other Formulas may be hydrogen. In other embodiments, $R^1$ may be $C_{1-6}$alkyl, e.g., methyl. In other embodiments, $R^{X1}$ may be $-C(O)OH$.

In certain embodiments, $R^{X2}$ may be hydrogen. In other embodiments, $R^{X2}$ may be $C_{1-6}$alkyl, e.g., methyl. In other embodiments, $R^{X2}$ may be $C_{1-6}$alkoxy substituted by phenyl, e.g., benzyloxy.

In certain embodiments, $R^{X3}$ may be hydrogen or cyano. In other embodiments, $R^{X3}$ may be halogen, e.g., fluoride, chloride, or bromide. In other embodiments, $R^{X3}$ may be $C_{1-6}$alkyl, e.g., methyl, ethyl, i-propyl, or t-butyl; or $C_{1-6}$alkyl substituted by one of more fluorides, e.g., trifluoromethyl. $R^{X3}$, for example, may be $C_{1-6}$alkoxy, e.g, methoxy, or $C_{1-6}$alkoxy substituted by phenyl, e.g., benzyloxy. In further embodiments, $R^{X3}$ may be $C_{3-6}$cycloalkyl, e.g., cyclopropyl. In another embodiment, $R^{X3}$ may be phenyl.

In one embodiment, $R^1$ may be $-C(O)OH$. In some embodiments, $R^1$ may be hydrogen or $-C(O)-C(O)OH$. In other embodiments, $R^1$ may be $C_{1-6}$alkyl substituted by hydroxyl, e.g., methyleneoxy, or substituted by $-C(O)OH$.

In certain embodiments, $R^2$ may be hydrogen. In other embodiments, $R^2$ may be $C_{1-6}$alkyl, e.g., methyl. $R^2$, for example, may be $C_{1-6}$alkoxy substituted by phenyl, e.g., benzyloxy.

In certain embodiments, $R^3$ may be hydrogen. In other embodiments, $R^3$ may be $C_{1-6}$alkyl, e.g., methyl. In other embodiments, $R^3$ may be $C_{1-6}$alkoxy, e.g, methoxy, or $C_{1-6}$alkoxy substituted by phenyl, e.g., benzyloxy. In further embodiments, $R^3$ may be $C_{3-6}$cycloalkoxy (which may be optionally substituted as described herein), e.g., cyclopropyloxy, cyclobutyloxy, or cyclohexyloxy. In some embodiments, cyclopropyloxy, cyclobutyloxy, and cyclohexyloxy may be substituted by phenyl or heteroaryl. In one embodiment, $R^3$ may be —O-phenyl. In other embodiments, $R^3$ may be —NH—C(O)-phenyl, —NH—C(O)—$CH_2$-phenyl, —O—C(O)—NH— phenyl, or —NH—C(O)—O-phenyl.

In certain embodiments, $R^{41}$ may be hydrogen. In other embodiments, $R^{41}$ may be halogen, e.g., chloride or bromide. In other embodiments, $R^{41}$ may be $C_{1-6}$alkyl, e.g., methyl, ethyl, or i-propyl. In one embodiment, $R^{41}$ may be $C_{2-6}$alkynyl, e.g., ethynyl. In some embodiments, $R^{41}$ may be $C_{3-6}$cycloalkyl, e.g., cyclopropyl or cyclohexyl. In another embodiment, $R^{41}$ may be phenyl. In further embodiments, $R^{41}$ may be $C_{1-6}$alkoxy, e.g, methoxy, or $C_{1-6}$alkoxy substituted by phenyl, e.g., benzyloxy. In other embodiments, $R^{41}$ may be —NHMe, —NH—$CH_2$-phenyl, —O—C(O)—NH-phenyl, or —NH—C(O)—O-phenyl.

In certain embodiments, $R^{42}$ may be hydrogen. In other embodiments, $R^{42}$ may be $C_{1-6}$alkyl, e.g., methyl.

Also provided herein are compounds disclosed in the Exemplification.

Also contemplated herein are pharmaceutical compositions that include a disclosed compound such as those compounds having Formula I and a pharmaceutically acceptable carrier or excipient. In certain embodiments, the compositions can include at least one additional CFTR modulator as described anywhere herein or at least two additional CFTR modulators, each independently as described anywhere herein.

The features and other details of the disclosure will now be more particularly described. Before further description of the present disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

It will be appreciated that the description of the present disclosure herein should be construed in congruity with the laws and principals of chemical bonding.

The term "alkyl", as used herein, unless otherwise indicated, refers to both branched and straight-chain saturated aliphatic hydrocarbon groups having the specified number of carbon atoms; for example, "$C_1$-$C_{10}$ alkyl" denotes alkyl having 1 to 10 carbon atoms, and straight or branched hydrocarbons of 1-6, 1-4, or 1-3 carbon atoms, referred to herein as $C_{1-6}$ alkyl, $C_{1-4}$ alkyl, and $C_{1-3}$ alkyl, respectively. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "carbonyl" as used herein refers to the radical —C(O)—.

The term "cyano" as used herein refers to the radical —CN.

The term, "alkenyl", as used herein, refers to both straight and branched-chain moieties having the specified number of carbon atoms and having at least one carbon-carbon double bond. Exemplary alkenyl groups include, but are not limited to, a straight or branched group of 2-6 or 3-4 carbon atoms, referred to herein as $C_{2-6}$ alkenyl, and $C_{3-4}$ alkenyl, respectively. Exemplary alkenyl groups include, but are not limited to, vinyl, allyl, butenyl, pentenyl, etc.

The term, "alkynyl", as used herein, refers to both straight and branched-chain moieties having the specified number or carbon atoms and having at least one carbon-carbon triple bond.

The term "cycloalkyl," as used herein, refers to saturated cyclic alkyl moieties having 3 or more carbon atoms, for example, 3-10, 3-6, or 4-6 carbons, referred to herein as $C_{3-10}$ cycloalkyl, $C_{3-6}$ cycloalkyl or $C_{4-6}$ cycloalkyl, respectively for example. Unless otherwise stated, such saturated cyclic alkyl moieties can contain up to 18 carbon atoms and include monocycloalkyl, polycycloalkyl, and benzocycloalkyl structures. Monocycloalkyl refers to groups having a single ring group. Polycycloalkyl denotes hydrocarbon systems containing two or more ring systems with one or more ring carbon atoms in common; i.e., a spiro, fused, or bridged structure. Benzocycloalkyl signifies a monocyclic alkyl group fused to a benzene ring, referred to herein as $C_{8-12}$benzocycloalkyl, for example. Examples of monocycloalkyl groups include, but are not limited to, cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, and cyclooctadecyl. Examples of polycycloalkyl groups include, but are not limited to, decahydronaphthalene, spiro[4.5]decyl, bicyclo[2.2.1]heptyl, bicyclo[3.2.1]octyl, pinanyl, norbornyl, adamantyl, and bicyclo[2.2.2]octyl. Examples of benzocycloalkyl groups include, but are not limited to, tetrahydronaphthyl, indanyl, and 1,2-benzocycloheptanyl.

The term "cycloalkoxy" refers to a cycloalkyl group as just described, that is a monocycloalkyl, polycycloalkyl, or benzocycloalkyl structure, bound to the remainder of the molecule through an ethereal oxygen atom. Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc. The term "benzocycloalkoxy" refers to a monocyclic cycloalkoxy group fused to a benzene ring, referred to herein for example as $C_{8-12}$benzocycloalkoxy. Examples of benzocycloalkoxy groups include, but are not limited to, tetrahydronaphthyloxy, indanyloxy, and 1,2-benzocycloheptanyloxy.

The term "cycloalkenyl," as used herein, refers to cyclic alkenyl moieties having 3 or more carbon atoms.

The term "cycloalkynyl," as used herein, refers to cyclic alkynyl moieties having 5 or more carbon atoms.

"Alkylene" means a straight or branched, saturated aliphatic divalent radical having the number of carbons indicated. "Cycloalkylene" refers to a divalent radical of carbocyclic saturated hydrocarbon group having the number of carbons indicated.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$ alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_{1-6}$alkoxy-$C_{1-6}$alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term "alkyoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkenyloxy" used herein refers to a straight or branched alkenyl group attached to oxygen (alkenyl-O—). Exemplary alkenyloxy groups include, but are not limited to, groups with an alkenyl group of 3-6 carbon atoms, referred to herein as $C_{3-6}$alkenyloxy. Exemplary "alkenyloxy" groups include, but are not limited to allyloxy, butenyloxy, etc.

The term "alkynyloxy" used herein refers to a straight or branched alkynyl group attached to oxygen (alkynyl-O). Exemplary alkynyloxy groups include, but are not limited to, groups with an alkynyl group of 3-6 carbon atoms, referred to herein as $C_{3-6}$alkynyloxy. Exemplary alkynyloxy groups include, but are not limited to, propynyloxy, butynyloxy, etc.

The term "heterocyclic" or "heterocycle" encompasses heterocycloalkyl, heterocycloalkenyl, heterobicycloalkyl, heterobicycloalkenyl, heteropolycycloalkyl, heteropolycycloalkenyl, and the like unless indicated otherwise. Heterocycloalkyl refers to cycloalkyl groups containing one or more heteroatoms (O, S, or N) within the ring. Heterocycloalkenyl as used herein refers to cycloalkenyl groups containing one or more heteroatoms (O, S or N) within the ring. Heterobicycloalkyl refers to bicycloalkyl groups containing one or more heteroatoms (O, S or N) within a ring. Heterobicycloalkenyl as used herein refers to bicycloalkenyl groups containing one or more heteroatoms (O, S or N) within a ring, a heterocycle can refer to, for example, a saturated or partially unsaturated 4- to 12 or 4-10-membered ring structure, including monocyclic, bridged bicyclic, fused bycyclic and spirocyclic rings, and whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran, etc.

The term "oxo" as used herein refers to the radical =O.

Cycloalkyl, cycloalkenyl, and heterocyclic groups also include groups similar to those described above for each of these respective categories, but which are substituted with one or more oxo moieties.

The term "heteroaryl", as used herein, refers to aromatic carbocyclic groups containing one or more heteroatoms (O, S, or N) within a ring. A heteroaryl group, unless indicated otherwise, can be monocyclic or polycyclic. A heteroaryl group may additionally be substituted or unsubstituted. Contemplated heteroaryl groups include ring systems substituted with one or more oxo moieties. A polycyclic heteroaryl can comprise fused rings, covalently attached rings or a combination thereof. A polycyclic heteroaryl is a polycyclic ring system that comprises at least one aromatic ring containing one or more heteroatoms within a ring. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, thiazolopyridinyl, oxazolopyridinyl and azaindolyl. The foregoing heteroaryl groups may be C-attached or heteroatom-attached (where such is possible). For instance, a group derived from pyrrole may be pyrrol-1-yl (N-attached) or pyrrol-3-yl (C-attached). In some embodiments, the heteroaryl is 4- to 12-membered heteroaryl. In yet other embodiments, the heteroaryl is a mono or bicyclic 4- to 10-membered heteroaryl.

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "halo" or "halogen" as used herein refer to F, Cl, Br, or I.

The term "haloalkyl" as used herein refers to an alkyl group having 1 to (2n+1) substituent(s) independently selected from F, Cl, Br or I, where n is the maximum number of carbon atoms in the alkyl group. It will be understood that haloalkyl is a specific example of an optionally substituted alkyl.

The terms "hydroxy" and "hydroxyl" as used herein refers to the radical —OH.

As will be understood by the skilled artisan, "H" is the symbol for hydrogen, "N" is the symbol for nitrogen, "S" is the symbol for sulfur, "O" is the symbol for oxygen. "Me" is an abbreviation for methyl.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of disclosed compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis"

represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic ring may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasterisomers of disclosed compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009. Where a particular compound is described or depicted, it is intended to encompass that chemical structure as well as tautomers of that structure.

The term "enantiomerically pure" means a stereomerically pure composition of a compound. For example, a stereochemically pure composition is a composition that is free or substantially free of other stereoisomers of that compound. In another example, for a compound having one chiral center, an enantiomerically pure composition of the compound is free or substantially free of the other enantiomer. In yet another example, for a compound having two chiral centers, an enantiomerically pure composition is free or substantially free of the other diastereomers.

Where a particular stereochemistry is described or depicted it is intended to mean that a particular enantiomer is present in excess relative to the other enantiomer. A compound has an R-configuration at a specific position when it is present in excess compared to the compound having an S-configuration at that position. A compound has an S-configuration at a specific position when it is present in excess compared to the compound having an R-configuration at that position.

The compounds disclosed herein can exist in solvated as well as unsolvated forms with pharmaceutically acceptable solvents such as water, ethanol, and the like, and it is intended that disclosed compounds include both solvated and unsolvated forms. In one embodiment, a disclosed compound is amorphous or, in another embodiment, a single polymorph. In another embodiment, a disclosed compound is a mixture of polymorphs. In another embodiment, a disclosed compound is in a crystalline form.

Isotopically labeled compounds are also contemplated herein, which are identical to those recited herein, except that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a disclosed compound may have one or more H atoms replaced with deuterium.

Certain isotopically labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly suitable for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be suitable in some circumstances. Isotopically labeled compounds can generally be prepared by following procedures analogous to those disclosed in the examples herein by substituting an isotopically labeled reagent for a non-isotopically labeled reagent.

In some embodiments one or more of the nitrogen atoms of a disclosed compound if present are oxidized to N-oxide.

Representative synthetic routes for the preparation of the compounds disclosed herein are provided throughout the Examples section. As will be understood by the skilled artisan, diastereomers can be separated from the reaction mixture using column chromatography.

Disclosed compounds may be also be prepared using methods described in the literature, including, but not limited to, *J. Med. Chem.* 2011, 54(13), 4350-64; *Russian Journal of Organic Chemistry*, 2011, 47(8), 1199-1203; U.S. Patent Application Publication No. 2009/0036451 A1; WO2008/046072 A2, and U.S. Pat. No. 4,336,264, the contents of each of which are expressly incorporated by reference herein.

As discussed above, contemplated herein in an embodiment is a method of increasing CFTR activity in a subject comprising administering an effective amount of a disclosed compound. Also contemplated herein is a method of treating a patient suffering from a condition associated with CFTR activity comprising administering to said patient an effective amount of a compound described herein.

"Treating" or "treatment" includes preventing or delaying the onset of the symptoms, complications, or biochemical indicia of a disease, alleviating or ameliorating the symptoms or arresting or inhibiting further development of the disease, condition, or disorder. A "subject" is an animal to be treated or in need of treatment. A "patient" is a human subject in need of treatment.

An "effective amount" refers to that amount of an agent that is sufficient to achieve a desired and/or recited effect. In the context of a method of treatment, an "effective amount" of the therapeutic agent that is sufficient to ameliorate of one or more symptoms of a disorder and/or prevent advancement of a disorder, cause regression of the disorder and/or to achieve a desired effect.

The term "modulating" encompasses increasing, enhancing, inhibiting, decreasing, suppressing, and the like. The terms "increasing" and "enhancing" mean to cause a net gain by either direct or indirect means. As used herein, the terms "inhibiting" and "decreasing" encompass causing a net decrease by either direct or indirect means.

In some examples, CFTR activity is enhanced after administration of a compound described herein when there is an increase in the CFTR activity as compared to that in the absence of the administration of the compound. CFTR activity encompasses, for example, chloride channel activity of the CFTR, and/or other ion transport activity (for example, $HCO_3^-$ transport). In certain of these embodiments, the activity of one or more (e.g., one or two) mutant CFTRs (e.g., ΔF508, S549N, G542X, G551D, R117H, N1303K, W1282X, R553X, 621+1G>T, 1717-1G>A, 3849+10kbC>T, 2789+5G>A, 3120+1G>A, I507del, R1162X, 1898+1G>A, 3659delC, G85E, D1152H, R560T, R347P, 2184insA, A455E, R334W, Q493X, and 2184delA CFTR) is enhanced (e.g., increased). Contemplated patients may have a CFTR mutation(s) from one or more classes, such as without limitation, Class I CFTR mutations, Class II CFTR mutations, Class III CFTR mutations, Class IV CFTR mutations, Class V CFTR mutations, and Class VI mutations. Contemplated subject (e.g., human subject) CFTR genotypes include, without limitation, homozygote mutations (e.g., ΔF508/ΔF508 and R117H/R117H) and compound heterozygote mutations (e.g., ΔF508/G551D; ΔF508/A455E; ΔF508/G542X; Δ508F/W1204X; R553X/W1316X; W1282X/N1303K, 591Δ18/E831X, F508del/R117H/N1303K/3849+10kbC>T; Δ303K/384; and DF508/G178R).

In certain embodiments, the mutation is a Class I mutation, e.g., a G542X; a Class II/I mutation, e.g., a ΔF508/G542X compound heterozygous mutation. In other embodiments, the mutation is a Class III mutation, e.g., a G551D; a Class II/Class III mutation, e.g., a ΔF508/G551D compound heterozygous mutation. In still other embodiments, the mutation is a Class V mutation, e.g., a A455E; Class II/Class V mutation, e.g., a ΔF508/A455E compound heterozygous mutation. Of the more than 1000 known mutations of the CFTR gene, ΔF508 is the most prevalent mutation of CFTR which results in misfolding of the protein and impaired trafficking from the endoplasmic reticulum to the apical membrane (Dormer et al. (2001). *J Cell Sci* 114, 4073-4081; http://www.genet.sickkids.on.ca/app). In certain embodiments, ΔF508 CFTR activity is enhanced (e.g., increased). In certain embodiments, ΔF508 CFTR activity and/or G542X CFTR activity and/or G551D CFTR activity and/or A455E CFTR activity is enhanced (e.g., increased). An enhancement of CFTR activity can be measured, for example, using literature described methods, including for example, Ussing chamber assays, patch clamp assays, and hBE Ieq assay (Devor et al. (2000), Am J Physiol Cell Physiol 279(2): C461-79; Dousmanis et al. (2002), J Gen Physiol 119(6): 545-59; Bruscia et al. (2005), PNAS 103(8): 2965-2971).

As discussed above, the disclosure also encompasses a method of treating cystic fibrosis. Methods of treating other conditions associated with CFTR activity, including conditions associated with deficient CFTR activity, comprising administering an effective amount of a disclosed compound, are also provided herein.

For example, provided herein is a method of treating a condition associated with deficient or decreased CFTR activity comprising administering an effective amount of a disclosed compound that enhances CFTR activity. Non-limiting examples of conditions associated with deficient CFTR activity are cystic fibrosis, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), chronic sinusitis, dry eye disease, protein C deficiency, Aβ-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome.

In some embodiments, disclosed methods of treatment further comprise administering an additional therapeutic agent. For example, in an embodiment, provided herein is a method of administering a disclosed compound and at least one additional therapeutic agent. In certain aspects, a disclosed method of treatment comprises administering a disclosed compound, and at least two additional therapeutic agents. Additional therapeutic agents include, for example, mucolytic agents, bronchodilators, antibiotics, anti-infective agents, anti-inflammatory agents, ion channel modulating agents, therapeutic agents used in gene therapy, CFTR correctors, and CFTR potentiators, or other agents that modulates CFTR activity. In some embodiments, at least one additional therapeutic agent is selected from the group consisting of a CFTR corrector and a CFTR potentiator. Non-limiting examples of CFTR correctors and potentiators include VX-770 (Ivacaftor), deuterated Ivacaftor, GLPG2851, GLPG2737, GLPG2451, VX-809 (3-(6-(1-(2, 2-difluorobenzo[d][1,3]dioxol-5-yl)cyclopropanecarbox-amido)-3-methylpyridin-2-yl)benzoic acid, VX-661 (1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide), VX-983, VX-152, VX-440, and Ataluren (PTC124) (3-[5-(2-fluorophenyl)-1,2,4-oxadiazol-3-yl]benzoic acid), FDL169, GLPG1837/ABBV-974 (for example, a CFTR potentiator), GLPG2665, GLPG2222 (for example, a CFTR corrector); and compounds described in, e.g., WO2014/144860 and 2014/176553, hereby incorporated by reference. Non-limiting examples of modulators include QBW-251, QR-010, NB-124, riociquat, and compounds described in, e.g., WO2014/045283; WO2014/081821, WO2014/081820, WO2014/152213; WO2014/160440, WO2014/160478, US2014027933; WO2014/0228376, WO2013/038390, WO2011/113894, WO2013/038386; and WO2014/180562, of which the disclosed modulators in those publications are contemplated as an additional therapeutic agent and incorporated by reference. Non-limiting examples of anti-inflammatory agents include N6022 (3-(5-(4-(1H-imidazol-1-yl) phenyl)-1-(4-carbamoyl-2-methylphenyl)-1H-pyrrol-2-yl) propanoic acid), CTX-4430, N1861, N1785, and N91115.

In some embodiments, the methods described herein can further include administering an additional therapeutic agent or administering at least two additional CFTR therapeutic agents. In some embodiments, the methods described herein can further include administering an additional CFTR modulator or administering at least two additional CFTR modulators. In certain embodiments, at least one CFTR modulator is a CFTR corrector (e.g., VX-809, VX-661, VX-983, VX-152, VX-440, and GLPG2222 or GLPG2665) or potentiator (e.g., ivacaftor, genistein and GLPG1837). In certain of these embodiments, one of the at least two additional therapeutic agents is a CFTR corrector (e.g., VX-809, VX-661, VX-152, VX-440, and VX-983) and the other is a CFTR potentiator (e.g., ivacaftor and genistein). In certain of these embodiments, one of the at least two additional therapeutic agents is a CFTR corrector (e.g., GLPG2222) and the other is a CFTR potentiator (e.g., GLPG1837). In certain of these embodiments, one of the at least two additional therapeutic agents is a CFTR corrector (e.g., VX-809 or VX-661) and the other is a CFTR potentiator (e.g., ivacaftor). In certain of these embodiments, at least one CFTR modulator is an agent that enhances read-through of stop codons (e.g., NB124 or ataluren). NB124 has the structure:

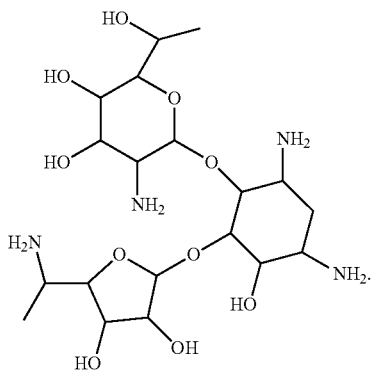 [SMILES: CC(N)C1OC(OC2C(O)C(N)CC(N)C2OC2OC(C(C)O)C(O)C(O)C2N)C(O)C1O]

In other embodiments, the methods described herein can further include administrating an epithelial sodium channel (ENaC) inhibitor (e.g., VX-371).

Accordingly, in another aspect, this disclosure provides a method of treating a condition associated with deficient or decreased CFTR activity (e.g., cystic fibrosis), which includes administering to a subject in need thereof (e.g., a human patient in need thereof) an effective amount of a disclosed compound and at least one or two additional CFTR therapeutic agent(s) (e.g., at least one or two additional CFTR therapeutic agents, e.g., in which one of the at least one or two additional therapeutic agents is optionally a CFTR corrector, modulator or amplifier (e.g., VX-809, VX-661, VX-983, GLPG2222, NB124, ataluren) and/or the other is a CFTR potentiator (e.g., ivacaftor, genistein, and GLPG1837); e.g., one of the at least two additional therapeutic agents is GLPG2222, and the other is GLPG1837; or one of the at least two additional therapeutic agents is VX-809 or VX-661, and the other is ivacaftor. Additional agents, e.g. amplifiers, are disclosed in co-pending applications PCT/US14/044100, PCT/US15/020460, PCT/US15/020499, and PCT/US15/036691, each incorporated by reference. For example, an exemplary amplifier is N-(3-(5-(hydroxymethyl)-1H-1,2,3-triazol-1-yl)propyl)-5-phenylisoxazole-3-carboxamide ("Compound A"). In certain embodiments, the subject's CFTR genotype includes, without limitation, one or more Class I CFTR mutations, one or more Class II CFTR mutations, one or more Class III CFTR mutations, one or more Class IV CFTR mutations, or one or more Class V CFTR mutations, or one or more Class VI CFTR mutations. In certain embodiments, the subject's CFTR genotype includes, without limitation, one or more homozygote mutations (e.g., ΔF508/ΔF508 or R117H/R117H) and/or one or more compound heterozygote mutations (e.g., ΔF508/G551D; ΔF508/A455E; ΔF508/G542X; Δ508F/W1204X; R553X/W1316X; W1282X/N1303K; F508del/R117H; N1303K/3849+10kbC>T; ΔF508/R334W; DF508/G178R, and 591Δ18/E831X). In certain embodiments, the subject's CFTR genotype includes a Class I mutation, e.g., a G542X Class I mutation, e.g., a ΔF508/G542X compound heterozygous mutation. In other embodiments, the subject's CFTR genotype includes a Class III mutation, e.g., a G551D Class III mutation, e.g., a ΔF508/G551D compound heterozygous mutation. In still other embodiments, the subject's CFTR genotype includes a Class V mutation, e.g., a A455E Class V mutation, e.g., a ΔF508/A455E compound heterozygous mutation. In certain embodiments, ΔF508 CFTR activity and/or G542X CFTR activity and/or G551D CFTR activity and/or A455E activity is enhanced (e.g., increased). In certain embodiments, the enhancement in activity (e.g., increase in activity) provided by the combination of the disclosed compound and one or two additional therapeutic agents is greater than additive when compared to the enhancement in activity provided by each therapeutic component individually.

| Class | Effect on CFTR protein | Example of mutation |
|-------|------------------------|---------------------|
| I | Shortened protein | W1282X Instead of inserting the amino acid tryptophan (W), the protein sequence is prematurely stopped (indicated by an X). |
| II | Protein fails to reach cell membrane | ΔF508 A phenylalanine amino acid (F) is deleted |
| III | Channel cannot be regulated properly | G551D A "missense" mutation: instead of a glycine amino acid (G), aspartate (D) is added |
| IV | Reduced chloride conductance | R117H Missense |
| V | Reduced due to incorrect splicing of gene | 3120+1G>A Splice-site mutation in gene intron 16 |
| VI | Reduced due to protein instability | N287Y a A –>T at 991 |

| Genotype | Description | Possible Symptoms |
|----------|-------------|-------------------|
| Δ508F/Δ508F | homozygote | Severe lung disease, pancreatic insufficient |
| R117H/R117H | homozygote | Congenital bilateral absence of the vas deferens, No lung or pancreas disease, |
| WT/Δ508F | heterozygote | Unaffected |
| WT/3120+1 G>A | heterozygote | Unaffected |
| Δ508F/W1204X | compound heterozygote | No lung disease, pancreatic insufficient |
| R553X and W1316X | compound heterozygote | Mild lung disease, pancreatic insufficient |
| 591Δ18/E831X | compound heterozygote | No lung or pancreas disease, nasal polyps |

For example, provided herein is a method of treating a patient having one or more of the following mutations in the CFTR gene: G1244E, G1349D, G178R, G551S, S1251N, S1255P, S549N, S549R, G970R, or R117H, and/or e.g., a patient with one or two copies of the F508del mutation, or one copy of the ΔF508 mutation and a second mutation that results in a gating effect in the CFTR protein (e.g., a patient that is heterozygous for ΔF508 and G551D mutation), a patient with one copy of the ΔF508 mutation and a second mutation that results in residual CFTR activity, or a patient with one copy of the ΔF508 mutation and a second mutation that results in residual CFTR activity, comprising administering an effective amount of a disclosed compound. As described herein, such exemplary methods (e.g., of a patient having one or mutations such as those described above) may include, for example, administering to such patient a combination therapy, e.g., administering (simultaneously or sequentially) an effective amount of ivacaftor to said patient and an effective amount of a disclosed compound that may act as an amplifier or a disclosed compound that may act as a corrector. Such administration may result, for example, in increased chloride transport in human bronchial epithelial cells with e.g., one or two copies of mutations, e.g, ΔF508 mutation, as compared to administration of ivacaftor alone. Another combination therapy that includes a disclosed compound may also include an effective amount of a readthrough agent (e.g., ataluren, NB124) and an effective amount of disclosed compound that may act as an amplifier or as a corrector.

Without being limited by theory, a disclosed compound may be advantageous as compared to known CFTR correctors. For example, using e.g., F508del-CFTR protein relative quantitation, exposure to a disclosed compound can result, at least in some embodiments, in a greater proportion of CFTR protein on the cell surface as compared to a known corrector. In another embodiment, using e.g., F508del-CFTR HBE, CFTR function of a disclosed compound administered with e.g., ivacaftor may be increased. For example, a disclosed compound co-dosed with ivacaftor (or another corrector) can restore chloride transport equal to, or greater than, the combination of lumacaftor and ivacaftor in CFTR HBE cells. In another embodiment, the combination of a disclosed compound, lumacaftor and ivacaftor may increase chloride transport e.g., over 1 fold, e.g., a further 1.4-fold. Disclosed compounds, for example, can maintain, in some embodiments, similar functional benefit whether ivacaftor is administered for 24 hours or acutely, in contrast to the combination of lumacaftor and ivacaftor that has attenuated response at 24 hours compared to acute ivacaftor administration.

The phrase "combination therapy," as used herein, refers to an embodiment where a patient is co-administered a disclosed compound, a CFTR potentiator agent (e.g., ivacaftor) and optionally, one or more CFTR corrector agent(s) (e.g, VX-661 and/or lumacaftor) as part of a specific treatment regimen intended to provide the beneficial effect from the co-action of these therapeutic agents. For example, a beneficial effect of a combination may include, but is not limited to, pharmacokinetic or pharmacodynamic co-action resulting from the combination of therapeutic agents. For example, administration of a disclosed compound with ivacaftor alone or with a CFTR corrector agent (e.g., lumacaftor or VX-661) may result in a level of function (e.g., as measured by chloride activity in HBE cells or patients that have a ΔF508 mutation, that achieves clinical improvement (or better) as compared to the chloride activity level in cells or patients with a G551D mutation receiving ivacaftor alone, or ivacaftor and a corrector agent (lumacaftor or VX-661; or for example, administration of a disclosed compound with ivacaftor alone or ivacaftor with a CFTR corrector agent (e.g., lumacaftor or VX-661) may result in a level of function (e.g., as measured by chloride activity in HBE cells or patients that have a A455E mutation, that achieves clinical improvement (or better) as compared to the chloride activity level at e.g., 50% or more of wild type cells; or upon administration of a disclosed compound and ivacaftor to a patient (e.g. having a G551D class III mutation) may show e.g., about two times or more improved activity of ivacaftor as compared to administration of ivacaftor alone. Administration of disclosed therapeutic agents in combination typically is carried out over a defined time period (usually a day, days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner Substantially simultaneous administration can be accomplished, for example, by administering to the subject a single tablet or capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, inhalational routes, intravenous routes, intramuscular routes, and direct absorption through mucous membrane tissues. The therapeutic agents can be administered by the same route or by different routes. For example, a first therapeutic agent of the combination selected may be administered by intravenous injection or inhalation or nebulizer while the other therapeutic agents of the combination may be administered orally. Alternatively, for example, all therapeutic agents may be administered orally or all therapeutic agents may be administered by intravenous injection, inhalation or nebulization.

Combination therapy also can embrace the administration of the therapeutic agents as described above in further combination with other biologically active ingredients and non-drug therapies. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by a day, days or even weeks.

The components of a disclosed combination may be administered to a patient simultaneously or sequentially. It will be appreciated that the components may be present in the same pharmaceutically acceptable carrier and, therefore, are administered simultaneously. Alternatively, the active ingredients may be present in separate pharmaceutical carriers, such as, conventional oral dosage forms, that can be administered either simultaneously or sequentially.

In a further aspect, a method of identifying a candidate agent that increases CFTR activity is provided, which includes: (i) contacting a cell that expresses a CFTR protein with the candidate agent and a disclosed compound; (ii) measuring the CFTR activity in the cell in the presence of the candidate agent and the disclosed compound; and (iii) comparing the CFTR activity to that in the absence of the test agent, wherein an increase in CFTR activity in the presence of the test agent indicates that the agent increases CFTR activity. In certain embodiments, the cell expresses a mutant CFTR protein. In certain embodiments, CFTR activity is measured by measuring chloride channel activity of the CFTR, and/or other ion transport activity. In certain of these embodiments, the method is high-throughput. In certain of these embodiments, the candidate agent is a CFTR corrector or a CFTR potentiator.

Provided herein, in an embodiment, is a method for treating a patient having CF or a condition associated with deficient or decreased CFTR activity, or suspected to have CF or a condition associated with deficient or decreased CFTR activity, comprising testing the patient (e.g., testing the patient's cells, mucosa and/or bodily fluids) for a specific functional or molecular profile, optionally assessing the results of such testing, and administering to the patient a disclosed compound based on the testing and/or assessment. For example, provided herein is a method for treating a patient having CF or a condition associated with deficient or decreased CFTR activity and a specific functional or molecular profile comprising administering to the patient a disclosed compound.

The term "pharmaceutically acceptable salt(s)" as used herein refers to salts of acidic or basic groups that may be present in a disclosed compounds used in disclosed compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, e.g., calcium, magnesium, sodium, lithium, zinc, potassium, and iron salts. Examples of such salts also include, e.g., ammonium salts and quaternary ammonium salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

In an embodiment, contemplated methods may include for example, administering prodrugs of the compounds described herein, for example, prodrugs of a compound of Formula I, or a pharmaceutical composition thereof.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al., *Nature Reviews Drug Discovery* 2008, 7, 255). For example, if a compound of the disclosure or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$alkylamino-$(C_{2-3})$alkyl (such as β-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino$(C_{2-3})$alkyl.

Similarly, if a compound of the disclosure contains an alcohol functional group, a prodrug can be formed by the replacement of the hydrogen atom of the alcohol group with a group such as $(C_{1-6})$alkylcarbonyloxymethyl, 1-($(C_{1-6})$alkylcarbonyloxy)ethyl, 1-methyl-1-($(C_{1-6})$alkylcarbonyloxy)ethyl $(C_{1-6})$alkoxycarbonyloxy)methyl, N—$(C_{1-6})$alkoxycarbonylaminomethyl, succinoyl, $(C_{1-6})$alkylcarbonyl, α-amino$(C_{1-4})$alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, P(O)(OH)$_2$, —P(O)(O$(C_{1-6})$alkyl)$_2$ or glycosyl (the radical resulting from the removal of a hydroxyl group of the hemiacetal form of a carbohydrate).

If a compound of the disclosure incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplício, et al., *Molecules* 2008, 13, 519 and references therein.

Also contemplated in certain embodiments is the use of clathrates of the compounds described herein, pharmaceutical compositions comprising the clathrates, and methods of use of the clathrates. Clathrates of a disclosed compound or a pharmaceutical composition thereof are also contemplated herein.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

As discussed above, the disclosure also contemplates administration of pharmaceutical compositions comprising a pharmaceutically acceptable carrier or excipient and a compound described herein. A disclosed compound, or a pharmaceutically acceptable salt, solvate, clathrate or prodrug thereof, can be administered in pharmaceutical compositions comprising a pharmaceutically acceptable carrier or excipient. The excipient can be chosen based on the expected route of administration of the composition in therapeutic applications. The route of administration of the composition depends on the condition to be treated. For example, intravenous injection may be suitable for treatment of a systemic disorder and oral administration may be suitable to treat a gastrointestinal disorder. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. A pharmaceutical composition comprising a disclosed compound or a pharmaceutically acceptable salt, solvate, clathrate or prodrug, can be administered by a variety of routes including, but not limited to, parenteral, oral, pulmonary, ophthalmic, nasal, rectal, vaginal, aural, topical, buccal, transdermal, intravenous, intramuscular, subcutaneous, intradermal, intraocular, intracerebral, intralymphatic, intraarticular, intrathecal and intraperitoneal. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

Disclosed compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are suitable liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above [Langer, *Science* 249: 1527, 1990 and Hanes, *Advanced Drug Delivery Reviews* 28: 97-119, 1997]. The compositions and pharmacologic agents described herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, transdermal applications and ocular delivery. For suppositories, binders and carriers include, for example, polyalkylene glycols or triglycerides; such suppositories can be formed from mixtures containing the active ingredient in the range of about 0.5% to about 10%, or about 1% to about 2%. Oral formulations include excipients, such as pharmaceutical grades of mannitol, lactose, starch, magnesium stearate, sodium saccharine, cellulose, and magnesium carbonate. Topical application can result in transdermal or intradermal delivery. Transdermal delivery can be achieved using a skin patch or using transferosomes. [Paul et al., *Eur. J. Immunol.* 25: 3521-24, 1995; Cevc et al., *Biochem. Biophys. Acta* 1368: 201-15, 1998].

For the purpose of oral therapeutic administration, the pharmaceutical compositions can be incorporated with excipients and used in the form of tablets, troches, capsules, elixirs, suspensions, syrups, wafers, chewing gums and the like. Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used. In another embodiment, the composition is administered as a tablet or a capsule.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The pharmaceutical composition can also be administered by nasal administration. As used herein, nasally administering or nasal administration includes administering the composition to the mucus membranes of the nasal passage or nasal cavity of the patient. As used herein, pharmaceutical compositions for nasal administration of a composition include therapeutically effective amounts of the compounds prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administered to the skin.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present disclosure, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

The disclosure also encompasses the treatment of a condition associated with a dysfunction in proteostasis in a subject comprising administering to said subject an effective amount of a disclosed compound that enhances, improves or restores proteostasis of a protein. Proteostasis refers to protein homeostasis. Dysfunction in protein homeostasis is a result of protein misfolding, protein aggregation, defective protein trafficking or protein degradation. For example, the disclosure contemplates s administering a disclosed compound e.g., Formula I that corrects protein misfolding, reduces protein aggregation, corrects or restores protein trafficking and/or affects protein degradation for the treatment of a condition associated with a dysfunction in proteostasis. In some aspects, a disclosed compound e.g., Formula I that corrects protein misfolding and/or corrects or restores protein trafficking is administered. In cystic fibrosis, the mutated or defective enzyme is the cystic fibrosis transmembrane conductance regulator (CFTR). One of the most common mutations of this protein is ΔF508 which is a deletion (Δ) of three nucleotides resulting in a loss of the amino acid phenylalanine (F) at the 508th (508) position on the protein. As described above, mutated cystic fibrosis transmembrane conductance regulator exists in a misfolded state and is characterized by altered trafficking as compared to the wild type CFTR. Additional exemplary proteins of which there can be a dysfunction in proteostasis, for example that can exist in a misfolded state, include, but are not limited to, glucocerebrosidase, hexosamine A, aspartyl-glucosaminidase, α-galactosidase A, cysteine transporter, acid ceremidase, acid α-L-fucosidase, protective protein, cathepsin A, acid β-glucosidase, acid β-galactosidase, iduronate 2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, N-acetylglucosamine-1-phosphotransferase, acid sphingmyelinase, NPC-1, acid α-glucosidase, β-hexosamine B, heparin N-sulfatase, α-N-acetylglucosaminidase, α-glucosaminide N-acetyltransferase, N-acetylglucosamine-6-sulfate sulfatase, α-N-acetylgalactosaminidase, α-neuramidase, β-glucuronidase, β-hexosamine A and acid lipase, polyglutamine, α-synuclein, TDP-43, superoxide dismutase (SOD), Aβ peptide, tau protein, transthyretin and insulin. The compounds of Formula I can be used to restore proteostasis (e.g., correct folding and/or alter trafficking) of the proteins described above.

Protein conformational diseases encompass gain of function disorders and loss of function disorders. In one embodiment, the protein conformational disease is a gain of function disorder. The terms "gain of function disorder," "gain of function disease," "gain of toxic function disorder" and "gain of toxic function disease" are used interchangeably herein. A gain of function disorder is a disease characterized by increased aggregation-associated proteotoxicity. In these diseases, aggregation exceeds clearance inside and/or outside of the cell. Gain of function diseases include, but are not limited to, neurodegenerative diseases associated with aggregation of polyglutamine, Lewy body diseases, amyotrophic lateral sclerosis, transthyretin-associated aggregation diseases, Alzheimer's disease, Machado-Joseph disease, cerebral B-amyloid angiopathy, retinal ganglion cell degeneration, tauopathies (progressive supranuclear palsy, corticobasal degeneration, frontotemporal lobar degeneration), cerebral hemorrhage with amyloidosis, Alexander disease, Serpinopathies, familial amyloidotic neuropathy, senile systemic amyloidosis, ApoAI amyloidosis, ApoAII amyloidosis, ApoAIV amyloidosis, familial amyloidosis of the Finnish type, lysozyme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amyloid, seminal vesical amyloid, sickle cell disease, critical illness myopathy, von Hippel-Lindau disease, spinocerebellar ataxia 1, Angelman syndrome, giant axon neuropathy, inclusion body myopathy with Paget disease of bone, frontotemporal dementia (IBMPFD) and prion diseases. Neurodegenerative diseases associated with aggregation of polyglutamine include, but are not limited to, Huntington's disease, dentatorubral and pallidoluysian atrophy, several forms of spino-cerebellar ataxia, and spinal and bulbar muscular atrophy Alzheimer's disease is characterized by the formation of two types of aggregates: extracellular aggregates of Aβ peptide and intracellular aggregates of the microtubule associated protein tau. Transthyretin-associated aggregation diseases include, for example, senile systemic amyloidoses and familial amyloidotic neuropathy. Lewy body diseases are characterized by an aggregation of α-synuclein protein and include, for example, Parkinson's disease, lewy body dementia (LBD) and multiple system atrophy (SMA). Prion diseases (also known as transmissible spongiform encephalopathies or TSEs) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome, Fatal Familial Insomnia and Kuru. In another embodiment, the misfolded protein is alpha-1 anti-trypsin.

In a further embodiment, the protein conformation disease is a loss of function disorder. The terms "loss of function disease" and "loss of function disorder" are used interchangeably herein. Loss of function diseases are a group of diseases characterized by inefficient folding of a protein resulting in excessive degradation of the protein. Loss of function diseases include, for example, lysosomal storage diseases. Lysosomal storage diseases are a group of diseases characterized by a specific lysosomal enzyme deficiency which may occur in a variety of tissues, resulting in the build-up of molecules normally degraded by the deficient enzyme. The lysosomal enzyme deficiency can be in a lysosomal hydrolase or a protein involved in the lysosomal trafficking. Lysosomal storage diseases include, but are not limited to, aspartylglucosaminuria, Fabry's disease, Batten disease, Cystinosis, Farber, Fucosidosis, Galactasidosialidosis, Gaucher's disease (including Types 1, 2 and 3), Gm1 gangliosidosis, Hunter's disease, Hurler-Scheie's disease, Krabbe's disease, α-Mannosidosis, β-Mannosidosis, Maroteaux-Lamy's disease, Metachromatic Leukodystrophy, Morquio A syndrome, Morquio B syndrome, Mucolipidosis II, Mucolipidosis III, Neimann-Pick Disease (including Types A, B and C), Pompe's disease, Sandhoff disease, Sanfilippo syndrome (including Types A, B, C and D), Schindler disease, Schindler-Kanzaki disease, Sialidosis, Sly syndrome, Tay-Sach's disease and Wolman disease.

In another embodiment, a disease associated with a dysfunction in proteostasis is a cardiovascular disease. Cardiovascular diseases include, but are not limited to, coronary artery disease, myocardial infarction, stroke, restenosis and arteriosclerosis. Conditions associated with a dysfunction of proteostasis also include ischemic conditions, such as, ischemia/reperfusion injury, myocardial ischemia, stable angina, unstable angina, stroke, ischemic heart disease and cerebral ischemia.

In yet another embodiment, a treatment of a disease associated with a dysfunction in proteostasis is diabetes and/or complications of diabetes, including, but not limited to, diabetic retinopathy, cardiomyopathy, neuropathy, nephropathy, and impaired wound healing is contemplated.

In a further embodiment, a treatment of a disease associated with a dysfunction in proteostasis is an ocular disease including, but not limited to, age-related macular degeneration (AMD), diabetic macular edema (DME), diabetic retinopathy, glaucoma, cataracts, retinitis pigmentosa (RP) and dry macular degeneration is contemplated.

In yet additional embodiments, a disclosed method is directed to treating a disease associated with a dysfunction in proteostasis, wherein the disease affects the respiratory system or the pancreas. In certain additional embodiments, a contemplated method encompass treating a condition selected from the group consisting of polyendocrinopathy/hyperinsulinemia, diabetes mellitus, Charcot-Marie Tooth syndrome, Pelizaeus-Merzbacher disease, and Gorham's Syndrome.

Additional conditions associated with a dysfunction of proteostasis include hemoglobinopathies, inflammatory diseases, intermediate filament diseases, drug-induced lung damage and hearing loss. For example, provided herein are methods for the treatment of hemoglobinopathies (such as sickle cell anemia), an inflammatory disease (such as inflammatory bowel disease, colitis, ankylosing spondylitis), intermediate filament diseases (such as non-alcoholic and alcoholic fatty liver disease) and drug induced lung damage (such as methotrexate-induced lung damage). In another embodiment, methods for treating hearing loss, such as noise-induced hearing loss, aminoglycoside-induced hearing loss, and cisplatin-induced hearing loss comprising administering a disclosed compound are provided.

Additional conditions include those associated with a defect in protein trafficking and that can be treated according to a disclosed methods include: PGP mutations, hERG trafficking mutations, nephrongenic diabetes insipidus mutations in the arginine-vasopressin receptor 2, persistent hyperinsulinemic hypoglycemia of infancy (PHH1) mutations in the sulfonylurea receptor 1, and α1AT.

The disclosure is illustrated by the following examples which are not meant to be limiting in any way.

EXEMPLIFICATION

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. At least some of the compounds identified as "intermediates" herein are contemplated as compounds of the disclosure.

General Procedures:

General procedures for the preparation of contemplated compounds are outlined in Scheme I and Scheme II. The disclosed compounds may be prepared, for example, either by base-mediated condensation of an aromatic aldehyde with a suitably functionalized isatin derivative (Scheme I), or three-component coupling between an aromatic aldehyde, a functionalized aniline, and an alpha-keto acid as shown in Scheme II.

Scheme I:

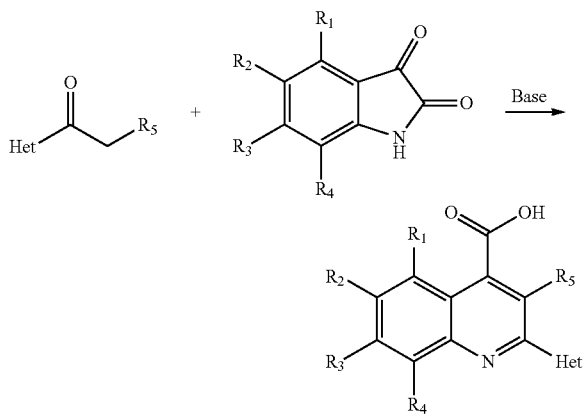

Scheme II:

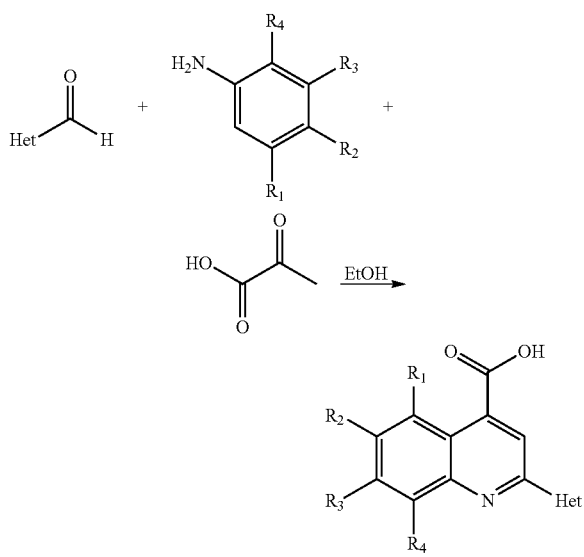

| List of Abbreviations | |
|---|---|
| Abbreviation | Name |
| rt | room temperature |
| THF | tetrahydrofuran |
| MeCN | acetonitrile |
| MTBE | tert-butyl methyl ether |
| DMSO | dimethylsulfoxide |
| DCM | dichloromethane |
| DCE | 1,2-dichloroethane |
| EtOH | ethanol |
| $Et_2O$ | diethyl ether |
| MeOH | methanol |
| IPA | isopropanol |
| EtOAc | ethyl acetate |
| DMF | N,N-dimethylformamide |
| TFA | trifluoroacetic acid |
| $Boc_2O$ | di-tert-butyl dicarbonate |
| TEOF | triethylorthoformate |
| DMAP | 4-(dimethylamino)pyridine |
| TsOH | 4-toluenesulfonic acid |
| $Ac_2O$ | acetic anhydride |
| AcOH | acetic acid |
| AcCl | acetyl chloride |
| BnBr | benzyl bromide |
| NaOMe | sodium methoxide |
| NaOAc | sodium acetate |
| BuLi | n-butyllithium |
| MeMgBr | methylmagnesium bromide |
| HATU | 1-[Bis(dimethylamino)methylene]-1H-1,2,3-triazolo[4,5-b]pyridinium-3-oxide hexafluorophosphate |
| DIEA | N,N-diisopropylethylamine |
| TEA | triethylamine |
| KOtBu | potassium tert-butoxide |
| TBHP | tert-butyl hydroperoxide |
| $PPh_3$ | triphenylphosphine |
| DIAD | diisopropyl azodicarboxylate |
| $Pd(OAc)_2$ | palladium(II) acetate |
| $Ni(OAc)_2$ | nickel(II) acetate |
| NIS | N-iodosuccinimide |
| NBS | N-bromosuccinimde |
| py | pyridine |
| MeI | iodomethane |
| dppf | 1,1'-bis(diphenylphosphino)ferrocene |
| atm | atmosphere |
| $NaBH(OAc)_3$ | sodium triacetoxyborohydride |
| mCPBA | meta-chloroperbenzoic acid |

| List of Abbreviations | |
|---|---|
| Abbreviation | Name |
| conc | concentrated |
| ESI | Electrospray Ionization |
| pos | positive |
| neg | negative |
| Calcd. | Calculated |

Preparation of Intermediates:

Intermediate 1: 7-Methyl-5-(trifluoromethyl)-2,3-dihydro-1H-indole-2,3-dione

A. tert-Butyl N-[2-Bromo-4-(trifluoromethyl)phenyl]carbamate. To a 100-mL round-bottom flask was placed a solution of 2-bromo-4-(trifluoromethyl)aniline (4.8 g, 20.00 mmol) in THF (20 mL) then DMAP (488 mg, 3.99 mmol) and $Boc_2O$ (8.72 g) were added. The reaction was heated to reflux overnight then concentrated under reduced pressure. The residue was purified by column chromatography eluting with EtOAc/petroleum ether (1:50) affording 7.9 g of the title compound as a white solid. $^1$H NMR (300 MHz, $CDCl_3$): δ 7.89 (s, 1H), 7.62-7.59 (d, J=9.0 Hz, 1H), 7.38-7.35 (d, J=9.0 Hz, 1H), 1.42 (s, 9H).

B. tert-Butyl N-[2-Methyl-4-(trifluoromethyl)phenyl]carbamate. To a 100-mL 3-necked round-bottom flask purged and maintained with an inert atmosphere of nitrogen was placed a solution of tert-butyl N-[2-bromo-4-(trifluoromethyl)phenyl]carbamate (6.75 g, 19.85 mmol, as prepared in the previous step) in dioxane/$H_2O$ (20:1; 20 mL) then methylboronic acid (2.98 g, 49.78 mmol), $K_3PO_4$ (25.25 g, 118.95 mmol), $Pd(OAc)_2$ (889 mg, 3.96 mmol), and $PCy_3 \cdot HBF_4$ (2.92 g, 7.93 mmol) were added. The reaction was stirred at 100° C. for 12 h then concentrated under reduced pressure. The residue was purified by column chromatography eluting with EtOAc/petroleum ether (1:2) affording 4.69 g (86%) of the title compound as a brown solid. $^1$H NMR (300 MHz, $CDCl_3$): δ 8.09-8.07 (d, J=6.0 Hz, 1H), 7.48-7.46 (d, J=6.0 Hz, 1H), 6.42 (s, 1H), 2.23 (s, 3H), 1.42 (s, 9H).

C. 2-Methyl-4-(trifluoromethyl)aniline. To a 100-mL round-bottom flask was placed a solution of tert-butyl N-[2-methyl-4-(trifluoromethyl)phenyl]carbamate (3.621 g, 13.15 mmol, as prepared in the previous step) in DCM (20 mL) then TFA (6 mL) was added. The reaction was stirred for 1 hour at rt, diluted with DCM, and extracted with water. The aqueous extracts were combined then the pH was adjusted to 8 with saturated aqueous $NaHCO_3$ solution and extracted with EtOAc. The organic extracts were combined, dried over anhydrous $Na_2SO_4$, and concentrated under reduced pressure affording 200 mg (9%) of the title compound as a yellow oil. Mass Spectrum (LCMS, ESI pos): Calcd. for $C_8H_9F_3N^+$: 176.1 (M+H); Found: 176.0.

D. 2-(N-Hydroxyimino)-N-[2-methyl-4-(trifluoromethyl)phenyl]acetamide. To a 100-mL round-bottom flask was placed a solution of 2,2,2-trichloroethane-1,1-diol (300 mg, 1.81 mmol), $NH_2OH \cdot HCl$ (300 mg, 4.32 mmol), and $Na_2SO_4$ (1 g, 7.04 mmol) in water (20 mL). A solution of 2-methyl-4-(trifluoromethyl)aniline (200 mg, 1.14 mmol, as prepared in the previous step) in conc. HCl/$H_2O$ (0.5/10 mL) was added then the reaction was stirred for 2 h at 100° C. The reaction mixture was cooled to rt then the precipitate was isolated by filtration affording 56 mg (20%) of the title compound as a yellow solid. Mass Spectrum (LCMS, ESI pos): Calcd. for $C_{10}H_{10}F_3N_2O_2^+$: 247.1 (M+H); Found: 247.1.

E. 7-Methyl-5-(trifluoromethyl)-2,3-dihydro-1H-indole-2,3-dione. To a 50-mL round-bottom flask was placed a solution of 2-(N-hydroxyimino)-N-[2-methyl-4-(trifluoromethyl)phenyl]acetamide (56 mg, 0.23 mmol, as prepared in the previous step) in conc. $H_2SO_4$ (2 mL) and stirred for 30 min at 90° C. The reaction was diluted with water and then the mixture was extracted with EtOAc (3×30 mL). The organic extracts were combined, dried over anhydrous $Na_2SO_4$, and concentrated under reduced pressure affording 46 mg of the title compound as an orange solid. Mass Spectrum (LCMS, ESI pos): Calcd. for $C_{10}H_7F_3NO_2^+$: 230.0 (M+H); Found: 230.0.

Intermediate 2:
5-Fluoro-7-methyl-2,3-dihydro-1H-indole-2,3-dione

A. (2E)-N-(4-Fluoro-2-methylphenyl)-2-(N-hydroxyimino)acetamide. To a 500-mL round-bottom flask was placed a solution of 4-fluoro-2-methylaniline (6 g, 47.94 mmol) in 10% HCl (80 mL) then 2,2,2-trichloroethane-1,1-diol (8.7 g, 52.60 mmol, 1.10 equiv) and $NH_2OH \cdot HCl$ (10.6 g, 152.54 mmol, 3.20 equiv) were added. The reaction was stirred for 1 h at 80° C. then cooled to rt and extracted with EtOAc (3×50 mL). The organic extracts were combined, dried over anhydrous $Na_2SO_4$, and concentrated under reduced pressure affording 4.4 g (47%) of the title compound as a brown oil. Mass Spectrum (LCMS, ESI pos): Calcd. for $C_9H_{10}FN_2O_2^+$: 197.1 (M+H); Found: 197.1.

B. 5-Fluoro-7-methyl-2,3-dihydro-1H-indole-2,3-dione. To a 100-mL round-bottom flask was placed a solution of (2E)-N-(4-fluoro-2-methylphenyl)-2-(N-hydroxyimino)acetamide (4.4 g, 22.43 mmol, as prepared in the previous step) in conc. $H_2SO_4$ (10 mL) then the mixture was stirred for 1 h at 80° C. The reaction was then quenched by the addition of water/ice and the precipitate was isolated by filtration affording 1.8 g (45%) of the title compound as a brown solid. Mass Spectrum (LCMS, ESI pos): Calcd. for $C_9H_7FNO_2^+$: 180.1 (M+H); Found: 180.0. $^1$H NMR (400 MHz, DMSO-$d_6$): δ 8.93 (s, 1H), 7.19-7.13 (m, 2H), 2.30 (s, 3H).

Intermediate 3:
5-Bromo-7-methyl-2,3-dihydro-1H-indole-2,3-dione

A. N-(4-Bromo-2-methylphenyl)-2-(N-hydroxyimino)acetamide. To a 1000-mL round-bottom flask was placed a solution of 2,2,2-trichloroethane-1,1-diol (12.78 g, 77.27 mmol, 1.20 equiv) in water (200 mL) and 2N HCl (100 mL). To this solution were added $Na_2SO_4$ (18.32 g), $NH_2OH \cdot HCl$ (8.9 g), and 4-bromo-2-methylaniline (12 g, 64.50 mmol) then the reaction was stirred for 1 h at 90° C. The reaction was quenched with water (200 mL) then the precipitate was isolated by filtration, washed with water (3×200 mL), and dried affording 7.38 g (45%) of the title compound as a brown solid. Mass Spectrum (LCMS, ESI pos): Calcd. for $C_9H_{10}BrN_2O_2^+$: 257.0 (M+H); Found: 256.8.

B. 5-Bromo-7-methyl-2,3-dihydro-1H-indole-2,3-dione. To a 250-mL round-bottom flask was placed a solution of N-(4-bromo-2-methylphenyl)-2-(N-hydroxyimino)acetamide (7.38 g, 28.71 mmol, as prepared in the previous step) in concentrated $H_2SO_4$ (70 mL). The solution was stirred for 2 h at 80° C. then quenched by the addition of 500 mL of water/ice. The precipitate was isolated by filtration, washed with water (3×200 mL), and dried affording 6.5 g (94%) of the title compound as a red solid. Mass Spectrum (LCMS, ESI pos): Calcd. for $C_9H_7BrNO_2^+$: 240.0 (M+H); Found: 240.0. $^1$H NMR (400 MHz, DMSO-$d_6$): δ 11.16 (s, 1H), 7.60 (s, 1H), 7.44 (s, 1H), 2.14 (s, 3H).

Intermediate 4: 4-(Benzyloxy)-2-methylaniline

A. 4-(Benzyloxy)-2-methyl-1-nitrobenzene. To a 100-mL round-bottom flask was placed a solution of 3-methyl-4-nitrophenol (1.53 g, 9.99 mmol) and $K_2CO_3$ (2.07 g, 14.98 mmol) in DMF (15 mL) then BnBr (2.04 g, 11.93 mmol) was added dropwise to the stirred solution. The reaction was stirred at rt overnight then quenched by the addition of water and extracted with EtOAc. The organic extracts were combined, washed with brine, dried over anhydrous $Na_2SO_4$, and concentrated under reduced pressure. The residue was purified by column chromatography eluting with EtOAc/petroleum ether (1:20) affording 2.2 g (91%) of the title compound as a white solid.

B. 4-(Benzyloxy)-2-methylaniline. To a 100-mL round-bottom flask purged and maintained with an inert atmosphere of $N_2$ was placed a solution of 4-(benzyloxy)-2-methyl-1-nitrobenzene (2.2 g, 9.04 mmol) in MeOH (20 mL), then Raney Ni (200 mg) was added. The reaction was purged with $H_2$ then stirred for 16 h at rt. The atmosphere was purged with $N_2$, then the solids were removed by filtration. The filtrate was concentrated under reduced pressure affording 1.8 g (93%) of the title compound as a dark red oil. Mass Spectrum (LCMS, ESI pos): Calcd. for $C_{14}H_{16}NO^+$: 214.1 (M+H); Found: 214.0.

Intermediate 5: 4-[2-[(tert-Butyldimethylsilyl)oxy]ethoxy]-2-methylaniline

A. tert-Butyldimethyl[2-(3-methyl-4-nitrophenoxy)ethoxy]silane. To a 250-mL round-bottom flask was placed a solution of 4-methyl-3-nitrophenol (1 g, 6.53 mmol, 1.00 equiv) in NMP (50 mL) then $Cs_2CO_3$ (2.77 g, 8.50 mmol), NaI (980 mg), and (2-bromoethoxy)(tert-butyl)dimethylsilane (3.10 g, 12.96 mmol) were added. The resulting solution was stirred for 6 h at 100° C. then the reaction was quenched with water and extracted with EtOAc. The organic extracts were combined, washed with brine, dried over anhydrous $Na_2SO_4$, and concentrated under reduced pressure affording 1.48 g (73%) of the title compound as a white solid. $^1$H NMR (300 MHz, $CDCl_3$): δ 8.14-8.03 (m, 1H), 6.84-6.81 (m, 2H), 4.14-4.11 (m, 2H), 4.01-3.98 (m, 2H), 2.64 (s, 3H), 0.92 (s, 9H), 0.11 (s, 6H).

B. 4-[2-[(tert-Butyldimethylsilyl)oxy]ethoxy]-2-methylaniline. To a 250-mL round-bottom flask purged and maintained with an inert atmosphere of $N_2$ was placed a solution of tert-butyldimethyl[2-(3-methyl-4-nitrophenoxy)ethoxy]silane (1.48 g, 4.75 mmol, as prepared in the previous step) in MeOH (50 mL), then Raney Ni (200 mg) was added. The reaction was purged with $H_2$ then stirred for 16 h at rt. The atmosphere was purged with $N_2$, then the solids were removed by filtration. The filtrate was concentrated under reduced pressure affording 1.2 g of the title compound as a dark red oil. Mass Spectrum (LCMS, ESI pos): Calcd. for $C_{15}H_{28}NO_2Si^+$: 282.2 (M+H); Found: 282.2.

Intermediate 6: 5-tert-Butyl-7-methyl-2,3-dihydro-1H-indole-2,3-dione

A. tert-Butyl N-(2-Bromo-4-tert-butylphenyl)carbamate. To a 250-mL round-bottom flask was placed a solution of 2-bromo-4-tert-butylaniline (4.56 g, 19.99 mmol) in THF (100 mL) then DMAP (244 mg, 2.00 mmol) and Boc$_2$O (8.72 g, 39.95 mmol) were added. The reaction was stirred for 2 h at 65° C., then diluted with 250 mL of H$_2$O and extracted with EtOAc (2×250 mL). The organic extracts were combined, was washed with brine (2×250 mL), dried over anhydrous Na$_2$SO$_4$, and concentrated under reduced pressure affording 7 g of the title compound as a yellow oil. Mass Spectrum (LCMS, ESI pos): Calcd. for C$_{15}$H$_{23}$BrNO$_2$$^+$: 328.1 (M+H); Found: 328.1.

B. tert-Butyl N-(4-tert-Butyl-2-methylphenyl)carbamate. To a 50-mL round-bottom flask was placed a solution of tert-butyl N-(2-bromo-4-tert-butylphenyl)carbamate (1.64 g, 5.00 mmol, as prepared in the previous step) in 1,4-dioxane/H$_2$O (20/0.5 mL), then PCy$_3$.HBF$_4$ (368 mg, 1.00 mmol), Pd(OAc)$_2$ (112 mg, 0.50 mmol), K$_3$PO$_4$ (3.18 g, 14.98 mmol) and methylboronic acid (450 mg, 7.52 mmol) were added. The resulting solution was purged with N$_2$, stirred for 16 h at 100° C., and diluted with 200 mL of H$_2$O. The mixture was extracted with EtOAc (2×200 mL) and the organic extracts were combined, was washed with brine (2×200 mL), dried over anhydrous Na$_2$SO$_4$, and concentrated under reduced pressure. The residue was purified by column chromatography eluting with petroleum ether/EtOAc (100:1) affording 520 mg (40%) of the title compound as a yellow oil. Mass Spectrum (LCMS, ESI pos): Calcd. for C$_{16}$H$_{26}$NO$_2$$^+$: 264.2 (M+H); Found: 264.2.

C. 4-tert-Butyl-2-methylaniline. To a 25-mL round-bottom flask was placed a solution of tert-butyl N-(4-tert-butyl-2-methylphenyl)carbamate (520 mg, 1.97 mmol, as prepared in the previous step) in DCM (6 mL) then TFA (3 mL) was added. The resulting solution was stirred for 2 h at rt then concentrated under reduced pressure. The residue was dissolved in 100 mL of aqueous NaHCO$_3$ then the solution was extracted with EtOAc (2×50 mL). The organic extracts were combined, washed with brine (2×50 mL), dried over anhydrous Na$_2$SO$_4$, and concentrated under reduced pressure affording 320 mg of the title compound as a yellow oil. Mass Spectrum (LCMS, ESI pos): Calcd. for C$_{11}$H$_{18}$N$^+$: 164.1 (M+H); Found: 164.1.

D. (2E)-N-(4-tert-Butyl-2-methylphenyl)-2-(N-hydroxyimino)acetamide. To a 250-mL round-bottom flask was placed a solution of 4-tert-butyl-2-methylaniline (320 mg, 1.96 mmol, as prepared in the previous step) in water (100 mL) followed by NH$_2$OH.HCl (420 mg, 6.00 mmol), Na$_2$SO$_4$ (10 g), conc. HCl (0.4 mL), and 2,2,2-trichloroethane-1,1-diol (396 mg, 2.39 mmol, 1.20 equiv). The resulting solution was stirred for 1 h at 90° C. then the reaction was cooled to rt. The solids were isolated by filtration and dried in an oven under reduced pressure affording 360 mg (78%) of the title compound as a brown solid. Mass Spectrum (LCMS, ESI pos): Calcd. for C$_{13}$H$_{19}$N$_2$O$_2$$^+$: 235.1 (M+H); Found: 235.1.

E. 5-tert-Butyl-7-methyl-2,3-dihydro-1H-indole-2,3-dione. To a 25-mL, round-bottom flask was placed a solution of (2E)-N-(4-tert-butyl-2-methylphenyl)-2-(N-hydroxyimino)acetamide (360 mg, 1.54 mmol, as prepared in the previous step) in conc. H$_2$SO$_4$ (3 mL). The resulting solution was stirred for 30 min at 70° C. then quenched by the addition of 100 mL of water/ice. The precipitate was isolated by filtration and dried in an oven under reduced pressure affording 150 mg (45%) of the title compound as a brown solid. Mass Spectrum (LCMS, ESI pos): Calcd. for C$_{13}$H$_{16}$NO$_2$$^+$: 218.1 (M+H); Found: 218.1.

Intermediate 7:
4,7-Dimethyl-2,3-dihydro-1H-indole-2,3-dione

A. (2E)-N-(2,5-Dimethylphenyl)-2-(N-hydroxyimino)acetamide. To a 3000-mL round-bottom flask was placed a solution of 2,2,2-trichloroethane-1,1-diol (36 g, 217.65 mmol), NH$_2$OH.HCl (44 g, 628.57 mmol) and Na$_2$SO$_4$ (300 g) in water (2000 mL) then 2,5-dimethylaniline (24.2 g, 199.70 mmol) in conc. HCl (20 mL) was added. The reaction was stirred at 100° C. for 1 h then cooled to rt and the precipitate was isolated by filtration and dried in an oven under reduced pressure affording 35.5 g (92%) of the title compound as a light brown solid. Mass Spectrum (LCMS, ESI pos): Calcd. for C$_{10}$H$_{13}$N$_2$O$_2$$^+$: 193.1 (M+H); Found: 193.1.

B. 4,7-Dimethyl-2,3-dihydro-1H-indole-2,3-dione. To a 50-mL round-bottom flask was placed a solution of (2E)-N-(2,5-dimethylphenyl)-2-(N-hydroxyimino)acetamide (3.5 g, 18.21 mmol, as prepared in the previous step) in conc H$_2$SO$_4$ (20 mL). The reaction was stirred for 30 min at 70° C. then quenched by the addition of 200 mL of water/ice. The solids were isolated by filtration and dried in an oven under reduced pressure affording 600 mg (19%) of the title compound as a red solid. Mass Spectrum (LCMS, ESI pos): Calcd. for C$_{10}$H$_{10}$NO$_2$$^+$: 176.1 (M+H); Found: 176.0.

General Procedure A. Representative Example

Intermediate 8:
1-(3-Ethyl-1-benzofuran-2-yl)ethan-1-one

A. Ethyl 2-(2-Propanoylphenoxy)acetate. To a 250-mL round-bottom flask was placed a solution of 1-(2-hydroxyphenyl)propan-1-one (4.5 g, 29.97 mmol) in acetone (30 mL) then ethyl 2-bromoacetate (6.012 g, 36.00 mmol) and K$_2$CO$_3$ (12.42 g, 89.86 mmol) were added. The reaction was heated to reflux overnight, cooled to rt, and the solids were removed by filtration. The filtrate was concentrated under reduced pressure affording 6.769 g (96%) of the title compound as a colorless liquid.

B. 2-(2-Propanoylphenoxy)acetic acid. To a 500-mL round-bottom flask was placed a solution of ethyl 2-(2-propanoylphenoxy)acetate (6.769 g, 28.65 mmol, as prepared in the previous step) in water (100 mL) then Na$_2$CO$_3$ (9.121 g, 86.06 mmol) was added. The reaction was stirred for 3 h at 100° C., cooled to rt, and the pH of the solution was adjusted to 2-3 with 6M HCl. The precipitate was isolated by filtration affording 5.79 g (97%) of the title compound as a white solid.

C. 3-Ethyl-1-benzofuran. To a 100-mL round-bottom flask was placed a solution of 2-(2-propanoylphenoxy)acetic acid (4.16 g, 19.98 mmol, as prepared in the previous step) in Ac$_2$O (20 mL), then NaOAc (8.2 g, 100.00 mmol) was added. The reaction was stirred at 140° C. overnight then cooled to rt, and the pH of the solution was adjusted to 6-7 with saturated aqueous NaHCO$_3$ solution. The resulting solution was extracted with EtOAc (3×100 mL) and the organic extracts were combined, dried over anhydrous Na$_2$SO$_4$, and concentrated under reduced pressure. The residue was purified by column chromatography eluting with petroleum ether affording 2.424 g (83%) of the title compound as a colorless liquid. $^1$H NMR (300 MHz, CDCl$_3$): δ 7.63-7.60 (m, 1H), 7.54-7.51 (m, 1H), 7.45 (s, 1H), 7.37-7.26 (m, 2H), 2.80-2.72 (q, J=6.0 Hz, 2H), 1.42-1.37 (t, J=6.0 Hz, 3H).

D. 1-(3-Ethyl-1-benzofuran-2-yl)ethan-1-one. To a 100-mL round-bottom flask was placed a solution of AlCl$_3$ (2.65 g, 19.92 mmol) and AcCl (1.56 g, 19.89 mmol) in DCM (30 mL). The mixture was stirred for 30 min then 3-ethyl-1-benzofuran (2.424 g, 16.58 mmol, as prepared in the previous step) was added. The reaction was stirred for 30 min at rt then the pH of the solution was adjusted to 7 with saturated aqueous NaHCO$_3$ solution. The solids were removed by filtration then the filtrate was dried over anhydrous Na$_2$SO$_4$ and concentrated under reduced pressure affording 2.348 g (75%) of the title compound as a yellow oil. Mass Spectrum (LCMS, ESI pos): Calcd. for C$_{12}$H$_{13}$O$_2$$^+$: 189.1 (M+H); Found: 189.1.

Using General Procedure A with reagents, starting materials, and conditions familiar to those skilled in the art, the following intermediates were prepared:

| Intermediate | Name and Data |
| --- | --- |
| 17 | 1-(3-Phenyl-1-benzofuran-2-yl)ethan-1-one. Mass Spectrum (LCMS, ESI pos): Calcd. for C$_{16}$H$_{13}$O$_2$$^+$: 237.1 (M + H); Found: 237.1. $^1$H NMR (400 MHz, DMSO-d$_6$): δ 7.81-7.79 (d, J = 8.0 Hz, 1H), 7.64-7.51 (m, 7H), 7.42-7.38 (m, 1H), 2.48 (s, 3H). |
| 64 | 1-(3,7-Dimethyl-1-benzofuran-2-yl)ethan-1-one. Mass Spectrum (LCMS, ESI pos): Calcd. for C$_{12}$H$_{13}$O$_2$$^+$: 189.1 (M + H); Found: 189.1. |

Intermediate 9:
3-Chloro-1-benzofuran-2-carbaldehyde

A. Methyl 2-(2-Ethoxy-2-oxoethoxy)benzoate. To a 1-L round-bottom flask was placed a solution of methyl 2-hydroxybenzoate (40 g, 262.90 mmol) in acetone (500 mL) followed by ethyl 2-bromoacetate (53 g, 317.36 mmol) and K$_2$CO$_3$ (110 g, 790.15 mmol). The resulting solution was stirred at 80° C. overnight, cooled to rt, and filtered. The filtrate was concentrated under reduced pressure affording 70 g of the title compound as yellow oil. Mass Spectrum (LCMS, ESI pos): Calcd. for C$_{12}$H$_{15}$O$_5$$^+$: 239.1 (M+H); Found: 239.2.

B. 2-(Carboxymethoxy)benzoic acid. To a 1-L round-bottom flask was placed a solution of methyl 2-(2-ethoxy-2-oxoethoxy)benzoate (30 g, 125.93 mmol, as prepared in the previous step) in MeOH/THF (1:1, 500 mL) then NaOH (10 g, 250.02 mmol) was added. The reaction was stirred at 80° C. overnight, cooled to rt, and concentrated under reduced pressure. The residue was dissolved in water and the pH was adjusted to 5 with HCl. The precipitate was isolated by filtration affording 15 g (61%) of the title compound as a white solid. Mass Spectrum (LCMS, ESI pos): Calcd. for C$_9$H$_9$O$_5$$^+$: 197.04 (M+H); Found: 197.1. $^1$H NMR (400 MHz, DMSO-d$_6$): δ 12.87 (s, 2H), 7.68-7.66 (m, 1H), 7.51-7.46 (m, 1H), 7.08-6.98 (m, 2H), 4.78 (s, 2H).

C. 2,3-Dihydro-1-benzofuran-3-one. To a 500-mL round-bottom flask was placed a solution of 2-(carboxymethoxy) benzoic acid (15 g, 76.47 mmol, as prepared in the previous step) in Ac$_2$O (150 mL) then NaOAc (20 g, 243.80 mmol) was added. The reaction was stirred at 140° C. overnight, cooled to rt, quenched by the addition of water, and extracted with EtOAc (3×50 mL). The organic extracts were combined, dried over anhydrous Na$_2$SO$_4$, and concentrated under reduced pressure. The residue was purified by column chromatography eluting with EtOAc/petroleum ether (1:50) affording 6 g (58%) of the title compound as a brown oil.

D. 3-Chloro-1-benzofuran-2-carbaldehyde. To a 100-mL round-bottom flask was placed a solution of 2,3-dihydro-1-benzofuran-3-one (1 g, 7.46 mmol, as prepared in the previous step) in DMF (3 mL) followed by the dropwise addition of POCl$_3$ (5.2 g, 33.91 mmol, 4.55 equiv) with stirring. The resulting solution was stirred at 100° C. overnight, cooled to rt, and quenched by the addition of water/ice. The precipitate was isolated by filtration affording 600 mg (45%) of the title compound as a brown solid. Mass Spectrum (LCMS, ESI pos): Calcd. for C$_9$H$_6$ClO$_2$$^+$: 181.0 (M+H); Found: 181.1.

Intermediate 10:
1-(3-Bromo-1-benzofuran-2-yl)ethan-1-one

A. 1-(3-Bromo-1-benzofuran-2-yl)ethan-1-one. To a 50-mL 3-necked round-bottom flask purged and maintained with an inert atmosphere of nitrogen was placed a solution of AlCl$_3$ (1.01 g, 7.57 mmol) in DCM (10 mL) followed by the addition of AcCl (594 mg, 7.57 mmol). The mixture was stirred 30 min at rt then 3-bromo-1-benzofuran (500 mg, 2.54 mmol) was added. The reaction was stirred for 30 min at rt, quenched by the addition of water, and extracted with EtOAc. The organic extracts were combined, washed with brine, dried over anhydrous Na$_2$SO$_4$, and concentrated under reduced pressure affording 620 mg of the title compound as a light yellow solid.

Intermediate 11: 2-(Benzyloxy)-5-methylaniline

A. 1-(Benzyloxy)-4-methyl-2-nitrobenzene. To a 100-mL round-bottom flask was placed a solution of 4-methyl-2-nitrophenol (3.06 g, 19.98 mmol) in DMF (30 mL) then K$_2$CO$_3$ (4.14 g, 29.95 mmol) and BnBr (4.08 g, 23.85 mmol) were added. The reaction was stirred for 2 h at rt, quenched by the addition of water, and extracted with EtOAc. The organic extracts were combined, washed with brine, dried over anhydrous Na$_2$SO$_4$, and concentrated under reduced pressure. The residue was purified by column chromatography eluting with EtOAc/petroleum ether (1:25) affording 4.5 g (93%) of the title compound as yellow oil.

B. 2-(Benzyloxy)-5-methylaniline. To a 250-mL round-bottom flask purged and maintained with an inert atmosphere of nitrogen was placed a solution of 1-(benzyloxy)-4-methyl-2-nitrobenzene (4.5 g, 18.50 mmol, as prepared in the previous step) in EtOAc (50 mL) then Raney Ni (200 mg) was added and the solution was degassed and back filled with H$_2$. The reaction was stirred for 1 h at rt then the atmosphere was purged with N$_2$ and the solids were removed by filtration. The filtrate was concentrated under reduced pressure affording 3.5 g (89%) of the title compound as an orange oil. Mass Spectrum (LCMS, ESI pos): Calcd. for C$_{14}$H$_{16}$NO$^+$: 214.1 (M+H); Found: 214.1.

Intermediate 12: 3-(Benzyloxy)-4-methylaniline

A. 2-(Benzyloxy)-1-methyl-4-nitrobenzene. To a 100-mL round-bottom flask was placed a solution of 2-methyl-5-nitrophenol (1.53 g, 9.99 mmol) in MeCN (20 mL) followed by K$_2$CO$_3$ (2.07 g, 14.98 mmol) and BnBr (2.04 g, 11.93 mmol). The reaction was stirred for 2 h at 80° C. then quenched by the addition of water/ice. The precipitate was isolated by filtration affording 2.35 g (97%) of the title compound as an off-white solid.

B. 3-(Benzyloxy)-4-methylaniline. To a 250-mL round-bottom flask was placed a solution of 2-(benzyloxy)-1-methyl-4-nitrobenzene (1.9 g, 7.81 mmol, as prepared in the previous step) in MeOH (80 mL) and THF (40 mL). To this solution was added Ni(OAc)$_2$·4H$_2$O (3.8 g, 15.32 mmol) then the solution was cooled to 0° C. and NaBH$_4$ (1.2 g, 31.72 mmol) was added in small portions. The reaction was stirred for 5 min at 0° C., quenched by the addition of water, and extracted with EtOAc. The organic extracts were combined, washed with brine, dried over anhydrous Na$_2$SO$_4$, and concentrated under reduced pressure affording 1.9 g of the title compound as a brown solid. Mass Spectrum (LCMS, ESI pos): Calcd. for $C_{14}H_{16}NO^+$: 214.1 (M+H); Found: 214.0.

Intermediate 13: 5-(Benzyloxy)-2-methylaniline

A. 4-(Benzyloxy)-1-methyl-2-nitrobenzene. To a 100-mL round-bottom flask was placed a solution of 4-methyl-3-nitrophenol (1.53 g, 9.99 mmol) in DMF (20 mL) then K$_2$CO$_3$ (2.07 g, 14.98 mmol) and BnBr (2.04 g, 11.93 mmol) were added. The resulting mixture was stirred for 16 h at rt then quenched by the addition of water. The resulting solution was extracted with EtOAc and the organic extracts were combined. The resulting solution was washed with brine, dried over anhydrous Na$_2$SO$_4$, and concentrated under reduced pressure. The crude product was purified by column chromatography eluting with EtOAc/petroleum ether (1:50) affording 1.6 g (66%) of the title compound as light yellow oil.

B. 5-(Benzyloxy)-2-methylaniline. To a 250-mL round-bottom flask purged and maintained with an inert atmosphere of N$_2$ was placed a solution of 4-(benzyloxy)-1-methyl-2-nitrobenzene (1.4 g, 5.76 mmol, as prepared in the previous step) in MeOH (30 mL), then Raney Ni (150 mg) was added. The reaction was purged with H$_2$ then stirred for 16 h at rt. The atmosphere was purged with N$_2$, then the solids were removed by filtration. The filtrate was concentrated under reduced pressure affording 1 g (81%) of the title compound as light red oil. Mass Spectrum (LCMS, ESI pos): Calcd. for $C_{14}H_{16}NO^+$: 214.1 (M+H); Found: 214.1.

General Procedure B: Representative Example

Intermediate 14:
3-(Propan-2-yl)-1-benzofuran-2-carbaldehyde

A. 1-[2-(Benzyloxy)phenyl]-2-methylpropan-1-one. To a 100-mL round-bottom flask was placed a solution of 2-(benzyloxy)benzonitrile (10 g, 47.79 mmol) and CuBr (140 mg, 0.98 mmol) in THF (15 mL) then isopropylmagnesium bromide (62 mL, 62 mmol) was added. The reaction was stirred for 5 h at 80° C., quenched by the addition of water, and extracted with EtOAc. The organic extracts were combined and concentrated under reduced pressure. The residue was purified by column chromatography eluting with EtOAc/petroleum ether (1:5) affording 5 g (41%) of the title compound as light yellow oil. Mass Spectrum (LCMS, ESI pos): Calcd. for $C_{17}H_{19}O_2^+$: 255.1 (M+H); Found: 255.1.

B. 1-(2-Hydroxyphenyl)-2-methylpropan-1-one. To a 100-mL round-bottom flask purged and maintained with an inert atmosphere of N$_2$ was placed a solution of 1-[2-(benzyloxy)phenyl]-2-methylpropan-1-one (2.4 g, 9.44 mmol, as prepared in the previous step) in MeOH (20 mL) followed by Pd on carbon (400 mg). The solution was degassed and back-filled with H$_2$ then stirred for 2 h at rt. The H$_2$ was vented then the solids were removed by filtration. The filtrate was concentrated under reduced pressure affording 1.5 g (97%) of the title compound as light yellow oil. Mass Spectrum (LCMS, ESI pos): Calcd. for $C_{10}H_{13}O_2^+$: 165.1 (M+H); Found: 165.0.

C. Ethyl 2-[2-(2-Methylpropanoyl)phenoxy]acetate. To a 100-mL round-bottom flask was placed a solution of 1-(2-hydroxyphenyl)-2-methylpropan-1-one (4.9 g, 29.84 mmol, as prepared in the previous step) in acetone (30 mL) then K$_2$CO$_3$ (12.4 g, 89.86 mmol) and ethyl 2-bromoacetate (4.99 g, 29.88 mmol) were added. The reaction was stirred for 3 h at 56° C., quenched by the addition of water, and extracted with EtOAc. The organic extracts were combined, washed with water, and concentrated under reduced pressure affording 7.5 g of the title compound as a yellow oil. Mass Spectrum (LCMS, ESI pos): Calcd. for $C_{14}H_{19}O_4^+$: 251.1 (M+H); Found: 251.1.

D. 2-[2-(2-Methylpropanoyl)phenoxy]acetic acid. To a 100-mL round-bottom flask was placed a solution of ethyl 2-[2-(2-methylpropanoyl)phenoxy]acetate (5 g, 19.98 mmol, as prepared in the previous step) and Na$_2$CO$_3$ (6.36 g, 59.44 mmol) in water (10 mL). The reaction was stirred at 95° C. for 2 h, quenched by the addition of dilute HCl/ice, and extracted with EtOAc. The organic extracts were combined, washed with water, dried over anhydrous Na$_2$SO$_4$, and concentrated under reduced pressure affording 3.8 g (86%) of the title compound as a yellow oil. $^1$H NMR (400 MHz, DMSO-d$_6$): δ 13.06 (s, 1H), 7.51-7.39 (m, 2H), 7.06-7.02 (m, 2H), 4.82 (s, 2H), 3.65-3.55 (m, 1H), 1.08-1.06 (d, J=8.0 Hz, 6H).

E. 3-(Propan-2-yl)-1-benzofuran. To a 100-mL round-bottom flask was placed a solution of 2-[2-(2-methylpropanoyl)phenoxy]acetic acid (3.8 g, 17.10 mmol, as prepared in the previous step) in Ac$_2$O (38 mL) then NaOAc (7.6 g) was added. The reaction was stirred at 140° C. overnight, quenched by the addition of saturated aqueous NaHCO$_3$, and extracted with EtOAc. The organic extracts were combined and concentrated under reduced pressure. The residue was purified by column chromatography eluting with EtOAc/petroleum ether (1:1000) affording 3.12 g of the title compound as colorless oil. Mass Spectrum (LCMS, ESI pos): Calcd. for $C_{11}H_{13}O^+$: 161.1 (M+H); Found: 161.1. $^1$H NMR (400 MHz, DMSO-d$_6$): δ 7.73 (s, 1H), 7.69-7.66 (m, 1H), 7.56-7.53 (m, 1H), 7.33-7.22 (m, 2H), 3.13-3.02 (m, 1H), 1.32-1.30 (d, J=8.0 Hz, 6H).

F. 3-(Propan-2-yl)-1-benzofuran-2-carbaldehyde. To a 50-mL 3-necked round-bottom flask purged and maintained with an inert atmosphere of nitrogen was placed a solution of 3-(propan-2-yl)-1-benzofuran (500 mg, 3.12 mmol, as prepared in the previous step) in THF (10 mL). The solution was cooled to −78° C. then BuLi (3.75 mL, 3.75 mmol) was added dropwise. The mixture was stirred 30 min at −78° C. then DMF (456 mg, 6.25 mmol) was added. The reaction was stirred for 30 min at −78° C., quenched by the addition of water, and extracted with EtOAc. The organic extracts were combined and concentrated under reduced pressure. The residue was purified by column chromatography eluting with EtOAc/petroleum ether (1;1000) affording 200 mg (34%) of the title compound as a yellow oil.

Using General Procedure B with reagents, starting materials, and conditions familiar to those skilled in the art, the following intermediates were prepared:

| Intermediate | Name and Data |
|---|---|
| 15 | 3-Cyclopropyl-1-benzofuran-2-carbaldehyde.<br>Mass Spectrum (LCMS, ESI pos): Calcd. for $C_{12}H_{11}O_2^+$: 187.1 (M + H); Found: 187.0. |
| 16 | 3-Cyclohexyl-1-benzofuran-2-carbaldehyde.<br>Mass Spectrum (LCMS, ESI pos): Calcd. for $C_{15}H_{17}O_2^+$: 229.1 (M + H); Found: 229.1. |

Intermediate 18:
3-Methoxy-1-benzofuran-2-carbaldehyde

A. Methyl 2-(2-Ethoxy-2-oxoethoxy)benzoate. To a 500-mL round-bottom flask was placed a solution of methyl 2-hydroxybenzoate (20 g, 131.45 mmol) in acetone (200 mL) then ethyl 2-bromoacetate (26.4 g, 158.08 mmol) and $K_2CO_3$ (54.8 g, 393.64 mmol) were added. The reaction was stirred at 80° C. overnight, cooled to rt, and the solids were removed by filtration. The filtrate was concentrated under reduced pressure affording 48 g of the title compound as yellow oil.

B. Methyl 3-Hydroxy-1-benzofuran-2-carboxylate. To a 250-mL round-bottom flask was placed a solution of methyl 2-(2-ethoxy-2-oxoethoxy)benzoate (11.9 g, 49.95 mmol, as prepared in the previous step) in MeOH (100 mL) then NaOMe (12.6 g, 70.00 mmol) was added. The reaction was stirred for 1.5 h at 65° C. then the solvent was removed under reduced pressure. The residue was dissolved in 200 mL of $H_2O$, then the pH of the solution was adjusted to 5-6 with AcOH. The precipitate was isolated by filtration and dried in an oven under reduced pressure affording 6 g (63%) of the title compound as a light yellow solid. Mass Spectrum (LCMS, ESI pos): Calcd. for $C_{10}H_9O_4^+$: 193.1 (M+H); Found: 193.0. $^1$H NMR (300 MHz, DMSO-$d_6$): δ 10.76 (s, 1H), 7.87-7.83 (m, 1H), 7.54-7.44 (m, 2H), 7.30-7.24 (m, 1H), 3.49 (s, 3H).

C. Methyl 3-Methoxy-1-benzofuran-2-carboxylate. To a 100-mL round-bottom flask was placed a solution of methyl 3-hydroxy-1-benzofuran-2-carboxylate (2.02 g, 10.51 mmol, as prepared in the previous step) and $K_2CO_3$ (1.6 g, 11.58 mmol) in acetone (30 mL) then dimethyl sulfate (1.6 g, 12.69 mmol) was added. The reaction was stirred for 1.5 h at 65° C., quenched by the addition of water, and extracted with EtOAc. The organic extracts were combined, washed with brine, dried over anhydrous $Na_2SO_4$, and concentrated under reduced pressure affording 2.5 g of the title compound as a yellow oil. Mass Spectrum (LCMS, ESI pos): Calcd. for $C_{11}H_{11}O_4^+$: 207.1 (M+H); Found: 207.0.

D. 3-Methoxy-1-benzofuran-2-carboxylic acid. To a 100-mL round-bottom flask was placed a solution of methyl 3-methoxy-1-benzofuran-2-carboxylate (2.5 g, 12.12 mmol, as prepared in the previous step) in a mixture of EtOH (15 mL) and water (10 mL). To this solution was added NaOH (1.3 g, 32.50 mmol) then the reaction was stirred at 80° C. overnight. The EtOH was removed under reduced pressure then the solution was washed with EtOAc, the pH was adjusted to 6 with 2N HCl, and extracted with EtOAc. The organic extracts were combined, was washed with brine, dried over anhydrous $Na_2SO_4$, and concentrated under reduced pressure affording 1.67 g (72%) of the title compound as a yellow solid. Mass Spectrum (LCMS, ESI pos): Calcd. for $C_{10}H_9O_4^+$: 193.1 (M+H); Found: 193.0.

E. N, 3-Dimethoxy-N-methyl-1-benzofuran-2-carboxamide. To a 250-mL round-bottom flask was placed a solution of 3-methoxy-1-benzofuran-2-carboxylic acid (1.67 g, 8.69 mmol, as prepared in the previous step) in DCM (50 mL) then methoxy(methyl)amine hydrochloride (1.69 g, 17.33 mmol), HATU (6.61 g, 17.38 mmol), and DIEA (3.37 g, 26.08 mmol) were added. The reaction was stirred for 2 h at rt, quenched by the addition of water, and extracted with EtOAc. The organic extracts were combined, washed with brine, dried over anhydrous $Na_2SO_4$, and concentrated under reduced pressure. The residue was purified by column chromatography eluting with EtOAc/petroleum ether (1:5) affording 1.8 g (88%) of the title compound as a yellow oil. Mass Spectrum (LCMS, ESI pos): Calcd. for $C_{12}H_{14}NO_4^+$: 236.1 (M+H); Found: 236.0. $^1$H NMR (300 MHz, CDCl$_3$): δ 7.73 (d, J=7.9 Hz, 1H), 7.51-7.36 (m, 2H), 7.30 (s, 1H), 4.15 (s, 3H), 3.86 (s, 3H), 3.39 (s, 3H).

F. 3-Methoxy-1-benzofuran-2-carbaldehyde. To a 100-mL round-bottom flask was placed a solution of N, 3-dimethoxy-N-methyl-1-benzofuran-2-carboxamide (350 mg, 1.49 mmol, as prepared in the previous step) in THF (15 mL) then the solution was cooled to −20° C. and LiAlH$_4$ (170 mg, 4.48 mmol) was added in small portions. The reaction was stirred for 5 min at −20° C. then quenched by the addition of $Na_2SO_4.10H_2O$ and the precipitate was removed by filtration. The filtrate was diluted with 50 mL of water and extracted with EtOAc. The organic extracts were combined, washed with brine, dried over anhydrous $Na_2SO_4$, and concentrated under reduced pressure affording 170 mg (65%) of the title compound as a light yellow solid. Mass Spectrum (LCMS, ESI pos): Calcd. for $C_{10}H_9O_3^+$: 177.1 (M+H); Found: 177.0.

General Procedure C: Representative Example

Intermediate 19:
3-(Benzyloxy)-1-benzofuran-2-carbaldehyde

A. Methyl 3-(Benzyloxy)-1-benzofuran-2-carboxylate. To a 25-mL round-bottom flask was placed a solution of methyl 3-hydroxy-1-benzofuran-2-carboxylate (192 mg, 1.00 mmol, as prepared in Intermediate 18, Step B) and KOtBu (224 mg, 2.00 mmol) in DMSO (5 mL). To this solution was added benzyl bromide (256 mg, 1.50 mmol) then the reaction was stirred at 100° C. for 2 h, diluted with 50 mL of $H_2O$, and extracted with EtOAc (2×50 mL). The organic extracts were combined, washed with brine (2×50 mL), dried over anhydrous $Na_2SO_4$, and concentrated under reduced pressure. The crude product was purified by Prep-TLC (petroleum ether/EtOAc=8:1) affording 160 mg (57%) of the title compound as a yellow solid. Mass Spectrum (LCMS, ESI pos): Calcd. for $C_{17}H_{15}O_4^+$: 283.1 (M+H); Found: 283.1.

B. 3-(Benzyloxy)-1-benzofuran-2-carboxylic acid. To a 25-mL round-bottom flask was placed a solution of methyl 3-(benzyloxy)-1-benzofuran-2-carboxylate (160 mg, 0.57 mmol, as prepared in the previous step) in EtOH/$H_2O$ (5/2 mL). To this solution was added KOH (95 mg, 1.69 mmol) then the reaction was stirred at 80° C. for 1 h, diluted with 50 mL of $H_2O$, and washed with EtOAc (1×50 mL). The pH of the solution was adjusted to 3-4 with conc. HCl then the precipitate was isolated by filtration and dried in an oven under reduced pressure affording 105 mg (69%) of the title compound as a yellow solid. Mass Spectrum (LCMS, ESI pos): Calcd. for $C_{16}H_{13}O_4^+$: 269.1 (M+H); Found: 269.0.

C. 3-(Benzyloxy)-N-methoxy-N-methyl-1-benzofuran-2-carboxamide. To a 25-mL round-bottom flask was placed a solution of 3-(benzyloxy)-1-benzofuran-2-carboxylic acid (105 mg, 0.39 mmol, as prepared in the previous step) in DCM (3 mL) then HATU (228 mg, 0.60 mmol), DIEA (155 mg, 1.20 mmol), and methoxy(methyl)amine hydrochloride (58.5 mg, 0.60 mmol) were added. The reaction was stirred for 1 h at rt, diluted with 50 mL of $H_2O$, and extracted with EtOAc (2×50 mL). The organic extracts were combined, washed with brine (2×50 mL), dried over anhydrous $Na_2SO_4$, and concentrated under reduced pressure. The crude product was purified by Prep-TLC (petroleum ether/EtOAc=5:1) affording 70 mg (57%) of the title compound as yellow oil. Mass Spectrum (LCMS, ESI pos): Calcd. for $C_{18}H_{18}NO_4^+$: 312.1 (M+H); Found: 312.2.

D. 3-(Benzyloxy)-1-benzofuran-2-carbaldehyde. To a 50-mL 3-necked round-bottom flask was placed a solution of 3-(benzyloxy)-N-methoxy-N-methyl-1-benzofuran-2-carboxamide (350 mg, 1.12 mmol, as prepared in the previous step) in THF (5 mL) then $LiAlH_4$ (128 mg, 3.37 mmol) was added. The reaction was stirred for 1 min at rt then quenched by the addition of $Na_2SO_4 \cdot 10H_2O$. The solids were removed by filtration then the filtrate was diluted with 50 mL of water and extracted with EtOAc. The organic extracts were combined, washed with water, dried over anhydrous $Na_2SO_4$, and concentrated under reduced pressure. The residue was purified by column chromatography eluting with EtOAc/petroleum ether (1:5) affording 150 mg (53%) of the title compound as a light yellow solid. Mass Spectrum (LCMS, ESI pos): Calcd. for $C_{16}H_{13}O_3^+$: 253.1 (M+H); Found: 253.1. $^1H$ NMR (DMSO-$d_6$, 300 MHz): δ 9.89 (s, 1H), 7.96-7.93 (m, 1H), 7.64-7.55 (m, 2H), 7.52-7.48 (m, 2H), 7.43-7.31 (m, 4H), 5.63 (s, 3H).

Using General Procedure C with reagents, starting materials, and conditions familiar to those skilled in the art, the following intermediates were prepared:

acetate (20 g, 97.46 mmol, as prepared in the previous step) was added dropwise with stirring. After completion of addition, the reaction was stirred at rt for 2 h, quenched by the addition of water, and extracted with EtOAc (3×200 mL). The organic extracts were combined, washed with brine (2×200 mL), dried over anhydrous $Na_2SO_4$, and concentrated under reduced pressure affording 17 g of the title compound as a yellow solid. Mass Spectrum (LCMS, ESI pos): Calcd. for $C_{11}H_{12}NO_3^+$: 206.1 (M+H); Found: 206.1.

C. Ethyl 3-[[(tert-Butoxy)carbonyl]amino]-1-benzofuran-2-carboxylate. To a 1000-mL round-bottom flask was placed a solution of ethyl 3-amino-1-benzofuran-2-carboxylate (5.5 g, 26.80 mmol, as prepared in the previous step), DMAP (3.3 g) and TEA (70 mL) in DCM (700 mL). To this solution was added $Boc_2O$ (8.8 g, 40.32 mmol) then the resulting solution was stirred for 6 h at 40° C. The reaction was washed with 1N HCl (3×300 mL), saturated aqueous $NaHCO_3$ (3×300 mL), and brine (3×200 mL), then dried over $Na_2SO_4$ and concentrated under reduced pressure affording 9.2 g of the title compound as a brown solid. Mass Spectrum (LCMS, ESI pos): Calcd. for $C_{16}H_{20}NO_5^+$: 306.1 (M+H); Found: 306.2.

D. 3-[[(tert-Butoxy)carbonyl]amino]-1-benzofuran-2-carboxylic acid. To a 500-mL round-bottom flask was placed a solution of ethyl 3-[[(tert-butoxy)carbonyl]amino]-1-benzofuran-2-carboxylate (9.2 g, 30.13 mmol, as prepared in the previous step) in $THF/H_2O$ (10:1; 220 mL) then LiOH (2.2 g, 91.86 mmol) was added. The reaction was stirred at 40° C. for 5 h then diluted with 100 mL of $H_2O$. The resulting mixture was concentrated under reduced pressure to 120 mL then washed with DCM (3×100 mL). The pH of the aqueous layer was adjusted to 4-5 with 1N HCl then the precipitate was isolated by filtration affording 4.8 g (57%) of the title compound as a light yellow solid. $^1H$ NMR (400 MHz, DMSO-$d_6$): δ 8.99 (s, 1H), 8.00 (d, J=8.0 Hz, 1H), 7.64 (d, J=8.4 Hz, 1H), 7.53 (m, 1H), 7.35 (m, 1H), 1.50 (s, 9H).

E. tert-Butyl N-[2-[Methoxy(methyl)carbamoyl]-1-benzofuran-3-yl]carbamate. To a 500-mL round-bottom flask was placed a solution of 3-[[(tert-butoxy)carbonyl]amino]-

| Intermediate | Name and Data |
|---|---|
| 47 | 3,6-Dimethyl-1-benzofuran-2-carbaldehyde.<br>Mass Spectrum (LCMS, ESI pos): Calcd. for $C_{11}H_{11}O_2^+$: 175.1 (M + H); Found: 175.0 |
| 48 | 7-Chloro-3-methylbenzofuran-2-carbaldehyde.<br>Mass Spectrum (LCMS, ESI pos): Calcd. for $C_{10}H_8ClO_2^+$: 195.0 (M + H); Found: 195.0. |

Intermediate 20: tert-Butyl N-(2-Formyl-1-benzofuran-3-yl)carbamate

A. Ethyl 2-(2-Cyanophenoxy)acetate. To a 1000-mL round-bottom flask was placed a solution of 2-hydroxybenzonitrile (30 g, 251.85 mmol) in MeCN (500 mL) then $K_2CO_3$ (104 g, 747.05 mmol) and ethyl 2-bromoacetate (50 g, 299.40 mmol) were added. The resulting solution was stirred overnight at rt then the solids were removed by filtration. The filtrate was concentrated under reduced pressure affording 46 g (89%) of the title compound as a light yellow solid.

B. Ethyl 3-Amino-1-benzofuran-2-carboxylate. To a 2000-mL round-bottom flask was placed a solution of KOtBu (18 g, 160.41 mmol) in THF (600 mL) then a THF solution (400 mL) solution of ethyl 2-(2-cyanophenoxy)

1-benzofuran-2-carboxylic acid (2 g, 7.21 mmol, as prepared in the previous step) in DCM (50 mL) then DIEA (4.7 g), HATU (5.5 g), and methoxy(methyl)amine hydrochloride (1.06 g, 10.87 mmol) were added. The reaction was stirred at rt for 3 h, quenched by the addition of 50 mL of water, and extracted with DCM (3×30 mL). The organic extracts were combined, washed with brine (1×20 mL), and concentrated under reduced pressure. The residue was purified by column chromatography eluting with EtOAc/petroleum ether (1:30) affording 1.9 g (82%) of the title compound as light yellow oil. Mass Spectrum (LCMS, ESI pos): Calcd. for $C_{16}H_{21}N_2O_5^+$: 321.1 (M+H); Found: 321.1.

F. tert-Butyl N-(2-Formyl-1-benzofuran-3-yl)carbamate. To a 500-mL 3-necked round-bottom flask purged and maintained with an inert atmosphere of nitrogen, was placed a solution of tert-butyl N-[2-[methoxy(methyl)carbamoyl]-

1-benzofuran-3-yl]carbamate (1.22 g, 3.81 mmol, as prepared in the previous step) in THF (200 mL) then LiAlH$_4$ (210 mg, 5.53 mmol) was added. The reaction was stirred at rt for 30 min then quenched by the addition of 3 g of Na$_2$SO$_4$.10H$_2$O. The solids were removed by filtration then the filtrate was concentrated under reduced pressure. The residue was purified by column chromatography eluting with EtOAc/petroleum ether (1:30) affording 0.7 g (70%) of the title compound as a light yellow solid. Mass Spectrum (LCMS, ESI pos): Calcd. for C$_{14}$H$_{16}$NO$_4^+$: 262.1 (M+H); Found: 262.1.

Intermediate 21:
4-(Benzyloxy)-2,3-dihydro-1H-indole-2,3-dione

A. 4-(Benzyloxy)-1H-indole. To a 250-mL round-bottom flask was placed a solution of 1H-indol-4-ol (3 g, 22.53 mmol) in acetone (100 mL), then K$_2$CO$_3$ (6.225 g, 45.04 mmol) and BnBr (3.471 g, 20.29 mmol) were added. The reaction was stirred for 20 h at 30° C. then the solids were removed by filtration and the filtrate was concentrated under reduced pressure. The residue was purified by column chromatography eluting with EtOAc/petroleum ether (1:20) affording 2.95 g (59%) of the title compound as a brown oil. Mass Spectrum (LCMS, ESI pos): Calcd. for C$_{15}$H$_{14}$NO$^+$: 224.1 (M+H); Found: 224.1.

B. 4-(Benzyloxy)-2,3-dihydro-1H-indole-2,3-dione. To a 100-mL round-bottom flask was placed a solution of 4-(benzyloxy)-1H-indole (1 g, 4.48 mmol, as prepared in the previous step) in DMSO (20 mL), then I$_2$ (1.36 g) and TBHP (2.02 g, 22.41 mmol) were added. The reaction was stirred at 80° C. for 16 h, quenched by the addition of 50 mL of aqueous Na$_2$S$_2$O$_3$, and extracted with EtOAc. The organic extracts were combined, dried over anhydrous Na$_2$SO$_4$, and concentrated under reduced pressure. The residue was purified by column chromatography eluting with EtOAc/petroleum ether (1:2) affording 801 mg (71%) of the title compound as a brown solid. Mass Spectrum (LCMS, ESI pos): Calcd. for C$_{15}$H$_{12}$NO$_3^+$: 254.1 (M+H); Found: 254.1.

Intermediate 22: 3-(Benzyloxy)-5-methylaniline

A. 1-(Benzyloxy)-3-methyl-5-nitrobenzene. To a 100-mL round-bottom flask was placed a solution of 3-methyl-5-nitrophenol (1 g, 6.53 mmol) in acetone (10 mL) then K$_2$CO$_3$ (1.8 g, 13.02 mmol) and BnBr (1.34 g) were added. The reaction was stirred at 80° C. for 16 h, the solids were filtered out then the filtrate was diluted with 50 mL of water and extracted with EtOAc. The organic extracts were combined and concentrated under reduced pressure affording 1.11 g (70%) of the title compound as a yellow oil.

B. 3-(Benzyloxy)-5-methylaniline. To a 100-mL round-bottom flask was placed a solution of 1-(benzyloxy)-3-methyl-5-nitrobenzene (600 mg, 2.47 mmol, as prepared in the previous step) and Ni(OAc)$_2$.4H$_2$O (874 mg) in MeOH/THF 2:1 (9 mL), then the solution was cooled to 0° C. and NaBH$_4$ (365 mg) was added in several portions over 5 min. The reaction was stirred at rt for 1 h, The solids were removed by filtration and the filtrate was concentrated under reduced pressure affording 527 mg of the title compound as a brown oil. Mass Spectrum (LCMS, ESI pos): Calcd. for C$_{14}$H$_{16}$NO$^+$: 214.1 (M+H); Found: 214.1.

Intermediate 23: 3-(Benzyloxy)-2-methylaniline

A. 1-(Benzyloxy)-2-methyl-3-nitrobenzene. To a 500-mL 3-necked round-bottom flask was placed a solution of 2-methyl-3-nitrophenol (10 g, 65.30 mmol) and K$_2$CO$_3$ (13 g, 94.06 mmol) in CH$_3$CN (100 mL) then BnBr (13 g, 76.01 mmol) was added. The reaction was stirred at 90° C. for 2 h, cooled to rt, filtered, and concentrated under reduced pressure. The crude product was purified by column chromatography eluting with EtOAc/petroleum ether (1:9) affording 8.6 g of the title compound as a yellow oil.

B. 3-(Benzyloxy)-2-methylaniline. To a 100-mL round-bottom flask purged and maintained with an inert atmosphere of N$_2$, was placed a solution of 1-(benzyloxy)-2-methyl-3-nitrobenzene (8.6 g, 35.35 mmol, as prepared in the previous step) in MeOH (10 mL) then Raney Ni (1 g) was added. The solution was degassed and back-filled with H$_2$, then stirred for 16 h at room temperature. The H$_2$ was purged then the solids were removed by filtration. The filtrate was concentrated under reduced pressure affording 4.4 g of the title compound as a light yellow oil. Mass Spectrum (LCMS, ESI pos): Calcd. for C$_{14}$H$_{16}$NO$^+$: 214.1 (M+H); Found: 214.1.

Intermediate 24:
2-Methyl-5-(2-phenylethoxy)aniline

A. 1-Methyl-2-nitro-4-(2-phenylethoxy)benzene. To a 100-mL round-bottom flask was placed a solution of 4-methyl-3-nitrophenol (5 g, 32.65 mmol) in DMF (10 mL) then K$_2$CO$_3$ (13.5 g, 96.97 mmol, 3.00 equiv) and BnBr (6.05 g, 32.69 mmol) were added. The reaction was stirred at 130° C. overnight, cooled to rt, quenched by the addition of water, and extracted with EtOAc. The organic extracts were combined and concentrated under reduced pressure. The residue was purified by column chromatography eluting with EtOAc/petroleum ether (1:50) affording 2.45 g (29%) of the title compound as a yellow solid. $^1$H NMR (400 MHz, DMSO-d$_6$): δ 7.54-7.51 (m, 1H), 7.42-7.30 (m, 5H), 7.26-7.21 (m, 1H), 4.28 (t, J=6.0 Hz, 2H), 3.05 (t, J=6.0 Hz, 2H), 2.42 (s, 3H).

B. 2-Methyl-5-(2-phenylethoxy)aniline. To a 100-mL round-bottom flask purged and maintained with an inert atmosphere of N$_2$, was placed a solution of 1-methyl-2-nitro-4-(2-phenylethoxy)benzene (1 g, 3.89 mmol, as prepared in the previous step) in MeOH (20 mL) then Pd on carbon (200 mg) was added. The resulting mixture was degassed and back-filled with H$_2$, then stirred for 2 h at rt. The solids were removed by filtration then the filtrate was concentrated under reduced pressure affording 1 g of the title compound as a colorless oil. Mass Spectrum (LCMS, ESI pos): Calcd. for C$_{15}$H$_{18}$NO$^+$: 228.1 (M+H); Found: 228.1.

General Procedure D: Representative Example

Intermediate 25:
2-Methyl-5-(3-phenylcyclobutoxy)aniline

A. 3-Phenylcyclobutan-1-ol. To a 50-mL round-bottom flask was placed a solution of 3-phenylcyclobutan-1-one (1 g, 6.64 mmol) in MeOH (5 mL) then NaBH$_4$ (130 mg, 3.53 mmol) was added. The reaction was stirred for 20 min at rt, quenched by the addition of water, and extracted with EtOAc. The organic extracts were combined, washed with water, dried over anhydrous Na$_2$SO$_4$, and concentrated under reduced pressure affording 1 g of the title compound as a colorless oil.

B. 1-Methyl-2-nitro-4-(3-phenylcyclobutoxy)benzene. To a 50-mL 3-necked round-bottom flask purged and maintained with an inert atmosphere of nitrogen, was placed a solution of 3-phenylcyclobutan-1-ol (484 mg, 3.27 mmol, as prepared in the previous step), 4-methyl-3-nitrophenol (500 mg, 3.27 mmol), and PPh$_3$ (1.03 g, 3.93 mmol) in THF (10 mL) then DIAD (792 mg, 3.92 mmol) was added dropwise. The reaction was stirred for 2 h at rt, quenched by the addition of water, and extracted with EtOAc. The organic extracts were combined and concentrated under reduced pressure. The residue was purified by column chromatography eluting with EtOAc/petroleum ether (1:5) affording 300 mg (32%) of the title compound as a yellow oil.

C. 2-Methyl-5-(3-phenylcyclobutoxy)aniline. To a 50-mL round-bottom flask purged and maintained with an inert atmosphere of N$_2$, was placed a solution of 1-methyl-2-nitro-4-(3-phenylcyclobutoxy)benzene (300 mg, 1.06 mmol, as prepared in the previous step) in MeOH (5 mL) then Raney Ni (30 mg) was added. The solution was degassed and back-filled with H$_2$ and stirred for 1 h at rt. The solids were removed by filtration then the filtrate was concentrated under reduced pressure affording 220 mg (82%) of the title compound as a light yellow oil. Mass Spectrum (LCMS, ESI pos): Calcd. for C17H20NO+: 254.2 (M+H); Found: 254.2.

Using General Procedure D with reagents, starting materials, and conditions familiar to those skilled in the art, the following intermediates were prepared:

| Intermediate | Name and Data |
|---|---|
| 26 | 2-Methyl-5-[(4-phenylcyclohexyl)oxy]aniline. Mass Spectrum (LCMS, ESI pos): Calcd. for C$_{19}$H$_{24}$NO$^+$: 282.2 (M + H); Found: 282.2. |
| 27 | 2-Methyl-5-[(3-phenylcyclohexyl)oxy]aniline. Mass Spectrum (LCMS, ESI pos): Calcd. for C$_{19}$H$_{24}$NO$^+$: 282.2 (M + H); Found: 282.2. |
| 50 | 5-(Cyclohexyloxy)-2-methylaniline. Mass Spectrum (LCMS, ESI pos): Calcd. for C$_{13}$H$_{20}$NO$^+$: 206.2 (M + H); Found: 206.1. |

Intermediate 28: 5-(Cyclohexyloxy)-2-methylaniline

A. 4-(Cyclohexyloxy)-1-methyl-2-nitrobenzene. To a 100-mL round-bottom flask was placed a solution of 4-methyl-3-nitrophenol (460 mg, 3.00 mmol), cyclohexanol (360 mg, 3.59 mmol), and PPh$_3$ (1.18 g, 4.50 mmol, 1.50 equiv) in THF (15 mL) then DIAD (909 mg, 4.50 mmol) was added. The reaction was stirred for 2 h at rt, quenched by the addition of water, and extracted with EtOAc. The organic extracts were combined, washed with brine, dried over anhydrous Na$_2$SO$_4$, and concentrated under reduced pressure. The residue was purified by column chromatography eluting with EtOAc/petroleum ether (1:100) affording 307 mg (43%) of the title compound as a white solid. $^1$H NMR (300 MHz, CDCl$_3$): δ 7.517.50 (m, 1H), 7.23-7.20 (d, J=8.5 Hz, 1H), 7.07-7.03 (m, 1H), 4.30-4.25 (m, 1H), 2.52 (s, 3H), 2.05-1.94 (m, 2H), 1.87-1.77 (m, 2H), 1.59-1.53 (m, 3H), 1.43-1.33 (m, 3H), 0.93-0.85 (m, 1H).

B. 5-(Cyclohexyloxy)-2-methylaniline. To a 50-mL round-bottom flask purged and maintained with an inert atmosphere of N$_2$, was placed a solution of 4-(cyclohexyloxy)-1-methyl-2-nitrobenzene (307 mg, 1.30 mmol, as prepared in the previous step) in MeOH (5 mL) then Pd on carbon (50 mg) and AcOH (0.1 mL) were added. The mixture was degassed and back-filled with H$_2$ and stirred for 4 h at rt. The H$_2$ was purged then the solids were removed by filtration. The filtrate was concentrated under reduced pressure affording 210 mg (78%) of the title compound as an orange oil. Mass Spectrum (LCMS, ESI pos): Calcd. for C$_{13}$H$_{20}$NO$^+$: 206.2 (M+H); Found: 206.1.

Intermediate 29: 2-Methyl-5-phenoxyaniline

A. 1-Methyl-2-nitro-4-phenoxybenzene. To a 30-mL sealed tube was placed a solution of 4-bromo-1-methyl-2-nitrobenzene (1.07 g, 4.95 mmol) in dioxane (18 mL) then phenol (470 mg, 4.99 mmol), Cs$_2$CO$_3$ (3.26 g, 10.01 mmol), and CuI (190 mg, 1.00 mmol) were added. The reaction was heated to 120° C. for 3 h under microwave irradiation, cooled to rt, quenched by the addition of water, and extracted with EtOAc. The organic extracts were combined, washed with brine, dried over anhydrous Na$_2$SO$_4$, and concentrated under reduced pressure. The residue was purified by column chromatography eluting with EtOAc/petroleum ether (1:100) affording 166 mg (15%) of the title compound as a light yellow oil. $^1$H NMR (400 MHz, CD$_3$OD): δ 7.54-7.53 (d, J=2.7 Hz, 1H), 7.46-7.42 (t, J=8.1 Hz, 3H), 7.27-7.18 (m, 2H), 7.09-7.07 (d, J=7.9 Hz, 2H), 2.54 (s, 3H).

B. 2-Methyl-5-phenoxyaniline. To a 50-mL round-bottom flask purged and maintained with an inert atmosphere of N$_2$, was placed a solution of 1-methyl-2-nitro-4-phenoxybenzene (165 mg, 0.72 mmol, as prepared in the previous step) in MeOH (4 mL) then Pd on carbon (20 mg) was added. The solution was degassed and back-filled with H$_2$, then stirred for 1 h at rt. The H$_2$ was purged then the solids were removed by filtration. The filtrate was concentrated under reduced pressure affording (98%) of the title compound as a yellow solid. Mass Spectrum (LCMS, ESI pos): Calcd. for C$_{13}$H$_{14}$NO$^+$: 200.1 (M+H); Found: 200.1.

Intermediate 30: N-(3-Amino-4-methylphenyl)benzamide

A. N-(4-Methyl-3-nitrophenyl)benzamide. To a solution of 4-methyl-3-nitroaniline (5 g, 32.86 mmol) and TEA (11.6 mL) in DCM (60 mL) was added benzoyl chloride (4 mL) dropwise with stirring at 0° C. The resulting solution was stirred for 2 h at rt then the solids were removed by filtration. The filtrate was concentrated under reduced pressure affording 7.8 g (93%) of the title compound as an off-white solid. Mass Spectrum (LCMS, ESI pos): Calcd. for C$_{14}$H$_{13}$N$_2$O$_3^+$: 257.1 (M+H); Found: 257.1.

B. N-(3-Amino-4-methylphenyl)benzamide. To a solution of N-(4-methyl-3-nitrophenyl)benzamide (1 g, 3.90 mmol, as prepared in the previous step) in EtOH (20 mL) was added Pd on carbon (200 mg) under N$_2$. The resulting solution was degassed and back-filled with H$_2$ then the reaction was stirred for 16 h at rt. The H$_2$ was purged then the solids were removed by filtration. The filtrate was concentrated under reduced pressure affording 650 mg (74%) of the title compound as a yellow solid. Mass Spectrum (LCMS, ESI pos): Calcd. for C$_{14}$H$_{15}$N$_2$O$^+$: 227.1 (M+H); Found: 227.1.

Intermediate 31:
N-(3-Amino-4-methylphenyl)-2-phenylacetamide

A. N-(4-Methyl-3-nitrophenyl)-2-phenylacetamide. To a solution of 4-methyl-3-nitroaniline (3 g, 19.72 mmol) and pyridine (1.78 mL) in THF (30 mL), was added 2-phenylacetyl chloride (2.66 mL) dropwise with stirring at 0° C. The reaction was stirred for 3 h at rt, quenched by the addition of 30 mL of aqueous $NH_4Cl$, and extracted with EtOAc (3×100 mL). The organic extracts were combined, washed with brine (2×100 mL), dried over anhydrous $Na_2SO_4$, and concentrated under reduced pressure affording 5 g (94%) of the title compound as a light yellow solid. Mass Spectrum (LCMS, ESI pos): Calcd. for $C_{18}H_{15}N_2O_3^+$: 271.1 (M+H); Found: 271.1.

B. N-(3-Amino-4-methylphenyl)-2-phenylacetamide. To a solution of N-(4-methyl-3-nitrophenyl)-2-phenylacetamide (2 g, 7.40 mmol, as prepared in the previous step) in EtOH (30 mL) was added Pd on carbon (200 mg) under nitrogen. The reaction was degassed and back-filled with $H_2$, then stirred for 16 h at rt. The $H_2$ was purged then the solids were removed by filtration, and the filtrate was concentrated under reduced pressure affording 1.7 g (96%) of the title compound as an off-white solid. Mass Spectrum (LCMS, ESI pos): Calcd. for $C_{15}H_{17}N_2O^+$: 241.1 (M+H); Found: 241.1.

Intermediate 32:
1-(2,1-Benzoxazol-3-yl)ethan-1-one

A. N-Methoxy-N-methyl-2,1-benzoxazole-3-carboxamide. To a 50-mL round-bottom flask was placed a solution of 2,1-benzoxazole-3-carboxylic acid (500 mg, 3.07 mmol) in DCM (20 mL) then HATU (2.33 g, 6.13 mmol), DIEA (2.4 g, 18.57 mmol), and methoxy(methyl)amine hydrochloride (598 mg, 6.13 mmol) were added. The reaction was stirred for 5 h at rt, quenched by the addition of 15 mL of water, and extracted with DCM (3×30 mL). The organic extracts were combined, washed with brine (1×20 mL), dried over $Na_2SO_4$, and concentrated under reduced pressure. The residue was purified by column chromatography eluting with EtOAc/petroleum ether (1:20) affording 158 mg (25%) of the title compound as a white solid. Mass Spectrum (LCMS, ESI pos): Calcd. for $C_{10}H_{11}N_2O_3^+$: 207.1 (M+H); Found: 207.1.

B. 1-(2,1-Benzoxazol-3-yl)ethan-1-one. To a 25-mL round-bottom flask purged and maintained with an inert atmosphere of nitrogen, was placed a solution of N-methoxy-N-methyl-2,1-benzoxazole-3-carboxamide (158 mg, 0.77 mmol, as prepared in the previous step) in THF (10 mL). The solution was cooled to 0° C. then MeMgBr (1.54 mmol, 0.53 mL of 2.9 M THF solution) was added dropwise with stirring. The reaction was stirred for 15 min at 0° C. then quenched by the addition of 10 mL of saturated aqueous $NH_4Cl$ solution and extracted with EtOAc (3×20 mL). The organic extracts were combined, washed with brine (1×20 mL), dried over $Na_2SO_4$, and concentrated under reduced pressure. The residue was purified by column chromatography eluting with EtOAc/petroleum ether (1:30) affording 98 mg (79%) of the title compound as a light yellow solid. Mass Spectrum (LCMS, ESI pos): Calcd. for $C_9H_8NO_2^+$: 162.1 (M+H); Found: 162.0.

General Procedure E: Representative Example

Intermediate 33: 4-(Benzyloxy)-7-methyl-2,3-dihydro-1H-indole-2,3-dione

A. 4-(Benzyloxy)-7-methyl-1H-indole. To a 500-mL 3-necked round-bottom flask purged and maintained with an inert atmosphere of nitrogen, was placed a solution of 4-(benzyloxy)-1-methyl-2-nitrobenzene (10 g, 41.11 mmol, as prepared in Intermediate 13, Step A) in THF (50 mL) then the solution was cooled to −40° C. and ethenylmagnesium bromide (200 mL) was added dropwise with stirring. The resulting solution was stirred for 3 h at −40° C., quenched by the addition of saturated aqueous $NH_4Cl$ solution, and extracted with EtOAc. The organic extracts were combined, dried over anhydrous $Na_2SO_4$, and concentrated under reduced pressure. The residue was purified by column chromatography eluting with EtOAc/petroleum ether (1:150) affording 2.3 g (24%) of the title compound as a brown oil. Mass Spectrum (LCMS, ESI pos): Calcd. for $C_{16}H_{16}NO^+$: 238.1 (M+H); Found: 238.1.

B. 4-(Benzyloxy)-7-methyl-2,3-dihydro-1H-indole-2,3-dione. To a 250-mL round-bottom flask was placed a solution of 4-(benzyloxy)-7-methyl-1H-indole (4.4 g, 18.54 mmol, as prepared in the previous step) in DMSO (50 mL) then $I_2$ (5.66 g, 22.30 mmol) was added followed by the dropwise addition of TBHP (8.36 g, 92.76 mmol). The reaction was stirred for 5 h at 80° C., quenched by the addition of water, and extracted with DCM. The organic extracts were combined, washed with aqueous $Na_2S_2O_3$ solution, dried over anhydrous $Na_2SO_4$, and concentrated under reduced pressure. The residue was purified by column chromatography eluting with EtOAc/petroleum ether (1:8) affording 2 g (40%) of the title compound as a brown solid. Mass Spectrum (LCMS, ESI pos): Calcd. for $C_{16}H_{14}NO_3^+$: 268.1 (M+H); Found: 268.1.

Using General Procedure E with reagents, starting materials, and conditions familiar to those skilled in the art, the following intermediates were prepared:

| Intermediate | Name and Data |
| --- | --- |
| 63 | 7-Methyl-4-(trifluoromethoxy)-2,3-dihydro-1H-indole-2,3-dione<br>Mass Spectrum (LCMS, ESI pos): Calcd. for $C_{10}H_7F_3NO_3^+$: 246.0 (M + H); Found: 246.2. |

Intermediate 34:
1-(2,1-Benzothiazol-3-yl)ethan-1-one

A. N-(Oxo-[4]-sulfanylidene)methanesulfonamide. To a 100-mL round-bottom flask was placed a solution of methanesulfonamide (17.8 g, 187.13 mmol) in toluene (50 mL) then thionyl chloride (20 mL) was added. The reaction was stirred overnight at 90° C. then concentrated under reduced pressure affording 26.4 g of the title compound as a brown oil.

B. N-(Chlorosulfinyl)-2-methylaniline. To a 100-mL round-bottom flask was placed a solution of 2-methylaniline (12.5 g, 117 mmol) in toluene (50 mL) then the solution was cooled to 0° C. and thionyl chloride (21 g, 177 mmol) was added dropwise with stirring. The reaction was heated to reflux for 5 h then cooled to rt and concentrated under reduced pressure affording 22.8 g of the title compound as a brown solid.

C. 2,1-Benzothiazole. To a 250-mL round-bottom flask was placed a solution of N-(oxo[4]-sulfanylidene)methanesulfonamide (25.4 g, 179.93 mmol, as prepared in Step A) and pyridine (9.5 g, 120.10 mmol) in toluene (50 mL), then a solution of N-(chlorosulfinyl)-2-methylaniline (22.8 g, 120.21 mmol, as prepared in the previous step) in toluene (20 mL) was added dropwise with stirring. The reaction was stirred overnight at 90° C. then cooled to rt and concentrated under reduced pressure. The residue was purified by column chromatography eluting with EtOAc/petroleum ether (1:10). The product was further purified by Flash-Prep-HPLC (IntelFlash-1: Column, C18; mobile phase, MeCN/$H_2$O (0.05% $NH_4HCO_3$)=20/80 increasing to MeCN/$H_2$O (0.05% $NH_4HCO_3$)=95/5 within 20 min; Detector, uv 254 nm) affording 3.275 g (20%) of the title compound as a brown liquid. Mass Spectrum (LCMS, ESI pos): Calcd. for $C_7H_6NS^+$: 136.0 (M+H); Found: 136.0.

D. 2,1-Benzothiazole-3-carbaldehyde. To a 100-mL 3-necked round-bottom flask purged and maintained with an inert atmosphere of nitrogen, was placed a solution of 2,1-benzothiazole (3.275 g, 24.23 mmol, as prepared in the previous step) in THF (50 mL), then the solution was cooled to −78° C. and BuLi (19.4 mL of 2.5 M hexanes solution, 48.5 mmol) was added dropwise with stirring. The resulting solution was stirred for 30 min at −40° C. then DMF (3.542 g, 48.46 mmol) was added dropwise with stirring. The reaction was stirred at −40° C. for 2 h, quenched by the addition of saturated aqueous $NH_4Cl$ solution, and extracted with EtOAc. The organic extracts were combined, dried over anhydrous $Na_2SO_4$, and concentrated under reduced pressure. The residue was purified by column chromatography eluting with EtOAc/petroleum ether (1:30) affording 1.846 g (47%) of the title compound as a brown solid.

E. 1-(2,1-Benzothiazol-3-yl)ethan-1-ol. To a 100-mL 3-necked round-bottom flask was placed a solution of 2,1-benzothiazole-3-carbaldehyde (560 mg, 3.43 mmol, as prepared in the previous step) in THF (30 mL), then the solution was cooled to 0° C. and MeMgBr (3.44 mL of a 3 M THF solution, 10.3 mmol) was added dropwise with stirring. The reaction was stirred for 1 h at rt, quenched by the addition of saturated aqueous $NH_4Cl$ solution, and extracted with EtOAc. The organic extracts were combined, dried over anhydrous $Na_2SO_4$, and concentrated under reduced pressure. The residue was purified by column chromatography eluting with EtOAc/petroleum ether (1:3) affording 414 mg (67%) of the title compound as a brown oil. Mass Spectrum (LCMS, ESI pos): Calcd. for $C_9H_{10}NOS^+$: 180.1 (M+H); Found: 180.0.

F. 1-(2,1-Benzothiazol-3-yl)ethan-1-one. To a 100-mL round-bottom flask was placed a solution of 1-(2,1-benzothiazol-3-yl)ethan-1-ol (414 mg, 2.31 mmol, as prepared in the previous step) in DCM (20 mL) then Dess-Martin Periodinane (1.972 g, 4.65 mmol) was added. The reaction was stirred for 2 h at rt then the solids were removed by filtration. The filtrate was concentrated under reduced pressure then the residue was purified by column chromatography eluting with EtOAc/petroleum ether (1:3) affording 322 mg (79%) of the title compound as a yellow solid. Mass Spectrum (LCMS, ESI pos): Calcd. for $C_9H_8NOS^+$: 178.0 (M+H); Found: 178.0.

Intermediate 35:
1-(3-Methyl-1-benzothiophen-2-yl)ethan-1-one

A. 1-(3-Methyl-1-benzothiophen-2-yl)ethan-1-one. To a 100-mL 3-necked round-bottom flask purged and maintained with an inert atmosphere of nitrogen, was placed a solution of $AlCl_3$ (3.2 g) in DCM (20 mL) then AcCl (1.9 g, 24.20 mmol) was added. This was followed by the addition of 3-methyl-1-benzothiophene (1.2 g, 8.10 mmol) dropwise with stirring. The solution was stirred for 3 h at rt, quenched by the addition of 50 mL of water, and extracted with DCM (3×30 mL). The organic extracts were combined, washed with brine (2×30 mL), dried over anhydrous $Na_2SO_4$, and concentrated under reduced pressure. The residue was purified by column chromatography eluting with EtOAc/petroleum ether (1:80) affording 1.25 g (81%) of the title compound as a white solid. Mass Spectrum (LCMS, ESI pos): Calcd. for $C_{11}H_{11}OS^+$: 191.1 (M+H); Found: 191.1. $^1$H NMR (300 MHz, DMSO-$d_6$): δ 8.00-7.97 (m, 2H), 7.55-7.43 (m, 2H), 2.60 (s, 3H), 2.60 (s, 3H).

General Procedure F: Representative Example

Intermediate 36:
5-(Benzyloxy)-2-cyclopropylaniline

A. 4-(Benzyloxy)-1-chloro-2-nitrobenzene. To a 250-mL round-bottom flask was placed a solution of 4-chloro-3-nitrophenol (5 g, 28.81 mmol) and $K_2CO_3$ (6 g, 43.41 mmol) in MeCN (50 mL) then BnBr (4.9 g, 28.65 mmol) was added. The reaction was stirred for 16 h at 90° C., cooled to rt, and the solids were removed by filtration. The filtrate was concentrated under reduced pressure. The residue was purified by column chromatography eluting with EtOAc/petroleum ether (2%) affording 6.7 g of the title compound as a yellow solid.

B. 4-(Benzyloxy)-1-cyclopropyl-2-nitrobenzene. To a 250-mL round-bottom flask purged and maintained with an inert atmosphere of nitrogen, was placed a solution of 4-(benzyloxy)-1-chloro-2-nitrobenzene (1 g, 3.79 mmol, as prepared in the previous step) in dioxane/$H_2O$ (20:1, 50 mL) then cyclopropylboronic acid (640 mg, 7.45 mmol), Pd(OAc)$_2$ (0.17 g), PCy$_3$·HBF$_4$ (0.27 g), and $K_2CO_3$ (4.7 g, 34.01 mmol) were added. The reaction was stirred for 4 h at 120° C., quenched by the addition of 15 mL of water, and extracted with EtOAc (2×30 mL). The organic extracts were combined and concentrated under reduced pressure. The residue was purified by column chromatography eluting with petroleum ether (100%) affording 850 mg of the title compound as a yellow solid.

C. 5-(Benzyloxy)-2-cyclopropylaniline. To a 25-mL round-bottom flask was placed a solution of 4-(benzyloxy)-1-cyclopropyl-2-nitrobenzene (500 mg, 1.86 mmol, as prepared in the previous step) in MeOH (5 mL) then Raney Ni (300 mg) was added. The solution was degassed and backfilled with $H_2$ and stirred for 16 h at rt. The $H_2$ was purged then the solids were removed by filtration. The filtrate was concentrated under reduced pressure affording 430 mg (97%) of the title compound as a yellow solid. Mass Spectrum (LCMS, ESI pos): Calcd. for $C_{16}H_{18}NO^+$: 240.1 (M+H); Found: 240.1.

Using General Procedure F with reagents, starting materials, and conditions familiar to those skilled in the art, the following intermediates were prepared:

| Intermediate | Name and Data |
|---|---|
| 37 | 5-(Benzyloxy)-2-ethylaniline.<br>Mass Spectrum (LCMS, ESI pos): Calcd. for $C_{15}H_{18}NO^+$: 228.1 (M + H); Found: 228.1. |
| 38 | 5-(Benzyloxy)-2-(propan-2-yl)aniline.<br>Mass Spectrum (LCMS, ESI pos): Calcd. for $C_{16}H_{20}NO^+$: 242.2 (M + H); Found: 242.1. |

Intermediate 39: 5-(Benzyloxy)-2-fluoroaniline

A. 4-(Benzyloxy)-1-fluoro-2-nitrobenzene. To a 50-mL 3-necked round-bottom flask purged and maintained with an inert atmosphere of nitrogen, was placed a solution of 4-fluoro-3-nitrophenol (1 g, 6.37 mmol) in acetone (20 mL) then $K_2CO_3$ (2.64 g, 18.96 mmol) and BnBr (1.31 g, 7.66 mmol) were added. The reaction was stirred overnight at rt then the solids were removed by filtration. The filtrate was concentrated under reduced pressure affording 1.1 g (70%) of the title compound as a light yellow solid.

B. 5-(Benzyloxy)-2-fluoroaniline. To a 25-mL round-bottom flask purged and maintained with an inert atmosphere of nitrogen, was placed a solution of 4-(benzyloxy)-1-fluoro-2-nitrobenzene (200 mg, 0.81 mmol, as prepared in the previous step) and Ni(OAc)$_2$ 4H$_2$O (287 mg, 2.44 mmol) in THF/MeOH (1:1, 6 mL). To this solution was added NaBH$_4$ (123 mg, 3.34 mmol) in several portions. The reaction was stirred for 1 h at rt, quenched by the addition of ice water, and extracted with EtOAc. The organic extracts were combined and concentrated under reduced pressure affording 220 mg of the title compound as a yellow solid. Mass Spectrum (LCMS, ESI pos): Calcd. for $C_{13}H_{13}FNO^+$: 218.1 (M+H); Found: 218.1.

Intermediate 40: 4-(Benzyloxy)-7-chloro-2,3-dihydro-1H-indole-2,3-dione

A. 4-(Benzyloxy)-1-chloro-2-nitrobenzene. To a 50-mL 3-necked round-bottom flask purged and maintained with an inert atmosphere of nitrogen, was placed a solution of 4-chloro-3-nitrophenol (1.7 g, 9.80 mmol) in acetone (10 mL) then $K_2CO_3$ (4.07 g, 29.24 mmol) and BnBr (2.02 g, 11.81 mmol) were added. The reaction was stirred overnight at rt then the solids were removed by filtration. The filtrate was concentrated under reduced pressure then the residue was triturated with petroleum ether and the solid was isolated by filtration affording 2.6 g of the title compound as a yellow solid. $^1$H NMR (400 MHz, DMSO-d$_6$): δ 7.81-7.79 (d, J=8.0 Hz, 1H), 7.77-7.66 (m, 1H), 7.49-7.34 (m, 6H), 5.22 (s, 2H).

B. 4-(Benzyloxy)-7-chloro-1H-indole. To a 50-mL 3-necked round-bottom flask purged and maintained with an inert atmosphere of nitrogen, was placed a solution of 4-(benzyloxy)-1-chloro-2-nitrobenzene (1 g, 3.79 mmol, as prepared in the previous step) in THF (15 mL), then the solution was cooled to −40° C. and ethenylmagnesium bromide (11.5 mL of 1 M THF solution, 11.5 mmol) was added. The reaction was stirred for 1 h at −40° C., quenched by the addition of water, and extracted with EtOAc. The organic extracts were combined and concentrated under vacuum. The residue was purified by column chromatography eluting with EtOAc/petroleum ether (1:5) affording 260 mg (27%) of the title compound as a yellow oil. Mass Spectrum (LCMS, ESI pos): Calcd. for $C_{15}H_{13}ClNO^+$: 258.1 (M+H); Found: 258.1.

C. 4-(Benzyloxy)-7-chloro-2,3-dihydro-1H-indole-2,3-dione. To a 25-mL round-bottom flask was placed a solution of 4-(benzyloxy)-7-chloro-1H-indole (260 mg, 1.01 mmol, as prepared in the previous step) in DMSO (5 mL) then I$_2$ (305 mg, 1.20 mmol) and TBHP (450 mg, 4.99 mmol) were added. The reaction was stirred overnight at 80° C., quenched by the addition of aqueous Na$_2$S$_2$O$_3$ solution, and extracted with EtOAc. The organic extracts were combined and concentrated under reduced pressure. The residue was purified by column chromatography eluting with EtOAc/petroleum ether (1:5) affording 100 mg (34%) of the title compound as a yellow solid. Mass Spectrum (LCMS, ESI pos): Calcd. for $C_{15}H_{11}ClNO_3^+$: 288.0 (M+H); Found: 288.0.

General Procedure G: Representative Example

Intermediate 41: 2-Methyl-5-(pyridin-3-ylmethoxy)aniline

A. 3-(4-Methyl-3-nitrophenoxymethyl)pyridine. To a 250-mL round-bottom flask was placed a solution of 4-methyl-3-nitrophenol (5 g, 32.65 mmol) and K$_2$CO$_3$ (6.5 g, 47.03 mmol, 1.50 equiv) in MeCN (50 mL) then 3-(bromomethyl)pyridine (6.5 g, 37.79 mmol) was added. The reaction was stirred for 16 h at 90° C., cooled to rt, and the solids were removed by filtration. The filtrate was concentrated under reduced pressure affording 3.7 g of the title compound as a yellow oil.

B. 2-Methyl-5-(pyridin-3-ylmethoxy)aniline. To a 50-mL round-bottom flask purged and maintained with an inert atmosphere of N$_2$, was placed a solution of 3-(4-methyl-3-nitrophenoxymethyl)pyridine (486 mg, 1.99 mmol, as prepared in the previous step) in MeOH (10 mL) then Raney Ni (1 g) was added and the solution was degassed and backfilled with H$_2$. The reaction was stirred for 4 h at rt then the H$_2$ was purged and the solids were removed by filtration. The filtrate was concentrated under reduced pressure affording 376 mg (88%) of the title compound as a colorless liquid. Mass Spectrum (LCMS, ESI pos): Calcd. for $C_{13}H_{15}N_2O^+$: 215.1 (M+H); Found: 215.1.

Using General Procedure G with reagents, starting materials, and conditions familiar to those skilled in the art, the following intermediates were prepared:

| Intermediate | Name and Data |
|---|---|
| 42 | 2-Methyl-5-(pyridin-2-ylmethoxy)aniline.<br>Mass Spectrum (LCMS, ESI pos): Calcd. for $C_{13}H_{15}N_2O^+$: 215.2 (M + H); |

| Intermediate Name and Data |
|---|
| Found: 215.1. $^1$H NMR (400 MHz, DMSO-d$_6$): δ 8.57-8.56 (m, 1H), 7.84-7.80 (m, 1H), 7.47-7.45 (d, J = 8.0 Hz, 1H), 7.34-7.31 (m, 1H), 6.81-6.78 (d, J = 9.6 Hz, 1H), 6.29 (s, 1H), 6.14-6.12 (m, 1H), 5.05 (s, 2H), 4.85 (brs, 2H), 1.97 (s, 3H). |

General Procedure H: Representative Example

Intermediate 43:
5-(Difluoromethoxy)-2-methylaniline 4-(Difluoromethoxy)-1-methyl-2-nitrobenzene. To a 250-mL round-bottom flask was placed a solution of 4-methyl-3-nitrophenol (5 g, 32.65 mmol) in DMF (50 mL). To the solution were added Cs$_2$CO$_3$ (9 g, 65.14 mmol), ClF$_2$COONa (10 g, 65.59 mmol). The resulting solution was stirred for 8 h at 100° C. in an oil bath. The solids were filtered out and the resulting solution was concentrated under vacuum to give 3.7 g (56%) of the title compound as yellow oil.

5-(Difluoromethoxy)-2-methylaniline. To a 100-mL round-bottom flask, was placed a solution of 4-(difluoromethoxy)-1-methyl-2-nitrobenzene (1 g, 4.92 mmol) in MeOH (7 mL). To the solution was added Raney Ni (100 mg, 1.69 mmol). The solution was degassed and back filled with hydrogen. The resulting solution was stirred for 2 h at room temperature. The solids were filtered out. The resulting solution was concentrated under vacuum to give 712 mg (84%) of the title compound as yellow oil. Mass Spectrum (LCMS, ESI pos): Calcd. for C$_8$H$_{10}$F$_2$NO$^+$: 174.1 (M+H); Found: 174.2.

Using General Procedure H with reagents, starting materials, and conditions familiar to those skilled in the art, the following intermediates were prepared:

| Intermediate | Name and Data |
|---|---|
| 45 | 4-(Difluoromethoxy)-2-methylaniline. Mass Spectrum (LCMS, ESI pos): Calcd. for C$_8$H$_{10}$F$_2$NO$^+$: 174.1 (M + H); Found: 174.2. |

General Procedure I: Representative Example

Intermediate 44:
5-(2,2-Difluoroethoxy)-2-methylaniline 4-(2,2-Difluoroethoxy)-1-methyl-2-nitrobenzene. To a 250-mL round-bottom flask was placed a solution of 4-methyl-3-nitrophenol (3 g, 19.59 mmol) in DMF (50 mL) then 2-bromo-1,1-difluoroethane (3.54 g, 24.42 mmol) and Cs$_2$CO$_3$ (32 g, 98.21 mmol) were added. The reaction was stirred for 16 h at 90° C., cooled to rt, and filtered. The filtrate was diluted with water and extracted with EtOAc. The combined organic layers were concentrated under reduced pressure affording 4.6 g of the title compound as a yellow solid.

5-(2,2-Difluoroethoxy)-2-methylaniline. To a 50-mL round-bottom flask purged and maintained with an inert atmosphere of N$_2$, was placed a solution of 4-(2,2-difluoroethoxy)-1-methyl-2-nitrobenzene (1 g, 4.60 mmol, as prepared in the previous step) in MeOH (10 mL) then Pd on carbon (200 mg) was added. The solution was degassed and back-filled with H$_2$ and stirred for 16 h at rt. The H$_2$ was purged then the solids were removed by filtration. The filtrate was concentrated under reduced pressure affording 682 mg (79%) of the title compound as a black solid. Mass Spectrum (LCMS, ESI pos): Calcd. for C$_9$H$_{12}$F$_2$NO$^+$: 188.1 (M+H); Found: 188.1.

Using General Procedure I with reagents, starting materials, and conditions familiar to those skilled in the art, the following intermediates were prepared:

| Intermediate | Name and Data |
|---|---|
| 46 | 4-(2,2-Difluoroethoxy)-2-methylaniline. Mass Spectrum (LCMS, ESI pos): Calcd. for C$_9$H$_{12}$F$_2$NO$^+$: 188.1 (M + H); Found: 188.1. |

Intermediate 49:
7-(Benzyloxy)-3-methyl-1-benzofuran-2-carbaldehyde

A. 3-Methyl-1-benzofuran-7-ol. To a 50-mL 3-necked round-bottom flask purged and maintained with an inert atmosphere of nitrogen, was placed a solution of 7-methoxy-3-methyl-1-benzofuran (400 mg, 2.47 mmol) in DCM (5 mL) then the solution was cooled to −78° C. and BBr$_3$ (3.7 mL) was added. The reaction was stirred for 5 h over which time the temperature was allowed to increase to rt. The reaction was quenched by the addition of water and extracted with DCM. The organic extracts were combined and concentrated under reduced pressure. The residue was purified by column chromatography eluting with EtOAc/petroleum ether (1:5) affording 320 mg (88%) of the title compound as a light yellow solid. Mass Spectrum (LCMS, ESI pos): Calcd. for C$_9$H$_9$O$_2^+$: 149.1 (M+H); Found: 149.1.

B. 7-(Benzyloxy)-3-methyl-1-benzofuran. To a 50-mL round-bottom flask was placed a solution of 3-methyl-1-benzofuran-7-ol (320 mg, 2.16 mmol, as prepared in the previous step) in acetone (10 mL) then K$_2$CO$_3$ (896 mg, 6.49 mmol) and BnBr (416 mg, 2.43 mmol) were added. The reaction was stirred overnight at rt then the solids were removed by filtration. The filtrate was concentrated under reduced pressure. The residue was purified by column chromatography eluting with EtOAc/petroleum ether (1:7) affording 490 mg (95%) of the title compound as a light yellow solid. Mass Spectrum (LCMS, ESI pos): Calcd. for $C_{16}H_{15}O_2^+$: 239.1 (M+H); Found: 239.1.

C. 7-(Benzyloxy)-3-methyl-1-benzofuran-2-carbaldehyde. To a 50-mL 3-necked round-bottom flask purged and maintained with an inert atmosphere of nitrogen, was placed a solution of 7-(benzyloxy)-3-methyl-1-benzofuran (490 mg, 2.06 mmol, as prepared in the previous step) in THF (5 mL) then the solution was cooled to −78° C. and BuLi (0.9 mL of 2.5M THF solution) was added. The reaction was stirred for 1 h at −78° C. then DMF (300 mg, 4.11 mmol) was added. The reaction was stirred for 1 h at −78° C. then quenched by the addition of saturated aqueous $NH_4Cl$ solution and extracted with EtOAc. The organic extracts were combined and concentrated under reduced pressure. The residue was purified by column chromatography eluting with EtOAc/petroleum ether (1:5) affording 300 mg (55%) of the title compound as a white solid. Mass Spectrum (LCMS, ESI pos): Calcd. for $C_{17}H_{15}O_3^+$: 267.1 (M+H); Found: 267.1.

General Procedure J: Representative Example

Intermediate 51: 5-(Cyclohexyloxy)-2-ethylaniline

A. 1-Chloro-4-(cyclohexyloxy)-2-nitrobenzene. To a 250-mL 3-necked round-bottom flask purged and maintained with an inert atmosphere of nitrogen, was placed a solution of 4-chloro-3-nitrophenol (5 g, 28.81 mmol), cyclohexanol (5.78 g, 57.71 mmol), and $PPh_3$ (11.36 g, 43.31 mmol) in THF (50 mL) then the solution was cooled to 0° C. and DIAD (8.76 g, 43.32 mmol) was added dropwise with stirring. The reaction was stirred for 2 h at rt, quenched by the addition of water, and extracted with EtOAc. The organic extracts were combined, washed with brine, dried over anhydrous $Na_2SO_4$, and concentrated under reduced pressure. The residue was purified by column chromatography eluting with EtOAc/petroleum ether (1:100) affording 3.5 g (48%) of the title compound as a light yellow solid.

B. 4-(Cyclohexyloxy)-1-ethenyl-2-nitrobenzene as yellow oil. To a 250-mL round-bottom flask was placed a solution of 1-chloro-4-(cyclohexyloxy)-2-nitrobenzene (2.8 g, 10.95 mmol, as prepared in the previous step) in dioxane/water (42 mL) then 2-ethenyl-4,4,5,5-tetramethyl-1,3,2-dioxaborolane (3.4 g, 22.08 mmol), $K_3PO_4$ (9.3 g, 43.81 mmol), $PCy_3 \cdot HBF_4$ (808 mg, 2.20 mmol), and $Pd(OAc)_2$ (492 mg, 2.19 mmol) were added under nitrogen. The reaction was stirred for 1 h at 100° C., quenched by the addition of water, and extracted with EtOAc. The organic extracts were combined, washed with brine, dried over anhydrous $Na_2SO_4$, and concentrated under reduced pressure. The residue was purified by column chromatography eluting with EtOAc/petroleum ether (1:100) affording 2 g (74%) of the title compound as a yellow oil. $^1$H NMR (300 MHz, $CDCl_3$): δ 7.53 (d, J=8.6 Hz, 1H), 7.42 (d, J=2.6 Hz, 1H), 7.17-7.01 (m, 2H), 5.64 (d, J=15 Hz, 1H), 5.38 (d, J=12 Hz, 1H), 4.36-4.28 (m, 1H), 1.97-1.80 (m, 4H), 1.62-1.35 (m, 6H).

C. 5-(Cyclohexyloxy)-2-ethylaniline. To a 100-mL round-bottom flask purged and maintained with an inert atmosphere of nitrogen, was placed a solution of 4-(cyclohexyloxy)-1-ethenyl-2-nitrobenzene (2 g, as prepared in the previous step) in MeOH (15 mL) then Pd on carbon (200 mg) was added. The resulting solution was degassed and back-filled with $H_2$ and stirred for 2 h at rt. The $H_2$ was purged then the solids were removed by filtration. The filtrate was concentrated under reduced pressure and the residue was purified by Flash-Prep-HPLC (IntelFlash-1: Column, C18; mobile phase, $MeCN/H_2O$=5/95 increasing to $MeCN/H_2O$=95/5 within 30 min; Detector, uv 254 nm) affording 900 mg of the title compound as light yellow oil. Mass Spectrum (LCMS, ESI pos): Calcd. for $C_{14}H_{22}NO^+$: 220.2 (M+H); Found: 220.1.

Using General Procedure J with reagents, starting materials, and conditions familiar to those skilled in the art, the following intermediates were prepared:

| Intermediate | Name and Data |
|---|---|
| 61 | 2-Ethyl-5-(1-phenylpropoxy)aniline.<br>Mass Spectrum (LCMS, ESI pos): Calcd. for $C_{17}H_{22}NO^+$: 256.2 (M + H); Found: 256.2. |

Intermediate 52:
2-Methyl-5-(1-phenylethoxy)aniline

A. 1-Methyl-2-nitro-4-(1-phenylethoxy)benzene. To a 50-mL round-bottom flask was placed a solution of 4-methyl-3-nitrophenol (1.5 g, 9.80 mmol) in acetone (20 mL) then $K_2CO_3$ (4.07 g, 29.49 mmol) and (1-bromoethyl)benzene (2 g, 10.81 mmol) were added. The reaction was stirred overnight at rt, the solids were removed by filtration, and concentrated under reduced pressure affording 2.8 g of the title compound as a yellow oil.

B. 2-Methyl-5-(1-phenylethoxy)aniline. To a 50-mL round-bottom flask purged and maintained with an inert atmosphere of nitrogen, was placed a solution of 1-methyl-2-nitro-4-(1-phenylethoxy)benzene (500 mg, 1.94 mmol, as prepared in the previous step) in MeOH (10 mL) then Raney Ni (50 mg) was added. The solution was degassed and back-filled with $H_2$ and stirred for 2 h at rt. The $H_2$ was purged then the solids were removed by filtration. The filtrate was concentrated under reduced pressure affording 430 mg (97%) of the title compound as a yellow solid. Mass Spectrum (LCMS, ESI pos): Calcd. for $C_{15}H_{18}NO^+$: 228.1 (M+H); Found: 228.1.

Intermediate 53: 4-tert-Butyl-2-ethylaniline

A. 4-tert-Butyl-2-ethenylaniline. To a 500-mL 3-necked round-bottom flask, was placed a solution of 2-bromo-4-tert-butylaniline (1.38 g, 6.05 mmol) in dioxane/water (120 mL) then $Pd(OAc)_2$ (135 mg, 0.60 mmol), 2-ethenyl-4,4,5,5-tetramethyl-1,3,2-dioxaborolane (1.41 g, 9.15 mmol), $PCy_3 \cdot HBF_4$ (440 mg, 1.19 mmol), and $K_3PO_4$ (3.81 g, 17.97 mmol) were added under nitrogen. The reaction was stirred for 12 h at 110° C., quenched by the addition of water, and extracted with EtOAc. The organic extracts were combined and concentrated under reduced pressure. The residue was purified by column chromatography eluting with EtOAc/petroleum ether (1:80) affording 436 mg (41%) of the title compound as a colorless oil. Mass Spectrum (LCMS, ESI pos): Calcd. for $C_{12}H_{18}N^+$: 176.1 (M+H); Found: 176.1.

B. 4-tert-Butyl-2-ethylaniline. To a 100-mL round-bottom flask was placed a solution of 4-tert-butyl-2-ethenylaniline (266 mg, 1.52 mmol, as prepared in the previous step) in MeOH (50 mL) then Pd on carbon (20 mg) was added. The solution was degassed and back-filled with $H_2$ then stirred for 30 min at rt. The $H_2$ was purged then the solids were removed by filtration. The filtrate was concentrated under reduced pressure affording 266 mg of the title compound as a colorless oil. Mass Spectrum (LCMS, ESI pos): Calcd. for $C_{12}H_{20}N^+$: 178.2 (M+H); Found: 178.2.

General Procedure K: Representative Example

Intermediate 54: 2-Ethyl-5-[(2-methylphenyl)methoxy]aniline

A. 1-Ethyl-4[(2-methylphenyl)methoxy]-2-nitrobenzene. To a 50-mL round-bottom flask was placed a solution of 4-ethyl-3-nitrophenol (600 mg, 3.59 mmol) in acetone (30 mL) then $K_2CO_3$ (1.48 g, 10.71 mmol) and 1-(bromomethyl)-2-methylbenzene (788 mg, 4.26 mmol) were added. The reaction was stirred for 4 h at 70° C. then cooled to rt and filtered. The filtrate was concentrated under reduced pressure. The residue was purified by column chromatography eluting with EtOAc/petroleum ether (1:40) affording 300 mg (31%) of the title compound as a yellow oil.

B. 2-Ethyl-5[(2-methylphenyl)methoxy]aniline. To a 50-mL round-bottom flask was placed a solution of 1-ethyl-4[(2-methylphenyl)methoxy]-2-nitrobenzene (300 mg, 1.11 mmol, as prepared in the previous step) in MeOH (10 mL) then Raney Ni (60 mg) was added. The solution was degassed and back-filled with $H_2$ then stirred for 3 h at rt. The $H_2$ was purged, the solids were removed by filtration, and the filtrate was concentrated under reduced pressure. The residue was purified by column chromatography eluting with EtOAc/petroleum ether (1:3) affording 160 mg (60%) of the title compound as a white solid. Mass Spectrum (LCMS, ESI pos): Calcd. for $C_{16}H_{20}NO^+$: 242.2 (M+H); Found: 242.1.

Using General Procedure K with reagents, starting materials, and conditions familiar to those skilled in the art, the following intermediates were prepared:

| Intermediate | Name and Data |
|---|---|
| 55 | 2-Ethyl-5-[(3-methylphenyl)methoxy]aniline. Mass Spectrum (LCMS, ESI pos): Calcd. for $C_{16}H_{20}NO^+$: 242.2 (M + H); Found: 242.1. |
| 56 | 2-Ethyl-5-[(4-methylphenyl)methoxy]aniline. Mass Spectrum (LCMS, ESI pos): Calcd. for $C_{16}H_{20}NO^+$: 242.2 (M + H); Found: 242.1. |

Intermediate 57: 2-(3-Amino-4-methylphenoxy)ethan-1-ol

A. 2-(4-Methyl-3-nitrophenoxy)ethan-1-ol. To a 100-mL round-bottom flask was placed a solution of 4-methyl-3-nitrophenol (1.53 g, 9.99 mmol) in NMP (40 mL) then $Cs_2CO_3$ (4.24 g, 13.01 mmol), NaI (1.5 g, 10.00 mmol), and (2-bromoethoxy)(tert-butyl)dimethylsilane (3.11 g, 13.00 mmol) were added. The reaction was stirred for 4 h at 100° C., quenched by the addition of water, and extracted with EtOAc. The organic extracts were combined, washed with brine, dried over anhydrous $Na_2SO_4$, and concentrated under reduced pressure. The residue was purified by column chromatography eluting with EtOAc/petroleum ether (1:5) affording 1 g (51%) of the title compound as a yellow solid. $^1$H NMR (300 MHz, DMSO-$d_6$): δ 7.50 (d, J=2.7 Hz, 1H), 7.39 (d, J=8.5 Hz, 1H), 7.23 (dd, J=8.5, 2.7 Hz, 1H), 4.95-4.80 (m, 1H), 4.05 (t, J=4.9 Hz, 2H), 3.71 (t, J=4.9 Hz, 2H), 2.42 (s, 3H).

B. 2-(3-Amino-4-methylphenoxy)ethan-1-ol. To a 100-mL round-bottom flask purged and maintained with an inert atmosphere of $N_2$, was placed a solution of 2-(4-methyl-3-nitrophenoxy)ethan-1-ol (770 mg, 3.90 mmol, as prepared in the previous step) in MeOH (10 mL) then Raney Ni (150 mg) was added. The solution was degassed and back-filled with $H_2$ then the reaction was stirred for 4 h at rt. The $H_2$ was purged then the solids were removed by filtration. The filtrate was concentrated under reduced pressure affording 600 mg (92%) of the title compound as a white solid. Mass Spectrum (LCMS, ESI pos): Calcd. for $C_9H_{14}NO_2^+$: 168.1 (M+H); Found: 168.0.

General Procedure L: Representative Example

Intermediate 58: 3,4-Dimethyl-1-benzofuran-2-carbaldehyde

A. Ethyl 2-(2-Acetyl-3-methylphenoxy)acetate. To a 100-mL round-bottom flask was placed a solution of 1-(2-hydroxy-6-methylphenyl)ethan-1-one (2 g, 13.32 mmol) in acetone (50 mL) then ethyl 2-bromoacetate (2.43 g, 14.55 mmol) and $K_2CO_3$ (13 g, 39.90 mmol) were added. The reaction was stirred for 16 h at 90° C., cooled to rt, and the solids were removed by filtration. The filtrate was concentrated under reduced pressure affording 3.5 g of the title compound as a yellow oil. Mass Spectrum (LCMS, ESI pos): Calcd. for $C_{13}H_{17}O_4^+$: 237.1 (M+H); Found: 237.1.

B. 2-(2-Acetyl-3-methylphenoxy)acetic acid. To a 100-mL round-bottom flask was placed a solution of ethyl 2-(2-acetyl-3-methylphenoxy)acetate (1.5 g, 6.35 mmol, as prepared in the previous step) in water (20 mL) then $Na_2CO_3$ (2 g, 19.06 mmol) was added. The resulting solution was stirred for 3 h at rt then the pH of the solution was adjusted to 5 with 6N HCl. The precipitate was isolated by filtration affording 989 mg (75%) of the title compound as a white solid. Mass Spectrum (LCMS, ESI pos): Calcd. for $C_{11}H_{13}O_4^+$: 209.1 (M+H); Found: 209.1.

C. 3,4-Dimethyl-1-benzofuran. To a 100-mL round-bottom flask and maintained with an inert atmosphere of $N_2$, was placed a solution of 2-(2-acetyl-3-methylphenoxy)acetic acid (1 g, 4.80 mmol, as prepared in the previous step) in $Ac_2O$ (20 mL) then NaOAc (2 g) was added. The reaction was stirred for 16 h at 140° C., cooled with an ice/salt bath, and the pH of the solution was adjusted to 8 with saturated aqueous $Na_2CO_3$ solution. The resulting mixture was extracted with EtOAc and the organic layers were combined and concentrated under reduced pressure. The residue was purified by column chromatography eluting with petroleum ether (100%) affording 351 mg (50%) of the title compound as a yellow oil. Mass Spectrum (LCMS, ESI pos): Calcd. for $C_{10}H_{11}O^+$: 147.1 (M+H); Found: 147.1.

D. 3,4-Dimethyl-1-benzofuran-2-carbaldehyde. To a 50-mL 3-necked round-bottom flask purged and maintained with an inert atmosphere of nitrogen, was placed a solution of 3,4-dimethyl-1-benzofuran (351 mg, 2.40 mmol, as prepared in the previous step) in THF (10 mL) then the solution was cooled to −78° C. and n-BuLi (1.2 mL of 2.4 M hexanes solution, 2.88 mmol) was added dropwise. The reaction was stirred for 30 min at −78° C. then DMF (350 mg, 4.79 mmol) was added. The reaction was stirred for 2 h at −40° C., quenched by the addition of water, and extracted with EtOAc. The organic extracts were combined and concentrated under reduced pressure. The residue was purified by column chromatography eluting with petroleum ether/EtOAc (50:1) affording 206 mg (49%) of the title compound as a yellow solid. Mass Spectrum (LCMS, ESI pos): Calcd. for $C_{11}H_{11}O_2^+$: 175.1 (M+H); Found: 175.1.

Using General Procedure L with reagents, starting materials, and conditions familiar to those skilled in the art, the following intermediates were prepared:

| Intermediate | Name and Data |
| --- | --- |
| 59 | 7-Fluoro-3-methyl-1-benzofuran-2-carbaldehyde.<br>Mass Spectrum (LCMS, ESI pos): Calcd. for $C_{10}H_8FO_2^+$: 179.1 (M + H); Found: 179.0. $^1$H NMR (300 MHz, DMSO-d$_6$): δ 10.05 (brs, 1H), 7.71 (d, J = 9.0 Hz, 1H), 7.53-7.35 (m, 2H), 2.62 (s, 1H). |

Intermediate 60: 2-Ethyl-5-(1-phenylethoxy)aniline

A. 1-Bromo-2-nitro-4-(1-phenylethoxy)benzene. To a 50-mL round-bottom flask was placed a solution of 4-bromo-3-nitrophenol (2 g, 9.17 mmol) in acetone (20 mL) then $K_2CO_3$ (3.8 g, 27.54 mmol) and (1-bromoethyl)benzene (1.86 g, 10.05 mmol) were added. The reaction was stirred overnight at rt then the solids were removed by filtration. The filtrate was concentrated under reduced pressure affording 3 g of the title compound as a yellow solid.

B. 1-Ethenyl-2-nitro-4-(1-phenylethoxy)benzene. To a 100-mL round-bottom flask was placed a solution of 1-bromo-2-nitro-4-(1-phenylethoxy)benzene (1 g, 3.10 mmol, as prepared in the previous step) in dioxane/H$_2$O (1:1, 21 mL) then Pd(OAc)$_2$ (139 mg, 0.62 mmol), PCy$_3$.HBF$_4$ (229 mg, 0.62 mmol), K$_3$PO$_4$ (3.95 g, 18.61 mmol), and 2-ethenyl-4,4,5,5-tetramethyl-1,3,2-dioxaborolane (960 mg, 6.23 mmol) were added under nitrogen. The reaction was stirred overnight at 120° C. then concentrated under reduced pressure. The residue was purified by column chromatography eluting with EtOAc/petroleum ether (1:100) affording 490 mg (59%) of the title compound as a yellow oil.

C. 2-Ethyl-5-(1-phenylethoxy)aniline. To a 50-mL round-bottom flask purged and maintained with an inert atmosphere of N$_2$, was placed a solution of 1-ethenyl-2-nitro-4-(1-phenylethoxy)benzene (490 mg, 1.82 mmol, as prepared in the previous step) in MeOH (10 mL) then Raney Ni (49 mg) was added. The solution was degassed and back-filled with H$_2$ then the solution was stirred for 1 h at rt. The H$_2$ was purged then the solids were removed by filtration. The filtrate was concentrated under reduced pressure affording 380 mg (87%) of the title compound as a light yellow solid. Mass Spectrum (LCMS, ESI pos): Calcd. for $C_{16}H_{20}NO^+$: 242.2 (M+H); Found: 242.1.

Intermediate 62: 2-Methyl-5-[[4-(1,3,4-oxadiazol-2-yl)cyclohexyl]oxy]aniline

A. Ethyl 4-(4-Methyl-3-nitrophenoxy)cyclohexane-1-carboxylate. To a 250-mL round-bottom flask was placed a solution of 4-methyl-3-nitrophenol (2 g, 13.06 mmol) in THF (100 mL) then ethyl 4-hydroxycyclohexane-1-carboxylate (2.5 g, 14.52 mmol), PPh$_3$ (5.11 g, 19.48 mmol) were added. The solution was cooled to 0° C. then DIAD (4.04 g, 19.98 mmol) was added dropwise with stirring. The reaction was stirred for 16 h at rt then concentrated under reduced pressure. The residue was purified by column chromatography eluting with petroleum ether/ethyl acetate (15:1) affording 2.1 g (52%) of the title compound as a yellow oil.

B. 4-(4-Methyl-3-nitrophenoxy)cyclohexane-1-carbohydrazide. To a 50-mL round-bottom flask was placed a solution of ethyl 4-(4-methyl-3-nitrophenoxy)cyclohexane-1-carboxylate (300 mg, 0.98 mmol, as prepared in the previous step) in EtOH (10 mL) then hydrazine (156 mg, 4.87 mmol) was added. The reaction was stirred for 16 h at 90° C. then concentrated under reduced pressure affording 210 mg (73%) of the title compound as a yellow solid. Mass Spectrum (LCMS, ESI pos): Calcd. for $C_{14}H_{20}N_3O_4^+$: 294.1 (M+H); Found: 294.1.

C. 2-[4-(4-Methyl-3-nitrophenoxy)cyclohexyl]-1,3,4-oxadiazole. To a 20-mL vial was placed a solution of 4-(4-methyl-3-nitrophenoxy)cyclohexane-1-carbohydrazide (500 mg, 1.70 mmol, as prepared in the previous step) in toluene (12.5 mL) then TEOF (722.5 mg, 4.88 mmol), and TsOH (100 mg, 0.63 mmol) were added. The reaction was stirred for 1 h at 110° C. under microwave irradiation then concentrated under reduced pressure. The residue was purified by column chromatography eluting with petroleum ether/ethyl acetate (20:1) affording 189 mg (37%) of the title compound as an off-white solid. Mass Spectrum (LCMS, ESI pos): Calcd. for $C_{15}H_{18}N_3O_4^+$: 304.1 (M+H); Found: 304.1.

D. 2-Methyl-5-[[4-(1,3,4-oxadiazol-2-yl)cyclohexyl]oxy]aniline. To a 50-mL round-bottom flask was placed a solution of 2-[4-(4-Methyl-3-nitrophenoxy)cyclohexyl]-1,3,4-oxadiazole (400 mg, 1.32 mmol, as prepared in the previous step) and Ni(OAc)$_2$.4H$_2$O (526 mg) in MeOH/THF (2:1) (10 mL) then the solution was cooled to 0° C. and NaBH$_4$ (220 mg, 5.82 mmol) was added in small portions with stirring. The reaction was stirred for 1 min at rt, quenched with saturated aqueous NH$_4$Cl solution, and extracted with EtOAc (3×30 mL). The organic extracts were combined and concentrated under reduced pressure 281 mg (78%) of the title compound as a colorless oil. Mass Spectrum (LCMS, ESI pos): Calcd. for $C_{15}H_{20}N_3O_2^+$: 274.2 (M+H); Found: 274.1.

Intermediate 65:
7-Methoxy-3-methyl-1-benzofuran-2-carbaldehyde

A. Methyl 2-(Benzyloxy)-3-methoxybenzoate. To a 250-mL round-bottom flask was placed a solution of methyl 2-hydroxy-3-methoxybenzoate (10 g, 54.89 mmol) in DMF (100 mL) then NaH (1.6 g, 66.67 mmol) was added. The solution was stirred for 10 min at rt then BnBr (10.3 g, 60.22 mmol) was added dropwise with stirring. The reaction was stirred overnight at 70° C., quenched by the addition of water, and extracted with EtOAc. The organic extracts were combined, washed with brine, dried over anhydrous $Na_2SO_4$, and concentrated under reduced pressure affording 17 g of the title compound as a yellow oil.

B. 2-(Benzyloxy)-3-methoxybenzoic acid. To a 500-mL round-bottom flask was placed a solution of methyl 2-(benzyloxy)-3-methoxybenzoate (21 g, 53.99 mmol) in MeOH/THF/$H_2O$ (150 mL) then NaOH (9 g, 225.00 mmol) was added. The reaction was stirred overnight at 50° C. then cooled to 5° C., and the pH was adjusted to 5 with 6N HCl. The precipitate was collected by filtration affording 13 g (93%) of the title compound as a light yellow solid.

C. 2-(Benzyloxy)-N,3-dimethoxy-N-methylbenzamide. To a 100-mL round-bottom flask was placed a solution of 2-(benzyloxy)-3-methoxybenzoic acid (3.2 g, 12.39 mmol, as prepared in the previous step) in DCM (20 mL) then methoxy(methyl)amine hydrochloride (1.44 g, 14.76 mmol), HATU (5.6 g, 14.73 mmol), and DIEA (4.8 g, 37.14 mmol) were added. The reaction was stirred for 2 h at rt, quenched by the addition of water, and extracted with EtOAc. The organic extracts were combined, washed with brine, dried over anhydrous $Na_2SO_4$, and concentrated under reduced pressure affording 6 g of the title compound as a yellow oil. Mass Spectrum (LCMS, ESI pos): Calcd. for $C_{17}H_{20}NO_4^+$: 302.1 (M+H); Found: 302.2.

D. 1-[2-(Benzyloxy)-3-methoxyphenyl]ethan-1-one. To a 250-mL 3-necked round-bottom flask purged and maintained with an inert atmosphere of nitrogen, was placed a solution of 2-(benzyloxy)-N,3-dimethoxy-N-methylbenzamide (6.5 g, 21.6 mmol, as prepared in the previous step) in THF (60 mL) then the solution was cooled to −40° C. and MeMgBr (16 mL of 3M THF solution, 84 mmol) was added dropwise with stirring. The reaction was stirred for 1 h at 0° C., quenched by the addition of water, and extracted with EtOAc. The organic extracts were combined, washed with brine, dried over anhydrous $Na_2SO_4$, and concentrated under reduced pressure. The residue was purified by column chromatography eluting with EtOAc/petroleum ether (1:10) affording 3 g (55%) of the title compound as a light yellow oil. Mass Spectrum (LCMS, ESI pos): Calcd. for $C_{16}H_{17}O_3^+$: 257.1 (M+H); Found: 257.1.

E. 1-(2-Hydroxy-3-methoxyphenyl)ethan-1-one. To a 100-mL round-bottom flask purged and maintained with an inert atmosphere of nitrogen, was placed a solution of 1-[2-(benzyloxy)-3-methoxyphenyl]ethan-1-one (3 g, 11.71 mmol, as prepared in the previous step) in MeOH (20 mL) then conc. HCl (0.1 mL) and Pd on carbon (300 mg) were added. The reaction was degassed and back-filled with $H_2$ and stirred for 24 h at rt. The $H_2$ was purged then the solids were removed by filtration. The filtrate was concentrated under reduced pressure affording 1.73 g (89%) of the title compound as a yellow solid. Mass Spectrum (LCMS, ESI pos): Calcd. for $C_9H_{11}O_3^+$: 167.1 (M+H); Found: 167.1. $^1$H NMR (300 MHz, $CDCl_3$): δ 12.58 (s, 1H), 7.35 (d, J=8.2 Hz, 1H), 7.07 (d, J=7.9 Hz, 1H), 6.86 (t, J=8.1 Hz, 1H), 3.91 (s, 3H), 2.65 (s, 3H).

F. Ethyl 2-(2-Acetyl-6-methoxyphenoxy)acetate. To a 100-mL round-bottom flask was placed a solution of 1-(2-hydroxy-3-methoxyphenyl)ethan-1-one (1.73 g, 10.41 mmol, as prepared in the previous step) in acetone (18 mL) then ethyl 2-bromoacetate (1.9 g, 11.38 mmol) and $K_2CO_3$ (4.3 g, 31.11 mmol) were added. The reaction was stirred for 2.5 h at 60° C., quenched by the addition of water, and extracted with EtOAc. The organic extracts were combined, washed with brine, dried over anhydrous $Na_2SO_4$, and concentrated under reduced pressure 2.5 g of the title compound as a yellow oil. Mass Spectrum (LCMS, ESI pos): Calcd. for $C_{13}H_{17}O_5^+$: 253.1 (M+H); Found: 253.1.

G. 2-(2-Acetyl-6-methoxyphenoxy)acetic acid. To a 100-mL round-bottom flask was placed a solution of ethyl 2-(2-acetyl-6-methoxyphenoxy)acetate (2.5 g, as prepared in the previous step) in water (20 mL) then $Na_2CO_3$ (4.3 g, 40.19 mmol) was added. The reaction was stirred for 1.5 h at 95° C. then cooled to rt and the pH was adjusted to 6 with 6N HCl. The precipitate was collected by filtration affording 2 g of the title compound as a white solid. Mass Spectrum (LCMS, ESI pos): Calcd. for $C_{11}H_{13}O_5^+$: 225.1 (M+H); Found: 225.1.

H. 7-Methoxy-3-methyl-1-benzofuran. To a 40-mL sealed tube was placed a solution of 2-(2-acetyl-6-methoxyphenoxy)acetic acid (2 g, 8.92 mmol, as prepared in the previous step) in $Ac_2O$ (20 mL) then NaOAc (5 g, 60.95 mmol) was added. The reaction was stirred overnight at 140° C., quenched by the addition of water/ice, the pH value of the solution was adjusted to 7-8 with 6M NaOH solution, and extracted with $Et_2O$. The organic extracts were combined, washed with brine, dried over anhydrous $Na_2SO_4$, and concentrated under reduced pressure. The residue was purified by column chromatography eluting with petroleum ether affording 1.4 g (97%) of the title compound as a white solid. $^1$H NMR (400 MHz, $CDCl_3$): δ 7.41 (s, 1H), 7.20-7.11 (m, 2H), 6.81 (d, J=4.5 Hz, 1H), 4.01 (s, 3H), 2.23 (s, 3H).

I. 7-Methoxy-3-methyl-1-benzofuran-2-carbaldehyde. To a 50-mL 3-necked round-bottom flask was placed a solution of 7-methoxy-3-methyl-1-benzofuran (243 mg, 1.50 mmol, as prepared in the previous step) in THF (3 mL) then the solution was cooled to −78° C. and BuLi (0.72 mL of 2.5N hexanes solution, 1.8 mmol) was added dropwise with stirring. The solution was stirred for 30 min at −78° C. then warmed to −40° C. and DMF (219 mg, 3.00 mmol) was added dropwise with stirring. The reaction was stirred for 30 min at −40° C., quenched by the addition of water, and extracted with EtOAc. The organic extracts were combined, washed with brine, dried over anhydrous $Na_2SO_4$, and concentrated under reduced pressure. The residue was purified by column chromatography eluting with EtOAc/petroleum ether (1:7) affording 200 mg (70%) of the title compound as a light yellow solid. Mass Spectrum (LCMS, ESI pos): Calcd. for $C_{11}H_{11}O_3^+$: 191.1 (M+H); Found: 191.0.

Intermediate 66:
1-(1-Methanesulfonylpiperidin-4-yl)ethan-1-ol

A. 1-(1-Methanesulfonylpiperidin-4-yl)ethan-1-one. To a 250-mL round-bottom flask was placed a solution of 1-(piperidin-4-yl)ethan-1-one (4.5 g, 35.38 mmol) in DCM (100 mL) then TEA (8.35 g, 82.52 mmol) was added. To the reaction mixture was added a solution of MsCl (4.86 g, 42.45 mmol) in DCM (50 mL) dropwise with stirring. The reaction was stirred for 8 h at rt, quenched with water, and extracted with DCM. The organic extracts were combined, dried over anhydrous $Na_2SO_4$, and concentrated under reduced pressure affording 6.17 g (85%) of the title compound as a white solid. Mass Spectrum (LCMS, ESI pos): Calcd. for $C_8H_{16}NO_3S^+$: 206.1 (M+H); Found: 206.1.

B. 1-(1-Methanesulfonylpiperidin-4-yl)ethan-1-ol. To a 250-mL round-bottom flask was placed a solution of 1-(1-methanesulfonylpiperidin-4-yl)ethan-1-one (6.17 g, 30.06 mmol, as prepared in the previous step) in a mixture of MeOH (120 mL) and THF (30 mL) then NaBH$_4$ (2.27 g, 60.01 mmol) was added. The reaction was stirred for 8 h at rt, quenched by the addition of water, and extracted with DCM. The organic extracts were combined, dried over anhydrous Na$_2$SO$_4$, and concentrated under reduced pressure affording 5.52 g (89%) of the title compound as a white solid. Mass Spectrum (LCMS, ESI pos): Calcd. for C$_8$H$_{18}$NO$_3$S$^+$: 208.1 (M+H); Found: 208.1.

Intermediate 67: 1-[Pyrazolo[1,5-a]pyridin-5-yl]ethan-1-ol

A. N-Methoxy-N-methylpyrazolo[1,5-a]pyridine-5-carboxamide. To a 100-mL round-bottom flask was placed a solution of pyrazolo[1,5-a]pyridine-5-carboxylic acid (3.24 g, 19.98 mmol) in DCM (50 mL) then methoxy(methyl)amine hydrochloride (2.925 g, 29.99 mmol), HATU (11.4 g, 29.98 mmol), and DIEA (7.74 g, 59.89 mmol) were added. The reaction was stirred for 2 h at rt then concentrated under reduced pressure. The residue was purified by column chromatography eluting with EtOAc/petroleum ether (1:1) affording 5.594 g of the title compound as a yellow oil. Mass Spectrum (LCMS, ESI pos): Calcd. for C$_{10}$H$_{12}$N$_3$O$_2$$^+$: 206.1 (M+H); Found: 206.1.

B. Pyrazolo[1,5-a]pyridine-5-carbaldehyde. To a 250-mL round-bottom flask was placed a solution of N-methoxy-N-methylpyrazolo[1,5-a]pyridine-5-carboxamide (5.594 g, 27.26 mmol, as prepared in the previous step) in THF (60 mL) then the solution was cooled to 0° C. and LAH (3.11 g, 81.95 mmol) was added in several batches. The reaction was stirred for 1 h at rt, quenched by the addition of Na$_2$SO$_4$.10H$_2$O, and the solids were removed by filtration. The filtrate was concentrated under reduced pressure. The residue was purified by column chromatography eluting with EtOAc/petroleum ether (1:5) affording 1.259 g (32%) of the title compound as a yellow solid. Mass Spectrum (LCMS, ESI pos): Calcd. for C$_8$H$_7$N$_2$O$^+$: 147.1 (M+H); Found: 147.2.

C. 1-[Pyrazolo[1,5-a]pyridin-5-yl]ethan-1-ol. To a 250-mL 3-necked round-bottom flask purged and maintained with an inert atmosphere of nitrogen was placed a solution of pyrazolo[1,5-a]pyridine-5-carbaldehyde (1.259 g, 8.61 mmol, as prepared in the previous step) in THF (70 mL) then the solution was cooled to 0° C. and 3M MeMgBr (5.75 mL) was added dropwise. The reaction was stirred for 1 h at rt, quenched by the addition of saturated aqueous NH4Cl solution, and extracted with EtOAc (3×50 mL). The organic extracts were combined, dried over anhydrous Na2SO4, and concentrated under reduced pressure. The residue was purified by column chromatography eluting with EtOAc/petroleum ether (1:1) affording 1.1 g (79%) of the title compound as a yellow solid. Mass Spectrum (LCMS, ESI pos): Calcd. for C$_9$H$_{11}$N$_2$O$^+$: 163.1 (M+H); Found: 163.2.

Intermediate 68: 2,5-Bis(benzyloxy)aniline

A. 1,4-Bis(benzyloxy)-2-nitrobenzene. To a 100-mL round-bottom flask was placed a solution of 2-nitrobenzene-1,4-diol (1 g, 6.45 mmol) in acetone (15 mL) then K$_2$CO$_3$ (4.45 g, 32.20 mmol) and (bromomethyl)benzene (2.64 g, 15.48 mmol) were added. The reaction was stirred for 10 h at rt, filtered, and concentrated under reduced pressure affording 1.302 g (60%) of the title compound as a yellow solid.

B. 2,5-Bis(benzyloxy)aniline. To a 100-mL 3-necked round-bottom flask was placed a solution of 1,4-bis(benzyloxy)-2-nitrobenzene (300 mg, 0.89 mmol, as prepared in the previous step) and Ni(OAc)$_2$.4H$_2$O (317 mg, 1.79 mmol) in MeOH/THF (1:1, 6 mL) then NaBH$_4$ (132 mg, 3.49 mmol) was added. The reaction was stirred for 4 h at rt, quenched with water, and extracted with EtOAc. The organic extracts were combined, dried over anhydrous Na$_2$SO$_4$, and concentrated under reduced pressure affording 220 mg (81%) of the title compound as a brown solid. Mass Spectrum (LCMS, ESI pos): Calcd. for C$_{20}$H$_{20}$NO$_2$$^+$: 306.1 (M+H); Found: 306.1.

Intermediate 69: 1-(4-(Methylsulfonyl)phenyl)ethanol

A. 1-(4-(Methylsulfonyl)phenyl)ethanol. To a 1000-mL 3-necked round-bottom flask was placed a solution of 1-(4-(methylsulfonyl)phenyl)ethanone (25 g, 126.26 mmol) in a mixture of THF (100 mL) and MeOH (200 mL) then the solution was cooled to 0° C. and NaBH$_4$ (4.80 g, 126.26 mmol) was added. The reaction was allowed to warm to rt and stirred for 2 h, then quenched by the addition of water and extracted with EtOAc. The organic extracts were combined, washed with brine, dried over anhydrous Na$_2$SO$_4$, and concentrated under reduced pressure affording 22 g (87%) of the title compound as white solid. Mass Spectrum (LCMS, ESI pos): Calcd. for C$_9$H$_{13}$O$_3$S$^+$: 201.1 (M+H); Found: 201.1.

Intermediate 70: (1s,3s)-3-Phenylcyclobutan-1-ol

A. (1s,3s)-3-Phenylcyclobutan-1-ol. To a 100-mL round-bottom flask was placed a solution of 3-phenylcyclobutan-1-one (1 g, 6.84 mmol) in MeOH (10 mL) then the solution was cooled to 0° C. and NaBH$_4$ (130 mg, 3.42 mmol) was added. The reaction was stirred for 10 min at 0° C., quenched by the addition of water, and extracted with EtOAc. The organic extracts were combined and concentrated under reduced pressure affording 1.022 g of the title compound as a colorless oil.

Intermediate 71: (1r,3r)-3-Phenylcyclobutan-1-ol

A. (1r,3r)-3-Phenylcyclobutyl 4-nitrobenzoate. To a 50-mL 3-necked round-bottom flask purged and maintained with an inert atmosphere of nitrogen was placed a solution of (1s,3s)-3-phenylcyclobutan-1-ol (1 g, 6.75 mmol, Intermediate 70) in THF (30 mL) then 4-nitrobenzoic acid (1.13 g, 6.76 mmol) and Ph$_3$P (2.66 g, 10.14 mmol) were added. The solution was cooled to 0° C. then DIAD (2.05 g, 10.15 mmol, 1.50 equiv) was added dropwise. The reaction was stirred for 30 min at rt then concentrated under reduced pressure. The residue was purified by column chromatography eluting with EtOAc/petroleum ether (1:50) affording 2.26 g of the title compound as a white solid.

B. (1r,3r)-3-Phenylcyclobutan-1-ol. To a 100-mL round-bottom flask was placed a solution of (1r,3r)-3-phenylcyclobutyl 4-nitrobenzoate (2 g, 2.88 mmol, as prepared in the previous step) in MeOH/THF=2:1 (60 mL) then K$_2$CO$_3$ (1.4 g, 10.08 mmol) was added. The reaction was stirred for 8 h at 40° C., quenched by the addition of water, and extracted with EtOAc. The organic extracts were combined, washed with brine, dried over anhydrous Na$_2$SO$_4$, and concentrated under reduced pressure affording 720 mg (72%) of the title compound as light yellow oil.

Intermediate 72: 1-[4-(Oxetan-3-yl)phenyl]ethan-1-ol

A. 1-[4-(Oxetan-3-yl)phenyl]ethan-1-one. To a 10-mL sealed tube was placed a solution of (4-acetylphenyl)boronic acid (328 mg, 2.00 mmol) in IPA (2 mL) then 3-iodooxetane (184 mg, 1.00 mmol), NiI$_2$ (18.6 mg, 0.10 mmol), (1R,2R)-2-aminocyclohexan-1-ol hydrochloride (15.2 mg, 0.10 mmol), and NaHMDS (2 mL, 2 mmol) were added under nitrogen. The reaction was irradiated with microwave radiation for 1 h at 85° C. then concentrated under reduced pressure. The residue was purified by column chromatography eluting with EtOAc/petroleum ether (1:3) affording 133 mg (38%) of the title compound as off-white oil.

B. 1-[4-(Oxetan-3-yl)phenyl]ethan-1-ol. To a 100-mL round-bottom flask was placed a solution of 1-[4-(oxetan-3-yl)phenyl]ethan-1-one (1.62 g, 9.19 mmol, as prepared in the previous step) in MeOH (20 mL) then the solution was cooled to −18° C. and NaBH$_4$ (700 mg, 18.50 mmol) was added in small portions. The reaction was stirred for 1 h at −18° C., quenched by the addition of water, and extracted with EtOAc. The organic extracts were combined and concentrated under reduced pressure affording 1.2 g (73%) of the title compound as a light yellow solid. Mass Spectrum (LCMS, ESI pos): Calcd. for $C_{11}H_{15}O_2^+$: 179.1 (M+H); Found: 179.2.

Intermediate 73:
1-(Tetrahydro-2H-pyran-4-yl)ethan-1-ol

A. 1-(Tetrahydro-2H-pyran-4-yl)ethan-1-ol. To a 100-mL round-bottom flask was placed a solution of 1-(tetrahydro-2H-pyran-4-yl)ethan-1-one (10 g, 78.0 mmol) in THF (200 mL) then the solution was cooled to 0° C. and NaBH$_4$ (1.50 g, 39.5 mmol) was added. The reaction was stirred for 30 min at 0° C., quenched by the addition of water, and extracted with EtOAc. The organic extracts were combined and concentrated under reduced pressure affording 10 g (98%) of the title compound as colorless oil. Mass Spectrum (LCMS, ESI pos): Calcd. for $C_7H_{15}O_2^+$: 131.1 (M+H); Found: 131.2.

Intermediate 74:
4-(1-hydroxyethyl)-N-methylbenzene-1-sulfonamide

A. Pentafluorophenyl 4-Acetylbenzenesulfonate. To a 100-mL round-bottom flask was placed a solution of 2,3,4,5,6-pentafluorophenol (900 mg, 4.89 mmol) in DCM (30 mL) then TEA (1.48 g, 14.67 mmol) was added. The solution was cooled to 0° C. then 4-acetylbenzene-1-sulfonyl chloride (1.28 g, 5.87 mmol) was added. The reaction was warmed to rt and stirred for 2 h then concentrated under reduced pressure. The residue was purified by column chromatography eluting with EtOAc/petroleum ether (1:50) affording 800 mg of the title compound as a yellow oil.

B. Pentafluorophenyl 4-(1-Hydroxyethyl)benzenesulfonate. To a 50-mL round-bottom flask was placed a solution of pentafluorophenyl 4-acetylbenzenesulfonate (800 mg, 2.18 mmol, as prepared in the previous step) in MeOH (20 mL) then the solution was cooled to 0° C. and NaBH$_4$ (1 g, 2.62 mmol) was added in several portions. The reaction was warmed to rt, stirred for 1 h, and concentrated under reduced pressure. The residue was purified by column chromatography eluting with EtOAc/petroleum ether (1:10) affording 552 mg (68%) of the title compound as a yellow oil. Mass Spectrum (LCMS, ESI pos): Calcd. for $C_{14}H_{10}F_5O_4S^+$: 369.0 (M+H); Found: 369.2.

C. 4-(1-Hydroxyethyl)-N-methylbenzene-1-sulfonamide. To a 50-mL round-bottom flask was placed a solution of pentafluorophenyl 4-(1-hydroxyethyl)benzene-1-sulfonate (552 mg, 1.50 mmol) in THF (10 mL) then TEA (454.5 mg, 4.49 mmol) and a solution of 2M methylamine in THF (1.5 mL, 3.0 mmol) were added. The reaction was stirred for 2 h at rt then concentrated under reduced pressure. The residue was purified by column chromatography eluting with EtOAc/petroleum ether (1:1) affording 286 mg (89%) of the title compound as a yellow oil.

Preparation of Compounds

Example 1: Preparation of 6,8-Dimethyl-2-(3-methyl-1-benzofuran-2-yl)quinoline-4-carboxylic acid (Compound 9)

A. 6,8-Dimethyl-2-(3-methyl-1-benzofuran-2-yl)quinoline-4-carboxylic acid. To a 100 mL round-bottom flask was placed a solution of 1-(3-methyl-1-benzofuran-2-yl)ethan-1-one (1 g, 5.74 mmol) in EtOH (20 mL) then 5,7-dimethyl-2,3-dihydro-1H-indole-2,3-dione (800 mg, 4.57 mmol) and KOH (800 mg) were added. The resulting solution was heated to 80° C. and stirred for 16 h. The reaction was cooled to rt and concentrated under reduced pressure. The residue was dissolved in 100 mL of H$_2$O, washed with MTBE (3×50 mL), and the pH of the solution was adjusted to 2-3 with 2N HCl. The resulting precipitate was isolated by filtration and washed with MeOH (3×50 mL) affording 485 mg (32%) of the title compound as a yellow solid. Mass Spectrum (LCMS, ESI pos): Calcd. for $C_{21}H_{18}NO_3^+$: 332.1 (M+H); Found: 332.0. $^1$H NMR (300 MHz, DMSO-d$_6$): δ 13.95 (s, 1H), 8.43 (s, 1H), 8.33 (s, 1H), 7.80-7.77 (d, J=7.5 Hz, 1H), 7.73-7.70 (d, J=8.1 Hz, 1H), 7.61 (s, 1H), 7.47-7.42 (t, J=7.5 Hz, 1H), 7.38-7.33 (t, J=7.5 Hz, 1H), 2.85 (s, 3H), 2.73 (s, 3H), 2.52 (s, 3H). HPLC purity (254 nm): 99.5%.

Using the procedure described in Example 1, with reagents, starting materials, and conditions familiar to those skilled in the art, the following compounds representative of the disclosure were prepared:

| Compound | Name and Data |
| --- | --- |
| 17 | 6-Chloro-8-methyl-2-(3-methylbenzofuran-2-yl)quinoline-4-carboxylic acid Mass Spectrum (LCMS, ESI pos): Calcd. for $C_{20}H_{15}ClNO_3^+$: 352.1 (M + H); Found: 352.0. $^1$H NMR (300 MHz, DMSO-d$_6$): δ 14.23 (s, 1H), 8.69 (s, 1H), 8.55 (s, 1H), 7.82-7.80 (m, 2H), 7.75-7.72 (d, J = 8.1 Hz, 1H), 7.49-7.43 (m, 1H), 7.39-7.37 (m, 1H), 2.85 (s, 3H), 2.81 (s, 3H). HPLC purity (254 nm): 98.3%. |
| 18 | 6,8-Dimethyl-2-(3-methylbenzo[b]thiophen-2-yl)quinoline-4-carboxylic acid Mass Spectrum (LCMS, ESI pos): Calcd. for $C_{21}H_{18}NO_2S^+$: 348.1 (M + H); Found: 348.0. $^1$H NMR (300 MHz, DMSO-d$_6$): δ 8.29-8.27 (d, J = 6.0 Hz, 2H), 8.04-8.01 (m, 1H), 7.96-7.93 (m, 1H), 7.60 (s, 1H), 7.48-7.45 (m, 2H), 2.83 (s, 3H), 2.78 (s, 3H), 2.50 (s, 3H). HPLC purity (254 nm): 95.1%. |
| 19 | 8-Methyl-2-(3-methyl-1-benzofuran-2-yl)-6-(trifluoromethyl)quinoline-4-carboxylic acid Mass Spectrum (LCMS, ESI pos): Calcd. for $C_{21}H_{15}F_3NO_3^+$: 386.1 (M + H); Found: 386.1. $^1$H NMR (400 MHz, DMSO-d$_6$): δ 9.03 (s, 1H), 8.58 (s, 1H), |

| Compound | Name and Data |
|---|---|
| | 7.99 (s, 1H), 7.81-7.79 (d, J = 7.6 Hz, 1H), 7.74-7.72 (d, J = 8.4 Hz, 1H), 7.50-7.46 (m, 1H), 7.38-7.35 (t, J = 7.2 Hz, 1H), 2.51-2.50 (m, 6H). HPLC purity (254 nm): 98.9%. |
| 20 | 6-Fluoro-8-methyl-2-(3-methylbenzofuran-2-yl)quinoline-4-carboxylic acid<br>Mass Spectrum (LCMS, ESI pos): Calcd. for $C_{20}H_{15}FNO_3^+$: 336.1 (M + H); Found: 336.0. $^1$H NMR (300 MHz, DMSO-$d_6$): δ 8.55 (s, 1H), 8.38-8.33 (m, 1H), 7.80-7.77 (d, J = 7.5 Hz, 1H), 7.73-7.70 (d, J = 8.4 Hz, 2H), 7.48-7.43 (m, 1H), 7.38-7.33 (m, 1H), 2.83 (s, 3H), 2.73 (s, 3H). HPLC purity (254 nm): 97.1%. |
| 21 | 6-Bromo-8-methyl-2-(3-methyl-1-benzofuran-2-yl)quinoline-4-carboxylic acid<br>Mass Spectrum (LCMS, ESI pos): Calcd. for $C_{20}H_{15}BrNO_3^+$: 396.0 (M + H); Found: 395.8. $^1$H NMR (300 MHz, DMSO-$d_6$): δ 14.33-14.30 (m, 1H), 8.88 (s, 1H), 8.52 (s, 1H), 7.91(s, 1H), 7.80-7.70 (m, 2H), 7.49-7.44 (m, 1H), 7.38-7.34 (m, 1H), 2.80 (d, J = 9.0 Hz, 6H). HPLC purity (254 nm): 98.1%. |
| 27 | 6-tert-Butyl-8-methyl-2-(3-methyl-1-benzofuran-2-yl)quinoline-4-carboxylic acid<br>Mass Spectrum (LCMS, ESI pos): Calcd. for $C_{24}H_{24}NO_3^+$: 374.2 (M + H); Found: 374.3. $^1$H NMR (400 MHz, DMSO-$d_6$): δ 13.93 (s, 1H), 8.52 (s, 1H), 8.43 (s, 1H), 7.88 (s, 1H), 7.78-7.77 (d, J = 7.2 Hz, 1H), 7.72-7.70 (d, J = 8.0 Hz, 1H), 7.46-7.42 (t, J = 8.0 Hz, 1H), 7.36-7.32 (t, J = 7.6 Hz, 1H), 2.84 (s, 3H), 2.81 (s, 3H), 1.39 (s, 9H). HPLC purity (254 nm): 98.4%. |
| 31 | 5,8-Dimethyl-2-(3-methyl-1-benzofuran-2-yl)quinoline-4-carboxylic acid<br>Mass Spectrum (LCMS, ESI pos): Calcd. for $C_{21}H_{18}NO_3^+$: 332.1 (M + H); Found: 332.1. $^1$H NMR (300 MHz, DMSO-$d_6$): δ 14.10 (brs, 1H), 8.01 (s, 1H), 7.81-7.78 (d, J = 7.8 Hz, 1H), 7.71-7.63 (m, 2H), 7.48-7.33 (m, 3H), 2.86 (s, 3H), 2.73 (s, 3H), 2.60 (s, 3H). HPLC purity (254 nm): 99.2%. |
| 32 | 2-(3-Ethyl-1-benzofuran-2-yl)-5,8-dimethylquinoline-4-carboxylic acid<br>Mass Spectrum (LCMS, ESI pos): Calcd. for $C_{22}H_{20}NO_3^+$: 346.1 (M + H); Found: 346.1. $^1$H NMR (400 MHz, DMSO-$d_6$): δ 14.17 (s, 1H), 8.00 (s, 1H), 7.83-7.81 (d, J = 7.6 Hz, 1H), 7.71-7.69 (d, J = 8.0 Hz, 1H), 7.65-7.63 (d, J = 7.2 Hz, 1H), 7.47-7.34 (m, 3H), 3.47-3.42 (q, J = 7.6 Hz, 2H), 2.77 (s, 3H), 2.64 (s, 3H), 1.40-1.36 (t, J = 7.6 Hz, 3H). HPLC purity (254 nm): 96.1%. |
| 39 | 2-(3-Bromo-1-benzofuran-2-yl)-5,8-dimethylquinoline-4-carboxylic acid<br>Mass Spectrum (LCMS, ESI pos): Calcd. for $C_{20}H_{15}BrNO_3^+$: 396.0 (M + H); Found: 395.9. $^1$H NMR (400 MHz, DMSO-$d_6$): δ 8.09 (s, 1H), 7.81-7.79 (m, 1H), 7.70-7.64 (m, 2H), 7.57-7.53 (m, 1H), 7.48-7.44 (m, 2H), 2.82 (s, 3H), 2.64 (s, 3H). HPLC purity (254 nm): 99.7%. |
| 59 | 5,8-Dimethyl-2-(3-phenyl-1-benzofuran-2-yl)quinoline-4-carboxylic acid<br>Mass Spectrum (LCMS, ESI pos): Calcd. for $C_{26}H_{20}NO_3^+$: 394.1 (M + H); Found: 394.3. $^1$H NMR (400 MHz, DMSO-$d_6$): δ 14.12 (s, 1H), 7.95 (s, 1H), 7.82-7.80 (m, 1H), 7.64-7.62 (m, 2H), 7.57-7.45 (m, 6H), 7.39-7.35 (m, 2H), 2.61 (s, 3H), 2.18 (s, 3H). HPLC purity (254 nm): 95.5%. |
| 67 | 5-(Benzyloxy)-2-(3-methyl-1-benzofuran-2-yl)quinoline-4-carboxylic acid<br>Mass Spectrum (LCMS, ESI pos): Calcd. for $C_{26}H_{20}NO_4^+$: 410.1 (M + H); Found: 410.3. $^1$H NMR (300 MHz, DMSO-$d_6$): δ 7.90 (s, 1H), 7.79-7.68 (m, 4H), 7.55 (d, J = 9.0 Hz, 2H), 7.22-6.52 (m, 1H), 5.36 (s, 2H), 2.84 (s, 3H). HPLC purity (254 nm): 97.8%. |
| 85 | 2-(2,1-Benzoxazol-3-yl)-5-(benzyloxy)-8-methylquinoline-4-carboxylic acid<br>Mass Spectrum (LCMS, ESI pos): Calcd. for $C_{25}H_{19}N_2O_4^+$: 411.1 (M + H); Found: 411.0. $^1$H NMR (400 MHz, CD$_3$OD): δ 8.50 (d, J = 8.8 Hz, 1H), 7.93 (s, 1H), 7.56-7.51 (m, 3H), 7.40-7.36 (m, 2H), 7.25 (d, J = 7.6 Hz, 2H), 7.17-7.13 (m, 2H), 6.81 (d, J = 8.0 Hz, 1H), 5.25 (s, 2H), 2.68 (s, 3H). HPLC purity (254 nm): 94.7%. |
| 104 | 6-Chloro-8-methyl-2-(3-methyl-1-benzothiophen-2-yl)quinoline-4-carboxylic acid<br>Mass Spectrum (LCMS, ESI pos): Calcd. for $C_{20}H_{15}ClNO_2S^+$: 368.1 (M + H); Found: 367.8. $^1$H NMR (400 MHz, DMSO-$d_6$): δ 8.67 (s, 1H), 8.43 (s, 1H), 8.05-8.03 (m, 1H), 7.98-7.96 (m, 1H), 7.83 (s, 1H), 7.51-7.46 (m, 2H), 2.85 (s, 3H), 2.82 (s, 3H). HPLC purity (254 nm): 99.2%. |
| 111 | 5-(Benzyloxy)-8-chloro-2-(3-methyl-1-benzofuran-2-yl)quinoline-4-carboxylic acid<br>Mass Spectrum (LCMS, ESI pos): Calcd. for $C_{26}H_{19}ClNO_4^+$: 444.1 (M + H); Found: 444.1. $^1$H NMR (300 MHz, DMSO-$d_6$): δ 13.74 (brs, 1H), 8.00-7.95 (m, 2H), 7.82-7.79 (d, J = 7.8 Hz, 1H), 7.71-7.69 (d, J = 8.1 Hz, 1H), 7.57-7.54 (d, J = 7.2 Hz, 2H), 7.51-7.31 (m, 5H), 7.21-7.18 (d, J = 8.7 Hz, 1H), 5.38 (s, 2H), 2.93 (s, 3H). HPLC purity (254 nm): 97.2%. |
| 121 | 8-Methyl-2-(3-methyl-1-benzofuran-2-yl)-5-(trifluoromethoxy)quinoline-4-carboxylic acid<br>Mass Spectrum (LCMS, ESI pos): Calcd. for $C_{21}H_{15}F_3NO_4^+$: 402.1 (M + H); 402.1. $^1$H NMR (400 MHz, CDCl$_3$): δ 8.07 (s, 1H), 7.73 (d, J = 7.6 Hz, 1H), 7.66 (d, J = 8.0 Hz, 1H), 7.59 (d, J = 8.4 Hz, 1H), 7.44-7.40 (m, 2H), 7.34 (t, J = 7.6 Hz, 1H), 2.92 (s, 3H), 2.85 (s, 3H). HPLC purity (254 nm): 97.5%. |
| 125 | 2-(3,7-Dimethyl-1-benzofuran-2-yl)-5,8-dimethylquinoline-4-carboxylic acid<br>Mass Spectrum (LCMS, ESI pos): Calcd. for $C_{22}H_{20}NO_3^+$: 346.1 (M + H); Found: 346.1. $^1$H NMR (300 MHz, DMSO-$d_6$): δ 14.21 (brs, 1H), 8.04 (s, 1H), 7.64-7.58 (m, 2H), 7.39 (d, J = 7.5 Hz, 1H), 7.26-7.21 (m, 1H), 2.84 (s, 3H), 2.76 (s, 3H), 2.64 (s, 3H), 2.59 (s, 3H). HPLC purity (254 nm): 96.5%. |

Example 2: Preparation of 2-(1,3-Benzothiazol-2-yl)-6,8-dimethylquinoline-4-carboxylic acid (Compound 2)

A. 2-(1,3-Benzothiazol-2-yl)-6,8-dimethylquinoline-4-carboxylic acid. To a 10 mL sealed tube was placed a solution of 2,4-dimethylaniline (150 mg, 1.24 mmol) in EtOH (4.5 mL) then 1,3-benzothiazole-2-carbaldehyde (202 mg, 1.24 mmol) and 2-oxopropanoic acid (164 mg, 1.86 mmol) were added. The reaction mixture was heated to 100° C. for 3 h under microwave irradiation. The reaction was cooled to rt and the solids were isolated by filtration affording 41.7 mg (10%) of the title compound as a light yellow solid. Mass Spectrum (LCMS, ESI pos): Calcd. for $C_{19}H_{15}N_2O_2S^+$: 335.1 (M+H); Found: 335.0. $^1$H NMR: (400 MHz, DMSO-$d_6$): δ 8.76 (s, 1H), 8.40 (s, 1H), 8.23-8.16 (m, 2H), 7.67 (s, 1H), 7.63-7.52 (m, 2H), 2.83 (s, 3H), 2.51 (s, 3H). HPLC purity (254 nm): 98.1%.

Using the procedure described in Example 2, with reagents, starting materials, and conditions familiar to those skilled in the art, the following compounds representative of the disclosure were prepared:

| Compound | Name and Data |
| --- | --- |
| 3 | 2-(1,3-Benzoxazol-2-yl)-6,8-dimethylquinoline-4-carboxylic acid<br>Mass Spectrum (LCMS, ESI pos): Calcd. for $C_{19}H_{15}N_2O_3^+$: 319.1 (M + H); Found: 319.0. $^1$H NMR (300 MHz, DMSO-$d_6$): δ 11.12-11.04 (m, 1H), 8.75 (s, 1H), 8.40 (s, 1H), 7.96-7.94 (d, 2H, J = 8.1 Hz), 7.69 (s, 1H), 7.57-7.47 (m, 2H), 2.85 (s, 3H), 2.55 (s, 3H). HPLC purity (254 nm): 98.7%. |
| 5 | 6,8-Dimethyl-2-(2-methyl-1-benzofuran-3-yl)quinoline-4-carboxylic acid<br>Mass Spectrum (LCMS, ESI pos): Calcd. for $C_{21}H_{18}NO_3^+$: 332.1 (M + H); Found: 332.2. $^1$H NMR (400 MHz, CDCl$_3$): δ 8.51 (s, 1H), 8.45 (s, 1H), 8.16-8.14 (m, 1H), 7.53-7.50 (m, 2H), 7.37-7.31 (m, 2H), 2.90-2.89 (m, 6H), 2.59 (s, 3H). HPLC purity (254 nm): 99.7%. |
| 6 | 2-(1-Benzofuran-2-yl)-6,8-dimethylquinoline-4-carboxylic acid<br>Mass Spectrum (LCMS, ESI pos): Calcd. for $C_{20}H_{16}NO_3^+$: 318.1; Found: 318.1. $^1$H NMR (300 MHz, DMSO-$d_6$): δ 13.97 (s, 1H), 8.42 (s, 1H), 8.28 (s, 1H), 7.86 (s, 1H), 7.80-7.75 (m, 2H), 7.60 (s, 1H), 7.46-7.41 (m, 1H), 27.36-7.31 (m, 2H), 2.81 (s, 3H), 2.49 (s, 3H). HPLC purity (254 nm): 95.4%. |
| 7 | 2-(1-Benzofuran-2-yl)-3,6,8-trimethylquinoline-4-carboxylic acid<br>Mass Spectrum (LCMS, ESI pos): Calcd. for $C_{21}H_{18}NO_3^+$: 332.1 (M + H); Found: 332.1. $^1$H NMR (300 MHz, DMSO-$d_6$): δ 7.81-7.78 (d, J = 7.5 Hz, 1H), 7.74-7.71 (d, J = 8.1 Hz, 1H), 7.64 (s, 1H), 7.51 (s, 1H), 7.45-7.31 (m, 3H), 2.77 (s, 3H), 2.70 (s, 3H), 2.49 (s, 3H). HPLC purity (254 nm): 99.6%. |
| 8 | 2-(1-Benzothiophen-3-yl)-6,8-dimethylquinoline-4-carboxylic acid<br>Mass Spectrum (LCMS, ESI pos): Calcd. for $C_{20}H_{16}NO_2S^+$: 334.1 (M + H ); Found: 334.1. $^1$H NMR (300 MHz, DMSO-$d_6$): δ 13.87 (s, 1H), 9.22-9.19 (d, J = 8.1 Hz, 1H), 8.74 (s, 1H), 8.43 (s, 1H), 8.23 (s, 1H), 8.13-8.10 (d, J = 8.1 Hz, 1H), 7.60-7.46 (m, 3H), 2.86 (s, 3H), 2.52 (s, 3H). HPLC purity (254 nm): 95.7%. |
| 9 | 6,8-Dimethyl-2-(3-methyl-1-benzofuran-2-yl)quinoline-4-carboxylic acid<br>Mass Spectrum (LCMS, ESI pos): Calcd. for $C_{21}H_{18}NO_3^+$: 332.1 (M + H); Found: 332.1. $^1$H NMR (400 MHz, DMSO-$d_6$): δ 8.43 (s, 1H), 8.33 (s, 1H), 7.80-7.78 (d, J = 7.6 Hz, 1H), 7.73-7.71 (d, J = 8.0 Hz, 1H), 7.62 (s, 1H), 7.46-7.42 (m, 1H), 7.38-7.34 (m, 1H), 2.86 (s, 3H), 2.79 (s, 3H), 2.51-2.50 (m, 3H). HPLC purity (254 nm): 97.6%. |
| 10 | 2-(1-Benzofuran-2-yl)-5,8-dimethylquinoline-4-carboxylic acid<br>Mass Spectrum (LCMS, ESI pos): Calcd. for $C_{20}H_{16}NO_3^+$: 318.1 (M + H); Found: 318.1. $^1$H NMR (300 MHz, DMSO-$d_6$): δ 14.18 (brs, 1H), 8.09 (s, 1H), 7.91 (s, 1H), 7.81-7.83 (m, 2H), 7.63-7.61 (m, 1H), 7.46-7.31 (m, 3H), 2.85 (s, 3H), 2.70 (s, 3H). HPLC purity (254 nm): 97.3%. |
| 11 | 2-(1-Benzofuran-2-yl)-6-methoxy-8-methylquinoline-4-carboxylic acid<br>Mass Spectrum (LCMS, ESI pos): Calcd. for $C_{20}H_{16}NO_4^+$: 334.1 (M + H); Found: 334.1. $^1$H NMR (400 MHz, DMSO-$d_6$): δ 8.20 (s, 1H), 8.10 (s, 1H), 7.77-7.68 (m, 3H), 7.42-7.38 (m, 1H), 7.31-7.29 (m, 2H), 7.15-7.10 (m, 2H), 3.86 (s, 3H), 2.76 (s, 3H). HPLC purity (254 nm): 95.5%. |
| 13 | 2-(1-Benzothiophen-2-yl)-5,8-dimethylquinoline-4-carboxylic acid<br>Mass Spectrum (LCMS, ESI pos): Calcd. for $C_{20}H_{16}NO_2S^+$: 334.1 (M + H); Found: 334.0. $^1$H NMR (400 MHz, DMSO-$d_6$): δ 8.47 (s, 1H), 8.16 (s, 1H), 8.05-8.03 (m, 1H), 7.91-7.89 (m, 1H), 7.60-7.58 (d, J = 7.6 Hz, 1H), 7.44-7.40 (m, 2H), 7.37-7.35 (d, J = 7.2 Hz, 1H), 2.76 (s, 3H), 2.64 (s, 3H). HPLC purity (254 nm): 97.8%. |
| 14 | 2-(1-Benzofuran-2-yl)-5-methoxy-8-methylquinoline-4-carboxylic acid<br>Mass Spectrum (LCMS, ESI pos): Calcd. for $C_{20}H_{16}NO_4^+$: 334.1 (M + H); Found: 334.1. $^1$H NMR (300 MHz, DMSO-$d_6$): δ 13.44 (brs, 1H), 8.00 (s, 1H), 7.91 (s, 1H), 7.80-7.73 (m, 2H), 7.66-7.64 (m, 1H), 7.46-7.41 (m, 1H), 7.36-7.31 (m, 1H), 7.08-7.05 (d, J = 8.1 Hz, 1H), 3.90 (s, 3H), 2.73 (s, 3H). HPLC purity (254 nm): 97.5%. |
| 15 | 2-(1-Benzofuran-2-yl)-5-(benzyloxy)-8-methylquinoline-4-carboxylic acid<br>Mass Spectrum (LCMS, ESI pos): Calcd. for $C_{26}H_{20}NO_4^+$: 410.1 (M + H); Found: 410.1. $^1$H NMR (300 MHz, DMSO-$d_6$): δ 13.51 (s, 1H), 8.02 (s, 1H), 7.92 (s, 1H), 7.81-7.73 (m, 2H), 7.62-7.53 (m, 3H), 7.47-7.29 (m, 5H), 7.13-7.10 (d, J = 8.1 Hz, 1H), 5.32 (s, 2H), 2.72 (s, 3H). HPLC purity (254 nm): 97.1%. |
| 16 | 2-(1-Benzofuran-2-yl)-6-chloro-8-methylquinoline-4-carboxylic acid<br>Mass Spectrum (LCMS, ESI pos): Calcd. for $C_{19}H_{13}ClNO_3^+$: 338.1 (M + H); Found: 338.0. $^1$H NMR (300 MHz, DMSO-$d_6$): δ 14.26 (brs, 1H), 8.66 (s, 1H), 8.55 (s, 1H), 7.94 (s, 1H), 7.82-7.76 (m, 3H), 7.48-7.43 (m, 1H), 7.37-7.33 (m, 1H), 2.84 (s, 3H). HPLC purity (254 nm): 96.7%. |

| Compound | Name and Data |
|---|---|
| 23 | 6-Methoxy-8-methyl-2-(3-methyl-1-benzofuran-2-yl)quinoline-4-carboxylic acid<br>Mass Spectrum (LCMS, ESI pos): Calcd. for $C_{21}H_{18}NO_4^+$: 348.1 (M + H);<br>Found: 343.1. $^1$H NMR (300 MHz, DMSO-$d_6$): δ 13.91 (brs, 1H), 8.46 (s, 1H), 8.04 (s, 1H), 7.76-7.68 (m, 2H), 7.44-7.31 (m, 3H), 3.89 (s, 3H), 2.80 (s, 3H), 2.76 (s, 3H). HPLC purity (254 nm): 97.6%. |
| 24 | 6-(Benzyloxy)-8-methyl-2-(3-methyl-1-benzofuran-2-yl)quinoline-4-carboxylic acid<br>Mass Spectrum (LCMS, ESI pos): Calcd. for $C_{27}H_{22}NO_4^+$: 424.2 (M + H);<br>Found: 424.2. $^1$H NMR (300 MHz, DMSO-$d_6$): δ 13.91 (s, 1H), 8.47 (s, 1H), 8.16 (s, 1H), 7.77-7.69 (m, 2H), 7.55-7.53 (m, H), 7.45-7.31 (m, 5H), 5.24 (s, 1H), 2.82 (s, 3H), 2.77 (s, 3H). HPLC purity (254 nm): 97.6%. |
| 30 | 5-(Benzyloxy)-8-methyl-2-(3-methyl-1-benzofuran-2-yl)quinoline-4-carboxylic acid<br>Mass Spectrum (LCMS, ESI pos): Calcd. for $C_{27}H_{22}NO_4^+$: 424.2 (M + H);<br>Found: 424.2. $^1$H NMR (400 MHz, DMSO-$d_6$): δ 13.54 (s, 1H), 7.92 (s, 1H), 7.81-7.79 (d, J = 7.6 Hz, 1H), 7.70-7.68 (d, J = 8.0 Hz, 1H), 7.64-7.62 (d, J = 8.0 Hz, 1H), 7.56-7.55 (d, J = 7.2 Hz, 2H), 7.48-7.31 (m, 5H), 7.13-7.11 (d, J = 8.0 Hz, 1H), 5.33 (s, 2H), 2.86 (s, 3H), 2.69 (s, 3H). HPLC purity (254 nm): 96.5%. |
| 33 | 5-(Benzyloxy)-8-methyl-2-(3-methyl-1-benzothiophen-2-yl)quinoline-4-carboxylic acid<br>Mass Spectrum (LCMS, ESI pos): Calcd. for $C_{27}H_{22}NO_3S^+$: 440.1 (M + H);<br>Found: 440.0. $^1$H NMR (300 MHz, DMSO-$d_6$): δ 13.47 (s, 1H), 8.04-8.01 (m, 2H), 7.97-7.94 (m, 1H), 7.81 (s, 1H), 7.62-7.60 (m, 1H), 7.56-7.54 (m, 2H), 7.51-7.49 (m, 2H), 7.47-7.29 (m, 3H), 7.12-7.10 (m, 1H), 5.34 (s, 2H), 2.83 (s, 3H), 2.69 (s, 3H). HPLC purity (254 nm): 99.0%. |
| 34 | 2-(-Benzothiophen-2-yl)-5-(benzyloxy)-8-methylquinoline-4-carboxylic acid<br>Mass Spectrum (LCMS, ESI pos): Calcd. for $C_{26}H_{20}NO_3S^+$: 426.5 (M + H);<br>Found: 425.8. $^1$H NMR (300 MHz, DMSO-$d_6$): δ 13.48 (brs, 1H), 8.51 (s, 1H), 8.24 (s, 1H), 8.05-8.02 (m, 1H), 7.96-7.86 (m, 1H), 7.60-7.54 (m, 3H), 7.46-7.27 (m, 5H), 7.11-7.08 (m, 1H), 5.32 (s, 2H), 2.69 (s, 3H). HPLC purity (254 nm): 96.7%. |
| 35 | 5-(Benzyloxy)-8-methyl-2-(2-methyl-1-benzofuran-3-yl)quinoline-4-carboxylic acid<br>Mass Spectrum (LCMS, ESI pos): Calcd. for $C_{27}H_{22}NO_4^+$: 424.2 (M + H);<br>Found: 424.0. $^1$H NMR (300 MHz, DMSO-$d_6$): δ 13.42 (brs, 1H), 8.20-8.17 (m, 1H), 7.96 (s, 1H), 7.74-7.54 (m, 4H), 7.42-7.26 (m, 5H), 7.10-7.07 (d, J = 8.1 Hz, 1H), 5.35 (s, 1H), 2.85 (s, 3H), 2.71 (s, 3H). HPLC purity (254 nm): 98.8%. |
| 38 | 2-(3-Chloro-1-benzofuran-2-yl)-5,8-dimethylquinoline-4-carboxylic acid<br>Mass Spectrum (LCMS, ESI pos): Calcd. for $C_{20}H_{15}ClNO_3^+$: 352.1 (M + H );<br>Found: 352.1. $^1$H NMR (300 MHz, DMSO-$d_6$): δ 7.94-7.74 (m, 3H), 7.57-7.53 (m, 2H), 7.48-7.44(m, 1H), 7.32-7.29 (m, 1H), 2.77 (s, 2H), 2.68 (s, 3H). HPLC purity (254 nm): 95.1%. |
| 40 | 8-(Benzyloxy)-5-methyl-2-(3-methyl-1-benzofuran-2-yl)quinoline-4-carboxylic acid<br>Mass Spectrum (LCMS, ESI pos): Calcd. for $C_{27}H_{22}NO_4^+$: 424.2 (M + H);<br>Found: 424.0. $^1$H NMR (400 MHz, DMSO-$d_6$): δ 14.16 (s, 1H), 8.01 (s, 1H), 7.77-7.75 (d, J = 7.6 Hz, 1H), 7.69-7.63 (m, 3H), 7.47-7.41 (m, 4H), 7.39-7.32 (m, 3H), 5.35 (s, 2H), 2.85 (s, 3H), 2.59 (s, 3H). HPLC purity (254 nm): 98.9%. |
| 41 | 7-(Benzyloxy)-6-methyl-2-(3-methyl-1-benzofuran-2-yl)quinoline-4-carboxylic acid<br>Mass Spectrum (LCMS, ESI pos): Calcd. for $C_{27}H_{22}NO_4^+$: 424.2 (M + H);<br>Found: 424.1. $^1$H NMR (400 MHz, DMSO-$d_6$): δ 13.95 (s, 1H), 8.52 (s, 1H), 8.30 (s, 1H), 7.77-7.69 (m, 2H), 7.58-7.56 (m, 3H), 7.42-7.42 (m, 3H), 7.39-7.33 (m, 2H), 5.38 (s, 1H), 2.86 (s, 3H), 2.44 (s, 3H). HPLC purity (254 nm): 96.9%. |
| 56 | 5,8-Dimethyl-2-[3-(propan-2-yl)-1-benzofuran-2-yl]quinoline-4-carboxylic acid<br>Mass Spectrum (LCMS, ESI pos): Calcd. for $C_{23}H_{22}NO_3^+$: 360.2 (M + H);<br>Found: 360.2. $^1$H NMR (400 MHz, DMSO-$d_6$): δ 14.15 (s, 1H), 7.99-7.97 (m, 1H), 7.71-7.63 (m, 2H), 7.46-7.41 (m, 2H), 7.34-7.30 (m, 1H), 4.77-4.70 (m, 1H), 2.75 (s, 3H), 2.65 (s, 3H), 1.54-1.53 (d, J = 7.2 Hz, 6H). HPLC purity (254 nm): 98.3%. |
| 57 | 2-(3-Cyclopropyl-1-benzofuran-2-yl)-5,8-dimethylquinoline-4-carboxylic acid<br>Mass Spectrum (LCMS, ESI pos): Calcd. for $C_{23}H_{20}NO_3^+$: 358.1 (M + H);<br>Found: 358.0. $^1$H NMR (400 MHz, DMSO-$d_6$): δ 14.16 (s, 1H), 8.02 (s, 1H), 7.70-7.62 (m, 3H), 7.44-7.40 (m, 2H), 7.30-7.26 (m, 1H), 3.50-3.46 (m, 1H), 2.72 (s, 3H), 2.65 (s, 3H), 1.23-1.15 (m, 4H). HPLC purity (254 nm): 94.6%. |
| 58 | 2-(3-Cyclohexyl-1-benzofuran-2-yl)-5,8-dimethylquinoline-4-carboxylic acid<br>Mass Spectrum (LCMS, ESI pos): Calcd. for $C_{26}H_{26}NO_3^+$: 400.2 (M + H); 400.0.<br>$^1$H NMR (300 MHz, DMSO-$d_6$): δ 8.02-8.00 (m, 2H), 7.71-7.64 (m, 2H), 7.46-7.42 (m, 2H), 7.35-7.30 (m, 1H), 4.59-4.54 (m, 1H), 2.80 (s, 3H), 2.64 (s, 3H), 2.07-2.05 (m, 2H), 1.92-1.81 (m, 5H), 1.47 (brs, 3H). HPLC purity (254 nm): 95.1%. |
| 60 | 2-(3-Methoxy-1-benzofuran-2-yl)-5,8-dimethylquinoline-4-carboxylic acid<br>Mass Spectrum (LCMS, ESI pos): Calcd. for $C_{21}H_{18}NO_4^+$: 348.1 (M + H);<br>Found: 348.1. $^1$H NMR (300 MHz, DMSO-$d_6$): δ 8.03 (s, 1H), 7.94-7.92 (d, J = 7.5 Hz, 1H), 7.72-7.70 (d, J = 8.1 Hz, 1H), 7.63-7.60 (d, J = 7.2 Hz, 1H), 7.50-7.45 (m, 1H), 7.40-7.33 (m, 2H), 4.27 (s, 3H), 2.78 (s, 3H), 2.63 (s, 3H). HPLC purity (254 nm): 97.5%. |
| 61 | 2-[3-(Benzyloxy)-1-benzofuran-2-yl]-5,8-dimethylquinoline-4-carboxylic acid<br>Mass Spectrum (LCMS, ESI pos): Calcd. for $C_{27}H_{22}NO_4^+$: 424.2 (M + H);<br>Found: 424.2. $^1$H NMR (400 MHz, DMSO-$d_6$): δ 8.11 (s, 1H), 7.91-7.89 (d, J = 8.0 Hz, 1H), 7.72-7.70 (d, J = 8.0 Hz, 1H), 7.62-7.60 (d, J = 8.0 Hz, 1H), 7.54-7.49 (m, 2H), 7.47-7.45 (m, 1H), 7.40-7.32 (m, 5H), 5.59 (s, 2H), 2.75 (s, 3H), 2.63 (s, 3H). HPLC purity (254 nm): 96.2%. |

-continued

| Compound | Name and Data |
|---|---|
| 68 | 5-(Benzyloxy)-7-methyl-2-(3-methyl-1-benzofuran-2-yl)quinoline-4-carboxylic acid<br>Mass Spectrum (LCMS, ESI pos): Calcd. for $C_{27}H_{22}NO_4^+$: 424.2 (M + H);<br>Found: 424.1. $^1$H NMR (400 MHz, DMSO-d$_6$): δ 7.82 (s, 1H), 7.78 (d, J = 7.6 Hz , 1H), 7.68 (d, J = 8.4 Hz, 1H), 7.58-7.53 (m, 3H), 7.47-7.37 (m, 3H), 7.35-7.32 (m, 2H), 7.10 (s, 1H), 5.34 (s, 2H), 2.83 (s, 3H), 2.50 (s, 3H). HPLC purity (254 nm): 98.4%. |
| 70 | 7-(Benzyloxy)-8-methyl-2-(3-methylbenzofuran-2-yl)quinoline-4-carboxylic acid<br>Mass Spectrum (LCMS, ESI pos): Calcd. for $C_{27}H_{22}NO_4^+$: 424.2 (M + H);<br>Found: 424.2. $^1$H NMR (300 MHz, DMSO-d$_6$): δ 13.94 (brs, 1H), 8.58-8.55 (d, J = 9.6 Hz, 1H), 8.32 (s, 1H), 7.80-7.67 (m, 3H), 7.55-7.52 (m, 2H), 7.48-7.33 (m, 5H), 5.38 (s, 2H), 2.86 (s, 3H), 2.71 (s, 3H). HPLC purity (254 nm): 98.6%. |
| 71 | 7-(Benzyloxy)-8-methyl-2-(3-methylbenzofuran-2-yl)quinoline-4-carboxylic acid<br>Mass Spectrum (LCMS, ESI pos): Calcd. for $C_{27}H_{22}NO_4^+$: 424.2 (M + H);<br>Found: 424.2. $^1$H NMR (300 MHz, DMSO-d$_6$): δ 13.94 (brs, 1H), 8.58-8.55 (d, J = 9.6 Hz, 1H), 8.32 (s, 1H), 7.80-7.67 (m, 3H), 7.55-7.52 (m, 2H), 7.48-7.33 (m, 5H), 5.38 (s, 2H), 2.86 (s, 3H), 2.71 (s, 3H). HPLC purity (254 nm): 98.6%. |
| 72 | 7-(Benzyloxy)-5-methyl-2-(3-methyl-1-benzofuran-2-yl)quinoline-4-carboxylic acid<br>Mass Spectrum (LCMS, ESI pos): Calcd. for $C_{27}H_{22}NO_4^+$: 424.2 (M + H);<br>Found: 424.2. $^1$H NMR (400 MHz, DMSO-d$_6$): δ 7.83 (s, 1H), 7.78 (d, J = 7.6 Hz , 1H), 7.68 (d, J = 8.4 Hz, 1H), 7.54 (d, J = 7.2 Hz, 2H), 7.50-7.42 (m, 4H), 7.39-7.34 (m, 2H), 7.28 (s, 1H), 5.34 (s, 2H), 2.84 (s, 3H), 2.64 (s, 3H). HPLC purity (254 nm): 99.2%. |
| 73 | 8-methyl-2-(3-methyl-1-benzofuran-2-yl)-5-(2-phenylethoxy)quinoline-4-carboxylic acid<br>Mass Spectrum (LCMS, ESI pos): Calcd. for $C_{28}H_{24}NO_4^+$: 438.2 (M + H);<br>Found: 438.2. $^1$H NMR (400 MHz, DMSO-d$_6$): δ 13.49 (brs, 1H), 7.92 (s, 1H), 7.82-7.80 (d, J = 8.0 Hz, 1H), 7.71-7.63 (m, 2H), 7.49-7.23 (m, 7H), 7.10-7.08 (d, J = 8.0 Hz, 1H), 4.35-4.31 (m, 2H), 3.19-3.15 (m, 2H), 2.86 (s, 3H), 2.70 (s, 3H). HPLC purity (254 nm): 98.7%. |
| 75 | 8-Methyl-2-(3-methyl-1-benzofuran-2-yl)-5-(3-phenylcyclobutoxy)quinoline-4-carboxylic acid<br>Mass Spectrum (LCMS, ESI pos): Calcd. for $C_{30}H_{26}NO_4^+$: 464.2 (M + H);<br>Found: 464.2. $^1$H NMR (300 MHz, DMSO-d$_6$): δ 13.56 (brs, 1H), 7.93-7.90 (m, 1H), 7.81-7.79 (d, J = 7.5 Hz, 1H), 7.71-7.62 (m, 2H), 7.49-7.44 (t, J = 7.5 Hz, 1H), 7.39-7.32 (m, 5H), 7.25-7.21 (m, 1H), 6.87-6.85 (d, J = 7.8 Hz, 1H), 5.17-5.14 (m, 0.7H), 4.97-4.95 (m, 0.3H), 3.77-3.75 (m, 1H), 2.87 (s, 3H), 2.71 (s, 3H), 2.65-2.57 (m, 3H). HPLC purity (254 nm): 95.5%. |
| 76 | 8-Methyl-2-(3-methyl-1-benzofuran-2-yl)-5-[[(1r,4r)-4-phenylcyclohexyl]oxy]quinoline-4-carboxylic acid<br>Mass Spectrum (LCMS, ESI pos): Calcd. for $C_{32}H_{30}NO_4^+$: 492.2 (M + H);<br>Found: 492.3. $^1$H NMR (400 MHz, DMSO-d$_6$): δ 13.39 (s, 1H), 7.87 (s, 1H), 7.81-7.79 (d, J = 8.0 Hz, 1H), 7.70-7.64 (m, 2H), 7.46-7.42 (m, 1H), 7.38-7.27 (m, 5H), 7.20-7.14 (m, 2H), 4.67-4.65 (m, 1H), 2.86 (s, 3H), 2.71 (s, 3H), 2.59-2.57 (m, 1H), 2.28-2.25 (m, 2H), 1.91-1.89 (m, 2H), 1.70-1.64 (m, 4H). HPLC purity (254 nm): 97.7%. |
| 77 | 8-Methyl-2-(3-methyl-1-benzofuran-2-yl)-5-[(3-phenylcyclohexyl)oxy]quinoline-4-carboxylic acid (cis, trans mixture)<br>Mass Spectrum (LCMS, ESI pos): Calcd. for $C_{32}H_{30}NO_4^+$: 492.2 (M + H);<br>Found: 492.3. $^1$H NMR (400 MHz, DMSO-d$_6$): δ 13.46 (brs, 1H), 7.92-7.86 (m, 1H), 7.81-7.78 (m, 1H), 7.72-7.67 (m, 1H), 7.63-7.61 (m, 1H), 7.48-7.45 (m, 1H), 7.38-7.32 (m, 1H), 7.30-7.28 (m, 4H), 7.21-7.15 (m, 1H), 7.08-7.03 (m, 1H), 4.99-4.98 (m, 0.7H), 4.73-4.70 (m, 0.3H), 3.40-3.33 (m, 5H), 3.16 (m, 1H), 2.87-2.85 (m, 3H), 2.70 (s, 3H), 2.35-2.20 (m, 1H), 2.19-1.90 (m, 3H), 1.90-1.80 (m, 1H), 1.80-1.60 (m, 3H), 1.60-1.56 (m, 6H), 1.38-1.36 (m, 1H). HPLC purity (254 nm): 99.8%. |
| 79 | 5-(Cyclohexyloxy)-8-methyl-2-(3-methyl-1-benzofuran-2-yl)quinoline-4-carboxylic acid<br>Mass Spectrum (LCMS, ESI pos): Calcd. for $C_{26}H_{26}NO_4^+$: 416.2 (M + H); 416.2.<br>$^1$H NMR (400 MHz, DMSO-d$_6$): δ 13.34 (s, 1H), 7.86 (s, 1H), 7.80-7.78 (d, J = 7.6 Hz, 1H), 7.69-7.67 (d, J = 8.4 Hz, 1H), 7.63-7.61 (d, J = 8.4 Hz, 1H), 7.47-7.43 (m, 1H), 7.38-7.34 (t, J = 7.2 Hz, 1H), 4.60-4.56 (m, 1H), 2.86 (s, 3H), 2.69 (s, 3H), 1.99-1.96 (m, 2H), 1.80-1.77 (m, 2H), 1.63-1.54 (m, 3H), 1.44-1.30 (m, 3H). HPLC purity (254 nm): 97.2%. |
| 80 | 8-Methyl-2-(3-methyl-1-benzofuran-2-yl)-5-phenoxyquinoline-4-carboxylic acid<br>Mass Spectrum (LCMS, ESI pos): Calcd. for $C_{26}H_{20}NO_4^+$: 410.1 (M + H);<br>Found: 410.1. $^1$H NMR (300 MHz, DMSO-d$_6$): δ 13.54 (s, 1H), 7.99 (s, 1H), 7.82-7.80 (d, J = 7.5 Hz, 1H), 7.70-7.65 (t, J = 7.8 Hz, 2H), 7.49-7.34 (m, 4H), 7.22-7.17 (m, 1H), 7.11-7.08 (d, J = 7.8 Hz, 2H), 6.95-6.92 (d, J = 8.1 Hz, 1H), 2.88 (s, 3H), 2.76 (s, 3H). HPLC purity (254 nm): 97.2%. |
| 82 | 5-Benzamido-8-methyl-2-(3-methyl-1-benzofuran-2-yl)quinoline-4-carboxylic acid<br>Mass Spectrum (LCMS, ESI pos): Calcd. for $C_{27}H_{21}N_2O_4^+$: 437.2 (M + H);<br>Found: 437.3. $^1$H NMR (400 MHz, DMSO-d$_6$): δ 8.04-8.03 (m, 3H), 7.81-7.76 (m, 2H), 7.00-7.68 (d, J = 8.0 Hz, 1H), 7.60-7.53 (m, 4H), 7.47-7.43 (m, 1H), 7.37-7.35 (m, 1H), 2.87 (s, 6H), 2.82 (s, 7H). HPLC purity (254 nm): 97.3%. |
| 83 | 8-Methyl-2-(3-methyl-1-benzofuran-2-yl)-5-(2-phenylacetamido)quinoline-4-carboxylic acid<br>Mass Spectrum (LCMS, ESI pos): Calcd. for $C_{28}H_{23}N_2O_4^+$: 451.2 (M + H); |

| Compound | Name and Data |
|---|---|
| | Found: 451.3. $^1$H NMR (400 MHz, DMSO-d$_6$): δ 9.90 (s, 1H), 8.02 (s, 1H), 7.81-7.79 (d, J = 7.6 Hz, 1H), 7.72-7.68 (m, 2H), 7.47-7.43 (m, 1H), 7.37-7.30 (m, 6H), 7.25-7.23 (m, 1H), 3.66 (s, 2H), 2.85 (s, 3H), 2.78 (s, 3H). HPLC purity (254 nm): 96.5%. |
| 94 | 5-(Benzyloxy)-8-methyl-2-(2-methyl-1-benzothiophen-3-yl)quinoline-4-carboxylic acid<br>Mass Spectrum (LCMS, ESI pos): Calcd. for C$_{27}$H$_{22}$NO$_3$S$^+$: 440.1 (M + H); Found: 439.9. $^1$H NMR (400 MHz, DMSO-d$_6$): δ 13.49 (s, 1H), 8.01-8.00 (d, J = 2.0 Hz, 1H), 7.99-7.91 (m, 1H), 7.65 (s, 1H), 7.62-7.55 (m, 3H), 7.43-7.32 (m, 5H), 7.13-7.11 (m, 1H), 5.36 (s, 1H), 2.71 (s, 3H), 2.65 (s, 3H). HPLC purity (254 nm): 98.7%. |
| 95 | 2-(1-Benzothiophen-3-yl)-5-(benzyloxy)-8-methylquinoline-4-carboxylic acid<br>Mass Spectrum (LCMS, ESI pos): Calcd. for C$_{26}$H$_{20}$NO$_3$S$^+$: 426.1 (M + H); Found: 426.0. $^1$H NMR (400 MHz, DMSO-d$_6$): δ 13.43 (s, 1H), 9.30-9.28 (d, J = 8.4 Hz, 1H), 8.85 (s, 1H), 8.13-8.11 (t, J = 4.0 Hz, 2H), 1.62-7.47 (m, 5H), 7.42-7.30 (m, 3H), 7.11-7.09 (d, J = 8.0 Hz, 1H), 5.34 (s, 2H), 2.77 (s, 3H). HPLC purity (254 nm): 99.5%. |
| 97 | 8-Methyl-2-(3-methyl-1-benzofuran-2-yl)-5-[[4-(1,3,4-oxadiazol-2-yl)cyclohexyl]oxy]quinoline-4-carboxylic acid<br>Mass Spectrum (LCMS, ESI pos): Calcd. for C$_{28}$H$_{26}$N$_3$O$_5^+$: 484.2 (M + H); Found: 484.2. $^1$H NMR (400 MHz, DMSO-d$_6$): δ 13.38 (s, 1H), 9.16 (s, 1H), 7.85 (s, 1H), 7.79 (d, J = 7.6 Hz, 1H), 7.69 (d, J = 8.4 Hz, 1H), 7.64 (d, J = 8.4 Hz, 1H), 7.45 (t, J = 8.0 Hz, 1H), 7.36 (t, J = 7.6 Hz, 1H), 7.07 (d, J = 8.0 Hz, 1H), 4.82 (s, 1H), 3.17-3.15 (m, 1H), 2.86 (s, 3H), 2.70 (s, 3H), 2.15-2.03 (m, 4H), 1.94-1.83 (m, 4H). HPLC purity (254 nm): 98.3%. |
| 103 | 8-Methyl-2-(3-methyl-1-benzofuran-2-yl)-5-[[(1s,4s)-4-phenylcyclohexyl]oxy]quinoline-4-carboxylic acid<br>Mass Spectrum (LCMS, ESI pos): Calcd. for C$_{32}$H$_{30}$NO$_4^+$: 492.2 (M + H); Found: 492.3. $^1$H NMR (300 MHz, DMSO-d$_6$): δ 13.44 (s, 1H), 7.91 (s, 1H), 7.80-7.78 (d, J = 7.5 Hz, 1H), 7.71-7.62 (m, 2H), 7.48-7.26 (m, 6H), 7.19-7.14 (m, 1H), 7.05-7.03 (d, J = 7.5 Hz, 1H), 4.90 (s, 1H), 2.86 (s, 3H), 2.70 (s, 3H), 2.64-2.56 (m, 1H), 2.20-2.16 (m, 2H), 2.07-1.96 (m, 2H), 1.79-1.70 (m, 2H), 1.59-1.55 (m, 2H). HPLC purity (254 nm): 98.2%. |
| 106 | 5-(Benzyloxy)-8-cyclopropyl-2-(2-methyl-1-benzofuran-3-yl)quinoline-4-carboxylic acid<br>Mass Spectrum (LCMS, ESI pos): Calcd. for C$_{29}$H$_{24}$NO$_4^+$: 450.2 (M + H); Found: 450.0. $^1$H NMR (300 MHz, DMSO-d$_6$): δ 13.42 (s, 1H), 8.24-8.18 (m, 1H), 7.76 (s, 1H), 7.64-7.60 (m, 1H), 7.55 (d, J = 7.2 Hz, 2H), 7.41-7.25 (m, 6H), 7.05 (d, J = 8.1 Hz, 1H), 5.33 (s, 2H), 3.02-2.92 (m, 1H), 2.85 (s, 3H), 1.08-1.02 (m, 2H), 1.02-0.79 (m, 2H). HPLC purity (254 nm): 95.3%. |
| 107 | 5-(Benzyloxy)-8-cyclopropyl-2-(3-methyl-1-benzofuran-2-yl)quinoline-4-carboxylic acid<br>Mass Spectrum (LCMS, ESI pos): Calcd. for C$_{29}$H$_{24}$NO$_4^+$: 450.2 (M + H); Found: 450.1. $^1$H NMR (400 MHz, DMSO-d$_6$): δ 13.49 (brs, 1H), 7.92 (s, 1H), 7.78-7.77 (d, J = 7.6 Hz, 1H), 7.69-7.67 (d, J = 8.0 Hz, 1H), 7.54-7.52 (d, J = 7.2 Hz, 2H), 7.46-7.28 (m, 6H), 7.09-7.07 (d, J = 8.4 Hz, 1H), 5.31 (s, 2H), 2.94-2.92 (m, 1H), 2.85 (s, 3H), 1.09-1.04 (m, 2H), 0.78-0.75 (m, 2H). HPLC purity (254 nm): 95.0%. |
| 108 | 5-(Benzyloxy)-8-ethyl-2-(3-methyl-1-benzofuran-2-yl)quinoline-4-carboxylic acid<br>Mass Spectrum (LCMS, ESI pos): Calcd. for C$_{28}$H$_{24}$NO$_4^+$: 438.2 (M + H); Found: 438.1. $^1$H NMR (400 MHz, DMSO-d$_6$): δ 13.51 (brs, 1H), 7.92 (s, 1H), 7.79 (d, J = 7.6 Hz, 1H), 7.69 (d, J = 8.0 Hz, 1H), 7.61 (d, J = 8.0 Hz, 1H), 7.56-7.55 (m, 2H), 7.48-7.31 (m, 5H), 7.14 (d, J = 8.0 Hz, 1H), 5.33 (s, 2H), 3.20 (q, J = 7.2 Hz, 2H), 2.86 (s, 3H), 1.33 (t, J = 7.2 Hz, 3H). HPLC purity (254 nm): 97.1%. |
| 109 | 5-(Benzyloxy)-2-(3-methyl-1-benzofuran-2-yl)-8-(propan-2-yl)quinoline-4-carboxylic acid<br>Mass Spectrum (LCMS, ESI pos): Calcd. for C$_{29}$H$_{26}$NO$_4^+$: 452.2 (M + H); Found: 452.2. $^1$H NMR (400 MHz, DMSO-d$_6$): δ 13.50 (brs, 1H), 7.92 (s, 1H), 7.79 (d, J = 7.6 Hz, 1H), 7.69 (d, J = 8.4 Hz, 1H), 7.63 (d, J = 8.4 Hz, 1H), 7.57-7.55 (m, 2H), 7.48-7.32 (m, 5H), 7.16 (d, J = 8.4 Hz, 1H), 5.33 (s, 2H), 4.21 (hept, J = 6.8 Hz, 1H), 2.86 (s, 3H), 1.36 (d, J = 6.8 Hz, 6H). HPLC purity (254 nm): 98.2%. |
| 110 | 5-(Benzyloxy)-8-fluoro-2-(3-methyl-1-benzofuran-2-yl)quinoline-4-carboxylic acid<br>Mass Spectrum (LCMS, ESI pos): Calcd. for C$_{26}$H$_{19}$FNO$_4^+$: 428.1 (M + H); Found: 428.3. $^1$H NMR (400 MHz, DMSO-d$_6$): δ 13.71 (brs, 1H), 8.00 (s, 1H), 7.80 (d, J = 7.6 Hz, 1H), 7.70 (d, J = 8.4 Hz, 1H), 7.64 (t, J = 8.8 Hz, 1H), 7.56-7.54 (m, 2H), 7.48 (t, J = 7.2 Hz, 1H), 7.43-7.32 (m, 4H), 7.16-7.14 (m, 1H), 5.34 (s, 2H), 2.86 (s, 3H). HPLC purity (254 nm): 97.8%. |
| 113 | 5-Ethyl-8-methyl-2-(3-methyl-1-benzofuran-2-yl)quinoline-4-carboxylic acid<br>Mass Spectrum (LCMS, ESI pos): Calcd. for C$_{22}$H$_{20}$NO$_3^+$: 346.1 (M + H); Found: 346.3. $^1$H NMR (400 MHz, DMSO-d$_6$): δ 14.18 (brs, 1H), 7.99 (s, 1H), 7.80-7.82 (d, J = 7.6 Hz, 1H), 7.70-7.68 (m, 2H), 7.47-7.44 (t, J = 6.4 Hz, 2H), 7.38-7.34 (t, J = 7.6 Hz, 1H), 3.08-3.02 (m, 2H), 2.85 (s, 3H), 2.77 (s, 3H), 1.28-1.23 (m, 3H). HPLC purity (254 nm): 99.1%. |
| 114 | 8-Methyl-2-(3-methyl-1-benzofuran-2-yl)-5-(pyridin-3-ylmethoxy)quinoline-4-carboxylic acid<br>Mass Spectrum (LCMS, ESI pos): Calcd. for C$_{26}$H$_{21}$N$_2$O$_4^+$: 425.2 (M + H); Found: 425.1. $^1$H NMR (400 MHz, DMSO-d$_6$): δ 8.76 (s, 1H), 8.57-8.56 (d, J = 3.6 Hz, 1H), 7.98-7.93 (m, 2H), 7.81-7.79 (d, J = 7.6 Hz, 1H), 7.70-7.66 (m, 2H), 7.48-7.44 (m, 2H), 7.38-7.34 (m, 2H), 7.21-7.19 (d, J = 8.0 Hz, 2H), 5.37 (s, 2H), 2.86 (s, 3H), 2.71 (s, 3H). HPLC purity (254 nm): 96.8%. |

| Compound | Name and Data |
|---|---|
| 115 | 8-Methyl-2-(3-methyl-1-benzofuran-2-yl)-5-(pyridin-2-ylmethoxy)quinoline-4-carboxylic acid<br>Mass Spectrum (LCMS, ESI pos): Calcd. for $C_{26}H_{21}N_2O_4^+$: 425.2(M + H); Found: 425.3. $^1$H NMR (400 MHz, DMSO-$d_6$): δ 8.53-8.52 (d, J = 4.4 Hz, 1H), 8.30-8.28 (d, J = 8.0 Hz, 1H), 7.89-7.85 (m, 1H), 7.79-7.77 (d, J = 7.6 Hz, 1H), 7.71-7.69 (m, 2H), 7.52-7.51 (d, J = 7.6 Hz, 1H), 7.46-7.42 (m, 1H), 7.38-7.31 (m, 2H), 6.94-6.92 (d, J = 7.6 Hz, 1H), 5.28 (s, 2H), 2.87 (s, 3H), 2.68 (s, 3H). HPLC purity (254 nm): 99.2%. |
| 117 | 8-Methyl-2-(3-methyl-1-benzofuran-2-yl)-6-(trifluoromethoxy)quinoline-4-carboxylic acid<br>Mass Spectrum (LCMS, ESI pos): Calcd. for $C_{21}H_{15}F_3NO_4^+$: 402.1 (M + H); Found: 402.1. $^1$H NMR (300 MHz, DMSO-$d_6$): δ 8.81 (s, 1H), 8.39 (s, 1H), 7.78 (d, J = 7.2 Hz, 1H), 7.71 (d, J = 8.7 Hz, 1H), 7.63 (s, 1H), 7.44 (t, J = 7.2 Hz, 1H), 7.34 (t, J = 7.2 Hz, 1H), 2.84 (s, 3H), 2.81 (s, 3H). HPLC purity (254 nm): 97.0%. |
| 118 | 6-(Difluoromethoxy)-8-methyl-2-(3-methyl-1-benzofuran-2-yl)quinoline-4-carboxylic acid<br>Mass Spectrum (LCMS, ESI pos): Calcd. for $C_{21}H_{16}F_2NO_4^+$: 384.1 (M + H); Found: 384.1. $^1$H NMR (300 MHz, DMSO-$d_6$): δ 8.49 (s, 1H), 8.42 (s, 1H), 7.78 (d, J = 7.6 Hz, 1H), 7.70 (d, J = 8.4 Hz, 1H), 7.55 (s, 1H), 7.44 (t, J = 7.2 Hz, 1H), 7.36-7.18 (m, 2H), 2.84 (s, 3H), 2.80 (s, 3H). HPLC purity (254 nm): 98.8%. |
| 119 | 6-(2,2-Difluoroethoxy)-8-methyl-2-(3-methyl-1-benzofuran-2-yl)quinoline-4-carboxylic acid<br>Mass Spectrum (LCMS, ESI pos): Calcd. for $C_{22}H_{18}F_2NO_4^+$: 398.1 (M + H); Found: 398.1. $^1$H NMR (300 MHz, DMSO-$d_6$): δ 13.94 (s, 1H), 8.49 (s, 1H), 8.10 (s, 1H), 7.77 (d, J = 7.8 Hz, 1H), 7.71 (d, J = 8.1 Hz, 1H), 7.54 (s, 1H), 7.44 (t, J = 7.5 Hz, 1H), 7.34 (t, J = 7.5 Hz, 1H), 6.54 (dt, $J_{H-H}$ = 9.0 Hz, $J_{H-F}$ = 15.3 Hz, 1H), 4.52-4.42 (m, 1H), 2.86 (s, 3H), 2.79 (s, 3H). HPLC purity (254 nm): 99.5%. |
| 120 | 5-(Difluoromethoxy)-8-methyl-2-(3-methyl-1-benzofuran-2-yl)quinoline-4-carboxylic acid<br>Mass Spectrum (LCMS, ESI pos): Calcd. for $C_{21}H_{16}F_2NO_4^+$: 384.1 (M + H); Found: 384.1. $^1$H NMR (300 MHz, DMSO-$d_6$): δ 7.87 (s, 1H), 7.82-7.77 (m, 1H), 7.69-7.66 (m, 2H), 7.45 (t, J = 7.5 Hz, 1H), 7.37-7.33 (m, 1H), 7.26-7.21 (m, 1H), 7.12-7.07 (m, 1H), 2.84(s, 3H), 2.74(s, 3H). HPLC purity (254 nm): 99.0%. |
| 122 | 5-(2,2-Difluoroethoxy)-8-methyl-2-(3-methyl-1-benzofuran-2-yl)quinoline-4-carboxylic acid<br>Mass Spectrum (LCMS, ESI pos): Calcd. for $C_{22}H_{18}F_2NO_4^+$: 398.1 (M + H); Found: 398.1. $^1$H NMR (, 300 MHz, DMSO-$d_6$): δ (brs, 1H), 7.93 (s, 1H), 7.80 (d, J = 7.5 Hz, 1H), 7.68 (d, J = 7.8 Hz, 2H), 7.46 (t, J = 7.5 Hz, H),7.36 (t, J = 7.8 Hz, 1H), 7.17 (d, J = 7.8 Hz, 1H), 6.36 (tt, $J_{H-F}$ = 54.9 Hz, $J_{H-H}$ = 3.9 Hz, 1H), 4.53-4.43 (m, 1H), 2.86 (s, 3H), 2.72 (s, 1H). HPLC purity (254 nm): 98.1%. |
| 123 | 5-(Difluoromethoxy)-8-methyl-2-(2-methyl-1-benzofuran-3-yl)quinoline-4-carboxylic acid<br>Mass Spectrum (LCMS, ESI pos): Calcd. for $C_{21}H_{16}F_2NO_4^+$: 384.1 (M + H); Found: 384.2. $^1$H NMR (300 MHz, DMSO-$d_6$): δ 8.21-8.18 (m, 1H), 7.87 (s, 1H), 7.74 (d, J = 7.8 Hz, 1H), 7.66-7.63 (m, 1H), 7.39-7.28 (m, 3H), 7.24 (t, $J_{H-F}$ = 63 Hz, 1H), 2.85 (s, 3H), 2.79 (s, 3H). HPLC purity (254 nm): 94.4%. |
| 124 | 5-(2,2-Difluoroethoxy)-8-methyl-2-(2-methyl-1-benzofuran-3-yl)quinoline-4-carboxylic acid<br>Mass Spectrum (LCMS, ESI pos): Calcd. For $C_{22}H_{18}F_2NO_4^+$: (M + H); 398.1; Found: 398.1. $^1$H NMR (300 MHz, DMSO-$d_6$): δ 13.39 (brs, 1H), 8.20-8.18 (m, 1H), 7.76 (s, 1H), 6.68-6.62 (m, 2H), 7.38-7.36 (m, 2H), 7.17 (d, J = 7.8 Hz, 1H), 6.37 (tt, $J_{H-F}$ = 54.0 Hz, $J_{H-H}$ = 3.6 Hz, 1H), 4.48 (td, $J_{H-F}$ = 14.1 Hz, $J_{H-H}$ = 3.9 Hz, 2H), 2.85 (s, 3H), 2.74 (s, 3H). HPLC purity (24 nm): 95.5%. |
| 126 | 2-(3,6-Dimethyl-1-benzofuran-2-yl)-5-hydroxy-8-methylquinoline-4-carboxylic acid<br>Mass Spectrum (LCMS, ESI pos): Calcd. for $C_{22}H_{20}NO_3^+$: 346.1 (M + H); Found: 346.1. $^1$H NMR (400 MHz, DMSO-$d_6$): δ 14.14 (s, 1H), 7.96 (s, 1H), 7.66-7.62 (m, 2H), 7.49 (s, 1H), 7.39 (d, J = 7.2 Hz, 1H), 7.18 (d, J = 8.0 Hz, 1H), 2.82 (s, 3H), 2.75 (s, 3H), 2.64 (s, 3H), 2.48 (s, 3H). HPLC purity (254 nm): 99.0%. |
| 127 | 2-(3,5-Dimethylbenzofuran-2-yl)-5,8-dimethylquinoline-4-carboxylic acid<br>Mass Spectrum (LCMS, ESI pos): Calcd. for $C_{22}H_{20}NO_3^+$: 346.1 (M + H); Found: 346.1. $^1$H NMR (400 MHz, DMSO-$d_6$): δ 14.13 (brs, 1H), 7.98 (s, 1H), 7.64 (d, J = 7.2 Hz, 1H), 7.57-7.55 (m, 2H), 7.40 (d, J = 7.2 Hz, 1H), 7.26 (d, J = 8.8 Hz, 1H), 2.83 (s, 3H), 2.76 (s, 3H), 2.64 (s, 3H), 2.46 (s, 3H). HPLC purity (254 nm): 99.6%. |
| 128 | 2-(3,4-Dimethyl-1-benzofuran-2-yl)-5,8-dimethylquinoline-4-carboxylic acid<br>Mass Spectrum (LCMS, ESI pos): Calcd. for $C_{22}H_{20}NO_3^+$: 346.1 (M + H); Found: 346.1. $^1$H NMR (300 MHz, CD$_3$OD): δ 7.94 (s, 1H), 7.47(d, J = 7.2 Hz, 1H), 7.36 (d, J = 8.1 Hz, 1H), 7.28-7.01 (m, 2H), 6.99 (d, J = 7.5 Hz, 1H), 3.18 (s, 3H), 2.84 (s, 3H), 2.77 (s, 6H). HPLC purity (254 nm): 93.1%. |
| 129 | 2-(7-Chloro-3-methylbenzofuran-2-yl)-5,8-dimethylquinoline-4-carboxylic acid<br>Mass Spectrum (LCMS, ESI pos): Calcd. for $C_{21}H_{17}ClNO_3^+$: 366.1. (M + H); Found: 366.0. $^1$H NMR (400 MHz, DMSO-$d_6$): δ 7.97 (s, 1H), 7.79 (d, J = 7.6 Hz, 1H), 7.66 (d, J = 6.8 Hz, 1H), 7.56 (d, J = 7.6 Hz, 1H), 7.40-7.36 (m, 2H), 2.87 (s, 3H), 2.77 (s, 3H), 2.66 (s, 3H). HPLC purity (254 nm): 96.4%. |
| 130 | 2-(7-Fluoro-3-methyl-1-benzofuran-2-yl)-5,8-dimethylquinoline-4-carboxylic acid<br>Mass Spectrum (LCMS, ESI pos): Calcd. for $C_{21}H_{17}FNO_3^+$: 350.1 (M + H); Found: 350.1. $^1$H NMR (400 MHz, CD$_3$OD): δ 7.97 (s, 1H), 7.52-7.50 (m, 2H), |

| Compound | Name and Data |
|---|---|
|  | 7.34-7.26 (m, 2H), 7.19-7.15 (m, 1H), 2.92 (s, 3H), 2.87 (s, 3H), 2.80 (s, 3H). HPLC purity (254 nm): 96.9%. |
| 131 | 2-(7-Methoxy-3-methyl-1-benzofuran-2-yl)-5,8-dimethylquinoline-4-carboxylic acid<br>Mass Spectrum (LCMS, ESI pos): Calcd. for $C_{22}H_{20}NO_4^+$: 362.1 (M + H); Found: 362.1. $^1$H NMR (300 MHz, DMSO-$d_6$): δ 7.95 (s, 1H), 7.65 (d, J = 7.2 Hz, 1H), 7.42-7.40 (d, J = 7.2 Hz, 1H), 7.36-7.25 (m, 2H), 7.07 (d, J = 6.6 Hz, 1H), 4.01 (s, 3H), 2.83 (s, 3H), 2.76 (s, 3H), 2.65 (s, 3H). HPLC purity (254 nm): 96.9%. |
| 132 | 2-[7-(Benzyloxy)-3-methyl-1-benzofuran-2-yl]-5,8-dimethylquinoline-4-carboxylic acid<br>Mass Spectrum (LCMS, ESI pos): Calcd. for $C_{28}H_{24}NO_4^+$: 438.2 (M + H); Found: 438.2. $^1$H NMR (400 MHz, DMSO-$d_6$): δ 14.16 (brs, 1H), 7.92 (s, 1H), 7.65 (d, J = 7.2 Hz, 1H), 7.57-7.56 (m, 2H), 7.45-7.35 (m, 5H), 7.25 (t, J = 8.0 Hz, 1H), 7.13 (d, J = 7.6 Hz, 1H), 5.40 (s, 2H), 2.83 (s, 3H), 2.76 (s, 3H), 2.64 (s, 3H). HPLC purity (254 nm): 97.9%. |
| 134 | 5-(Cyclohexyloxy)-8-methyl-2-(3-methyl-1-benzothiophen-2-yl)quinoline-4-carboxylic acid<br>Mass Spectrum (LCMS, ESI pos): Calcd. for $C_{26}H_{26}NO_3S^+$: 432.2 (M + H); Found: 432.1. $^1$H NMR(400 MHz, DMSO-$d_6$): δ 13.29 (brs, 1H), 8.04-8.01 (m, 1H), 7.96-7.93 (m, 1H), 7.74 (s, 1H), 7.61 (d, J = 8.4 Hz, 1H), 7.50-7.44 (m, 2H), 7.07 (d, J = 8.4 Hz, 1H), 4.60-4.56 (m, 1H), 3.81 (s, 3H), 2.68 (s, 3H), 1.99-1.97 (m, 2H), 1.80-1.77 (m, 2H), 1.62-1.53 (m, 3H), 1.44-1.38 (m, 3H). HPLC purity (254 nm): 96.6%. |
| 135 | 5-(Cyclohexyloxy)-8-ethyl-2-(3-methyl-1-benzothiophen-2-yl)quinoline-4-carboxylic acid.<br>Mass Spectrum (LCMS, ESI pos): Calcd. for $C_{27}H_{28}NO_3S^+$: 446.2 (M + H); Found: 446.1. $^1$H NMR (400 MHz, DMSO-$d_6$): δ 13.28 (brs, 1H), 8.04-8.02 (m, 1H), 7.95-7.93 (m, 1H), 7.75 (s, 1H), 7.60 (d, J = 8.4 Hz, 1H), 7.50-7.44 (m, 2H), 7.09 (d, J = 8.0 Hz, 1H), 4.62-4.56 (m, 1H), 3.18 (q, J = 7.2 Hz, 2H), 2.81 (s, 3H), 2.00-1.97 (m, 2H), 1.80-1.77 (m, 2H), 1.63-1.55 (m, 3H), 1.44-1.36 (m, 3H), 1.35 (t, J = 7.2 Hz, 3H). HPLC purity (254 nm): 99.5%. |
| 146 | 5-(Benzyloxy)-8-ethyl-2-(3-methyl-1H-indol-2-yl)quinoline-4-carboxylic acid<br>Mass Spectrum (LCMS, ESI pos): Calcd. for $C_{28}H_{25}N_2O_3^+$: 437.2 (M + H); Found: 437.2. $^1$H NMR (400 MHz, DMSO-$d_6$): δ 13.50 (brs, 1H), 11.58 (s, 1H), 7.99 (s, 1H), 7.67 (d, J = 8.0 Hz, 1H), 7.58-7.56 (m, 3H), 7.48-7.32 (m, 4H), 7.22 (t, J = 8.4 Hz, 1H), 7.10-7.06 (m, 2H), 5.34 (s, 2H), 3.24 (q, J = 7.6 Hz, 2H), 2.80 (s, 3H), 1.33 (t, J = 7.6 Hz, 3H). HPLC purity (254 nm): 95.0%. |
| 147 | 5-(Benzyloxy)-2-(1,3-dimethyl-1H-indol-2-yl)-8-ethylquinoline-4-carboxylic acid<br>Mass Spectrum (LCMS, ESI pos): Calcd. for $C_{29}H_{27}N_2O_3^+$: 451.2 (M + H); Found: 451.3. $^1$H NMR (400 MHz, DMSO-$d_6$): δ 7.68(s, 1H), 7.65-7.54 (m, 5H), 7.42-7.38 (m, 2H), 7.34-7.26 (m, 2H), 7.15-7.11 (m, 2H), 5.36 (s, 2H), 3.93 (s, 3H), 3.17 (q, J = 7.6 Hz, 2H), 2.45 (s, 3H), 1.28 (t, J = 7.6 Hz, 3H). HPLC purity (254 nm): 99.0%. |
| 158 | 2-(1-Benzothiophen-3-yl)-5-(benzyloxy)-8-ethylquinoline-4-carboxylic acid<br>Mass Spectrum (LCMS, ESI pos): Calcd. for $C_{27}H_{22}NO_3S^+$: 440.1 (M + H); Found: 440.1. $^1$H NMR (300 MHz, DMSO-$d_6$): δ 13.40 (brs, 1H), 9.26 (d, J = 8.4 Hz, 1H), 8.85 (s, 1H), 8.14-8.12 (m, 2H), 7.61-7.29 (m, 8H), 7.13 (d, J = 8.1 Hz, 1H), 5.34 (s, 2H), 3.36 (q, J = 7.5 Hz, 2H), 1.36 (t, J = 7.5 Hz, 3H). HPLC purity (254 nm): 99.4%. |
| 159 | 2-(1-Benzothiophen-3-yl)-5-(cyclohexyloxy)-8-ethylquinoline-4-carboxylic acid<br>Mass Spectrum (LCMS, ESI pos): Calcd. for $C_{26}H_{26}NO_3S^+$: 432.2 (M + H); Found: 432.1. $^1$H NMR (300 MHz, DMSO-$d_6$): δ 13.20 (brs, 1H), 9.27 (d, J = 7.8 Hz, 1H), 8.83 (s, 1H), 8.12 (d, J = 7.8 Hz, 1H), 8.05 (s, 1H), 7.61-7.45 (m, 3H), 7.08 (d, J = 8.1 Hz, 1H), 4.62-4.56 (m, 1H), 3.28 (q, J = 7.5 Hz, 2H), 2.00-1.97 (m, 2H), 1.80-1.77 (m, 2H), 1.64-1.54 (m, 3H), 1.45-1.39 (m, 3H), 1.37 (t, J = 7.5 Hz, 3H). HPLC purity (254 nm): 99.7%. |
| 161 | 2-(1-Benzothiophen-3-yl)-6-tert-butyl-8-ethylquinoline-4-carboxylic acid<br>Mass Spectrum (LCMS, ESI pos): Calcd. for $C_{24}H_{24}NO_2S^+$: 390.2 (M + H); Found: 390.1. $^1$H NMR (300 MHz, DMSO-$d_6$): δ 13.86 (brs, 1H), 9.17 (d, J = 8.1 Hz, 1H), 8.74 (s, 1H), 8.43-8.41 (m, 2H), 8.11 (d, J = 7.8 Hz, 1H), 7.84 (d, J = 1.8 Hz, 1H), 7.58-7.45 (m, 2H), 3.36 (q, J = 7.8 Hz, 2H), 1.42-1.37 (m, 12H). HPLC purity (254 nm): 99.4%. |
| 169 | 2-(1-Benzofuran-3-yl)-5-(benzyloxy)-8-ethylquinoline-4-carboxylic acid<br>Mass Spectrum (LCMS, ESI pos): Calcd. for $C_{27}H_{22}NO_4^+$: 424.2 (M + H); Found: 424.2. $^1$H NMR (400 MHz, DMSO-$d_6$): δ 13.41 (brs, 1H), 9.16 (s, 1H), 8.78-8.76 (m, 1H), 8.09 (s, 1H), 7.73-7.71 (m, 1H), 7.60-7.55 (m, 3H), 7.49-7.30 (m, 5H), 7.11 (d, J = 8.4 Hz, 1H), 5.33 (s, 2H), 3.32 (s, 1H), 3.28 (q, J = 7.6 Hz, 2H), 1.38 (t, J = 7.6 Hz, 3H). HPLC purity (254 nm): 98.1%. |
| 170 | 2-(1-Benzofuran-3-yl)-5-(cyclohexyloxy)-8-ethylquinoline-4-carboxylic acid<br>Mass Spectrum (LCMS, ESI pos): Calcd. for $C_{26}H_{26}NO_4^+$: 416.2 (M + H); Found: 416.1. $^1$H NMR (300 MHz, DMSO-$d_6$): δ 13.20 (brs, 1H), 9.13 (s, 1H), 8.79-8.76 (m, 1H), 8.02 (s, 1H), 7.73-7.70 (m, 1H), 7.58 (d, J = 7.8 Hz, 1H), 7.50-7.42 (m, 2H), 7.07 (d, J = 8.4 Hz, 1H), 4.61-4.55 (m, 1H), 3.28 (q, J = 8.1 Hz, 2H), 2.00-1.97 (m, 2H), 1.80-1.77 (m, 2H), 1.64-1.54 (m, 3H), 1.45-1.27 (m, 3H), 1.39 (t, J = 8.1 Hz, 3H). HPLC purity (254 nm): 99.5%. |
| 172 | 2-(1-Benzofuran-3-yl)-6-tert-butyl-8-ethylquinoline-4-carboxylic acid<br>Mass Spectrum (LCMS, ESI pos): Calcd. for $C_{24}H_{24}NO_3^+$: 374.2 (M + H); Found: 374.1. $^1$H NMR (300 MHz, DMSO-$d_6$): □ 13.85 (brs, 1H), 9.11 (s, 1H), 8.76-8.74 (m, 1 H), 8.39-8.37 (m, 2H), 7.83 (s, 1H), 7.72-7.69 (m, 1H), 7.49-7.44 (m, 2H), 3.39 (q, J = 7.2 Hz, 1.42 (t, J = 7.2 Hz, 3H), 1.39 (s, 9H). HPLC purity (254 nm): 97.5%. |

-continued

| Compound | Name and Data |
|---|---|
| 173 | 5-(Benzyloxy)-8-ethyl-2-(2-methyl-1-benzofuran-3-yl)quinoline-4-carboxylic acid<br>Mass Spectrum (LCMS, ESI pos): Calcd. for $C_{28}H_{24}NO_4^+$: 438.2 (M + H);<br>Found: 438.1. $^1$H NMR (400 MHz, DMSO-$d_6$): δ 13.43 (brs, 1H), 8.17-8.13 (m, 1H),<br>7.74 (s, 1H), 7.66-7.55 (m, 4H), 7.42-7.30 (m, 5H), 7.12 (d, J = 8.4 Hz, 1H), 5.35<br>(s, 2H), 3.21 (q, J = 7.2 Hz, 2H), 2.84 (s, 3H), 1.30 (t, J = 7.2 Hz, 3H). HPLC purity<br>(254 nm): 96.9%. |
| 174 | 5-(Cyclohexyloxy)-8-ethyl-2-(2-methyl-1-benzofuran-3-yl)quinoline-4-carboxylic acid<br>Mass Spectrum (LCMS, ESI pos): Calcd. for $C_{27}H_{28}NO_4^+$: 430.2 (M + H);<br>Found: 430.1. $^1$H NMR (300 MHz, DMSO-$d_6$): δ 13.21 (brs, 1H), 8.15-8.12 (m,<br>1H), 7.66 (s, 1H), 7.64-7.58 (m, 2H), 7.40-7.35 (m, 2H), 7.07 (d, J = 8.4 Hz, 1H),<br>4.62-4.56 (m, 1H), 3.25-3.16 (m, 2H), 2.83 (s, 3H), 2.00-1.97 (m, 2H), 1.80-1.77<br>(m, 2H), 1.64-1.54 (m, 3H), 1.45-1.27 (m, 6H). HPLC purity (254 nm): 99.5%. |
| 178 | 6-tert-Butyl-8-ethyl-2-(2-methyl-1-benzofuran-3-yl)quinoline-4-carboxylic acid<br>Mass Spectrum (LCMS, ESI pos): Calcd. for $C_{25}H_{26}NO_3^+$: 388.2 (M + H);<br>Found: 388.2. $^1$H NMR (300 MHz, DMSO-$d_6$): □ 8.48 (s, 1 H), 8.18 (s, 2 H), 8.15-8.13<br>(m, 1H), 7.83 (s, 1 H), 7.64-7.61 (m, 1 H), 7.37-7.34 (m, 2 H), 3.0 (s, 2 H), 2.84<br>(s, 3 H), 1.39 (s, 9H), 1.36-1.33 (m, 3 H). HPLC purity (254 nm): 99.1%. |
| 185 | 2-(1-Benzothiophen-3-yl)-8-ethyl-5-[(2-methylphenyl)methoxy]quinoline-4-<br>carboxylic acid<br>Mass Spectrum (LCMS, ESI pos): Calcd. for $C_{28}H_{24}NO_3S^+$: 454.2 (M + H);<br>Found: 453.9. $^1$H NMR (400 MHz, DMSO-$d_6$): δ 13.34 (s, 1H), 9.28 (d, J = 8.4<br>Hz, 1H), 8.85 (s, 1H), 8.16-8.08 (m, 2H), 7.66-7.45 (m, 4H), 7.30-7.19 (m, 3H),<br>7.16 (d, J = 8.1 Hz, 1H), 5.29 (s, 2H), 3.30 (q, J = 7.6 Hz, 2H), 2.38 (s, 3H), 1.37<br>(t, J = 7.4 Hz, 3H). HPLC purity (254 nm): 98.7%. |
| 186 | 2-(1-Benzothiophen-3-yl)-8-ethyl-5-[(3-methylphenyl)methoxy]quinoline-4-<br>carboxylic acid<br>Mass Spectrum (LCMS, ESI pos): Calcd. for $C_{28}H_{24}NO_3S^+$: 454.2 (M + H);<br>Found: 453.9. $^1$H NMR (400 MHz, DMSO-$d_6$): δ 13.42 (s, 1H), 9.27 (d, J = 8.2<br>Hz, 1H), 8.85 (s, 1H), 8.16-8.09 (m, 2H), 7.63-7.44 (m, 3H), 7.40-7.23 (m, 3H),<br>7.17-7.07 (m, 2H), 5.30 (s, 2H), 3.27 (q, J = 7.6 Hz, 2H), 2.33 (s, 3H), 1.36 (t, J =<br>7.4 Hz, 3H). HPLC purity (254 nm): 99.9%. |
| 187 | 2-(1-Benzothiophen-3-yl)-8-ethyl-5-[(4-methylphenyl)methoxy]quinoline-4-<br>carboxylic acid<br>Mass Spectrum (LCMS, ESI pos): Calcd. for $C_{28}H_{24}NO_3S^+$: 454.2 (M + H);<br>Found: 454.1. $^1$H NMR (400 MHz, DMSO-$d_6$): δ 9.21 (d, J = 8.1 Hz, 1H), 8.63<br>(s, 1H), 8.10 (d, J = 7.9 Hz, 1H), 7.76 (s, 1H), 7.65-7.42 (m, 6H), 7.15 (d, J = 7.8<br>Hz, 2H), 6.95 (d, J = 8.0 Hz, 1H), 5.22 (s, 2H), 3.23 (q, J = 7.4 Hz, 2H), 2.29 (s,<br>3H), 1.33 (t, J = 7.4 Hz, 3H). HPLC purity (254 nm): 99.3%. |
| 227 | 2-(1-Benzofuran-2-yl)-5-(2-hydroxyethoxy)-8-methylquinoline-4-carboxylic acid<br>Mass Spectrum (LCMS, ESI pos): Calcd. for $C_{21}H_{18}NO_5^+$: 364.1 (M + H);<br>Found: 364.0. $^1$H NMR (400 MHz, DMSO-$d_6$): δ 13.56 (brs, 1H), 8.01 (s, 1H), 7.92 (s,<br>1H), 7.81-7.79 (d, J = 7.6 Hz, 1H), 7.76-7.74 (d, J = 8.4 Hz, 1H), 7.65-7.63 (d, J =<br>8.0 Hz, 1H), 7.46-7.43 (t, J = 7.2 Hz, 1H), 7.36-7.33 (t, J = 7.2 Hz, 1H), 7.10-7.08<br>(d, J = 8.0 Hz, 1H), 4.17-4.14 (t, J = 5.6 Hz, 2H), 3.84-3.81 (t, J = 5.6 Hz,<br>2H), 2.73 (s, 3H). HPLC purity (254 nm): 98.1%. |
| 273 | 6-(Difluoromethoxy)-8-methyl-2-(2-methyl-1-benzofuran-3-yl)quinoline-4-<br>carboxylic acid<br>Mass Spectrum (LCMS, ESI pos): Calcd. for $C_{21}H_{16}F_2NO_4^+$: 384.1 (M + H);<br>Found: 384.0. $^1$H NMR (400 MHz, CDCl$_3$): δ 8.55 (s, 1H), 8.52-8.51 (m, 1H),<br>8.14-8.12 (m, 1H), 7.54-7.49 (m, 2H), 7.38-7.32 (m, 2H), 6.73 (t, $J_{H-F}$ = 73.6 Hz,<br>1H), 2.92 (s, 3H), 2.90 (s, 3H). HPLC purity (254 nm): 96.4%. |

Example 3: Preparation of 2-(1-Benzothiophen-2-yl)-6,8-dimethylquinazoline-4-carboxylic acid (Compound 4)

A. 2-(1-Benzothiophene-2-amido)-3,5-dimethylbenzoic acid. To a 100-mL round-bottom flask was placed a solution of 1-benzothiophene-2-carboxylic acid (1.0 g, 5.61 mmol) in DCM (30 mL) followed by the dropwise addition of oxalyl chloride (1.426 g, 11.23 mmol) with stirring at 0° C. To the solution was added DMF (0.01 mL) then the reaction was stirred for 1 h at rt. The solvent was removed under reduced pressure affording 1.1 g of 1-benzothiophene-2-carbonyl chloride as a yellow solid.

To a 100-mL 3-necked round-bottom flask was placed a solution of 2-amino-3,5-dimethylbenzoic acid (0.973 g, 5.89 mmol) in THF (20 mL) and a solution of Na$_2$CO$_3$ (1.79 g, 16.73 mmol) in water (20 mL). This was followed by the dropwise addition of 1-benzothiophene-2-carbonyl chloride (1.1 g, 5.59 mmol, as prepared above) in THF (20 mL) with stirring at 0° C. over 30 min. The resulting solution was stirred for 1 h at rt then the reaction was diluted with 20 mL of water and the pH was adjusted to 2 with aqueous 2N HCl. The resulting solution was extracted with EtOAc (3×30 mL) and the organic extracts were combined. The solution was washed with brine (2×20 mL), dried over anhydrous Na$_2$SO$_4$, and concentrated under reduced pressure affording 1 g (55%) of the title compound as a yellow solid. Mass Spectrum (LCMS, ESI neg): Calcd. for $C_{18}H_{16}NO_3S^+$: 324.1 (M−H); Found: 324.

B. N-(2-Carbamoyl-4,6-dimethylphenyl)-1-benzothiophene-2-carboxamide. To a 100-mL round-bottom flask was placed a solution of 2-(1-benzothiophene-2-amido)-3,5-dimethylbenzoic acid (460 mg, 1.41 mmol, as prepared in the previous step), NH$_4$HCO$_3$ (560 mg, 7.09 mmol) and HATU (807 mg, 2.12 mmol) in DMF (10 mL). This was followed by the dropwise addition of DIEA (914 mg, 7.07 mmol) then the reaction was stirred for 18 h at rt. The solution was diluted with 60 mL of water/ice then the precipitate was isolated by filtration, washed with 30 mL water, and dried in an oven under reduced pressure affording 350 mg (76%) of the title compound as a light yellow solid. Mass Spectrum (LCMS, ESI pos): Calcd. for $C_{18}H_{17}N_2O_2S^+$: 325.1 (M+H); Found: 325.1.

C. 2-(1-Benzothiophen-2-yl)-6,8-dimethyl-3,4-dihydroquinazolin-4-one. To a 100-mL round-bottom flask was placed a solution of N-(2-carbamoyl-4,6-dimethylphenyl)-1-benzothiophene-2-carboxamide (350 mg, 1.08 mmol, as prepared in the previous step) in EtOH (20 mL) followed by the addition of 1M NaOH (40 mL). The reaction was stirred for 1 h at 80° C. then diluted with 50 mL of water/ice. The pH of the solution was adjusted to 6 with 2N HCl then the precipitate was isolated by filtration and dried in an oven under reduced pressure affording 300 mg (91%) of the title compound as an off-white solid. Mass Spectrum (LCMS, ESI pos): Calcd. for $C_{18}H_{15}N_2OS^+$: 307.1 (M+H); Found: 307.1.

D. 2-(1-Benzothiophen-2-yl)-4-chloro-6,8-dimethylquinazoline. To a 100-mL round-bottom flask was placed a solution of 2-(1-benzothiophen-2-yl)-6,8-dimethyl-3,4-dihydroquinazolin-4-one (300 mg, 0.98 mmol, as prepared in the previous step) and $POCl_3$ (3 mL) in toluene (10 mL). This was followed by the dropwise addition of DIEA (380 mg, 2.94 mmol) to the stirred solution at 0° C. The reaction was stirred for 12 h at 90° C. then quenched by the addition of 50 mL of water/ice. The resulting solution was extracted with EtOAc (3×30 mL) and the organic extracts were combined, washed with brine (3×20 mL), dried over anhydrous $Na_2SO_4$, and concentrated under reduced pressure. The residue was purified by column chromatography eluting with EtOAc/petroleum ether (1:5) affording 250 mg (79%) of the title compound as a yellow solid. Mass Spectrum (LCMS, ESI pos): Calcd. for $C_{18}H_{14}ClN_2S^+$: 325.1 (M+H); Found: 324.8.

E. 2-(1-Benzothiophen-2-yl)-6,8-dimethylquinazoline-4-carbonitrile. To an 8-mL vial was placed a solution of 2-(1-benzothiophen-2-yl)-4-chloro-6,8-dimethylquinazoline (100 mg, 0.31 mmol, as prepared in the previous step), CuCN (41.6 mg, 0.46 mmol) and CuI (5.87 mg, 0.03 mmol) in DMF (5 mL). The reaction stirred at 130° C. for 6 h under microwave irradiation then diluted with 30 mL of water/ice. The resulting solution was extracted with EtOAc (3×30 mL) and the organic extracts were combined, washed with brine (3×20 mL), dried over anhydrous $Na_2SO_4$, and concentrated under reduced pressure. The residue was purified by column chromatography eluting with EtOAc/petroleum ether (1:10) affording 80 mg (82.4%) of the title compound as a yellow solid. Mass Spectrum (LCMS, ESI pos): Calcd. for $C_{19}H_{14}N_3S^+$: 316.1 (M+H); Found: 316.1.

F. 2-(1-Benzothiophen-2-yl)-6,8-dimethylquinazoline-4-carboxylic acid (Compound 4). To a 20-mL sealed tube was placed a solution of 2-(1-benzothiophen-2-yl)-6,8-dimethylquinazoline-4-carbonitrile (80 mg, 0.25 mmol, as prepared in the previous step) in conc HCl (10 mL) then the resulting solution was stirred for 12 h at 100° C. The reaction was concentrated under reduced pressure then the crude product was purified by Prep-HPLC (Column, XBridge Prep Phenyl OBD Column, 19*150 mm 5 um 13 nm; mobile phase, Water (10 mmol/L $NH_4HCO_3$) and MeCN (20.0% MeCN up to 55.0% in 8 min); Detector, UV 220/254 nm) affording 35.5 mg (42%) of the title compound as a yellow solid. Mass Spectrum (LCMS, ESI pos): Calcd. for $C_{19}H_{15}N_2O_2S^+$: 335.1 (M+H); Found: 335.0. $^1$H NMR (400 MHz, $CD_3OD$): δ 8.42 (s, 1H), 7.97 (s, 1H), 7.93-7.89 (m, 2H), 7.69 (s, 1H), 7.43-7.38 (m, 2H), 2.80 (s, 3H), 2.53 (s, 3H). HPLC purity (254 nm): 98.0%.

Example 4: Preparation of 2-(1-Benzofuran-2-yl)-6-chloro-8-methylquinoline-3-carboxylic acid (Compound 12)

A. Ethyl 2,6-Dichloro-8-methylquinoline-3-carboxylate. To a 25-mL round-bottom flask was placed a solution of 2,6-dichloro-8-methylquinoline-3-carbaldehyde (480 mg, 2.00 mmol) in EtOH (10 mL) then NIS (75 mg, 0.33 mmol) and $K_2CO_3$ (552 mg, 3.99 mmol) were added. The reaction was stirred for 2 h at 80° C., then diluted with 50 mL of $H_2O$ and extracted with EtOAc (2×50 mL). The organic extracts were combined, was washed with brine (2×50 mL), dried over anhydrous $Na_2SO_4$, and concentrated under reduced pressure. The crude product was purified by Prep-TLC (petroleum ether/EtOAc=4:1) affording 100 mg (18%) of the title compound as yellow oil. Mass Spectrum (LCMS, ESI pos): Calcd. for $C_{13}H_{12}Cl_2NO_2^+$: 284.0; Found: 284.0.

B. Ethyl 2-(1-Benzofuran-2-yl)-6-chloro-8-methylquinoline-3-carboxylate. To a 25-mL round-bottom flask was placed a solution of ethyl 2,6-dichloro-8-methylquinoline-3-carboxylate (100 mg, 0.35 mmol, as prepared in the previous step) in 1,4-dioxane/$H_2O$ (2/0.1 mL), then $Pd(PPh_3)_4$ (46 mg, 0.04 mmol), $K_2CO_3$ (96.6 mg, 0.70 mmol), and (1-benzofuran-2-yl)boronic acid (85 mg, 0.52 mmol) were added. The reaction was purged with $N_2$, then stirred for 16 h at 100° C. The resulting solution was diluted with 50 mL of $H_2O$ and extracted with EtOAc (2×50 mL). The organic extracts were combined, washed with brine (2×50 mL), dried over anhydrous $Na_2SO_4$, and concentrated under reduced pressure. The crude product was purified by Prep-TLC (petroleum ether/EtOAc=3:1) affording 65 mg (50%) of the title compound as yellow oil. Mass Spectrum (LCMS, ESI pos): Calcd. for $C_{21}H_{17}ClNO_3^+$: 366.1 (M+H); Found: 366.1.

C. 2-(1-Benzofuran-2-yl)-6-chloro-8-methylquinoline-3-carboxylic acid. To a 25-mL round-bottom flask was placed a solution of ethyl 2-(1-benzofuran-2-yl)-6-chloro-8-methylquinoline-3-carboxylate (90 mg, 0.25 mmol, as prepared in the previous step) in EtOH (3 mL), KOH (42 mg, 0.75 mmol), and water (1 mL). The reaction was stirred for 1 h at 80° C. then diluted with 20 mL of $H_2O$. The pH of the solution was adjusted to 3-4 with conc HCl then the precipitate was isolated by filtration. The crude product was purified by Flash-Prep-HPLC (CombiFlash-1: Column, C18; mobile phase, X: $H_2O$ (0.5% TFA), Y: MeCN, X/Y=90/10 increasing to X/Y=20/80 within 30 min; Detector, UV 254 nm) affording 27 mg (32%) of the title compound as a light yellow solid. Mass Spectrum (LCMS, ESI pos): Calcd. for $C_{19}H_{13}ClNO_3^+$: 338.1 (M+H); Found: 338.0. $^1$H NMR (300 MHz, DMSO-$d_6$): δ 13.67 (s, 1H), 8.72 (s, 1H), 8.11 (s, 1H), 7.82-7.80 (m, 2H), 7.65-7.62 (m, 2H), 7.45-7.32 (m, 2H), 2.80 (s, 3H). HPLC purity (254 nm): 98.9%.

Example 5: Preparation of 6-Cyano-8-methyl-2-(3-methyl-1-benzofuran-2-yl)quinoline-4-carboxylic acid (Compound 22)

A. 6-Cyano-8-methyl-2-(3-methyl-1-benzofuran-2-yl)quinoline-4-carboxylic acid. To a 10-mL sealed tube was placed a solution of 6-bromo-8-methyl-2-(3-methyl-1-benzofuran-2-yl)quinoline-4-carboxylic acid (100 mg, 0.25 mmol, Compound 21) in DMF (3 mL) then $Pd(PPh_3)_4$ (29 mg, 0.03 mmol) and $Zn(CN)_2$ (59 mg, 0.50 mmol) were added under nitrogen. The reaction was heated to 120° C. for 2 h under microwave irradiation then quenched by the addition of water. The solution was extracted with EtOAc, the organic extracts were combined, washed with water, dried over anhydrous $Na_2SO_4$, and concentrated under reduced pressure. The residue was purified by column chromatography eluting with EtOAc/petroleum ether (1:1) affording 43.2 mg (50%) of the title compound as a yellow solid. Mass Spectrum (LCMS, ESI pos): Calcd. for $C_{21}H_{15}N_2O_3^+$: 343.1 (M+H); Found: 343.1. $^1$H NMR (300 MHz, DMSO-$d_6$): δ 14.44-14.41 (m, 1H), 9.06 (s, 1H), 8.54 (s, 1H), 8.01 (s, 1H), 7.81-7.79 (m, 1H), 7.73-7.71 (m, 1H), 7.51-7.46 (m, 1H), 7.39-7.34 (m, 1H), 2.82 (s, 3H), 2.80 (s, 3H). HPLC purity (254 nm): 95.1%.

Example 6: Preparation of 6-(2-Hydroxyethoxy)-8-methyl-2-(3-methyl-1-benzofuran-2-yl)quinoline-4-carboxylic acid (Compound 25)

A. 6-[2-[(tert-Butyldimethylsilyl)oxy]ethoxy]-8-methyl-2-(3-methyl-1-benzofuran-2-yl)quinoline-4-carboxylic acid. To a 30-mL sealed tube was placed a solution of 4-[2-[(tert-butyldimethylsilyl)oxy]ethoxy]-2-methylaniline (798 mg, 2.84 mmol, Intermediate 5) in EtOH (10 mL) then 3-methyl-1-benzofuran-2-carbaldehyde (500 mg, 3.12 mmol) and 2-oxopropanoic acid (375 mg, 4.26 mmol) were added. The reaction was heated to 100° C. for 3 h under microwave irradiation then concentrated under reduced pressure. The crude product was purified by Flash-Prep-HPLC (IntelFlash-1: Column, $C_{18}$; mobile phase, MeCN/$H_2O$=5:95 increasing to MeCN/$H_2O$=95:5 within 30 min; Detector, UV 254 nm) affording 270 mg of the title compound as a yellow solid. Mass Spectrum (LCMS, ESI pos): Calcd. for $C_{28}H_{34}NO_5Si^+$: 492.2 (M+H); Found: 492.3.

B. 6-(2-Hydroxyethoxy)-8-methyl-2-(3-methyl-1-benzofuran-2-yl)quinoline-4-carboxylic acid. To a 50-mL round-bottom flask was placed a solution of 6-[2-[(tert-butyldimethylsilyl)oxy]ethoxy]-8-methyl-2-(3-methyl-1-benzofuran-2-yl)quinoline-4-carboxylic acid (200 mg, 0.41 mmol, as prepared in the previous step) in MeOH (5 mL) then py.HF (1 mL) was added. The reaction was stirred for 3 h at rt, quenched by the addition of water, and extracted with DCM. The organic extracts were combined, washed with brine, dried over anhydrous $Na_2SO_4$, and concentrated under reduced pressure. The residue was purified by column chromatography eluting with EtOAc/petroleum ether (2:1) affording 35.1 mg (23%) of the title compound as a yellow solid. Mass Spectrum (LCMS, ESI pos): Calcd. for $C_{22}H_{20}NO_5^+$: 378.1 (M+H); Found: 378.0. $^1$H NMR (300 MHz, DMSO-$d_6$): δ 8.46 (s, 1H), 8.07-8.06 (m, 1H), 7.78-7.69 (m, 2H), 7.45-7.32 (m, 3H), 4.95 (brs, 1H), 4.14-4.11 (m, 2H), 3.82-3.81 (m, 2H), 2.83 (s, 3H), 2.78 (s, 3H). HPLC purity (254 nm): 95.9%.

Example 7: Preparation of 6-Ethyl-8-methyl-2-(3-methyl-1-benzofuran-2-yl)quinoline-4-carboxylic acid (Compound 26)

A. 6-Ethenyl-8-methyl-2-(3-methyl-1-benzofuran-2-yl)quinoline-4-carboxylic acid. To a 10-mL sealed tube purged and maintained with an inert atmosphere of nitrogen was placed a solution of 6-bromo-8-methyl-2-(3-methyl-1-benzofuran-2-yl)quinoline-4-carboxylic acid (90 mg, 0.23 mmol, Compound 21) in dioxane/$H_2O$=20:1 (6 mL) then 2-ethenyl-4,4,5,5-tetramethyl-1,3,2-dioxaborolane (70 mg, 0.45 mmol), $K_3PO_4$ (289 mg, 1.36 mmol), Pd(OAc)$_2$ (5.1 mg, 0.02 mmol), and PCy$_3$.HBF$_4$ (17 mg, 0.05 mmol) were added. The reaction was stirred at 100° C. overnight then concentrated under reduced pressure. The crude product was purified by Flash-Prep-HPLC (IntelFlash-1: Column, C18; mobile phase, MeCN/$H_2O$=40:60 increasing to MeCN/$H_2O$=95:5 within 30 min; Detector, UV 254 nm) affording 120 mg of the title compound as a brown solid. Mass Spectrum (LCMS, ESI pos): Calcd. for $C_{22}H_{18}NO_3^+$: 344.1 (M+H); Found: 344.1.

B. 6-Ethyl-8-methyl-2-(3-methyl-1-benzofuran-2-yl)quinoline-4-carboxylic acid. To a 50-mL round-bottom flask was placed a solution of 6-ethenyl-8-methyl-2-(3-methyl-1-benzofuran-2-yl)quinoline-4-carboxylic acid (126 mg, 0.37 mmol, as prepared in the previous step) in MeOH (10 mL), then Pd on carbon (20 mg) was added. The solution was degassed and back filled with $H_2$ then stirred for 30 min at rt under an atmosphere of $H_2$. The atmosphere was purged with $N_2$ then the solids were removed by filtration. The filtrate was concentrated under reduced pressure. The crude product was purified by Prep-HPLC (HPLC-10: Column, Gemini-NX C18 AXAI Packed, 21.2*150 mm 5 um; mobile phase, Water (0.05% TFA) and MeCN (75.0% MeCN up to 95.0% in 6 min); Detector, UV 254 nm) affording 20 mg (16%) of the title compound as a yellow solid. Mass Spectrum (LCMS, ESI pos): Calcd. for $C_{22}H_{20}NO_3^+$: 346.1 (M+H); Found: 346.1. $^1$H NMR (400 MHz, DMSO-$d_6$): δ 13.99 (brs, 1H), 8.43 (s, 1H), 8.35 (s, 1H), 7.93-7.77 (m, 1H), 7.73-7.71 (m, 1H), 7.65 (s, 1H), 7.47-7.43 (t, J=7.6 Hz, 1H), 7.37-7.34 (t, J=7.6 Hz, 1H), 2.85-2.79 (m, 8H), 1.31-1.27 (t, J=7.6 Hz, 3H). HPLC purity (254 nm): 99.0%.

Using the procedure described in Example 7, with reagents, starting materials, and conditions familiar to those skilled in the art, the following compounds representative of the disclosure were prepared:

| Compound | Name and Data |
| --- | --- |
| 36 | 8-Methyl-2-(3-methyl-1-benzofuran-2-yl)-6-(propan-2-yl)quinoline-4-carboxylic acid<br>Mass Spectrum (LCMS, ESI pos): Calcd. for $C_{23}H_{22}NO_3^+$: 360.2 (M + H); Found: 360.2. $^1$H NMR (400 MHz, DMSO-$d_6$): δ 14.00 (s, 1H), 8.44 (s, 1H), 8.39 (s, 1H), 7.79-7.71 (m, 3H), 7.47-7.43 (m, 1H), 7.37-7.34 (t, J = 7.2 Hz, 1H), 3.12-3.05 (m, 1H), 2.85 (s, 3H), 2.80 (s, 3H), 1.33-1.31 (d, J = 6.8 Hz, 6H). HPLC purity (254 nm): 99.6%. |

Example 8: Preparation of 6-Cyclopropyl-8-methyl-2-(3-methyl-1-benzofuran-2-yl)quinoline-4-carboxylic acid (Compound 28)

A. 6-Cyclopropyl-8-methyl-2-(3-methyl-1-benzofuran-2-yl)quinoline-4-carboxylic acid. To a 50-mL round-bottom flask was placed a solution of 6-bromo-8-methyl-2-(3-methyl-1-benzofuran-2-yl)quinoline-4-carboxylic acid (100 mg, 0.25 mmol, Compound 21) in dioxane/$H_2O$=20/1 (2.5 mL) then Pd(OAc)$_2$ (20 mg, 0.09 mmol), PCy$_3$.HBF$_4$ (40 mg, 0.11 mmol), $K_3PO_4$ (320 mg, 1.51 mmol), and cyclopropylboronic acid (43 mg, 0.50 mmol) were added under nitrogen. The reaction was stirred at 120° C. overnight then quenched by the addition of water and extracted with DCM.

The organic extracts were combined and concentrated under reduced pressure. The residue was purified by column chromatography eluting with EtOAc/petroleum ether (1:10), followed by Prep-HPLC (HPLC-10: Column, Gemini-NX C18 AXAI Packed, 21.2*150 mm 5 um; mobile phase, Water (0.05% TFA) and MeCN (80.0% MeCN up to 95.0% in 6 min); Detector, UV 254 nm) affording 14.5 mg (16%) of the title compound as a yellow solid. Mass Spectrum (LCMS, ESI pos): Calcd. for $C_{23}H_{20}NO_3^+$: 358.1 (M+H); Found: 357.9. $^1$H NMR (300 MHz, DMSO-$d_6$): δ 13.93 (s, 8.43 (s, 1H), 8.30 (s, 1H), 7.79-7.77 (d, J=7.5 Hz, 1H), 7.73-7.70 (d, J=8.1 Hz, 1H), 7.47-7.42 (m, 2H), 7.38-7.33 (m, 1H), 2.84 (s, 3H), 2.78 (s, 3H), 2.12-2.07 (m, 1H), 1.12-1.06 (m, 2H), 0.90-0.80 (m, 2H). HPLC purity (254 nm): 98.6%.

Using the procedure described in Example 8, with reagents, starting materials, and conditions familiar to those skilled in the art, the following compounds representative of the disclosure were prepared:

| Compound | Name and Data |
| --- | --- |
| 37 | 8-Methyl-2-(3-methyl-1-benzofuran-2-yl)-6-phenylquinoline-4-carboxylic acid Mass Spectrum (LCMS, ESI pos): Calcd. for $C_{26}H_{20}NO_3^+$: 394.1 (M + H); Found: 393.9. $^1$H NMR (400 MHz, DMSO-$d_6$): δ 14.04 (s, 1H), 8.84 (s, 1H), 8.51 (s, 1H), 8.10 (s, 1H), 7.82-7.80 (m, 3H), 7.74-7.72 (d, J = 8.4 Hz, 1H), 7.57-7.53 (m, 2H), 7.46-7.44 (m, 2H), 7.39-7.36 (m, 1H), 2.88 (s, 3H), 2.87 (s, 3H). HPLC purity (254 nm): 98.9%. |

Example 9: Preparation of [6,8-Dimethyl-2-(3-methyl-1-benzofuran-2-yl)quinolin-4-yl]methanol (Compound 29)

A. [6,8-Dimethyl-2-(3-methyl-1-benzofuran-2-yl)quinolin-4-yl]methanol. To a 50-mL round-bottom flask was placed a solution of 6,8-dimethyl-2-(3-methyl-1-benzofuran-2-yl)quinoline-4-carboxylic acid (100 mg, 0.30 mmol, Compound 9) in THF (5 mL) then NaBH$_4$ (17 mg, 0.46 mmol) was added. The reaction was stirred at 50° C. overnight then quenched by the addition of water and extracted with EtOAc. The organic extracts were combined, washed with brine, dried over anhydrous Na$_2$SO$_4$, and concentrated under reduced pressure. The residue was purified by column chromatography eluting with EtOAc/petroleum ether (1:1) affording 11.2 mg (12%) of the title compound as a light yellow solid. Mass Spectrum (LCMS, ESI pos): Calcd. for $C_{21}H_{20}NO_2^+$: 318.2 (M+H); Found: 318.0. $^1$H NMR (300 MHz, DMSO-$d_6$): δ 8.21 (s, 1H), 7.78-7.69 (m, 2H), 7.64 (s, 1H), 7.52 (s, 1H), 7.45-7.32 (m, 2H), 5.70-5.66 (m, 1H), 5.09-5.07 (m, 2H), 2.86 (s, 3H), 2.77 (s, 3H). HPLC purity (254 nm): 99.8%.

Example 10: Preparation of 5,8-Dimethyl-2-[3-(methylamino)-1-benzofuran-2-yl]quinoline-4-carboxylic acid (Compound 62)

A. tert-Butyl N-[2-[Methoxy(methyl)carbamoyl]-1-benzofuran-3-yl]-N-methylcarbamate. To a 100-mL round-bottom flask was placed a solution of tert-butyl N-[2-[methoxy(methyl)carbamoyl]-1-benzofuran-3-yl]carbamate (1.2 g, 3.75 mmol, as prepared in Intermediate 20, Step E) in MeCN (50 mL) then NaH (300 mg, 7.50 mmol) was added. The resulting solution was stirred for 20 min at rt then MeI (2.66 g, 18.74 mmol) was added. The reaction was stirred at rt for 2 h, filtered, and concentrated under reduced pressure. The residue was purified by column chromatography eluting with petroleum ether/EtOAc (20:1) affording 0.585 g (47%) of the title compound as light yellow oil. Mass Spectrum (LCMS, ESI pos): Calcd. for $C_{17}H_{23}N_2O_5^+$: 335.2 (M+H); Found: 335.2.

B. tert-Butyl N-(2-Formyl-1-benzofuran-3-yl)-N-methylcarbamate. To a 100-mL round-bottom flask purged and maintained with an inert atmosphere of nitrogen was placed a solution of tert-butyl N-[2-[methoxy(methyl)carbamoyl]-1-benzofuran-3-yl]-N-methylcarbamate (585 mg, 1.75 mmol, as prepared in the previous step) in THF (50 mL) then LiAlH$_4$ (67 mg, 1.77 mmol) was added. The reaction was stirred at rt for 10 min, then quenched by the addition of 5 g of Na$_2$SO$_4$.10H$_2$O. The solids were removed by filtration then the filtrate was concentrated under reduced pressure. The residue was purified by column chromatography eluting with EtOAc/petroleum ether (1:30) affording 200 mg (42%) of the title compound as a light yellow solid.

C. 2-(3-[[(tert-Butoxy)carbonyl](methyl)amino]-1-benzofuran-2-yl)-5,8-dimethylquinoline-4-carboxylic acid. To a 5-mL sealed tube was placed a solution of tert-butyl N-(2-formyl-1-benzofuran-3-yl)-N-methylcarbamate (200 mg, 0.73 mmol, as prepared in the previous step) in EtOH (2 mL) then 2-oxopropanoic acid (79 mg, 0.90 mmol) and 2,5-dimethylaniline (72 mg, 0.59 mmol) were added. The reaction was heated to 100° C. for 3 h under microwave irradiation. The crude product (3 mL) was purified by Flash-Prep-HPLC (IntelFlash-1: Column, C18; mobile phase, MeCN/H$_2$O=30/70 increasing to MeCN/H$_2$O=85/15 within 30 min; Detector, UV 254 nm) affording 26 mg (8%) of the title compound as a yellow solid. Mass Spectrum (LCMS, ESI pos): Calcd. for $C_{26}H_{27}N_2O_5^+$: 447.2 (M+H); Found: 447.2.

D. 5,8-Dimethyl-2-[3-(methylamino)-1-benzofuran-2-yl]quinoline-4-carboxylic acid. To a 25-mL round-bottom flask was placed a solution of 2-(3-[[(tert-butoxy)carbonyl](methyl)amino]-1-benzofuran-2-yl)-5,8-dimethylquinoline-4-carboxylic acid (26 mg, 0.06 mmol, as prepared in the previous step) in DCM (6 mL) then TFA (2 mL) was added. The reaction was stirred at 40° C. for 2 h then concentrated under reduced pressure. The residue was purified by Prep-HPLC (HPLC-10: Column, X Bridge C18 OBD Prep Column, 100 Å, 10 μm, 19 mm×250 mm; mobile phase, Water (0.05% TFA) and MeCN (80.0% MeCN up to 83.0% in 10 min); Detector, uv 254 nm) affording 6.8 mg (34%) of the title compound as a brown solid. Mass Spectrum (LCMS, ESI pos): Calcd. for $C_{21}H_{19}N_2O_3^+$: 347.1 (M+H); Found: 347.0. $^1$H NMR (400 MHz, DMSO-$d_6$): δ 8.11-8.09 (d, J=8.0 Hz, 1H), 7.73 (s, 1H), 7.62-7.57 (m, 2H), 7.48-7.44 (t, J=7.2 Hz, 1H), 7.30-7.26 (m, 2H), 3.44 (s, 3H), 2.66 (s, 3H), 2.61 (s, 3H). HPLC purity (254 nm): 95.1%.

Using the procedure described in Example 10, with reagents, starting materials, and conditions familiar to those skilled in the art, the following compounds representative of the disclosure were prepared:

| Compound | Name and Data |
|---|---|
| 63 | 2-[3-(Benzylamino)-1-benzofuran-2-yl]-5,8-dimethylquinoline-4-carboxylic acid<br>Mass Spectrum (LCMS, ESI pos): Calcd. for $C_{27}H_{23}N_2O_3^+$: 423.2 (M + H);<br>Found: 423.0. $^1$H NMR (400 MHz, DMSO-$d_6$): δ 14.11 (brs, 1H), 8.07-8.05 (d, J = 8.0 Hz, 1H), 7.89-7.86 (m, 1H), 7.75 (s, 1H), 7.62-7.60 (d, J = 8.4 Hz, 1H), 7.52-7.42 (m, 4H), 7.36-7.32 (t, J = 7.6 Hz, 2H), 7.29-7.24 (m, 3H), 4.99-4.98 (d, J = 5.6 Hz, 2H), 2.60 (s, 3H), 2.29 (s, 3H). HPLC purity (254 nm): 98.0%. |

Example 11: Preparation of 5,8-Dimethyl-2-[3-[(phenoxycarbonyl)amino]-1-benzofuran-2-yl]quinoline-4-carboxylic acid (Compound 65)

A. 2-(3-[[(tert-Butoxy)carbonyl]amino]-1-benzofuran-2-yl)-5,8-dimethylquinoline-4-carboxylic acid. To a 5-mL sealed tube was placed a solution of tert-butyl N-(2-formyl-1-benzofuran-3-yl)carbamate (350 mg, 1.34 mmol, Intermediate 20) in EtOH (2 mL) then 2,5-dimethylaniline (118 mg, 0.97 mmol) and 2-oxopropanoic acid (135 mg, 1.53 mmol) were added. The reaction was heated to 100° C. for 3 h under microwave irradiation then the reaction was cooled to rt and the resulting solid was isolated by filtration affording 90 mg (16%) of the title compound as a yellow solid. Mass Spectrum (LCMS, ESI pos): Calcd. for $C_{25}H_{25}N_2O_5^+$: 433.2 (M+H); Found: 433.2.

B. 2-(3-Amino-1-benzofuran-2-yl)-5,8-dimethylquinoline-4-carboxylic acid. To a 100-mL round-bottom flask was placed a solution of 2-(3-[[(tert-butoxy)carbonyl]amino]-1-benzofuran-2-yl)-5,8-dimethylquinoline-4-carboxylic acid (80 mg, 0.18 mmol, as prepared in the previous step) in DCM (5 mL) then TFA (2 mL) was added. The resulting solution was stirred at rt for 3 h then concentrated under reduced pressure affording 76 mg of the title compound as a brown solid. Mass Spectrum (LCMS, ESI pos): Calcd. for $C_{20}H_{17}N_2O_3^+$: 333.1 (M+H); Found: 333.1.

C. 5,8-Dimethyl-2-[3-[(phenoxycarbonyl)amino]-1-benzofuran-2-yl]quinoline-4-carboxylic acid. To a 100-mL 3-necked round-bottom flask purged and maintained with an inert atmosphere of nitrogen was placed a solution of 2-(3-amino-1-benzofuran-2-yl)-5,8-dimethylquinoline-4-carboxylic acid (76 mg, 0.23 mmol, as prepared in the previous step) and TEA (70 mg) in DCM (20 mL). The solution was cooled to 0° C. then phenyl chloroformate (32 mg, 0.20 mmol) was added dropwise with stirring. The reaction was stirred at rt for 30 min, quenched by the addition of 50 mL of water, and extracted with DCM (3×20 mL). The organic extracts were combined, washed with brine (1×20 mL), and concentrated under reduced pressure. The crude product was purified by Prep-HPLC (HPLC-10: Column, X Bridge C18 OBD Prep Column, 5 um, 19 mm*250 mm; mobile phase, Water (0.05% TFA) and MeCN (80.0% MeCN up to 90.0% in 10 min); Detector, uv 254 nm) affording 16.8 mg (16%) of the title compound as a yellow solid. Mass Spectrum (LCMS, ESI pos): Calcd. for $C_2H_{21}N_2O_5^+$: 453.1 (M+H); Found 453.0. $^1$H NMR (400 MHz, DMSO-$d_6$): δ 14.30 (brs, 1H), 10.93 (s, 1H), 8.20-8.17 (m, 1H), 8.00 (s, 1H), 7.76-7.74 (d, J=8.0 Hz, 1H), 7.69-7.67 (d, J=7.6 Hz, 1H), 7.55-7.44 (m, 4H), 7.42-7.31 (m, 4H), 2.85 (s, 3H), 2.66 (s, 3H). HPLC purity (254 nm): 99.3%.

Example 12: Preparation of 8-Methyl-2-(3-methyl-1-benzofuran-2-yl)-5-[(phenylcarbamoyl)oxy]quinoline-4-carboxylic acid (Compound 81)

A. 5-Hydroxy-8-methyl-2-(3-methyl-1-benzofuran-2-yl)quinoline-4-carboxylic acid. To a 100-mL round-bottom flask was placed a solution of 5-(benzyloxy)-8-methyl-2-(3-methyl-1-benzofuran-2-yl)quinoline-4-carboxylic acid (150 mg, 0.35 mmol, Compound 30) in MeOH (5 mL) then Pd on carbon (50 mg) was added. The resulting solution was degassed and back-filled with $H_2$ then the reaction was stirred for 5 h at rt. The $H_2$ was purged then the solid was removed by filtration. The filtrate was concentrated under reduced pressure affording 100 mg of the title compound as a yellow solid. Mass Spectrum (LCMS, ESI pos): Calcd. for $C_{20}H_{16}NO_4^+$: 334.1 (M+H); Found: 334.1.

B. 8-Methyl-2-(3-methyl-1-benzofuran-2-yl)-5-[(phenylcarbamoyl)oxy]quinoline-4-carboxylic acid. To a 50-mL round-bottom flask purged and maintained with an inert atmosphere of nitrogen, was placed a solution of 5-hydroxy-8-methyl-2-(3-methyl-1-benzofuran-2-yl)quinoline-4-carboxylic acid (100 mg, 0.30 mmol, as prepared in the previous step) and TEA (20 mg, 0.20 mmol) in DCM (2 mL) then isocyanatobenzene (53.6 mg, 0.45 mmol) was added. The reaction was stirred for 4 h at rt, quenched by the addition of water, and extracted with DCM. The organic extracts were combined and concentrated under reduced pressure. The crude product was purified by Flash-Prep-HPLC (IntelFlash-1: Column, C18; mobile phase, MeCN/$H_2O$=5/95 increasing to MeCN/$H_2O$=30/70 within 15 min; Detector, uv 254 nm) affording 11.5 mg (8%) of the title compound as a yellow solid. Mass Spectrum (LCMS, ESI pos): Calcd. for $C_{27}H_{21}N_2O_5^+$: 453.1 (M+H); Found: 453.1. $^1$H NMR (300 MHz, DMSO-$d_6$): δ 10.22 (brs, 1H), 8.04 (s, 1H), 7.83-7.78 (m, 2H), 7.69 (d, J=8.1 Hz, 1H), 7.55 (d, J=8.7 Hz, 2H), 7.49-7.30 (m, 6H), 7.08-7.05 (m, 1H), 2.88 (s, 3H), 2.81 (s, 3H). HPLC purity (254 nm): 97.2%.

Example 13: Preparation of 2-(2,1-Benzothiazol-3-yl)-5-(benzyloxy)-8-methylquinoline-4-carboxylic acid (Compound 86)

A. 2-(2,1-Benzothiazol-3-yl)-5-(benzyloxy)-8-methylquinoline-4-carboxylic acid. To a 50-mL round-bottom flask was placed a solution of 4-(benzyloxy)-7-methyl-2,3-dihydro-1H-indole-2,3-dione (160.2 mg, 0.60 mmol, Intermediate 33) in EtOH (6 mL) then 1-(2,1-benzothiazol-3-yl)ethan-1-one (106.2 mg, 0.60 mmol, Intermediate 34), KOH (50.4 mg, 0.90 mmol), and $NaAuCl_4.2H_2O$ (68.4 mg, 0.18 mmol) were added. The reaction was stirred for 3 h at 80° C. then cooled to rt and concentrated under reduced pressure. The residue was purified by Prep-TLC with EtOAc/petroleum ether (1:1) and further purified by Prep-HPLC (HPLC-10: Column, T3 OBD Prep Column, 19*250 mm 10 um; mobile phase, Water (0.05% TFA) and MeCN (80.0% MeCN up to 85.0% in 10 min); Detector, uv 254 nm) affording 6 mg (2%) of the title compound as a brown solid. Mass Spectrum (LCMS, ESI pos): Calcd. for $C_{25}H_{19}N_2O_3S^+$: 427.1 (M+H); Found: 427.1. $^1$H NMR (400 MHz, DMSO-$d_6$): δ 8.80 (d, J=8.8 Hz, 1H), 8.06 (s, 1H), 7.88 (d, J=8.8 Hz, 1H), 7.68-7.60 (m, 4H), 7.54-7.35 (m, 4H), 7.15 (d, J=8.4 Hz, 1H), 5.38 (s, 2H), 2.85 (s, 3H). HPLC purity (254 nm): 95.5%.

Example 14: Preparation of 6,8-Dimethyl-2-(3-methyl-1-benzofuran-2-yl)quinoline-3-carboxylic acid (Compound 105)

A. (3-Methyl-1-benzofuran-2-yl)boronic acid. To a 50-mL 3-necked round-bottom flask was placed a solution of 3-methyl-1-benzofuran (792 mg, 5.99 mmol) in THF (30 mL) then the solution was cooled to −78° C. and BuLi (3.6 mL of a 2.5 M hexanes solution, 9.00 mmol) was added dropwise with stirring over 10 min then the reaction was stirred for 30 min at −78° C. To this was added B(OMe)$_3$ (1.2 g, 11.55 mmol) dropwise with stirring at −78° C. over 5 min then the reaction was stirred for 16 h at rt. The reaction was quenched by the addition of 150 mL of water and extracted with EtOAc (2×100 mL). The organic extracts were combined, dried over Na$_2$SO$_4$, and concentrated under reduced pressure. The residue was purified by column chromatography eluting with petroleum ether/EtOAc (10:1) affording 520 mg (49%) of the title compound as a yellow solid.

B. N-(2,4-Dimethylphenyl)acetamide. To a 50-mL round-bottom flask was placed a solution of 2,4-dimethylaniline (5 g, 41.26 mmol) in Ac$_2$O (10 mL) then the reaction was stirred for 20 min at rt and quenched by the addition of 100 mL of water. The solids were isolated by filtration affording 6 g (89%) of the title compound as an off-white solid. Mass Spectrum (LCMS, ESI pos): Calcd. for $C_{10}H_{14}NO^+$: 164.1 (M+H); Found: 164.1.

C. 2-Chloro-6,8-dimethylquinoline-3-carbaldehyde. To a 50-mL round-bottom flask was placed DMF (2.5 g, 34.20 mmol) then the solution was cooled to 0° C. and POCl$_3$ (13.1 g, 85.44 mmol) was added dropwise with stirring over 10 min. The resulting solution was stirred for 2 h at 100° C., then N-(2,4-dimethylphenyl)acetamide (1.4 g, 8.58 mmol, as prepared in the previous step) was added. The reaction was stirred for 16 h at 90° C. then quenched by the addition of 150 mL of water/ice. The solids were isolated by filtration and purified by column chromatography eluting with EtOAc/petroleum ether (1:100) affording 500 mg (27%) of the title compound as a white solid. Mass Spectrum (LCMS, ESI pos): Calcd. for $C_{12}H_{11}ClNO^+$: 220.1 (M+H); Found: 220.0.

D. Ethyl 2-Chloro-6,8-dimethylquinoline-3-carboxylate. To a 50-mL round-bottom flask was placed a solution of 2-chloro-6,8-dimethylquinoline-3-carbaldehyde (500 mg, 2.28 mmol, as prepared in the previous step) in EtOH (20 mL) then NIS (765 mg, 3.40 mmol) and K$_2$CO$_3$ (635 mg, 4.59 mmol) were added. The reaction was stirred for 16 h at 80° C., quenched by the addition of 100 mL of water, and extracted with EtOAc (2×100 mL). The organic extracts were combined, washed with brine (2×100 mL), dried over anhydrous Na$_2$SO$_4$, and concentrated under reduced pressure. The residue was purified by column chromatography eluting with petroleum ether/EtOAc (50:1) affording 340 mg (57%) of the title compound as a yellow oil. Mass Spectrum (LCMS, ESI pos): Calcd. for $C_{14}H_{15}ClNO_2^+$: 264.1 (M+H); Found: 264.0.

E. 2-Chloro-6,8-dimethylquinoline-3-carboxylic acid. To a 50-mL round-bottom flask was placed a solution of ethyl 2-chloro-6,8-dimethylquinoline-3-carboxylate (340 mg, 1.29 mmol, as prepared in the previous step) in EtOH (15 mL) then KOH (217 mg, 3.87 mmol) and water (5 mL) were added. The reaction was stirred for 2 h at 80° C., quenched by the addition of 100 mL of water, and washed with EtOAc (1×100 mL). The pH of the aqueous layer was adjusted to 4-5 with concentrated HCl then the resulting solution was extracted with EtOAc (2×50 mL). The organic extracts were combined, washed with brine (2×50 mL), dried over anhydrous Na$_2$SO$_4$, and concentrated under reduced pressure affording 145 mg (48%) of the title compound as yellow oil. Mass Spectrum (LCMS, ESI pos): Calcd. for $C_{12}H_{11}ClNO_2^+$: 236.1 (M+H); Found: 236.0.

F. 6,8-Dimethyl-2-(3-methyl-1-benzofuran-2-yl)quinoline-3-carboxylic acid. To a 25-mL round-bottom flask was placed a solution of 2-chloro-6,8-dimethylquinoline-3-carboxylic acid (80 mg, 0.34 mmol, as prepared in the previous step) in dioxane/H$_2$O (5/0.1 mL), then Pd(PPh$_3$)$_4$ (35 mg, 0.03 mmol), K$_2$CO$_3$ (94 mg, 0.68 mmol), and (3-methyl-1-benzofuran-2-yl)boronic acid (90 mg, 0.51 mmol, as prepared in Example 14, Step A) under nitrogen. The reaction was stirred for 3 h at 100° C., diluted with 50 mL of H$_2$O, and extracted with EtOAc (2×50 mL). The organic extracts were combined, washed with brine (2×50 mL), dried over anhydrous Na$_2$SO$_4$, and concentrated under reduced pressure. The crude product was purified by Prep-HPLC (HPLC-10: Column, Gemini-NX C18 AXAI Packed, 21.2*150 mm 5 um; mobile phase, Water (0.05% TFA) and MeCN (65.0% MeCN up to 90.0% in 6 min); Detector, uv 254 nm) affording 8.6 mg (8%) of the title compound as a light yellow solid. Mass Spectrum (LCMS, ESI pos): Calcd. for $C_{21}H_{18}NO_3^+$: 332.1 (M+H); Found: 332.2. $^1$H NMR (300 MHz, DMSO-d$_6$): δ 13.34 (s, 1H), 8.62 (s, 1H), 7.77-7.74 (m, 2H), 7.63 (s, 1H), 7.56-7.53 (d, J=8.1 Hz, 1H), 7.42-7.32 (m, 2H), 2.71 (s, 3H), 2.61 (s, 3H), 2.50 (s, 3H). HPLC purity (254 nm): 99.8%.

Example 15: Preparation of 5-(benzyloxy)-8-cyano-2-(3-methyl-1-benzofuran-2-yl)quinoline-4-carboxylic acid (Compound 112)

A. 5-(Benzyloxy)-8-bromo-2-(3-methyl-1-benzofuran-2-yl)quinoline-4-carboxylic acid. To a 100-mL round-bottom flask was placed a solution of 5-(benzyloxy)-2-(3-methyl-1-benzofuran-2-yl)quinoline-4-carboxylic acid (200 mg, 0.49 mmol, Compound 67) in DCM (30 mL), then NBS (86 mg, 1.46 mmol) was added. The reaction was stirred for 1 h at rt then concentrated under reduced pressure. The residue was purified by column chromatography eluting with DCM/MeOH (15:1) affording 140 mg (85%) of the title compound as a yellow solid. Mass Spectrum (LCMS, ESI pos): Calcd. for $C_{26}H_{19}BrNO_4^+$: 488.1 (M+H); Found: 488.0.

B. 5-(Benzyloxy)-8-cyano-2-(3-methyl-1-benzofuran-2-yl)quinoline-4-carboxylic acid. To a 10-mL sealed tube was placed 5-(benzyloxy)-8-bromo-2-(3-methyl-1-benzofuran-2-yl)quinoline-4-carboxylic acid (140 mg, 0.29 mmol, as prepared in the previous step) in DMF (3 mL) then Pd(PPh$_3$)$_4$ (120 mg, 0.10 mmol) and Zn(CN)$_2$ (72 mg, 0.62 mmol) were added under nitrogen. The reaction was heated to 120° C. for 2 h under microwave irradiation, then cooled to rt and the solids were removed by filtration. The filtrate was concentrated under reduced pressure then the residue was purified by column chromatography eluting with EtOAc/petroleum ether (1:1). The resulting product was purified by Prep-HPLC (HPLC-10: Column, X Bridge C18 OBD Prep Column, 19 mm*250 mm; mobile phase, Water (0.05% TFA) and MeCN (60.0% MeCN up to 77.0% in 10 min); Detector, uv 254 nm) affording 12.5 mg (10%) of the title compound as a yellow solid. Mass Spectrum (LCMS, ESI pos): Calcd. for $C_{27}H_{19}N_2O_4^+$: 435.1 (M+H); Found: 435.1. $^1$H NMR (300 MHz, DMSO-d$_6$): δ 8.38 (d, J=8.1 Hz, 1H), 8.02 (s, 1H), 7.83 (d, J=8.1 Hz, 1H), 7.71 (d, J=8.1 Hz, 1H), 7.59-7.56 (m, 2H), 7.50 (t, J=7.2 Hz, 1H), 7.41-7.29 (m, 5H), 5.47 (s, 2H), 2.92 (s, 3H). HPLC purity (254 nm): 97.6%.

Example 16: Preparation of 8-Methyl-2-(3-methyl-1-benzothiophen-2-yl)-5-[(1R)-1-phenylethoxy]quinoline-4-carboxylic acid (Compound 137) and 8-Methyl-2-(3-methyl-1-benzothiophen-2-yl)-5-[(1S)-1-phenylethoxy]quinoline-4-carboxylic acid (Compound 138)

A. 8-Methyl-2-(3-methyl-1-benzothiophen-2-yl)-5-[(1R)-1-phenylethoxy]quinoline-4-carboxylic acid and 8-Methyl-2-(3-methyl-1-benzothiophen-2-yl)-5-[(1S)-1-phenylethoxy]quinoline-4-carboxylic acid. To a 10-mL sealed tube was placed a solution of 2-methyl-5-(1-phenylethoxy)aniline (730 mg, 3.21 mmol, Intermediate 52) in EtOH (5 mL) then 3-methyl-1-benzothiophene-2-carbaldehyde (566 mg, 3.21 mmol) and 2-oxopropanoic acid (849 mg, 9.64 mmol) were added. The reaction was heated to 100° C. for 2 h under microwave irradiation, cooled to rt, and concentrated under reduced pressure. The residue was purified by column chromatography eluting with DCM/MeOH (15:1). The resulting mixture was separated by Chiral-Prep-HPLC (Prep-HPLC-004: Column, CHIRALPAK ADH, 21.2*250 mm, 5 um; mobile phase, Hex (0.1% TFA) and IPA (hold 50.0% IPA in 19 min); Detector, uv 254 nm) affording 34.7 mg (2%) of 8-methyl-2-(3-methyl-1-benzothiophen-2-yl)-5-[(1R)-1-phenylethoxy]quinoline-4-carboxylic acid (Compound 137) as a yellow solid and 34.6 mg (2%) of 8-methyl-2-(3-methyl-1-benzothiophen-2-yl)-5-[(1S)-1-phenylethoxy]quinoline-4-carboxylic acid (Compound 138) as a yellow solid.

8-Methyl-2-(3-methyl-1-benzothiophen-2-yl)-5-[(1R)-1-phenylethoxy]quinoline-4-carboxylic acid (Compound 137)

Mass Spectrum (LCMS, ESI pos): Calcd. for $C_{28}H_{24}NO_3S^+$: 454.2 (M+H); Found: 454.1. $^1$H NMR (400 MHz, DMSO-$d_6$): δ 13.60 (brs 1H), 8.04-8.03 (m, 2H), 7.97-7.94 (m, 2H), 7.81 (s, 1H), 7.51-7.45 (m, 5H), 7.34-7.30 (m, 2H), 7.23 (t, J=7.2 Hz, 1H), 6.79 (d, J=8.0 Hz, 1H), 5.71 (q, J=6.4 Hz, 1H), 2.82 (s, 3H), 2.62 (s, 3H), 1.64 (d, J=6.4 Hz, 3H). HPLC purity (254 nm): 96.4%.

8-Methyl-2-(3-methyl-1-benzothiophen-2-yl)-5-[(1S)-1-phenylethoxy]quinoline-4-carboxylic acid (Compound 138)

Mass Spectrum (LCMS, ESI pos): Calcd. for $C_{28}H_{24}NO_3S^+$: 454.2 (M+H); Found: 454.1. $^1$H NMR (400 MHz, DMSO-$d_6$): δ 8.05-8.02 (m, 2H), 7.97-7.94 (m, 2H), 7.81 (s, 1H), 7.51-7.45 (m, 5H), 7.34-7.30 (m, 2H), 7.23 (t, J=7.2 Hz, 1H), 6.79 (d, J=8.0 Hz, 1H), 5.71 (q, J=6.4 Hz, 1H), 2.82 (s, 3H), 2.62 (s, 3H), 1.64 (d, J=6.4 Hz, 3H). HPLC purity (254 nm): 99.6%.

Using the procedure described in Example 16, with reagents, starting materials, and conditions familiar to those skilled in the art, the following compounds representative of the disclosure were prepared:

| Compound | Name and Data |
|---|---|
| 160 | 2-(1-Benzothiophen-3-yl)-8-methyl-5-[(1R)-1-phenylethoxy]quinoline-4-carboxylic acid<br>Mass Spectrum (LCMS, ESI pos): Calcd. for $C_{27}H_{22}NO_3S^+$: 440.1 (M + H); Found: 440.2. $^1$H NMR (300 MHz, DMSO-$d_6$): δ 9.27 (d, J = 8.1 Hz, 1H), 8.85 (s, 1H), 8.13-8.11 (m, 2H), 7.58-7.44 (m, 5H), 7.35-7.21 (m, 3H), 6.78 (d, J = 8.1 Hz, 1H), 5.71 (q, J = 6.3 Hz, 1H), 2.70 (s, 3H), 1.64 (d, J = 6.3 Hz, 3H). HPLC purity (254 nm): 96.0%. |
| 161 | 2-(1-Benzothiophen-3-yl)-8-methyl-5-[(1S)-1-phenylethoxy]quinoline-4-carboxylic acid<br>Mass Spectrum (LCMS, ESI pos): Calcd. for $C_{21}H_{22}NO_3S^+$: 440.1 (M + H); Found: 440.0. $^1$H NMR (300 MHz, DMSO-$d_6$): δ 9.27 (d, J = 8.1 Hz, 1H), 8.85 (s, 1H), 8.13-8.11 (m, 2H), 7.58-7.44 (m, 5H), 7.35-7.21 (m, 3H), 6.78 (d, J = 8.1 Hz, 1H), 5.71 (q, J = 6.3 Hz, 1H), 2.70 (s, 3H), 1.64 (d, J = 6.3 Hz, 3H). HPLC purity (254 nm): 95.5%. |
| 163 | 2-(1-Benzothiophen-3-yl)-8-ethyl-5-[(1R)-1-phenylethoxy]quinoline-4-carboxylic acid<br>Mass Spectrum (LCMS, ESI pos): Calcd. for $C_{28}H_{24}NO_3S^+$: 454.2 (M + H); Found: 454.2. $^1$H NMR (400 MHz, DMSO-$d_6$): δ 13.46 (br, 1H), 9.24 (d, J = 8.0 Hz, 1H), 8.85 (s, 1H), 8.13-8.11 (m, 2H), 7.57-7.44 (m, 5H), 7.33 (t, J = 6.8 Hz, 2H), 7.26-7.21 (m, 1H), 6.80 (d, J = 8.0 Hz, 1H), 5.71 (q, J = 6.0 Hz, 1H), 3.21 (q, J = 7.2 Hz, 2H), 1.64 (d, J = 6.4 Hz, 3H), 1.33 (t, J = 7.2 Hz, 3H). HPLC purity (254 nm): 96.8%. |
| 164 | 2-(1-Benzothiophen-3-yl)-8-ethyl-5-[(1S)-1-phenylethoxy]quinoline-4-carboxylic acid<br>Mass Spectrum (LCMS, ESI pos): Calcd. for $C_{28}H_{24}NO_3S^+$: 454.2 (M + H); Found: 454.2. $^1$H NMR (400 MHz, DMSO-$d_6$): δ 9.24 (d, J = 8.0 Hz, 1H), 8.85 (s, 1H), 8.13-8.11 (m, 2H), 7.57-7.44 (m, 5H), 7.33 (t, J = 6.8 Hz, 2H), 7.26-7.21 (m, 1H), 6.80 (d, J = 8.0 Hz, 1H), 5.71 (q, J = 6.0 Hz, 1H), 3.21 (q, J = 7.2 Hz, 2H), 1.64 (d, J = 6.4 Hz, 3H), 1.33 (t, J = 7.2 Hz, 3H). HPLC purity (254 nm): 96.1%. |
| 171 | 2-(1-Benzofuran-3-yl)-8-ethyl-5-[(1R)-1-phenylethoxy]quinoline-4-carboxylic acid<br>Mass Spectrum (LCMS, ESI pos): Calcd. for $C_{28}H_{24}NO_4^+$: 438.2 (M + H); Found: 438.2. $^1$H NMR (400 MHz, DMSO-$d_6$): δ 13.51 (brs, 1H), 9.16 (s, 1H), 8.76-8.74 (m, 1H), 8.10 (s, 1H), 7.73-7.71 (m, 1H), 7.55-7.41 (m, 5H), 7.35-7.22 (m, 3H), 6.79 (d, J = 8.0 Hz, 1H), 5.72-5.67 (q, J = 6.4 Hz, 1H), 3.24 (q, J = 8.0 Hz, 2H), 1.64 (d, J = 6.4 Hz, 3H), 1.35-1.31 (t, J = 8.0 Hz, 3H). HPLC purity (254 nm): 96.4%. |

| Compound | Name and Data |
|---|---|
| 172 | 2-(1-Benzofuran-3-yl)-8-ethyl-5-[(1S)-1-phenylethoxy]quinoline-4-carboxylic acid<br>Mass Spectrum (LCMS, ESI pos): Calcd. for $C_{28}H_{24}NO_4^+$: 438.2 (M + H); Found: 438.1. $^1$H NMR (400 MHz, DMSO-$d_6$): δ 13.50 (brs, 1H), 9.16 (s, 1H), 8.76-8.74 (m, 1H), 8.10 (s, 1H), 7.73-7.71 (m, 1H), 7.55-7.41 (m, 5H), 7.35-7.22 (m, 3H), 6.79 (d, J = 8.0 Hz, 1H), 5.72-5.67 (q, J = 6.4 Hz, 1H), 3.24 (q, J = 8.0 Hz, 2H), 1.64 (d, J = 6.4 Hz, 3H), 1.35-1.31 (t, J = 8.0 Hz, 3H). HPLC purity (254 nm): 97.5%. |
| 183 | 2-(1-Benzothiophen-3-yl)-8-ethyl-5-[(1R)-1-phenylpropoxy]quinoline-4-carboxylic acid<br>Mass Spectrum (LCMS, ESI pos): Calcd. for $C_{29}H_{26}NO_3S^+$: 468.2 (M + H); Found: 468.1. $^1$H NMR (400 MHz, $CD_3OD$): δ 9.23 (d, J = 8.0 Hz, 1H), 8.43 (s, 1H), 8.00-7.99 (m, 2H), 7.52-7.23 (m, 8H), 6.76 (d, J = 8.4 Hz, 1H), 5.37 (t, J = 6.2 Hz, 1H), 3.27 (q, J= 7.2 Hz, 2H), 2.28-2.17 (m, 1H), 2.02-1.91 (m, 1H), 1.38 (t, J = 7.6 Hz, 3H), 1.12 (t, J = 7.2 Hz, 3H). HPLC purity (254 nm): 98.8%. |
| 185 | 2-(1-Benzothiophen-3-yl)-8-ethyl-5-[(1S)-1-phenylpropoxy]quinoline-4-carboxylic acid<br>Mass Spectrum (LCMS, ESI pos): Calcd. for $C_{29}H_{26}NO_3S^+$: 468.2 (M + H); Found: 468.1. $^1$H NMR (400 MHz, $CD_3OD$): δ 9.23 (d, J = 8.0 Hz, 1H), 8.43 (s, 1H), 8.00-7.99 (m, 2H), 7.52-7.23 (m, 8H), 6.76 (d, J = 8.4 Hz, 1H), 5.37 (t, J = 6.2 Hz, 1H), 3.27 (q, J = 7.2 Hz, 2H), 2.28-2.17 (m, 1H), 2.02-1.91 (m, 1H), 1.38 (t, J = 7.6 Hz, 3H), 1.10 (t, J = 7.2 Hz, 3H). HPLC purity (254 nm): 99.0%. |

Example 17: 5-(Benzyloxy)-8-ethyl-2-(3-methyl-1-benzothiophen-2-yl)quinoline-4-carboxylic acid (Compound 133)

A. 5-(Benzyloxy)-2-(3-methyl-1-benzothiophen-2-yl)quinoline-4-carboxylic acid. To a 5-mL sealed tube was placed a solution of 1-(3-methyl-1-benzothiophen-2-yl)ethan-1-one (165 mg, 0.87 mmol) in EtOH (2 mL) then 4-(benzyloxy)-2,3-dihydro-1H-indole-2,3-dione (200 mg, 0.79 mmol, Intermediate 21) and KOH (88 mg, 1.57 mmol) were added. The reaction was stirred overnight at 80° C. then concentrated under reduced pressure. The residue was dissolved in 5 mL of $H_2O$, the pH was adjusted to 4-5 with 2 N HCl, and the resulting solution was extracted with EtOAc (3×30 mL). The organic extracts were combined and concentrated under reduced pressure. The residue was purified by column chromatography eluting with EtOAc/petroleum ether (1:1) affording 78 mg (23%) of the title compound as a yellow solid. Mass Spectrum (LCMS, ESI pos): Calcd. for $C_{26}H_{20}NO_3S^+$: 426.1 (M+H); Found: 426.1.

B. 5-(Benzyloxy)-8-bromo-2-(3-methyl-1-benzothiophen-2-yl)quinoline-4-carboxylic acid. To a 10-mL 3-necked round-bottom flask was placed a solution of 5-(benzyloxy)-2-(3-methyl-1-benzothiophen-2-yl)quinoline-4-carboxylic acid (68 mg, 0.16 mmol, as prepared in the previous step) in DCM (1 mL) then NBS (26 mg, 0.15 mmol) in DCM (1 mL) was added. The reaction was stirred for 1 h at rt, quenched by the addition of 5 mL of water, and extracted with DCM (3×20 mL). The organic extracts were combined and concentrated under reduced pressure affording 90 mg of the title compound as a yellow solid. Mass Spectrum (LCMS, ESI pos): Calcd. for $C_{26}H_{19}BrNO_3S^+$: 504.0 (M+H); Found: 504.4.

C. 5-(Benzyloxy)-2-(3-methylbenzo[b]thiophen-2-yl)-8-vinylquinoline-4-carboxylic acid. To a 10-mL sealed tube was placed a solution of 5-(benzyloxy)-8-bromo-2-(3-methyl-1-benzothiophen-2-yl)quinoline-4-carboxylic acid (90 mg, 0.18 mmol, as prepared in the previous step) in dioxane/$H_2O$ (20:1) (3 mL) then Pd(OAc)$_2$ (8 mg, 0.04 mmol), PCy$_3$.HBF$_4$ (26 mg), and 2-ethenyl-4,4,5,5-tetramethyl-1,3,2-dioxaborolane (41 mg, 0.27 mmol) were added under nitrogen. The reaction was stirred for 4 h at 100° C., quenched by the addition of 10 mL of water, and extracted with EtOAc (3×20 mL). The organic extracts were combined, dried over $Na_2SO_4$, and concentrated under reduced pressure. The residue was purified by column chromatography eluting with EtOAc/petroleum ether (1:1) affording 78 mg (84%) of the title compound as a light yellow solid. Mass Spectrum (LCMS, ESI pos): Calcd. for $C_{28}H_{22}NO_3S^+$: 452.1 (M+H); Found: 452.1.

D. 5-(Benzyloxy)-8-ethyl-2-(3-methyl-1-benzothiophen-2-yl)quinoline-4-carboxylic acid. To a 25-mL round-bottom flask was placed a solution of 5-(benzyloxy)-8-ethenyl-2-(3-methyl-1-benzothiophen-2-yl)quinoline-4-carboxylic acid (78 mg, 0.17 mmol, as prepared in the previous step) in MeOH (5 mL) then Pd on carbon (8 mg) was added. The solution was degassed and back-filled with $H_2$ then stirred for 10 min at rt. The $H_2$ was purged then the solids were removed by filtration. The filtrate was concentrated under reduced pressure and the residue was purified by Prep-HPLC (HPLC-10: Column, Atlantis Prep T3 OBD Column, 19*250 mm 10 um; mobile phase, Water (0.05% TFA) and MeCN (hold 95.0% MeCN in 10 min); Detector, UV 254/220 nm) affording 5.7 mg (7%) of the title compound as a yellow solid. Mass Spectrum (LCMS, ESI pos): Calcd. for $C_{28}H_{24}NO_3S^+$: 454.2 (M+H); Found: 454.1. $^1$H NMR (400 MHz, DMSD-$d_6$): δ 13.50 (s, 1H), 8.05-8.03 (m, 1H), 8.02-7.94 (m, 1H), 7.82 (s, 1H), 7.61-7.54 (m, 3H), 7.50-7.46 (m, 2H), 7.42-7.38 (m, 2H), 7.34-7.32 (m, 1H), 7.13 (d, J=8.0 Hz, 1H), 5.35 (s, 2H), 3.18 (q, J=7.2 Hz, 2H), 2.82 (s, 3H), 1.33 (t, J=7.2 Hz, 3H). HPLC purity (254 nm): 97.8%.

Example 18: Preparation of 5-(Benzyloxy)-8-methyl-2-(3-methyl-1-benzofuran-2-yl)quinazoline-4-carboxylic acid (Compound 101)

A. 2-Amino-6-(benzyloxy)-3-methylbenzoic acid. To a 50-mL round-bottom flask was placed a solution of 4-(benzyloxy)-7-methyl-2,3-dihydro-1H-indole-2,3-dione (1 g, 3.74 mmol, Intermediate 33) in water (13 mL) then NaOH (780 mg, 19.50 mmol) was added. The resulting solution was stirred for 2 h at 50° C. then $H_2O_2$ (13 mL) was added dropwise with stirring at 50° C. The reaction was stirred for 3 h at 50° C. then cooled to room temperature and the pH was adjusted to 4-5 with 2N HCl. The precipitate was collected by filtration and dried affording 520 mg (54%) of the title compound as a gray solid. Mass Spectrum (LCMS, ESI pos): Calcd. for $C_{15}H_{16}NO_3^+$: 258.1 (M+H); Found: 258.1.

B. 3-Methyl-1-benzofuran-2-carbonyl chloride. To a 50-mL 3-necked round-bottom flask purged and maintained with an inert atmosphere of nitrogen, was placed a solution of 3-methyl-1-benzofuran-2-carboxylic acid (500 mg, 2.84 mmol) and DMF (0.1 mL) in DCM (10 mL) then the solution was cooled to 0° C. and oxalyl chloride (470 mg, 3.70 mmol) was added dropwise with stirring. The reaction was stirred for 2 h at 0° C. then concentrated under reduced pressure affording 500 mg (91%) of the title compound as an off-white solid.

C. 6-(Benzyloxy)-3-methyl-2-(3-methyl-1-benzofuran-2-amido)benzoic acid. To a 250-mL round-bottom flask purged and maintained with an inert atmosphere of nitrogen, was placed a solution of 2-amino-6-(benzyloxy)-3-methylbenzoic acid (687 mg, 2.67 mmol, as prepared in Step A) in THF/H$_2$O (2/1, 93 mL) then Na$_2$CO$_3$ (809.8 mg, 7.64 mmol) was added and the mixture was cooled to 0° C. A solution of 3-methyl-1-benzofuran-2-carbonyl chloride (494 mg, 2.54 mmol, as prepared in the previous step) in THF (10 mL) was added dropwise then the resulting solution was stirred for 30 min at rt. The reaction was diluted with H$_2$O and the solids were isolated by filtration affording 498 mg (47%) of the title compound as a gray solid. Mass Spectrum (LCMS, ESI pos): Calcd. for $C_{25}H_{22}NO_5^+$: 416.2 (M+H); Found: 416.1.

D. N-[3-(Benzyloxy)-2-carbamoyl-6-methylphenyl]-3-methyl-1-benzofuran-2-carboxamide. To a 50-mL round-bottom flask was placed a solution of 6-(benzyloxy)-3-methyl-2-(3-methyl-1-benzofuran-2-amido)benzoic acid (260 mg, 0.63 mmol, as prepared in the previous step) in DMF (12 mL) then HATU (476 mg, 1.25 mmol), NH$_4$HCO$_3$ (495 mg), and DIEA (404 mg, 3.13 mmol) were added. The reaction was stirred for 3 h at rt then quenched by the addition of water and extracted with EtOAc. The organic extracts were combined, washed with brine, dried over anhydrous Na$_2$SO$_4$, and concentrated under reduced pressure affording 223 mg (86%) of the title compound as a gray solid. Mass Spectrum (LCMS, ESI pos): Calcd. for $C_{25}H_{23}N_2O_4^+$: 415.2 (M+H); Found: 415.2.

E. 5-(Benzyloxy)-8-methyl-2-(3-methyl-1-benzofuran-2-yl)quinazolin-4-ol. To a 50-mL round-bottom flask was placed a solution of N-[3-(benzyloxy)-2-carbamoyl-6-methylphenyl]-3-methyl-1-benzofuran-2-carboxamide (163 mg, 0.4 mmol, as prepared in the previous step) in EtOH (5 mL) then NaOH (47 mg, 1.17 mmol) was added. The reaction was stirred for 3 h at 80° C., then quenched by the addition of water. The precipitate was isolated by filtration and dried affording 150 mg (96%) of the title compound as a gray solid. Mass Spectrum (LCMS, ESI pos): Calcd. for $C_{25}H_{21}N_2O_3^+$: 397.2 (M+H); Found: 397.1. $^1$H NMR (400 MHz, DMSO-d$_6$): δ 7.69-7.63 (m, 2H), 7.59 (d, J=8.0 Hz, 1H), 7.44-7.19 (m, 7H), 6.60 (d, J=8.0 Hz, 1H), 5.14 (s, 2H), 2.77 (s, 3H), 2.44 (s, 6H).

F. 5-(Benzyloxy)-4-chloro-8-methyl-2-(3-methyl-1-benzofuran-2-yl)quinazoline. To a 25-mL 3-necked round-bottom flask purged and maintained with an inert atmosphere of nitrogen, was placed a solution of 5-(benzyloxy)-8-methyl-2-(3-methyl-1-benzofuran-2-yl)quinazolin-4-ol (120 mg, 0.30 mmol, as prepared in the previous step) in DCM (5 mL) then the solution was cooled to 0° C. and oxalyl chloride (50 mg, 0.39 mmol) was added dropwise. The resulting solution was stirred for 2 h at 0° C. then concentrated under reduced pressure affording 122 mg (97%) of the title compound as a gray solid. Mass Spectrum (LCMS, ESI pos): Calcd. for $C_{25}H_{20}ClN_2O_2^+$: 415.1 (M+H); Found: 415.1.

G. Methyl 5-(Benzyloxy)-8-methyl-2-(3-methyl-1-benzofuran-2-yl)quinazoline-4-carboxylate. To a 20-mL pressure tank reactor was placed a solution of 5-(benzyloxy)-4-chloro-8-methyl-2-(3-methyl-1-benzofuran-2-yl)quinazoline (122 mg, 0.29 mmol, as prepared in the previous step), Pd(dppf)Cl$_2$ (159 mg, 0.22 mmol), and NaOAc (122 mg) in MeOH (5 mL) under nitrogen then CO was introduced into the reactor. The reaction was stirred for 18 h at 120° C. under 40 atm of CO then the solution was concentrated under reduced pressure. The residue was purified by column chromatography eluting with EtOAc/petroleum ether (1:1) affording 28 mg (22%) of the title compound as a gray solid. Mass Spectrum (LCMS, ESI pos): Calcd. for $C_{27}H_{23}N_2O_4^+$: 439.2 (M+H); Found: 439.2.

H. 5-(Benzyloxy)-8-methyl-2-(3-methyl-1-benzofuran-2-yl)quinazoline-4-carboxylic acid. To a 25-mL round-bottom flask was placed a solution of methyl 5-(benzyloxy)-8-methyl-2-(3-methyl-1-benzofuran-2-yl)quinazoline-4-carboxylate (23 mg, 0.05 mmol, as prepared in the previous step) in THF/MeOH/H$_2$O (10/10/1, 4.2 mL) then NaOH (8 mg, 0.20 mmol) was added. The reaction was stirred for 4 h at 100° C. then concentrated under reduced pressure. The pH of the solution was adjusted to 2-3 using 2N HCl then the precipitate was isolated by filtration affording 5.1 mg (23%) of the title compound as a light yellow solid. Mass Spectrum (LCMS, ESI pos): Calcd. for $C_{26}H_{21}N_2O_4^+$: 425.2 (M+H); Found: 425.1. $^1$H NMR (400 MHz, CD$_3$OD): δ 7.74-7.55 (m, 5H), 7.45-7.21 (m, 5H), 6.94 (d, J=8.0 Hz, 1H), 5.37 (s, 2H), 2.88 (s, 3H), 2.68 (s, 3H). HPLC purity (254 nm): 96.9%.

Example 19: Preparation of 5-(Benzyloxy)-6,8-dimethyl-2-(3-methyl-1-benzofuran-2-yl)quinoline-4-carboxylic acid (Compound 66)

A. 5-(Benzyloxy)-6-bromo-8-methyl-2-(3-methyl-1-benzofuran-2-yl)quinoline-4-carboxylic acid. To a 50-mL round-bottom flask was placed a solution of 5-(benzyloxy)-8-methyl-2-(3-methyl-1-benzofuran-2-yl)quinoline-4-carboxylic acid (169.2 mg, 0.40 mmol, Compound 30) in DCM/THF (1:1, 10 mL) then the solution was cooled to −30° C. and NBS (71.2 mg, 0.40 mmol) was added in small portions. The cooling bath was removed then the reaction was stirred overnight. The resulting mixture was concentrated under reduced pressure and the residue was purified by Prep-TLC with ethyl acetate/petroleum ether (1:1) affording 120 mg (60%) of the title compound as a yellow solid. Mass Spectrum (LCMS, ESI pos): Calcd. for $C_{27}H_{21}BrNO_4^+$: 502.1 (M+H); Found: 502.4.

B. 5-(Benzyloxy)-6,8-dimethyl-2-(3-methyl-1-benzofuran-2-yl)quinoline-4-carboxylic acid. To an 8-mL sealed tube purged and maintained with an inert atmosphere of nitrogen, was placed a solution of 5-(benzyloxy)-6-bromo-8-methyl-2-(3-methyl-1-benzofuran-2-yl)quinoline-4-carboxylic acid (60 mg, 0.12 mmol, as prepared in the previous step) in dioxane/H$_2$O (20:1, 1 mL) then methylboronic acid (14 mg, 0.23 mmol), K$_3$PO$_4$ (128 mg, 0.60 mmol), Pd(OAc)$_2$ (2 mg, 0.01 mmol), and PCy$_3$.HBF$_4$ (8 mg, 0.02 mmol) were added. The reaction was stirred overnight at 100° C. then concentrated under vacuum. The residue was purified by Prep-TLC with ethyl acetate/petroleum ether (1:1). The product was further purified by Prep-HPLC (HPLC-10: Column, X Bridge C18 OBD Prep Column, 100*10 μm, 19 mm*250 mm; mobile phase, Water (0.05% TFA) and MeCN (80.0% MeCN up to 95.0% in 6 min);

Detector, uv 254 nm) affording 5 mg (10%) of the title compound as a yellow solid. Mass Spectrum (LCMS, ESI pos): Calcd. for $C_{28}H_{24}NO_4^+$: 438.2 (M+H); Found: 438.3. $^1$H NMR (400 MHz, $CD_3OD$): δ 8.03 (s, 1H), 7.74 (d, J=8.0 Hz, 1H), 7.69-7.61 (m, 4H), 7.46-7.32 (m, 5H), 4.89 (s, 2H), 2.93 (s, 3H), 2.82 (s, 3H), 2.49 (s, 3H). HPLC purity (254 nm): 97.5%.

Example 20: Preparation of 6-tert-Butyl-8-methyl-2-(3-methyl-1-benzofuran-2-yl)quinazoline-4-carboxylic acid (Compound 102)

A. 4-tert-Butyl-2-methylaniline. To a 1000-mL round-bottom flask was placed a solution of 2-bromo-4-tert-butylaniline (9.2 g, 40.33 mmol) in dioxane/water (500 mL) then $Pd(OAc)_2$ (900 mg, 4.01 mmol), $PCy_3 \cdot HBF_4$ (2.95 g, 8.01 mmol), methylboronic acid (3.6 g, 60.14 mmol), and $K_3PO_4$ (26 g, 122.64 mmol) were added under nitrogen. The reaction was stirred for 12 h at 110° C. then quenched by the addition of water and extracted with DCM. The organic extracts were combined and concentrated under reduced pressure. The residue was purified by column chromatography eluting with EtOAc/petroleum ether (1:80) affording 5.7 g (87%) of the title compound as a dark red oil. Mass Spectrum (LCMS, ESI pos): Calcd. for $C_{11}H_{18}N^+$: 164.1 (M+H); Found: 164.1.

B. 2-Bromo-4-tert-butyl-6-methylaniline. To a 500-mL 3-necked round-bottom flask was placed a solution of 4-tert-butyl-2-methylaniline (2.37 g, 14.52 mmol, as prepared in the previous step) in DCM (300 mL) then the solution was cooled to −30° C. and NBS (2.96 g, 13.10 mmol) was added. The reaction was stirred for 3 h at −30° C., washed with $H_2O$, dried over anhydrous $Na_2SO_4$, and concentrated under reduce pressure. The residue was purified by column chromatography eluting with EtOAc/petroleum ether (1:80) affording 3.4 g (97%) of the title compound as a dark red oil. Mass Spectrum (LCMS, ESI pos): Calcd. for $C_{11}H_{17}BrN^+$: 242.1 (M+H); Found: 242.1.

C. 2-Amino-5-tert-butyl-3-methylbenzonitrile. To a 20-mL sealed tube was placed a solution of 2-bromo-4-tert-butyl-6-methylaniline (1.85 g, 7.64 mmol, as prepared in the previous step) in DMF (15 mL) then $Pd(PPh_3)_4$ (890 mg, 0.77 mmol) and $ZnCN_2$ (1.61 g) were added under nitrogen. The reaction was heated to 130° C. for 2 h under microwave radiation then quenched by the addition of water and extracted with DCM. The organic extracts were combined, dried over anhydrous $Na_2SO_4$, and concentrated under reduced pressure. The residue was purified by column chromatography eluting with EtOAc/petroleum ether (1:10) affording 0.99 g (69%) of the title compound as a dark red oil. Mass Spectrum (LCMS, ESI pos): Calcd. for $C_{12}H_{17}N_2^+$: 189.1 (M+H); Found: 189.1.

D. 2-Amino-5-tert-butyl-3-methylbenzamide. To a 50-mL round-bottom flask was placed a solution of 2-amino-5-tert-butyl-3-methylbenzonitrile (510 mg, 2.71 mmol, as prepared in the previous step) in DMSO (10 mL) then $H_2O_2$ (2 mL) and $K_2CO_3$ (1.1 g, 7.96 mmol) were added. The reaction was stirred for 2 h at rt then quenched by the addition of aqueous $NaHSO_3$ solution and extracted with DCM. The organic extracts were combined, dried over anhydrous $Na_2SO_4$, and concentrated under reduced pressure affording 0.48 g (86%) of the title compound as a colorless oil. Mass Spectrum (LCMS, ESI pos): Calcd. for $C_{12}H_{19}N_2O^+$: 207.2 (M+H); Found: 207.1.

E. N-(4-tert-Butyl-2-carbamoyl-6-methylphenyl)-3-methyl-1-benzofuran-2-carboxamide. To a 100-mL round-bottom flask was placed a solution of 3-methyl-1-benzofuran-2-carbonyl chloride (234 mg, 1.20 mmol, as prepared in Example 18, Step B) in DCM then 2-amino-5-tert-butyl-3-methylbenzamide (268 mg, 1.30 mmol, as prepared in the previous step) and TEA (1.0 mL) were added. The reaction was stirred for 30 min at rt, quenched by the addition of water, and extracted with DCM. The organic extracts were combined, dried over anhydrous $Na_2SO_4$, and concentrated under reduced pressure. The residue was purified by column chromatography eluting with EtOAc/petroleum ether (1:3) affording 130 mg (30%) of the title compound as a white solid. Mass Spectrum (LCMS, ESI pos): Calcd. for $C_{22}H_{25}N_2O_3^+$: 365.2 (M+H); Found: 365.2.

F. 6-tert-Butyl-8-methyl-2-(3-methyl-1-benzofuran-2-yl)quinazolin-4-ol. To a 50-mL round-bottom flask was placed a solution of N-(4-tert-butyl-2-carbamoyl-6-methylphenyl)-3-methyl-1-benzofuran-2-carboxamide (130 mg, 0.36 mmol, as prepared in the previous step) in EtOH then NaOH (44 mg, 1.10 mmol) was added. The reaction was stirred for 3 h at 80° C. then quenched by the addition of water, and extracted with DCM. The organic extracts were combined, dried over anhydrous $Na_2SO_4$, and concentrated under reduced pressure affording 124 mg of the title compound as a white solid. Mass Spectrum (LCMS, ESI pos): Calcd. for $C_{22}H_{23}N_2O_2^+$: 347.2 (M+H); Found: 347.2.

G. 6-tert-Butyl-4-chloro-8-methyl-2-(3-methyl-1-benzofuran-2-yl)quinazoline. To a 50-mL round-bottom flask was placed a solution of 6-tert-butyl-8-methyl-2-(3-methyl-1-benzofuran-2-yl)quinazolin-4-ol (124 mg, 0.36 mmol, as prepared in the previous step) in DCM then DMF (0.2 mL) and oxalyl chloride (91 mg, 0.72 mmol) were added. The reaction was stirred for 30 min at rt then quenched by the addition of ice-water and extracted with DCM. The organic extracts were combined, dried over anhydrous $Na_2SO_4$, and concentrated under reduced pressure affording 130 mg of the title compound as a light yellow solid. Mass Spectrum (LCMS, ESI pos): Calcd. for $C_{22}H_{22}ClN_2O^+$: 365.1 (M+H); Found: 365.1.

H. 6-tert-Butyl-8-methyl-2-(3-methyl-1-benzofuran-2-yl)quinazoline-4-carbonitrile. To a 25-mL round-bottom flask was placed a solution of 6-tert-butyl-4-chloro-8-methyl-2-(3-methyl-1-benzofuran-2-yl)quinazoline (130 mg, 0.36 mmol, as prepared in the previous step) in DMF then $ZnCN_2$ (76 mg) and $Pd(PPh_3)_4$ (41 mg, 0.04 mmol) were added under nitrogen. The reaction was heated to 130° C. for 2 h under microwave irradiation then quenched by the addition of water and extracted with DCM. The organic extracts were combined, dried over anhydrous $Na_2SO_4$, and concentrated under reduced pressure affording 110 mg (87%) of the title compound as a yellow solid. Mass Spectrum (LCMS, ESI pos): Calcd. for $C_{23}H_{22}N_3O^+$: 356.2 (M+H); Found: 356.2.

I. 6-tert-Butyl-8-methyl-2-(3-methylbenzofuran-2-yl)quinazoline-4-carboxamide. To a 100-mL round-bottom flask was placed a solution of 6-tert-butyl-8-methyl-2-(3-methyl-1-benzofuran-2-yl)quinazoline-4-carbonitrile (100 mg, 0.28 mmol, as prepared in the previous step) in THF then $K_2CO_3$ (117 mg, 0.85 mmol) and $H_2O_2$ (4 mL) were added. The reaction was stirred for 3 h at rt then quenched by the addition of aqueous $NaHSO_3$ solution and extracted with DCM. The organic extracts were combined, dried over anhydrous $Na_2SO_4$, and concentrated under reduced pressure affording 120 mg of the title compound as a yellow solid. Mass Spectrum (LCMS, ESI pos): Calcd. for $C_{23}H_{24}N_3O_2^+$: 374.2 (M+H); Found: 374.2.

J. 6-tert-Butyl-8-methyl-2-(3-methyl-1-benzofuran-2-yl)quinazoline-4-carboxylic acid. To a 100-mL round-bottom flask was placed a solution of the 6-tert-butyl-8-methyl-2-(3-methylbenzofuran-2-yl)quinazoline-4-carboxamide (105 mg, 0.280 mmol, as prepared in the previous step) in EtOH then NaOH (112 mg, 2.80 mmol) was added. The reaction was stirred for 5 h at 75° C. then quenched by the addition of water. The pH of the solution was adjusted to 3 with 2N HCl and the precipitate was isolated by filtration, washed with water, and dried affording 48 mg of the title compound as a yellow solid. Mass Spectrum (LCMS, ESI pos): Calcd. for $C_{23}H_{23}N_2O_3^+$: 375.2 (M+H); Found: 375.0. $^1$H NMR (300 MHz, CD$_3$OD): δ 8.09 (s, 1H), 7.97 (s, 1H), 7.71 (d, J=7.8 Hz, 1H), 7.60 (d, J=8.1 Hz, 1H), 7.41 (t, J=7.5 Hz, 1H), 7.32 (t, J=7.2 Hz, 1H), 2.89 (s, 3H), 2.83 (s, 3H), 1.44 (s, 9H). HPLC purity (254 nm): 95.0%.

Example 21: Preparation of 5-(Benzylamino)-8-methyl-2-(3-methyl-1-benzofuran-2-yl)quinoline-4-carboxylic acid (Compound 116)

A. N-Benzyl-4-methyl-3-nitroaniline. To a 100-mL round-bottom flask was placed a solution of 4-methyl-3-nitroaniline (1 g, 6.57 mmol) and benzaldehyde (0.8 mL) in DCE (20 mL) then the solution was cooled to 0° C. and NaBH(OAc)$_3$ (2.1 g, 9.91 mmol) was added in several portions with stirring. The reaction was stirred for 16 h at 60° C., quenched by the addition of water, and extracted with DCM. The organic extracts were combined, washed with brine, dried over Na$_2$SO$_4$, and concentrated under reduced pressure. The residue was purified by column chromatography eluting with petroleum ether/EtOAc (10:1) affording 760 mg (48%) of the title compound as a red solid.

B. $N^1$—Benzyl-4-methylbenzene-1,3-diamine. To a 25-mL round-bottom flask purged and maintained with an inert atmosphere of N$_2$, was placed a solution of N-benzyl-4-methyl-3-nitroaniline (243 mg, 1.00 mmol, as prepared in the previous step) in MeOH (5 mL) then Pd on carbon (20 mg) was added. The solution was degassed and back-filled with H$_2$ and stirred for 5 h at rt. The H$_2$ was purged then the solids were removed by filtration. The filtrate was concentrated under reduced pressure affording 200 mg (94%) of the title compound as a yellow solid. Mass Spectrum (LCMS, ESI pos): Calcd. for $C_{14}H_{17}N_2^+$: 213.1 (M+H); Found: 213.1.

C. 1-Benzyl-6-methyl-4-(3-methylbenzofuran-2-yl)pyrrolo[4,3,2-de]quinolin-2(1H)-one. To an 8-mL vial was placed a solution of $N^1$-benzyl-4-methylbenzene-1,3-diamine (212 mg, 1.00 mmol, as prepared in the previous step) in EtOH (3 mL) then added 3-methyl-1-benzofuran-2-carbaldehyde (160 mg, 1.00 mmol) and 2-oxopropanoic acid (352 mg, 4.00 mmol) were added. The reaction was heated to 100° C. for 2 h under microwave irradiation, cooled to rt, and the precipitate was isolated by filtration affording 70 mg (17%) of the title compound as a yellow solid. Mass Spectrum (LCMS, ESI pos): Calcd. for $C_{27}H_{21}N_2O_2^+$: 405.2 (M+H); Found: 405.2.

D. 5-(Benzylamino)-8-methyl-2-(3-methyl-1-benzofuran-2-yl)quinoline-4-carboxylic acid. To a 25-mL round-bottom flask was placed a solution of 1-benzyl-6-methyl-4-(3-methylbenzofuran-2-yl)pyrrolo[4,3,2-de]quinolin-2(1H)-one (15 mg, 0.04 mmol, as prepared in the previous step) in water (3 mL) then NaOH (15 mg, 0.38 mmol) was added. The reaction was stirred for 1 h at rt then concentrated under reduced pressure. The crude product was purified by Flash-Prep-HPLC (IntelFlash-1: Column, C18; mobile phase, MeCN/H$_2$O=5% increasing to MeCN/H$_2$O=30% within 9.6 min; Detector, UV 254 nm) and further purified by Prep-HPLC (Column: X Bridge C18 OBD Prep Column, 19 mm*250 mm; mobile phase, Water (0.05% NH$_4$HCO$_3$) and MeCN (40.0% MeCN up to 55.0% in 10 min; Detector, uv 254 nm) affording 9.8 mg (63%) of the title compound as a yellow solid. Mass Spectrum (LCMS, ESI pos): Calcd. for $C_{27}H_{23}N_2O_3^+$: 423.2 (M+H); Found: 423.2. $^1$H NMR (300 MHz, DMSO-d$_6$): δ 7.82 (s, 1H), 7.75 (d, J=7.5 Hz, 1H), 7.66 (d, J=8.7 Hz, 1H), 7.53-7.46 (m, 3H), 7.42-7.39 (m, 5H), 7.35-7.23 (m, 5H), 6.39 (d, J=7.2 Hz, 1H), 4.36 (s, 2H), 2.84 (s, 3H), 2.62 (s, 3H). HPLC purity (254 nm): 95.1%.

Example 22: Preparation of 8-Ethyl-2-(3-methyl-1-benzothiophen-2-yl)-5-[2-(pyridin-3-yl)ethoxy]quinoline-4-carboxylic acid (Compound 141)

A. 5-(Benzyloxy)-8-ethyl-2-(3-methyl-1-benzothiophen-2-yl)quinoline-4-carbonyl chloride. To a 25-mL round-bottom flask purged and maintained with an inert atmosphere of nitrogen, was placed a solution of 5-(benzyloxy)-8-ethyl-2-(3-methyl-1-benzothiophen-2-yl)quinoline-4-carboxylic acid (71 mg, 0.16 mmol, Compound 133) and DMF (20 mg, 0.27 mmol) in DCM (5 mL) then the solution was cooled to 0° C. and oxalyl chloride (20 mg, 0.16 mmol) was added dropwise with stirring. The reaction was stirred for 30 min at rt then concentrated under reduced pressure affording 78 mg of the title compound as a yellow solid. Mass Spectrum (LCMS, ESI pos): Calcd. for $C_{28}H_{23}ClNO_2S^+$: 472.1 (M+H); Found: 473.0.

B. Methyl 5-(Benzyloxy)-8-ethyl-2-(3-methyl-1-benzothiophen-2-yl)quinoline-4-carboxylate. To a 25-mL round-bottom flask was placed 5-(benzyloxy)-8-ethyl-2-(3-methyl-1-benzothiophen-2-yl)quinoline-4-carbonyl chloride (78 mg, 0.17 mmol, as prepared in the previous step) then MeOH (10 mL) was added. The resulting solution was stirred for 5 min at rt then concentrated under reduced pressure affording 73 mg (94%) of the title compound as a yellow solid. Mass Spectrum (LCMS, ESI pos): Calcd. for $C_{29}H_{26}NO_3S^+$: 468.2 (M+H); Found: 468.3.

C. Methyl 8-Ethyl-5-hydroxy-2-(3-methyl-1-benzothiophen-2-yl)quinoline-4-carboxylate. To a 50-mL round-bottom flask purged and maintained with an inert atmosphere of N$_2$, was placed a solution of methyl 5-(benzyloxy)-8-ethyl-2-(3-methyl-1-benzothiophen-2-yl)quinoline-4-carboxylate (94 mg, 0.20 mmol, as prepared in the previous step) in MeOH (10 mL) then Pd on carbon (20 mg) was added. The reaction was stirred for 10 h at rt under an atmosphere of H$_2$ then the H$_2$ was purged and the solids were removed by filtration. The filtrate was concentrated under reduced pressure affording 68 mg (90%) of the title compound as a yellow solid. Mass Spectrum (LCMS, ESI pos): Calcd. for $C_{22}H_{20}NO_3S^+$: 378.1 (M+H); Found: 378.5.

D. Methyl 8-Ethyl-2-(3-methyl-1-benzothiophen-2-yl)-5-[2-(pyridin-3-yl)ethoxy]quinoline-4-carboxylate. To a 50-mL 3-necked round-bottom flask purged and maintained with an inert atmosphere of nitrogen, was placed a solution of methyl 8-ethyl-5-hydroxy-2-(3-methyl-1-benzothiophen-2-yl)quinoline-4-carboxylate (50 mg, 0.13 mmol, as prepared in the previous step) in THF (10 mL) then 2-(pyridin-3-yl)ethan-1-ol (24.47 mg, 0.20 mmol), PPh$_3$ (42 mg) were added. The solution was cooled to 0° C. then DIAD (32.3 mg) was added dropwise with stirring. The reaction was stirred for 2 h at rt, quenched by the addition of water, and extracted with EtOAc. The organic extracts were combined, dried over Na$_2$SO$_4$, and concentrated under reduced pressure. The residue was purified by column chromatography eluting with EtOAc/petroleum ether (1:1) affording 53 mg (83%) of the title compound as a yellow solid. Mass Spectrum (LCMS, ESI pos): Calcd. for $C_{29}H_{27}N_2O_3S^+$: 483.2 (M+H); Found: 483.6.

E. 8-Ethyl-2-(3-methyl-1-benzothiophen-2-yl)-5-[2-(pyridin-3-yl)ethoxy]quinoline-4-carboxylic acid. To a 50-mL round-bottom flask was placed a solution of methyl 8-ethyl-2-(3-methyl-1-benzothiophen-2-yl)-5-[2-(pyridin-3-yl)ethoxy]quinoline-4-carboxylate (53 mg, 0.11 mmol, as prepared in the previous step) in MeOH (5 mL) then KOH (38 mg, 0.68 mmol) was added. The reaction was stirred for 24 h at 100° C. then concentrated under vacuum. The crude product was purified by Flash-Prep-HPLC (IntelFlash-1: Column, C18; mobile phase, MeCN/H$_2$O=60% increasing to MeCN/H$_2$O=95% within 25 min; Detector, UV 254 nm) affording 5.8 mg (11%) of the title compound as a yellow solid. Mass Spectrum (LCMS, ESI pos): Calcd. for C$_{28}$H$_{25}$N$_2$O$_3$S$^+$: 469.2 (M+H); Found: 469.2. $^1$H NMR (400 MHz, DMSO-d$_6$): δ 8.89 (s, 1H), 8.69 (d, J=5.2 Hz, 1H), 8.58 (d, J=8.4 Hz, 1H), 7.96-7.91 (m, 3H), 7.78 (s, 1H), 7.61 (d, J=8.0 Hz, 1H), 7.49-7.42 (m, 2H), 7.08 (d, J=8.0 Hz, 1H), 4.56 (t, J=5.6 Hz, 2H), 3.47 (t, J=5.6 Hz, 2H), 3.28 (q, J=7.2 Hz, 2H), 2.92 (s, 3H), 1.41 (t, J=7.2 Hz, 3H). HPLC purity (254 nm): 98.9%.

Example 23: Preparation of 8-Ethyl-5-[(3-methanesulfonylphenyl)methoxy]-2-(3-methyl-1-benzofuran-2-yl)quinoline-4-carboxylic acid (Compound 143)

A. 5-(Benzyloxy)-8-ethyl-2-(3-methyl-1-benzofuran-2-yl)quinoline-4-carbonyl chloride. To a 250-mL 3-necked round-bottom flask purged and maintained with an inert atmosphere of nitrogen, was placed a solution of 5-(benzyloxy)-8-ethyl-2-(3-methyl-1-benzofuran-2-yl)quinoline-4-carboxylic acid (500 mg, 1.14 mmol, Compound 108) and DMF (0.2 mL) in DCM (6 mL) then oxalyl chloride (189 mg, 1.49 mmol) was added dropwise with stirring. The reaction was stirred for 30 min at rt then concentrated under reduced pressure affording 485 mg of the title compound as a yellow solid.

B. Methyl 5-(Benzyloxy)-8-ethyl-2-(3-methyl-1-benzofuran-2-yl)quinoline-4-carboxylate. To a 100-mL round-bottom flask was placed 5-(benzyloxy)-8-ethyl-2-(3-methyl-1-benzofuran-2-yl)quinoline-4-carbonyl chloride (1 g, 2.19 mmol, as prepared in the previous step) then MeOH (40 mL) was added. The resulting solution was stirred for 10 min at rt then concentrated under reduced pressure affording 900 mg (91%) of the title compound as a yellow solid. Mass Spectrum (LCMS, ESI pos): Calcd. for C$_{29}$H$_{26}$NO$_4$$^+$: 452.2 (M+H); Found: 452.5.

C. Methyl 8-Ethyl-5-hydroxy-2-(3-methyl-1-benzofuran-2-yl)quinoline-4-carboxylate. To a 250-mL round-bottom flask was placed a solution of methyl 5-(benzyloxy)-8-ethyl-2-(3-methyl-1-benzofuran-2-yl)quinoline-4-carboxylate (700 mg, 1.55 mmol, as prepared in the previous step) in MeOH (20 mL) then concH$_2$SO$_4$ (4 mL) was added. The reaction was stirred for 12 h at 100° C. then quenched by the addition of water and extracted with EtOAc. The organic extracts were combined and concentrated under reduced pressure affording 550 mg (98%) of the title compound as a yellow solid. Mass Spectrum (LCMS, ESI pos): Calcd. for C$_{22}$H$_{20}$NO$_4$$^+$: 362.1 (M+H); Found: 362.4.

D. Methyl 8-Ethyl-5-[(3-methanesulfonylphenyl)methoxy]-2-(3-methyl-1-benzofuran-2-yl)quinoline-4-carboxylate. To a 100-mL round-bottom flask was placed a solution of methyl 8-ethyl-5-hydroxy-2-(3-methyl-1-benzofuran-2-yl)quinoline-4-carboxylate (140 mg, 0.39 mmol, as prepared in the previous step) in acetone (6 mL) then 1-(bromomethyl)-3-methanesulfonylbenzene (98 mg, 0.39 mmol) and K$_2$CO$_3$ (108 mg, 0.78 mmol) were added. The reaction was stirred for 3 h at 80° C. then the solids were removed by filtration. The filtrate was concentrated under reduced pressure affording 100 mg (49%) of the title compound as a yellow solid. Mass Spectrum (LCMS, ESI pos): Calcd. for C$_{30}$H$_{28}$NO$_6$S$^+$: 530.2 (M+H); Found: 530.6.

E. 8-Ethyl-5-[(3-methanesulfonylphenyl)methoxy]-2-(3-methyl-1-benzofuran-2-yl)quinoline-4-carboxylic acid. To a 100-mL round-bottom flask was placed a solution of methyl 8-ethyl-5-[(3-methanesulfonylphenyl)methoxy]-2-(3-methyl-1-benzofuran-2-yl)quinoline-4-carboxylate (100 mg, 0.19 mmol, as prepared in the previous step) in MeOH/water (6 mL) then KOH (5 mg, 0.09 mmol) was added. The reaction was stirred for 12 h at 80° C. then concentrated under reduced pressure. The crude product was purified by Prep-HPLC (HPLC-10: Column, X Bridge C18 OBD Column 19*150 mm 5 um C-0013; mobile phase, Water (0.05% TFA) and ACN (60% ACN up to 95% in 15 min); Detector, 254 nm) affording 15.4 mg (16%) of the title compound as a light yellow solid. Mass Spectrum (LCMS, ESI pos): Calcd. for C$_{29}$H$_{26}$NO$_6$S$^+$: 516.2 (M+H); Found: 516.2. $^1$H NMR (300 MHz, DMSO-d$_6$): δ 13.48 (brs, 1H), 8.09 (s, 1H), 7.91 (s, 1H), 7.90-7.88 (m, 2H), 7.78 (d, J=7.2 Hz, 1H), 7.71-7.62 (m, 3H), 7.44 (t, J=6.3 Hz, 1H), 7.34 (t, J=7.2 Hz, 1H), 7.18 (d, J=8.1 Hz, 1H), 5.43 (s, 2H), 3.25 (s, 3H), 3.19 (q, J=7.5 Hz, 5H), 2.80 (s, 3H), 1.33 (t, J=7.5 Hz, 3H). HPLC purity (254 nm): 99.0%.

Example 24: Preparation of 8-Ethyl-5-[(3-methanesulfinylphenyl)methoxy]-2-(3-methyl-1-benzofuran-2-yl)quinoline-4-carboxylic acid (Compound 142)

A. Methyl 8-Ethyl-2-(3-methylbenzofuran-2-yl)-5-((3-(methylthio)benzyl)oxy)quinoline-4-carboxylate. To a 100-mL 3-necked round-bottom flask was placed a solution of methyl 8-ethyl-5-hydroxy-2-(3-methyl-1-benzofuran-2-yl)quinoline-4-carboxylate (300 mg, 0.83 mmol, as prepared in Example 23, Step C) in THF (5 mL) then [3-(methylthio)phenyl]methanol (153 mg, 0.99 mmol) and PPh$_3$ (261 mg) were added. The solution was cooled to 0° C. then DIAD (201 mg) was added dropwise with stirring. The reaction was stirred for 2 h at rt then quenched by the addition of water and concentrated under reduced pressure. The residue was purified by column chromatography eluting with EtOAc/petroleum ether (1:4) affording 280 mg (68%) of the title compound as a yellow solid. Mass Spectrum (LCMS, ESI pos): Calcd. for C$_{30}$H$_{28}$NO$_4$S$^+$: 498.2 (M+H); Found: 498.6.

B. Methyl 8-Ethyl-5-[(3-methanesulfinylphenyl)methoxy]-2-(3-methyl-1-benzofuran-2-yl)quinoline-4-carboxylate. To a 50-mL round-bottom flask was placed a solution of methyl 8-ethyl-2-(3-methylbenzofuran-2-yl)-5-((3-(methylthio)benzyl)oxy)quinoline-4-carboxylate (90 mg, 0.18 mmol, as prepared in the previous step) in DCM (3 mL) then the solution was cooled to 0° C. and mCPBA (35 mg) was added in several portions with stirring. The reaction was stirred for 5 min at 0° C. then quenched by the addition of water and extracted with EtOAc. The organic extracts were combined and concentrated under reduced pressure affording 40 mg (43%) of the title compound as a yellow solid. Mass Spectrum (LCMS, ESI pos): Calcd. for C$_{30}$H$_{28}$NO$_5$S$^+$: 514.2 (M+H); Found: 514.6.

C. 8-Ethyl-5-[(3-methanesulfinylphenyl)methoxy]-2-(3-methyl-1-benzofuran-2-yl)quinoline-4-carboxylic acid. To a 50-mL round-bottom flask was placed a solution of methyl 8-ethyl-5-[(3-methanesulfinylphenyl)methoxy]-2-(3-methyl-1-benzofuran-2-yl)quinoline-4-carboxylate (126 mg, 0.25 mmol, as prepared in the previous step) in MeOH/water (5 mL) then KOH (13 mg, 0.23 mmol) was added. The reaction was stirred for 12 h at 80° C. then concentrated under reduced pressure. The crude product was purified by Flash-Prep-HPLC (IntelFlash-1: Column, C18; mobile phase, ACN/H$_2$O: 10/90 increasing to ACN/H$_2$O: 95/5 within 20 min; Detector, UV 254 nm) affording 15.4 mg (13%) of the title compound as a light yellow solid. Mass Spectrum (LCMS, ESI pos): Calcd. for C$_{29}$H$_{26}$NO$_5$S$^+$: 500.2 (M+H); Found: 500.2. $^1$H NMR (300 MHz, DMSO-d$_6$): δ 13.53 (brs, 1H), 7.90 (s, 1.04), 7.83-7.77 (m, 2H), 7.68-7.59 (m, 5H), 7.44 (t, J=8.0 Hz, 1H), 7.34 (t, J=7.6 Hz, 1H), 7.16 (d, J=8.0 Hz, 1H), 5.39 (s, 2H), 3.19 (q, J=7.6 Hz, 2H), 2.85 (s, 3H), 2.78 (s, 3H), 1.32 (t, J=7.6 Hz, 3H). HPLC purity (254 nm): 99.8%.

Using the procedure described in Example 24, with reagents, starting materials, and conditions familiar to those skilled in the art, the following compounds representative of the disclosure were prepared:

was purified by column chromatography eluting with petroleum ether/EtOAc (15:1) affording 5.0 g (78%) of the title compound as a yellow solid.

C. 2-Ethyl-5-[(3-methylcyclohexyl)oxy]aniline. To a 500-mL round-bottom flask was placed a solution of 1-ethenyl-4[(3-methylcyclohexyl)oxy]-2-nitrobenzene (4.5 g, 17.22 mmol, as prepared in the previous step) in MeOH (150 mL) then Pd on carbon (500 mg) was added. The solution was degassed and back-filled with H$_2$. The reaction was stirred for 2 h at rt then the H$_2$ was purged and the solids were removed by filtration. The filtrate was concentrated under reduced pressure affording 3.8 g (95%) of the title compound as a yellow oil. Mass Spectrum (LCMS, ESI pos): Calcd. for C$_{15}$H$_{24}$NO$^+$: 234.2 (M+H); Found: 234.3.

D. 2-(1-Benzothiophen-3-yl)-8-ethyl-5-[[(1S,3R)-3-methylcyclohexyl]oxy]quinoline-4-carboxylic acid (Compound 181), 2-(Benzo[b]thiophen-3-yl)-8-ethyl-5-(((1R,

| Compound | Name and Data |
|---|---|
| 144 | 8-Ethyl-5-[(4-methanesulfinylphenyl)methoxy]-2-(3-methyl-1-benzofuran-2-yl)quinoline-4-carboxylic acid<br>Mass Spectrum (LCMS, ESI pos): Calcd. for C$_{29}$H$_{26}$NO$_5$S$^+$: 500.2 (M + H); Found: 500.2. $^1$H NMR (300 MHz, DMSO-d$_6$): δ 13.55 (brs, 1H), 7.92 (s, 1H), 7.79-7.60 (m, 7H), 7.44 (t, J = 7.2 Hz, 1H), 7.34 (t, J = 7.8 Hz, 1H), 7.15 (d, J = 8.1 Hz, 1H), 5.38 (s, 1H), 3.18 (q, J = 6.9 Hz, 2H), 2.84 (s, 3H), 2.74-2.71 (s, 3H), 1.32 (t, J = 7.5 Hz, 3H). HPLC purity (254 nm): 98.8%. |
| 145 | 8-Ethyl-5-[(4-methanesulfonylphenyl)methoxy]-2-(3-methyl-1-benzofuran-2-yl)quinoline-4-carboxylic acid<br>Mass Spectrum (LCMS, ESI pos): Calcd. for C$_{29}$H$_{26}$NO$_6$S$^+$: 516.2 (M + H); Found: 516.2. $^1$H NMR (300 MHz, DMSO-d$_6$): δ 13.55 (brs, 1H), 7.97-7.93 (m, 3H), 7.81-7.77 (m, 3H), 7.69-7.61 (m, 2H), 7.44 (t, J = 7.8 Hz, 1H), 7.36 (t, J = 6.9 Hz, 1H), 7.15 (d, J = 7.8 Hz, 1H), 5.44 (s, 2H), 3.22 (s, 3H), 3.21-3.16 (m, 2H), 2.85 (s, 3H), 1.35-1.30 (t, J = 7.5 Hz, 3H). HPLC purity (254 nm): 95.8%. |

Example 25: Preparation of 2-(1-Benzo[b]thiophen-3-yl)-8-ethyl-5-[[(1S,3R)-3-methylcyclohexyl]oxy] quinoline-4-carboxylic acid (Compound 181), 2-(Benzo[b]thiophen-3-yl)-8-ethyl-5-(((1R,3S)-3-methylcyclohexyl)oxy)quinoline-4-carboxylic acid (Compound 182), 2-(Benzo[b]thiophen-3-yl)-8-ethyl-5-(((1S,3S)-3-methylcyclohexyl)oxy)quinoline-4-carboxylic acid (Compound 183), and 2-(Benzo[b]thiophen-3-yl)-8-ethyl-5-(((1R,3R)-3-methylcyclohexyl)oxy)quinoline-4-carboxylic acid (Compound 184)

A. 1-Chloro-4-[(3-methylcyclohexyl)oxy]-2-nitrobenzene. To a 500-mL round-bottom flask purged and maintained with an inert atmosphere of nitrogen, was placed a solution of 4-chloro-3-nitrophenol (8.5 g, 48.98 mmol) in THF (300 mL) then 3-methylcyclohexan-1-ol (5.6 g, 49.04 mmol) and PPh$_3$ (15.4 g, 58.71 mmol) were added. The solution was cooled to 0° C. and DIAD (11.9 g, 58.85 mmol) was added dropwise with stirring. The reaction was stirred for 2 h at 0° C. then concentrated under reduced pressure. The residue was purified by column chromatography eluting with EtOAc/petroleum ether (1/16) affording 6.9 g (52%) of the title compound as a yellow solid.

B. 1-Ethenyl-4-[(3-methylcyclohexyl)oxy]-2-nitrobenzene. To a 250-mL round-bottom flask purged and maintained with an inert atmosphere of nitrogen, was placed a solution of 1-chloro-4[(3-methylcyclohexyl)oxy]-2-nitrobenzene (6.6 g, 24.47 mmol, as prepared in the previous step) in dioxane (40 mL) then 2-ethenyl-4,4,5,5-tetramethyl-1,3,2-dioxaborolane (8.24 g, 53.50 mmol), PCy$_3$.HBF$_4$ (7.2 g), K$_3$PO$_4$ (31.2 g, 146.98 mmol), and Pd(OAc)$_2$ (2.2 g, 9.80 mmol) were added. The reaction was stirred for 3 h at 110° C. then concentrated under reduced pressure. The residue 3S)-3-methylcyclohexyl)oxy)quinoline-4-carboxylic acid (Compound 182), 2-(Benzo[b]thiophen-3-yl)-8-ethyl-5-(((1S,3S)-3-methylcyclohexyl) oxy)quinoline-4-carboxylic acid (Compound 183), and 2-(Benzo[b]thiophen-3-yl)-8-ethyl-5-(((1R,3R)-3-methylcyclohexyl)oxy)quinoline-4-carboxylic acid (Compound 184). To a 20-mL sealed tube purged and maintained with an inert atmosphere of nitrogen, was placed a solution of 2-ethyl-5-[(3-methylcyclohexyl)oxy]aniline (1.0 g, 4.29 mmol, as prepared in the previous step) in EtOH (10 mL) then 2-oxopropanoic acid (1.13 g, 12.83 mmol) and 1-benzothiophene-3-carbaldehyde (626 mg, 3.86 mmol) were added. The reaction was stirred overnight at 120° C. then concentrated under reduced pressure. The crude product was purified by Flash-Prep-HPLC (IntelFlash-1: Column, C18; mobile phase, ACN, water (0.5% TFA) and ACN (80.0% ACN up to 95.0% in 15 min); Detector, UV 254 nm) then the isomers were separated by Prep-SFC (Prep SFC350-2: Column, CHIRALPAK AD-H SFC, 5*25 cm, 5 um; mobile phase, CO$_2$ (50%), ethanol (2 mM NH$_3$-MeOH); Detector, UV 254 nm) affording 56.7 mg (3%) of 2-(1-benzothiophen-3-yl)-8-ethyl-5-[[(1R,3S)-3-methylcyclohexyl]oxy]quinoline-4-carboxylic acid (Compound 182) as a light yellow solid, 53.9 mg (4%) of 2-(1-benzothiophen-3-yl)-8-ethyl-5-[[(1R,3R)-3-methylcyclohexyl]oxy]quinoline-4-carboxylic acid (Compound 184) as a light yellow solid and a mixture of Compound 181 and Compound 183. This mixture was separated by Chiral-Prep-HPLC (HPLC-09: Column: CHIRALPAK-AD-H-SL002, 20*250 mm; Mobile Phase A: Hex—HPLC, Mobile Phase B: IPA—HPLC; Flow rate: 15 mL/min; Gradient: 40 B to 40 B in 16 min; 254 nm) affording 55.7 mg (3%) of 2-(1-benzothiophen-3-yl)-8-ethyl-5-[[(1S,3R)-3-methylcyclohexyl]oxy]quinoline-4-carboxylic acid (Compound 181) as a brown solid and 56.8 mg (3%) of 2-(1-benzothiophen-3- yl)-8-ethyl-5-[[(1S,3S)-3-methylcyclohexyl]oxy]quinoline-4-carboxylic acid (Compound 183) as a brown solid.

2-(1-Benzothiophen-3-yl)-8-ethyl-5-[[(1S,3R)-3-methylcyclohexyl]oxy]quinoline-4-carboxylic acid (Compound 181)

Mass Spectrum (LCMS, ESI pos): Calcd. for $C_{27}H_{28}NO_3S^+$: 446.2 (M+H); Found: 446.2. $^1$H NMR (300 MHz, DMSO-$d_6$): δ 13.14 (brs, 1H), 9.26 (d, J=7.5 Hz, 1H), 8.81 (s, 1H), 8.12 (d, J=7.8 Hz, 1H), 8.04 (s, 1H), 7.46-7.61 (m, 3H), 7.02 (d, J=8.1 Hz, 1H), 4.86-4.85 (m, 1H), 3.25 (q, J=7.5 Hz, 2H), 1.97-1.72 (m, 4H), 1.70-1.61 (m, 1H), 1.60-1.45 (m, 2H), 1.37 (t, J=7.5 Hz, 3H), 1.10-0.93 (m, 1H), 0.87 (d, J=6.3 Hz, 1H). HPLC purity (254 nm): 99.5%.

2-(Benzo[b]thiophen-3-yl)-8-ethyl-5-(((1R,3S)-3-methylcyclohexyl)oxy)quinoline-4-carboxylic acid (Compound 182)

Mass Spectrum (LCMS, ESI pos): Calcd. for $C_{27}H_{28}NO_3S^+$: 446.2 (M+H); Found: 446.2. $^1$H NMR (300 MHz, DMSO-$d_6$): δ 13.14 (brs, 1H), 9.26 (d, J=7.5 Hz, 1H), 8.81 (s, 1H), 8.12 (d, J=7.8 Hz, 1H), 8.04 (s, 1H), 7.46-7.61 (m, 3H), 7.02 (d, J=8.1 Hz, 1H), 4.86-4.85 (m, 1H), 3.25 (q, J=7.5 Hz, 2H), 1.97-1.72 (m, 4H), 1.70-1.61 (m, 1H), 1.60-1.45 (m, 2H), 1.37 (t, J=7.5 Hz, 3H), 1.10-0.93 (m, 1H), 0.87 (d, J=6.3 Hz, 1H). HPLC purity (254 nm): 99.7%.

2-(Benzo[b]thiophen-3-yl)-8-ethyl-5-(((1S,3S)-3-methylcyclohexyl)oxy)quinoline-4-carboxylic acid (Compound 183)

Mass Spectrum (LCMS, ESI pos): Calcd. for $C_{27}H_{28}NO_3S^+$: 446.2 (M+H); Found: 446.2. $^1$H NMR (300 MHz, DMSO-$d_6$): δ 13.14 (s, 1H), 9.27 (d, J=7.8 Hz, 1H), 8.81 (s, 1H), 8.12 (d, J=7.8 Hz, 1H), 8.04 (s, 1H), 7.46-7.61 (m, 3H), 7.11 (d, J=8.1 Hz, 1H), 4.50-4.57 (m, 1H), 3.24 (q, J=7.5 Hz, 2H), 2.10-2.13 (m, 2H), 1.47-1.80 (m, 3H), 1.29-1.43 (m, 5H), 1.10-1.28 (m, 1H), 0.94 (d, J=6.6 Hz, 3H), 0.79-0.89 (m, 1H). HPLC purity (254 nm): 99.6%.

2-(Benzo[b]thiophen-3-yl)-8-ethyl-5-(((1R,3R)-3-methylcyclohexyl)oxy)quinoline-4-carboxylic acid (Compound 184)

Mass Spectrum (LCMS, ESI pos): Calcd. for $C_{27}H_{28}NO_3S^+$: 446.2 (M+H); Found: 446.2. $^1$H NMR (300 MHz, DMSO-$d_6$): δ 13.14 (s, 1H), 9.27 (d, J=7.8 Hz, 1H), 8.81 (s, 1H), 8.12 (d, J=7.8 Hz, 1H), 8.04 (s, 1H), 7.46-7.61 (m, 3H), 7.11 (d, J=8.1 Hz, 1H), 4.50-4.57 (m, 1H), 3.24 (q, J=7.5 Hz, 2H), 2.10-2.13 (m, 2H), 1.47-1.80 (m, 3H), 1.29-1.43 (m, 5H), 1.10-1.28 (m, 1H), 0.94 (d, J=6.6 Hz, 3H), 0.79-0.89 (m, 1H). HPLC purity (254 nm): 99.7%.

Using the procedure described in Example 25, with reagents, starting materials, and conditions familiar to those skilled in the art, the following compounds representative of the disclosure were prepared:

| Compound | Name and Data |
|---|---|
| 214 | Sodium 8-Ethyl-2-(3-methyl-1-benzothiophen-2-yl)-5-[[(1R,3S)-3-methylcyclohexyl]oxy]quinoline-4-carboxylate<br>Mass Spectrum (LCMS, ESI pos): Calcd. for $C_{28}H_{30}NO_3S^+$: 460.2 (M + H); Found: 460.3. $^1$H NMR (300 MHz, DMSO-$d_6$): δ 8.02-7.99 (m, 1H), 7.92-7.89 (m, 1H), 7.48-7.40 (m, 3H), 7.38 (s, 1H), 6.77 (d, J = 8.1 Hz, 1H), 4.71 (br s, 1H), 3.14 (q, J = 7.2 Hz, 2H), 2.80 (s, 3H), 2.21-2.13 (m, 2H), 2.02-1.91 (m, 2H), 1.64-1.61 (m, 1H), 1.42-1.29 (m, 5H), 1.18-1.14 (m, 1H), 0.93-0.88 (m, 1H), 0.81 (d, J = 6.9 Hz, 3H). HPLC purity (254 nm): 98.2%. |
| 215 | Sodium 8-Ethyl-2-(3-methyl-1-benzothiophen-2-yl)-5-[[(1S,3R)-3-methylcyclohexyl]oxy]quinoline-4-carboxylate<br>Mass Spectrum (LCMS, ESI pos): Calcd. for $C_{28}H_{30}NO_3S^+$: 460.2 (M + H); Found: 460.2. $^1$H NMR (300 MHz, DMSO-$d_6$): δ 8.02-7.99 (m, 1H), 7.92-7.88 (m, 1H), 7.48-7.40 (m, 3H), 7.37 (s, 1H), 6.77 (d, J = 8.1 Hz, 1H), 4.71 (br s, 1H), 3.13 (q, J = 7.5 Hz, 2H), 2.79 (s, 3H), 2.22-2.13 (m, 2H), 2.02-1.91 (m, 2H), 1.64-1.60 (m, 1H), 1.41-1.35 (m, 2H), 1.32 (t, J = 7.5 Hz, 3H), 1.18-1.13 (m, 1H), 0.92-0.87 (m, 1H), 0.81 (d, J = 6.9 Hz, 3H). HPLC purity (254 nm): 99.6%. |
| 216 | Sodium 8-Ethyl-2-(3-methyl-1-benzothiophen-2-yl)-5-[[(1S,3S)-3-methylcyclohexyl]oxy]quinoline-4-carboxylate<br>Mass Spectrum (LCMS, ESI pos): Calcd. for $C_{28}H_{30}NO_3S^+$: 460.2 (M + H); Found: 460.3. $^1$H NMR (300 MHz, DMSO-$d_6$): δ 8.02-7.99 (m, 1H), 7.92-7.88 (m, 1H), 7.48-7.40 (m, 3H), 7.36 (s, 1H), 6.88 (d, J = 8.1 Hz, 1H), 4.35-4.33 (m, 1H), 3.14 (q, J = 7.5 Hz, 2H), 2.79 (s, 3H), 2.06-2.03 (m, 2H), 1.76-1.59 (m, 2H), 1.48-1.35 (m, 3H), 1.32 (t, J = 7.5 Hz, 3H), 1.26-1.18 (m, 1H), 0.93 (d, J = 6.6 Hz, 3H), 0.88-0.84 (m, 1H). HPLC purity (254 nm): 97.7%. |
| 217 | Sodium 8-Ethyl-2-(3-methyl-1-benzothiophen-2-yl)-5-[[(1R,3R)-3-methylcyclohexyl]oxy]quinoline-4-carboxylate<br>Mass Spectrum (LCMS, ESI pos): Calcd. for $C_{28}H_{30}NO_3S^+$: 460.2 (M + H); Found: 460.2. $^1$H NMR (300 MHz, DMSO-$d_6$): δ 8.02-7.99 (m, 1H), 7.92-7.88 (m, 1H), 7.48-7.39 (m, 3H), 7.37 (s, 1H), 6.88 (d, J = 8.1 Hz, 1H), 4.36-4.29 (m, 1H), 3.14 (q, J = 7.5 Hz, 2H), 2.79 (s, 3H), 2.07-2.03 (m, 2H), 1.76-1.59 (m, 2H), 1.48-1.40 (m, 3H), 1.32 (t, J = 7.5 Hz, 6H), 1.26-1.18 (m, 1H), 0.93 (d, J = 6.6 Hz, 3H), 0.88-0.84 (m, 1H). HPLC purity (254 nm): 99.4%. |

Example 26: Preparation of Sodium 5-(Cyclohexylsulfonyl)-8-ethyl-2-(3-methylbenzo[b]thiophen-2-yl)quinoline-4-carboxylate (Compound 139)

A. 4-(Cyclohexylsulfanyl)-1-ethyl-2-nitrobenzene. To a 500-mL round-bottom flask was placed a solution of 4-ethyl-3-nitroaniline (12 g, 72.21 mmol) in conc. HCl (216 mL), then the solution was cooled to 0° C. and NaNO$_2$ (5.2 g, 75.36 mmol) was added. The resulting solution was stirred for 30 min at 0° C., then cyclohexanethiol (8.8 g, 75.72 mmol), NaOH (41 g, 1.03 mol), and Cu (7.8 g) were added. The resulting solution was stirred at 60° C. for 8 h. The resulting solution was diluted with water and extracted with DCM. The organic extracts were combined, dried over anhydrous Na$_2$SO$_4$, and concentrated under reduced pressure affording 6.33 g (33%) of the title compound as a light yellow solid.

B. 5-(Cyclohexylsulfanyl)-2-ethylaniline. To a 500-mL round-bottom flask was placed a solution of 4-(cyclohexylsulfanyl)-1-ethyl-2-nitrobenzene (6.33 g, 23.85 mmol, as prepared in the previous step) in MeOH then SnCl$_2$ (21.05 g, 111.01 mmol) was added. The resulting solution was stirred at 75° C. for 8 h then quenched by the addition of water. The pH value of the solution was adjusted to 10 with 1M NaOH solution then extracted with DCM. The organic extracts were combined, dried over anhydrous Na$_2$SO$_4$, and concentrated under reduced pressure affording 5.23 g (93%) of the title compound as a colorless oil. Mass Spectrum (LCMS, ESI pos): Calcd. for C$_{14}$H$_{22}$NS$^+$: 236.2 (M+H); Found: 236.1.

C. 5-(Cyclohexylsulfanyl)-8-ethyl-2-(3-methyl-1-benzothiophen-2-yl)quinoline-4-carboxylic acid. To a 25-mL sealed tube was placed a solution of 5-(cyclohexylsulfanyl)-2-ethylaniline (1.5 g, 6.37 mmol, as prepared in the previous step) in EtOH (15 mL) then 3-methyl-1-benzothiophene-2-carbaldehyde (1.24 g, 7.04 mmol) and 2-oxopropanoic acid (676 mg, 7.68 mmol) were added. The reaction was stirred at 110° C. for 12 h then quenched by the addition of water and extracted with DCM. The organic extracts were combined, dried over anhydrous Na$_2$SO$_4$, and concentrated under reduced pressure. The residue was purified by column chromatography eluting with DCM/MeOH (13:1) affording 200 mg (7%) of the title compound as a yellow solid. Mass Spectrum (LCMS, ESI pos): Calcd. for C$_{27}$H$_{28}$NO$_2$S$_2^+$: 462.2 (M+H); Found: 462.1.

D. 5-(Cyclohexanesulfonyl)-8-ethyl-2-(3-methyl-1-benzothiophen-2-yl)quinoline-4-carboxylic acid. To a 100-mL round-bottom flask was placed a solution of 5-(cyclohexylsulfanyl)-8-ethyl-2-(3-methyl-1-benzothiophen-2-yl)quinoline-4-carboxylic acid (100 mg, 0.22 mmol, as prepared in the previous step) in DCM (15 mL) then m-CPBA (76 mg, 0.44 mmol) was added. The reaction was stirred for 2 h at rt then quenched by the addition of water and extracted with DCM. The organic extracts were combined, dried over anhydrous Na$_2$SO$_4$, and concentrated under reduced pressure. The residue was purified by column chromatography eluting with DCM/MeOH (13:1) affording 15 mg (14%) of the title compound as a yellow solid. Mass Spectrum (LCMS, ESI pos): Calcd. for C$_{27}$H$_{28}$NO$_4$S$_2^+$: 494.2 (M+H); Found: 494.3.

E. Sodium 5-(Cyclohexanesulfonyl)-8-ethyl-2-(3-methyl-1-benzothiophen-2-yl)quinoline-4-carboxylate (Compound 274). To a 50-mL round-bottom flask was placed a solution of 5-(cyclohexanesulfonyl)-8-ethyl-2-(3-methyl-1-benzothiophen-2-yl)quinoline-4-carboxylic acid (15 mg, 0.03 mmol, as prepared in the previous step) in MeOH (10 mL) then 0.05 M NaOH (0.6 mL) was added. The reaction was stirred for 0.5 h at rt then the solvent was removed under reduced pressure affording 11.3 mg (72%) of the title compound as a light yellow solid. Mass Spectrum (LCMS, ESI pos): Calcd. for C$_{27}$H$_{28}$NO$_4$S$_2^+$: 494.2 (M+H); Found: 494.3. $^1$H NMR (400 MHz, DMSO-d$_6$): δ 8.04 (s, 1H), 8.03-8.01 (m, 2H), 7.95-7.94 (m, 1H), 7.73 (d, J=8.0 Hz, 1H), 7.47-7.45 (m, 2H), 4.91-4.85 (m, 1H), 3.32-3.30 (m, 2H), 2.84 (s, 1H), 2.09-2.05 (m, 2H), 1.86-1.83 (m, 2H), 1.68-1.67 (m, 1H), 1.52-1.49 (m, 2H), 1.38 (t, J=7.6 Hz, 3H), 1.26-1.20 (m, 3H). HPLC purity (254 nm): 97.0%.

Example 27: Preparation of Sodium 5-(Cyclohexanesulfinyl)-8-ethyl-2-(3-methyl-1-benzothiophen-2-yl)quinoline-4-carboxylate (Compound 140)

A. To a 50-mL round-bottom flask was placed a solution of 5-(cyclohexylsulfanyl)-8-ethyl-2-(3-methyl-1-benzothiophen-2-yl)quinoline-4-carboxylic acid (70 mg, 0.15 mmol, as prepared in Example 26, Step C) in DCM (10 mL) then m-CPBA (25.8 mg, 0.15 mmol) was added. The reaction was stirred for 0.5 h at rt then quenched by the addition of water and extracted with DCM. The organic extracts were combined, dried over anhydrous Na$_2$SO$_4$, and concentrated under reduced pressure. The residue was purified by column chromatography eluting with DCM/MeOH (13:1) affording 30 mg (41%) of the title compound as a yellow solid. Mass Spectrum (LCMS, ESI pos): Calcd. for C$_{27}$H$_{28}$NO$_3$S$_2^+$: 478.2 (M+H); Found: 478.2.

B. Sodium 5-(Cyclohexanesulfinyl)-8-ethyl-2-(3-methyl-1-benzothiophen-2-yl)quinoline-4-carboxylate (Compound 275). To a 50-mL round-bottom flask was placed a solution of 5-(cyclohexanesulfinyl)-8-ethyl-2-(3-methyl-1-benzothiophen-2-yl)quinoline-4-carboxylic acid (30 mg, 0.06 mmol, as prepared in the previous step) in MeOH (10 mL) then 0.05 M NaOH (1.3 mL) was added. The reaction was stirred for 0.5 h at rt then the solvent was removed under reduced pressure affording 6.9 mg (22%) of the title compound as a light yellow solid. Mass Spectrum (LCMS, ESI pos): Calcd. for C$_{27}$H$_{28}$NO$_3$S$_2^+$: 478.2 (M+H); Found: 478.2. $^1$H NMR (400 MHz, DMSO-d$_6$): δ 8.03-8.01 (m, 1H), 7.95-7.93 (m, 2H), 7.77 (d, J=7.6 Hz, 1H), 7.58 (s, 1H), 7.48-7.43 (m, 2H), 3.36-3.23 (m, 2H), 2.99-2.96 (m, 1H), 2.81 (s, 3H), 2.18-2.16 (m, 1H), 1.79-1.76 (m, 1H), 1.66-1.63 (m, 1H), 1.55-1.52 (m, 1H), 1.45-1.41 (m, 1H), 1.40 (t, J=7.8 Hz, 3H), 1.38-1.14 (m, 3H), 1.05-0.95 (m, 3H). HPLC purity (254 nm): 99.1%.

Example 28: Preparation of Sodium 8-Methyl-2-(3-methyl-1-benzothiophen-2-yl)-5-[(1R)-1-(4-methylphenyl)ethoxy]quinoline-4-carboxylate (Compound 226) and Sodium 8-Methyl-2-(3-methyl-1-benzothiophen-2-yl)-5-[(1S)-1-(4-methylphenyl)ethoxy]quinoline-4-carboxylate (Compound 227)

A. Methyl 5-(Benzyloxy)-8-methyl-2-(3-methyl-1-benzothiophen-2-yl)quinoline-4-carboxylate. To a 50-mL round-bottom flask was placed a solution of 5-(benzyloxy)-8-methyl-2-(3-methyl-1-benzothiophen-2-yl)quinoline-4-carboxylic acid (310 mg, 0.71 mmol, Compound 33) in DCM (10 mL) then oxalyl chloride (108 mg, 0.85 mmol) and DMF (1 drop) were added. The reaction was stirred for 1 h at rt then concentrated under reduced pressure. The residue was dissolved in MeOH (10 mL) and 1 M NaOMe in MeOH (2 mL) was added. The resulting solution stirred for 3 h at rt then the solids were collected by filtration affording 209 mg (65%) of the title compound as a brown solid. Mass Spectrum (LCMS, ESI pos): Calcd. for C$_{28}$H$_{24}$NO$_3$S$^+$: 454.1 (M+H); Found: 454.6.

B. Methyl 5-Hydroxy-8-methyl-2-(3-methyl-1-benzothiophen-2-yl)quinoline-4-carboxylate. To a 50-mL round-bottom flask was placed a solution of methyl 5-(benzyloxy)-8-methyl-2-(3-methyl-1-benzothiophen-2-yl)quinoline-4-carboxylate (209 mg, 0.46 mmol, as prepared in the previous step) in MeOH (2 mL) then concentrated H$_2$SO$_4$ (4 mL) was added. The reaction was stirred overnight at 80° C. then concentrated under reduced pressure. The residue was purified by column chromatography eluting with EtOAc/petroleum ether (1:2) affording 100 mg (60%) of the title compound as a yellow solid. Mass Spectrum (LCMS, ESI pos): Calcd. for $C_{21}H_{18}NO_3S^+$: 364.1 (M+H); Found: 364.3.

C. Methyl 8-Methyl-2-(3-methyl-1-benzothiophen-2-yl)-5-[1-(4-methylphenyl)ethoxy]quinoline-4-carboxylate. To a 50-mL 3-necked round-bottom flask purged and maintained with an inert atmosphere of nitrogen was placed a solution of methyl 5-hydroxy-8-methyl-2-(3-methyl-1-benzothiophen-2-yl)quinoline-4-carboxylate (277 mg, 0.76 mmol, as prepared in the previous step) in THF (10 mL) then 1-(4-methylphenyl)ethan-1-ol (125 mg, 0.92 mmol) and $PPh_3$ (185 mg, 0.71 mmol) were added. The solution was cooled to 0° C. then DIAD (240 mg, 1.19 mmol) was added dropwise with stirring. The reaction was stirred for 3 h at rt then concentrated under reduced pressure. The residue was purified by Prep-TLC developing with EtOAc/petroleum ether (1:4) affording 100 mg (27%) of the title compound as a yellow solid. Mass Spectrum (LCMS, ESI pos): Calcd. for $C_{30}H_{28}NO_3S^+$: 482.2 (M+H); Found: 482.7.

D. 8-Methyl-2-(3-methyl-1-benzothiophen-2-yl)-5-[1-(4-methylphenyl)ethoxy]quinoline-4-carboxylic acid. To a 50-mL round-bottom flask was placed a solution of methyl 8-methyl-2-(3-methyl-1-benzothiophen-2-yl)-5-[1-(4-methylphenyl)ethoxy]quinoline-4-carboxylate (100 mg, 0.21 mmol, as prepared in the previous step) in THF/MeOH (1:1, 10 mL) then NaOH (42 mg, 1.05 mmol) and $H_2O$ (2 mL) were added. The reaction was stirred for 2 h at 90° C., cooled to rt, and the pH value of the solution was adjusted to 2-3 with 2 M HCl solution. The resulting mixture was concentrated under reduced pressure. The residue was purified by Prep-TLC developed with EtOAc/petroleum ether (1:2) and by Flash-Prep-HPLC (IntelFlash-1: Column, C18; mobile phase, MeCN/$H_2O$ (0.05% TFA)=50:50 increasing to MeCN/$H_2O$ (0.05% TFA)=95:5 within 20 min; Detector, UV 254 nm) affording 86 mg (89%) of the title compound as a yellow solid. Mass Spectrum (LCMS, ESI pos): Calcd. for $C_{29}H_{26}NO_3S^+$: 468.2 (M+H); Found: 468.2.

E. 8-Methyl-2-(3-methyl-1-benzothiophen-2-yl)-5-[(1R)-1-(4-methylphenyl)ethoxy]quinoline-4-carboxylic acid and 8-Methyl-2-(3-methyl-1-benzothiophen-2-yl)-5-[(1S)-1-(4-methylphenyl)ethoxy]quinoline-4-carboxylic acid. 8-Methyl-2-(3-methyl-1-benzothiophen-2-yl)-5-[1-(4-methylphenyl)ethoxy]quinoline-4-carboxylic acid (86 mg, 0.18 mmol, as prepared in the previous step) was purified by Chiral-Prep-HPLC (Prep-HPLC-009: Column, Chiralpak ID-2, 2*25 cm, 5 um; mobile phase, Hex (0.1% TFA) and EtOH (hold 5.0% EtOH in 19 min); Detector, UV 220/254 nm) affording 34 mg (40%) of 8-methyl-2-(3-methyl-1-benzothiophen-2-yl)-5-[(1R)-1-(4-methylphenyl)ethoxy]quinoline-4-carboxylic acid as a yellow solid and 33 mg (38%) of 8-methyl-2-(3-methyl-1-benzothiophen-2-yl)-5-[(1S)-1-(4-methylphenyl)ethoxy]quinoline-4-carboxylic acid as a yellow solid.

F. Sodium 8-Methyl-2-(3-methyl-1-benzothiophen-2-yl)-5-[(1R)-1-(4-methylphenyl)ethoxy]quinoline-4-carboxylate (Compound 225). To a 10-mL round-bottom flask was placed a solution of 8-methyl-2-(3-methyl-1-benzothiophen-2-yl)-5-[(1R)-1-(4-methylphenyl)ethoxy]quinoline-4-carboxylic acid (34 mg, 0.07 mmol, as prepared in the previous step) in MeOH (2 mL) then 0.05M NaOH solution (1.5 mL) was added. The resulting solution was stirred for 30 min at rt then the solvent was removed under reduced pressure affording 24.2 mg (68%) of the title compound as a yellow solid. Mass Spectrum (LCMS, ESI pos): Calcd. for $C_{29}H_{26}NO_3S^+$: 468.2 (M+H); Found: 468.2. $^1$H NMR (400 MHz, DMSO-$d_6$): δ 8.00 (d, J=6.8 Hz, 1H), 7.90 (d, J=6.8 Hz, 1H), 7.54 (d, J=8.0 Hz, 2H), 7.48-7.41 (m, 3H), 7.28 (d, J=7.6 Hz, 1H), 7.05 (d, J=8.0 Hz, 2H), 6.59 (d, J=8.0 Hz, 1H), 5.52 (q, J=5.6 Hz, 1H), 2.84 (s, 3H), 2.57 (s, 3H), 2.25 (s, 3H), 1.56 (d, J=6.0 Hz, 3H). HPLC purity (254 nm): 95.7%.

G. Sodium 8-Methyl-2-(3-methyl-1-benzothiophen-2-yl)-5-[(1S)-1-(4-methylphenyl)ethoxy]quinoline-4-carboxylate (Compound 226). To a 10-mL round-bottom flask was placed a solution of 8-methyl-2-(3-methyl-1-benzothiophen-2-yl)-5-[(1S)-1-(4-methylphenyl)ethoxy]quinoline-4-carboxylic acid (13 mg, 0.03 mmol, as prepared in Step E) in MeOH (2 mL) then 0.01M NaOH solution (2.8 mL) was added. The resulting solution was stirred for 30 min at rt then the solvent was removed under reduced pressure affording 12.4 mg (97%) of the title compound as a yellow solid. Mass Spectrum (LCMS, ESI pos): Calcd. for $C_{29}H_{26}NO_3S^+$: 468.2 (M+H); Found: 468.2. $^1$H NMR (400 MHz, DMSO-$d_6$): δ 8.02-8.00 (m, 1H), 7.94-7.92 (m, 1H), 7.65 (br s, 1H), 7.49-7.45 (m, 4H), 7.42-7.37 (m, 1H), 7.08 (d, J=8.0 Hz, 2H), 6.70 (d, J=8.0 Hz, 1H), 5.59 (q, J=6.0 Hz, 1H), 2.84 (s, 3H), 2.59 (s, 3H), 2.33 (s, 3H), 1.59 (d, J=6.0 Hz, 3H). HPLC purity (254 nm): 96.6%.

Using the procedure described in Example 28, with reagents, starting materials, and conditions familiar to those skilled in the art, the following compounds representative of the disclosure were prepared:

| Compound | Name and Data |
| --- | --- |
| 190 | 2-(1-Benzothiophen-3-yl)-8-ethyl-5-[[2-(pyrazin-2-yl)phenyl]methoxy]quinoline-4-carboxylic acid<br>Mass Spectrum (LCMS, ESI pos): Calcd. for $C_{31}H_{24}N_3O_3S^+$: 518.2 (M + H); Found: 518.2. $^1$H NMR (300 MHz, $CD_3OD$): δ 9.21 (d , J = 8.4 Hz , 1H), 8.93 (s, 1H), 8.67-8.66 (m, 1H), 8.51 (d, J = 2.7 Hz, 1H), 8.39 (s, 1H), 8.02-7.97 (m, 1H), 7.93 (s, 1H), 7.84-7.81 (m, 1H), 7.65-7.62 (m, 1H), 7.59-7.42 (m, 5H), 6.89 (d, J = 8.1 Hz, 1H), 5.44 (s, 2H), 3.37-3.32 (m, 2H), 1.41 (t, J = 7.5 Hz, 3H). HPLC purity (254 nm): 92.1%. |
| 191 | 2-(1-Benzothiophen-3-yl)-8-ethyl-5-[[3-(pyrazin-2-yl)phenyl]methoxy]quinoline-4-carboxylic acid<br>Mass Spectrum (LCMS, ESI pos): Calcd. for $C_{31}H_{24}N_3O_3S^+$: 518.2 (M + H); Found: 518.1. $^1$H NMR (400 MHz, DMSO-$d_6$): 13.49 (brs, 1H), 9.38 (s, 1H), 9.27 (d, J = 8.0 Hz, 1H), 8.85 (s, 1H), 8.75 (s, 1H), 8.64 (s, 1H), 8.36 (s, 1H), 8.15-8.12 (m, 3H), 7.72-7.48 (m, 5H), 7.21 (d, J = 8.0 Hz, 1H), 5.46 (s, 2H), 3.28 (q, J = 7.2 Hz, 2H), 1.38 (t, J = 7.2 Hz, 3H). HPLC purity (254 nm): 98.7%. |
| 192 | 2-(1-Benzothiophen-3-yl)-8-ethyl-5-[[4-(pyrazin-2-yl)phenyl]methoxy]quinoline-4-carboxylic acid<br>Mass Spectrum (LCMS, ESI pos): Calcd. for $C_{31}H_{24}N_3O_3S^+$: 518.2 (M + H); |

| Compound | Name and Data |
|---|---|
|  | Found: 518.2. $^1$H NMR (400 MHz, DMSO-$d_6$): δ 13.44 (s, 1H), 9.30 (s, 1H), 9.27 (d, J = 8.0 Hz, 2H), 8.86 (s, 1H), 8.74-8.73 (m, 1H), 8.62 (d, J = 2.4 Hz, 1H), 8.20-8.12 (m, 4H), 7.73 (d, J = 8.4 Hz, 2H), 7.63-7.55 (m, 2H), 7.51-7.47 (m, 1H), 7.22 (d, J = 8.4 Hz, 1H), 5.43 (s, 2H), 3.31-3.25 (m, 2H), 1.36 (t, J = 7.6 Hz, 3H). HPLC purity (254 nm): 98.1%. |
| 193 | 2-(1-Benzothiophen-3-yl)-8-ethyl-5-[[4-(pyrazin-2-yl)phenyl]methoxy]quinoline-4-carboxylic acid<br>Mass Spectrum (LCMS, ESI pos): Calcd. for $C_{32}H_{25}N_2O_3S^+$: 517.2 (M + H); Found: 517.1. $^1$H NMR (400 MHz, $CD_3OD$): δ 9.22 (d, J = 8.0 Hz, 1H), 8.91 (s, 1H), 8.64 (d, J = 5.2 Hz, 1H), 8.48 (d, J = 8.0 Hz, 1H), 8.39 (s, 1H), 7.98 (d, J = 8.0 Hz, 1H), 7.94 (s, 1H), 7.83-7.76 (m, 2H), 7.61-7.60 (m, 2H), 7.56-7.44 (m, 4H), 6.94 (d, J = 8.4 Hz, 1H), 5.10 (s, 2H), 3.37-3.35 (m, 2H), 1.41 (t, J = 7.6 Hz, 3H). HPLC purity (254 nm): 97.4%. |
| 295 | Sodium 5-(2H-1,3-Benzodioxol-5-ylmethoxy)-8-methyl-2-(3-methyl-1-benzothiophen-2-yl)quinoline-4-carboxylate<br>Mass Spectrum (LCMS, ESI pos): Calcd. for $C_{28}H_2NO_5S^+$: 484.1 (M + H); Found: 484.1. $^1$H NMR (400 MHz, DMSO-$d_6$): δ 8.00 (d, J = 7.6 Hz, 1H), 7.91 (d, J = 7.6 Hz, 1H), 7.55 (s, 1H), 7.48-7.41 (m, 4H), 7.11 (d, J = 8.0 Hz, 1H), 6.87-6.83 (m, 2H), 5.97 (s, 2H), 5.15 (s, 2H), 2.82 (s, 3H), 2.63 (s, 3H). HPLC purity (254 nm): 98.9%. |

Example 29: Preparation of Sodium 5-((1R)-1-(tetrahydro-2H-pyran-4-yl)ethoxy)-8-methyl-2-(3-methyl-1-benzofuran-2-yl)quinoline-4-carboxylate (Compound 245) and Sodium 5-((1S)-1-(tetrahydro-2H-pyran-4-yl)ethoxy)-8-methyl-2-(3-methyl-1-benzofuran-2-yl)quinoline-4-carboxylate (Compound 246)

A. 4-(1-(4-Methyl-3-nitrophenoxy)ethyl)tetrahydro-2H-pyran. To a 1000-mL 3-necked round-bottom flask purged and maintained with an inert atmosphere of nitrogen was placed a solution of 1-(tetrahydro-2H-pyran-4-yl)ethan-1-ol (10 g, 76.8 mmol, Intermediate 73) in THF (400 mL) then 4-methyl-3-nitrophenol (10.6 g, 69.2 mmol) and $PPh_3$ (30.2 g, 115.1 mmol) were added. This was followed by the addition of DIAD (23.3 g, 115.2 mmol) at rt. The reaction was stirred for 5 h at rt and concentrated under reduced pressure. The residue was treated with water and extracted with DCM. The organic extracts were combined, dried over anhydrous $Na_2SO_4$, and concentrated under reduced pressure. The residue was purified by column chromatography eluting with EtOAc/petroleum ether (1:50) affording 10 g (49%) of the title compound as a yellow oil.

B. 2-Methyl-5-(1-(tetrahydro-2H-pyran-4-yl)ethoxy)aniline. To a 500-mL round-bottom flask purged and maintained with an inert atmosphere of $N_2$ was placed a solution of 4-(1-(4-Methyl-3-nitrophenoxy)ethyl)tetrahydro-2H-pyran (3.00 g, 11.3 mmol, as prepared in the previous step) in MeOH (200 mL) then Raney Ni (300 mg) was added. The solution was degassed and back filled with hydrogen and stirred for 2 h at rt. The $H_2$ was purged then the solids were removed by filtration. The filtrate was concentrated under reduced pressure affording 2.70 g of the title compound as a yellow oil. Mass Spectrum (LCMS, ESI pos): Calcd. for $C_{14}H_{22}NO_2^+$: 236.2 (M+H); Found: 236.2.

C. 5-((1R)-1-(tetrahydro-2H-pyran-4-yl)ethoxy)-8-methyl-2-(3-methyl-1-benzofuran-2-yl)quinoline-4-carboxylic acid and 5-((1S)-1-(tetrahydro-2H-pyran-4-yl)ethoxy)-8-methyl-2-(3-methyl-1-benzofuran-2-yl)quinoline-4-carboxylic acid. To a 20-mL sealed tube was placed a solution of 2-methyl-5-(1-(tetrahydro-2H-pyran-4-yl)ethoxy)aniline (1.00 g, 4.26 mmol, as prepared in the previous step) in EtOH (10 mL) then 3-methyl-1-benzofuran-2-carbaldehyde (680 mg, 4.26 mmol) and 2-oxopropanoic acid (749 mg, 8.52 mmol) were added. The reaction was stirred overnight at 110° C. then the reaction was cooled to rt and the solids were collected by filtration. The isomers were separated by Prep-SFC (Column, EnantioPak-A1, 250 mm*50 mm, 5 um; mobile phase, $CO_2$ (50%), MeOH Preparative (50%); Detector, UV 254 nm) affording 210 mg (11%) of 5-((1R)-1-(tetrahydro-2H-pyran-4-yl)ethoxy)-8-methyl-2-(3-methyl-1-benzofuran-2-yl)quinoline-4-carboxylic acid as a yellow solid and 190 mg (10%) of 5-((1S)-1-(tetrahydro-2H-pyran-4-yl)ethoxy)-8-methyl-2-(3-methyl-1-benzofuran-2-yl)quinoline-4-carboxylic acid as a yellow solid.

D. Sodium 5-((1R)-1-(Tetrahydro-2H-pyran-4-yl)ethoxy)-8-methyl-2-(3-methyl-1-benzofuran-2-yl)quinoline-4-carboxylate (Compound 245). To a 50-mL round-bottom flask purged and maintained with an inert atmosphere of nitrogen was placed a solution of 5-((1R)-1-(tetrahydro-2H-pyran-4-yl)ethoxy)-8-methyl-2-(3-methyl-1-benzofuran-2-yl)quinoline-4-carboxylic acid (210 mg, 0.45 mmol) in MeOH (1 mL) then 0.05N NaOH (9.0 mL, 0.45 mmol) was added. The reaction was stirred for 3 h at rt then the solvent was removed under reduced pressure affording 219.6 mg (99%) of the title compound as a light yellow solid. Mass Spectrum (LCMS, ESI pos): Calcd. for $C_{27}H_{28}NO_5^+$: 446.2 (M+H); Found: 446.2. $^1$H NMR (300 MHz, DMSO-$d_6$): δ 7.74 (d, J=7.2 Hz, 1H), 7.66 (d, J=8.1 Hz, 1H), 7.56 (s, 1H), 7.45-7.30 (m, 3H), 6.80 (d, J=8.1 Hz, 1H), 4.36-4.34 (m, 1H), 3.91-3.84 (m, 2H), 3.30-3.26 (m, 2H), 2.84 (s, 3H), 2.64 (s, 3H), 1.99-1.92 (m, 2H), 1.79-1.74 (m, 1H), 1.39-1.31 (m, 2H), 1.20 (d, J=6.0 Hz, 3H). HPLC purity (254 nm): 99.3%.

E. Sodium 5-((1S)-1-(Tetrahydro-2H-pyran-4-yl)ethoxy)-8-methyl-2-(3-methyl-1-benzofuran-2-yl)quinoline-4-carboxylate (Compound 246). To a 25-mL round-bottom flask, was placed a solution of 5-((1S)-1-(tetrahydro-2H-pyran-4-yl)ethoxy)-8-methyl-2-(3-methyl-1-benzofuran-2-yl)quinoline-4-carboxylic acid (60 mg, 0.13 mmol, as prepared in Step C) in THF (0.5 mL) then 0.05N NaOH (2.7 mL, 0.13 mmol) was added. The reaction was stirred for 1 h at rt then concentrated under reduced pressure affording 55.9 mg (89%) of the title compound as a light yellow solid. Mass Spectrum (LCMS, ESI pos): Calcd. for $C_{27}H_{28}NO_5^+$: 446.2 (M+H); Found: 446.2. $^1$H NMR (400 MHz, DMSO-$d_6$): δ 7.74 (d, J=7.6 Hz, 1H), 7.66 (d, J=8.0 Hz, 1H), 7.54 (s, 1H), 7.44-7.33 (m, 3H), 6.80 (d, J=8.0 Hz, 1H), 4.35-4.30 (m, 1H), 3.89-3.88 (m, 2H), 3.33-3.31 (m, 2H), 2.85 (s, 3H), 2.65 (s, 3H), 2.02-1.80 (m, 3H), 1.40-1.30 (m, 2H), 1.19 (d, J=6.0 Hz, 3H). HPLC purity (254 nm): 99.7%.

Using the procedure described in Example 29, with reagents, starting materials, and conditions familiar to those skilled in the art, the following compounds representative of the disclosure were prepared:

| Compound | Name and Data |
|---|---|
| 242 | Sodium 5-((1R)-1-Cyclohexylethoxy)-8-methyl-2-(3-methyl-1-benzofuran-2-yl)quinoline-4-carboxylate<br>Mass Spectrum (LCMS, ESI pos): Calcd. for $C_{28}H_{30}NO_4^+$: 444.2 (M + H); Found: 444.3. $^1$H NMR (400 MHz, DMSO-$d_6$): δ 7.74 (d, J = 7.6 Hz, 1H), 7.66 (d, J = 8.0 Hz, 1H), 7.55 (s, 1H), 7.43-7.39 (m, 2H), 7.32 (t, J = 7.6 Hz, 1H), 6.76 (d, J = 7.6 Hz, 1H), 4.34-4.32 (m, 1H), 2.85 (s, 3H), 2.64 (s, 3H), 1.95-1.87 (m, 2H), 1.70-1.63 (m, 4H), 1.12-1.15 (m, 8H). HPLC purity (254 nm): 98.2%. |
| 243 | Sodium 5-((1S)-1-Cyclohexylethoxy)-8-methyl-2-(3-methyl-1-benzofuran-2-yl)quinoline-4-carboxylate<br>Mass Spectrum (LCMS, ESI pos): Calcd. for $C_{28}H_{30}NO_4^+$: 444.2 (M + H); Found: 444.3. $^1$H NMR (400 MHz, DMSO-$d_6$): δ 7.74 (d, J = 7.6 Hz, 1H), 7.66 (d, J = 8.0 Hz, 1H), 7.54 (s, 1H), 7.43-7.39 (m, 2H), 7.32 (t, J = 7.6 Hz, 3H), 6.76 (d, J = 8.0 Hz, 1H), 4.34-4.32 (m, 1H), 2.84 (s, 3H), 2.64 (s, 3H), 1.95-1.87 (m, 2H), 1.69-1.62 (m, 4H), 1.19-1.15 (m, 8H). HPLC purity (254 nm): 97.7%. |
| 202 | Sodium 2-[Imidazo[1,2-a]pyridin-2-yl]-8-methyl-5-[(1R)-1-phenylethoxy]quinoline-4-carboxylate<br>Mass Spectrum (LCMS, ESI pos): Calcd. for $C_{26}H_{22}N_3O_3^+$: 424.2 (M + H); Found: 424.3. $^1$H NMR (400 MHz, CD$_3$OD): δ 8.92 (s, 1H), 8.78 (d, J = 7.2 Hz, 1H), 8.13 (s, 1H), 7.95-7.87 (m, 2H), 7.52 (d, J = 7.6 Hz, 2H), 7.46-7.40 (m, 2H), 7.36-7.32 (m, 2H), 7.27-7.24 (m, 1H), 6.78 (d, J = 6.4 Hz, 1H), 5.63 (q, J = 6.4 Hz, 1H), 2.78 (s, 3H), 1.75 (d, J = 6.4 Hz, 3H). HPLC purity (254 nm): 96.8%. |
| 203 | Sodium 2-[Imidazo[1,2-a]pyridin-2-yl]-8-methyl-5-[(1S)-1-phenylethoxy]quinoline-4-carboxylate<br>Mass Spectrum (LCMS, ESI pos): Calcd. for $C_{26}H_{22}N_3O_3^+$: 424.2 (M + H); Found: 424.3. $^1$H NMR (400 MHz, CD$_3$OD): δ 8.89 (s, 1H), 8.76 (d, J = 6.8 Hz , 1H), 8.13 (s, 1H), 7.92-7.85 (m, 2H), 7.52 (d, J = 7.6 Hz, 2H), 7.44 (d, J = 8.0 Hz, 2H), 7.40-7.32 (m, 3H), 7.27-7.24 (m, 1H), 6.77 (d, J = 8.0 Hz, 1H), 5.62 (q, J = 6.4 Hz, 1H), 2.78 (s, 3H), 1.75 (d, J = 6.4 Hz, 3H). HPLC purity (254 nm): 97.9%. |
| 247 | Sodium 5-[(1R)-1-(1-Methanesulfonylpiperidin-4-yl)ethoxy]-8-methyl-2-(3-methyl-1-benzofuran-2-yl)quinoline-4-carboxylate<br>Mass Spectrum (LCMS, ESI pos): Calcd. for $C_{28}H_{31}N_2O_6S^+$: 523.2 (M + H); Found: 523.3. $^1$H NMR (400 MHz, DMSO-$d_6$): δ 7.72 (d, J = 8.0 Hz, 1H), 7.65 (d, J = 8.0 Hz, 1H), 7.55 (s, 1H), 7.45-7.38 (m, 2H), 7.32 (t, J = 6.8 Hz, 1H), 6.81 (d, J = 7.6 Hz, 1H), 4.45-4.42 (m, 1H), 3.64-3.59 (m, 2H), 2.89 (s, 3H), 2.84 (s, 3H), 2.72-2.65 (m, 2H), 2.64 (s, 3H), 2.13-1.99 (m, 2H), 1.82-1.76 (m, 1H), 1.48-1.36 (m, 2H), 1.21 (d, J = 6.0 Hz, 3H). HPLC purity (254 nm): 99.8%. |
| 248 | Sodium 5-[(1S)-1-(1-Methanesulfonylpiperidin-4-yl)ethoxy]-8-methyl-2-(3-methyl-1-benzofuran-2-yl)quinoline-4-carboxylate<br>Mass Spectrum (LCMS, ESI pos): Calcd. for $C_{28}H_{31}N_2O_6S^+$: 523.2 (M + H); Found: 523.3. $^1$H NMR (400 MHz, DMSO-$d_6$): δ 7.74 (d, J = 8.0 Hz, 1H), 7.66 (d, J = 8.4 Hz, 1H), 7.59 (s, 1H), 7.46-7.39 (m, 2H), 7.33 (t, J = 7.2 Hz, 1H), 6.83 (d, J = 7.6 Hz, 1H), 4.46-4.42 (m, 1H), 3.64-3.59 (m, 2H), 2.87 (s, 3H), 2.84 (s, 3H), 2.73-2.65 (m, 2H), 2.65 (s, 3H), 2.13-2.10 (m, 1H), 2.02-1.98 (m, 1H), 1.85-1.78 (m, 1H), 1.45-1.39 (m, 2H), 1.21 (d, J = 6.0 Hz, 3H). HPLC purity (254 nm): 99.4%. |
| 229 | Sodium 5-[(1R)-1-(4-methanesulfonylphenyl)ethoxy]-8-methyl-2-(3-methyl-1-benzofuran-2-yl)quinoline-4-carboxylate<br>Mass Spectrum (LCMS, ESI pos): Calcd. for $C_{29}H_{26}NO_6S^+$: 516.1 (M + H); Found: 516.2. $^1$H NMR (400 MHz, DMSO-$d_6$): δ 8.06 (d, J = 8.4 Hz, 2H), 7.82 (d, J = 8.4 Hz, 2H), 7.75 (d, J = 8.0 Hz, 1H), 7.68-7.66 (m, 1H), 7.66 (s, 1H), 7.44-7.40 (m, 1H), 7.35-7.32 (m, 2H), 6.70 (d, J = 8.0 Hz, 1H), 5.78 (q, J = 6.4 Hz, 1H), 3.18 (s, 3H), 2.83 (s, 3H), 2.59 (s, 3H), 1.58 (d, J = 6.4 Hz, 3H). HPLC purity (254 nm): 99.6%. |
| 230 | Sodium 5-[(1S)-1-(4-methanesulfonylphenyl)ethoxy]-8-methyl-2-(3-methyl-1-benzofuran-2-yl)quinoline-4-carboxylate<br>Mass Spectrum (LCMS, ESI pos): Calcd. for $C_{29}H_{26}NO_6S^+$: 516.1 (M + H); Found: 516.3. $^1$H NMR (400 MHz, DMSO-$d_6$): δ 8.05 (d, J = 8.4 Hz, 2H), 7.83 (d, J = 8.4 Hz, 2H), 7.75 (d, J = 7.6 Hz, 1H), 7.68 (s, 1H), 7.68-7.66 (m, 1H), 7.44-7.40 (m, 1H), 7.35-7.31 (m, 2H), 6.70 (d, J = 8.4 Hz, 1H), 5.78 (q, J = 6.4 Hz, 1H), 3.18 (s, 3H), 2.83 (s, 3H), 2.60 (s, 3H), 1.59 (d, J = 6.4 Hz, 3H). HPLC purity (254 nm): 99.2%. |
| 285 | Sodium 8-Methyl-2-(3-methyl-1-benzofuran-2-yl)-5-[(1R)-1-[4-(oxetan-3-yl)phenyl]ethoxy]quinoline-4-carboxylate<br>Mass Spectrum (LCMS, ESI pos): Calcd. for $C_{31}H_{28}NO_5^+$: 494.2 (M + H); Found: 494.2. $^1$H NMR (300 MHz, DMSO-$d_6$): δ 7.74 (d, J = 8.0 Hz, 1H), 7.70-7.66 (m, 3H), 7.64 (s, 1H), 7.42 (t, J = 8.0 Hz, 1H), 7.33 (t, J = 7.6 Hz, 1H), 7.29 (d, J = 8.0 Hz, 3H), 6.62 (d, J = 8.0 Hz, 1H), 5.58 (q, J = 6.4 Hz, 1H), 4.90-4.86 (m, 2H), 4.60-4.56 (m, 2H), 4.22-4.15 (m, 1H), 2.83 (s, 3), 2.58 (s, 3H), 1.57 (d, J = 6.4 Hz, 3H). HPLC purity (254 nm): 93.8%. |
| 286 | Sodium 8-Methyl-2-(3-methyl-1-benzofuran-2-yl)-5-[(1S)-1-[4-(oxetan-3-yl)phenyl]ethoxy]quinoline-4-carboxylate<br>Mass Spectrum (LCMS, ESI pos): Calcd. for $C_{31}H_{28}NO_5^+$: 494.2 (M + H); Found: 494.3. $^1$H NMR (400 MHz, DMSO-$d_6$): δ 7.74 (d, J = 7.6 Hz, 1H), 7.71-7.66 (m, 3H), 7.63 (s, 1H), 7.41 (t, J = 7.6 Hz, 1H), 7.35-7.28 (m, 4H), 6.61 (d, J = 8.0 Hz, 1H), 5.57 (q, J = 6.0 Hz, 1H), 4.90-4.86 (m, 2H), 4.60-4.56 (m, 2H), 4.22-4.15 (m, 1H), 2.83 (s, 3), 2.58 (s, 3H), 1.57 (d, J = 6.0 Hz, 3H). HPLC purity (254 nm): 97.2%. |

| Compound | Name and Data |
|---|---|
| 287 | Sodium 8-Methyl-2-(3-methyl-1-benzothiophen-2-yl)-5-[(1R)-1-[4-(oxetan-3-yl)phenyl]ethoxy]quinoline-4-carboxylate<br>Mass Spectrum (LCMS, ESI pos): Calcd. for $C_{31}H_{28}NO_4S^+$: 510.2 (M + H); Found: 510.2. $^1$H NMR (400 MHz, DMSO-$d_6$): δ 8.00 (d, J = 8.4 Hz, 1H), 7.91 (d, J = 8.4 Hz, 1H), 7.69 (d, J = 8.0 Hz, 2H), 7.47-7.42 (m, 2H), 7.41 (s, 1H), 7.29-7.26 (m, 3H), 6.61 (d, J = 8.0 Hz, 1H), 5.57 (q, J = 6.0 Hz, 1H), 4.90-4.86 (m, 2H), 4.60-4.56 (m, 2H), 4.20-4.16 (m, 1H), 2.81 (s, 3H), 2.57 (s, 3H), 1.56 (d, J = 6.4 Hz, 3H). HPLC purity (254 nm): 93.6%. |
| 288 | Sodium 8-Methyl-2-(3-methyl-1-benzothiophen-2-yl)-5-[(1S)-1-[4-(oxetan-3-yl)phenyl]ethoxy]quinoline-4-carboxylate<br>Mass Spectrum (LCMS, ESI pos): Calcd. for $C_{31}H_{28}NO_4S^+$: 510.2 (M + H); Found: 510.3. $^1$H NMR (300 MHz, DMSO-$d_6$): δ 8.00 (d, J = 8.4 Hz, 1H), 7.91 (d, J = 8.8 Hz, 1H), 7.69 (d, J = 8.4 Hz, 2H), 7.46-7.42 (m, 2H), 7.41 (s, 1H), 7.29-7.27 (m, 3H), 6.61 (d, J = 8.0 Hz, 1H), 5.57 (q, J = 6.0 Hz, 1H), 4.90-4.86 (m, 2H), 4.60-4.56 (m, 2H), 4.20-4.16 (m, 1H), 2.81 (s, 3H), 2.57 (s, 3H), 1.56 (d, J = 6.4 Hz, 3H). HPLC purity (254 nm): 96.2%. |
| 222 | Sodium 8-Methyl-2-(3-methyl-1-benzothiophen-2-yl)-5-[[(1S,2S)-2-methylcyclohexyl]oxy]quinoline-4-carboxylate<br>Mass Spectrum (LCMS, ESI pos): Calcd. for $C_{27}H_{28}NO_3S^+$: 446.2 (M + H); Found: 446.2. $^1$H NMR (400 MHz, DMSO-$d_6$): δ 8.02-8.00 (m, 1H), 7.94-7.92 (m, 1H), 7.54-7.47 (m, 2H), 7.46-7.45 (m, 2H), 7.02-6.94 (m, 1H), 4.16-4.08 (m, 1H), 2.80 (s, 3H), 2.66 (s, 3H), 2.10-2.09 (m, 1H), 1.82-1.72 (m, 3H), 1.65-1.60 (m, 1H), 1.35-1.00 (m, 4H), 1.00 (d, J = 6.4 Hz, 3H). HPLC purity (254 nm): 98.1%. |
| 223 | Sodium 8-Methyl-2-(3-methyl-1-benzothiophen-2-yl)-5-[[(1S,2R)-2-methylcyclohexyl]oxy]quinoline-4-carboxylate<br>Mass Spectrum (LCMS, ESI pos): Calcd. for $C_{27}H_{28}NO_3S^+$: 446.2 (M + H); Found: 446.1. $^1$H NMR (400 MHz, DMSO-$d_6$): δ 8.00 (d, J = 6.8 Hz, 1H), 7.91 (d, J = 7.2 Hz, 1H), 7.48-7.42 (m, 4H), 6.82-6.75 (m, 1H), 4.56-4.53 (m, 1H), 2.81 (s, 3H), 2.64 (m, 3H), 2.10-1.96 (m, 1H), 1.84-1.62 (m, 3H), 1.48-1.23 (m, 5H), 0.99 (d, J = 6.8 Hz, 3H). HPLC purity (254 nm): 98.0%. |
| 224 | Sodium 8-Methyl-2-(3-methyl-1-benzothiophen-2-yl)-5-[[(1R,2R)-2-methylcyclohexyl]oxy]quinoline-4-carboxylate<br>Mass Spectrum (LCMS, ESI pos): Calcd. for $C_{27}H_{28}NO_3S^+$: 446.2 (M + H); Found: 446.2. $^1$H NMR (400 MHz, DMSO-$d_6$): δ 8.02-8.00 (m, 1H), 7.94-7.92 (m, 1H), 7.74-7.58 (m, 2H), 7.48-7.46 (m, 2H), 7.02-6.94 (m, 1H), 4.16-4.08 (m, 1H), 2.81 (s, 3H), 2.68 (s, 3H), 2.10-2.09 (m, 1H), 1.82-1.72 (m, 3H), 1.65-1.60 (m, 1H), 1.35-1.04 (m, 4H), 1.00 (d, J = 6.4 Hz, 3H). HPLC purity (254 nm): 98.8%. |
| 225 | Sodium 8-Methyl-2-(3-methyl-1-benzothiophen-2-yl)-5-[[(1R,2S)-2-methylcyclohexyl]oxy]quinoline-4-carboxylate<br>Mass Spectrum (LCMS, ESI pos): Calcd. for $C_{27}H_{28}NO_3S^+$: 446.2 (M + H); Found: 446.2. $^1$H NMR (400 MHz, DMSO-$d_6$): δ 8.00 (d, J = 6.8 Hz, 1H), 7.91 (d, J = 7.2 Hz, 1H), 7.48-7.42 (m, 4H), 6.83-6.80 (m, 1H), 4.57 (br s, 1H), 2.81 (s, 3H), 2.64 (s, 3H), 2.08-2.00 (m, 1H), 1.82-1.62 (m, 3H), 1.46-1.35 (m, 2H), 1.26-1.23 (m, 2H), 0.99 (d, J = 6.4 Hz, 3H). HPLC purity (254 nm): 97.3%. |
| 277* | Sodium 8-Methyl-2-(3-methyl-1-benzothiophen-2-yl)-5-(3-methylcyclobutoxy)quinoline-4-carboxylate<br>Mass Spectrum (LCMS, ESI pos): Calcd. for $C_{25}H_{24}NO_3S^+$: 418.1 (M + H); Found: 418.1. $^1$H NMR (400 MHz, DMSO-$d_6$): δ 7.99-7.97 (m, 1H), 7.90-7.87 (m, 1H), 7.44-7.40 (m, 3H), 7.34 (s, 1H), 6.54-6.52 (m, 1H), 4.90-4.87 (m, 0.7 H), 4.56-4.52 (m, 0.3H), 2.79 (s, 3H), 2.61 (s, 3H), 2.60-2.48 (m, 1H), 2.40-2.26 (m, 2H), 2.05-1.90 (m, 1.4H), 1.82-1.73 (m, 0.6H), 1.16-1.08 (m, 3H). HPLC purity (254 nm): 98.8%. |
| 281* | Sodium 8-Methyl-2-(3-methyl-1-benzofuran-2-yl)-5-[(1r,3r)-3-phenylcyclobutoxy]quinoline-4-carboxylate<br>Mass Spectrum (LCMS, ESI pos): Calcd. for $C_{30}H_{26}NO_4^+$: 464.2 (M + H); Found: 464.2. $^1$H NMR (400 MHz, DMSO-$d_6$): δ 7.75 (d, J = 7.2 Hz, 1H), 7.67-7.62 (m, 2H), 7.46-7.42 (m, 2H), 7.39-7.31 (m, 5H), 7.23-7.19 (m, 1H), 6.62 (d, J = 7.8 Hz, 1H), 5.05-4.95 (m, 1H), 3.83-3.78 (m, 1H), 2.85 (s, 3H), 2.73-2.66 (m, 5H), 2.54-2.49 (m, 2H). HPLC purity (254 nm): 98.8%. |
| 282* | Sodium 8-Methyl-2-(3-methyl-1-benzofuran-2-yl)-5-[(1s,3s)-3-phenylcyclobutoxy]quinoline-4-carboxylate<br>Mass Spectrum (LCMS, ESI pos): $C_{30}H_{26}NO_4^+$: 464.2 (M + H); Found: 464.3. $^1$H NMR (400 MHz, DMSO-$d_6$): δ 7.76 (d, J = 8.0 Hz, 1H), 7.66 (d, J = 8.4 Hz, 2H), 7.50 (d, J = 7.6 Hz, 1H), 7.44-7.28 (m, 6H), 7.20-7.17 (m, 1H), 6.82-6.80 (m, 1H), 4.88-4.84 (m, 1H), 3.15-3.11 (m, 1H), 2.90-2.85 (m, 2H), 2.84 (s, 3H), 2.66 (s, 3H), 2.33-2.27 (m, 2H). HPLC purity (254 nm): 98.2%. |
| 283* | Sodium 8-Methyl-2-(3-methyl-1-benzothiophen-2-yl)-5-[(1r,3r)-3-phenylcyclobutoxy]quinoline-4-carboxylate<br>Mass Spectrum (LCMS, ESI pos): Calcd. for $C_{30}H_{26}NO_3S^+$: 480.2 (M + H); Found: 480.2. $^1$H NMR (400 MHz, DMSO-$d_6$): δ 8.00 (d, J = 8.4 Hz, 1H), 7.91 (d, J = 8.8 Hz, 1H), 7.48-7.34 (m, 4H), 7.24-7.18 (m, 4H), 6.62 (d, J = 8.0 Hz, 1H), 5.03-4.98 (m, 1H), 3.81-3.77 (m, 1H), 2.82 (s, 3H), 2.71-2.67 (m, 2H), 2.65 (s, 3H), 2.54-2.50 (m, 2H). HPLC purity (254 nm): 95.3%. |
| 284* | Sodium 8-Methyl-2-(3-methyl-1-benzothiophen-2-yl)-5-[(1s,3s)-3-phenylcyclobutoxy]quinoline-4-carboxylate |

| Compound | Name and Data |
|---|---|
|  | Mass Spectrum (LCMS, ESI pos): Calcd. for $C_{30}H_{26}NO_3S^+$: 480.2 (M + H); Found: 480.2. $^1$H NMR (400 MHz, DMSO-d$_6$): δ 7.90-7.86 (m, 2H), 7.69 (s, 1H), 7.49-7.37 (m, 5H), 7.31 (t, J = 8.7 Hz, 2H), 7.15 (t, J = 7.2 Hz, 1H), 6.81 (d, J= 8.1 Hz, 1H), 4.84-4.81 (m, 1H), 3.21-3.15 (m, 1H), 3.02-2.96 (m, 2H), 2.86 (s, 3H), 2.72 (s, 3H), 2.58-2.52 (m, 2H). HPLC purity (254 nm): 98.5%. |
| 292* | Sodium 5-[(2-Methoxyphenyl)methoxy]-8-methyl-2-(3-methyl-1-benzothiophen-2-yl)quinoline-4-carboxylate<br>Mass Spectrum (LCMS, ESI pos): Calcd. for $C_{28}H_{24}NO_4S^+$: 470.1 (M + H); Found: 470.2. $^1$H NMR (400 MHz, DMSO-d$_6$): δ 8.11 (d, J = 7.6 Hz, 1H), 8.02-8.00 (m, 1H), 7.93-7.90 (m, 1H), 7.48-7.42 (m, 3H), 7.44 (s, 1H), 7.27-7.23 (t, J = 7.2 Hz, 1H), 7.00 (d, J = 8.0 Hz, 1H), 6.93 (t, J = 7.2 Hz, 1H), 6.79 (d, J = 8.0 Hz, 1H), 5.17 (s, 2H), 3.88 (s, 3H), 2.83 (s, 3H), 2.51 (s, 3H). HPLC purity (254 nm): 97.1%. |

*Chiral separation step was omitted.

Example 30: Preparation of 3-[8-Methyl-2-(3-methyl-1-benzofuran-2-yl)-5-[(1R)-1-phenylethoxy]quinolin-4-yl]-1H-pyrazol-5-ol (Compound 274)

A. 8-Methyl-2-(3-methyl-1-benzofuran-2-yl)-5-[(1R)-1-phenylethoxy]quinoline-4-carbonyl chloride. To a 50-mL 3-necked round-bottom flask purged and maintained with an inert atmosphere of nitrogen was placed a solution of 8-methyl-2-(3-methyl-1-benzofuran-2-yl)-5-[(1R)-1-phenylethoxy]quinoline-4-carboxylic acid (100 mg, 0.23 mmol, Compound 211) in DCM (10 mL) then DMF (0.1 mL) was added and the solution was cooled to 0° C. Oxalyl chloride (37.7 mg, 0.30 mmol) was added dropwise with stirring then the reaction was stirred for 1 h at rt. The resulting mixture was concentrated under reduced pressure affording 95 mg (91%) of the title compound as a yellow solid.

B. Ethyl 3-[8-Methyl-2-(3-methyl-1-benzofuran-2-yl)-5-[(1R)-1-phenylethoxy]quinolin-4-yl]-3-oxopropanoate. To a 50-mL 3-necked round-bottom flask purged and maintained with an inert atmosphere of nitrogen was placed a solution of EtOAc (35 mg, 0.40 mmol) in THF (10 mL), then the solution was cooled to −78° C. and LiHMDS (0.45 mL, 0.8 mmol) was added dropwise with stirring. The reaction was stirred at −78° C. for 0.5 h, then a solution of 8-methyl-2-(3-methyl-1-benzofuran-2-yl)-5-[(1R)-1-phenylethoxy]quinoline-4-carbonyl chloride (95 mg, 0.21 mmol, as prepared in the previous step) in THF (10 mL) was added dropwise. After completion of addition the reaction was warmed to rt and stirred for 1 h, then quenched by the addition of 1M aqueous NH$_4$Cl solution, and extracted with EtOAc. The organic extracts were combined, washed with brine, dried over anhydrous Na$_2$SO$_4$, and concentrated under reduced pressure affording 78 mg (74%) of the title compound as a yellow solid. Mass Spectrum (LCMS, ESI pos): Calcd. for $C_{32}H_{30}NO_5^+$: 508.2 (M+H); Found: 508.2.

C. 3-[8-Methyl-2-(3-methyl-1-benzofuran-2-yl)-5-[(1R)-1-phenylethoxy]quinolin-4-yl]-1H-pyrazol-5-ol. To a 25-mL round-bottom flask was placed a solution of ethyl 3-[8-methyl-2-(3-methyl-1-benzofuran-2-yl)-5-[(1R)-1-phenylethoxy]quinolin-4-yl]-3-oxopropanoate (70 mg, 0.14 mmol, as prepared in the previous step) in EtOH (10 mL) then N$_2$H$_4$·H$_2$O (43 mg) was added. The reaction was stirred at 95° C. for 12 h, cooled to rt, then the solvent was removed under reduced pressure. The residue was triturated with DCM/hexane (1/10) and the solid was collected by filtration affording 35.9 mg (55%) of the title compound as a yellow solid. Mass Spectrum (LCMS, ESI pos): Calcd. for $C_{30}H_{26}N_3O_3^+$: 476.2 (M+H); Found: 476.3. $^1$H NMR (400 MHz, DMSO-d$_6$): δ 11.83 (brs, 1H), 9.57 (brs, 1H), 7.89 (s, 1H), 7.78 (d, J=8.0 Hz, 1H), 7.68 (d, J=8.0 Hz, 1H), 7.44 (t, J=7.2 Hz, 2H), 7.37-7.26 (m, 5H), 7.22-7.19 (m, 1H), 6.72 (d, J=8.0 Hz, 1H), 5.77 (s, 1H), 5.44 (q, J=6.4 Hz, 1H), 2.85 (s, 3H), 2.65 (s, 3H), 1.26 (d, J=6.4 Hz, 3H). HPLC purity (254 nm): 95.1%.

Using the procedure described in Example 30, with reagents, starting materials, and conditions familiar to those skilled in the art, the following compounds representative of the disclosure were prepared:

| Compound | Name and Data |
|---|---|
| 275 | 3-[8-Methyl-2-(3-methyl-1-benzofuran-2-yl)-5-[(1R)-1-phenylethoxy]quinolin-4-yl]-1H-pyrazol-5-ol<br>Mass Spectrum (LCMS, ESI pos): Calcd. for $C_{30}H_{26}N_3O_3$: 476.2 (M + H); Found: 476.3. $^1$H NMR (400 MHz, DMSO-d$_6$): δ 11.81 (brs, 1H), 9.57 (brs, 1H), 7.88 (s, 1H), 7.77 (d, J = 7.2 Hz, 1H), 7.66 (d, J = 8.0 Hz, 1H), 7.44 (t, J = 7.2 Hz, 2H), 7.35-7.24 (m, 5H), 7.20-7.17 (m, 1H), 6.71 (d, J = 8.0 Hz, 1H), 5.75 (s, 1H), 5.42 (q, J = 6.4 Hz, 1H), 2.84 (s, 3H), 2.63 (s, 3H), 1.24 (d, J = 6.0 Hz, 3H). HPLC purity (254 nm): 96.1%. |

Example 31: Preparation of Sodium 5-[(2-Cyanophenyl)methoxy]-8-methyl-2-(3-methyl-1-benzothiophen-2-yl)quinoline-4-carboxylate (Compound 297)

A. Methyl 5-R2-Cyanophenyl)methoxyl-8-methyl-2-(3-methyl-1-benzothiophen-2-yl)quinoline-4-carboxylate. To a 100-mL round-bottom flask was placed a solution of methyl 5-hydroxy-8-methyl-2-(3-methyl-1-benzothiophen-2-yl)quinoline-4-carboxylate (175 mg, 0.48 mmol, as prepared in Example 28, Step B) in MeCN (20 mL) then 2-(bromomethyl)benzonitrile (99 mg, 0.50 mmol) and K$_2$CO$_3$ (331 mg, 2.39 mmol) were added. The reaction was stirred for 5 h at rt, quenched by the addition of water, and extracted with DCM. The organic extracts were combined, dried over anhydrous Na$_2$SO$_4$, and concentrated under reduced pressure. The residue was purified by column chromatography eluting with EtOAc/petroleum ether (1:10) affording 225 mg (98%) of the title compound as a light yellow solid. Mass Spectrum (LCMS, ESI pos): Calcd. for $C_{29}H_{23}N_2O_3S^+$: 479.1 (M+H); Found: 479.1.

B. 5-[(2-Cyanophenyl)methoxy]-8-methyl-2-(3-methyl-1-benzothiophen-2-yl)quinoline-4-carboxylic acid. To a 25-mL sealed tube was placed a solution of methyl 5-[(2-cyanophenyl)methoxy]-8-methyl-2-(3-methyl-1-benzothiophen-2-yl)quinoline-4-carboxylate (100 mg, 0.21 mmol, as prepared in the previous step) in MeOH (10 mL) and water (2 mL) then LiOH (225 mg, 9.39 mmol) was added. The reaction was stirred for 5 h at 80° C., cooled to rt, adjusted to pH 3 with 6N HCl, and extracted with DCM. The organic extracts were combined and concentrated under reduced pressure. The residue was purified by column chromatography eluting with DCM/MeOH (10:1) affording 90 mg (93%) of the title compound as a yellow solid. Mass Spectrum (LCMS, ESI pos): Calcd. for $C_{28}H_{21}N_2O_3S^+$: 465.1 (M+H); Found: 465.2.

C. Sodium 5-[(2-Cyanophenyl)methoxy]-8-methyl-2-(3-methyl-1-benzothiophen-2-yl)quinoline-4-carboxylate. To a 50-mL round-bottom flask was placed a solution of 5-[(2-cyanophenyl)methoxy]-8-methyl-2-(3-methyl-1-benzothiophen-2-yl)quinoline-4-carboxylic acid (63 mg, 0.14 mmol, as prepared in the last step) in MeOH (5 mL) then 0.05M NaOH solution (2.8 mL) was added. The reaction was stirred for 15 min at rt then the solvent was removed under reduced pressure affording 50.9 mg (77%) of the title compound as a white solid. Mass Spectrum (LCMS, ESI pos): Calcd. for $C_{28}H_{21}N_2O_3S^+$: 465.1 (M+H); Found: 465.2. $^1$H NMR (400 MHz, DMSO-$d_6$): δ 8.53 (d, J=7.6 Hz, 1H), 8.01 (d, J=6.8 Hz, 1H), 7.92 (d, J=8.4 Hz, 1H), 7.85 (d, J=8.0 Hz, 1H), 7.74 (t, J=8.0 Hz, 1H), 7.52-7.44 (m, 5H), 6.92 (d, J=8.0 Hz, 1H), 5.41 (s, 2H), 2.83 (s, 3H), 2.67 (s, 3H). HPLC purity (254 nm): 99.2%.

Using the procedure described in Example 31, with reagents, starting materials, and conditions familiar to those skilled in the art, the following compounds representative of the disclosure were prepared:

| Compound | Name and Data |
|---|---|
| 289 | Sodium 5-[(2-Fluorophenyl)methoxy]-8-methyl-2-(3-methyl-1-benzothiophen-2-yl)quinoline-4-carboxylate<br>Mass Spectrum (LCMS, ESI pos): Calcd. for $C_{27}H_{21}FNO_3S^+$: 458.1 (M + H); Found: 458.2. $^1$H NMR (400 MHz, DMSO-$d_6$): δ 8.31 (t, J = 7.2 Hz, 1H), 8.01 (d, J = 7.2 Hz, 1H), 7.92 (d, J = 7.2 Hz, 1H), 7.48-7.44 (m, 3H), 7.42 (s, 1H), 7.36-7.31 (m, 1H), 7.22-7.17 (m, 2H), 6.90 (d, J = 8.0 Hz, 1H), 5.28 (s, 2H), 2.83 (s, 3H), 2.65 (s, 3H). HPLC purity (254 nm): 98.4%. |
| 290 | Sodium 5-[(3-Fluorophenyl)methoxy]-8-methyl-2-(3-methyl-1-benzothiophen-2-yl)quinoline-4-carboxylate<br>Mass Spectrum (LCMS, ESI pos): Calcd. for $C_{27}H_{21}FNO_3S^+$: 458.1 (M + H); Found: 458.2. $^1$H NMR (400 MHz, DMSO-$d_6$): δ 8.01 (d, J = 7.2 Hz, 1H), 7.92 (d, J = 7.2 Hz, 1H), 7.85 (d, J = 10.8 Hz, 1H), 7.52 (d, J = 7.6 Hz, 1H), 7.48-7.43 (m, 3H), 7.42 (s, 1H), 7.40-7.34 (m, 1H), 7.08-7.04 (m, 1H), 6.87 (d, J = 7.6 Hz, 1H), 5.26 (s, 2H), 2.83 (s, 3H), 2.64 (s, 3H). HPLC purity (254 nm): 98.8%. |
| 291 | Sodium 5-[(4-Fluorophenyl)methoxy]-8-methyl-2-(3-methyl-1-benzothiophen-2-yl)quinoline-4-carboxylate<br>Mass Spectrum (LCMS, ESI pos): Calcd. for $C_{27}H_{21}FNO_3S^+$: 458.1 (M + H); Found: 458.2. $^1$H NMR (400 MHz, DMSO-$d_6$): δ 8.01 (d, J = 7.6 Hz, 1H), 7.91 (d, J = 7.6 Hz, 1H), 7.88-7.84 (m, 2H), 7.48-7.45 (m, 3H), 7.43 (s, 1H), 7.15 (t, J = 8.8 Hz, 2H), 6.88 (d, J = 8.0 Hz, 1H), 5.22 (s, 2H), 2.82 (s, 3H), 2.64 (s, 3H). HPLC purity (254 nm): 99.1%. |
| 293 | Sodium 5-[(3-Methoxyphenyl)methoxy]-8-methyl-2-(3-methyl-1-benzothiophen-2-yl)quinoline-4-carboxylate<br>Mass Spectrum (LCMS, ESI pos): Calcd. for $C_{28}H_{24}NO_4S^+$: 470.1 (M + H); Found: 470.2. $^1$H NMR (400 MHz, DMSO-$d_6$): δ 8.01 (d, J = 7.2 Hz, 1H), 7.92 (d, J = 7.6 Hz, 1H), 7.71 (s, 1H), 7.48-7.41 (m, 4H), 7.21 (t, J = 7.6 Hz, 1H), 7.14 (d, J = 7.2 Hz, 1H), 6.88 (d, J = 8.0 Hz, 1H), 6.78 (d, J = 8.0 Hz, 1H), 5.21 (s, 2H), 3.88 (s, 3H), 2.82 (s, 3H), 2.64 (s, 3H). HPLC purity (254 nm): 98.6%. |
| 294 | Sodium 5-[(2,6-Difluorophenyl)methoxy]-8-methyl-2-(3-methyl-1-benzothiophen-2-yl)quinoline-4-carboxylate<br>Mass Spectrum (LCMS, ESI pos): Calcd. for $C_{27}H_{20}F_2NO_3S^+$: 476.1 (M + H); Found: 476.2. $^1$H NMR (400 MHz, DMSO-$d_6$): δ 8.01 (d, J = 7.2 Hz, 1H), 7.91 (d, J = 7.6 Hz, 1H), 7.55-7.42 (m, 5H), 7.15 (t, J = 7.6 Hz, 2H), 6.90-6.85 (m, 1H), 5.16 (s, 2H), 2.80 (s, 3H), 2.67 (s, 3H). HPLC purity (254 nm): 96.6%. |
| 298 | Sodium 5-[(3-Cyanophenyl)methoxy]-8-methyl-2-(3-methyl-1-benzothiophen-2-yl)quinoline-4-carboxylate<br>Mass Spectrum (LCMS, ESI pos): Calcd. for $C_{28}H_{21}N_2O_3S^+$: 465.1 (M + H); Found: 465.2. $^1$H NMR (300 MHz, DMSO-$d_6$): δ 8.45 (s, 1H), 8.14 (d, J = 8.4 Hz, 1H), 8.03-8.00 (m, 1H), 7.93-7.90 (m, 1H), 7.72 (d, J = 7.5 Hz, 1H), 7.55 (t, J = 8.4 Hz, 1H), 7.48-7.43 (m, 4H), 6.91 (d, J = 8.4 Hz, 1H), 5.28 (s, 2H), 2.83 (s, 3H), 2.65 (s, 3H). HPLC purity (254 nm): 99.7%. |

Example 32: Preparation of 2-[8-Methyl-2-(3-methyl-1-benzofuran-2-yl)-5-(1-phenylethoxy)quinolin-4-yl]acetic acid (Compound 276)

A. 2-[8-Methyl-2-(3-methyl-1-benzofuran-2-yl)-5-(1-phenylethoxy)quinolin-4-yl]acetic acid. To a 100-mL round-bottom flask was placed a solution of 2-methyl-5-(1-phenylethoxy)aniline (1 g, 4.40 mmol, Intermediate 52) in THF (30 mL) then 3-methyl-1-benzofuran-2-carbaldehyde (700 mg, 4.37 mmol), CuCl (430 mg, 4.39 mmol), and but-3-ynoic acid (300 mg, 3.57 mmol) were added. The reaction was stirred at 80° C. for 12 h, quenched by the addition of water, and extracted with EtOAc. The organic extracts were combined, washed with brine, dried over anhydrous $Na_2SO_4$, and concentrated under reduced pressure. The crude product was purified by Prep-HPLC (Column, X Bridge™ Prep C18 5 um OBD™ 19*100 mm; mobile phase, water with 0.05% TFA and $CH_3CN$ (10.0% $CH_3CN$ up to 85.0% in 10 min, up to 95.0% in 1.5 min, down to 10.0% in 1.5 min); Detector, uv 254 nm) affording 11 mg (1%) of the title compound as a yellow solid. Mass Spectrum (LCMS, ESI pos): Calcd. for $C_{29}H_{26}NO_4^+$: 452.2 (M+H); Found: 452.2. $^1H$ NMR (400 MHz, DMSO-$d_6$): δ 12.48 (brs, 1H), 7.95 (s, 1H), 7.78 (d, J=7.6 Hz, 1H), 7.67 (d, J=8.4 Hz, 1H), 7.47-7.43 (m, 3H), 7.37-7.31 (m, 4H), 7.26-7.23 (m, 1H), 6.64 (d, J=8.4 Hz, 1H), 5.61 (q, J=6.0 Hz, 1H), 4.56 (d, J=16.8 Hz, 1H), 4.39 (d, J=16.8 Hz, 1H), 2.84 (s, 3H), 2.61 (s, 3H), 1.69 (d, J=6.0 Hz, 3H). HPLC purity (254 nm): 98.7%.

Example 33: Preparation of Sodium 8-Methyl-2-(3-methyl-1-benzothiophen-2-yl)-5-[[(1R,3S)-3-methylcyclohexyl]oxy]quinoline-4-carboxylate (Compound 218), 8-Methyl-2-(3-methyl-1-benzothiophen-2-yl)-5-[[(1S,3R)-3-methylcyclohexyl]oxy]quinoline-4-carboxylic acid (Compound 219), 8-Methyl-2-(3-methyl-1-benzothiophen-2-yl)-5-[[(1S,3S)-3-methylcyclohexyl]oxy]quinoline-4-carboxylic acid (Compound 220), and 8-methyl-2-(3-methyl-1-benzothiophen-2-yl)-5-[[(1R,3R)-3-methylcyclohexyl]oxy]quinoline-4-carboxylic acid (Compound 221)

A. 1-Methyl-4-[(3-methylcyclohexyl)oxy]-2-nitrobenzene. To a 250-mL 3-necked round-bottom flask purged and maintained with an inert atmosphere of nitrogen was placed a solution of 4-methyl-3-nitrophenol (5 g, 32.65 mmol) in THF (100 mL) then 3-methylcyclohexan-1-ol (3.7 g, 32.40 mmol) and $PPh_3$ (17.3 g, 65.96 mmol) were added. The solution was stirred at rt and DIAD (13.3 g, 65.77 mmol) was added dropwise then stirring was continued at rt for 5 h. The reaction was quenched by the addition of water and concentrated under reduced pressure. The residue was purified by column chromatography eluting with EtOAc/petroleum ether (1:10) affording 6.6 g (81%) of the title compound as yellow oil.

B. 2-Methyl-5-[(3-methylcyclohexyl)oxy]aniline. To a 250-mL round-bottom flask purged and maintained with an inert atmosphere of nitrogen was placed a solution of 1-methyl-4-[(3-methylcyclohexyl)oxy]-2-nitrobenzene (6 g, 24.07 mmol, as prepared in the previous step) in MeOH (100 mL) then Raney Ni (600 mg) was added. The solution was degassed and back filled with hydrogen and stirred for 5 h at rt. The $H_2$ was purged then the solids were removed by filtration. The filtrate was concentrated under reduced pressure affording 4.7 g of the title compound as a yellow solid. Mass Spectrum (LCMS, ESI pos): Calcd. for $C_{14}H_{22}NO^+$: 220.2 (M+H); Found: 220.2.

C. 8-Methyl-2-(3-methyl-1-benzothiophen-2-yl)-5-[[(1R,3S)-3-methylcyclohexyl]oxy]quinoline-4-carboxylic acid, 8-Methyl-2-(3-methyl-1-benzothiophen-2-yl)-5-[[(1S,3R)-3-methylcyclohexyl]oxy]quinoline-4-carboxylic acid, 8-Methyl-2-(3-methyl-1-benzothiophen-2-yl)-5-[[(1S,3S)-3-methylcyclohexyl]oxy]quinoline-4-carboxylic, and 8-Methyl-2-(3-methyl-1-benzothiophen-2-yl)-5-[[(1R,3R)-3-methylcyclohexyl]oxy]quinoline-4-carboxylic acid. To a 30-mL vial was placed a solution of 2-methyl-5-[(3-methylcyclohexyl)oxy]aniline (2.5 g, 11.40 mmol, as prepared in the previous step) in EtOH (10 mL) then 3-methyl-1-benzothiophene-2-carbaldehyde (2 g, 11.35 mmol) and 2-oxopropanoic acid (2 g, 22.71 mmol) were added. The reaction was stirred overnight at 130° C. then cooled to rt and concentrated under reduced pressure. The crude product was purified by Flash-Prep-HPLC (Column, C18 silica gel; mobile phase, ACN/$H_2O$=60% increasing to ACN/$H_2O$=100% within 15 min; Detector, UV 254 nm) affording 804 mg (16%) of the title compound as a yellow solid. The isomers were separated by Prep-SFC (Column, Chiralpak AD-H, 2*25 cm (5 um); mobile phase, $CO_2$ (50%), EtOH—(50%); Detector, UV 254 nm) affording 150 mg (19%) of 8-methyl-2-(3-methyl-1-benzothiophen-2-yl)-5-[[(1R,3S)-3-methylcyclohexyl]oxy]quinoline-4-carboxylic acid as a yellow solid, 76 mg (10%) of 8-methyl-2-(3-methyl-1-benzothiophen-2-yl)-5-[[(1S,3R)-3-methylcyclohexyl]oxy]quinoline-4-carboxylic acid as a yellow solid, 86 mg (11%) of 8-methyl-2-(3-methyl-1-benzothiophen-2-yl)-5-[[(1S,3S)-3-methylcyclohexyl]oxy]quinoline-4-carboxylic acid as a yellow solid and 60 mg (8%) of 8-methyl-2-(3-methyl-1-benzothiophen-2-yl)-5-[[(1R,3R)-3-methylcyclohexyl]oxy]quinoline-4-carboxylic acid as a yellow solid.

D. Sodium 8-Methyl-2-(3-methyl-1-benzothiophen-2-yl)-5-[[(1R,3S)-3-methylcyclohexyl]oxy]quinoline-4-carboxylate (Compound 218). To a 50-mL round-bottom flask was placed a solution of 8-methyl-2-(3-methyl-1-benzothiophen-2-yl)-5-[[(1R,3S)-3-methylcyclohexyl]oxy]quinoline-4-carboxylic acid (60 mg, 0.13 mmol, as prepared in the previous step) in MeOH (3 mL) then NaOH (5.4 mg, 0.14 mmol) and $H_2O$ (20 mL) were added. The reaction was stirred for 2 min at rt then the solvent was removed under reduced pressure affording 50.8 mg (81%) of the title compound as a yellow solid. Mass Spectrum (LCMS, ESI pos): Calcd. for $C_{27}H_{28}NO_3S^+$: 446.2 (M+H); Found: 446.3. $^1H$ NMR (300 MHz, DMSO-$d_6$): δ 8.01-7.98 (m, 1H), 7.92-7.89 (m, 1H), 7.48-7.41 (m, 3H), 7.36 (s, 1H), 6.75 (d, J=8.1 Hz, 1H), 4.71-4.68 (m, 1H), 2.81 (s, 3H), 2.63 (s, 3H), 2.21-2.13 (m, 2H), 2.02-1.91 (m, 2H), 1.64-1.61 (m, 1H), 1.46-1.33 (m, 2H), 1.17-1.09 (m, 1H), 0.96-0.89 (m, 1H), 0.86 (d, J=6.6 Hz, 3H). HPLC purity (254 nm): 99.2%.

E. Sodium 8-Methyl-2-(3-methyl-1-benzothiophen-2-yl)-5-[[(1S,3R)-3-methylcyclohexyl]oxy]quinoline-4-carboxylic acid (Compound 219). To a 50-mL round-bottom flask was placed a solution of 8-methyl-2-(3-methyl-1-benzothiophen-2-yl)-5-[[(1S,3R)-3-methylcyclohexyl]oxy]quinoline-4-carboxylic acid (60 mg, 0.13 mmol, as prepared in Step C) in MeOH (3 mL), then NaOH (5.4 mg, 0.14 mmol) and $H_2O$ (20 mL) were added. The reaction was stirred for 2 min at rt then the solvent was removed under reduced pressure affording 42.3 mg (72%) of the title compound as a yellow solid. Mass Spectrum (LCMS, ESI pos): Calcd. for $C_{27}H_{28}NO_3S^+$: 446.2 (M+H); Found: 446.3. $^1H$ NMR (300 MHz, DMSO-$d_6$): δ 8.00 (d, J=6.6 Hz, 1H), 7.90 (d, J=6.9 Hz, 1H), 7.48-7.42 (m, 3H), 7.37 (s, 1H), 6.76 (d, J=8.1 Hz, 1H), 4.71-4.70 (m, 1H), 2.81 (s, 3H), 2.73 (s, 3H), 2.26-2.12 (m, 2H), 2.02-1.91 (m, 2H), 1.64-1.61 (m, 1H), 1.46-1.36 (m, 2H), 1.23-1.11 (m, 1H), 0.96-0.89 (m, 1H), 0.86 (d, J=6.6 Hz, 3H). HPLC purity (254 nm): 97.5%.

F. Sodium 8-Methyl-2-(3-methyl-1-benzothiophen-2-yl)-5-[[(1S,3S)-3-methylcyclohexyl]oxy]quinoline-4-carboxylate (Compound 220). To a 50-mL round-bottom flask was placed a solution of 8-methyl-2-(3-methyl-1-benzothiophen-2-yl)-5-[[(1S,3S)-3-methylcyclohexyl]oxy]quinoline-4-carboxylic acid (60 mg, 0.13 mmol, as prepared in Step C) in MeOH (3 mL), then NaOH (5.4 mg, 0.14 mmol) and $H_2O$ (20 mL) were added. The reaction was stirred for 2 min at rt then the solvent was removed under reduced pressure affording 56.2 mg (82%) of the title compound as a yellow solid. Mass Spectrum (LCMS, ESI pos): Calcd. for $C_{27}H_{28}NO_3S^+$: 446.2 (M+H); Found: 446.2. $^1H$ NMR (300 MHz, DMSO-$d_6$): δ 8.01-7.98 (m, 1H), 7.91-7.89 (m, 1H), 7.48-7.42 (m, 3H), 7.33 (s, 1H), 6.84 (d, J=8.1 Hz, 1H), 4.37-4.30 (m, 1H), 2.80 (s, 3H), 2.72 (s, 3H), 2.04-2.01 (m, 2H), 1.76-1.72 (m, 1H), 1.63-1.59 (m, 1H), 1.52-1.14 (m, 4H), 0.94 (d, J=6.6 Hz, 3H), 0.93-0.82 (m, 1H). HPLC purity (254 nm): 98.8%.

G. Sodium 8-Methyl-2-(3-methyl-1-benzothiophen-2-yl)-5-[[(1R,3R)-3-methylcyclohexyl]oxy]quinoline-4-carboxylate (Compound 221). To a 50-mL round-bottom flask was placed a solution of 8-methyl-2-(3-methyl-1-benzothiophen-2-yl)-5-[[(1R,3R)-3-methylcyclohexyl]oxy]quinoline-4-carboxylic acid (60 mg, 0.13 mmol, as prepared in Step C) in MeOH (3 mL), then NaOH (5.4 mg, 0.14 mmol) and H$_2$O (20 mL) were added. The reaction was stirred for 2 min at rt then the solvent was removed under reduced pressure affording 50 mg (77%) of the title compound as a yellow solid. Mass Spectrum (LCMS, ESI pos): Calcd. for C$_{27}$H$_{28}$NO$_3$S$^+$: 446.2 (M+H); Found: 446.2. $^1$H NMR (300 MHz, DMSO-d$_6$): δ 8.01-7.98 (m, 1H), 7.92-7.89 (m, 1H), 7.48-7.40 (m, 3H), 7.33 (s, 1H), 6.85 (d, J=7.8 Hz, 1H), 4.37-4.30 (m, 1H), 2.80 (s, 3H), 2.64 (s, 3H), 2.06-2.01 (m, 2H), 1.76-1.72 (m, 1H), 1.63-1.60 (m, 1H), 1.52-1.14 (m, 4H), 0.92 (d, J=6.6 Hz, 3H), 0.90-0.82 (m, 1H). HPLC purity (254 nm): 97.0%.

Example 34: Preparation of Sodium 8-Methyl-2-(3-methyl-1-benzofuran-2-yl)-5-[(1R)-1-(4-sulfamoylphenyl)ethoxy]quinoline-4-carboxylate (Compound 237) and Sodium 8-Methyl-2-(3-methyl-1-benzofuran-2-yl)-5-[(1 S)-1-(4-sulfamoylphenyl)ethoxy]quinoline-4-carboxylate (Compound 238)

A. Methyl 5-(Benzyloxy)-8-methyl-2-(3-methyl-1-benzofuran-2-yl)quinoline-4-carboxylate. To a 100-mL round-bottom flask purged and maintained with an inert atmosphere of nitrogen was placed a solution of 5-(benzyloxy)-2-methylaniline (5 g, 23.45 mmol, Intermediate 13) in EtOH (50 mL) then methyl 2-oxopropanate (7.2 g, 81.5 mmol), and 3-methyl-1-benzofuran-2-carbaldehyde (3.75 g, 23.45 mmol) were added. The reaction was stirred for 12 h at 120° C. then concentrated under reduced pressure. The residue was purified by column chromatography eluting with EtOAc/petroleum ether (1:1) affording 4.25 g (43%) of the title compound as a yellow solid. Mass Spectrum (LCMS, ESI pos): Calcd. for C$_{28}$H$_{24}$NO$_4^+$: 438.2 (M+H); Found: 438.5.

B. Methyl 5-Hydroxy-8-methyl-2-(3-methyl-1-benzofuran-2-yl)quinoline-4-carboxylate. To a 250-mL round-bottom flask was placed a solution of methyl 5-(benzyloxy)-8-methyl-2-(3-methyl-1-benzofuran-2-yl)quinoline-4-carboxylate (2.2 g, 5.03 mmol, as prepared in the previous step) in MeOH (30 mL) then conc. H$_2$SO$_4$ (10 mL) was added. The reaction was stirred for 6 h at 80° C. then quenched by the addition of water/ice. The solids were collected by filtration affording 1.4 g (80%) of the title compound as a brown solid. Mass Spectrum (LCMS, ESI pos): Calcd. for C$_{21}$H$_{18}$NO$_4^+$: 348.1 (M+H); Found: 348.3.

C. Methyl 5-[1-[4-(tert-Butylsulfamoyl)phenyl]ethoxy]-8-methyl-2-(3-methyl-1-benzofuran-2-yl)quinoline-4-carboxylate. To a 100-mL 3-necked round-bottom flask purged and maintained with an inert atmosphere of nitrogen was placed a solution of methyl 5-hydroxy-8-methyl-2-(3-methyl-1-benzofuran-2-yl)quinoline-4-carboxylate (500 mg, 1.44 mmol, as prepared in the previous step) in THF (20 mL) then PPh$_3$ (566 mg, 2.16 mmol), N-tert-butyl-4-(1-hydroxyethyl)benzene-1-sulfonamide (407 mg, 1.58 mmol) were added. DIAD (436 mg, 2.16 mmol) was added dropwise then the reaction was stirred for 3 h at rt and concentrated under reduced pressure. The residue was purified by column chromatography eluting with EtOAc/petroleum ether (1:4) affording 250 mg (30%) of the title compound as a yellow solid. Mass Spectrum (LCMS, ESI pos): Calcd. for C$_{33}$H$_{35}$N$_2$O$_6$S$^+$: 587.2 (M+H); Found: 587.5.

D. 5-[1-[4-(tert-Butylsulfamoyl)phenyl]ethoxy]-8-methyl-2-(3-methyl-1-benzofuran-2-yl)quinoline-4-carboxylic acid. To a 40-mL sealed tube was placed a solution of methyl 5-[1-[4-(tert-butylsulfamoyl)phenyl]ethoxy]-8-methyl-2-(3-methyl-1-benzofuran-2-yl)quinoline-4-carboxylate (250 mg, 0.43 mmol, as prepared in the previous step) in MeOH (20 mL) then NaOH (171 mg, 4.28 mmol) and water (2 mL) were added. The reaction was stirred for 6 h at 100° C. then concentrated under reduced pressure. Then the pH of the aqueous layer was adjusted to 3 with 1N HCl and the solid was collected by filtration affording 190 mg (78%) of the title compound as a light yellow solid. Mass Spectrum (LCMS, ESI pos): Calcd. for C$_{32}$H$_{33}$N$_2$O$_6$S$^+$: 573.2 (M+H); Found: 573.2.

E. 8-Methyl-2-(3-methyl-1-benzofuran-2-yl)-5-[(1R)-1-(4-sulfamoylphenyl)ethoxy]quinoline-4-carboxylic acid and 8-Methyl-2-(3-methyl-1-benzofuran-2-yl)-5-[(1S)-1-(4-sulfamoylphenyl)ethoxy]quinoline-4-carboxylic acid. To a 25-mL round-bottom flask was placed a solution of 5-[1-[4-(tert-butylsulfamoyl)phenyl]ethoxy]-8-methyl-2-(3-methyl-1-benzofuran-2-yl)quinoline-4-carboxylic acid (190 mg, 0.33 mmol, as prepared in the previous step) in DCM (3 mL) then TFA (1 mL) was added. The reaction was stirred for 3 h at rt then the solvent was removed under reduced pressure. The residue was purified by column chromatography eluting with DCM/MeOH (25:1). The isomers were separated by Chiral-Prep-HPLC (Prep-HPLC-004: Column, Chiralpak IA, 2*25 cm, 5 um; mobile phase, Hex (0.1% TFA) and EtOH (hold 30.0% EtOH—in 24 min); Detector, uv 254 nm) affording 47 mg (28%) of 8-methyl-2-(3-methyl-1-benzofuran-2-yl)-5-[(1R)-1-(4-sulfamoylphenyl)ethoxy]quinoline-4-carboxylic acid as a yellow solid and 44 mg (26%) of 8-methyl-2-(3-methyl-1-benzofuran-2-yl)-5-[(1S)-1-(4-sulfamoylphenyl)ethoxy]quinoline-4-carboxylic acid as a yellow solid.

F. Sodium 8-Methyl-2-(3-methyl-1-benzofuran-2-yl)-5-[(1R)-1-(4-sulfamoylphenyl)ethoxy]quinoline-4-carboxylate (Compound 237). To a 25-mL round-bottom flask was placed a solution of 8-methyl-2-(3-methyl-1-benzofuran-2-yl)-5-[(1R)-1-(4-sulfamoylphenyl)ethoxy]quinoline-4-carboxylic acid (47 mg, 0.09 mmol, as prepared in the previous step) in MeOH (1 mL) then NaOH (3.6 mg, 0.09 mmol) was added. The reaction was stirred for 2 h at rt then the solvent was removed under reduced pressure affording 39.1 mg (80%) of the title compound as a yellow solid. Mass Spectrum (LCMS, ESI pos): Calcd. for C$_{28}$H$_{25}$N$_2$O$_6$S$^+$: 517.1 (M+H); Found: 517.1. $^1$H NMR (300 MHz, DMSO-d$_6$): δ 7.86 (s, 1H), 7.78-7.72 (m, 3H), 7.68-7.65 (m, 3H), 7.46-7.41 (m, 2H), 7.36-7.31 (m, 1H), 6.73 (d, J=7.8 Hz, 1H), 5.76 (q, J=6.6 Hz, 1H), 2.82 (s, 3H), 2.60 (s, 3H), 1.61 (d, J=6.0 Hz, 3H). HPLC purity (254 nm): 97.2%.

G. Sodium 8-Methyl-2-(3-methyl-1-benzofuran-2-yl)-5-[(1S)-1-(4-sulfamoylphenyl)ethoxy]quinoline-4-carboxylate (Compound 238). To a 25-mL round-bottom flask was placed a solution of 8-methyl-2-(3-methyl-1-benzofuran-2-yl)-5-[(1S)-1-(4-sulfamoylphenyl)ethoxy]quinoline-4-carboxylic acid (44 mg, 0.09 mmol, as prepared in Step E) in MeOH (1 mL) then NaOH (3.4 mg, 0.09 mmol) was added. The reaction was stirred for 2 h at rt then the solvent was removed under reduced pressure affording 40.3 mg (88%) of the title compound as a yellow solid. Mass Spectrum (LCMS, ESI pos): Calcd. for C$_{28}$H$_{25}$N$_2$O$_6$S$^+$: 517.1 (M+H); Found: 517.3. $^1$H NMR (300 MHz, DMSO-d$_6$): δ 7.95 (s, 1H), 7.81-7.77 (m, 3H), 7.72-7.67 (m, 3H), 7.57-7.55 (m, 2H), 7.47-7.39 (m, 1H), 6.79 (d, J=8.1 Hz, 1H), 5.84 (q, J=6.3 Hz, 1H), 2.74 (s, 3H), 2.64 (s, 3H), 1.65 (d, J=6.3 Hz, 3H). HPLC purity (254 nm): 98.0%.

Using the procedure described in Example 34, with reagents, starting materials, and conditions familiar to those skilled in the art, the following compounds representative of the disclosure were prepared:

| Compound | Name and Data |
|---|---|
| 239 | Sodium 8-Methyl-2-(3-methyl-1-benzofuran-2-yl)-5-[(1R)-1-[4-(methylsulfamoyl)phenyl]ethoxy]quinoline-4-carboxylate<br>Mass Spectrum (LCMS, ESI pos): Calcd. for $C_{29}H_{27}N_2O_6S^+$: 531.2 (M + H); Found: 531.2. $^1$H NMR (400 MHz, CD$_3$OD): δ 7.98 (s, 1H), 7.85-7.79 (m, 4H), 7.71 (d, J = 8.0 Hz, 1H), 7.59 (d, J = 8.4 Hz, 1H), 7.41 (t, J = 7.2 Hz, 1H), 7.38-7.30 (m, 2H), 6.62 (d, J = 8.0 Hz, 1H), 5.69 (q, J = 6.4 Hz, 1H), 2.89 (s, 3H), 2.68 (s, 3H), 2.50 (s, 3H), 1.80 (d, J = 6.4 Hz, 3H). HPLC purity (254 nm): 97.6%. |
| 240 | Sodium 8-Methyl-2-(3-methyl-1-benzofuran-2-yl)-5-[(1S)-1-[4-(methylsulfamoyl)phenyl]ethoxy]quinoline-4-carboxylate<br>Mass Spectrum (LCMS, ESI pos): Calcd. for $C_{29}H_{27}N_2O_6S^+$: 531.2 (M + H); Found: 531.2. $^1$H NMR (400 MHz, CD$_3$OD): δ 7.97 (s, 1H), 7.87-7.79 (m, 4H), 7.70 (d, J = 7.6 Hz, 1H), 7.59 (d, J = 8.0 Hz, 1H), 7.41 (t, J = 7.2 Hz, 1H), 7.33-7.30 (m, 2H), 6.61 (d, J = 8.0 Hz, 1H), 5.68 (q, J = 6.4 Hz, 1H), 2.90 (s, 3H), 2.68 (s, 3H), 2.50 (s, 3H), 1.79 (d, J = 6.4 Hz, 3H). HPLC purity (254 nm): 96.9%. |
| 257 | Sodium 8-Methyl-2-((1R)-3-methyl-1-benzofuran-2-yl)-5-(1-[pyrazolo[1,5-a]pyridin-5-yl]ethoxy)quinoline-4-carboxylate<br>Mass Spectrum (LCMS, ESI pos): Calcd. for $C_{29}H_{24}N_3O_4^+$: 478.2 (M + H); Found: 478.3. $^1$H NMR (400 MHz, DMSO-d$_6$): δ 8.53 (d, J = 7.2 Hz, 1H), 8.01 (s, 1H), 7.93 (s, 1H), 7.75 (d, J = 7.6 Hz, 1H), 7.69-7.64 (m, 2H), 7.44-7.40 (m, 2H), 7.36-7.32 (m, 2H), 6.74 (d, J = 8.0 Hz, 1H), 6.49 (s, 1H), 5.69 (q, J = 6.4 Hz, 1H), 2.83 (s, 3H), 2.59 (s, 3H), 1.61 (d, J = 6.4 Hz, 3H). HPLC purity (254 nm): 98.3%. |
| 258 | Sodium 8-Methyl-2-((1S)-3-methyl-1-benzofuran-2-yl)-5-(1-[pyrazolo[1,5-a]pyridin-5-yl]ethoxy)quinoline-4-carboxylate<br>Mass Spectrum (LCMS, ESI pos): Calcd. for $C_{29}H_{24}N_3O_4^+$: 478.2 (M + H); Found: 478.3. $^1$H NMR (400 MHz, DMSO-d$_6$): δ 8.55 (d, J = 7.2 Hz, 1H), 7.96-7.93 (m, 2H), 7.75 (d, J = 7.6 Hz, 1H), 7.71-7.66 (m, 2H), 7.43 (t, J = 7.6 Hz, 1H), 7.36-7.32 (m, 3H), 6.76 (d, J = 8.0 Hz, 1H), 6.51 (s, 1H), 5.70 (q, J = 6.4 Hz, 1H), 2.83 (s, 3H), 2.59 (s, 3H), 1.62 (d, J = 6.4 Hz, 3H). HPLC purity (254 nm): 98.8%. |

Example 35: CFTR Activity Assays i. Ussing Measurements

As discussed above, Ussing measurements are used to measure CFTR activity. In this method, primary lung epithelial cells (hBEs) homozygous for the Cystic Fibrosis-causing ΔF508 mutation are differentiated for a minimum of 4 weeks in an air-liquid interface on SnapWell filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% CO$_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages are stabilized, the chambers are clamped, and data is recorded by pulse readings every 5 seconds. Following baseline current stabilization, the following additions can be applied and the changes in current and resistance of the cells can be monitored:
 1. Benzamil to the apical chamber to inhibit ENaC sodium channel
 2. Forskolin to both chambers to activate ΔF508-CFTR by phosphorylation.
 3. VX-770 to the apical chamber to potentiate ΔF508-CFTR channel opening.
 4. CFTRinh-172 to the apical chamber to inhibit ΔF508-CFTR Cl— conductance.

The inhibitable current (that current that is blocked by CFTRinh-172) is measured as the specific activity of the ΔF508-CFTR channel, and increases in response to compound in this activity over that observed in vehicle-treated samples are identified as the correction of ΔF508-CFTR function imparted by the compound tested.

ii. hBE Equivalent Current (Ieq) Assay

Primary lung epithelial cells homozygous for the Cystic Fibrosis-causing ΔF508 mutation were differentiated for a minimum of 4 weeks in an air-liquid interface on Costar 24 well HTS filter plates prior to the equivalent current (Ieq) measurements. Cells were apically mucus-washed for 30 minutes 24 h prior to treatment with compounds. The basolateral media was removed and replaced with media containing the compound of interest diluted to its final concentration from DMSO stocks. Treated cells were incubated at 37° C. and 5% CO$_2$ for 24 hours. At the end of the treatment period, the media was changed to the Ieq experimental solution for 2 hours before the experiment and plates are maintained in a CO$_2$-free incubator during this period. The plates containing the cells were then placed in pre-warmed heating blocks at 36° C.±0.5 for 15 minutes before measurements are taken. The transepithelial voltage ($V_T$) and conductance ($G_T$) were measured using a custom 24 channel current clamp (TECC-24) with 24 well electrode manifold. The Ieq assay measurements were made following additions with standardized time periods:
 1. The baseline $V_T$ and $G_T$ values were measured for approximately 20 minutes.
 2. Benzamil was added to block ENaC for 15 minutes.
 3. Forskolin plus VX-770 were added to maximally activate ΔF508-CFTR for 27 minutes.

4. Bumetanide was added to inhibit the NaK$_2$Cl cotransporter and shut-off secretion of chloride.

The activity data captured was the area under the curve (AUC) for the traces of the equivalent chloride current. The AUC was collected from the time of the forskolin/VX-770 addition until the inhibition by bumetanide addition. Correction in response to compound treatment was scored as the increase in the AUC for compound-treated samples over that of vehicle-treated samples.

The results are shown below in Table 1. (+ indicates activity <50% of an CFTR amplifier (Compound A)+VX-809 (3 uM) with compound at 10 uM and Compound A at 3 uM; ++ indicates activity >50% of CFTR amplifier+VX-809 (3 uM) with compound at 10 uM and Compound A at 3 uM.

TABLE 1

| Compound # | Structure | Activity |
|---|---|---|
| 1 | 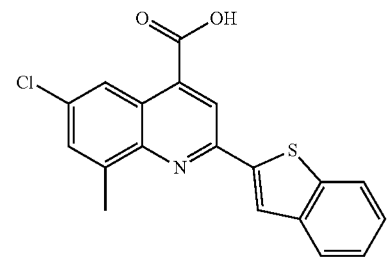 [SMILES: Cc1cc(Cl)cc2c(C(=O)O)cc(-c3cc4ccccc4s3)nc12] | + |
| 2 | 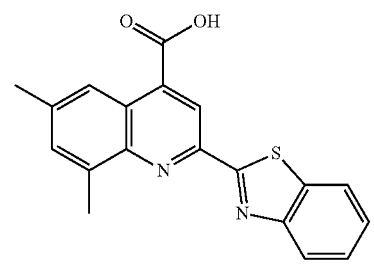 [SMILES: Cc1cc(C)c2nc(-c3nc4ccccc4s3)cc(C(=O)O)c2c1] | + |
| 3 | 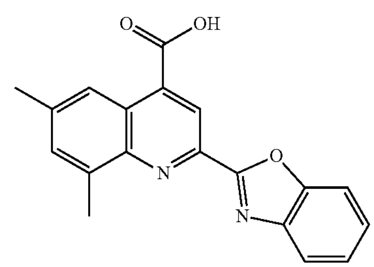 [SMILES: Cc1cc(C)c2nc(-c3nc4ccccc4o3)cc(C(=O)O)c2c1] | + |
| 4 | 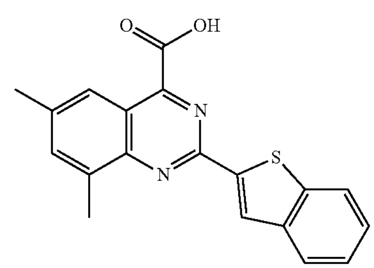 [SMILES: Cc1cc(C)c2nc(-c3cc4ccccc4s3)nc(C(=O)O)c2c1] | + |
| 5 | 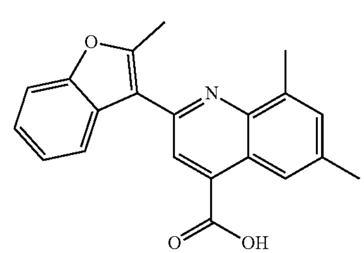 [SMILES: Cc1cc(C)c2nc(-c3c(C)oc4ccccc34)cc(C(=O)O)c2c1] | + |

TABLE 1-continued

| Compound # | Structure | Activity |
|---|---|---|
| 6 | 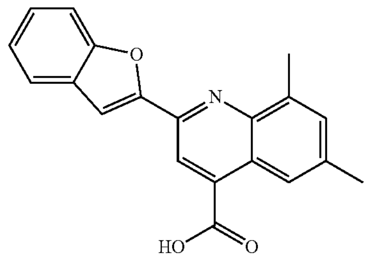 [SMILES: Cc1cc(C)c2nc(-c3cc4ccccc4o3)cc(C(=O)O)c2c1] | + |
| 7 | 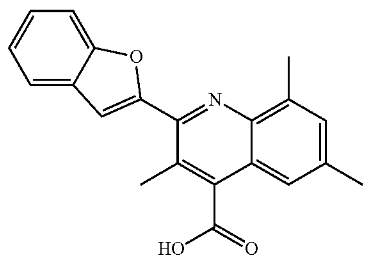 [SMILES: Cc1cc(C)c2nc(-c3cc4ccccc4o3)c(C)c(C(=O)O)c2c1] | + |
| 8 | 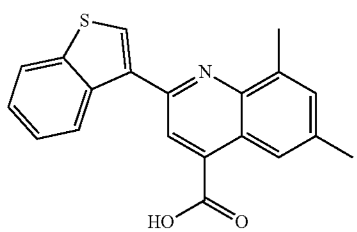 [SMILES: Cc1cc(C)c2nc(-c3csc4ccccc34)cc(C(=O)O)c2c1] | + |
| 9 | 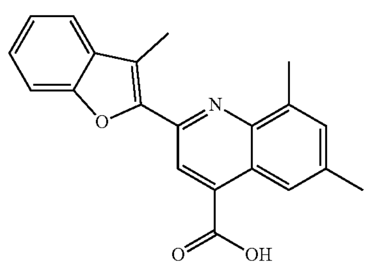 [SMILES: Cc1cc(C)c2nc(-c3oc4ccccc4c3C)cc(C(=O)O)c2c1] | ++ |
| 10 | 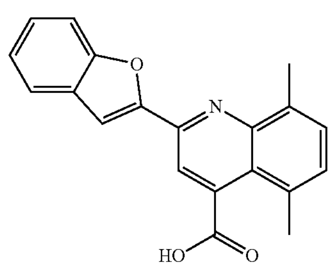 [SMILES: Cc1ccc(C)c2c(C(=O)O)cc(-c3cc4ccccc4o3)nc12] | + |
| 11 | 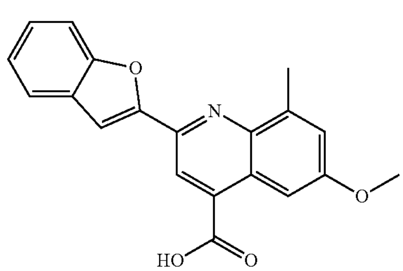 [SMILES: COc1cc(C)c2nc(-c3cc4ccccc4o3)cc(C(=O)O)c2c1] | + |

TABLE 1-continued

| Compound # | Structure | Activity |
|---|---|---|
| 12 | 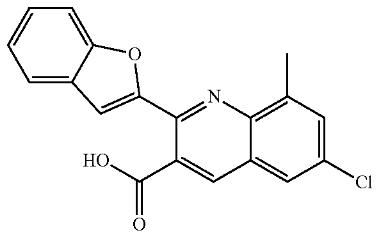 [SMILES: Cc1cc(Cl)cc2cc(C(=O)O)c(-c3cc4ccccc4o3)nc12] | + |
| 13 | 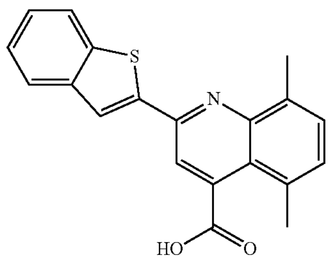 [SMILES: Cc1ccc(C)c2c(C(=O)O)cc(-c3cc4ccccc4s3)nc12] | + |
| 14 | 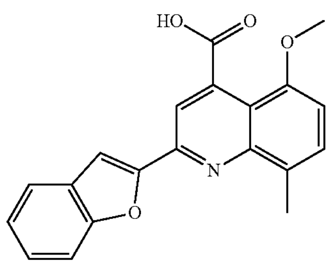 [SMILES: COc1ccc(C)c2nc(-c3cc4ccccc4o3)cc(C(=O)O)c12] | + |
| 15 | 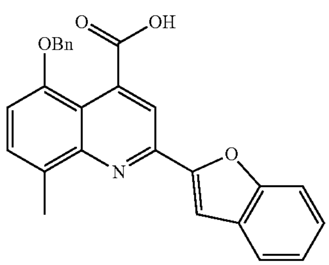 [SMILES: Cc1ccc(OCc2ccccc2)c2c(C(=O)O)cc(-c3cc4ccccc4o3)nc12] | ++ |
| 16 | 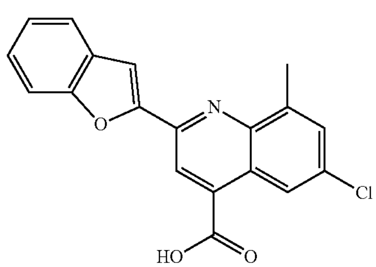 [SMILES: Cc1cc(Cl)cc2c(C(=O)O)cc(-c3cc4ccccc4o3)nc12] | + |
| 17 | 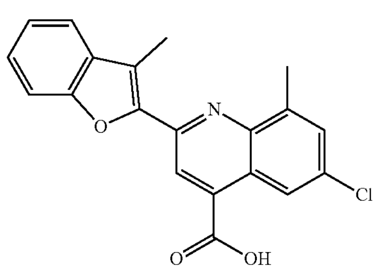 [SMILES: Cc1c(-c2cc(C(=O)O)c3cc(Cl)cc(C)c3n2)oc2ccccc12] | ++ |

TABLE 1-continued

| Compound # | Structure | Activity |
|---|---|---|
| 18 | 2-(3-methylbenzo[b]thiophen-2-yl)-6,8-dimethylquinoline-4-carboxylic acid | + |
| 19 | 2-(3-methylbenzofuran-2-yl)-8-methyl-6-(trifluoromethyl)quinoline-4-carboxylic acid | ++ |
| 20 | 2-(3-methylbenzofuran-2-yl)-6-fluoro-8-methylquinoline-4-carboxylic acid | ++ |
| 21 | 2-(3-methylbenzofuran-2-yl)-6-bromo-8-methylquinoline-4-carboxylic acid | ++ |
| 22 | 2-(3-methylbenzofuran-2-yl)-6-cyano-8-methylquinoline-4-carboxylic acid | + |
| 23 | 2-(3-methylbenzofuran-2-yl)-6-methoxy-8-methylquinoline-4-carboxylic acid | ++ |

TABLE 1-continued

| Compound # | Structure | Activity |
|---|---|---|
| 24 | 2-(3-methylbenzofuran-2-yl)-8-methyl-6-(benzyloxy)quinoline-4-carboxylic acid | ++ |
| 25 | 2-(3-methylbenzofuran-2-yl)-8-methyl-6-(2-hydroxyethoxy)quinoline-4-carboxylic acid | + |
| 26 | 2-(3-methylbenzofuran-2-yl)-8-methyl-6-ethylquinoline-4-carboxylic acid | ++ |
| 27 | 2-(3-methylbenzofuran-2-yl)-8-methyl-6-tert-butylquinoline-4-carboxylic acid | ++ |
| 28 | 2-(3-methylbenzofuran-2-yl)-8-methyl-6-cyclopropylquinoline-4-carboxylic acid | ++ |
| 29 | 2-(3-methylbenzofuran-2-yl)-6,8-dimethyl-4-(hydroxymethyl)quinoline | + |

TABLE 1-continued

| Compound # | Structure | Activity |
|---|---|---|
| 30 | 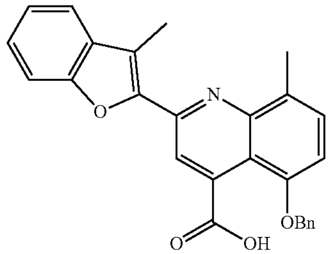 [SMILES: Cc1c(-c2cc(C(=O)O)c3c(OCc4ccccc4)ccc(C)c3n2)oc2ccccc12] | ++ |
| 31 | 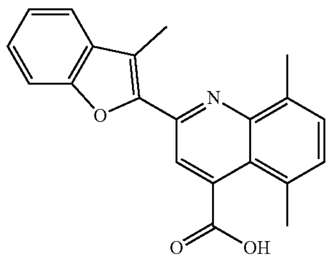 [SMILES: Cc1c(-c2cc(C(=O)O)c3c(C)ccc(C)c3n2)oc2ccccc12] | ++ |
| 32 | 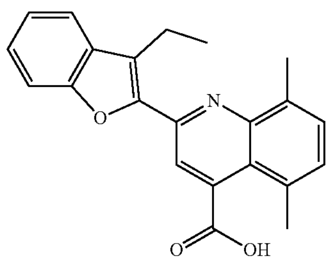 [SMILES: CCc1c(-c2cc(C(=O)O)c3c(C)ccc(C)c3n2)oc2ccccc12] | ++ |
| 33 | 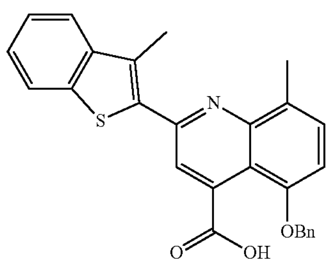 [SMILES: Cc1c(-c2cc(C(=O)O)c3c(OCc4ccccc4)ccc(C)c3n2)sc2ccccc12] | ++ |
| 34 | 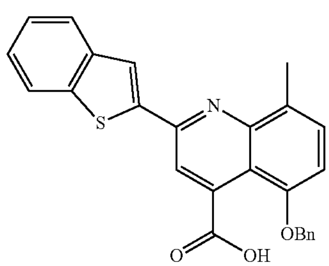 [SMILES: Cc1ccc(OCc2ccccc2)c2c(C(=O)O)cc(-c3cc4ccccc4s3)nc12] | ++ |
| 35 | 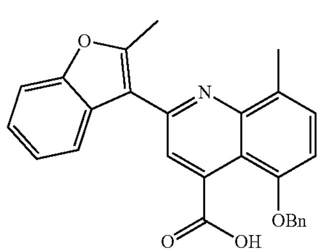 [SMILES: Cc1oc2ccccc2c1-c1cc(C(=O)O)c2c(OCc3ccccc3)ccc(C)c2n1] | ++ |

TABLE 1-continued

| Compound # | Structure | Activity |
|---|---|---|
| 36 | 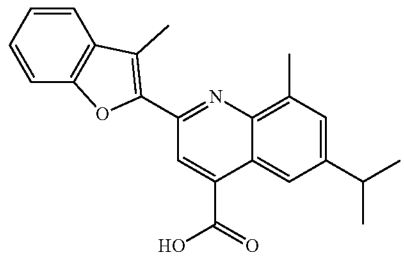 [SMILES: Cc1c(-c2cc(C(=O)O)c3cc(C(C)C)cc(C)c3n2)oc2ccccc12] | ++ |
| 37 | 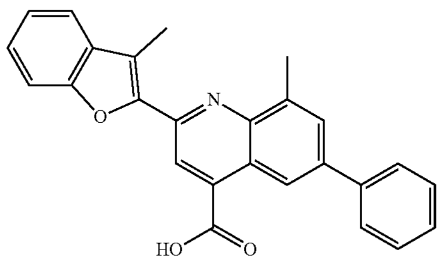 [SMILES: Cc1c(-c2cc(C(=O)O)c3cc(-c4ccccc4)cc(C)c3n2)oc2ccccc12] | ++ |
| 38 | 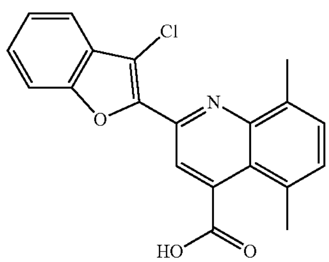 [SMILES: Cc1ccc(C)c2c(C(=O)O)cc(-c3oc4ccccc4c3Cl)nc12] | + |
| 39 | 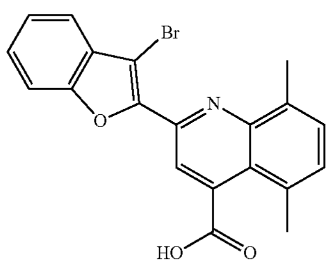 [SMILES: Cc1ccc(C)c2c(C(=O)O)cc(-c3oc4ccccc4c3Br)nc12] | + |
| 40 | 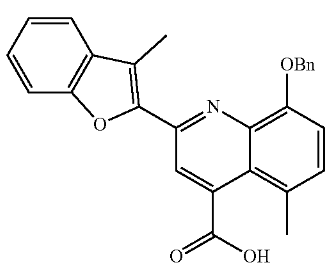 [SMILES: Cc1c(-c2cc(C(=O)O)c3c(C)ccc(OCc4ccccc4)c3n2)oc2ccccc12] | + |
| 41 | 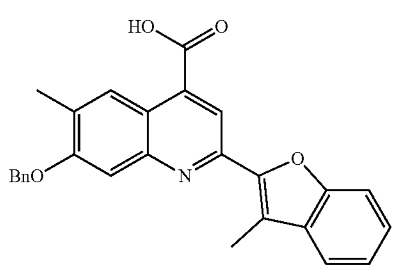 [SMILES: Cc1cc2c(C(=O)O)cc(-c3oc4ccccc4c3C)nc2cc1OCc1ccccc1] | + |

TABLE 1-continued

| Compound # | Structure | Activity |
|---|---|---|
| 42 | 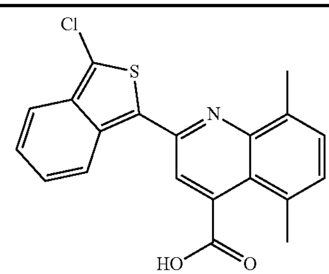 | |
| 43 | 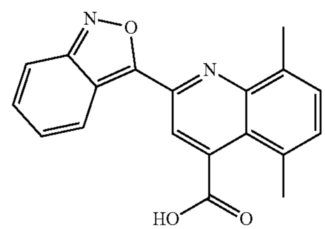 [SMILES: Cc1ccc(C)c2c(C(=O)O)cc(-c3onc4ccccc34)nc12] | |
| 44 | 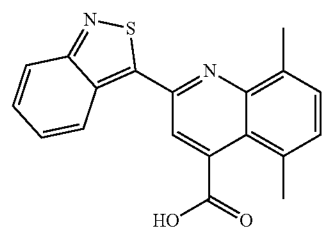 [SMILES: Cc1ccc(C)c2c(C(=O)O)cc(-c3snc4ccccc34)nc12] | |
| 45 | 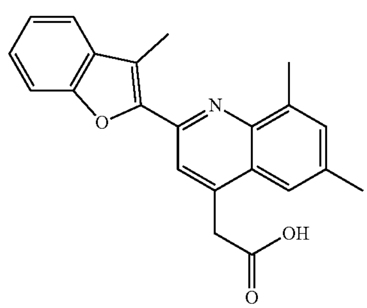 [SMILES: Cc1cc(C)c2nc(-c3oc4ccccc4c3C)cc(CC(=O)O)c2c1] | |
| 46 | 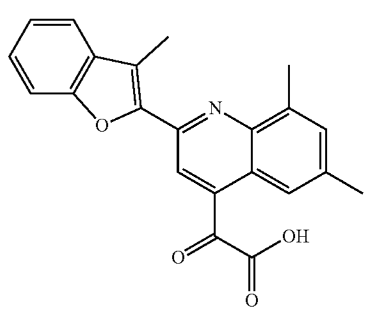 [SMILES: Cc1cc(C)c2nc(-c3oc4ccccc4c3C)cc(C(=O)C(=O)O)c2c1] | |
| 47 | 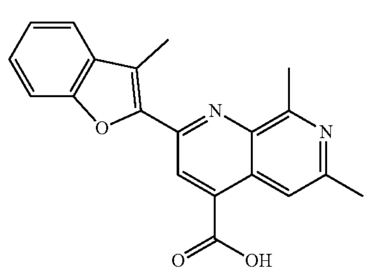 [SMILES: Cc1cc2c(C(=O)O)cc(-c3oc4ccccc4c3C)nc2c(C)n1] | |

TABLE 1-continued
| Compound # | Structure | Activity |
|---|---|---|
| 48 | 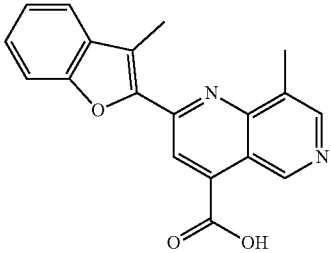 [SMILES: Cc1c(-c2cc(C(=O)O)c3cncc(C)c3n2)oc2ccccc12] | |
| 49 | 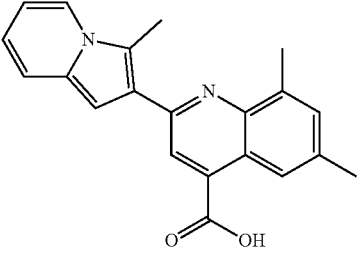 [SMILES: Cc1cc(C)c2nc(-c3cc4ccccn4c3C)cc(C(=O)O)c2c1] | |
| 50 | 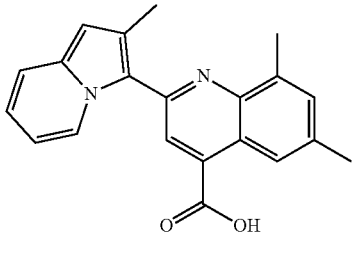 [SMILES: Cc1cc(C)c2nc(-c3c(C)cc4ccccn34)cc(C(=O)O)c2c1] | |
| 51 | 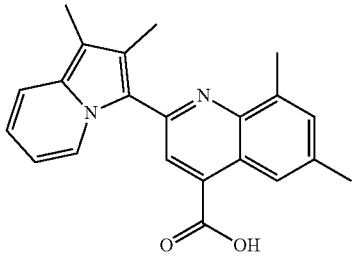 [SMILES: Cc1cc(C)c2nc(-c3c(C)c(C)c4ccccn34)cc(C(=O)O)c2c1] | |
| 52 | 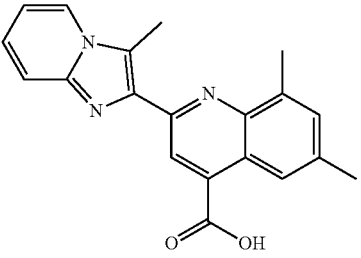 [SMILES: Cc1cc(C)c2nc(-c3nc4ccccn4c3C)cc(C(=O)O)c2c1] | |
| 53 | 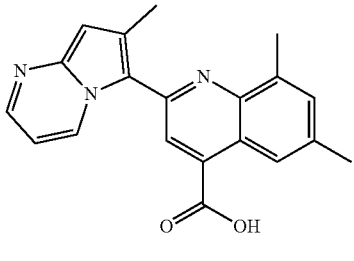 [SMILES: Cc1cc(C)c2nc(-c3c(C)cc4ncccn34)cc(C(=O)O)c2c1] | |

TABLE 1-continued
| Compound # | Structure | Activity |
|---|---|---|
| 54 | 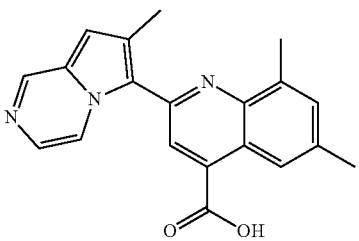 [SMILES: Cc1cc(C)c2nc(-c3c(C)cc4cnccn34)cc(C(=O)O)c2c1] | |
| 55 | 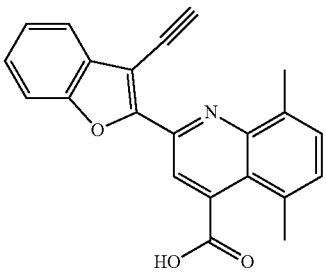 [SMILES: C#Cc1c(-c2cc(C(=O)O)c3c(C)ccc(C)c3n2)oc2ccccc12] | |
| 56 | 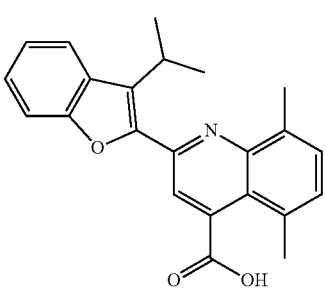 [SMILES: Cc1ccc(C)c2c(C(=O)O)cc(-c3oc4ccccc4c3C(C)C)nc12] | |
| 57 | 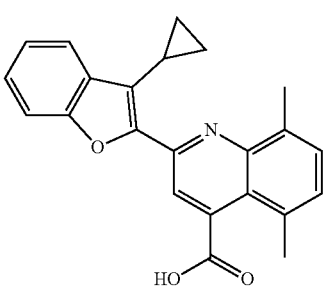 [SMILES: Cc1ccc(C)c2c(C(=O)O)cc(-c3oc4ccccc4c3C3CC3)nc12] | |
| 58 | 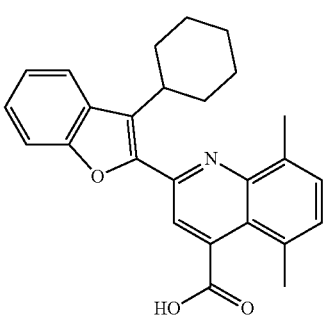 [SMILES: Cc1ccc(C)c2c(C(=O)O)cc(-c3oc4ccccc4c3C3CCCCC3)nc12] | |

TABLE 1-continued

| Compound # | Structure | Activity |
|---|---|---|
| 59 | 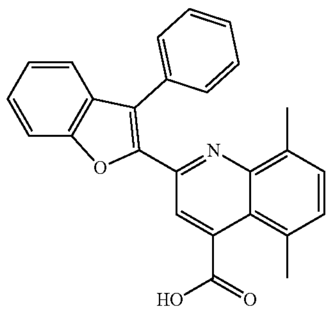 [SMILES: Cc1ccc(C)c2c(C(=O)O)cc(-c3oc4ccccc4c3-c3ccccc3)nc12] | |
| 60 | 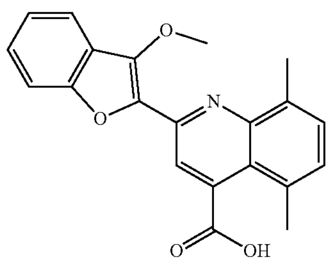 [SMILES: COc1c(-c2cc(C(=O)O)c3c(C)ccc(C)c3n2)oc2ccccc12] | |
| 61 | 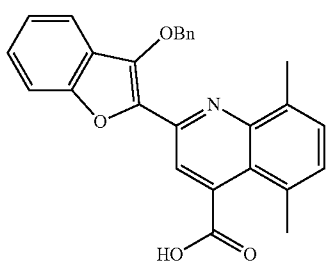 [SMILES: Cc1ccc(C)c2c(C(=O)O)cc(-c3oc4ccccc4c3OCc3ccccc3)nc12] | |
| 62 | 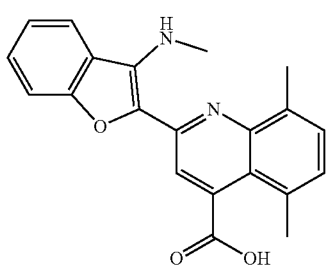 [SMILES: CNc1c(-c2cc(C(=O)O)c3c(C)ccc(C)c3n2)oc2ccccc12] | |
| 63 | 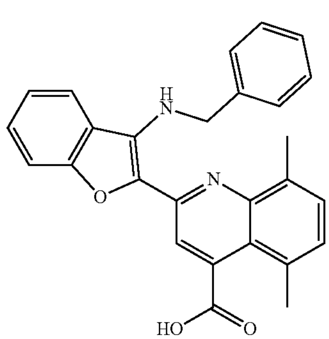 [SMILES: Cc1ccc(C)c2c(C(=O)O)cc(-c3oc4ccccc4c3NCc3ccccc3)nc12] | |

TABLE 1-continued
| Compound # | Structure | Activity |
|---|---|---|
| 64 | 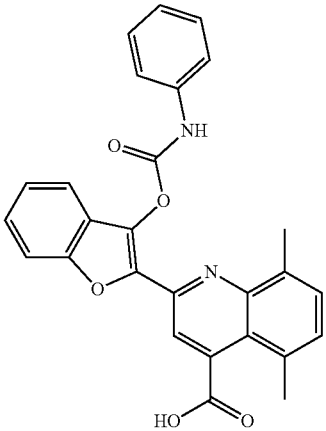 [SMILES: Cc1ccc(C)c2c(C(=O)O)cc(-c3oc4ccccc4c3OC(=O)Nc3ccccc3)nc12] | |
| 65 | 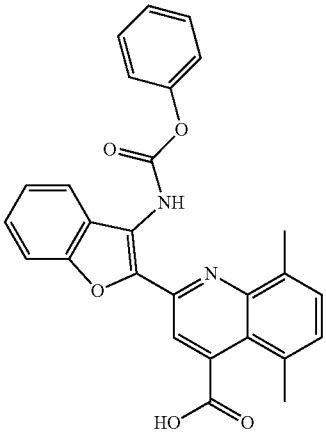 [SMILES: Cc1ccc(C)c2c(C(=O)O)cc(-c3oc4ccccc4c3NC(=O)Oc3ccccc3)nc12] | |
| 66 | 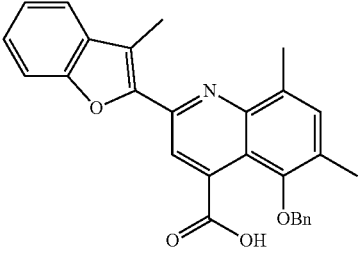 [SMILES: Cc1cc(C)c2nc(-c3oc4ccccc4c3C)cc(C(=O)O)c2c1OCc1ccccc1] | |
| 67 | 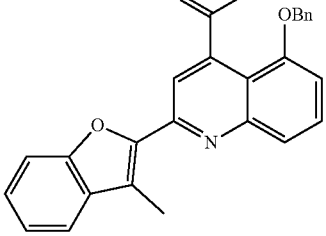 | |

TABLE 1-continued

| Compound # | Structure | Activity |
| --- | --- | --- |
| 68 | 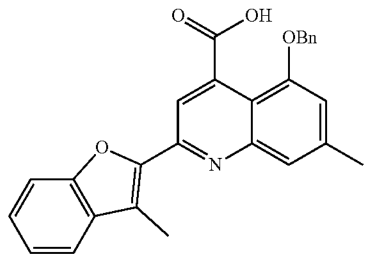 [SMILES: Cc1cc(OCc2ccccc2)c2c(C(=O)O)cc(-c3oc4ccccc4c3C)nc2c1] | |
| 69 | 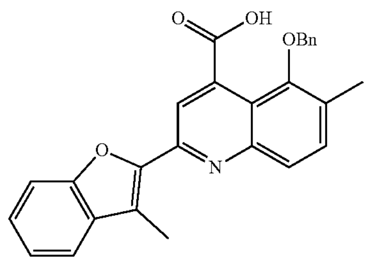 [SMILES: Cc1ccc2nc(-c3oc4ccccc4c3C)cc(C(=O)O)c2c1OCc1ccccc1] | |
| 70 | 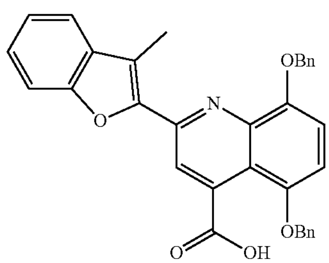 [SMILES: Cc1c(-c2cc(C(=O)O)c3c(OCc4ccccc4)ccc(OCc4ccccc4)c3n2)oc2ccccc12] | |
| 71 | 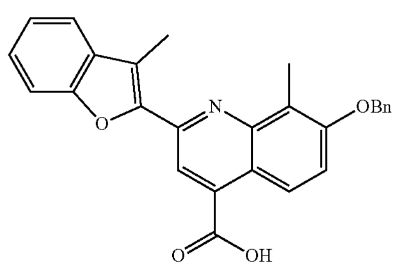 [SMILES: Cc1c(-c2cc(C(=O)O)c3ccc(OCc4ccccc4)c(C)c3n2)oc2ccccc12] | |
| 72 | 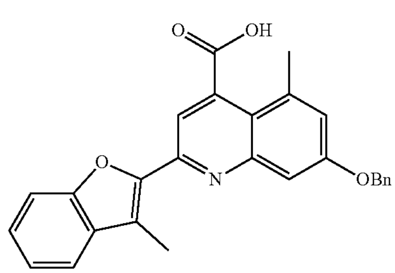 [SMILES: Cc1c(-c2cc(C(=O)O)c3c(C)cc(OCc4ccccc4)cc3n2)oc2ccccc12] | |

TABLE 1-continued
| Compound # | Structure | Activity |
|---|---|---|
| 73 | 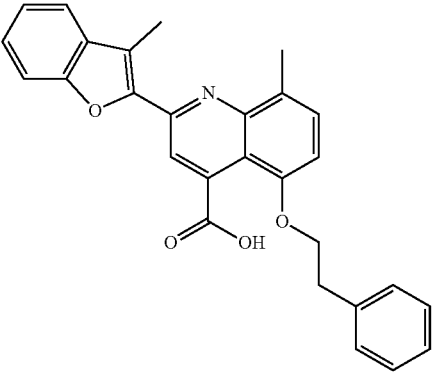 [SMILES: Cc1c(-c2cc(C(=O)O)c3c(OCCc4ccccc4)ccc(C)c3n2)oc2ccccc12] | ++ |
| 74 | 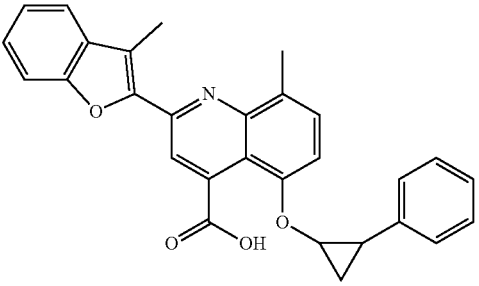 [SMILES: Cc1c(-c2cc(C(=O)O)c3c(OC4CC4c4ccccc4)ccc(C)c3n2)oc2ccccc12] |  |
| 75 | 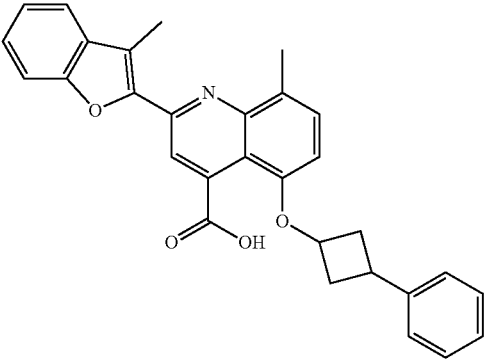 [SMILES: Cc1c(-c2cc(C(=O)O)c3c(OC4CC(c5ccccc5)C4)ccc(C)c3n2)oc2ccccc12] | ++ |
| 76 | 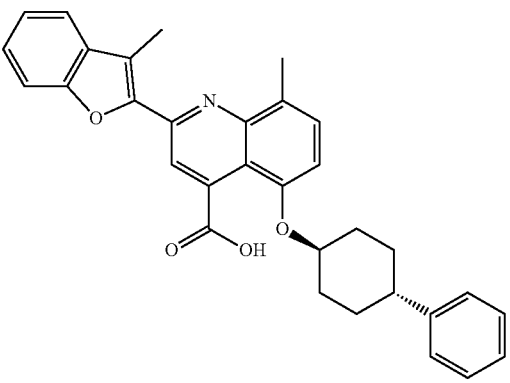 [SMILES: Cc1c(-c2cc(C(=O)O)c3c(O[C@H]4CC[C@H](c5ccccc5)CC4)ccc(C)c3n2)oc2ccccc12] | ++ |

TABLE 1-continued

| Compound # | Structure | Activity |
|---|---|---|
| 77 | 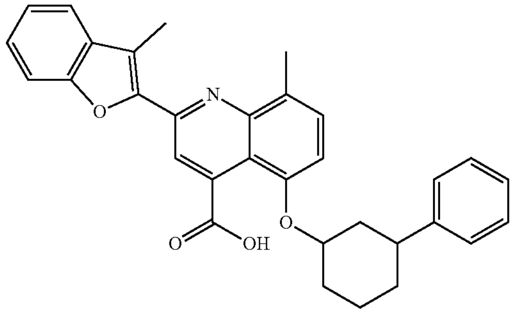 [SMILES: Cc1c(-c2cc(C(=O)O)c3c(OC4CCCC(c5ccccc5)C4)ccc(C)c3n2)oc2ccccc12] | ++ |
| 78 | 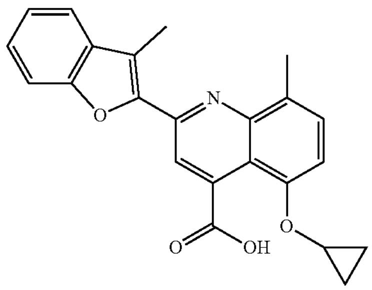 [SMILES: Cc1c(-c2cc(C(=O)O)c3c(OC4CC4)ccc(C)c3n2)oc2ccccc12] | |
| 79 | 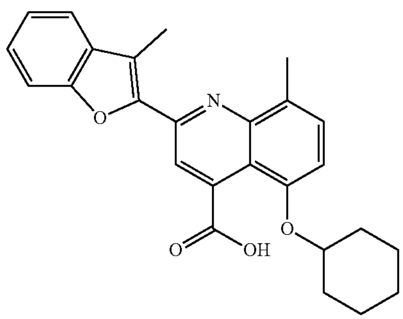 [SMILES: Cc1c(-c2cc(C(=O)O)c3c(OC4CCCCC4)ccc(C)c3n2)oc2ccccc12] | ++ |
| 80 | 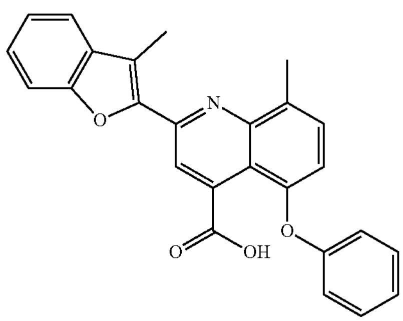 [SMILES: Cc1c(-c2cc(C(=O)O)c3c(Oc4ccccc4)ccc(C)c3n2)oc2ccccc12] | |
| 81 | 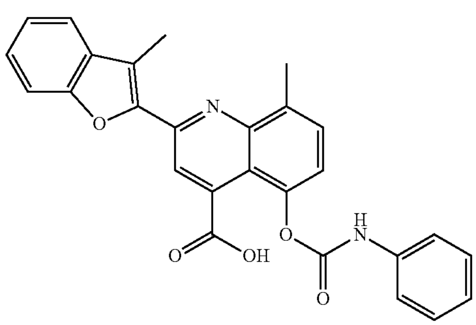 [SMILES: Cc1c(-c2cc(C(=O)O)c3c(OC(=O)Nc4ccccc4)ccc(C)c3n2)oc2ccccc12] | + |

TABLE 1-continued

| Compound # | Structure | Activity |
|---|---|---|
| 82 | 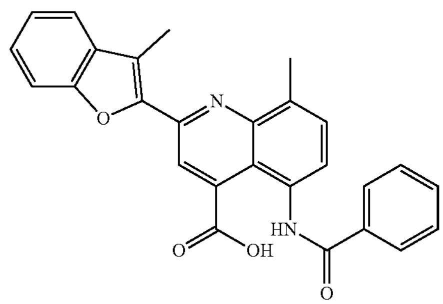 [SMILES: Cc1c(-c2cc(C(=O)O)c3c(NC(=O)c4ccccc4)ccc(C)c3n2)oc2ccccc12] | |
| 83 | 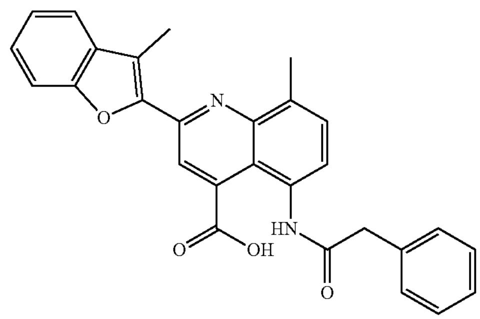 [SMILES: Cc1c(-c2cc(C(=O)O)c3c(NC(=O)Cc4ccccc4)ccc(C)c3n2)oc2ccccc12] | |
| 84 | 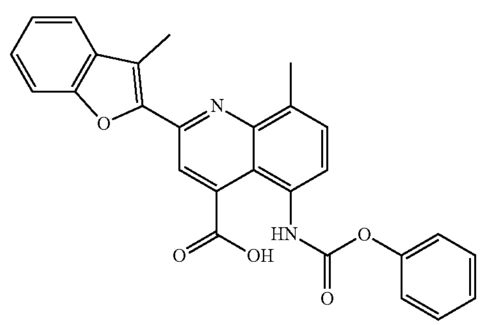 [SMILES: Cc1c(-c2cc(C(=O)O)c3c(NC(=O)Oc4ccccc4)ccc(C)c3n2)oc2ccccc12] | |
| 85 | 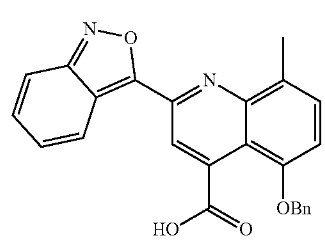 [SMILES: Cc1ccc(OCc2ccccc2)c2c(C(=O)O)cc(-c3onc4ccccc34)nc12] | |
| 86 | 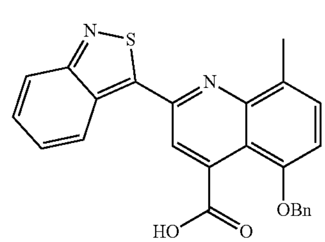 [SMILES: Cc1ccc(OCc2ccccc2)c2c(C(=O)O)cc(-c3snc4ccccc34)nc12] | ++ |

TABLE 1-continued

| Compound # | Structure | Activity |
|---|---|---|
| 87 | 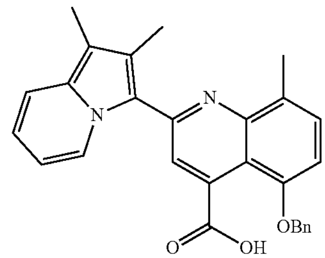 [SMILES: Cc1c(C)c2ccccn2c1-c1cc(C(=O)O)c2c(OCc3ccccc3)ccc(C)c2n1] | |
| 88 | 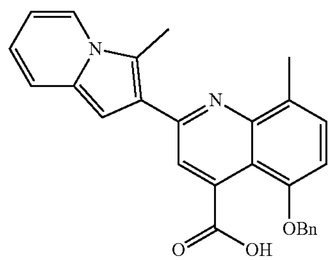 [SMILES: Cc1ccc(OCc2ccccc2)c2c(C(=O)O)cc(-c3cc4ccccn4c3C)nc12] | |
| 89 | 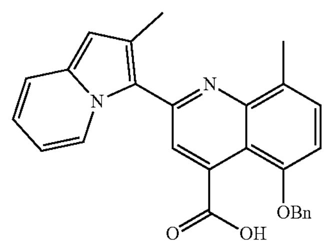 [SMILES: Cc1cc2ccccn2c1-c1cc(C(=O)O)c2c(OCc3ccccc3)ccc(C)c2n1] | |
| 90 | 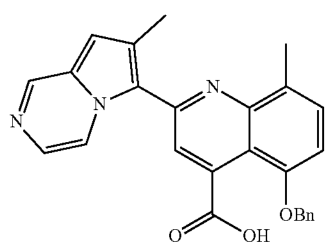 [SMILES: Cc1cc2cnccn2c1-c1cc(C(=O)O)c2c(OCc3ccccc3)ccc(C)c2n1] | |
| 91 | 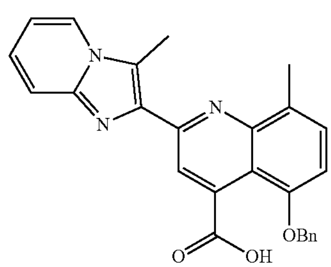 [SMILES: Cc1ccc(OCc2ccccc2)c2c(C(=O)O)cc(-c3nc4ccccn4c3C)nc12] | |
| 92 | 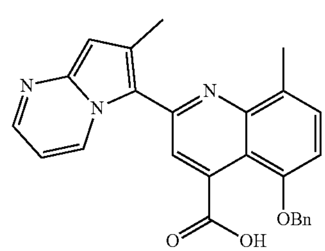 [SMILES: Cc1cc2ncccn2c1-c1cc(C(=O)O)c2c(OCc3ccccc3)ccc(C)c2n1] | |

TABLE 1-continued

| Compound # | Structure | Activity |
|---|---|---|
| 93 | 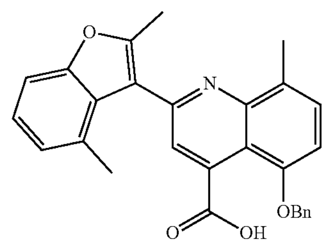 [SMILES: Cc1oc2cccc(C)c2c1-c1cc(C(=O)O)c2c(OCc3ccccc3)ccc(C)c2n1] | |
| 94 | 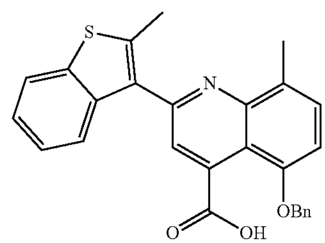 | |
| 95 | 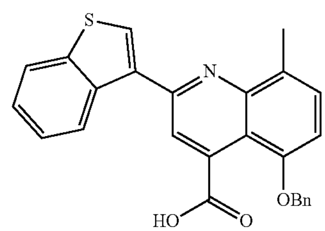 [SMILES: Cc1ccc(OCc2ccccc2)c2c(C(=O)O)cc(-c3csc4ccccc34)nc12] | ++ |
| 96 | 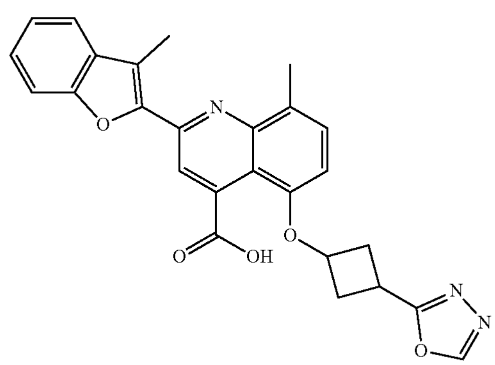 [SMILES: Cc1c(-c2cc(C(=O)O)c3c(OC4CC(c5nnco5)C4)ccc(C)c3n2)oc2ccccc12] | |
| 97 | 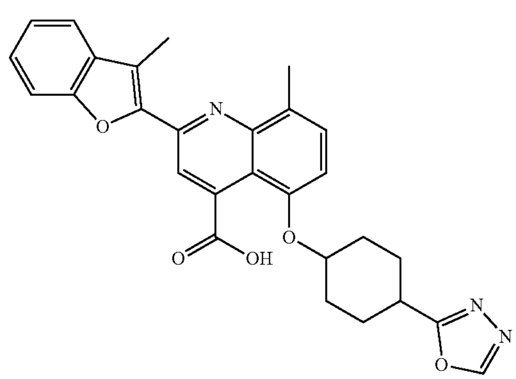 [SMILES: Cc1c(-c2cc(C(=O)O)c3c(OC4CCC(c5nnco5)CC4)ccc(C)c3n2)oc2ccccc12] | ++ |

TABLE 1-continued

| Compound # | Structure | Activity |
|---|---|---|
| 98 | 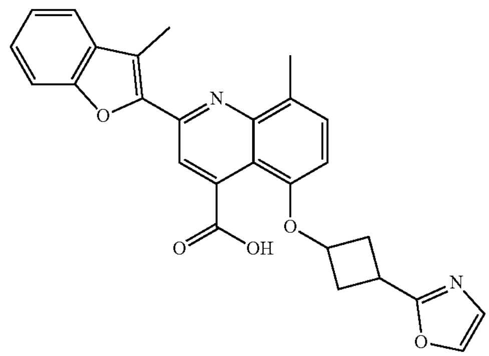 [SMILES: Cc1c(-c2cc(C(=O)O)c3c(OC4CC(c5ncco5)C4)ccc(C)c3n2)oc2ccccc12] | |
| 99 | 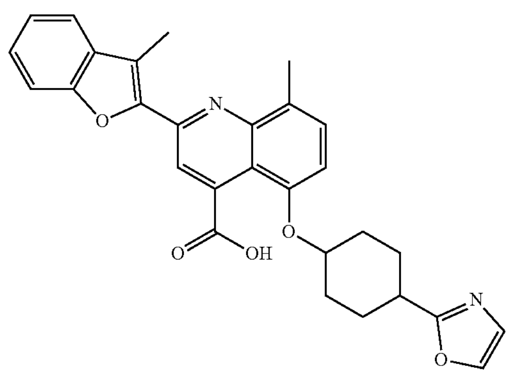 [SMILES: Cc1c(-c2cc(C(=O)O)c3c(OC4CCC(c5ncco5)CC4)ccc(C)c3n2)oc2ccccc12] | |
| 100 | 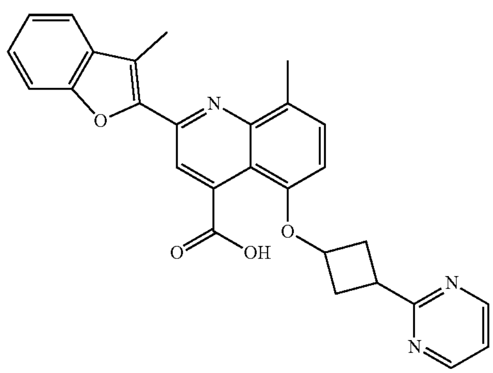 [SMILES: Cc1c(-c2cc(C(=O)O)c3c(OC4CC(c5ncccn5)C4)ccc(C)c3n2)oc2ccccc12] | |
| 101 | 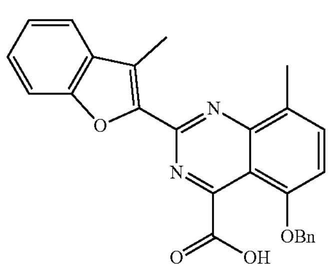 | ++ |
| 102 | 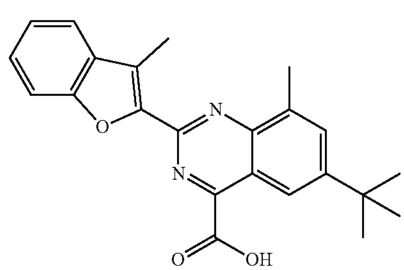 [SMILES: Cc1c(-c2nc(C(=O)O)c3cc(C(C)(C)C)cc(C)c3n2)oc2ccccc12] | |

TABLE 1-continued
| Compound # | Structure | Activity |
|---|---|---|
| 103 | 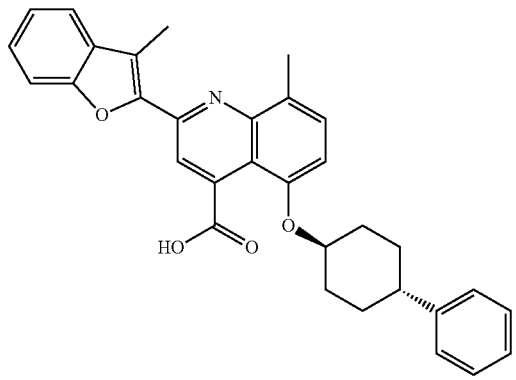 [SMILES: Cc1c(-c2cc(C(=O)O)c3c(O[C@H]4CC[C@H](c5ccccc5)CC4)ccc(C)c3n2)oc2ccccc12] | ++ |
| 104 | 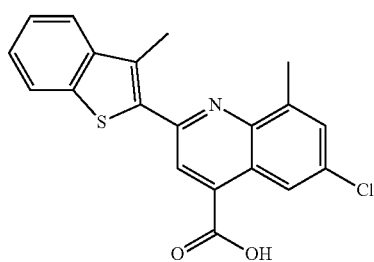 [SMILES: Cc1c(-c2cc(C(=O)O)c3cc(Cl)cc(C)c3n2)sc2ccccc12] | ++ |
| 105 | 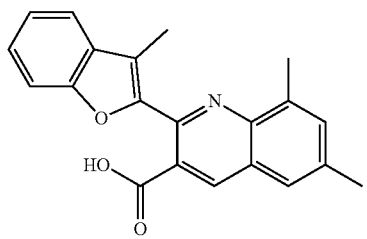 [SMILES: Cc1cc(C)c2nc(-c3oc4ccccc4c3C)c(C(=O)O)cc2c1] | + |
| 106 | 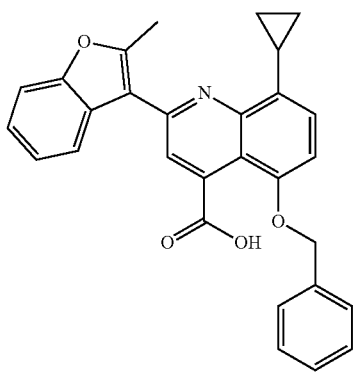 [SMILES: Cc1oc2ccccc2c1-c1cc(C(=O)O)c2c(OCc3ccccc3)ccc(C3CC3)c2n1] | ++ |

TABLE 1-continued

| Compound # | Structure | Activity |
|---|---|---|
| 107 | 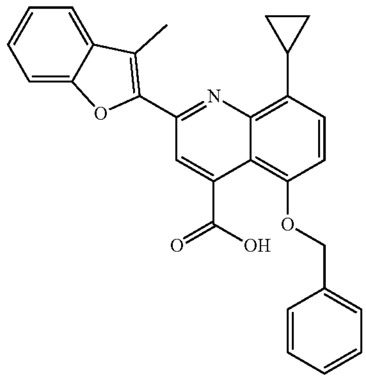 [SMILES: Cc1c(-c2cc(C(=O)O)c3c(OCc4ccccc4)ccc(C4CC4)c3n2)oc2ccccc12] | ++ |
| 108 | 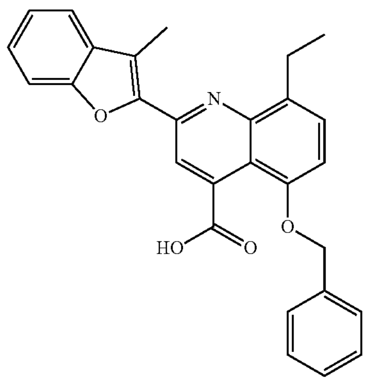 [SMILES: CCc1ccc(OCc2ccccc2)c2c(C(=O)O)cc(-c3oc4ccccc4c3C)nc12] | ++ |
| 109 | 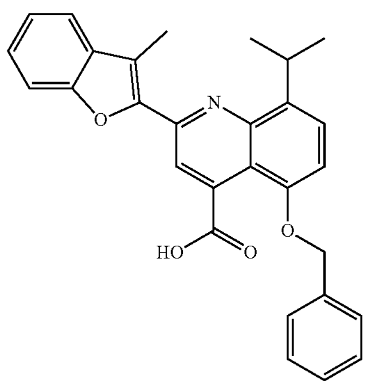 [SMILES: Cc1c(-c2cc(C(=O)O)c3c(OCc4ccccc4)ccc(C(C)C)c3n2)oc2ccccc12] | ++ |
| 110 | 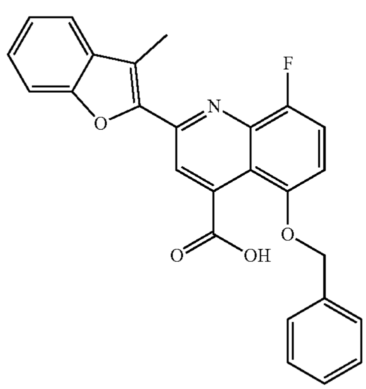 [SMILES: Cc1c(-c2cc(C(=O)O)c3c(OCc4ccccc4)ccc(F)c3n2)oc2ccccc12] | ++ |

TABLE 1-continued

| Compound # | Structure | Activity |
|---|---|---|
| 111 | 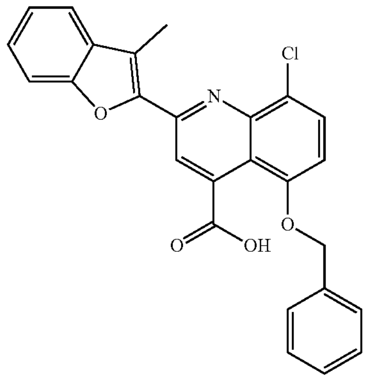 [SMILES: Cc1c(-c2cc(C(=O)O)c3c(OCc4ccccc4)ccc(Cl)c3n2)oc2ccccc12] | + |
| 112 | 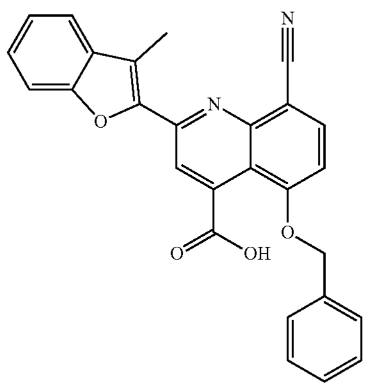 [SMILES: Cc1c(-c2cc(C(=O)O)c3c(OCc4ccccc4)ccc(C#N)c3n2)oc2ccccc12] | ++ |
| 113 | 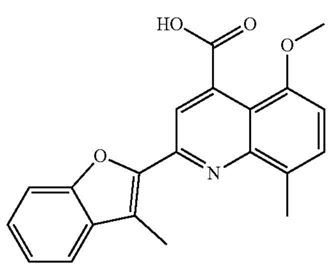 [SMILES: COc1ccc(C)c2nc(-c3oc4ccccc4c3C)cc(C(=O)O)c12] | + |
| 114 | 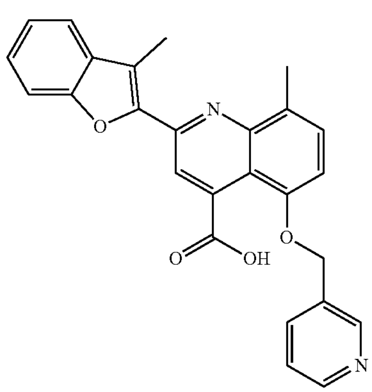 [SMILES: Cc1c(-c2cc(C(=O)O)c3c(OCc4cccnc4)ccc(C)c3n2)oc2ccccc12] | + |

TABLE 1-continued

| Compound # | Structure | Activity |
|---|---|---|
| 115 | 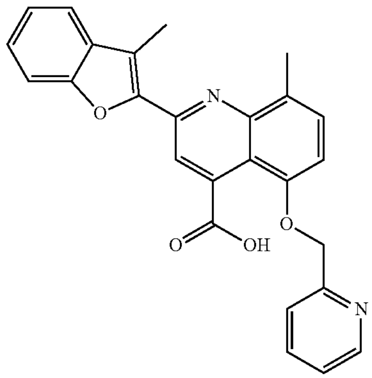 [SMILES: Cc1c(-c2cc(C(=O)O)c3c(OCc4ccccn4)ccc(C)c3n2)oc2ccccc12] | + |
| 116 | 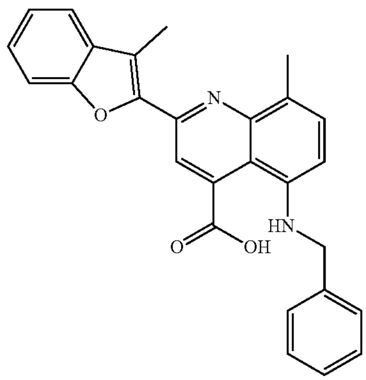 [SMILES: Cc1c(-c2cc(C(=O)O)c3c(NCc4ccccc4)ccc(C)c3n2)oc2ccccc12] | ++ |
| 117 | 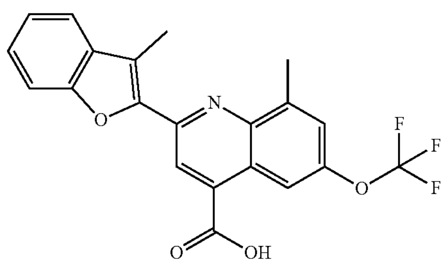 [SMILES: Cc1c(-c2cc(C(=O)O)c3cc(OC(F)(F)F)cc(C)c3n2)oc2ccccc12] | ++ |
| 118 | 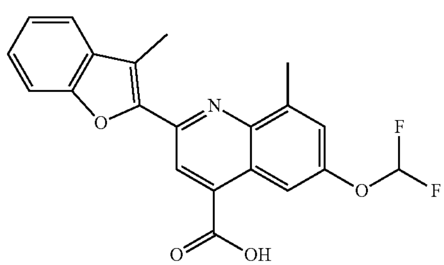 [SMILES: Cc1c(-c2cc(C(=O)O)c3cc(OC(F)F)cc(C)c3n2)oc2ccccc12] | ++ |
| 119 | 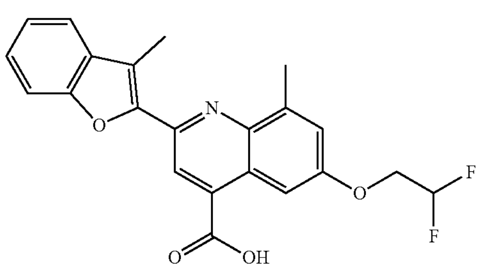 [SMILES: Cc1c(-c2cc(C(=O)O)c3cc(OCC(F)F)cc(C)c3n2)oc2ccccc12] | + |

TABLE 1-continued

| Compound # | Structure | Activity |
|---|---|---|
| 120 | 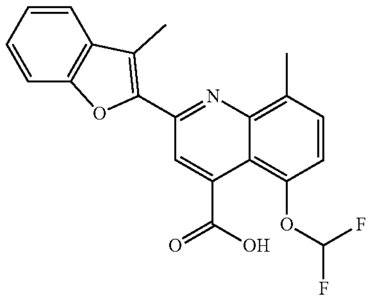 [SMILES: Cc1c(-c2cc(C(=O)O)c3c(OC(F)F)ccc(C)c3n2)oc2ccccc12] | ++ |
| 121 | 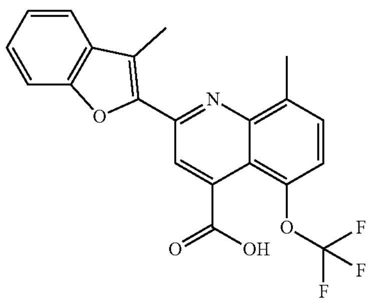 [SMILES: Cc1c(-c2cc(C(=O)O)c3c(OC(F)(F)F)ccc(C)c3n2)oc2ccccc12] | + |
| 122 | 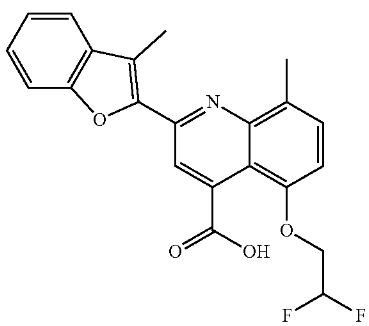 [SMILES: Cc1c(-c2cc(C(=O)O)c3c(OCC(F)F)ccc(C)c3n2)oc2ccccc12] | ++ |
| 123 | 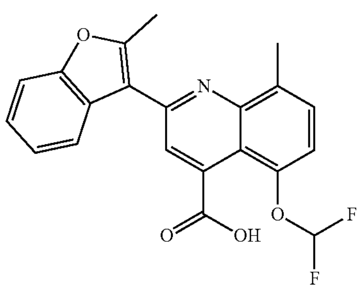 [SMILES: Cc1oc2ccccc2c1-c1cc(C(=O)O)c2c(OC(F)F)ccc(C)c2n1] | + |
| 124 | 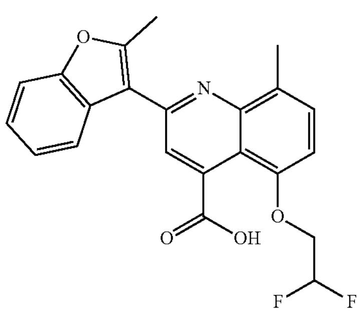 [SMILES: Cc1oc2ccccc2c1-c1cc(C(=O)O)c2c(OCC(F)F)ccc(C)c2n1] | + |

TABLE 1-continued

| Compound # | Structure | Activity |
|---|---|---|
| 125 | 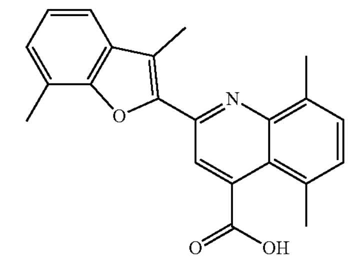 [SMILES: Cc1c(-c2cc(C(=O)O)c3c(C)ccc(C)c3n2)oc2c(C)cccc12] | ++ |
| 126 | 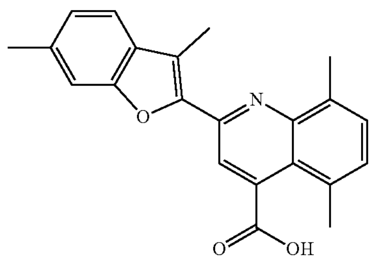 [SMILES: Cc1ccc2c(C)c(-c3cc(C(=O)O)c4c(C)ccc(C)c4n3)oc2c1] | ++ |
| 127 | 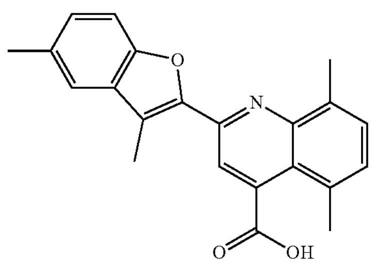 [SMILES: Cc1ccc2oc(-c3cc(C(=O)O)c4c(C)ccc(C)c4n3)c(C)c2c1] | ++ |
| 128 | 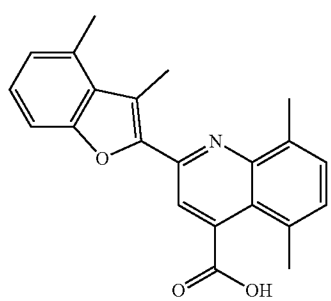 [SMILES: Cc1ccc(C)c2c(C(=O)O)cc(-c3oc4cccc(C)c4c3C)nc12] | + |
| 129 | 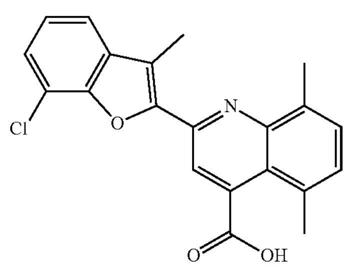 [SMILES: Cc1c(-c2cc(C(=O)O)c3c(C)ccc(C)c3n2)oc2c(Cl)cccc12] | + |
| 130 | 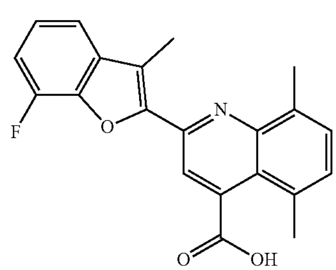 [SMILES: Cc1c(-c2cc(C(=O)O)c3c(C)ccc(C)c3n2)oc2c(F)cccc12] | + |

TABLE 1-continued

| Compound # | Structure | Activity |
|---|---|---|
| 131 | 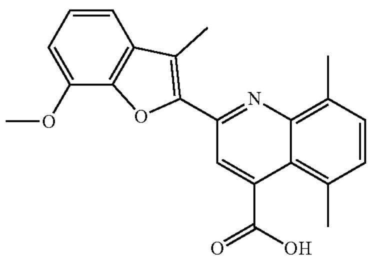 [SMILES: COc1cccc2c(C)c(-c3cc(C(=O)O)c4c(C)ccc(C)c4n3)oc12] | |
| 132 | 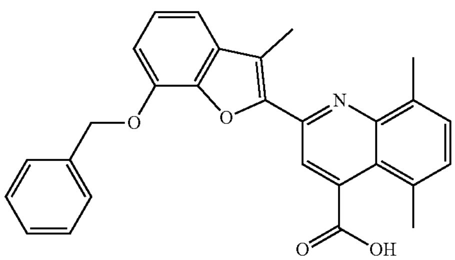 [SMILES: Cc1c(-c2cc(C(=O)O)c3c(C)ccc(C)c3n2)oc2c(OCc3ccccc3)cccc12] | ++ |
| 133 | 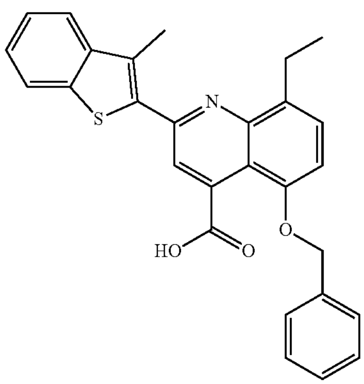 [SMILES: CCc1ccc(OCc2ccccc2)c2c(C(=O)O)cc(-c3sc4ccccc4c3C)nc12] | ++ |
| 134 | 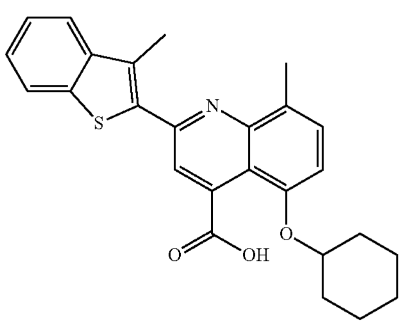 [SMILES: Cc1c(-c2cc(C(=O)O)c3c(OC4CCCCC4)ccc(C)c3n2)sc2ccccc12] | ++ |
| 135 | 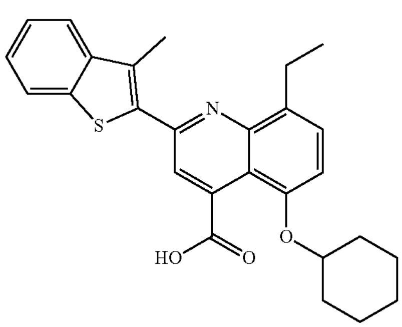 [SMILES: CCc1ccc(OC2CCCCC2)c2c(C(=O)O)cc(-c3sc4ccccc4c3C)nc12] | ++ |

TABLE 1-continued

| Compound # | Structure | Activity |
|---|---|---|
| 136 | 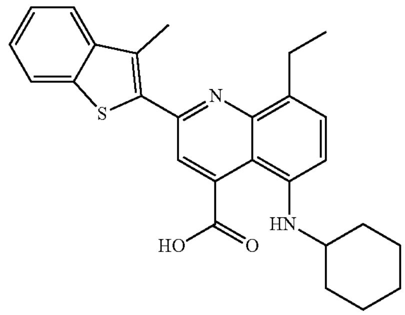 [SMILES: CCc1ccc(NC2CCCCC2)c2c(C(=O)O)cc(-c3sc4ccccc4c3C)nc12] | |
| 137 | 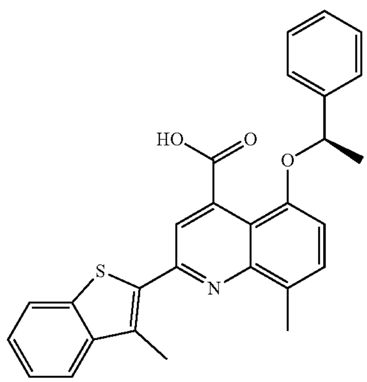 [SMILES: Cc1c(-c2cc(C(=O)O)c3c(O[C@H](C)c4ccccc4)ccc(C)c3n2)sc2ccccc12] | ++ |
| 138 | 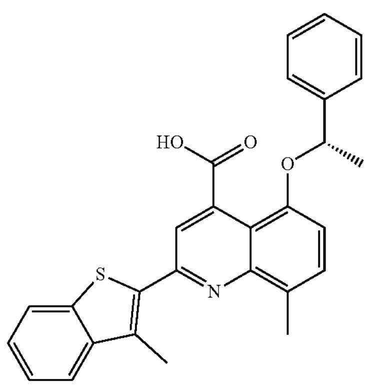 [SMILES: Cc1c(-c2cc(C(=O)O)c3c(O[C@@H](C)c4ccccc4)ccc(C)c3n2)sc2ccccc12] | ++ |
| 139 | 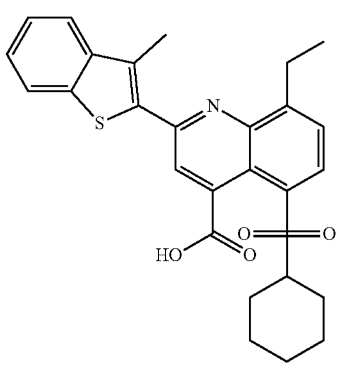 | |

TABLE 1-continued

| Compound # | Structure | Activity |
|---|---|---|
| 140 | 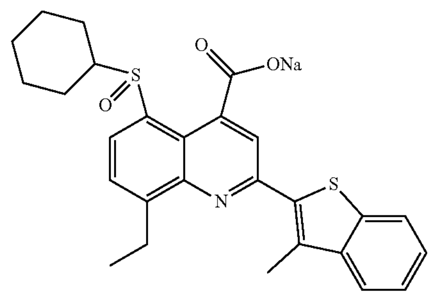 | ++ |
| 141 | 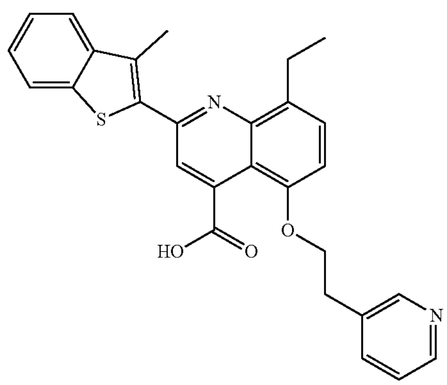 [SMILES: CCc1ccc(OCCc2cccnc2)c2c(C(=O)O)cc(-c3sc4ccccc4c3C)nc12] | + |
| 142 | 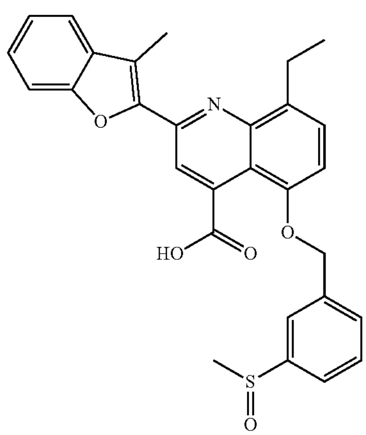 [SMILES: CCc1ccc(OCc2cccc(S(C)=O)c2)c2c(C(=O)O)cc(-c3oc4ccccc4c3C)nc12] | ++ |
| 143 | 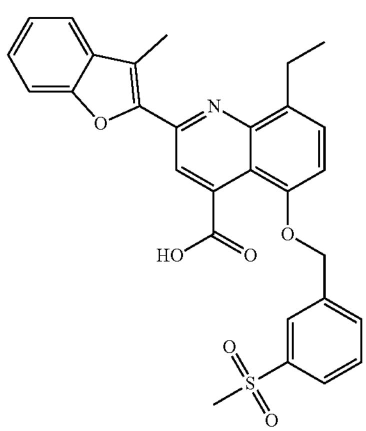 [SMILES: CCc1ccc(OCc2cccc(S(C)(=O)=O)c2)c2c(C(=O)O)cc(-c3oc4ccccc4c3C)nc12] | ++ |

TABLE 1-continued

| Compound # | Structure | Activity |
|---|---|---|
| 144 | 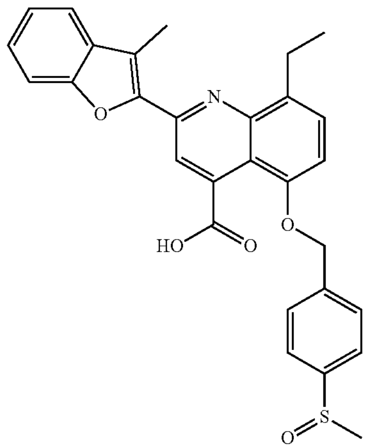 [SMILES: CCc1ccc(OCc2ccc(S(C)=O)cc2)c2c(C(=O)O)cc(-c3oc4ccccc4c3C)nc12] | ++ |
| 145 | 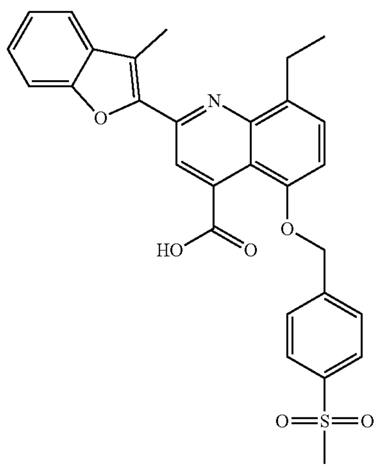 [SMILES: CCc1ccc(OCc2ccc(S(C)(=O)=O)cc2)c2c(C(=O)O)cc(-c3oc4ccccc4c3C)nc12] | ++ |
| 146 | 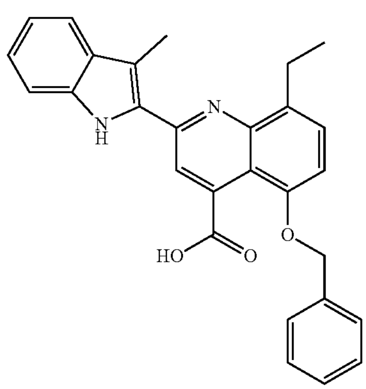 [SMILES: CCc1ccc(OCc2ccccc2)c2c(C(=O)O)cc(-c3[nH]c4ccccc4c3C)nc12] | ++ |

TABLE 1-continued
| Compound # | Structure | Activity |
|---|---|---|
| 147 | 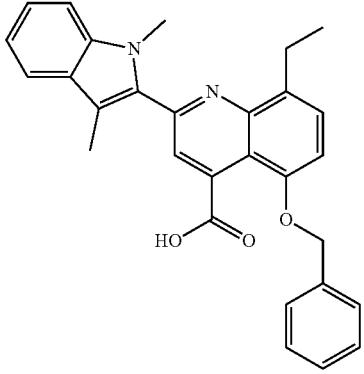 [SMILES: CCc1ccc(OCc2ccccc2)c2c(C(=O)O)cc(-c3c(C)c4ccccc4n3C)nc12] | + |
| 148 | 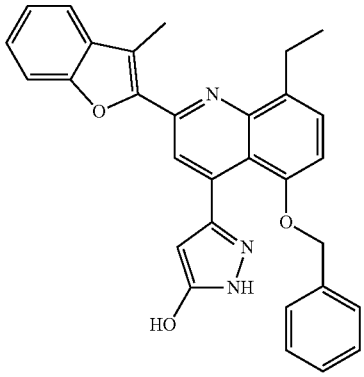 [SMILES: CCc1ccc(OCc2ccccc2)c2c(-c3cc(O)[nH]n3)cc(-c3oc4ccccc4c3C)nc12] | |
| 149 | 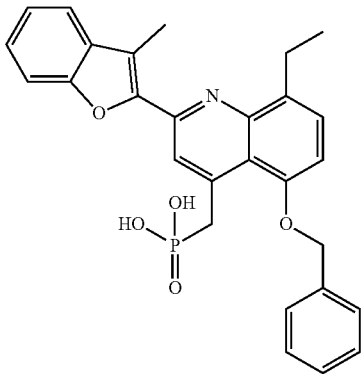 [SMILES: CCc1ccc(OCc2ccccc2)c2c(CP(=O)(O)O)cc(-c3oc4ccccc4c3C)nc12] | |
| 150 | 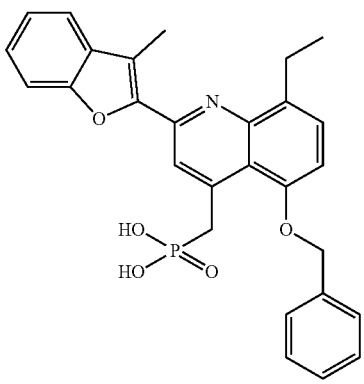 [SMILES: CCc1ccc(OCc2ccccc2)c2c(CP(=O)(O)O)cc(-c3oc4ccccc4c3C)nc12] | |

TABLE 1-continued

| Compound # | Structure | Activity |
|---|---|---|
| 151 | 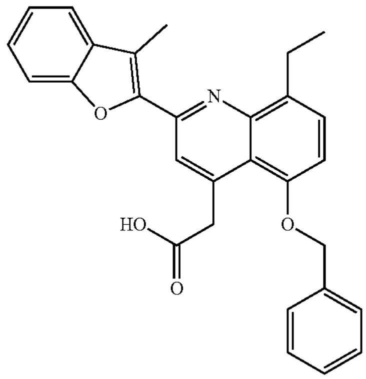 [SMILES: CCc1ccc(OCc2ccccc2)c2c(CC(=O)O)cc(-c3oc4ccccc4c3C)nc12] | |
| 152 | 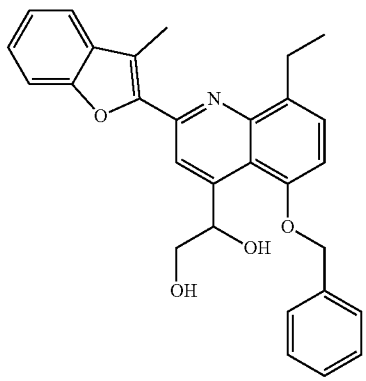 [SMILES: CCc1ccc(OCc2ccccc2)c2c(C(O)CO)cc(-c3oc4ccccc4c3C)nc12] | |
| 153 | 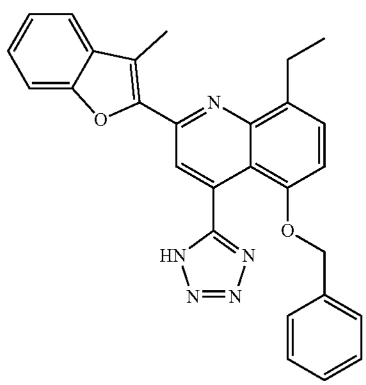 [SMILES: CCc1ccc(OCc2ccccc2)c2c(-c3nnn[nH]3)cc(-c3oc4ccccc4c3C)nc12] | |
| 154 | 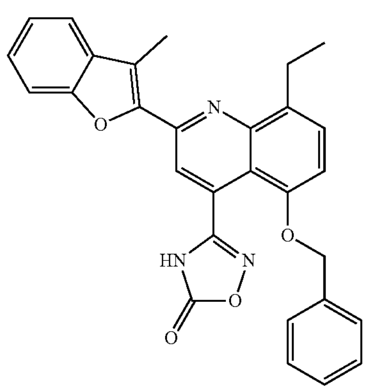 [SMILES: CCc1ccc(OCc2ccccc2)c2c(-c3noc(=O)[nH]3)cc(-c3oc4ccccc4c3C)nc12] | |

TABLE 1-continued

| Compound # | Structure | Activity |
|---|---|---|
| 155 | 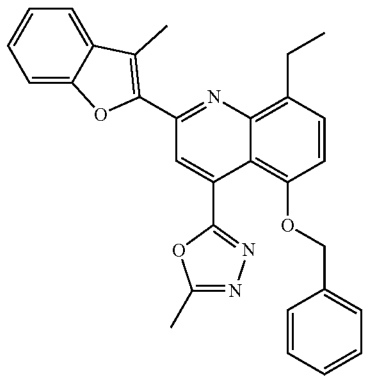 [SMILES: CCc1ccc(OCc2ccccc2)c2c(-c3nnc(C)o3)cc(-c3oc4ccccc4c3C)nc12] | |
| 156 | 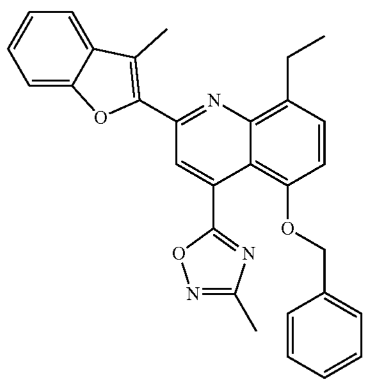 [SMILES: CCc1ccc(OCc2ccccc2)c2c(-c3nc(C)no3)cc(-c3oc4ccccc4c3C)nc12] | |
| 157 | 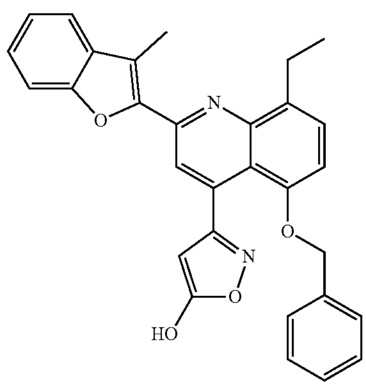 [SMILES: CCc1ccc(OCc2ccccc2)c2c(-c3cc(O)on3)cc(-c3oc4ccccc4c3C)nc12] | |
| 158 | 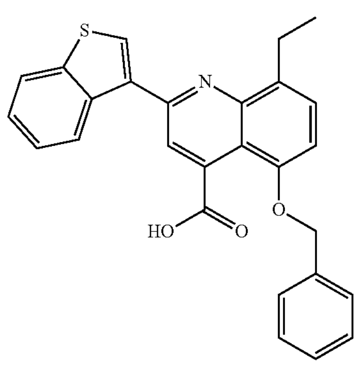 [SMILES: CCc1ccc(OCc2ccccc2)c2c(C(=O)O)cc(-c3csc4ccccc34)nc12] | ++ |

TABLE 1-continued

| Compound # | Structure | Activity |
|---|---|---|
| 159 | 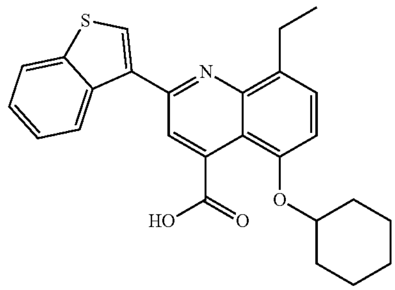 | ++ |
| 160 | 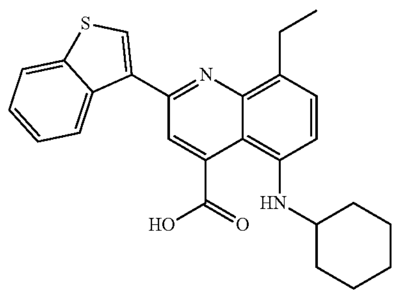 | |
| 161 | 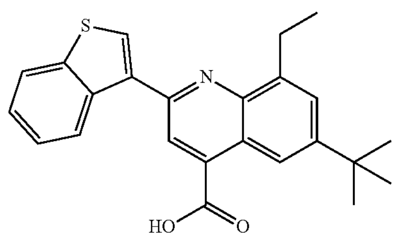 | ++ |
| 162 | 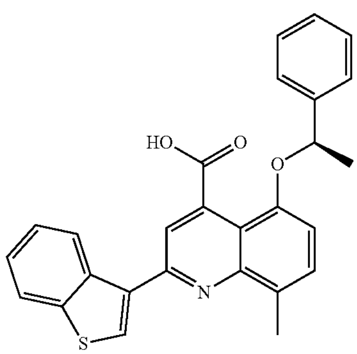 [SMILES: Cc1ccc(O[C@H](C)c2ccccc2)c2c(C(=O)O)cc(-c3csc4ccccc34)nc12] | ++ |
| 163 | 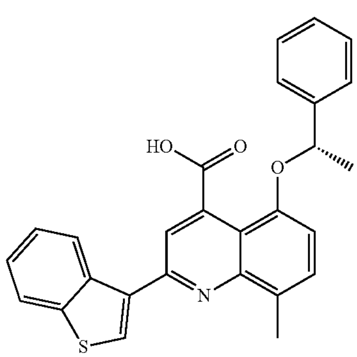 [SMILES: Cc1ccc(O[C@@H](C)c2ccccc2)c2c(C(=O)O)cc(-c3csc4ccccc34)nc12] | ++ |

TABLE 1-continued

| Compound # | Structure | Activity |
|---|---|---|
| 164 | 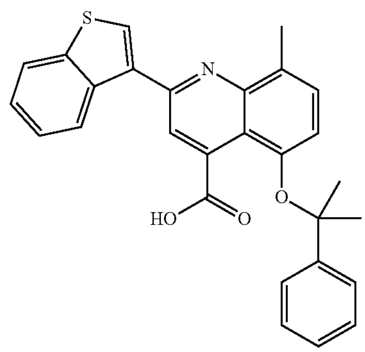 [SMILES: Cc1ccc(OC(C)(C)c2ccccc2)c2c(C(=O)O)cc(-c3csc4ccccc34)nc12] | |
| 165 | 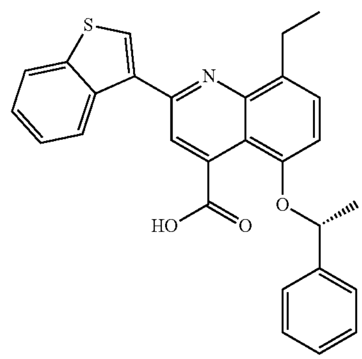 [SMILES: CCc1ccc(O[C@H](C)c2ccccc2)c2c(C(=O)O)cc(-c3csc4ccccc34)nc12] | ++ |
| 166 | 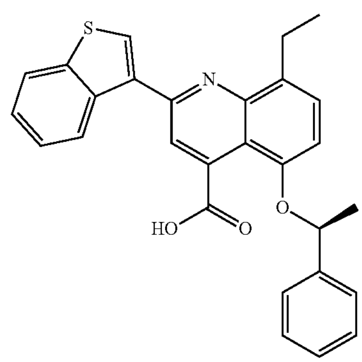 [SMILES: CCc1ccc(O[C@@H](C)c2ccccc2)c2c(C(=O)O)cc(-c3csc4ccccc34)nc12] | ++ |
| 167 | 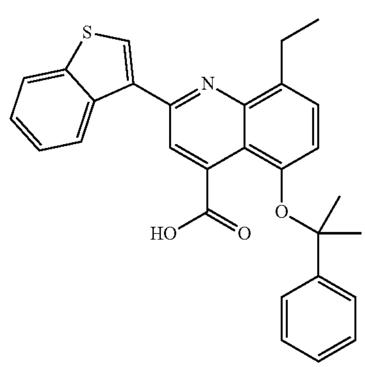 [SMILES: CCc1ccc(OC(C)(C)c2ccccc2)c2c(C(=O)O)cc(-c3csc4ccccc34)nc12] | |

TABLE 1-continued

| Compound # | Structure | Activity |
|---|---|---|
| 168 | 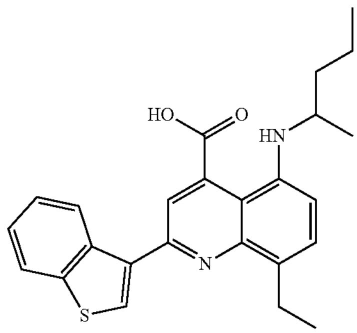 [SMILES: CCCC(C)Nc1ccc(CC)c2nc(-c3csc4ccccc34)cc(C(=O)O)c12] | |
| 169 | 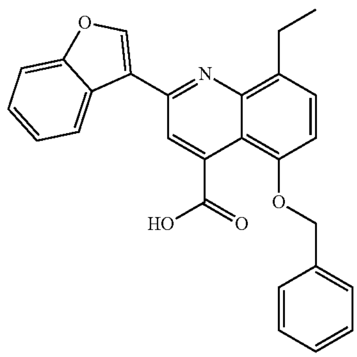 [SMILES: CCc1ccc(OCc2ccccc2)c2c(C(=O)O)cc(-c3coc4ccccc34)nc12] | ++ |
| 170 | 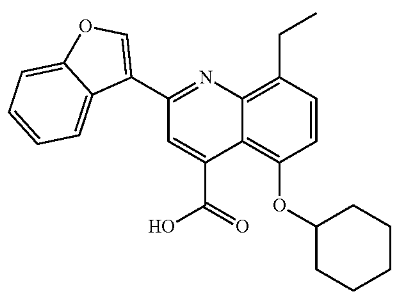 [SMILES: CCc1ccc(OC2CCCCC2)c2c(C(=O)O)cc(-c3coc4ccccc34)nc12] | ++ |
| 171 | 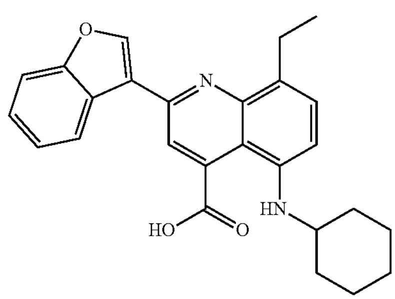 [SMILES: CCc1ccc(NC2CCCCC2)c2c(C(=O)O)cc(-c3coc4ccccc34)nc12] | |
| 172 | 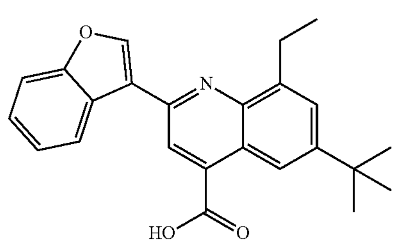 [SMILES: CCc1cc(C(C)(C)C)cc2c(C(=O)O)cc(-c3coc4ccccc34)nc12] | |

TABLE 1-continued

| Compound # | Structure | Activity |
|---|---|---|
| 173 | 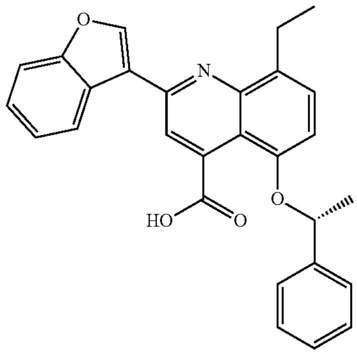 [SMILES: CCc1ccc(O[C@H](C)c2ccccc2)c2c(C(=O)O)cc(-c3coc4ccccc34)nc12] | ++ |
| 174 | 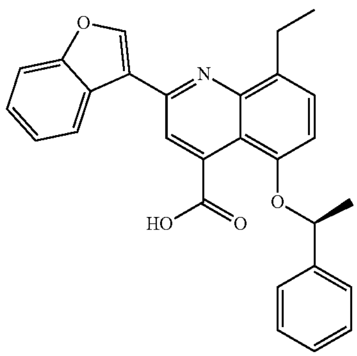 [SMILES: CCc1ccc(O[C@@H](C)c2ccccc2)c2c(C(=O)O)cc(-c3coc4ccccc34)nc12] | ++ |
| 175 | 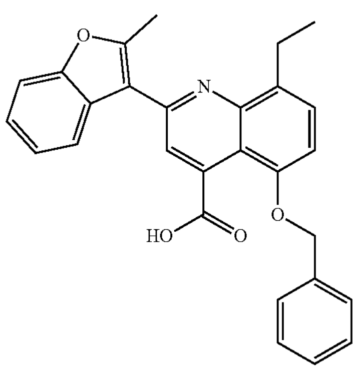 [SMILES: CCc1ccc(OCc2ccccc2)c2c(C(=O)O)cc(-c3c(C)oc4ccccc34)nc12] | ++ |
| 176 | 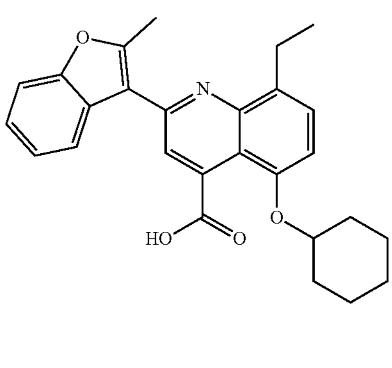 [SMILES: CCc1ccc(OC2CCCCC2)c2c(C(=O)O)cc(-c3c(C)oc4ccccc34)nc12] | ++ |

TABLE 1-continued

| Compound # | Structure | Activity |
|---|---|---|
| 177 | 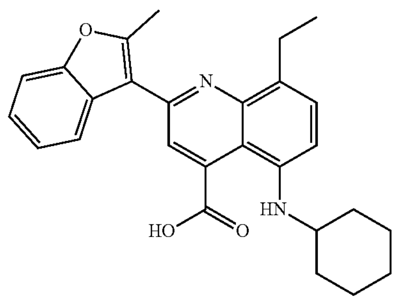 [SMILES: CCc1ccc(NC2CCCCC2)c2c(C(=O)O)cc(-c3c(C)oc4ccccc34)nc12] | |
| 178 | 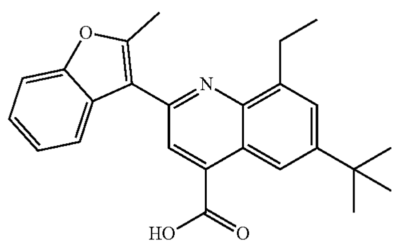 [SMILES: CCc1cc(C(C)(C)C)cc2c(C(=O)O)cc(-c3c(C)oc4ccccc34)nc12] | ++ |
| 179 | 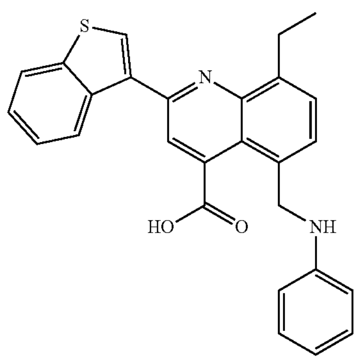 [SMILES: CCc1ccc(CNc2ccccc2)c2c(C(=O)O)cc(-c3csc4ccccc34)nc12] | |
| 180 | 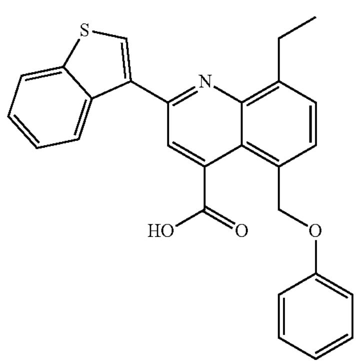 [SMILES: CCc1ccc(COc2ccccc2)c2c(C(=O)O)cc(-c3csc4ccccc34)nc12] | ++ |
| 181 | 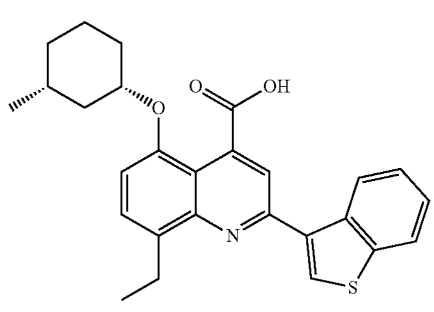 [SMILES: CCc1ccc(O[C@H]2CCC[C@@H](C)C2)c2c(C(=O)O)cc(-c3csc4ccccc34)nc12] | ++ |

TABLE 1-continued

| Compound # | Structure | Activity |
|---|---|---|
| 182 | 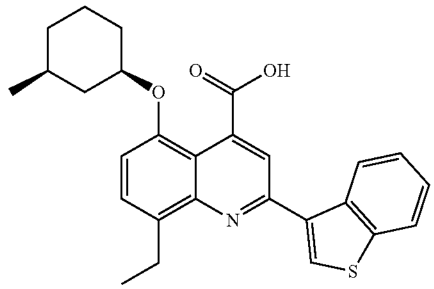 [SMILES: CCc1ccc(O[C@@H]2CCC[C@H](C)C2)c2c(C(=O)O)cc(-c3csc4ccccc34)nc12] | ++ |
| 183 | 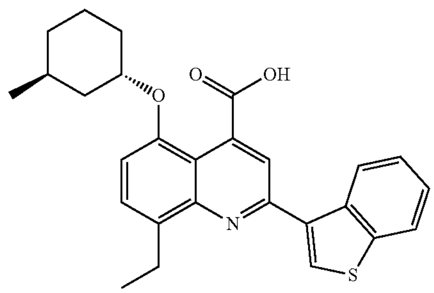 [SMILES: CCc1ccc(O[C@H]2CCC[C@H](C)C2)c2c(C(=O)O)cc(-c3csc4ccccc34)nc12] | ++ |
| 184 | 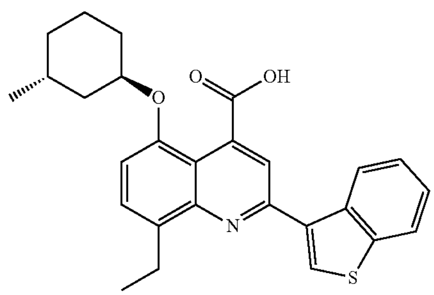 [SMILES: CCc1ccc(O[C@@H]2CCC[C@@H](C)C2)c2c(C(=O)O)cc(-c3csc4ccccc34)nc12] | ++ |
| 185 | 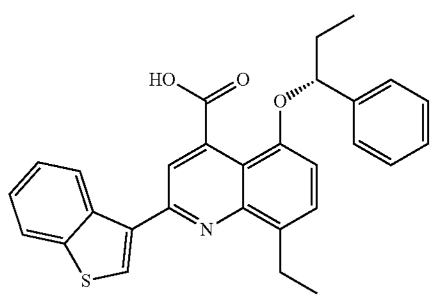 [SMILES: CCc1ccc(O[C@H](CC)c2ccccc2)c2c(C(=O)O)cc(-c3csc4ccccc34)nc12] | ++ |
| 186 | 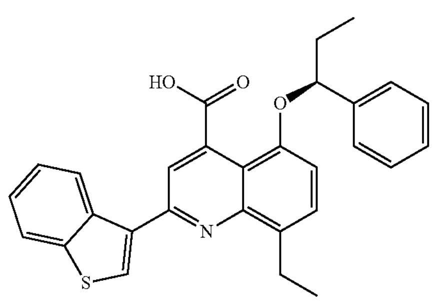 [SMILES: CCc1ccc(O[C@@H](CC)c2ccccc2)c2c(C(=O)O)cc(-c3csc4ccccc34)nc12] | ++ |

TABLE 1-continued

| Compound # | Structure | Activity |
|---|---|---|
| 187 | 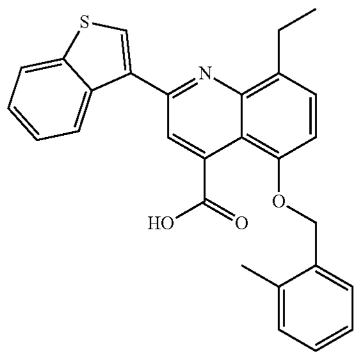 [SMILES: CCc1ccc(OCc2ccccc2C)c2c(C(=O)O)cc(-c3csc4ccccc34)nc12] | ++ |
| 188 | 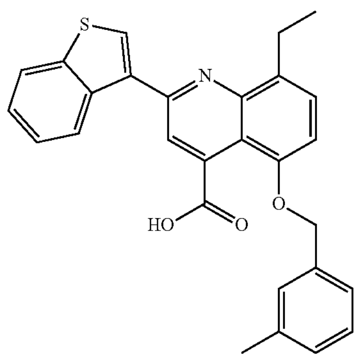 [SMILES: CCc1ccc(OCc2cccc(C)c2)c2c(C(=O)O)cc(-c3csc4ccccc34)nc12] | ++ |
| 189 | 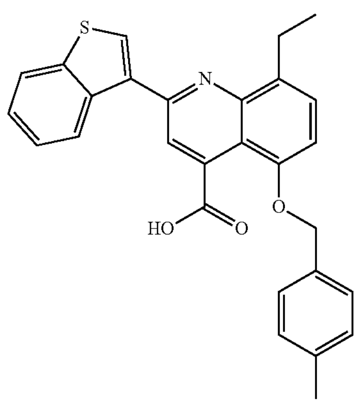 [SMILES: CCc1ccc(OCc2ccc(C)cc2)c2c(C(=O)O)cc(-c3csc4ccccc34)nc12] | ++ |
| 190 | 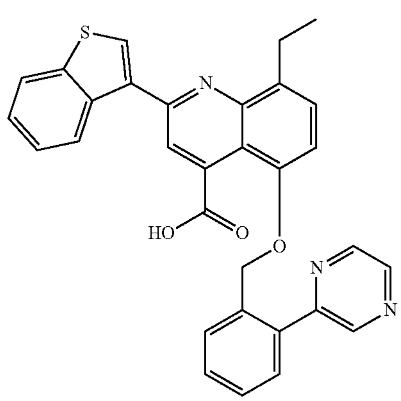 [SMILES: CCc1ccc(OCc2ccccc2-c2cnccn2)c2c(C(=O)O)cc(-c3csc4ccccc34)nc12] | |

TABLE 1-continued

| Compound # | Structure | Activity |
|---|---|---|
| 191 | 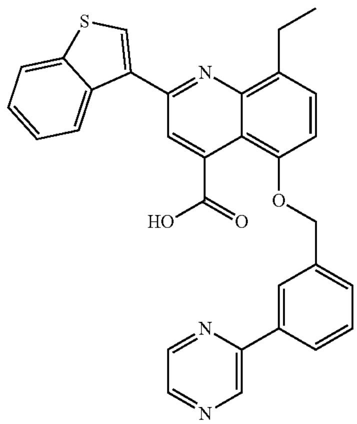 [SMILES: CCc1ccc(OCc2cccc(-c3cnccn3)c2)c2c(C(=O)O)cc(-c3csc4ccccc34)nc12] | |
| 192 | 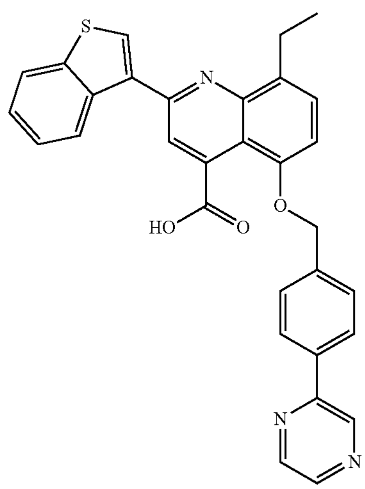 [SMILES: CCc1ccc(OCc2ccc(-c3cnccn3)cc2)c2c(C(=O)O)cc(-c3csc4ccccc34)nc12] | ++ |
| 193 | 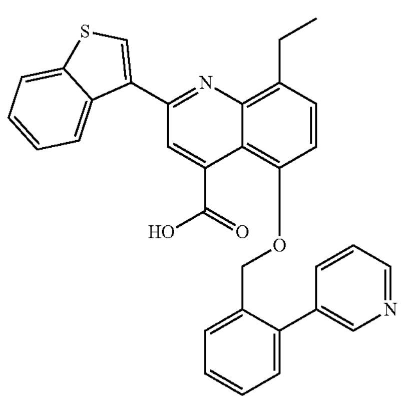 [SMILES: CCc1ccc(OCc2ccccc2-c2cccnc2)c2c(C(=O)O)cc(-c3csc4ccccc34)nc12] | |

TABLE 1-continued

| Compound # | Structure | Activity |
|---|---|---|
| 194 | 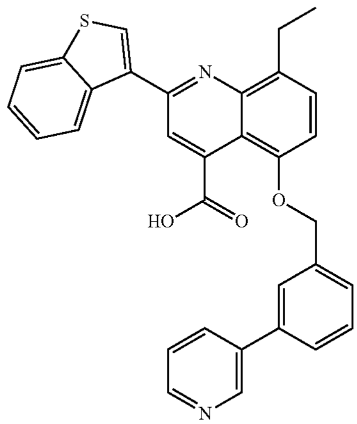 [SMILES: CCc1ccc(OCc2cccc(-c3cccnc3)c2)c2c(C(=O)O)cc(-c3csc4ccccc34)nc12] | + |
| 195 | 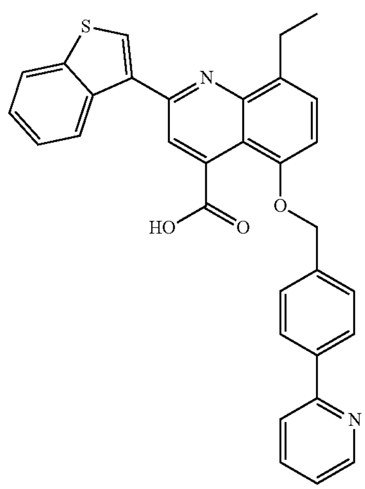 [SMILES: CCc1ccc(OCc2ccc(-c3ccccn3)cc2)c2c(C(=O)O)cc(-c3csc4ccccc34)nc12] | ++ |
| 196 | 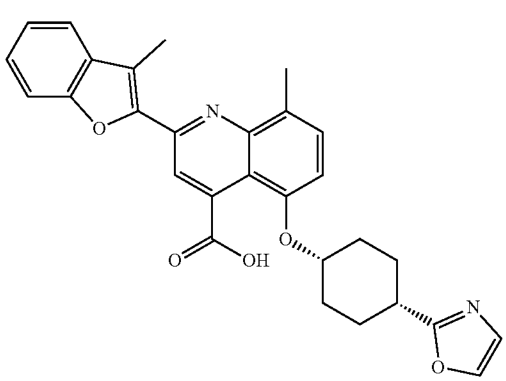 [SMILES: Cc1c(-c2cc(C(=O)O)c3c(O[C@H]4CC[C@@H](c5ncco5)CC4)ccc(C)c3n2)oc2ccccc12] | ++ |

TABLE 1-continued

| Compound # | Structure | Activity |
|---|---|---|
| 197 | 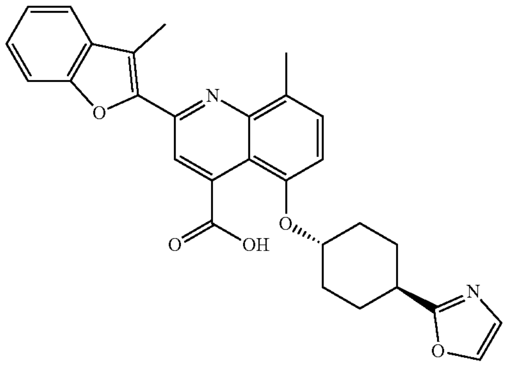 [SMILES: Cc1c(-c2cc(C(=O)O)c3c(O[C@H]4CC[C@H](c5ncco5)CC4)ccc(C)c3n2)oc2ccccc12] | ++ |
| 198 | 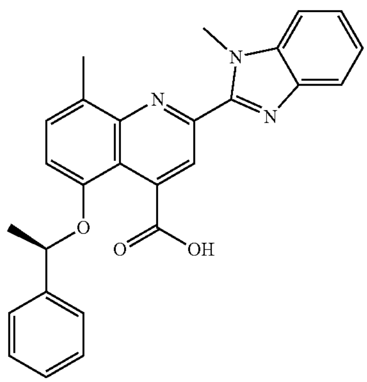 [SMILES: Cc1ccc(O[C@H](C)c2ccccc2)c2c(C(=O)O)cc(-c3nc4ccccc4n3C)nc12] | |
| 199 | 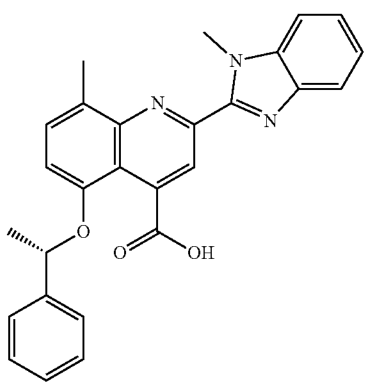 [SMILES: Cc1ccc(O[C@@H](C)c2ccccc2)c2c(C(=O)O)cc(-c3nc4ccccc4n3C)nc12] | |
| 200 | 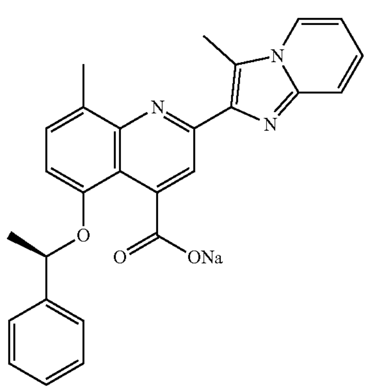 | + |

TABLE 1-continued

| Compound # | Structure | Activity |
|---|---|---|
| 201 | 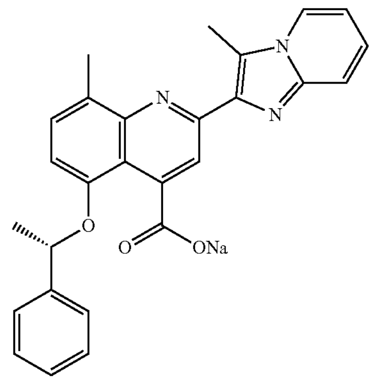 | ++ |
| 202 | 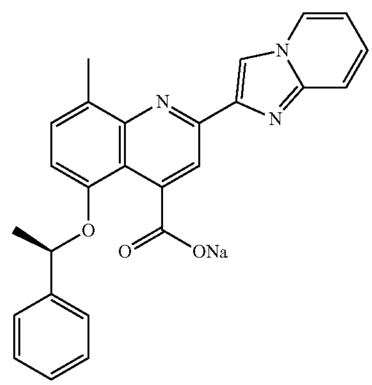 | + |
| 203 | 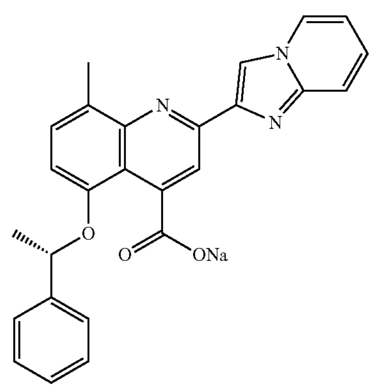 | + |
| 204 | 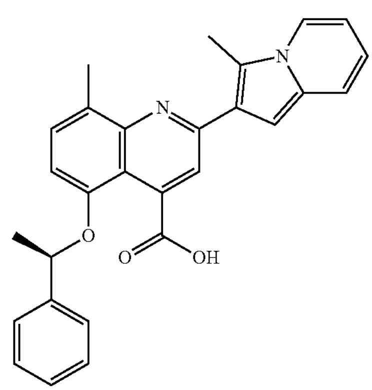 [SMILES: Cc1ccc(O[C@H](C)c2ccccc2)c2c(C(=O)O)cc(-c3cc4ccccn4c3C)nc12] | |

TABLE 1-continued

| Compound # | Structure | Activity |
|---|---|---|
| 205 | 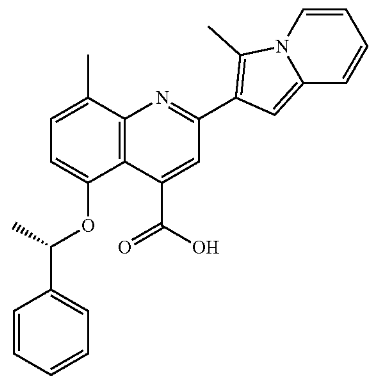 [SMILES: Cc1ccc(O[C@@H](C)c2ccccc2)c2c(C(=O)O)cc(-c3cc4ccccn4c3C)nc12] | |
| 206 | 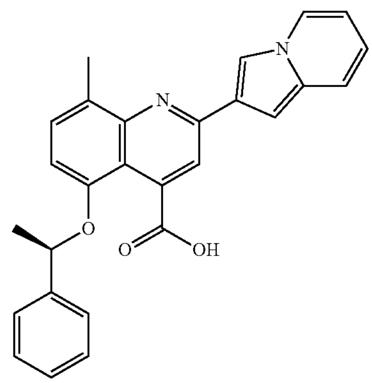 [SMILES: Cc1ccc(O[C@H](C)c2ccccc2)c2c(C(=O)O)cc(-c3cc4ccccn4c3)nc12] | |
| 207 | 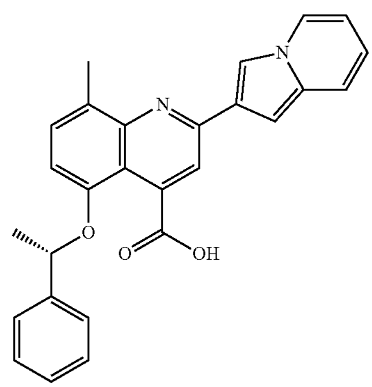 [SMILES: Cc1ccc(O[C@@H](C)c2ccccc2)c2c(C(=O)O)cc(-c3cc4ccccn4c3)nc12] | |
| 208 | 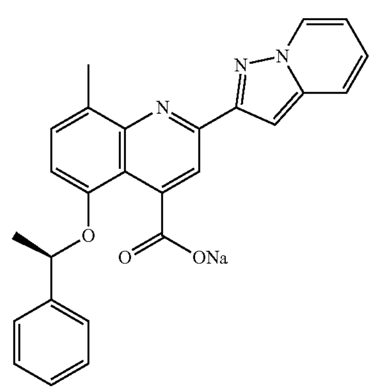 | ++ |

TABLE 1-continued

| Compound # | Structure | Activity |
|---|---|---|
| 209 | 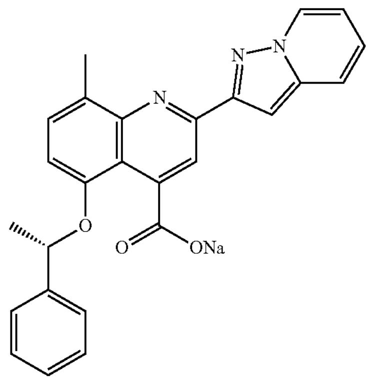 | + |
| 210 | 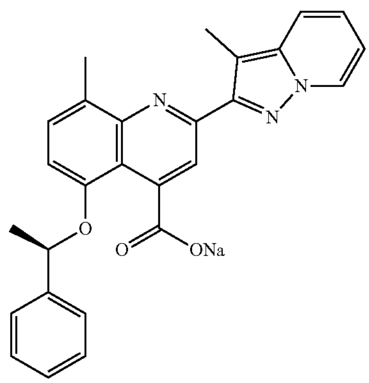 | |
| 211 | 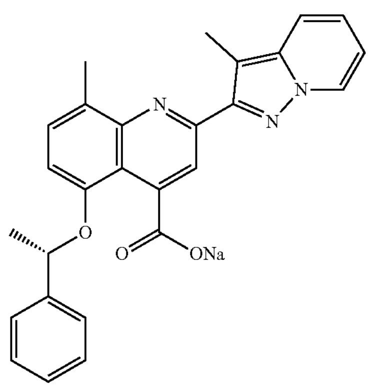 | |
| 212 | 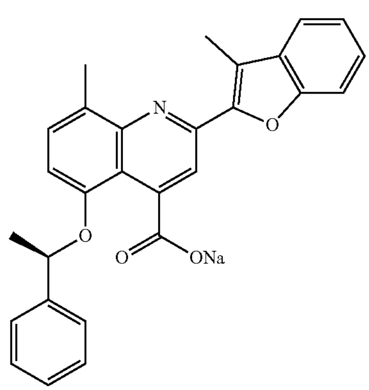 | ++ |

TABLE 1-continued
| Compound # | Structure | Activity |
|---|---|---|
| 213 | 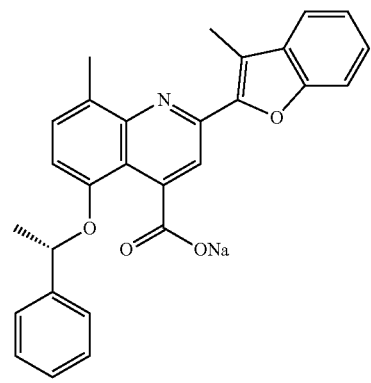 | ++ |
| 214 | 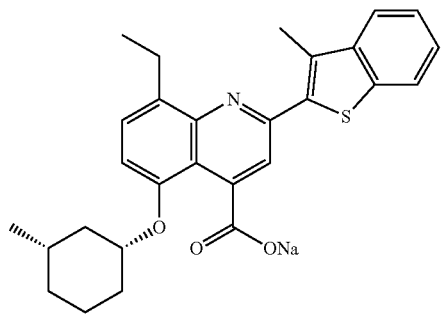 | ++ |
| 215 | 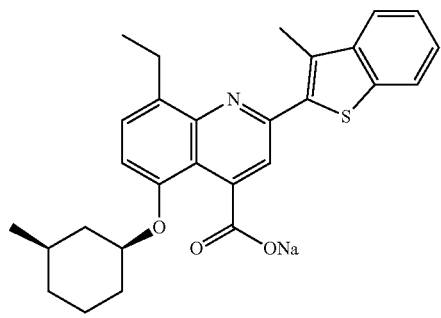 | ++ |
| 216 | 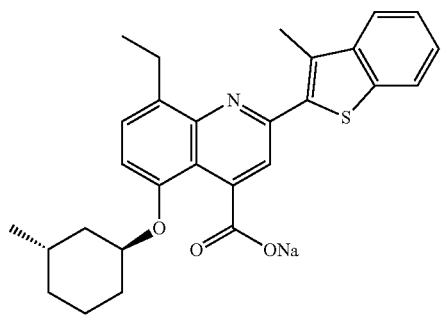 | ++ |

TABLE 1-continued

| Compound # | Structure | Activity |
|---|---|---|
| 217 | 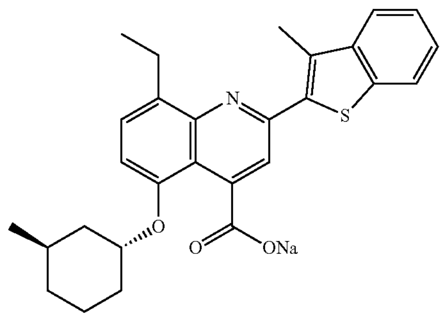 | ++ |
| 218 | 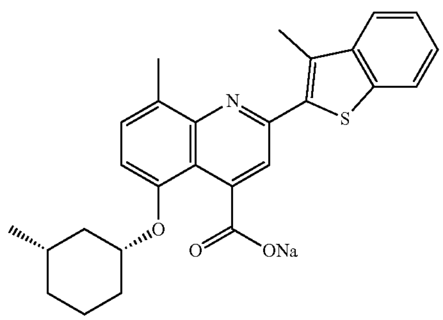 | ++ |
| 219 | 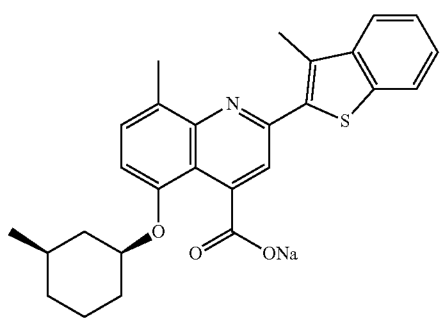 | ++ |
| 220 | 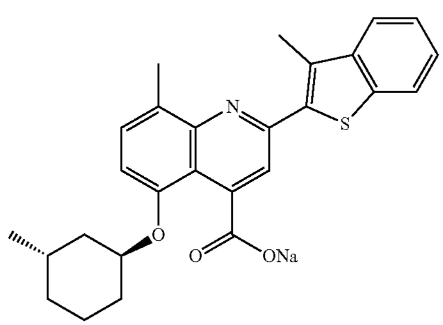 | ++ |
| 221 | 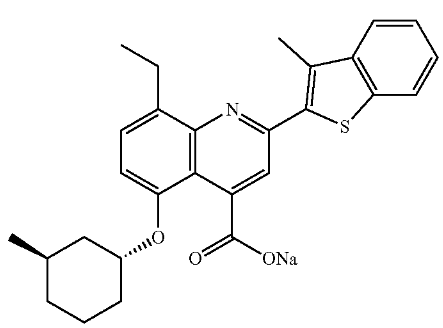 | ++ |

TABLE 1-continued
| Compound # | Structure | Activity |
|---|---|---|
| 222 | 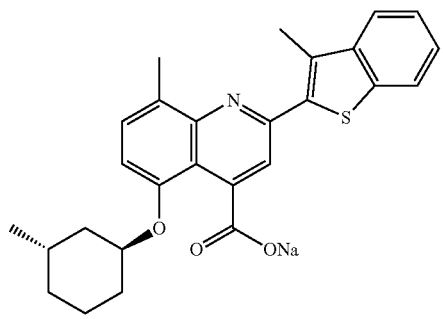 | ++ |
| 223 | 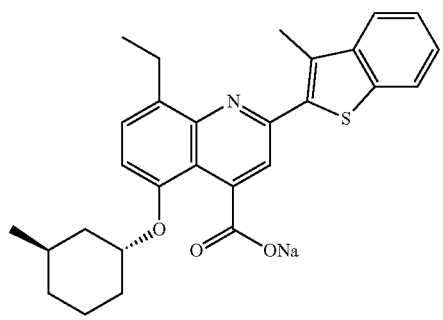 | ++ |
| 224 | 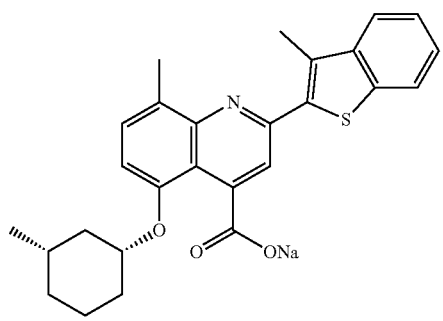 | ++ |
| 225 | 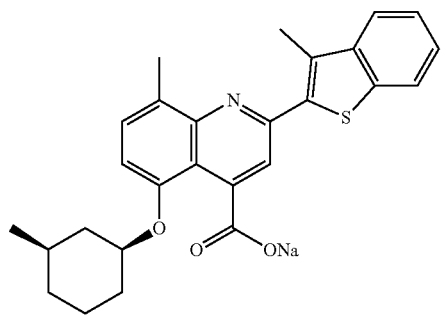 | ++ |

TABLE 1-continued

| Compound # | Structure | Activity |
|---|---|---|
| 226 | 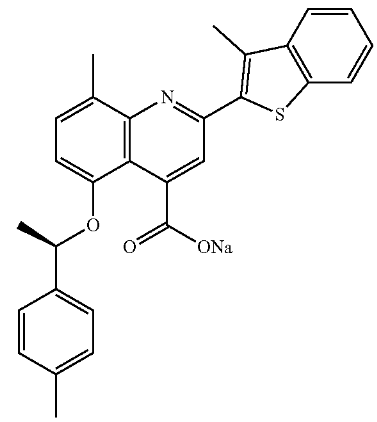 | ++ |
| 227 | 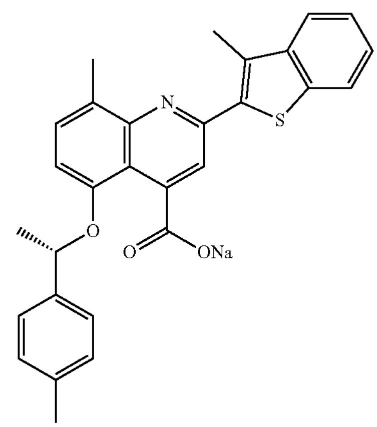 | ++ |
| 228 | 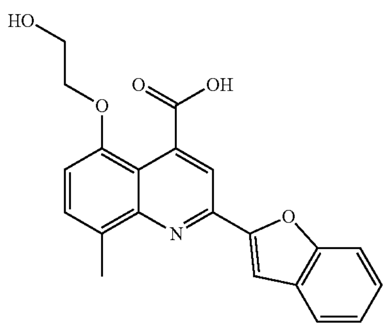 [SMILES: Cc1ccc(OCCO)c2c(C(=O)O)cc(-c3cc4ccccc4o3)nc12] | |
| 229 | 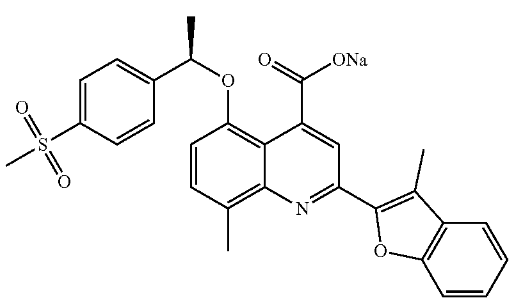 | ++ |

TABLE 1-continued
| Compound # | Structure | Activity |
|---|---|---|
| 230 | 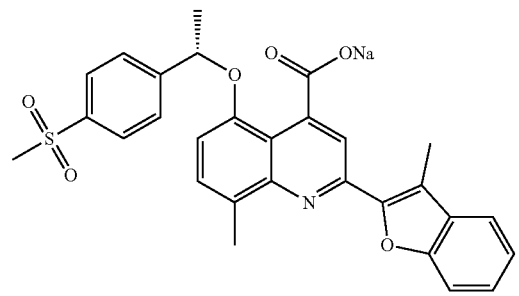 | ++ |
| 231 | 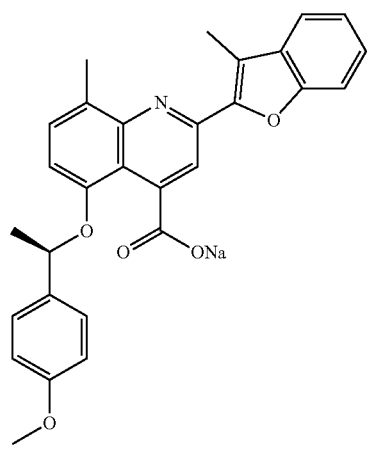 | |
| 232 | 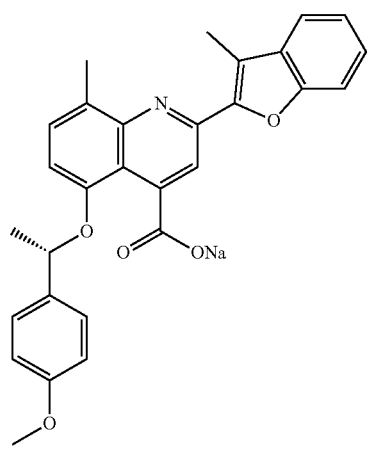 | |

TABLE 1-continued
| Compound # | Structure | Activity |
|---|---|---|
| 233 | 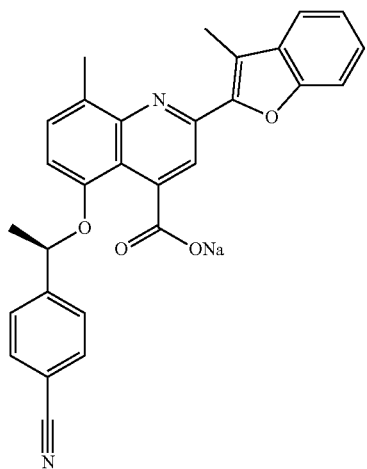 | ++ |
| 234 | 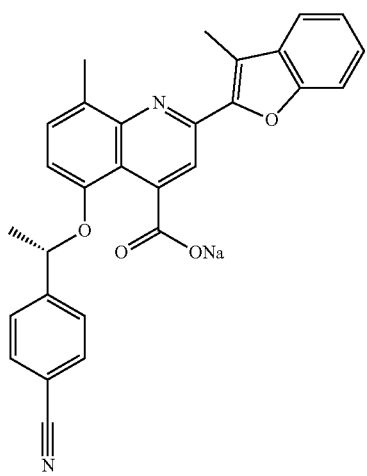 | ++ |
| 235 | 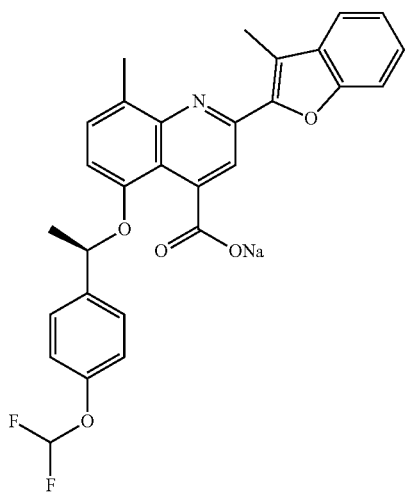 | ++ |

TABLE 1-continued

| Compound # | Structure | Activity |
|---|---|---|
| 236 | 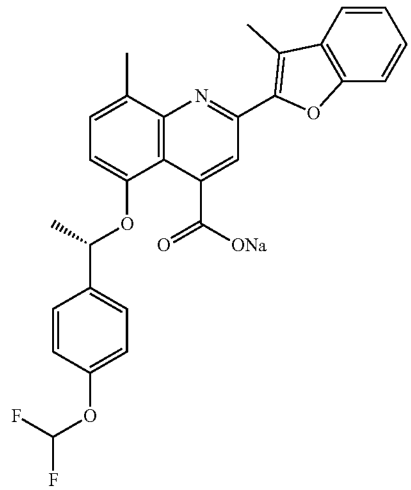 | ++ |
| 237 | 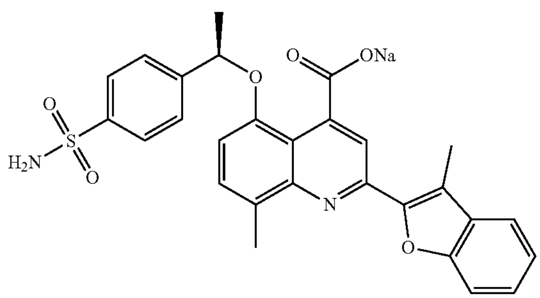 | + |
| 238 | 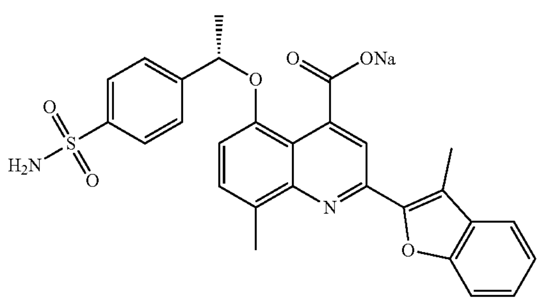 | ++ |
| 239 | 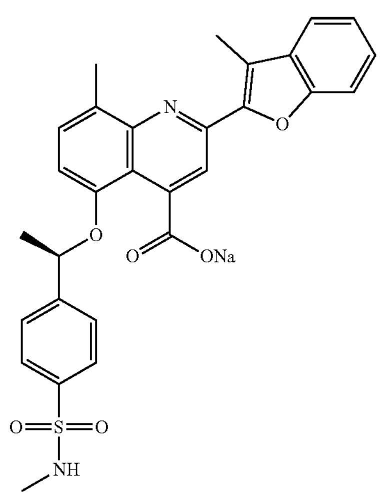 | ++ |

TABLE 1-continued
| Compound # | Structure | Activity |
|---|---|---|
| 240 | 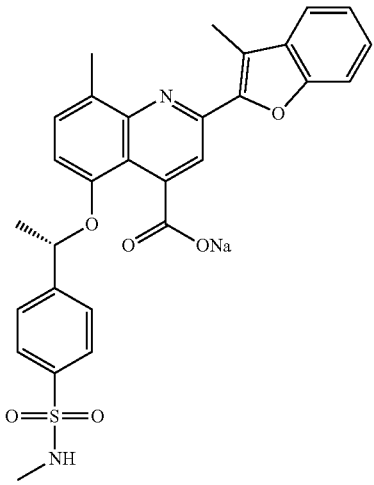 | ++ |
| 241 | 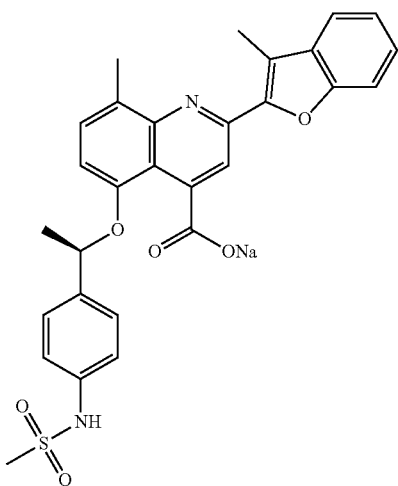 | |
| 242 | 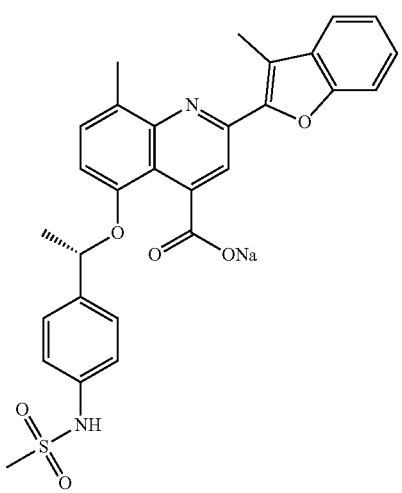 | |

TABLE 1-continued
| Compound # | Structure | Activity |
|---|---|---|
| 243 | 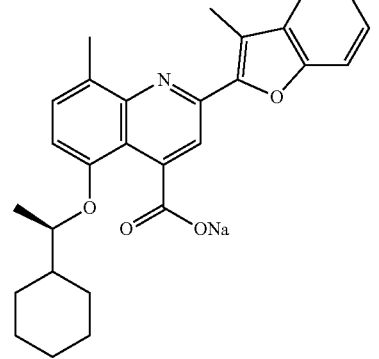 | ++ |
| 244 | 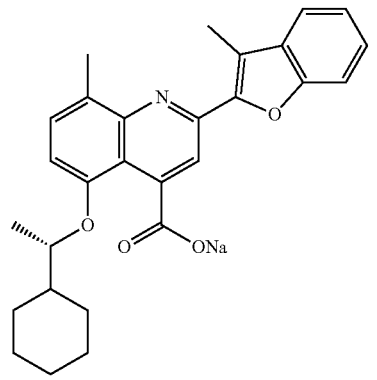 | ++ |
| 245 | 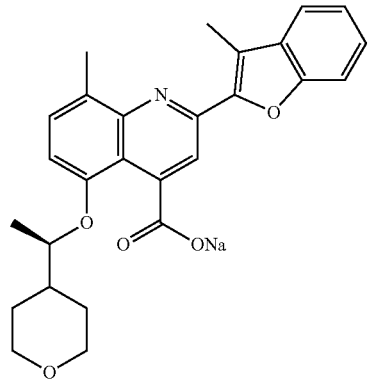 | ++ |
| 246 | 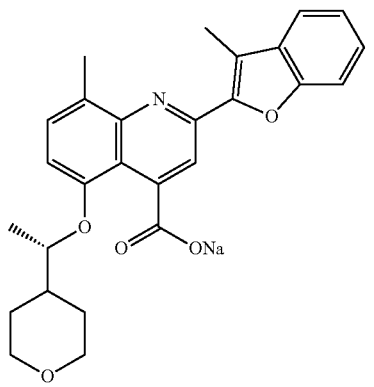 | ++ |

TABLE 1-continued
| Compound # | Structure | Activity |
|---|---|---|
| 247 | 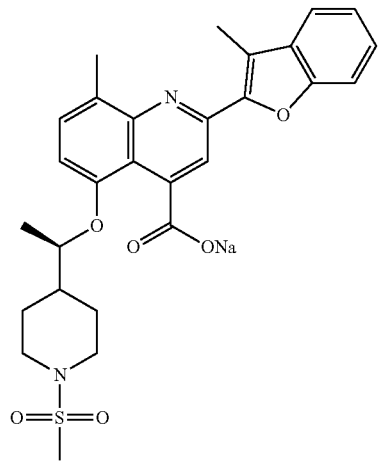 | ++ |
| 248 | 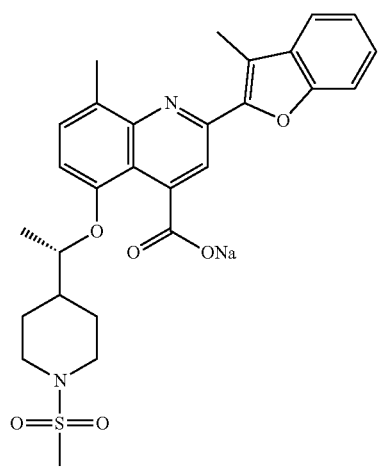 | ++ |
| 249 | 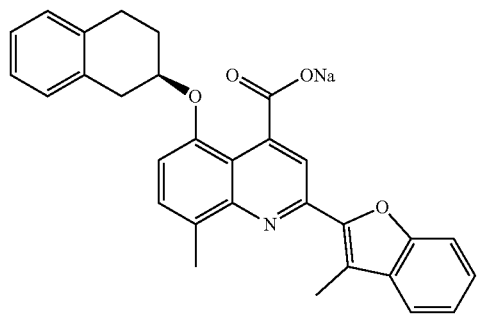 | ++ |

TABLE 1-continued
| Compound # | Structure | Activity |
|---|---|---|
| 250 | 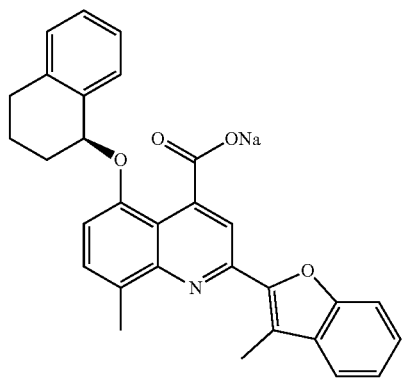 | |
| 251 | 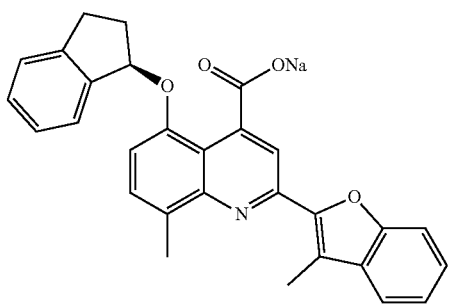 | |
| 252 | 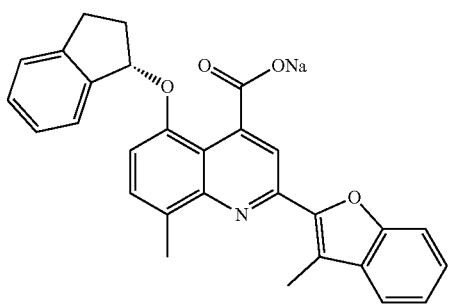 | |
| 253 | 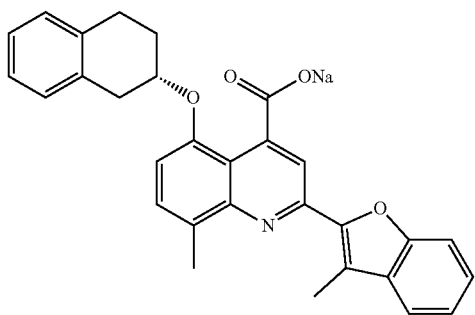 | ++ |

TABLE 1-continued

| Compound # | Structure | Activity |
|---|---|---|
| 254 | 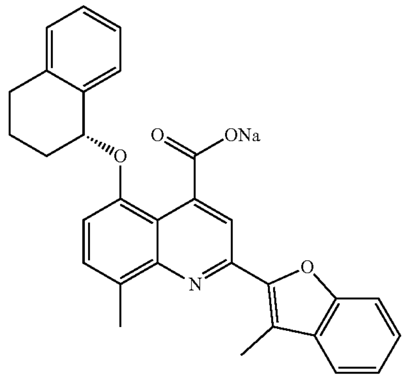 | |
| 255 | 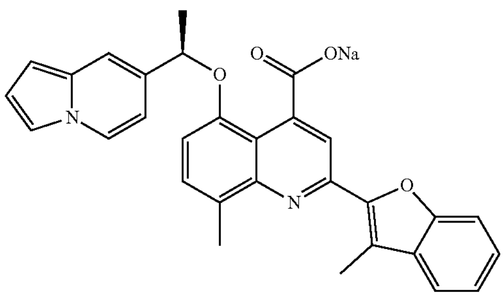 | |
| 256 | 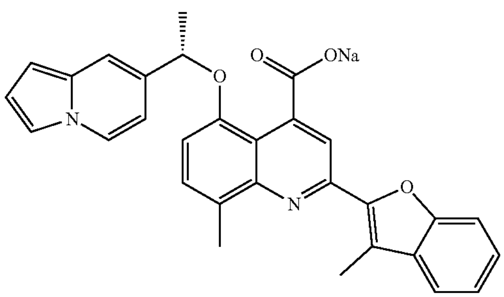 | |
| 257 | 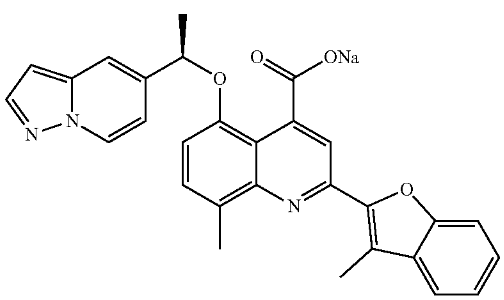 | ++ |
| 258 | 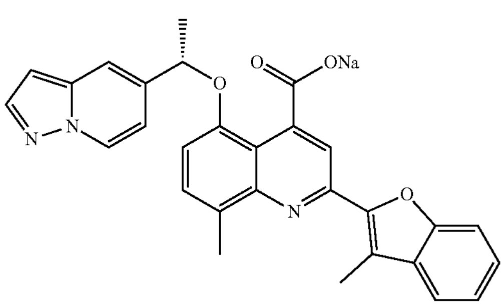 | ++ |

TABLE 1-continued

| Compound # | Structure | Activity |
|---|---|---|
| 259 | 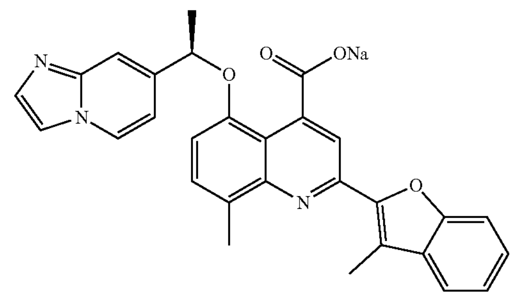 | |
| 260 | 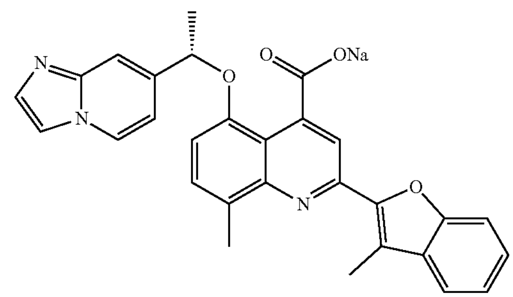 | |
| 261 | 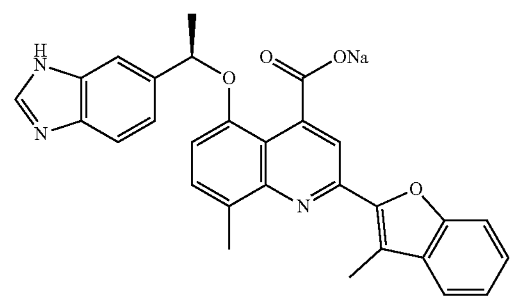 | |
| 262 | 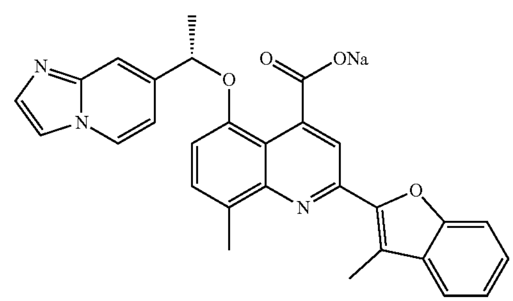 | |
| 263 | 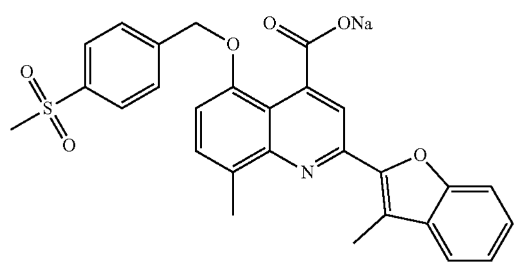 | ++ |

TABLE 1-continued
| Compound # | Structure | Activity |
|---|---|---|
| 264 | 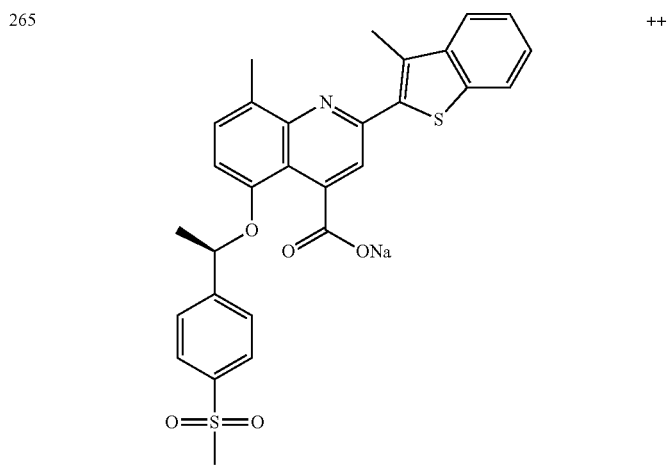 | ++ |
| 265 | 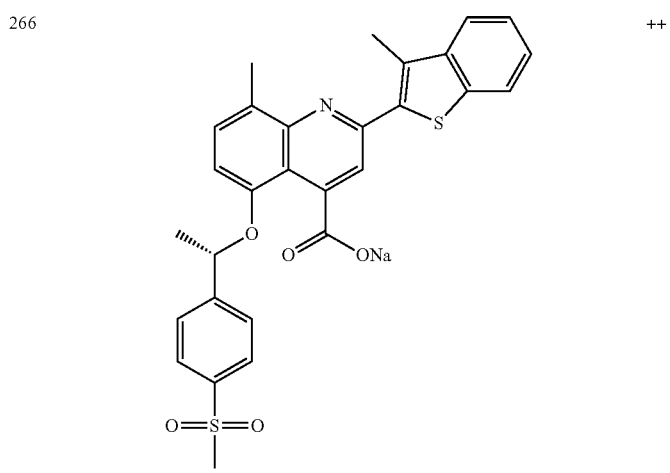 | ++ |
| 266 | 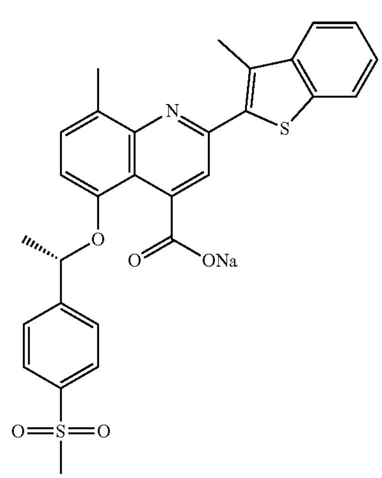 | ++ |

TABLE 1-continued
| Compound # | Structure | Activity |
|---|---|---|
| 267 | 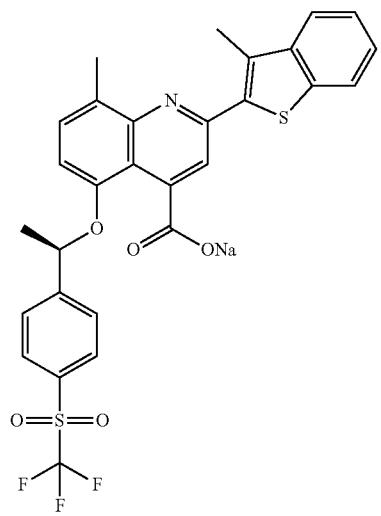 | |
| 268 | 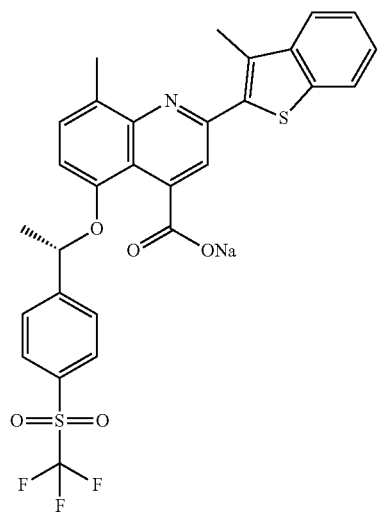 | |
| 269 | 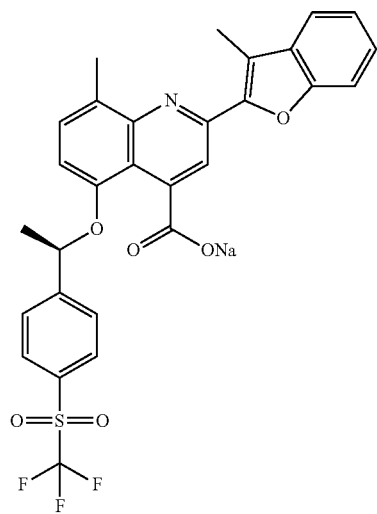 | |

TABLE 1-continued
| Compound # | Structure | Activity |
|---|---|---|
| 270 | 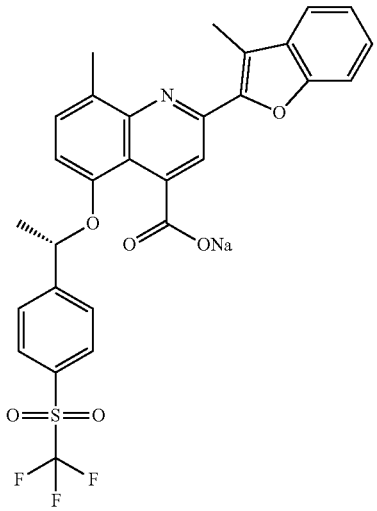 | |
| 271 | 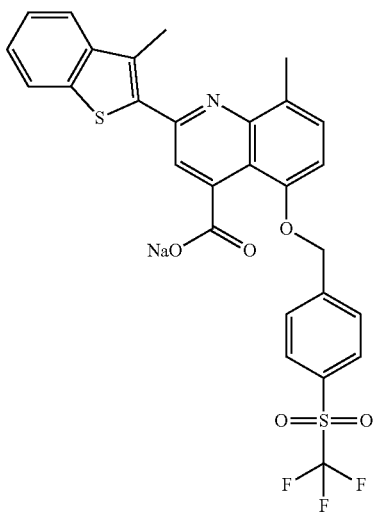 | |
| 272 | 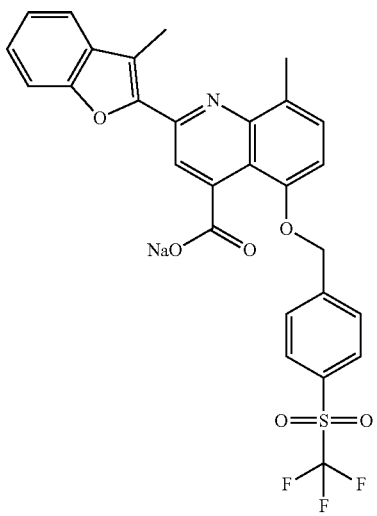 | |

TABLE 1-continued

| Compound # | Structure | Activity |
|---|---|---|
| 273 | 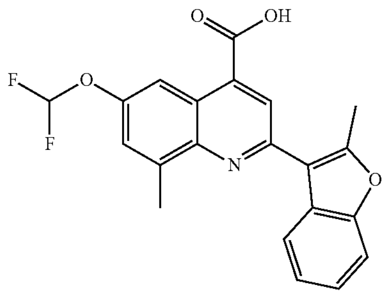 [SMILES: Cc1oc2ccccc2c1-c1cc(C(=O)O)c2cc(OC(F)F)cc(C)c2n1] | |
| 274 | 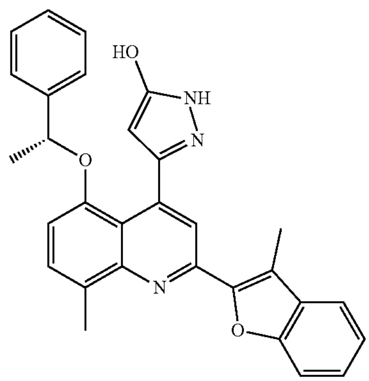 [SMILES: Cc1c(-c2cc(-c3cc(O)[nH]n3)c3c(O[C@H](C)c4ccccc4)ccc(C)c3n2)oc2ccccc12] | + |
| 275 | 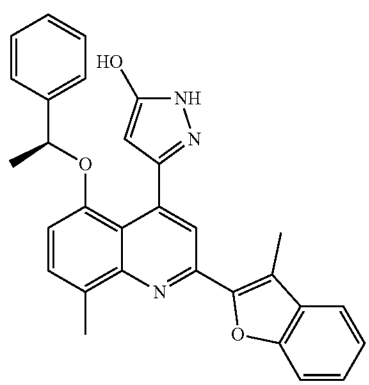 [SMILES: Cc1c(-c2cc(-c3cc(O)[nH]n3)c3c(O[C@@H](C)c4ccccc4)ccc(C)c3n2)oc2ccccc12] | + |
| 276 | 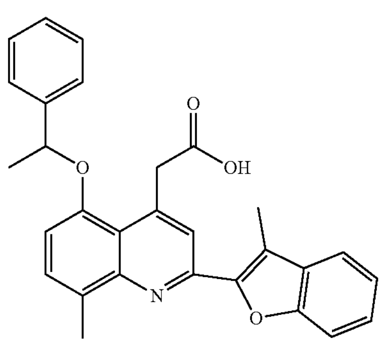 [SMILES: Cc1c(-c2cc(CC(=O)O)c3c(OC(C)c4ccccc4)ccc(C)c3n2)oc2ccccc12] | ++ |

TABLE 1-continued

| Compound # | Structure | Activity |
|---|---|---|
| 277 | 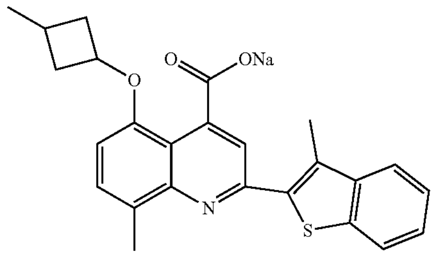 | ++ |
| 278 | 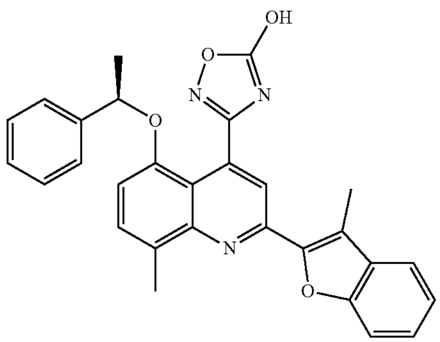 [SMILES: Cc1c(-c2cc(-c3noc(O)n3)c3c(O[C@H](C)c4ccccc4)ccc(C)c3n2)oc2ccccc12] | |
| 279 | 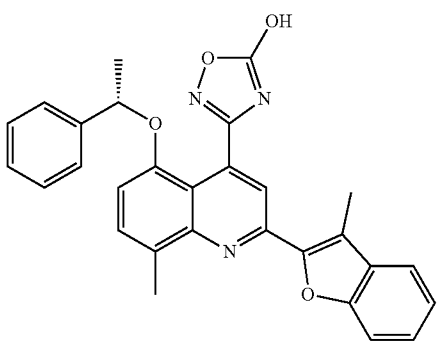 [SMILES: Cc1c(-c2cc(-c3noc(O)n3)c3c(O[C@@H](C)c4ccccc4)ccc(C)c3n2)oc2ccccc12] | |
| 280 | 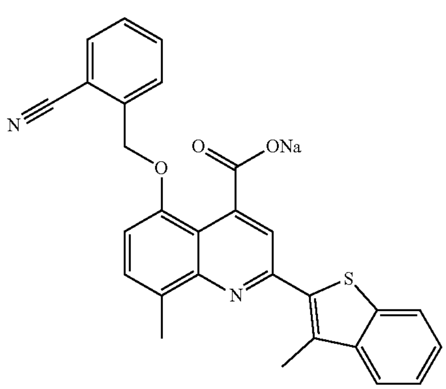 | ++ |

TABLE 1-continued

| Compound # | Structure | Activity |
|---|---|---|
| 281 | 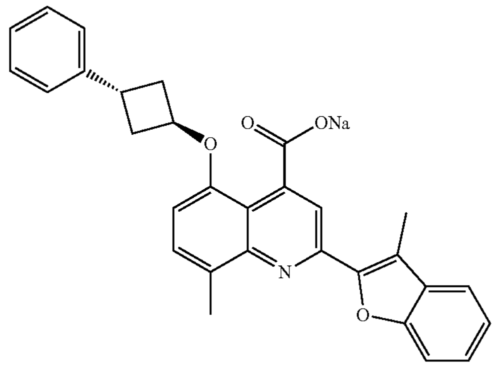 | ++ |
| 282 | 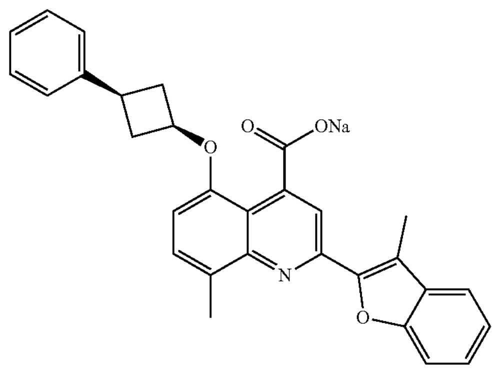 | ++ |
| 283 | 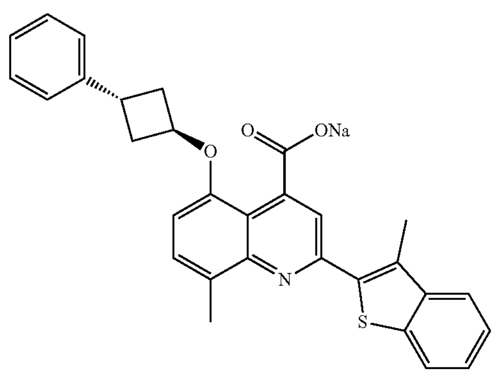 | ++ |
| 284 | 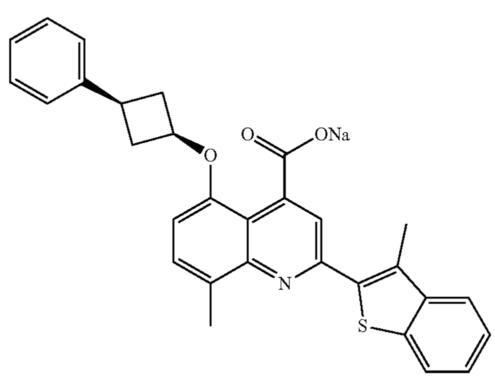 | ++ |

TABLE 1-continued
| Compound # | Structure | Activity |
|---|---|---|
| 285 | 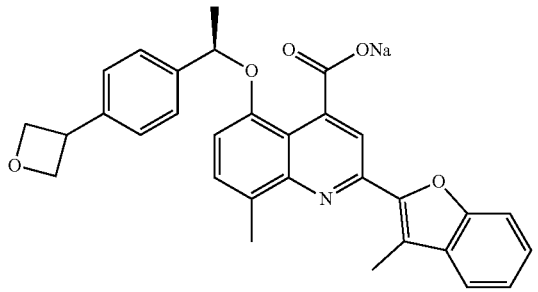 | ++ |
| 286 | 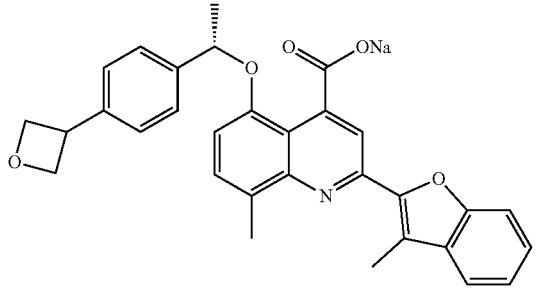 | ++ |
| 287 | 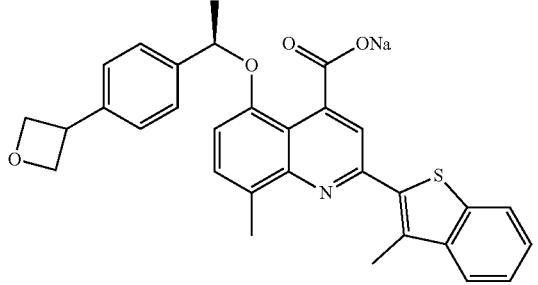 | |
| 288 | 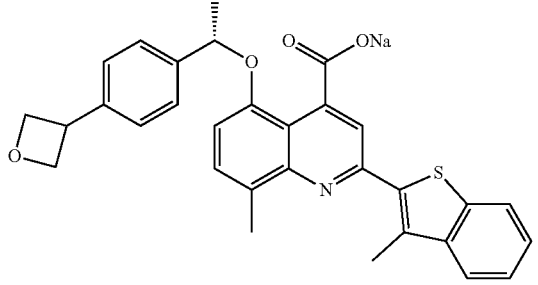 | |
| 289 | 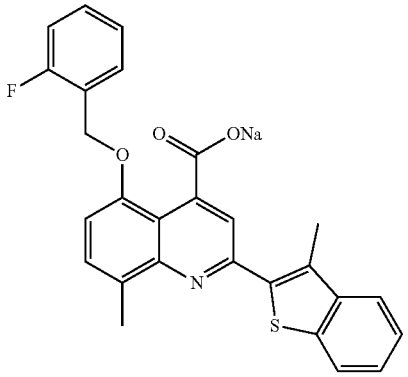 | ++ |

TABLE 1-continued

| Compound # | Structure | Activity |
|---|---|---|
| 290 | 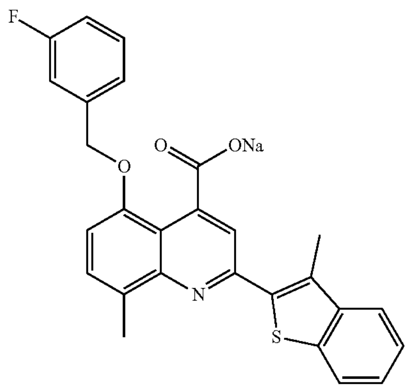 | ++ |
| 291 | 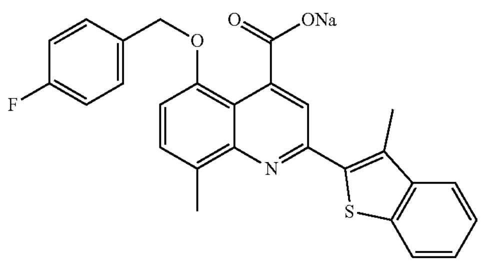 | ++ |
| 292 | 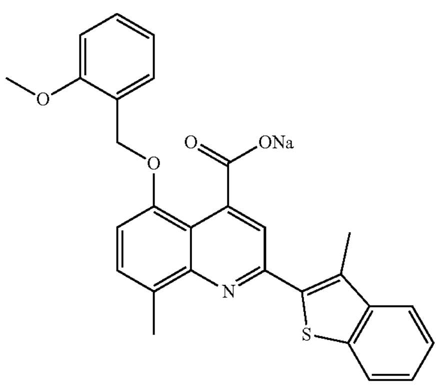 | ++ |
| 293 | 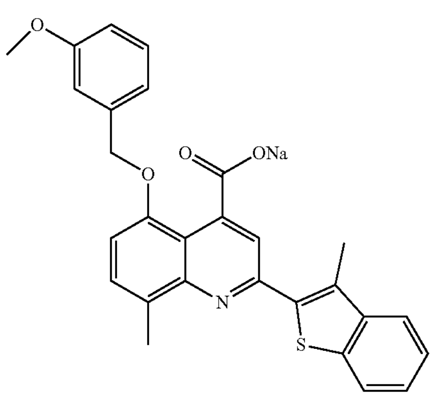 | ++ |

TABLE 1-continued

| Compound # | Structure | Activity |
|---|---|---|
| 294 | 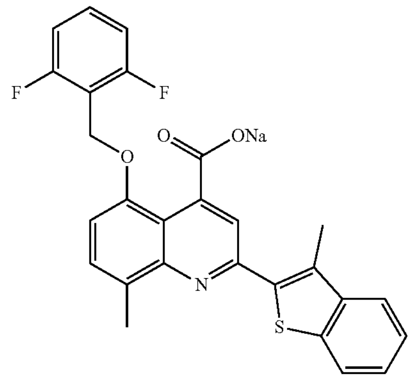 | ++ |
| 295 | 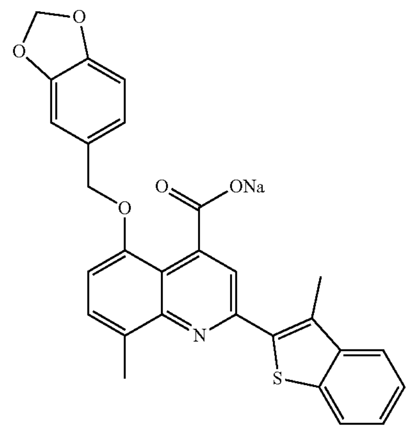 | ++ |
| 296 | 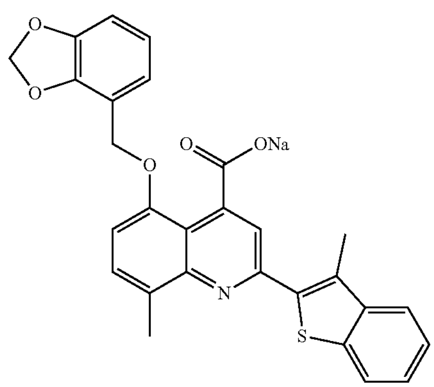 | ++ |
| 297 | 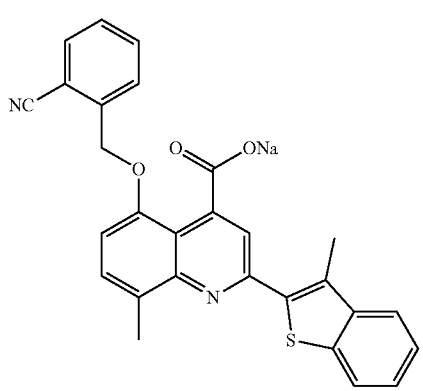 | ++ |

TABLE 1-continued
| Compound # | Structure | Activity |
|---|---|---|
| 298 | 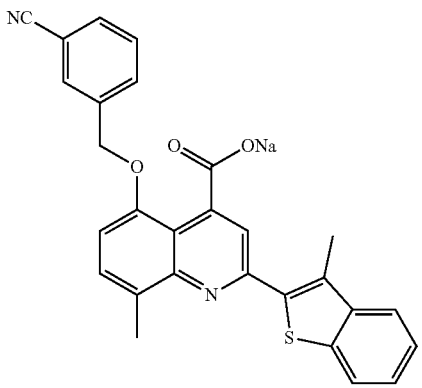 | ++ |
| 299 | 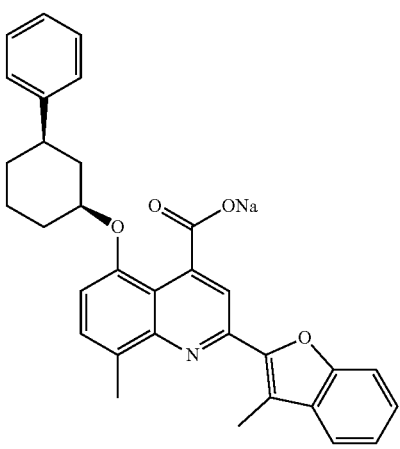 | ++ |
| 300 | 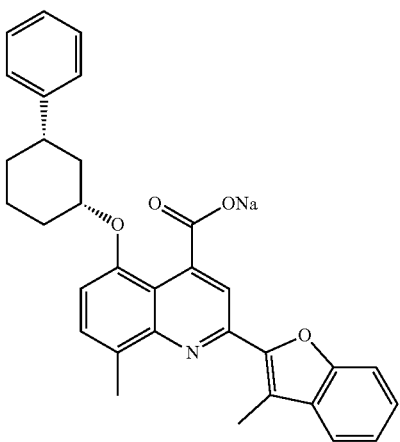 | ++ |

TABLE 1-continued
| Compound # | Structure | Activity |
|---|---|---|
| 301 | 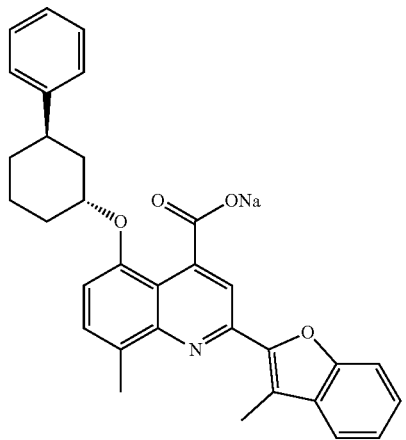 | ++ |
| 302 | 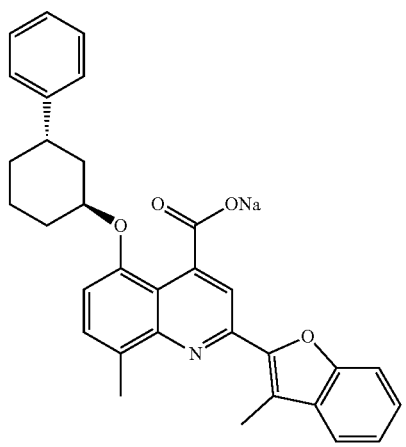 | ++ |
| 303 | 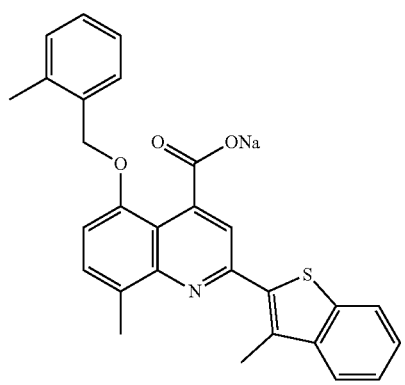 | ++ |

TABLE 1-continued
| Compound # | Structure | Activity |
|---|---|---|
| 304 | 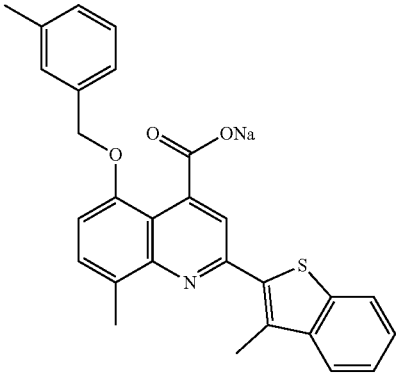 | ++ |
| 305 | 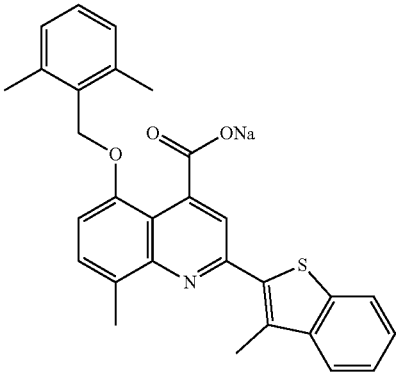 | ++ |
| 306 | 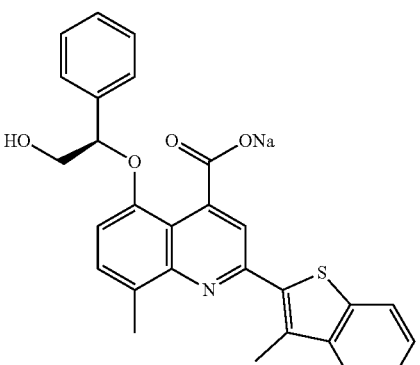 | ++ |
| 307 | 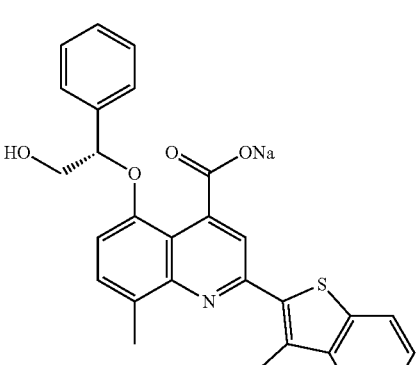 | ++ |

TABLE 1-continued

| Compound # | Structure | Activity |
|---|---|---|
| 308 | 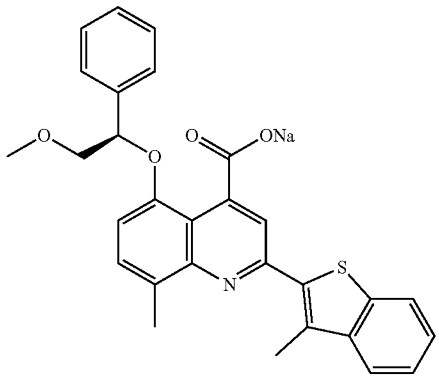 | ++ |
| 309 | 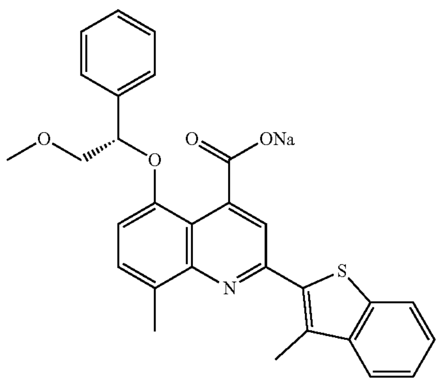 | ++ |
| 310 | 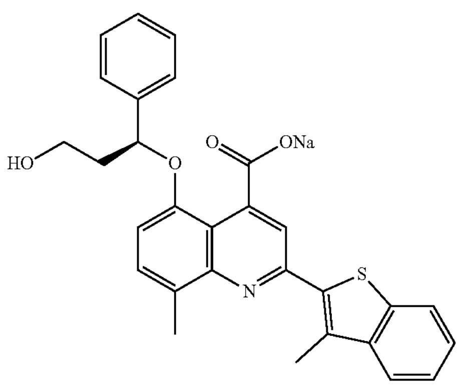 | ++ |
| 311 | 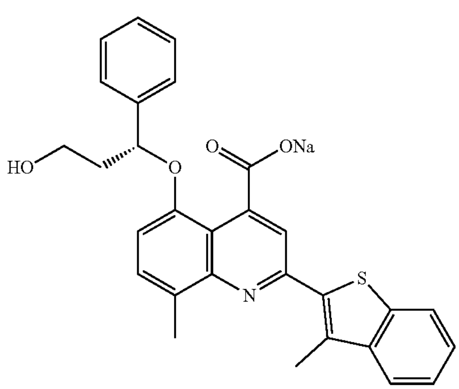 | ++ |

TABLE 1-continued
| Compound # | Structure | Activity |
|---|---|---|
| 312 | 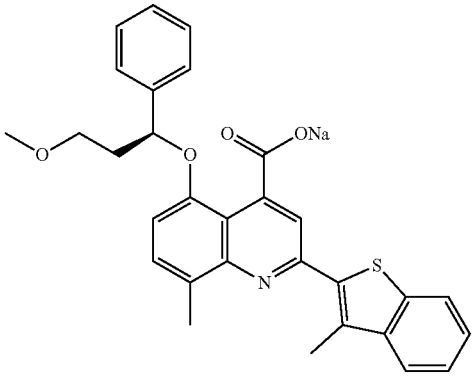 | ++ |
| 313 | 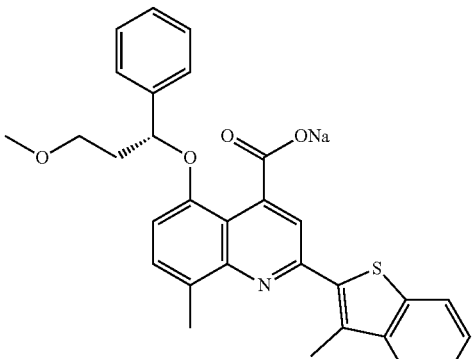 | ++ |
| 314 | 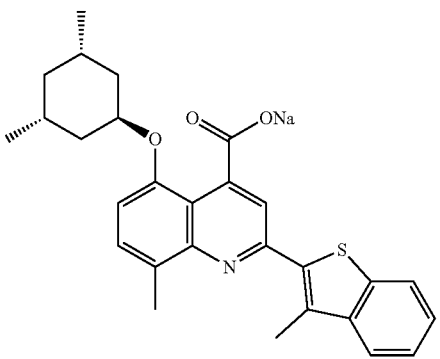 | ++ |
| 315 | 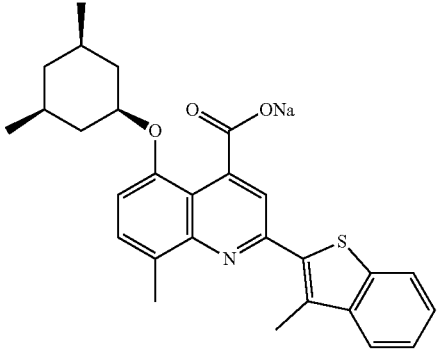 | ++ |

US 10,550,106 B2
TABLE 1-continued
| Compound # | Structure | Activity |
|---|---|---|
| 316 | 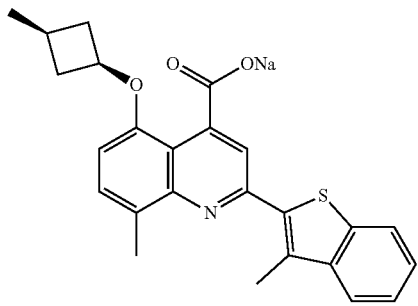 | |
| 317 | 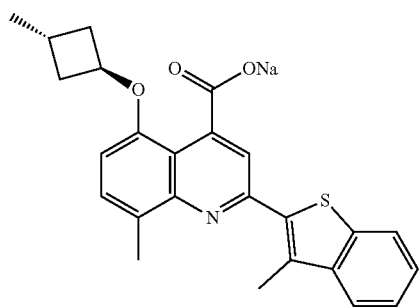 | |
| 318 | 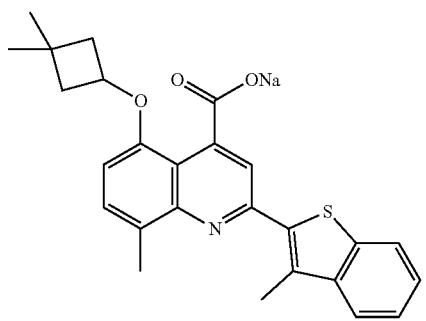 | ++ |
| 319 | 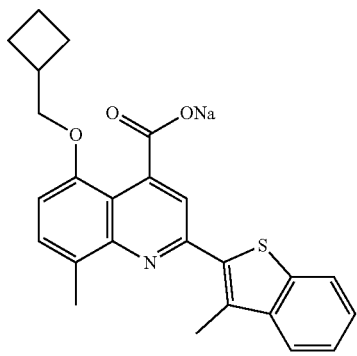 | ++ |

TABLE 1-continued
| Compound # | Structure | Activity |
|---|---|---|
| 320 | 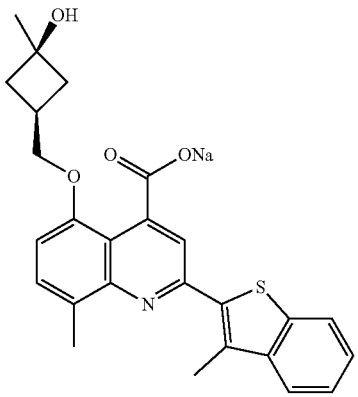 | ++ |
| 321 | 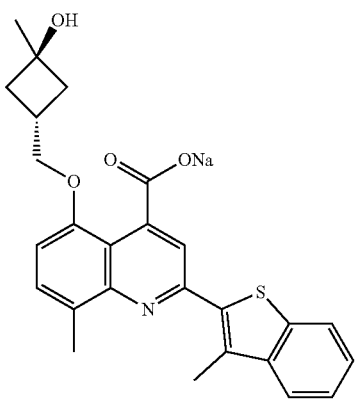 | ++ |
| 322 | 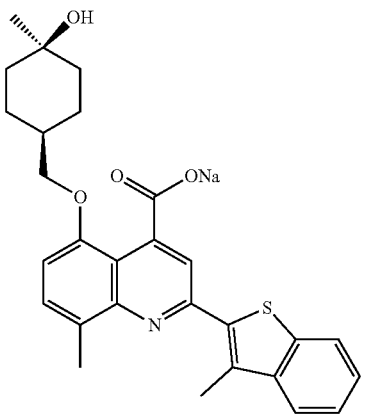 | ++ |

287
288
TABLE 1-continued
| Compound # | Structure | Activity |
|---|---|---|
| 323 | 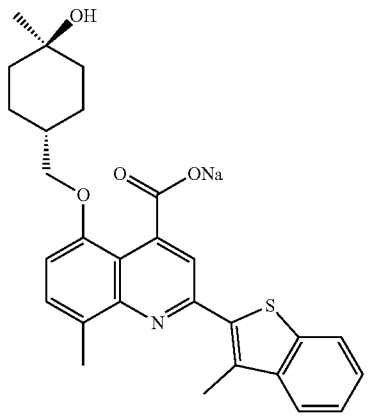 | ++ |
| 324 | 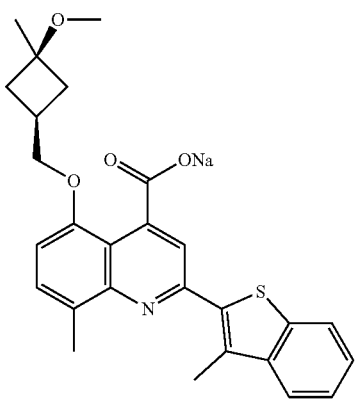 | ++ |
| 325 | 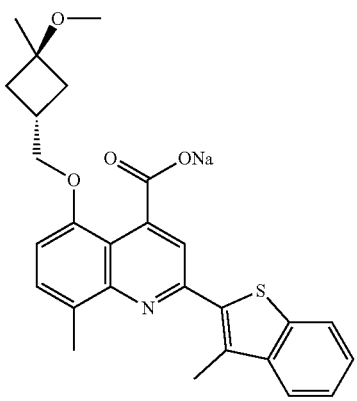 | ++ |

TABLE 1-continued
| Compound # | Structure | Activity |
|---|---|---|
| 326 | 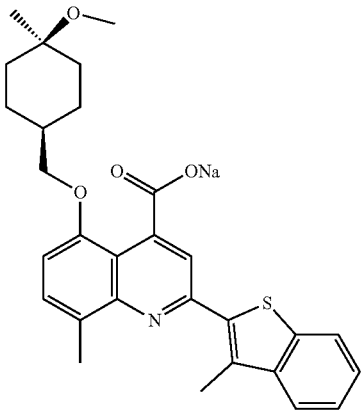 | ++ |
| 327 | 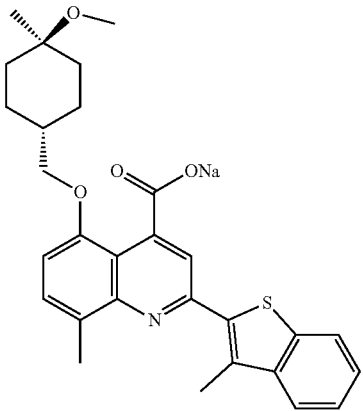 | ++ |
| 328 | 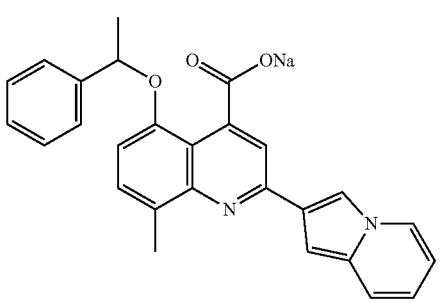 | ++ |
| 329 | 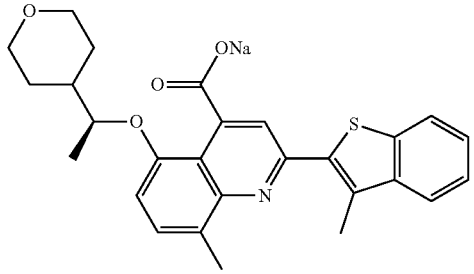 | ++ |

TABLE 1-continued

| Compound # | Structure | Activity |
|---|---|---|
| 330 | 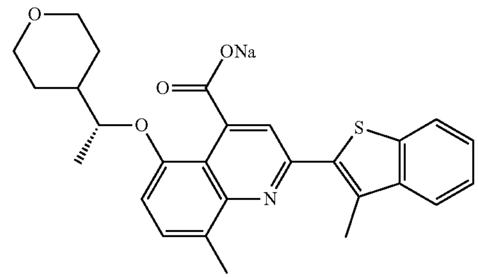 | ++ |
| 331 | 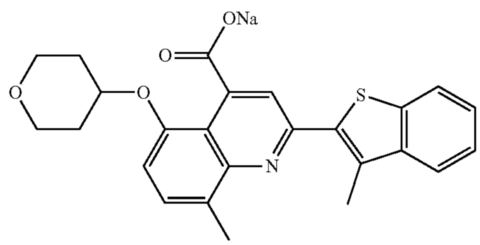 | ++ |
| 332 | 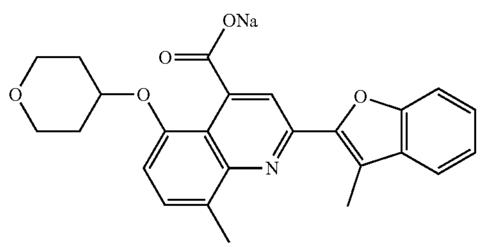 | ++ |
| 333 | 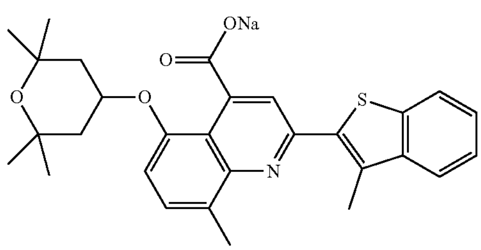 | ++ |
| 334 | 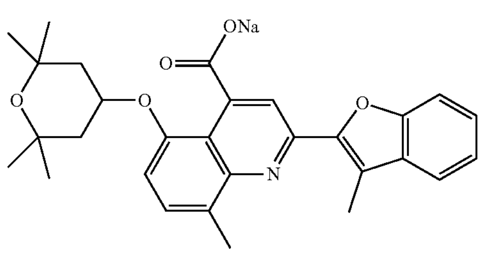 | ++ |

TABLE 1-continued

| Compound # | Structure | Activity |
|---|---|---|
| 335 | 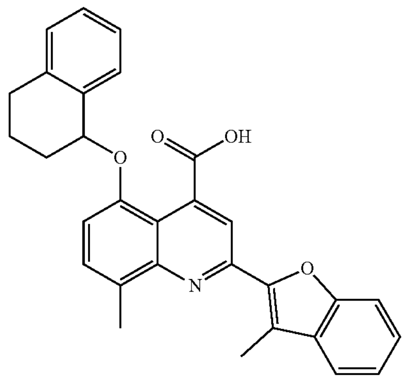 [SMILES: Cc1c(-c2cc(C(=O)O)c3c(OC4CCCc5ccccc54)ccc(C)c3n2)oc2ccccc12] | ++ |
| 336 | 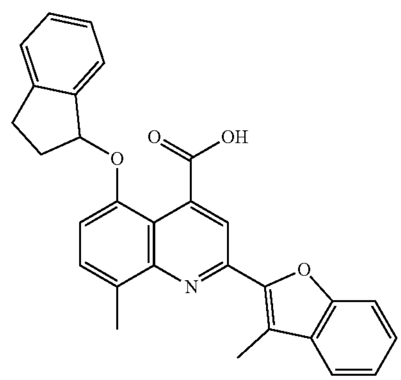 [SMILES: Cc1c(-c2cc(C(=O)O)c3c(OC4CCc5ccccc54)ccc(C)c3n2)oc2ccccc12] | ++ |
| 337 | 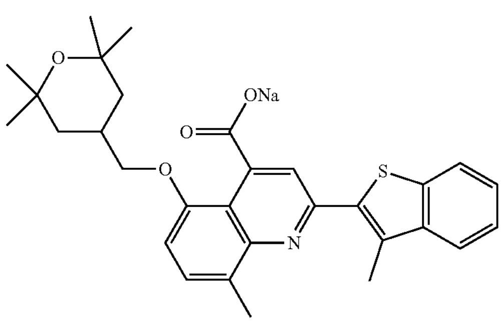 | ++ |
| 338 | 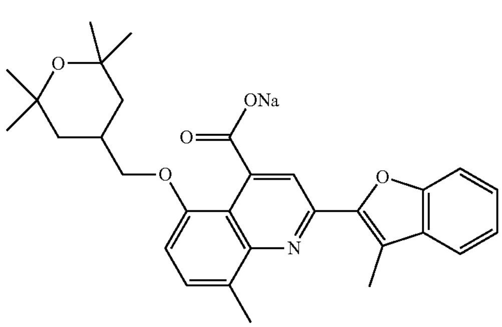 | ++ |

TABLE 1-continued

| Compound # | Structure | Activity |
|---|---|---|
| 339 | 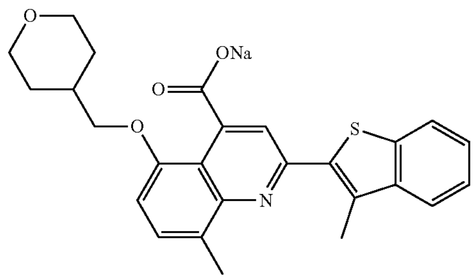 | |
| 340 | 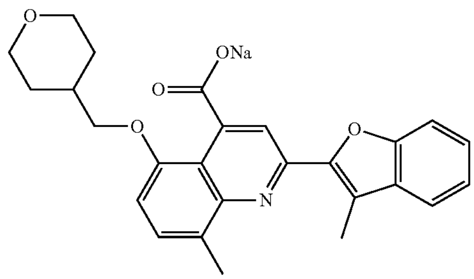 | |
| 341 | 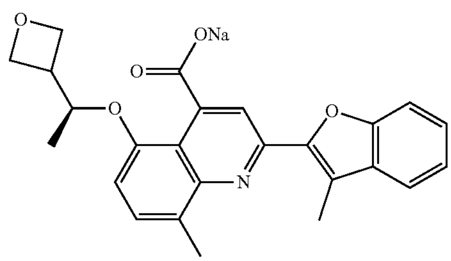 | |
| 342 | 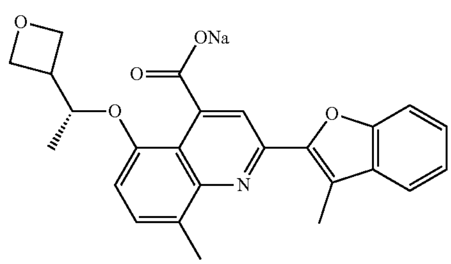 | |
| 343 | 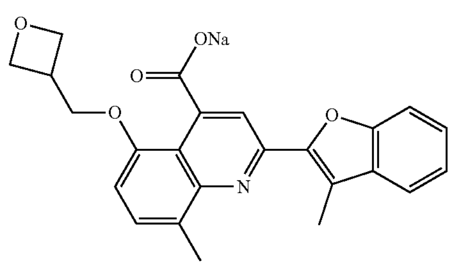 | ++ |
| 344 | 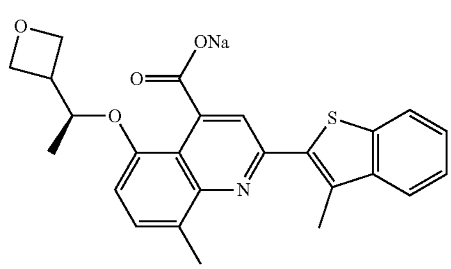 | |

TABLE 1-continued

| Compound # | Structure | Activity |
|---|---|---|
| 345 | 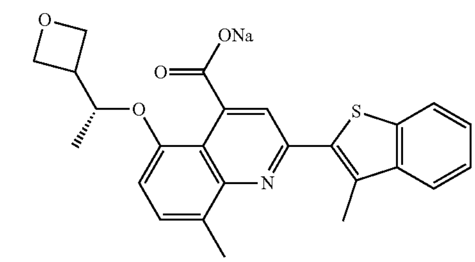 | |
| 346 | 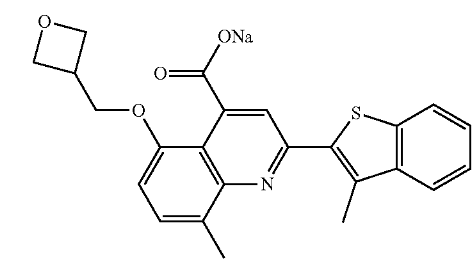 | ++ |
| 347 | 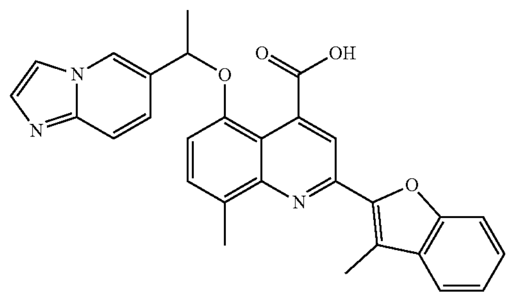 [SMILES: Cc1c(-c2cc(C(=O)O)c3c(OC(C)c4ccc5nccn5c4)ccc(C)c3n2)oc2ccccc12] | + |
| 348 | 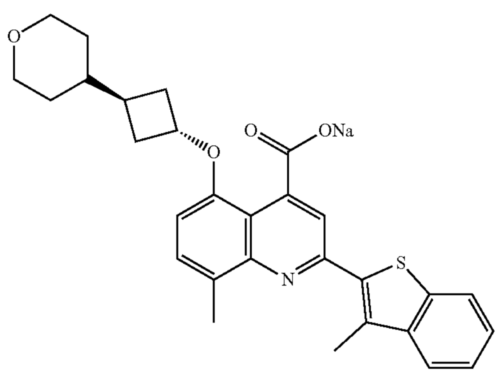 | |
| 349 | 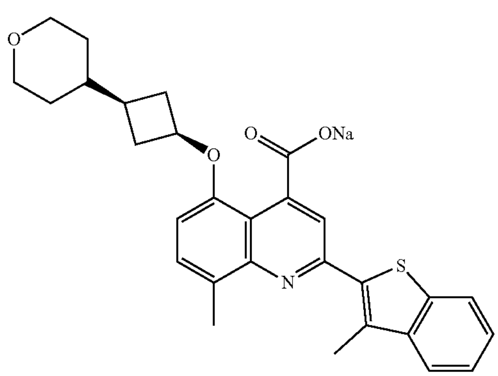 | |

TABLE 1-continued
| Compound # | Structure | Activity |
|---|---|---|
| 350 | 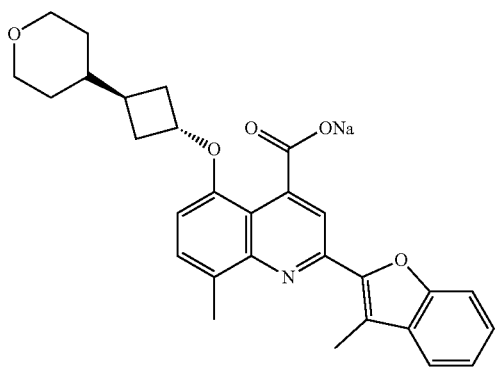 | ++ |
| 351 | 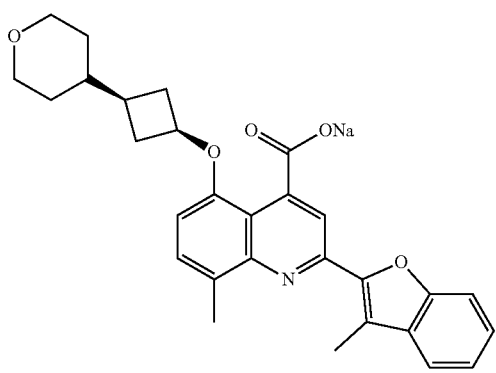 | |
| 352 | 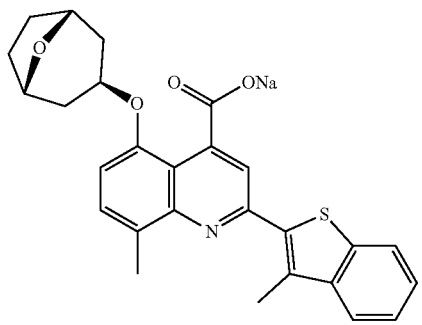 | ++ |
| 353 | 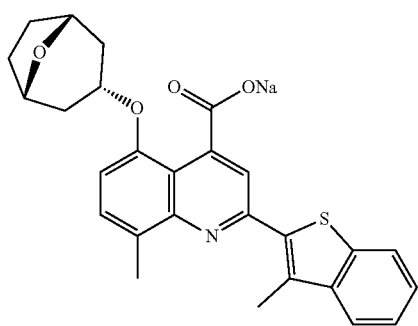 | ++ |

TABLE 1-continued

| Compound # | Structure | Activity |
|---|---|---|
| 354 | 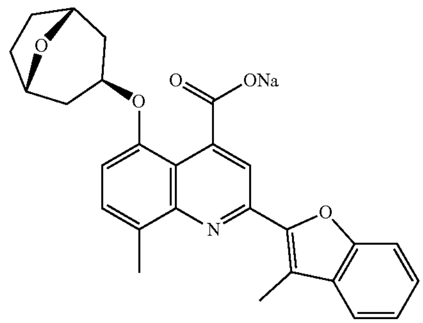 | ++ |
| 355 | 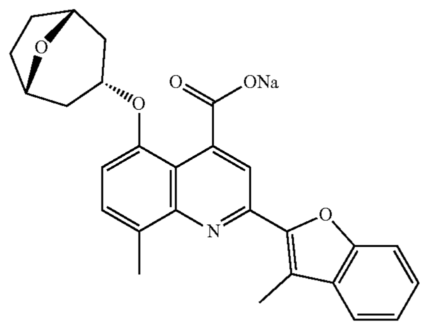 | ++ |
| 356 | 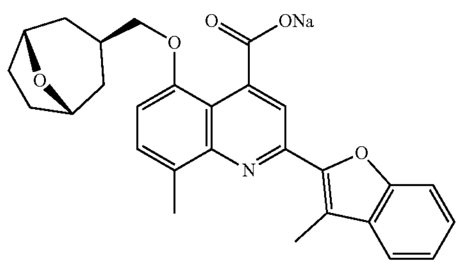 | ++ |
| 357 | 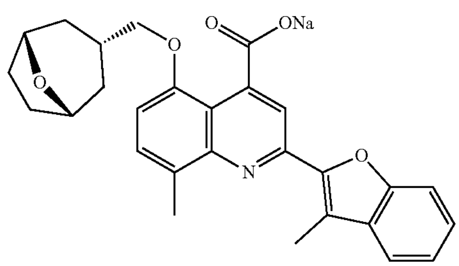 | ++ |
| 358 | 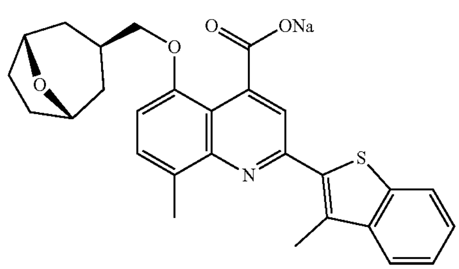 | ++ |

TABLE 1-continued

| Compound # | Structure | Activity |
|---|---|---|
| 359 | 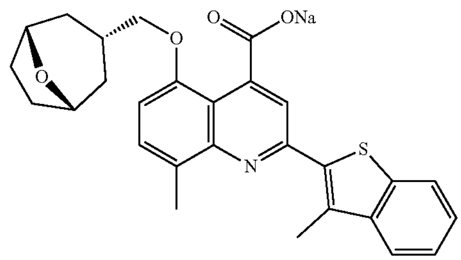 | ++ |
| 360 | 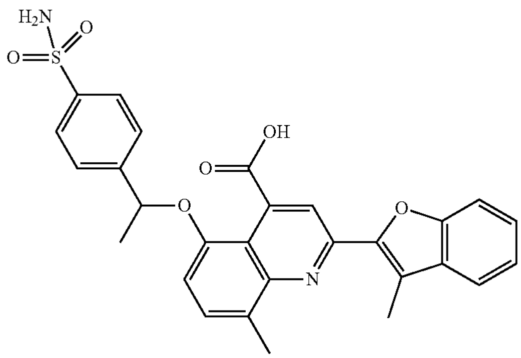 [SMILES: Cc1c(-c2cc(C(=O)O)c3c(OC(C)c4ccc(S(N)(=O)=O)cc4)ccc(C)c3n2)oc2ccccc12] | ++ |
| 361 | 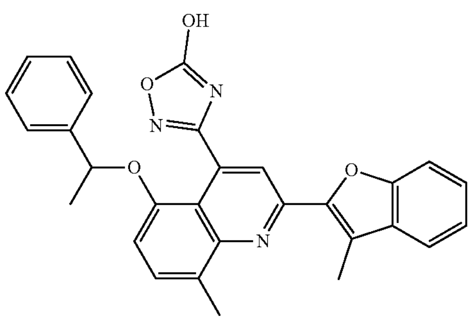 [SMILES: Cc1c(-c2cc(-c3noc(O)n3)c3c(OC(C)c4ccccc4)ccc(C)c3n2)oc2ccccc12] | ++ |
| 362 | 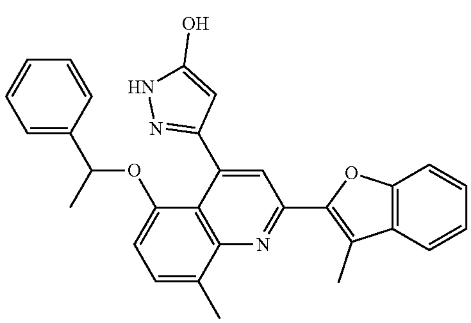 [SMILES: Cc1c(-c2cc(-c3cc(O)[nH]n3)c3c(OC(C)c4ccccc4)ccc(C)c3n2)oc2ccccc12] | + |
| 363 | 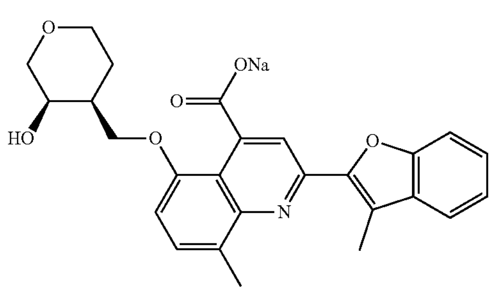 | |

TABLE 1-continued
| Compound # | Structure | Activity |
|---|---|---|
| 364 | 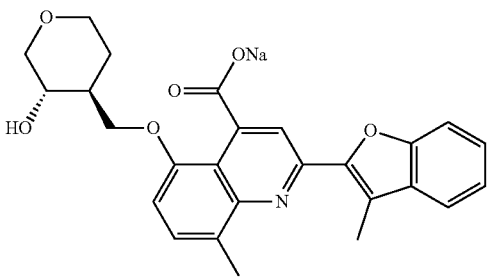 | |
| 365 | 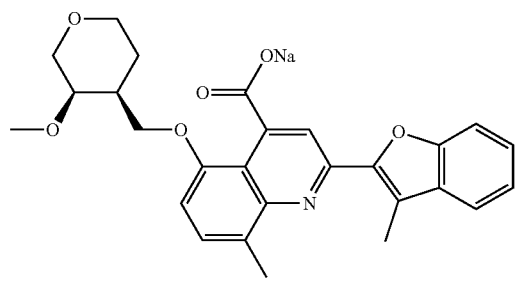 | |
| 366 | 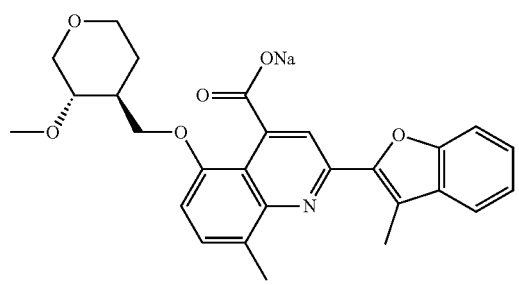 | |
| 367 | 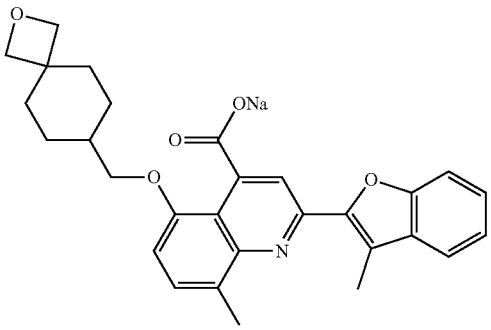 | ++ |
| 368 | 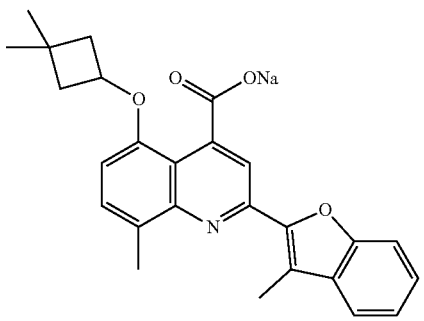 | ++ |

TABLE 1-continued
| Compound # | Structure | Activity |
|---|---|---|
| 369 | 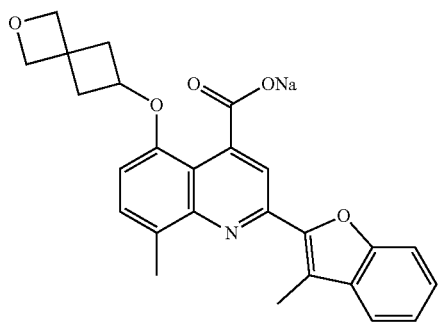 | ++ |
| 370 | 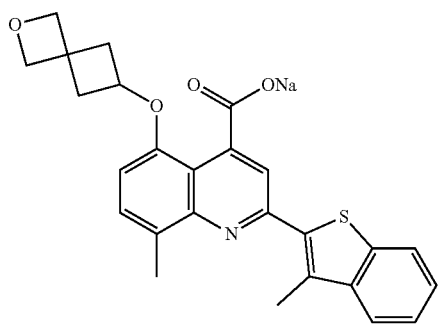 | ++ |
| 371 | 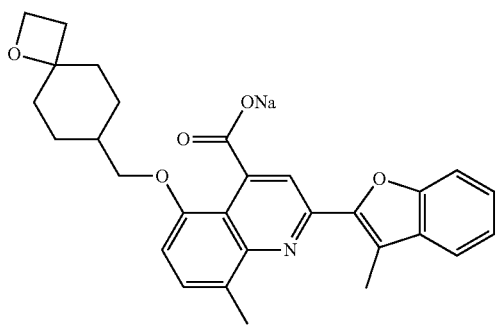 | |
| 372 | 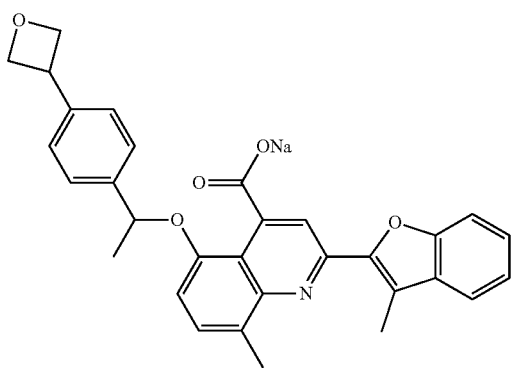 | ++ |

TABLE 1-continued

| Compound # | Structure | Activity |
|---|---|---|
| 373 | 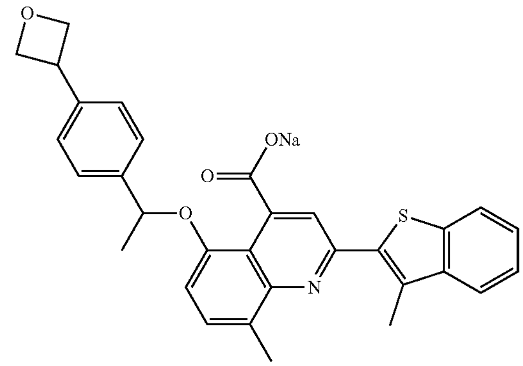 | ++ |
| 374 | 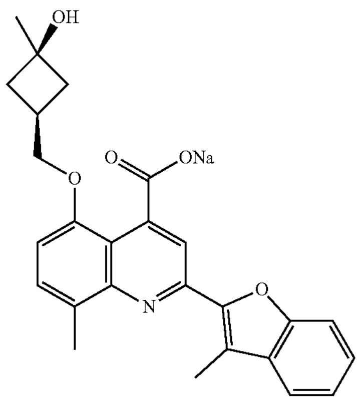 | ++ |
| 375 | 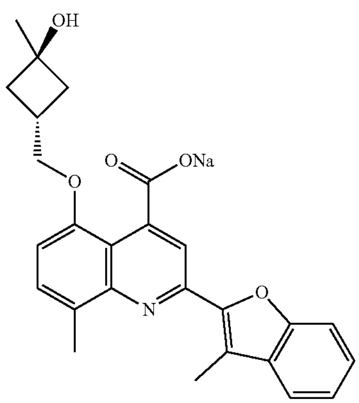 | ++ |
| 376 | 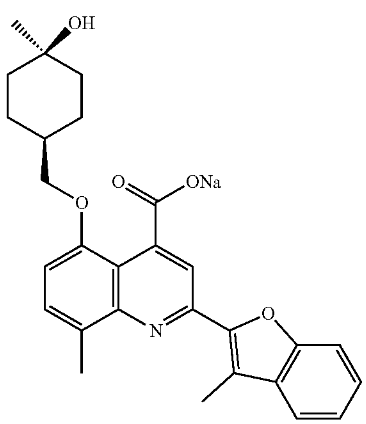 | ++ |

US 10,550,106 B2
311
312
TABLE 1-continued
| Compound # | Structure | Activity |
|---|---|---|
| 377 | 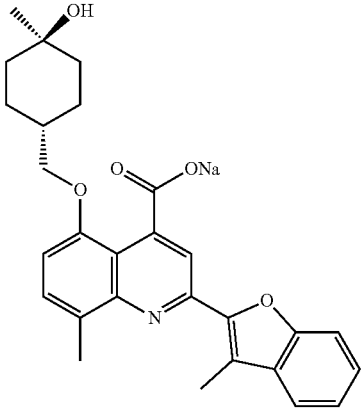 | ++ |
| 378 | 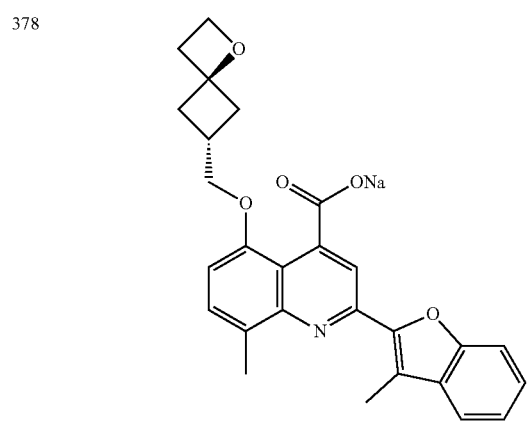 | |
| 379 | 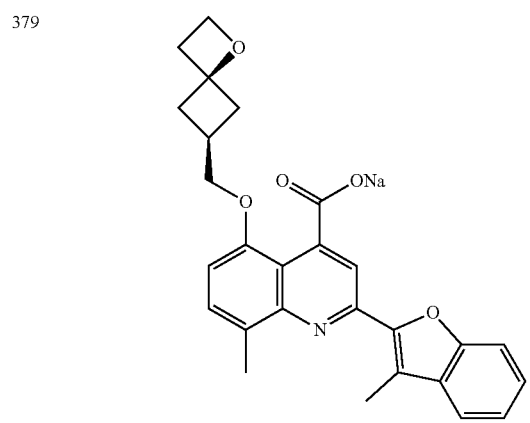 | |

TABLE 1-continued
| Compound # | Structure | Activity |
|---|---|---|
| 380 | 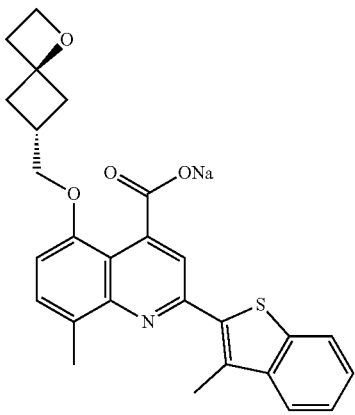 | |
| 381 | 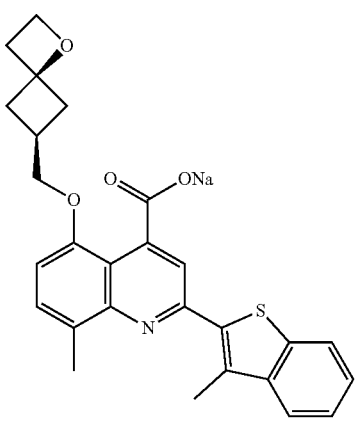 | |
| 382 | 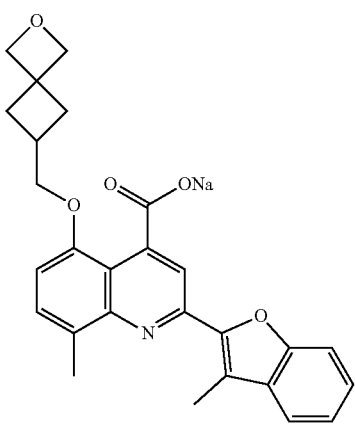 | |

TABLE 1-continued

| Compound # | Structure | Activity |
|---|---|---|
| 383 | 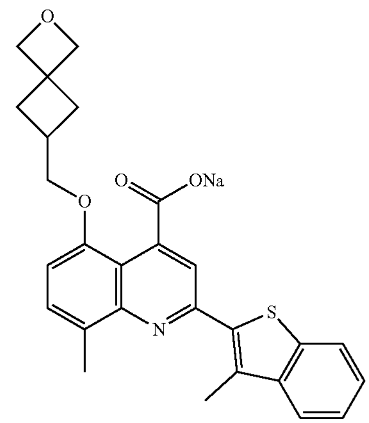 | |
| 384 | 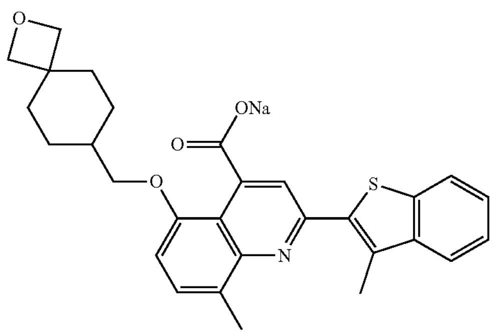 | ++ |
| 385 | 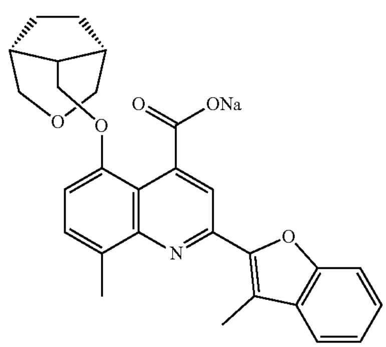 | |
| 386 | 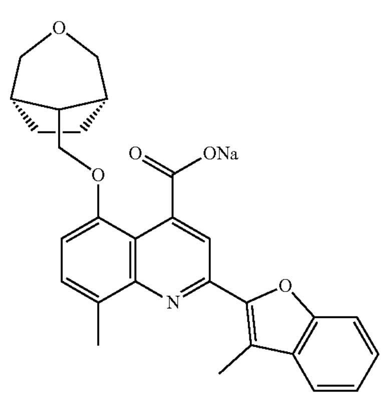 | |

TABLE 1-continued
| Compound # | Structure | Activity |
|---|---|---|
| 387 | 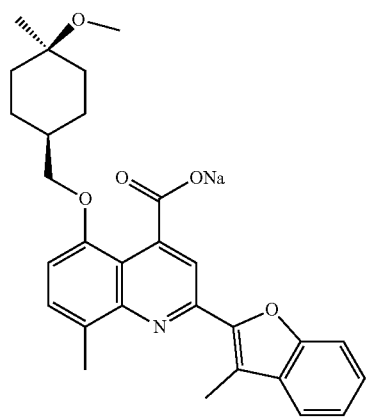 | ++ |
| 388 | 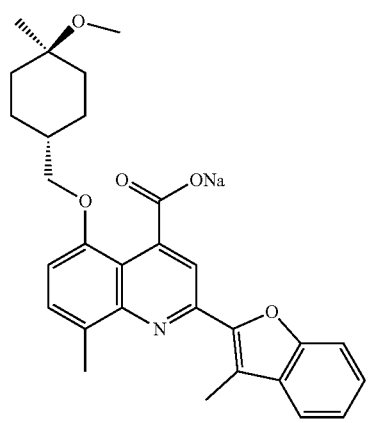 | ++ |
| 389 | 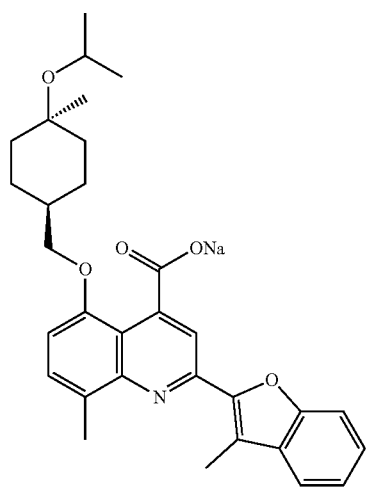 | |

TABLE 1-continued
| Compound # | Structure | Activity |
|---|---|---|
| 390 | 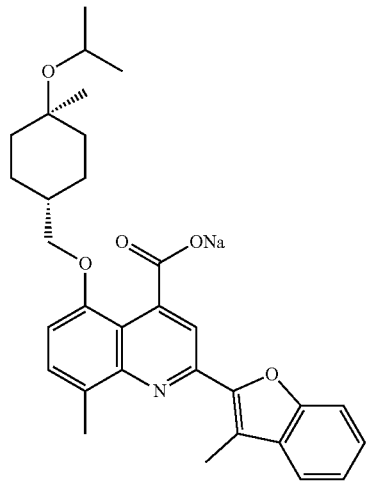 | |
| 391 | 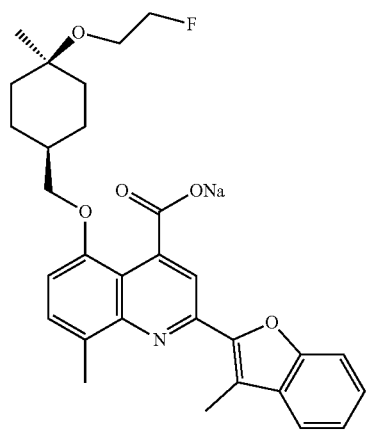 | |
| 392 | 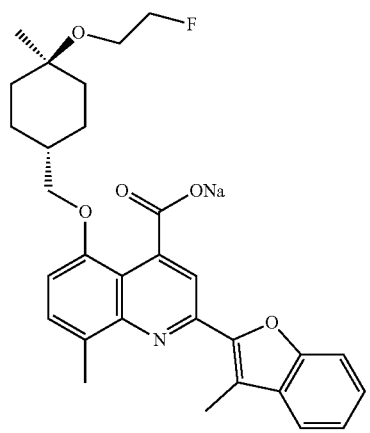 | |

US 10,550,106 B2
321                                                                                       322
TABLE 1-continued
| Compound # | Structure | Activity |
|---|---|---|
| 393 | 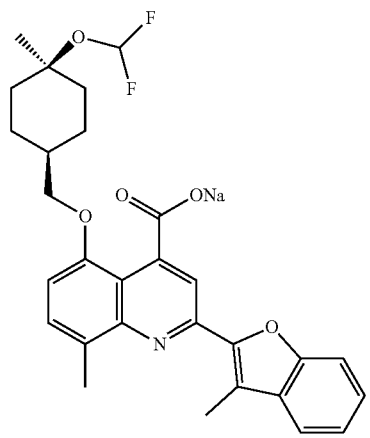 | |
| 394 | 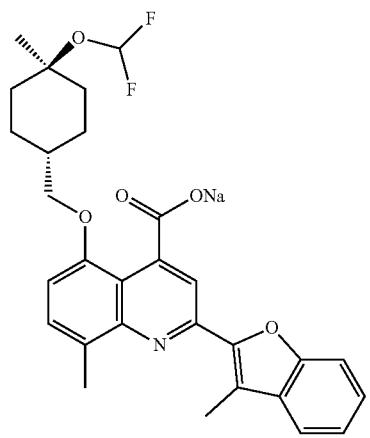 | |
| 395 | 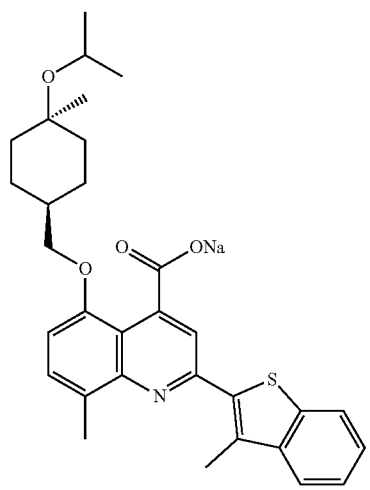 | |

TABLE 1-continued

| Compound # | Structure | Activity |
|---|---|---|
| 396 | 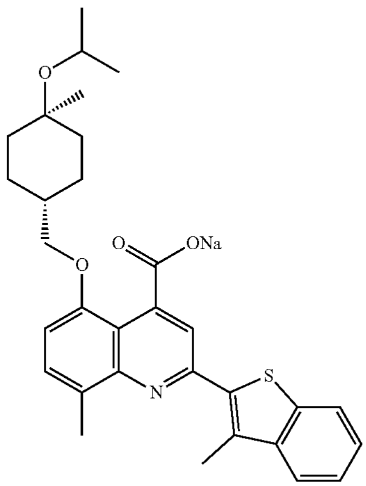 | |
| 397 | 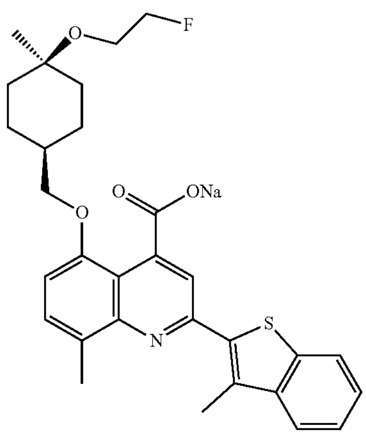 | |
| 398 | 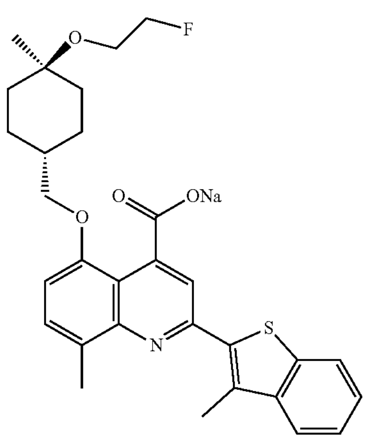 | |

TABLE 1-continued

| Compound # | Structure | Activity |
|---|---|---|
| 399 | 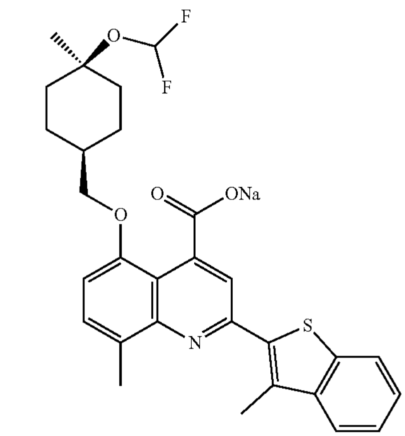 | |
| 400 | 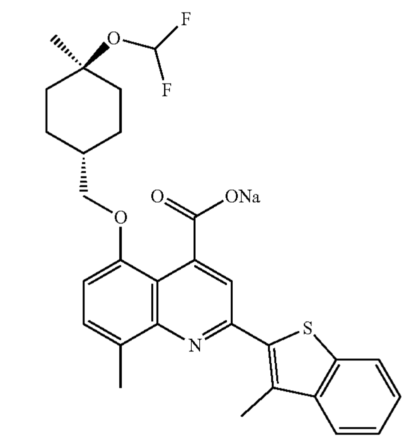 | |
| 401 | 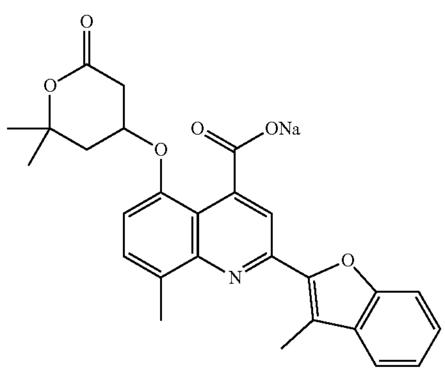 | |
| 402 | 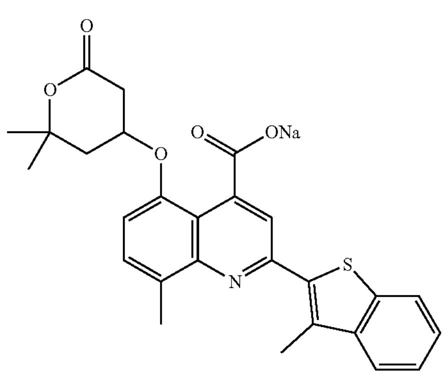 | |

TABLE 1-continued

| Compound # | Structure | Activity |
|---|---|---|
| 403 | 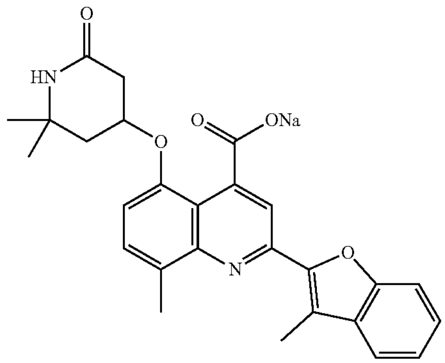 | |
| 404 | 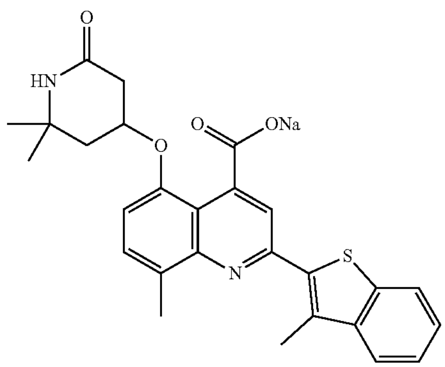 | |
| 405 | 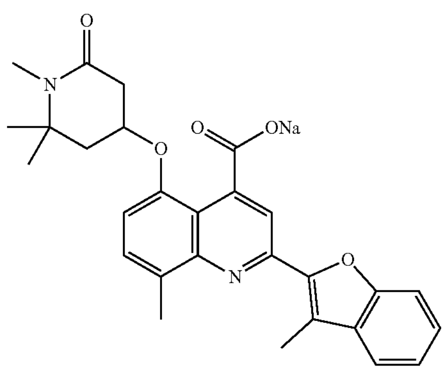 | |
| 406 | 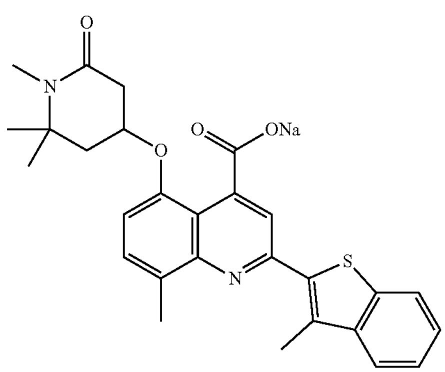 | |

TABLE 1-continued

| Compound # | Structure | Activity |
|---|---|---|
| 407 | 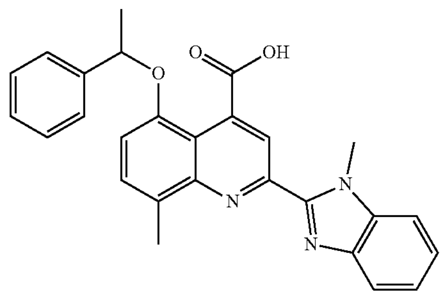 [SMILES: Cc1ccc(OC(C)c2ccccc2)c2c(C(=O)O)cc(-c3nc4ccccc4n3C)nc12] | + |

While this disclosure has been particularly shown and described with references to embodiments thereof, it will be understood by those skilled in the art that various changes in form and details may be made therein without departing from the scope of the disclosure encompassed by the appended claims.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:

1. A compound represented by:

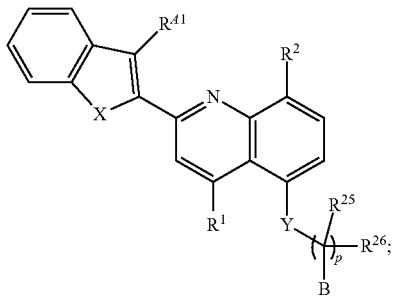

or a pharmaceutically acceptable salt or stereoisomer thereof, wherein
X is O or S;
$R^{41}$ is selected from the group consisting of hydrogen and $C_{1-6}$ alkyl;
$R^1$ is selected from the group consisting of —C(O)OH and a 5-6 membered monocyclic heteroaryl having one, two, three, or four heteroatoms each selected from the group consisting of O, N, and S; wherein said heteroaryl may optionally be substituted by one or two substituents each independently selected from the group consisting of halogen, hydroxyl, and $C_{1-4}$ alkyl;
$R^2$ is selected from the group consisting of hydrogen, halogen, cyano, $C_{1-6}$ alkyl, $C_{1-6}$alkoxy, and $C_{3-6}$ cycloalkyl;
Y is O or $S(O)_w$ (where w is 0, 1 or 2);
$R^{25}$ and $R^{26}$ are each independently selected from the group consisting of hydrogen and $C_{1-6}$alkyl;
p is 0 or 1; and
B is a 4-10 membered monocyclic, bridged bicyclic, or spirocyclic heterocyclic ring having one or two heteroatoms each independently selected from the group consisting of O, N, and S; wherein if said heterocyclic ring contains an NH moiety, that nitrogen may optionally be substituted by a substituent selected from the group consisting of $C_{1-6}$alkyl, —C(O)—$C_{1-6}$alkyl, —C(O)—O—$C_{1-6}$alkyl, and —S(O)$_w$$C_{1-3}$ alkyl (where w is 0, 1, or 2); and wherein said heterocyclic ring may optionally be substituted by one, two, three, or four substituents each independently selected from hydroxyl, $C_{1-6}$alkyl, $C_{1-6}$alkoxy, and oxo.

2. The compound of claim 1, wherein X is O.
3. The compound of claim 1, wherein $R^{41}$ is methyl.
4. The compound of claim 1, wherein $R^1$ is —C(O)OH.
5. The compound of claim 1, wherein p is 1.
6. The compound of claim 1, represented by

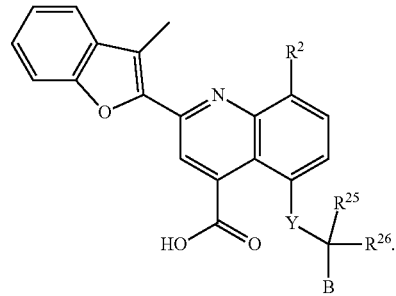

7. The compound of claim 1, wherein Y is O.
8. The compound of claim 1, wherein R² is C$_{1-6}$alkyl.
9. A compound selected from the group consisting of:
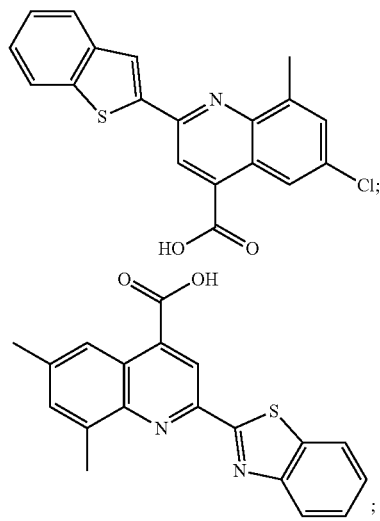
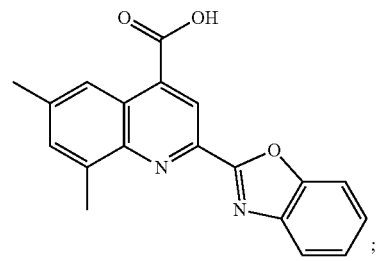
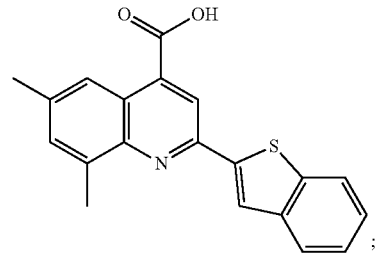
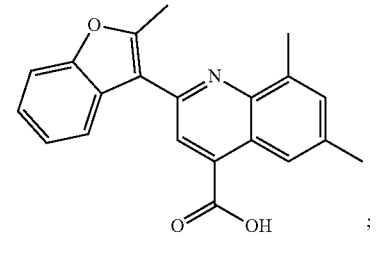
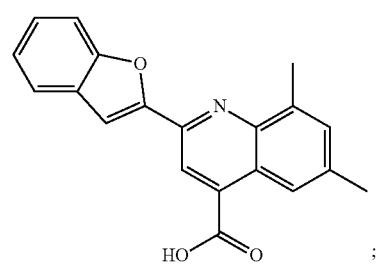
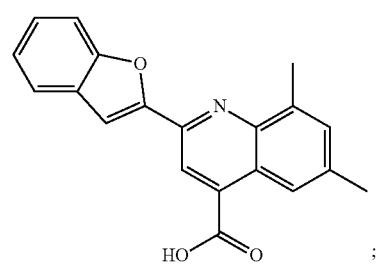
-continued
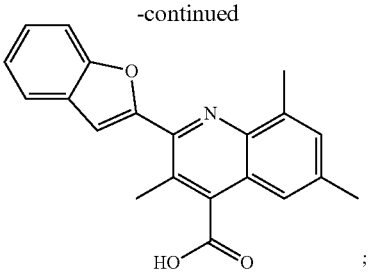
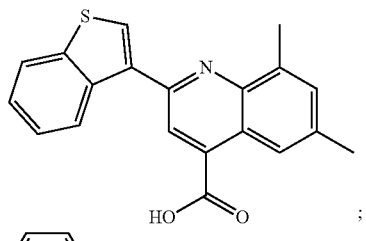
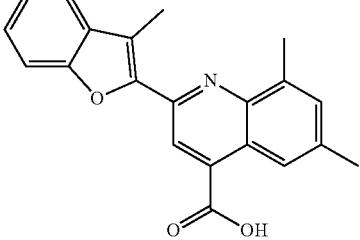
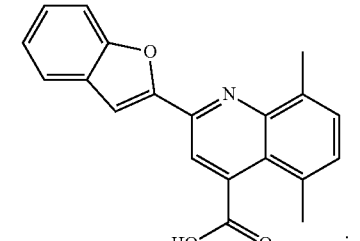
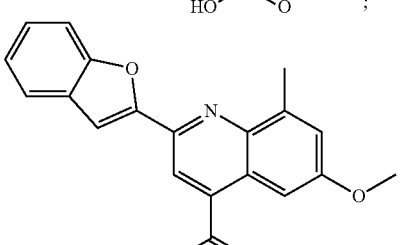
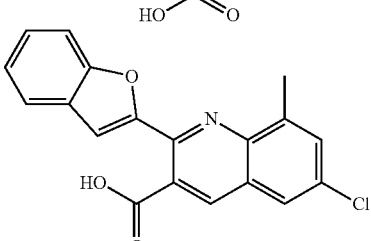
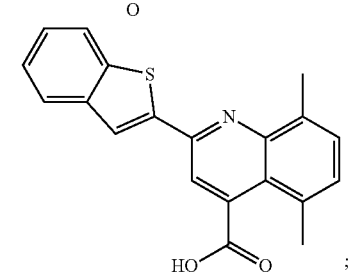

333
-continued
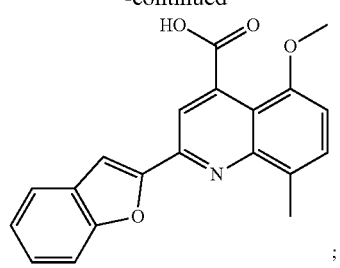
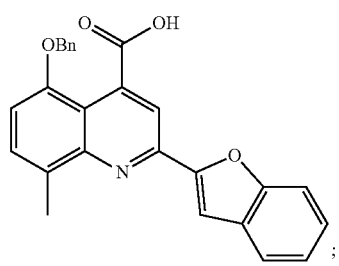
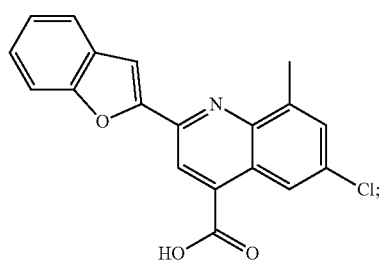
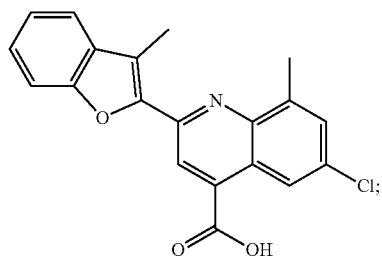
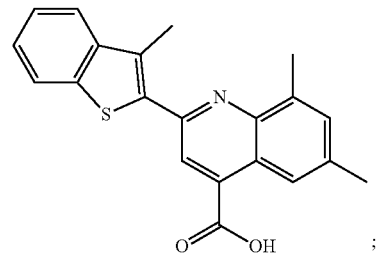
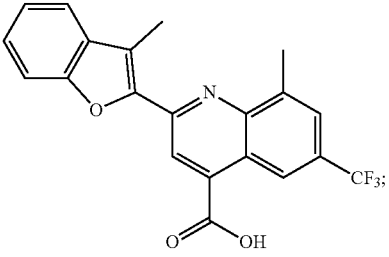
334
-continued
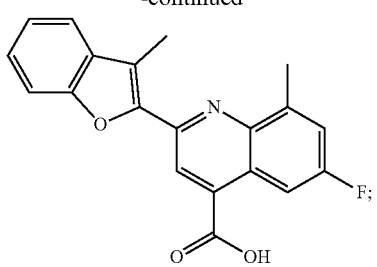
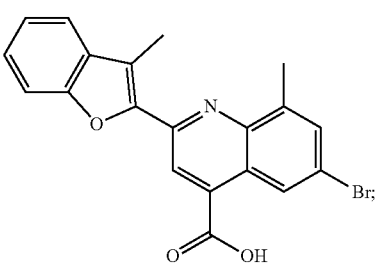
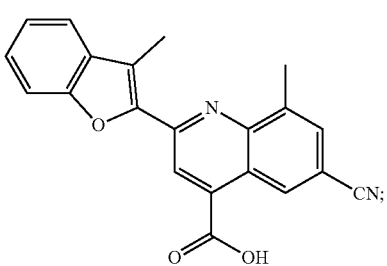
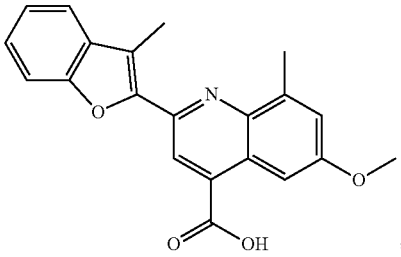
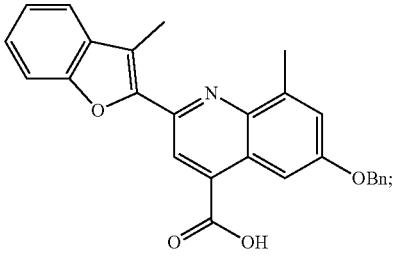
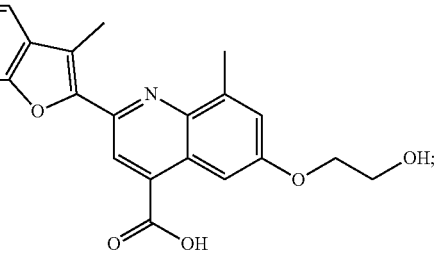

335
-continued
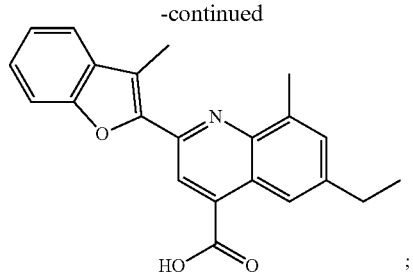
336
-continued
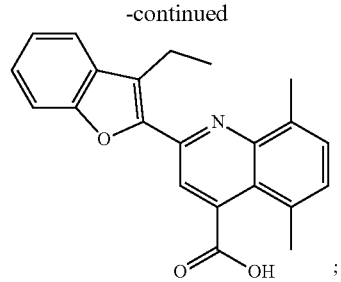
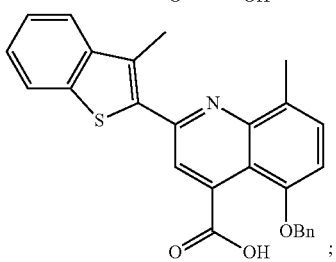
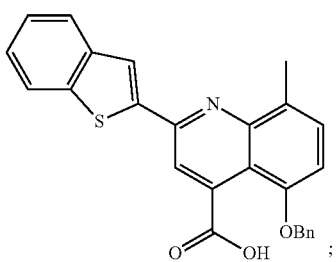
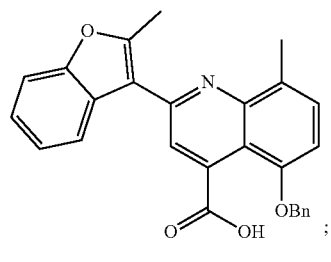
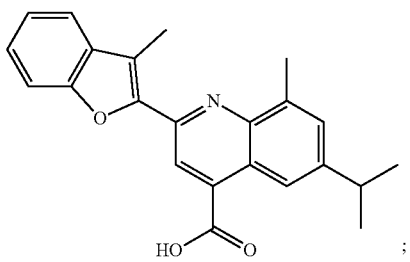
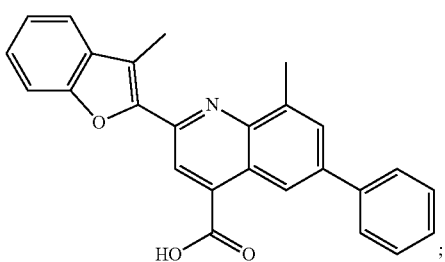

337
-continued
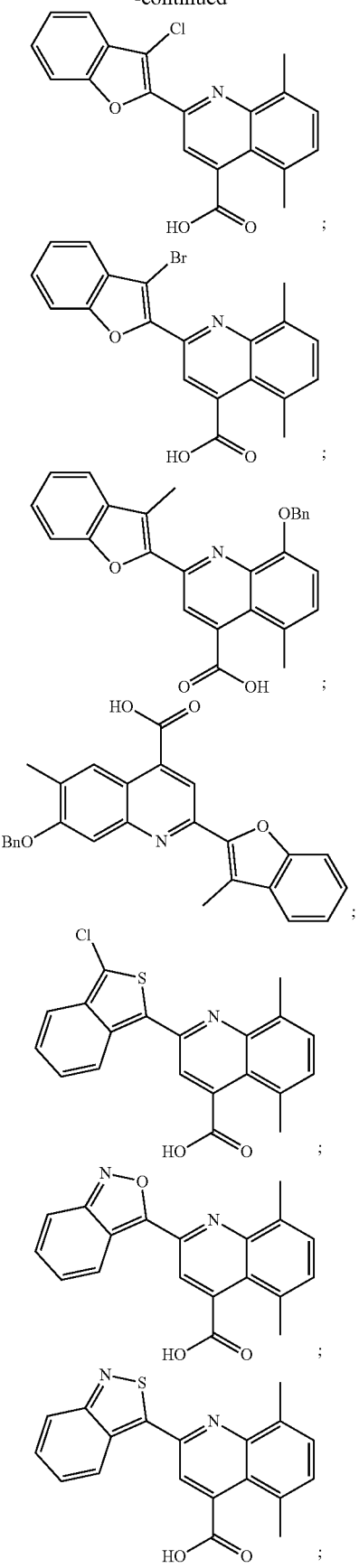
338
-continued
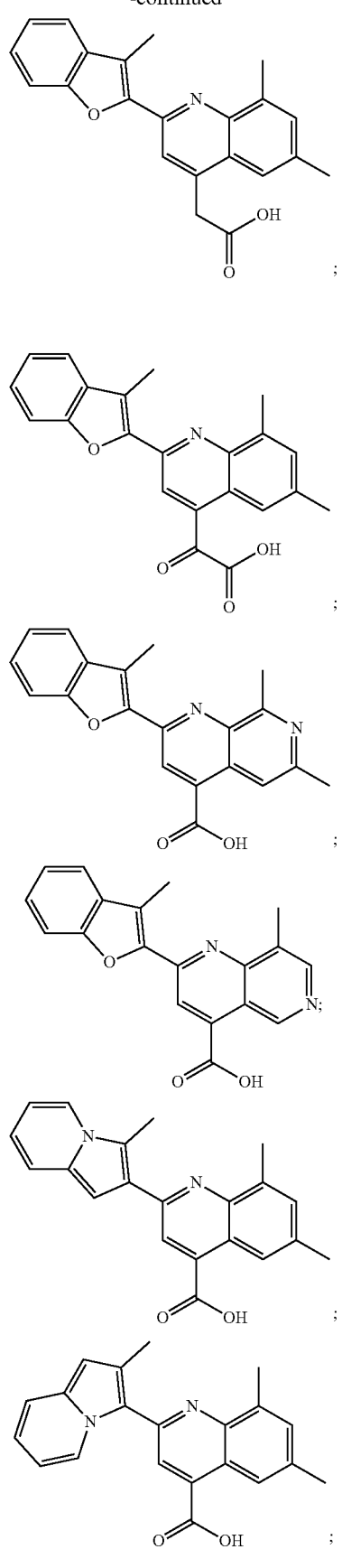

339
-continued
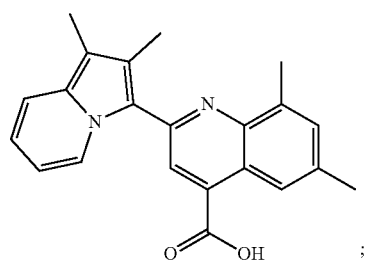
;
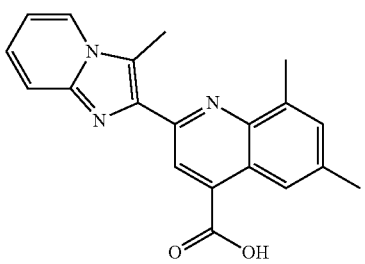
;
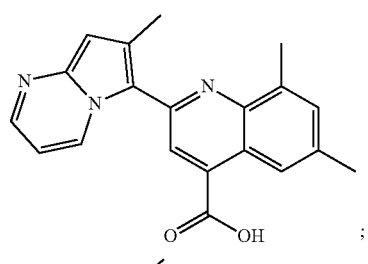
;
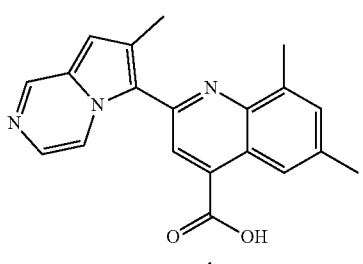
;
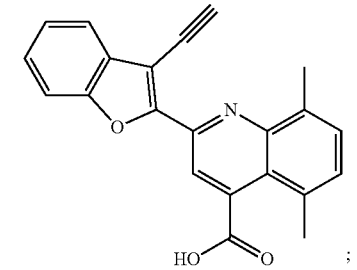
;
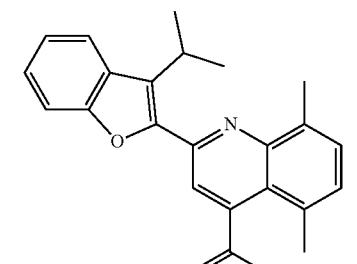
;
340
-continued
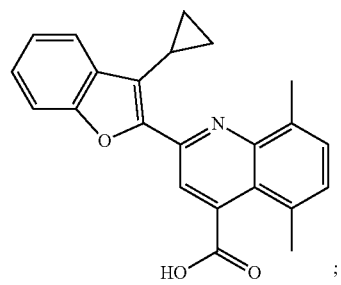
;
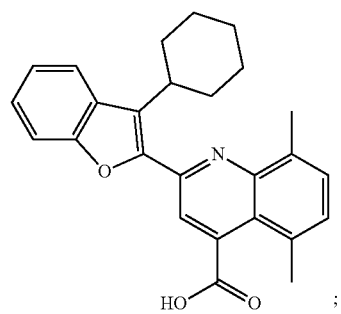
;
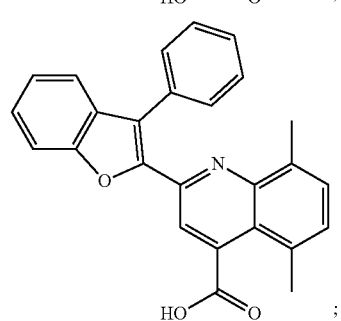
;
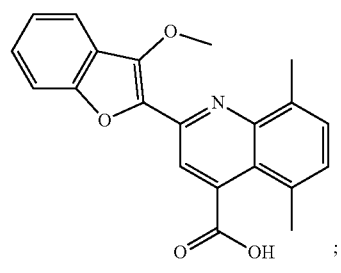
;
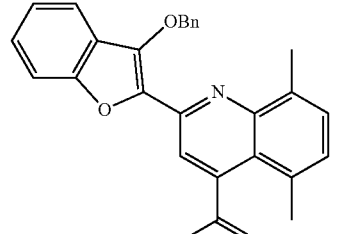
;
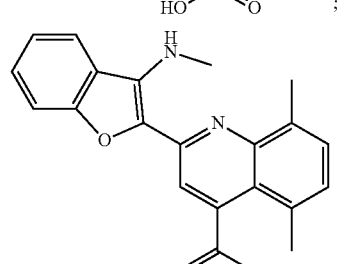
;

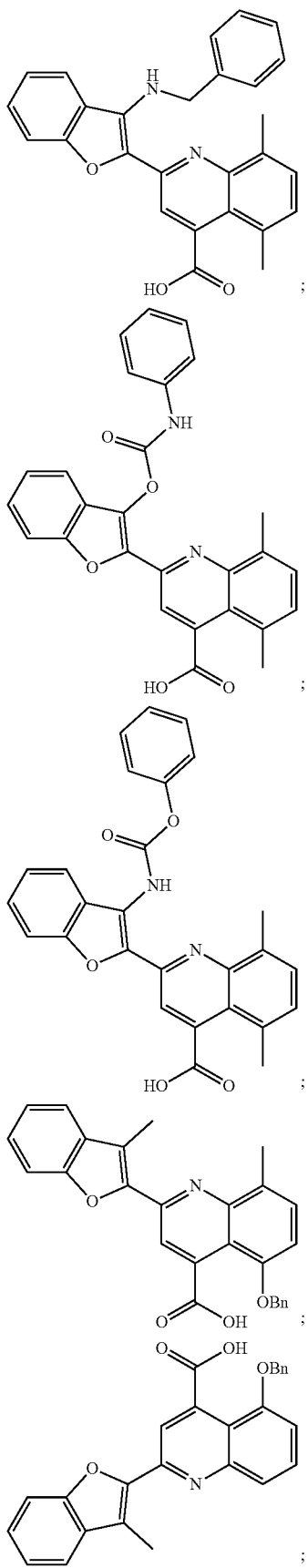
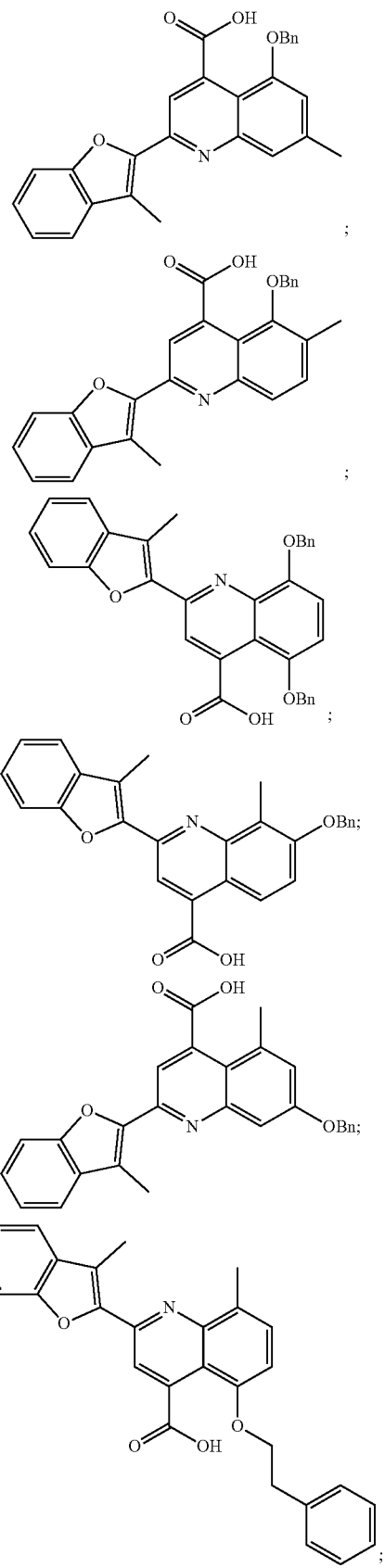

343
-continued
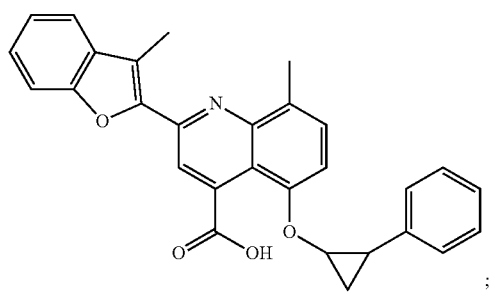
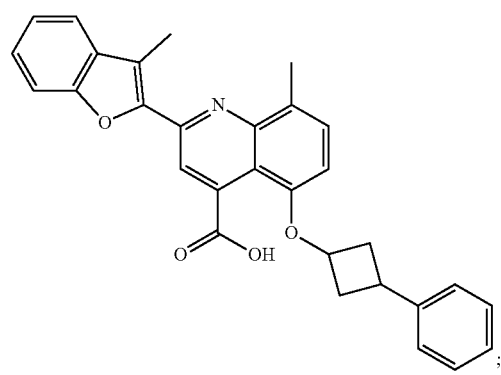
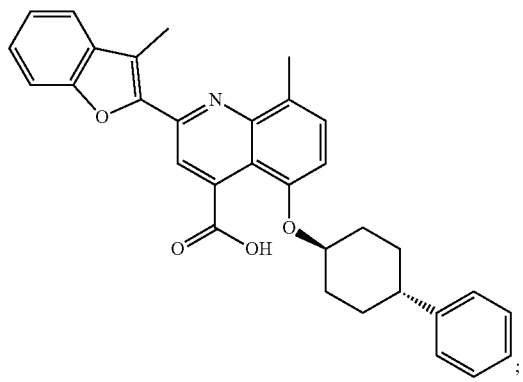
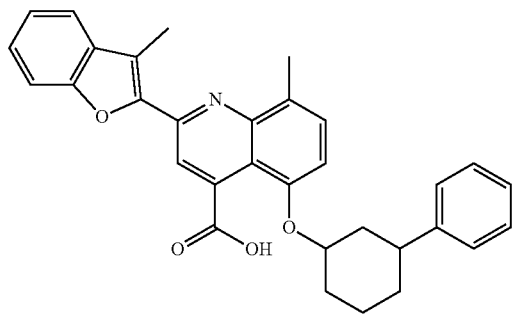
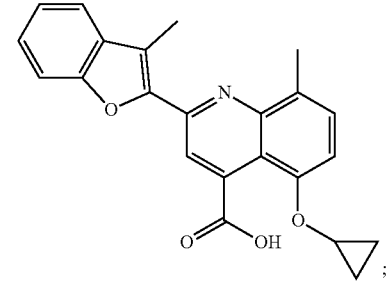
344
-continued
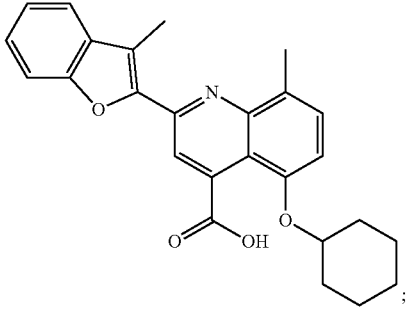
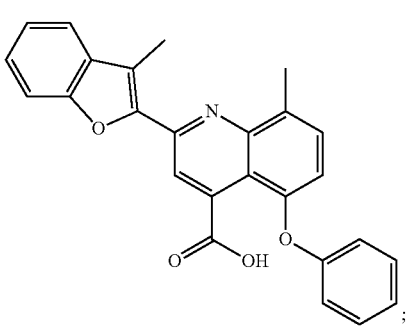
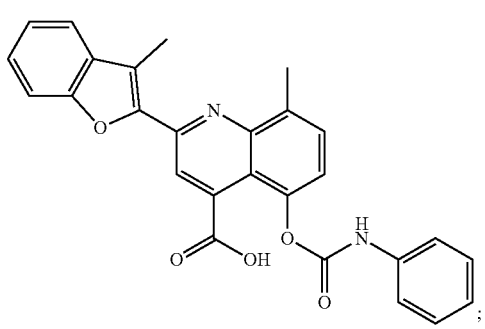
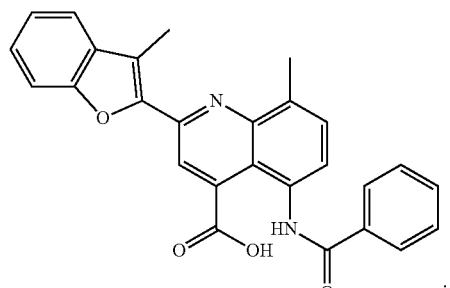
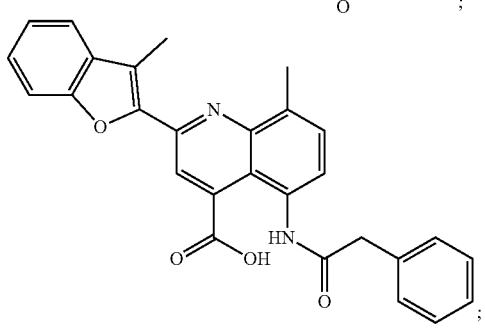

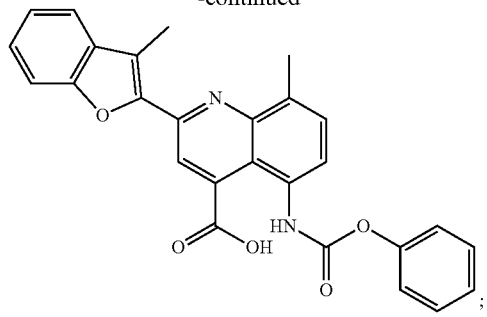
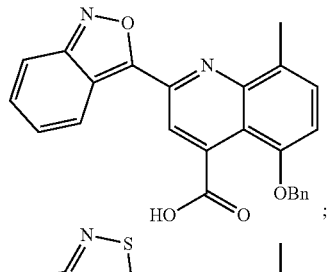
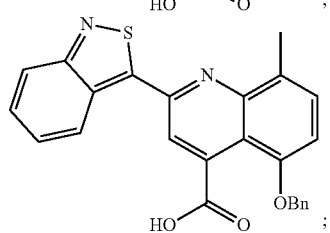
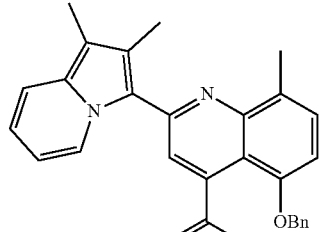
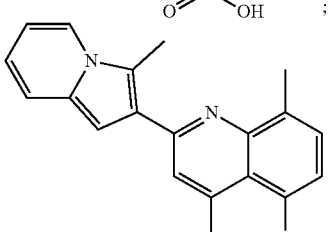
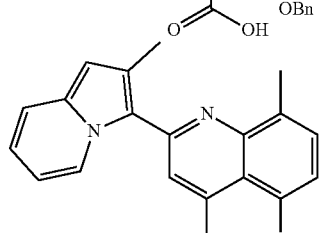
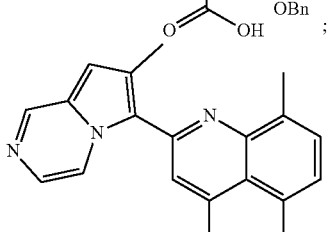
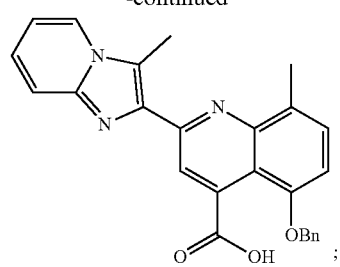
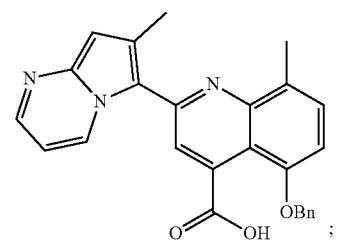
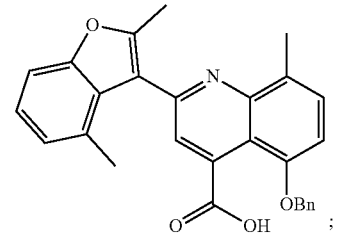
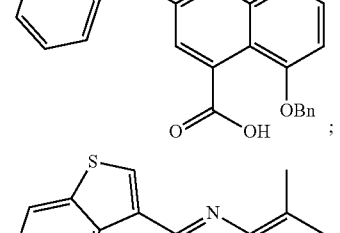
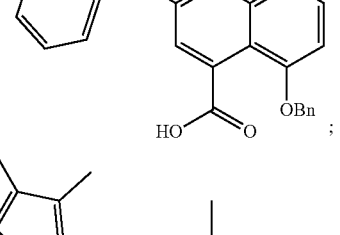
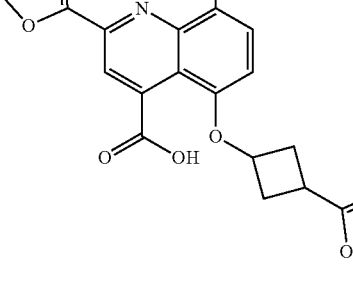

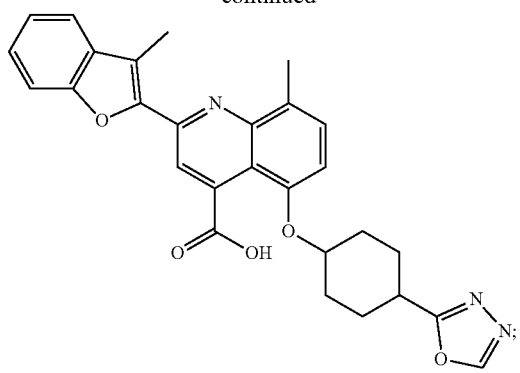
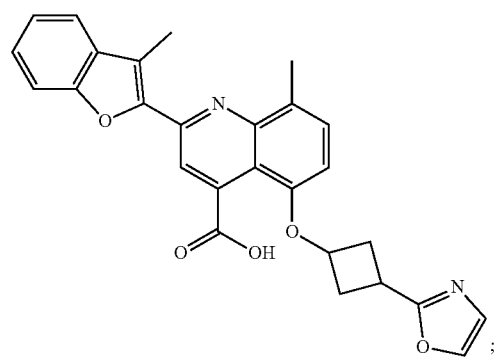
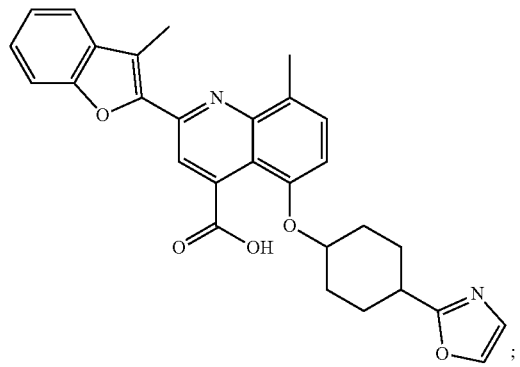
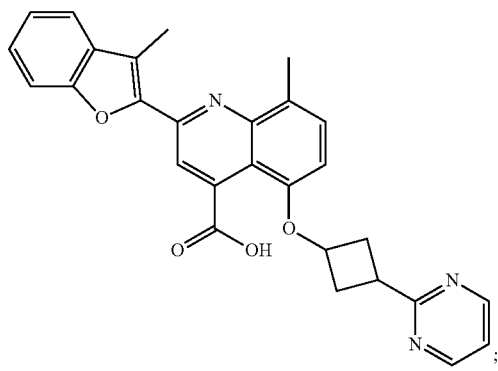
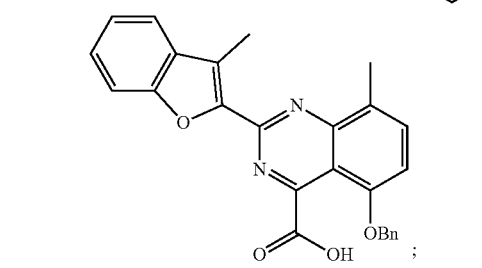
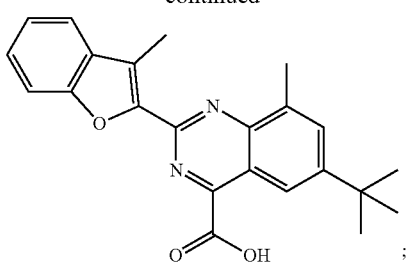
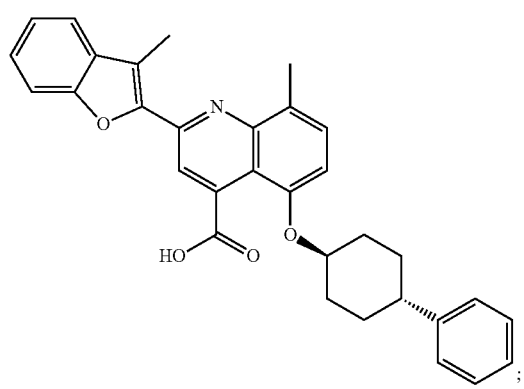
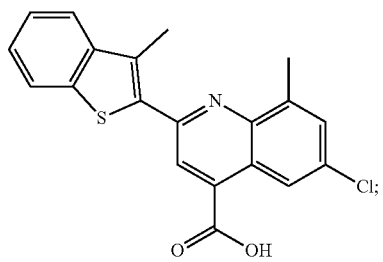
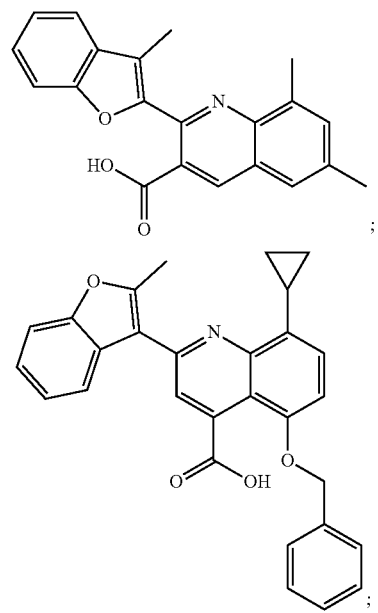

349
-continued
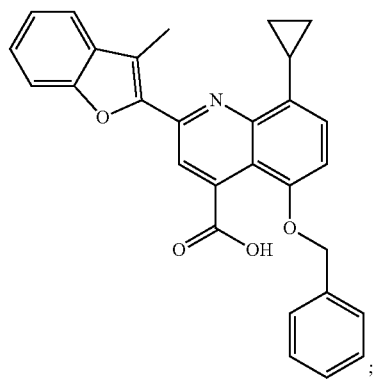
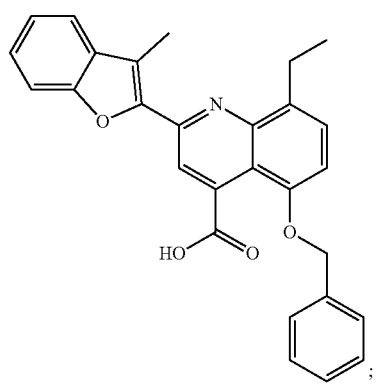
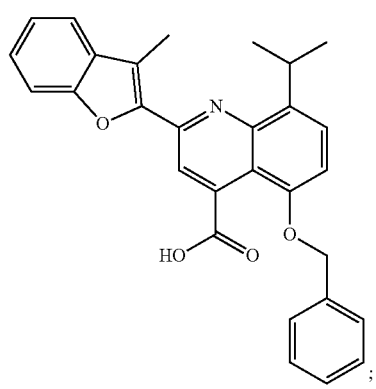
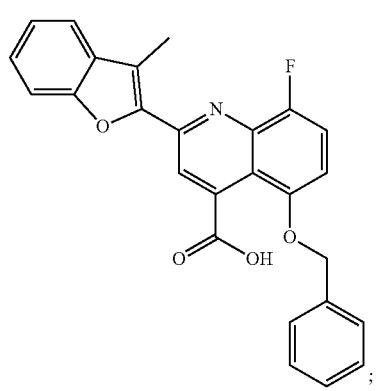
350
-continued
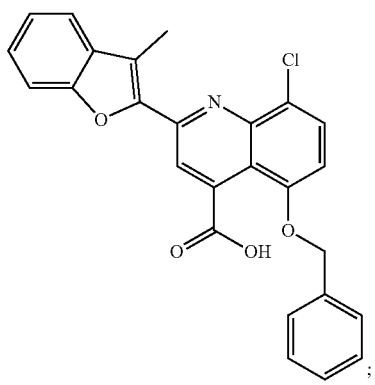
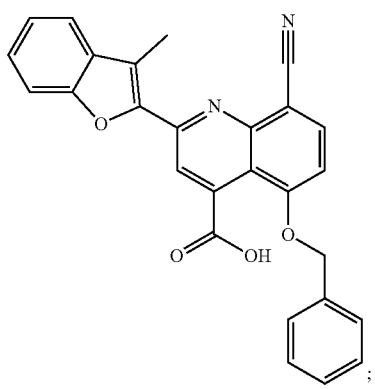
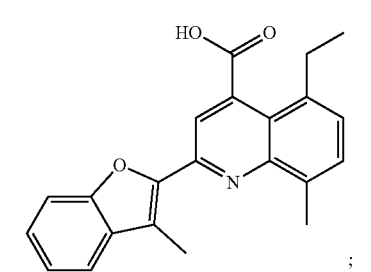
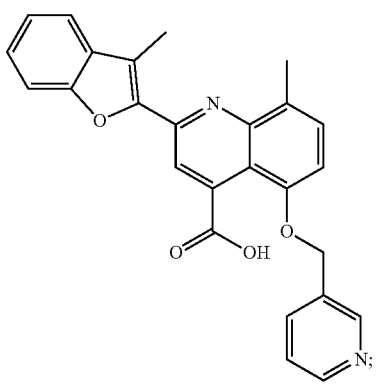

351
-continued
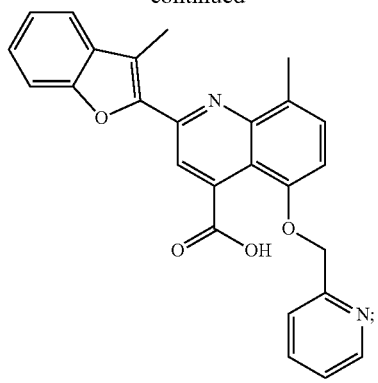
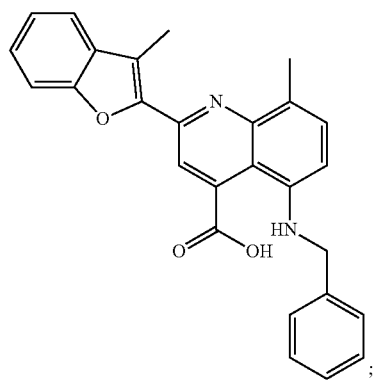
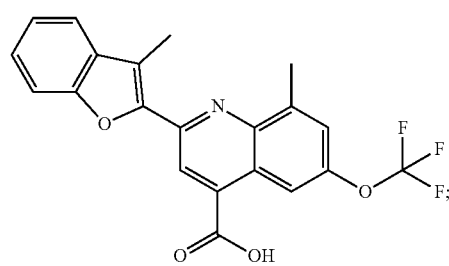
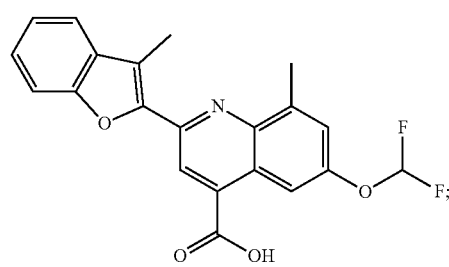
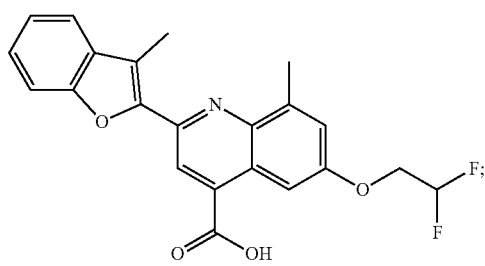
352
-continued
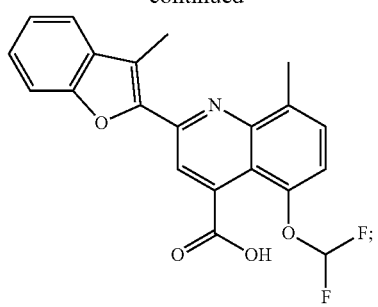
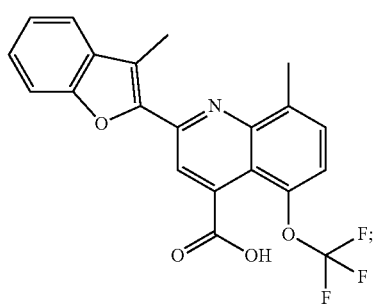
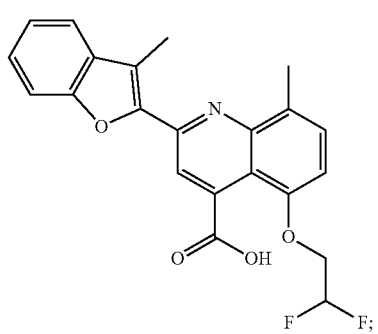
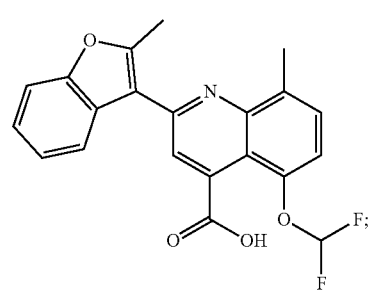
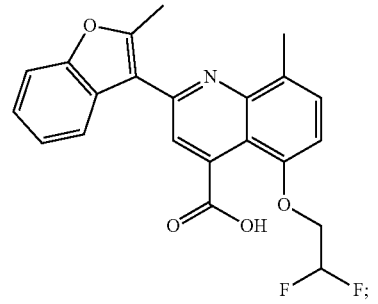

353
-continued

354
-continued

355
-continued
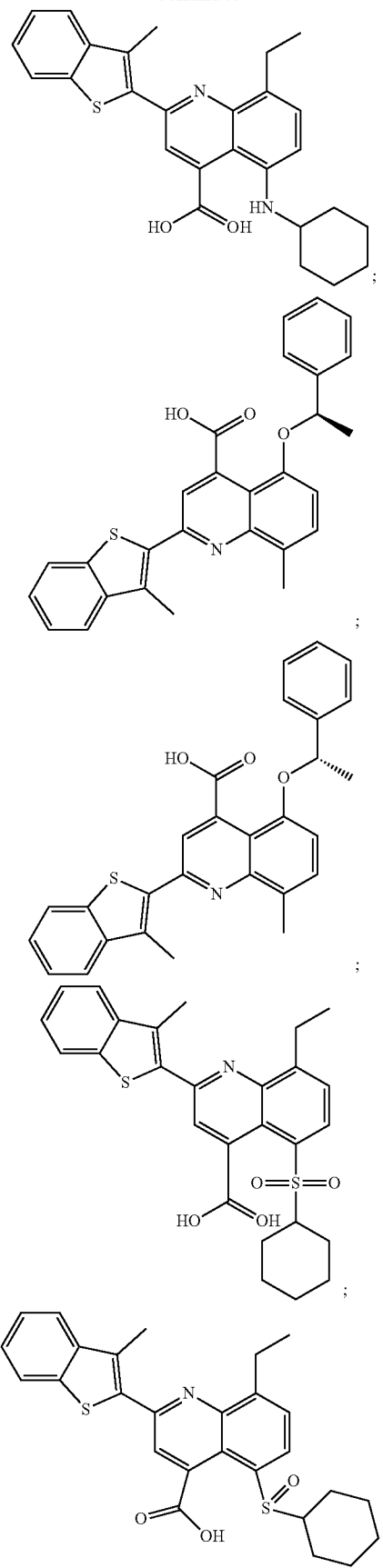
356
-continued
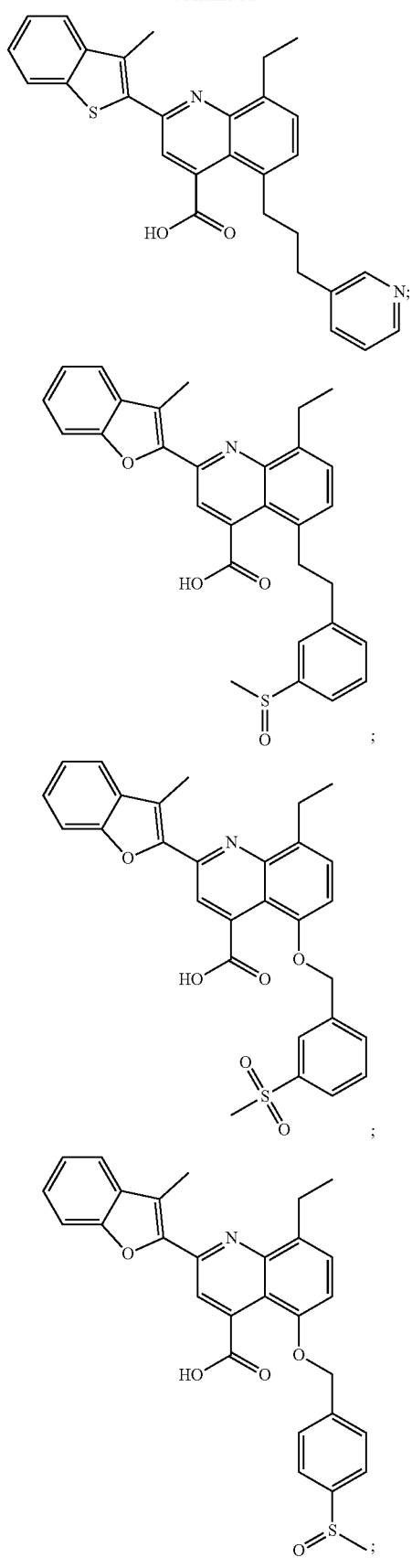

357
-continued
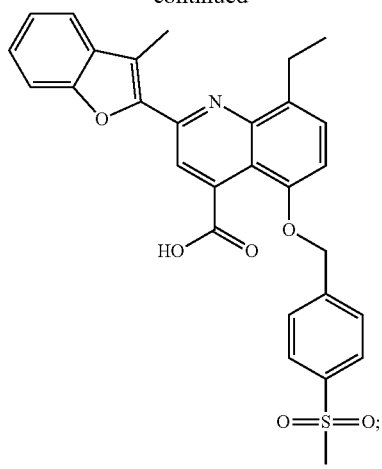
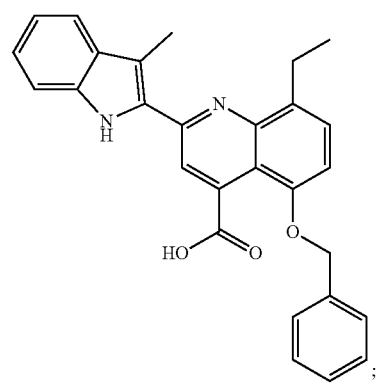
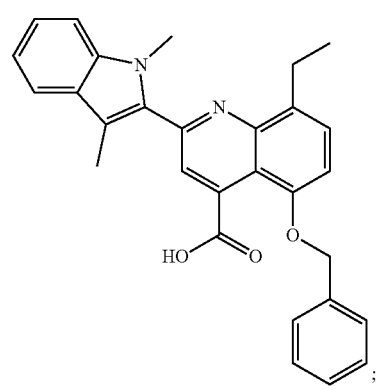
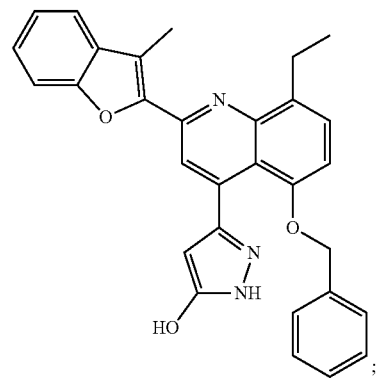
358
-continued
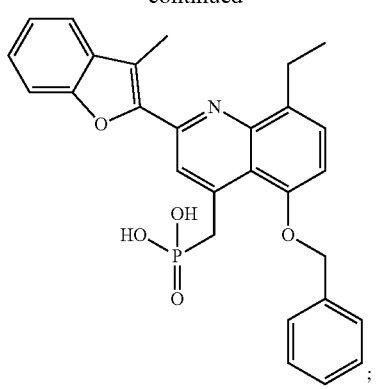
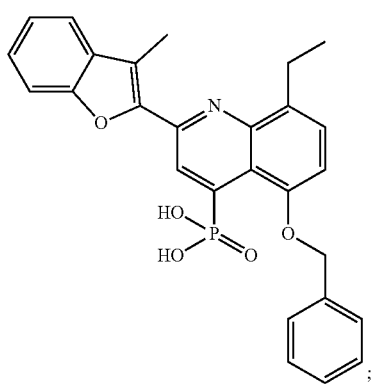
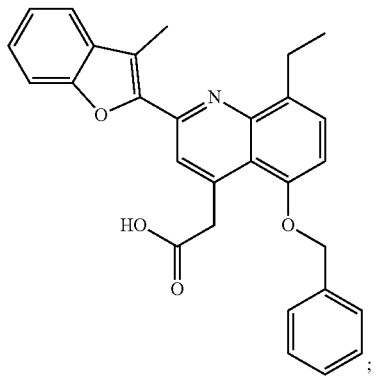

359
-continued

360
-continued

361
-continued
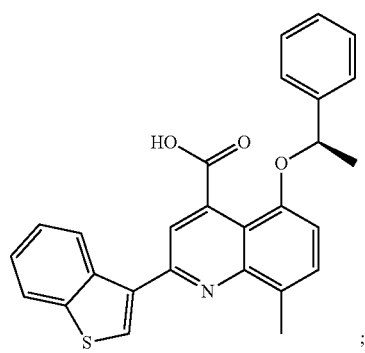
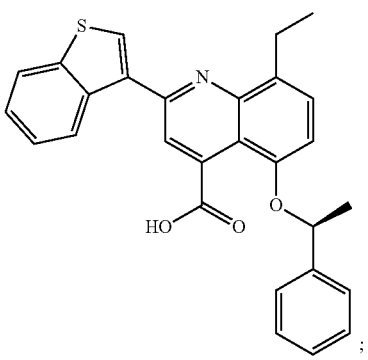
362
-continued
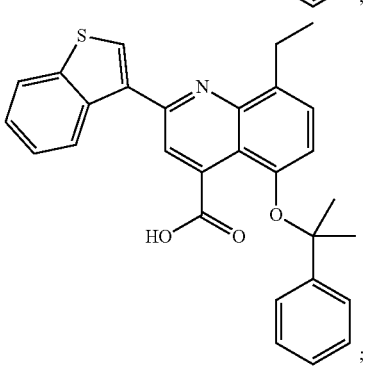
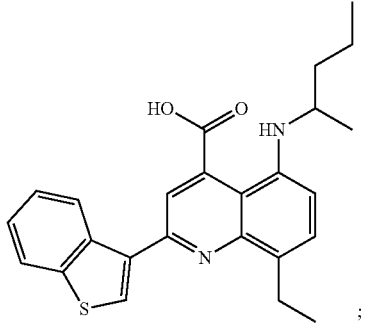
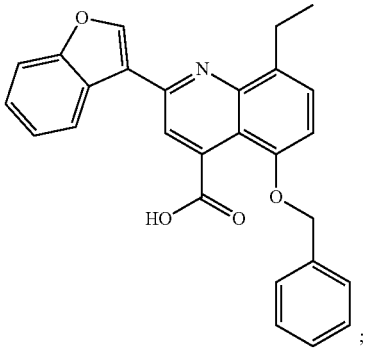
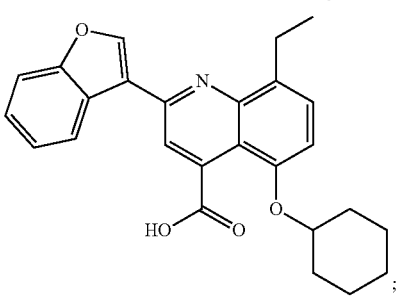

363
-continued
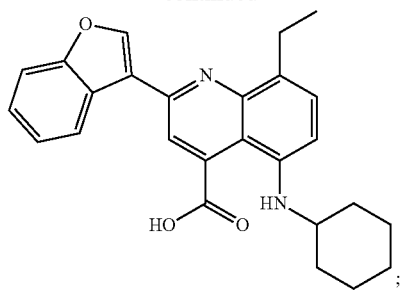
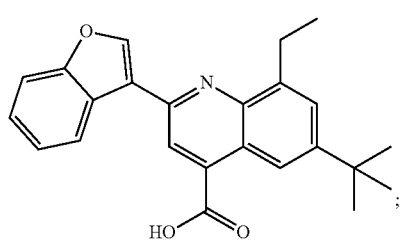
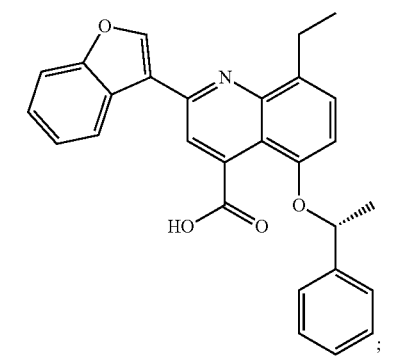
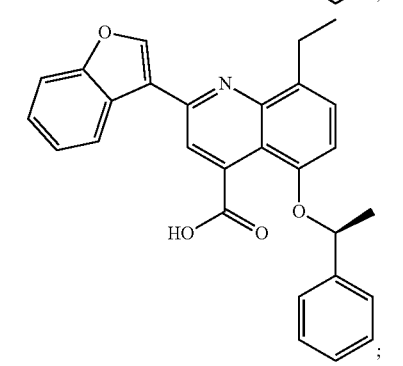
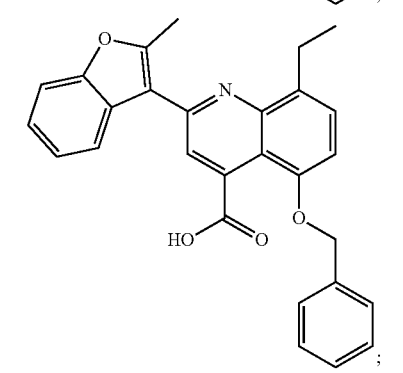
364
-continued
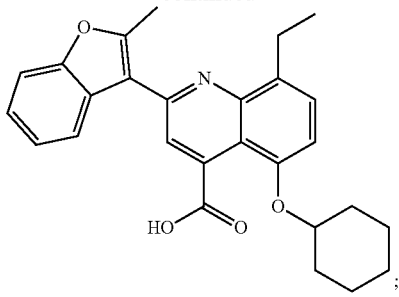
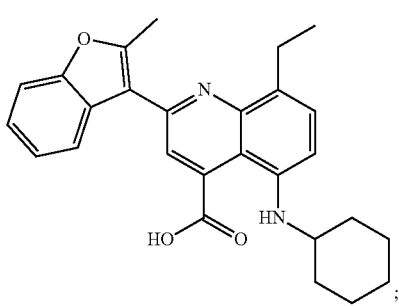
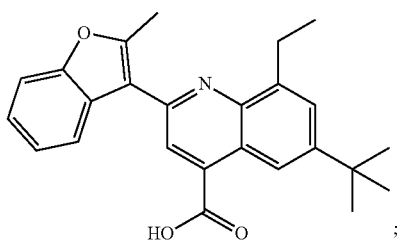
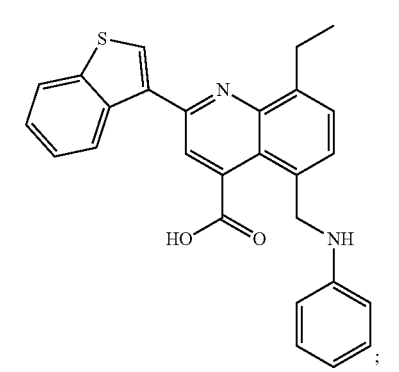
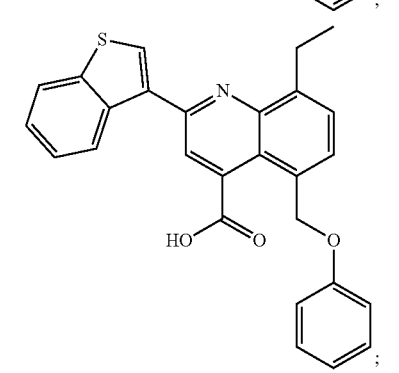

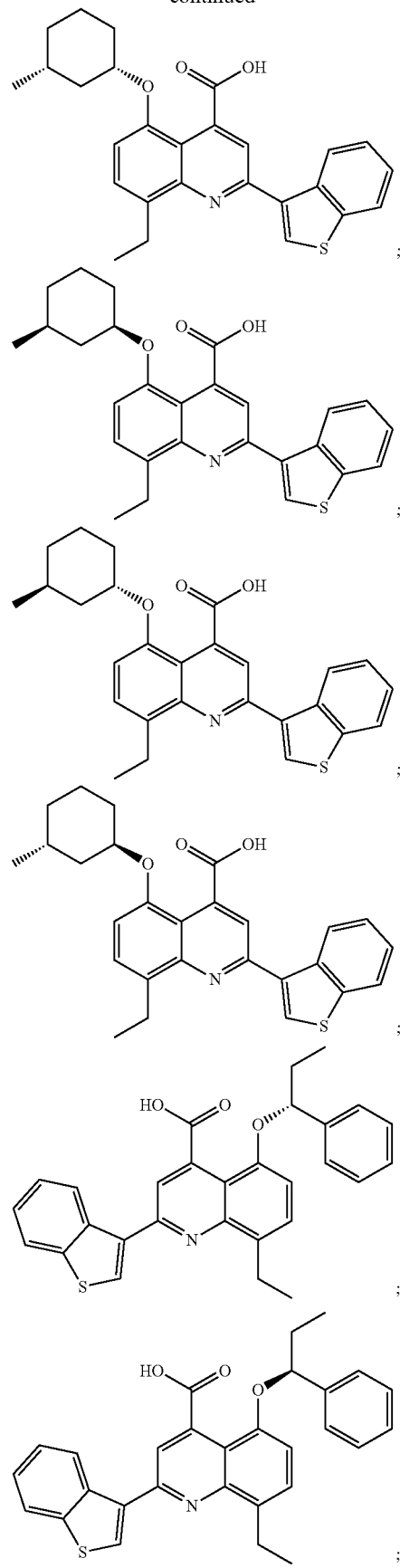
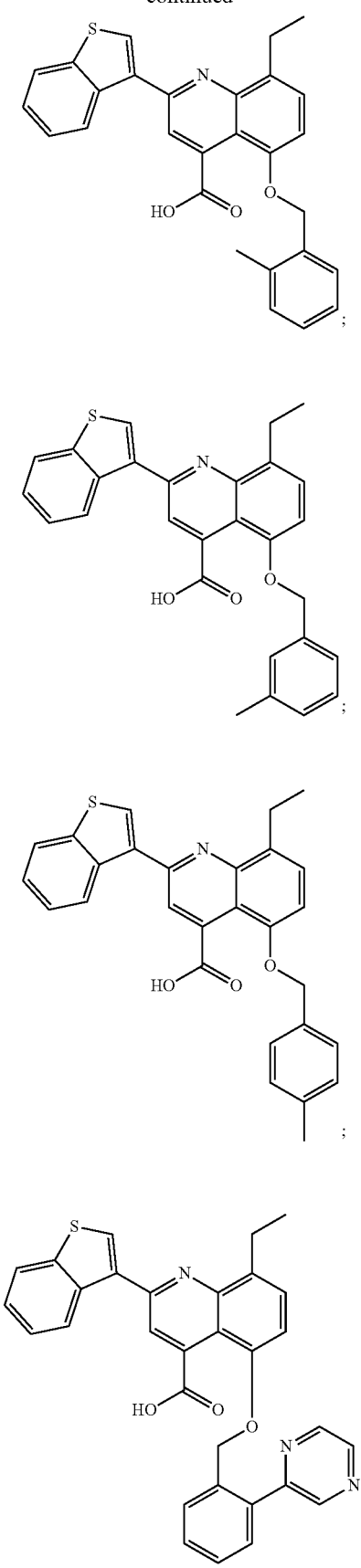

367
-continued
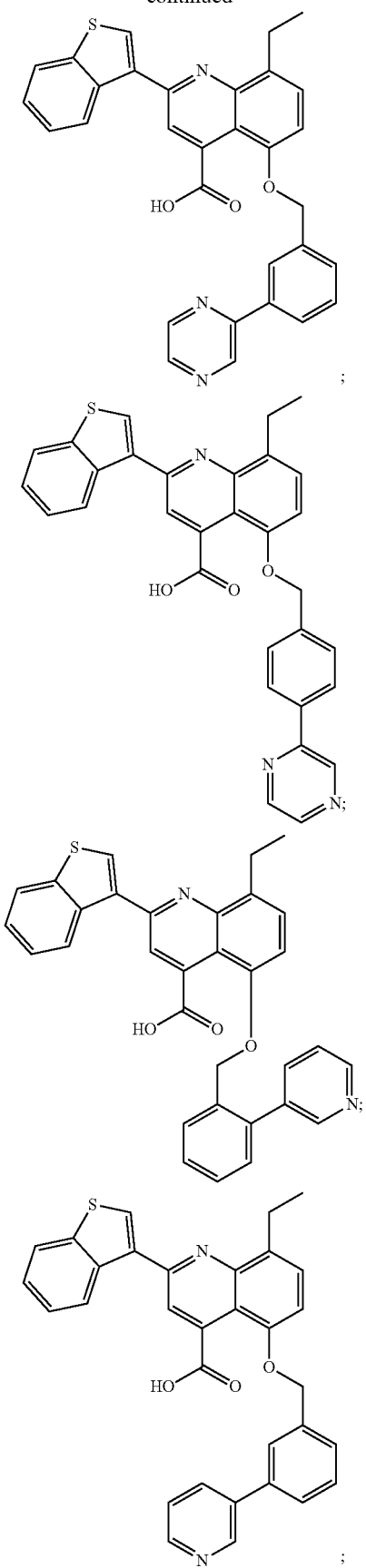
368
-continued
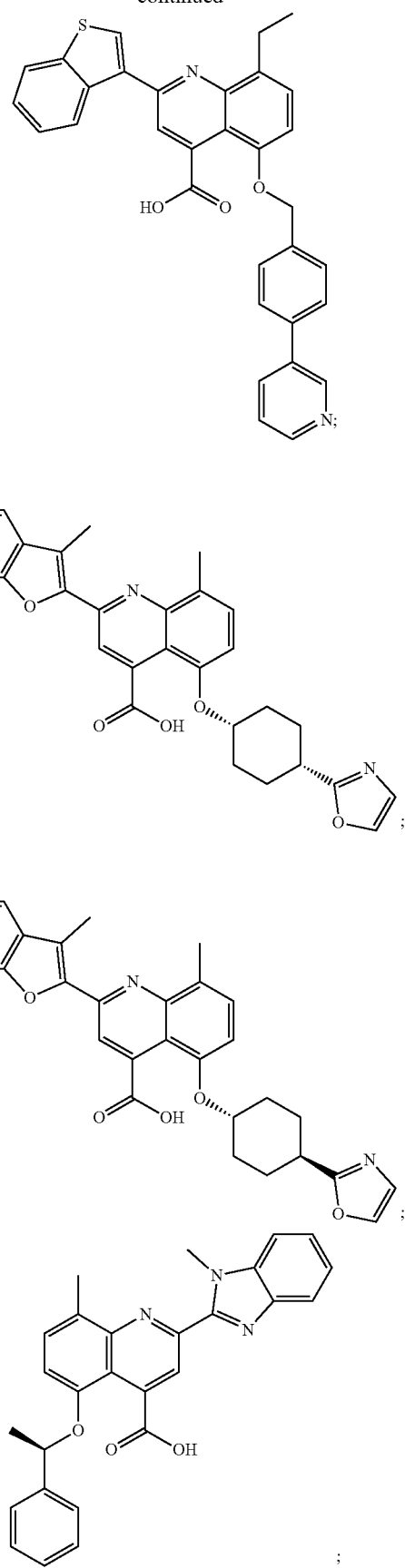

369
-continued
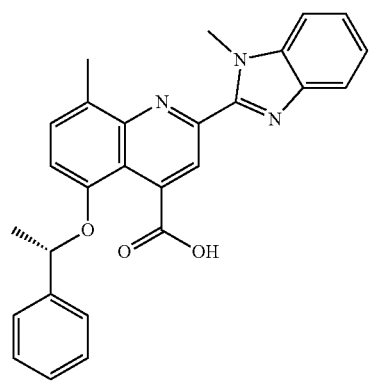
;
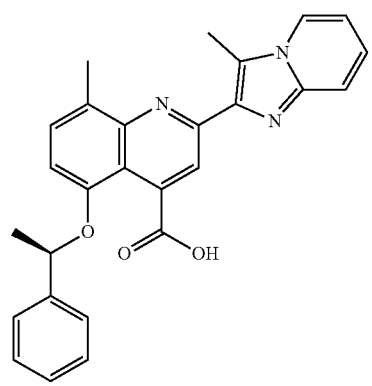
;
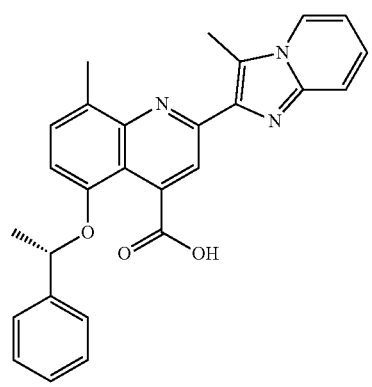
;
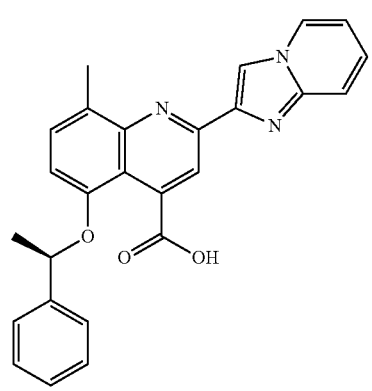
;
370
-continued
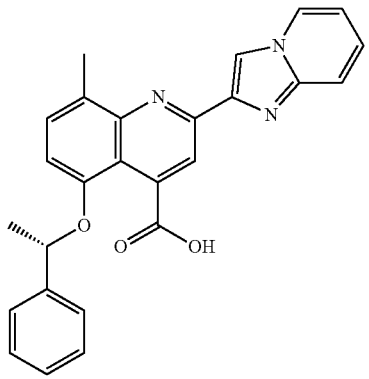
;
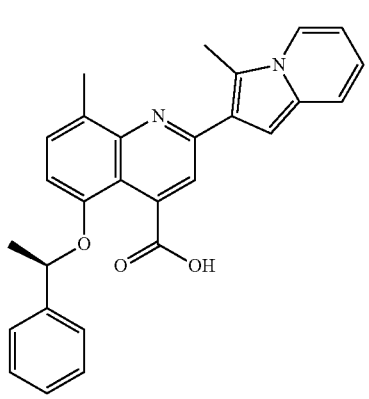
;
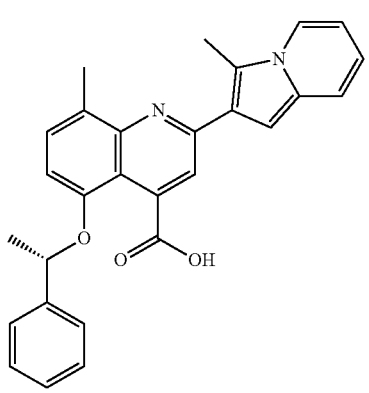
;
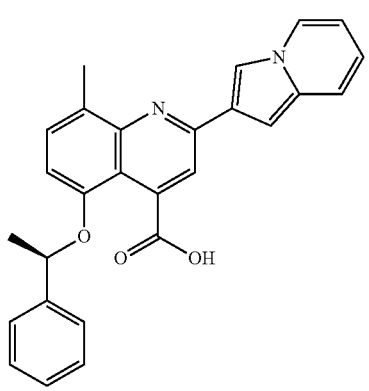
;

371
-continued
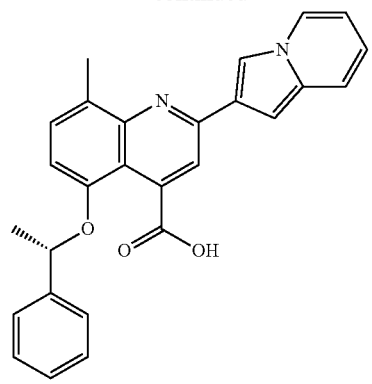
;
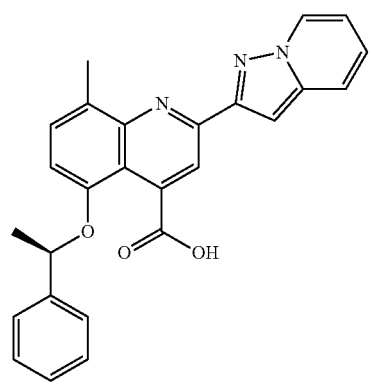
;
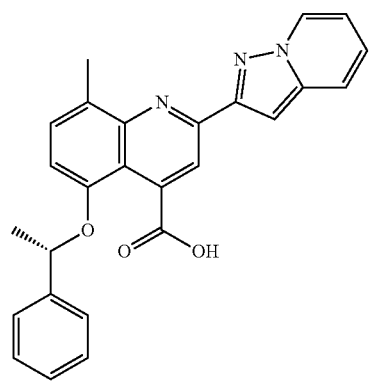
;
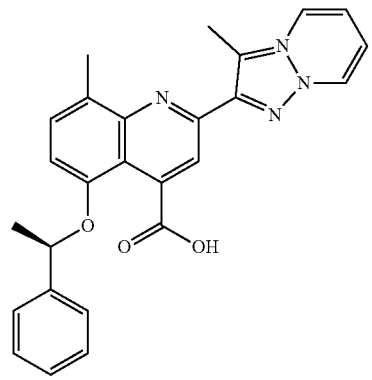
;
372
-continued
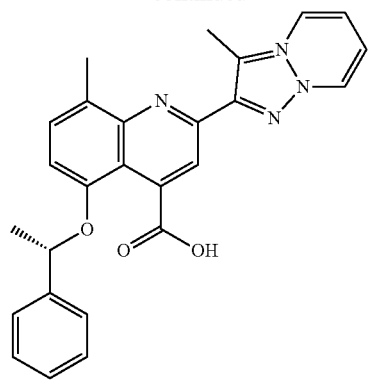
;
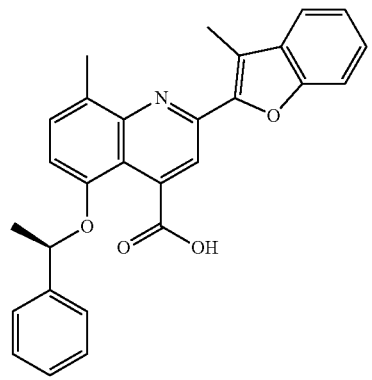
;
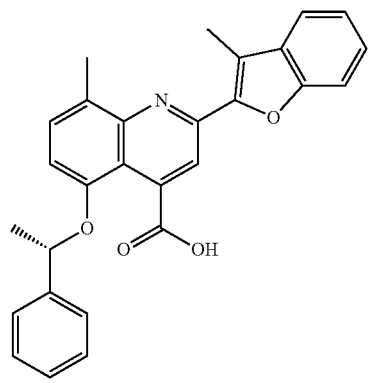
;
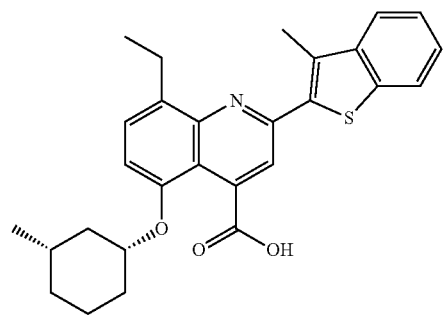
;

373
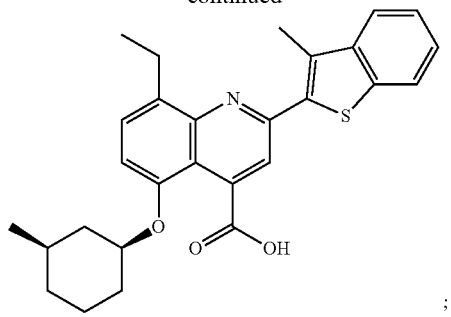
;
374
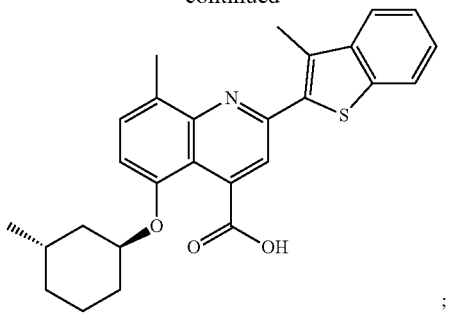
;

375
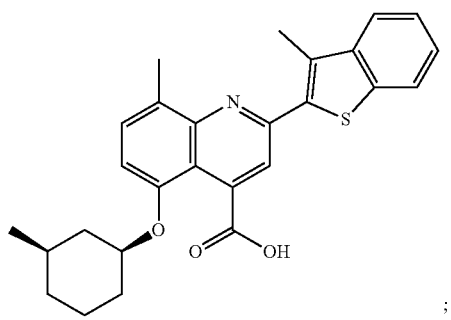
;
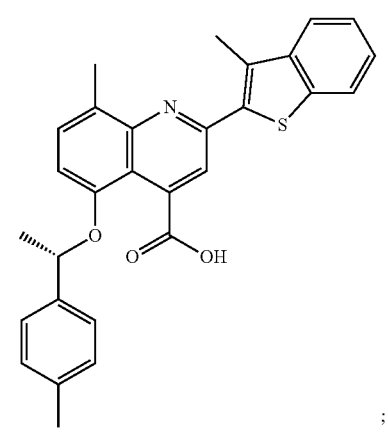
;
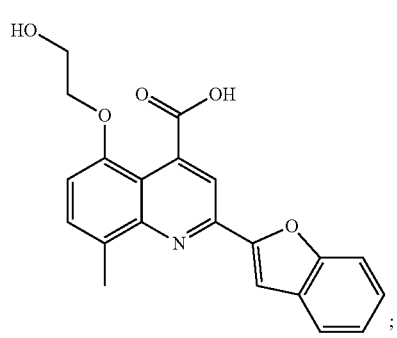
;
376
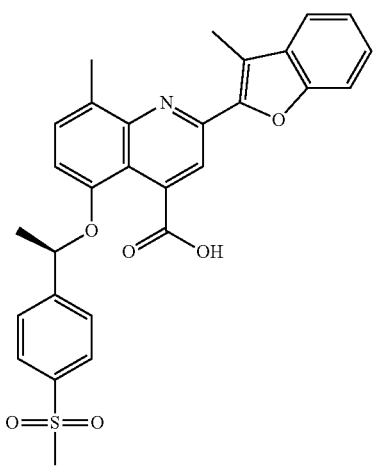
;
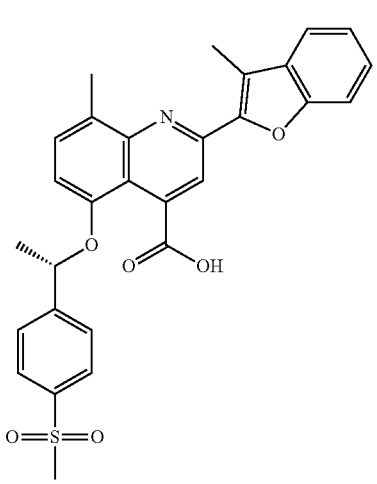
;
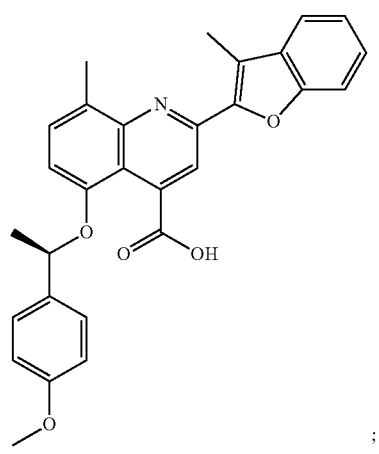
;

377
-continued
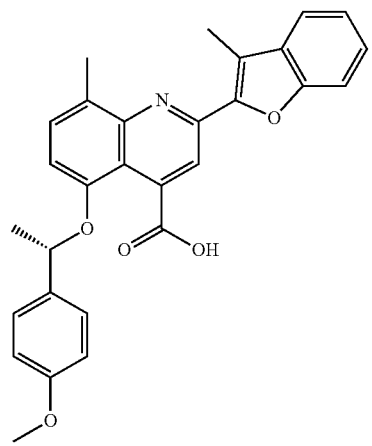
;
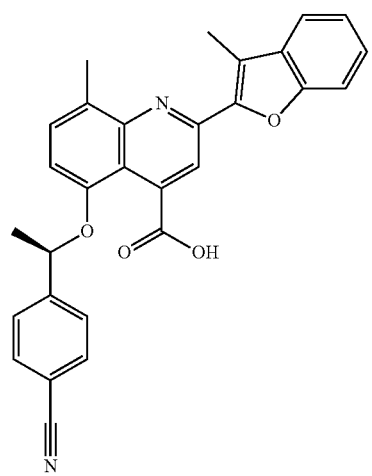
;
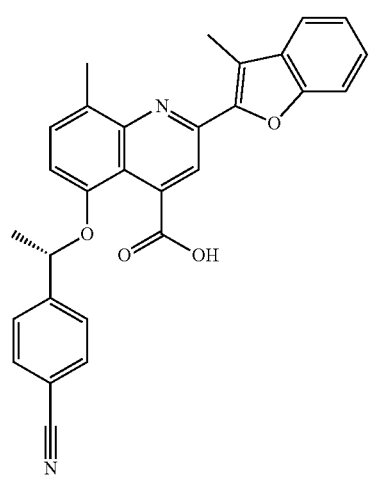
;
378
-continued
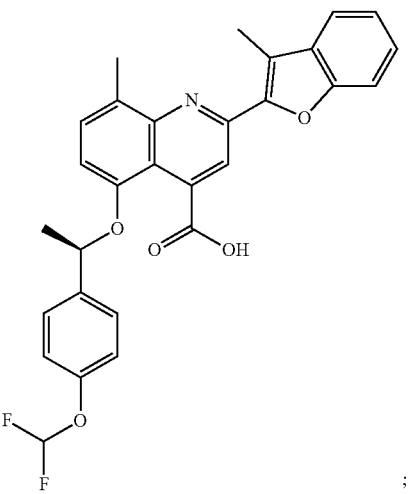
;
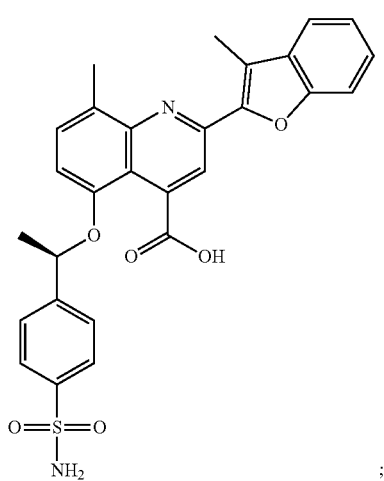
;

379
-continued
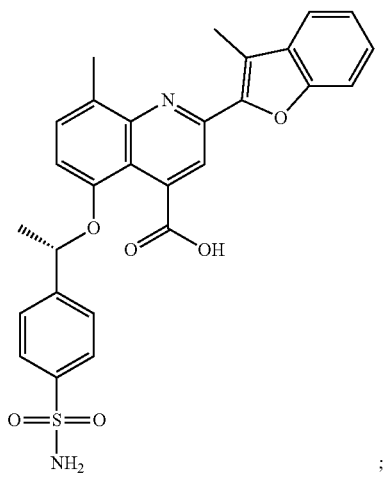
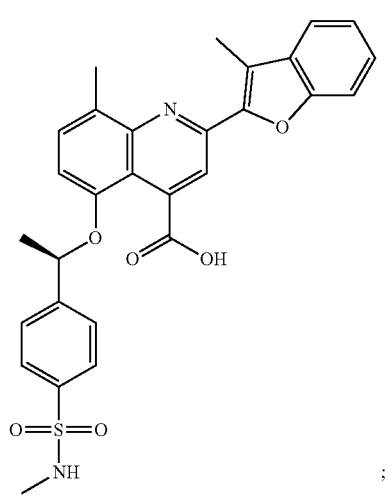
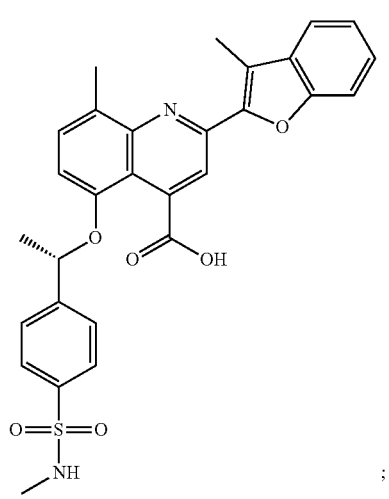
380
-continued
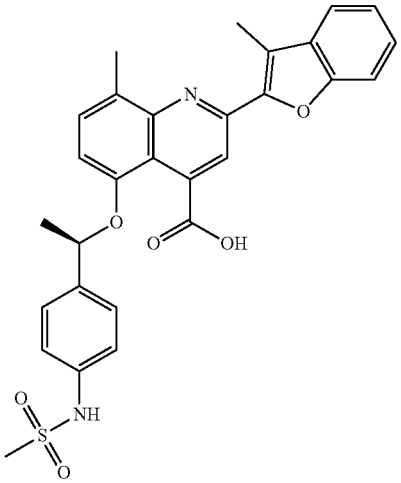
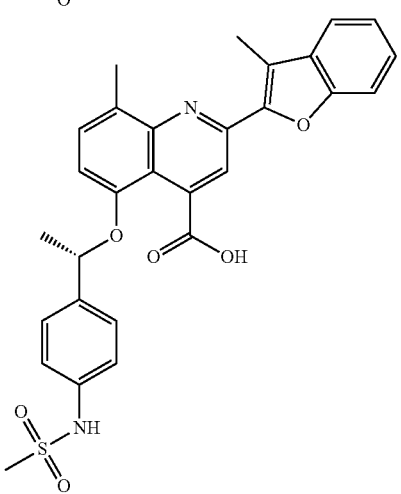
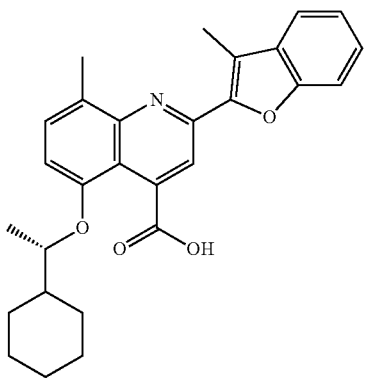

381
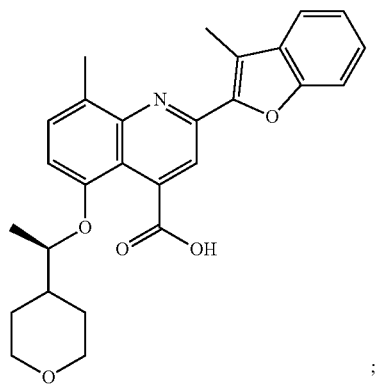
;
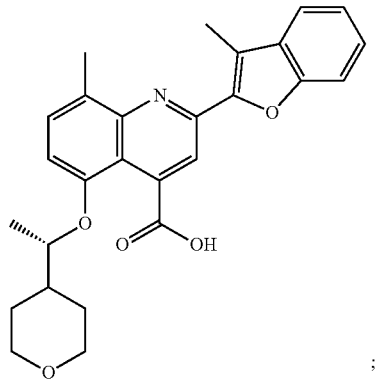
;
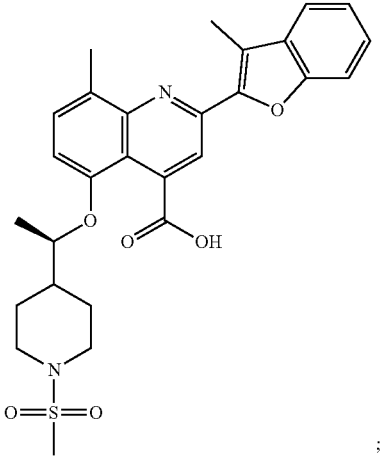
;
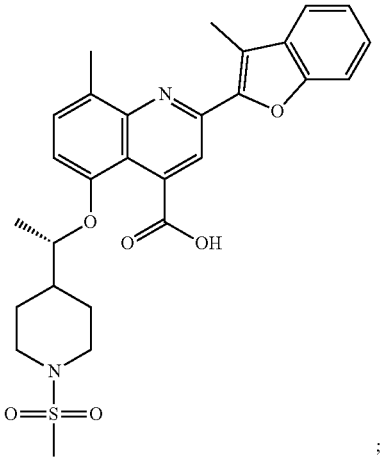
;
382
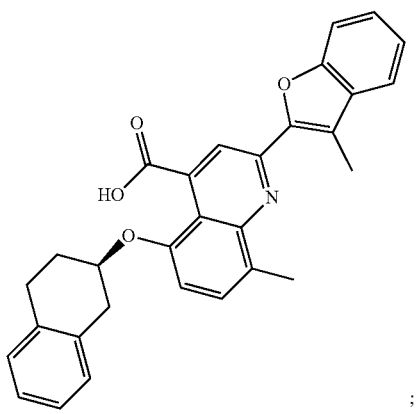
;
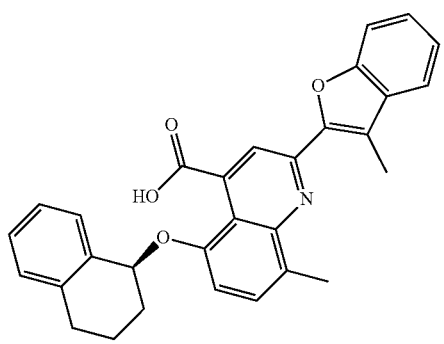
;
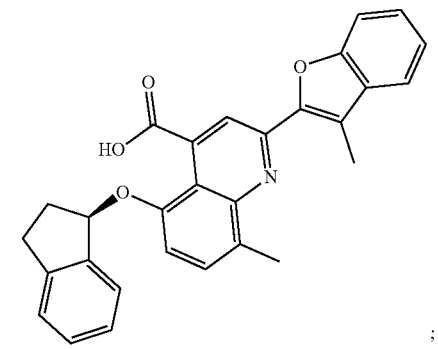
;
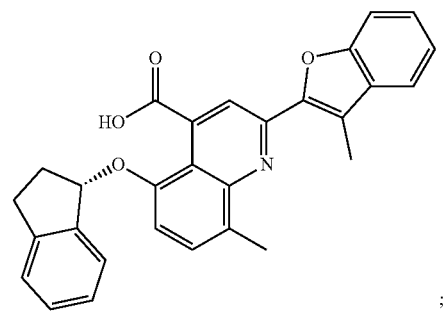
;

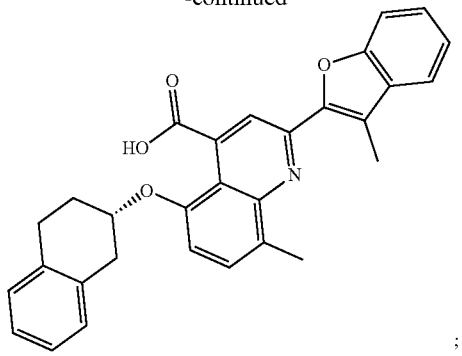
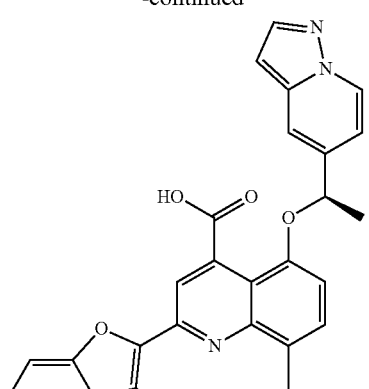

385
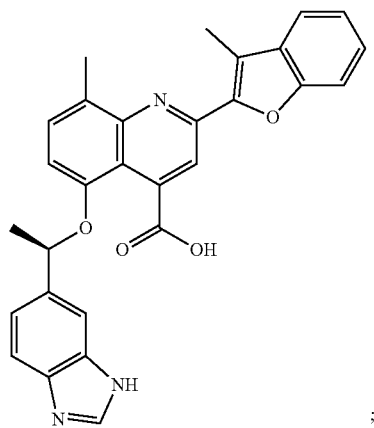
;
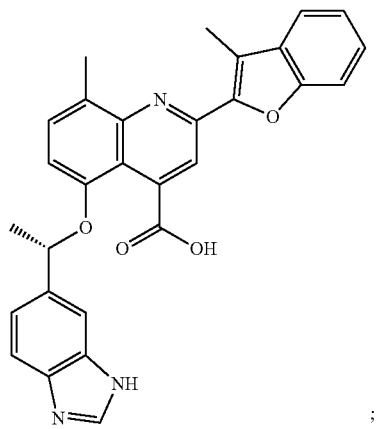
;
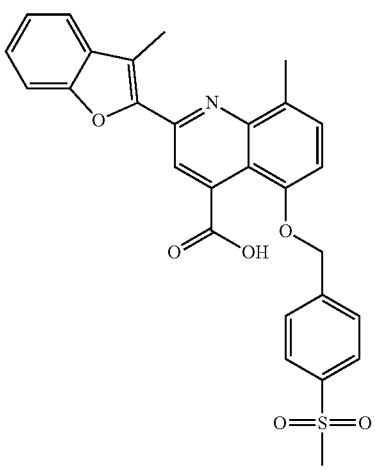
;
386
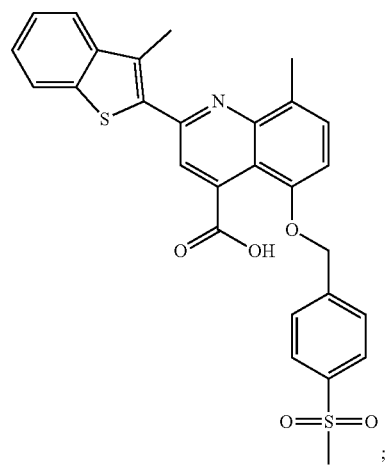
;
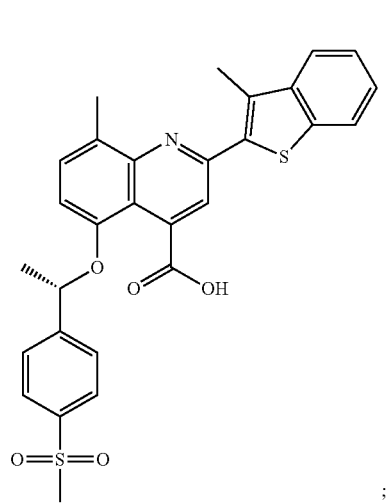
;

387
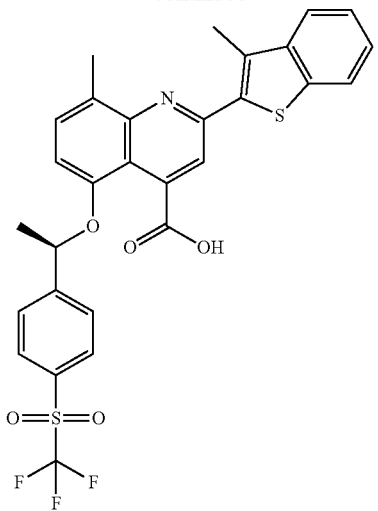
;
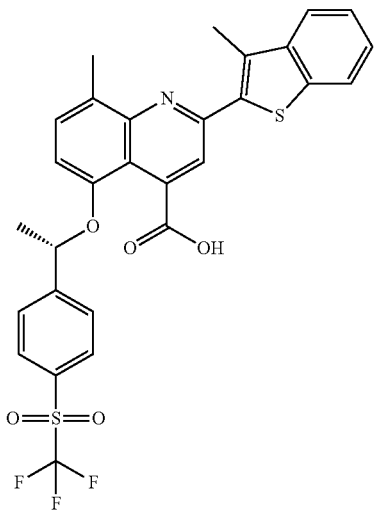
;
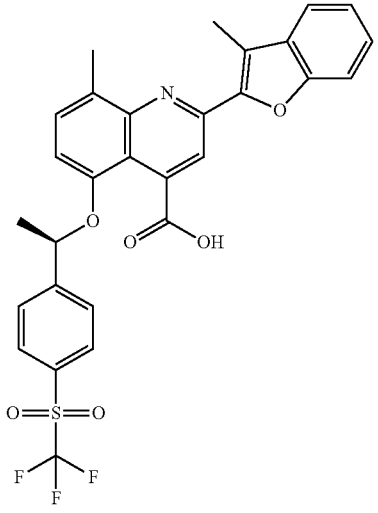
;
388
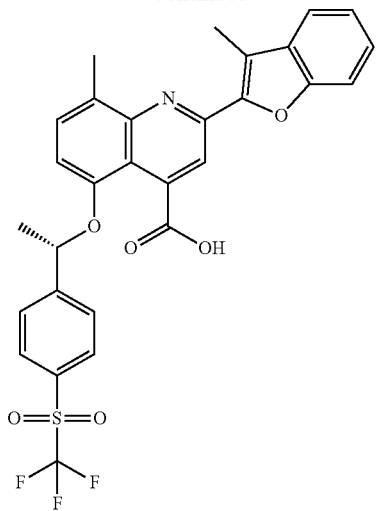
;
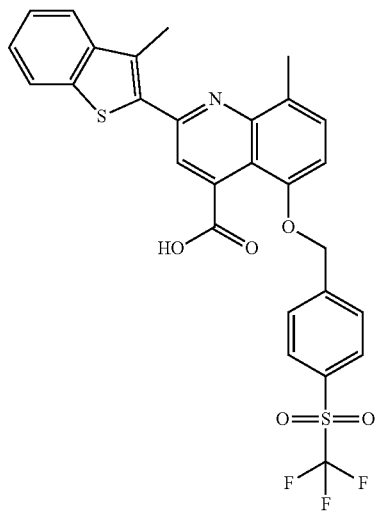
;

389
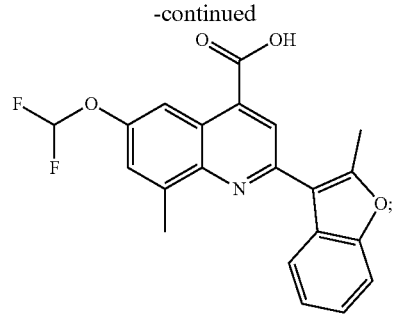
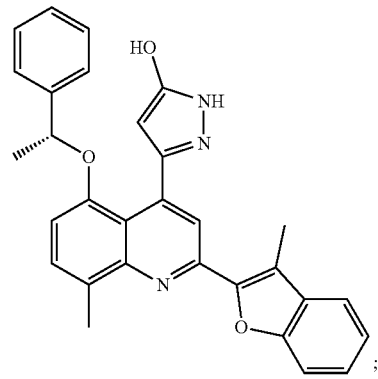
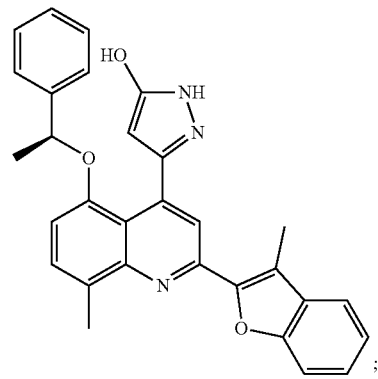
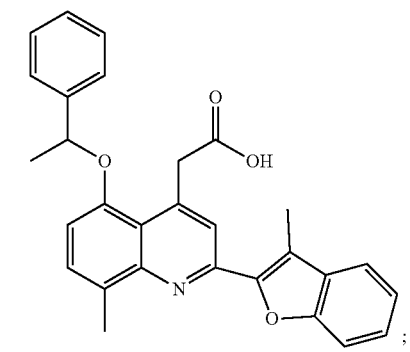
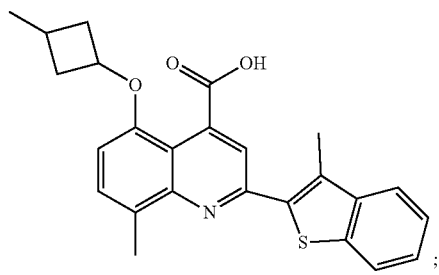
390
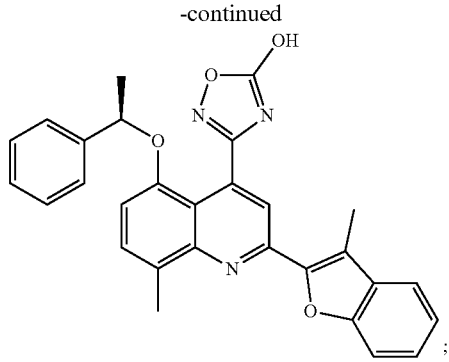
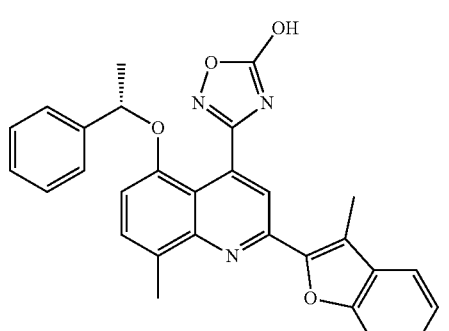
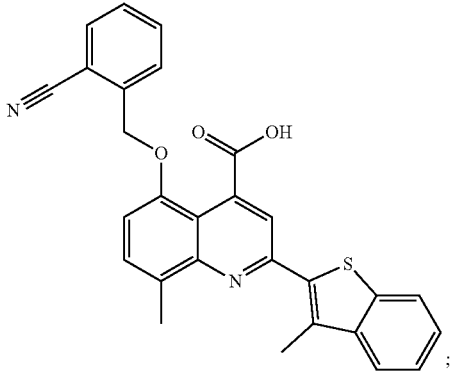
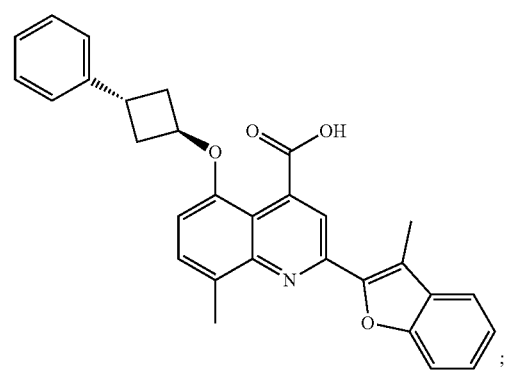

391
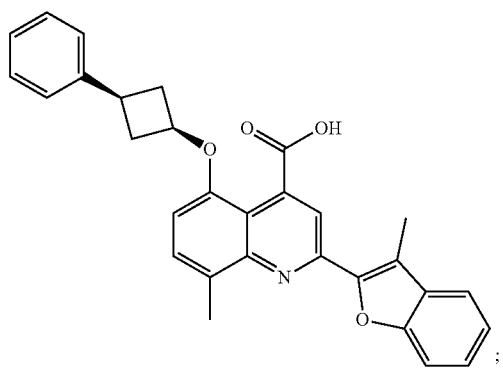
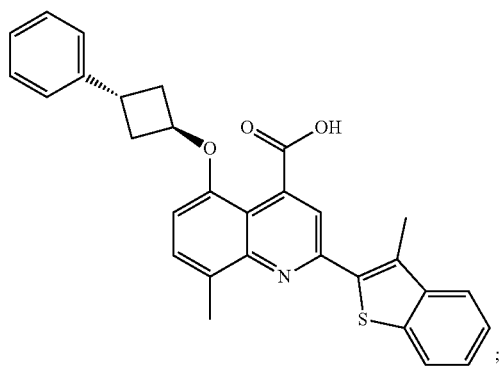
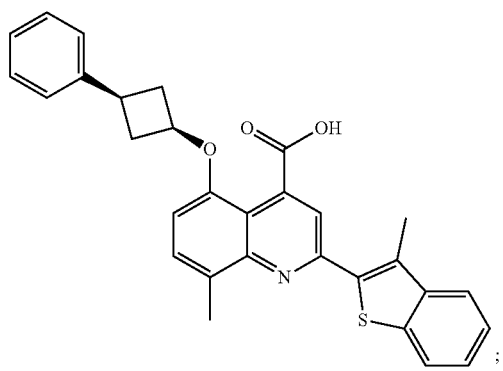
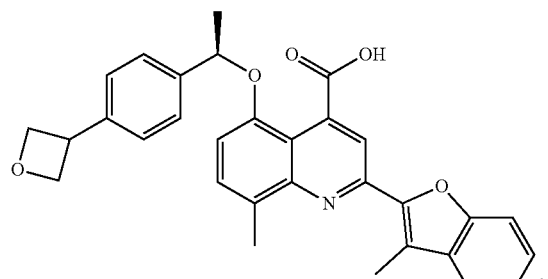
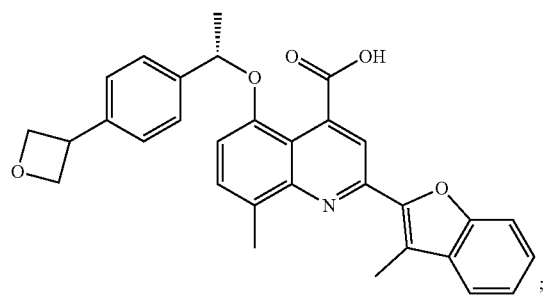
392
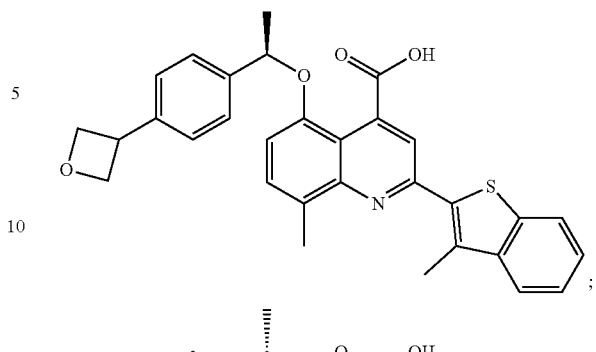
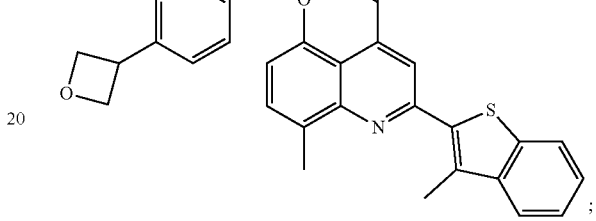
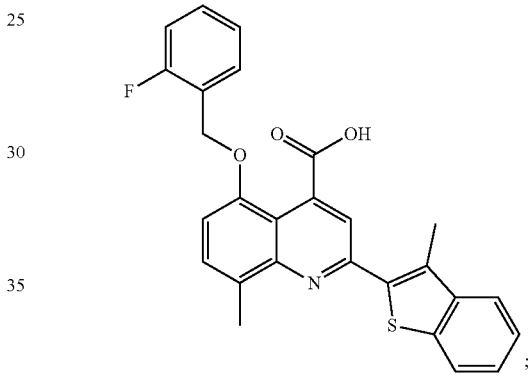
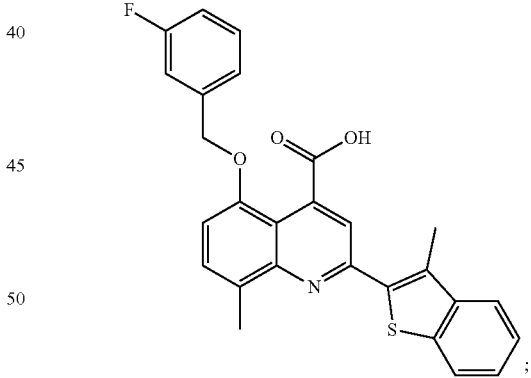
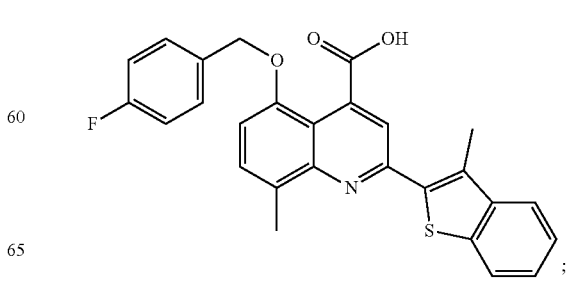

393
-continued
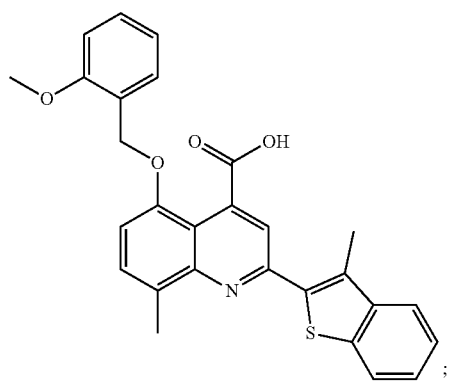
;
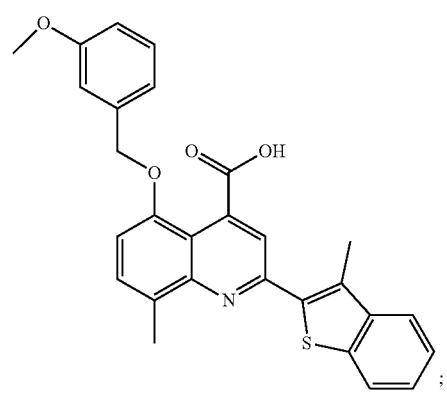
;
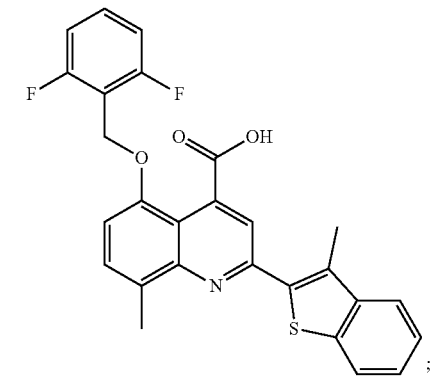
;
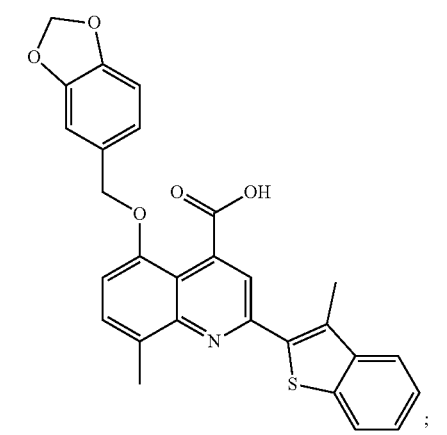
;
394
-continued
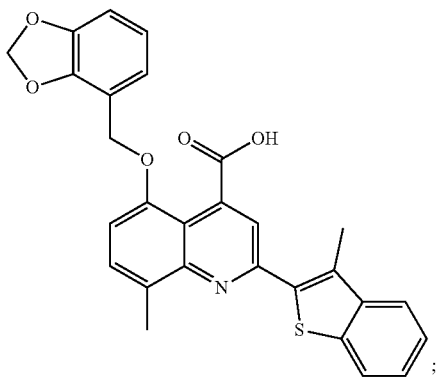
;
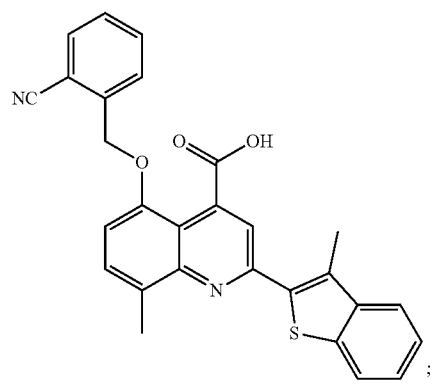
;
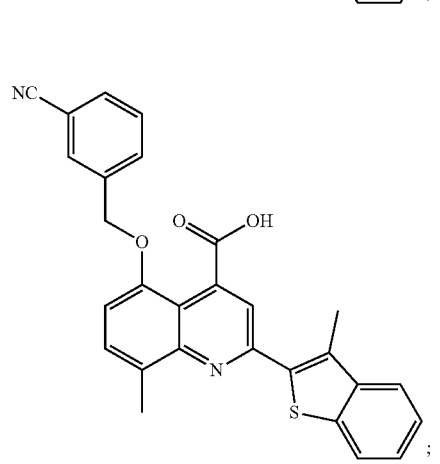
;
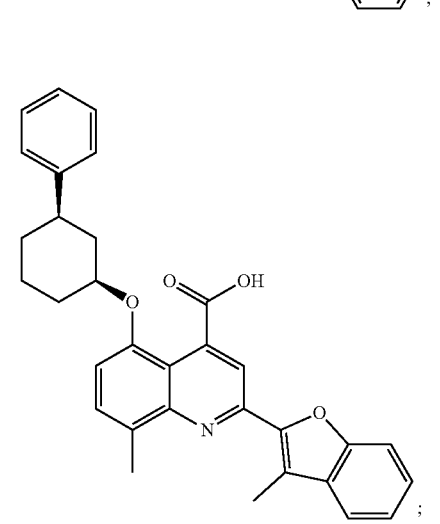
;

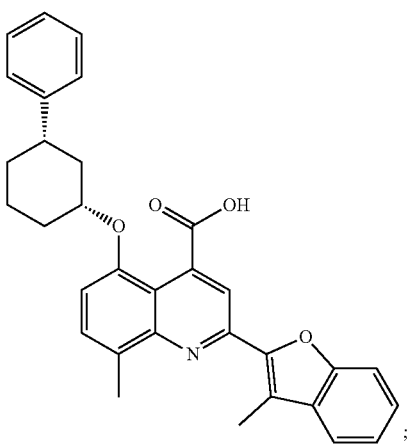
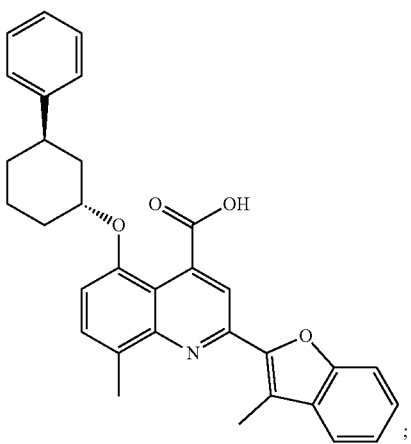
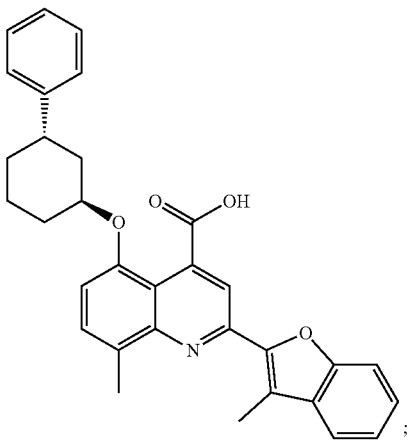
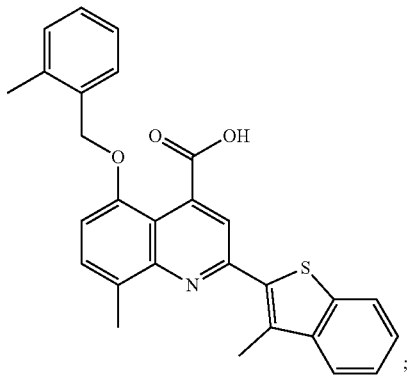
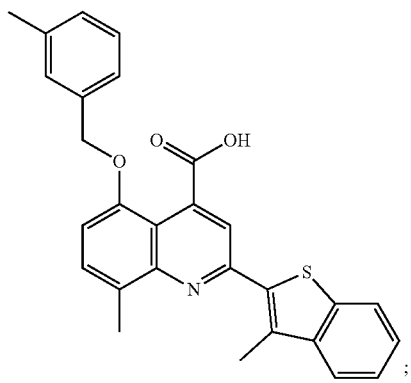
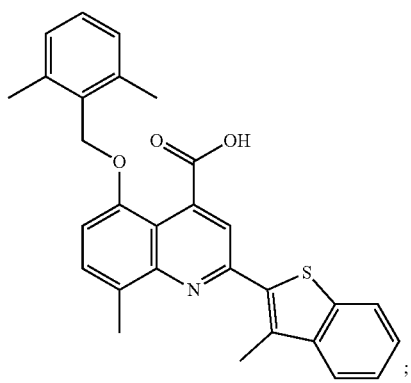
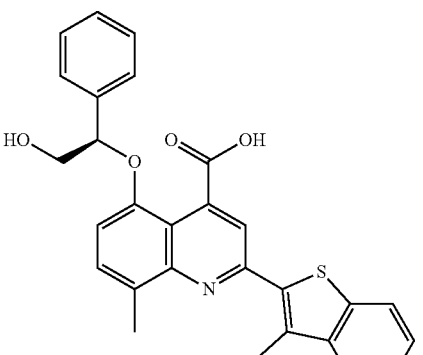
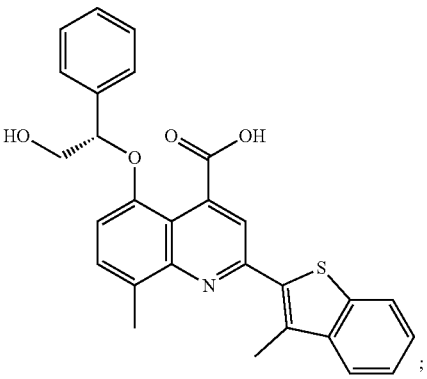

397
-continued
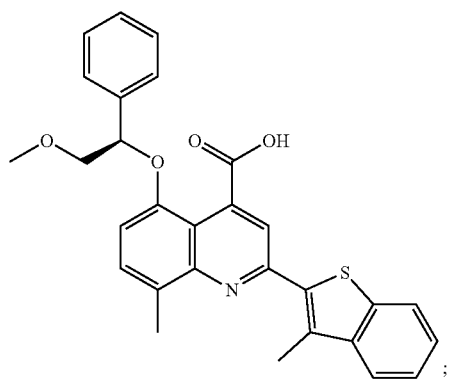
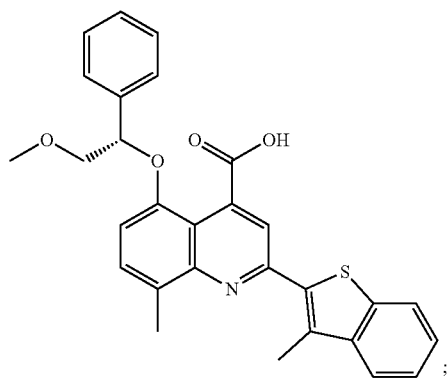
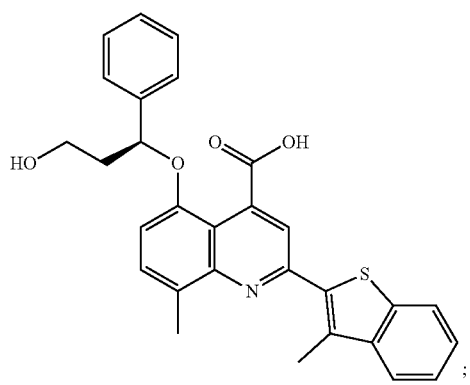
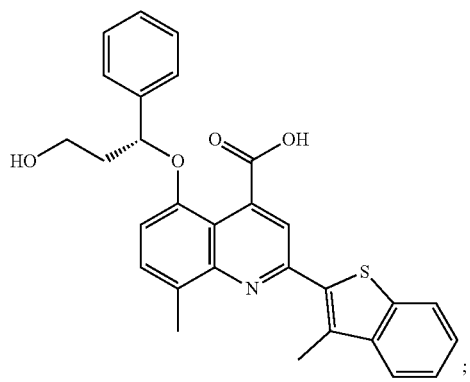
398
-continued
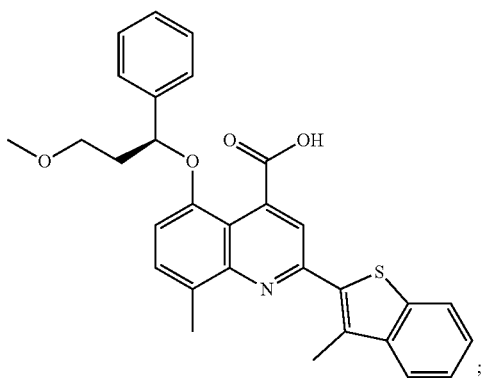
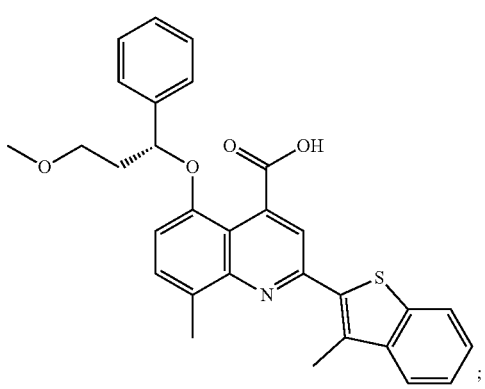
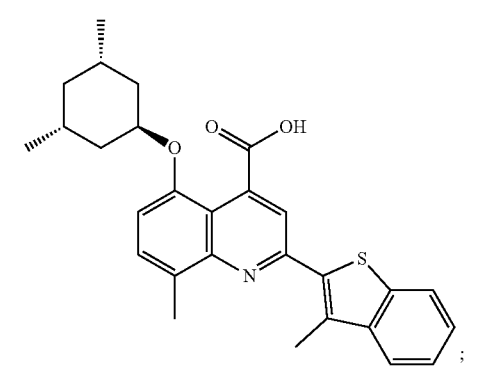
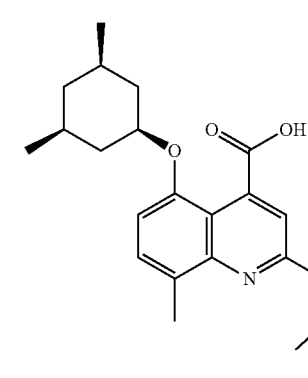

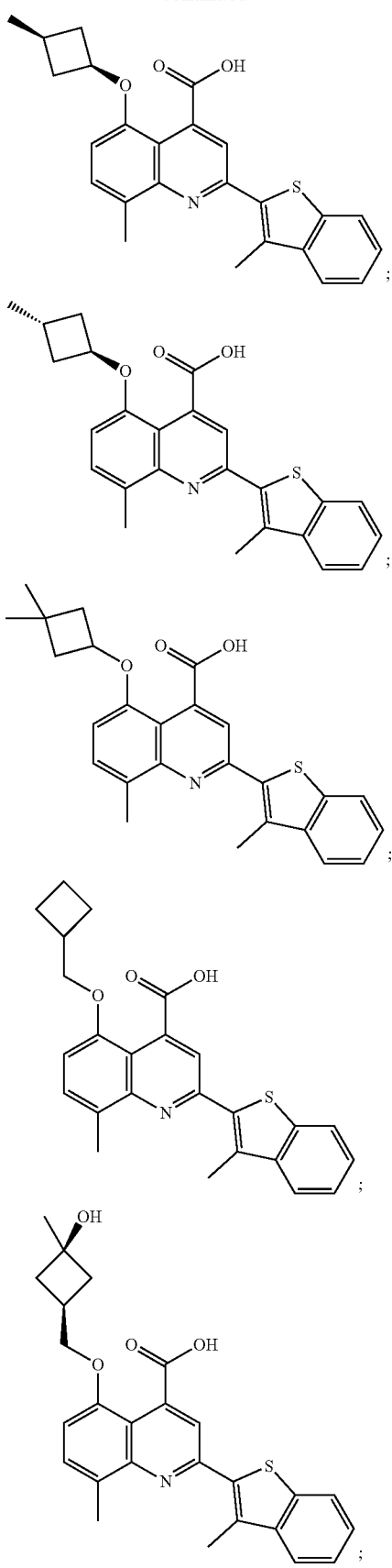 [SMILES: Cc1c(-c2cc(C(=O)O)c3c(O[C@H]4C[C@@H](C)C4)ccc(C)c3n2)sc2ccccc12 ; Cc1c(-c2cc(C(=O)O)c3c(O[C@H]4C[C@H](C)C4)ccc(C)c3n2)sc2ccccc12 ; Cc1c(-c2cc(C(=O)O)c3c(OC4CC(C)(C)C4)ccc(C)c3n2)sc2ccccc12 ; Cc1c(-c2cc(C(=O)O)c3c(OCC4CCC4)ccc(C)c3n2)sc2ccccc12 ; Cc1c(-c2cc(C(=O)O)c3c(OC[C@H]4C[C@@](C)(O)C4)ccc(C)c3n2)sc2ccccc12]

401
-continued
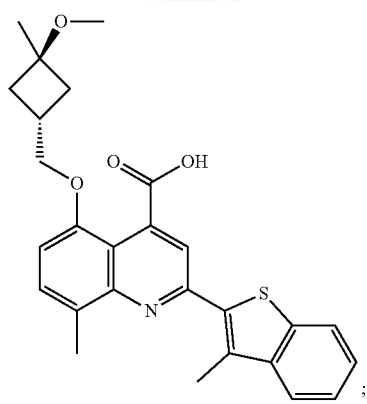
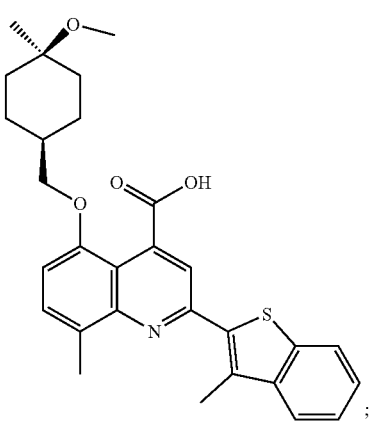
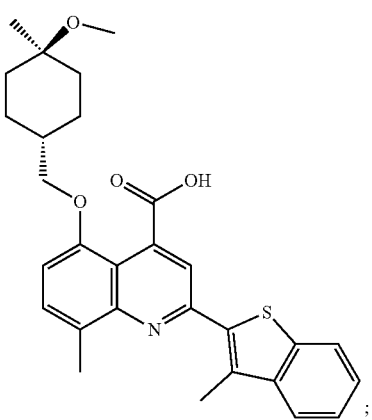
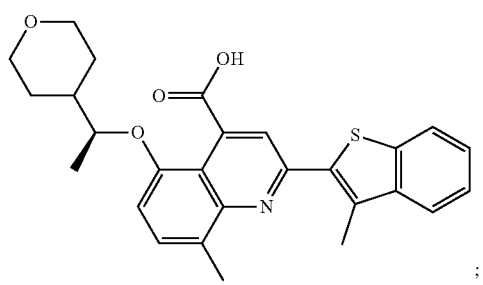
402
-continued
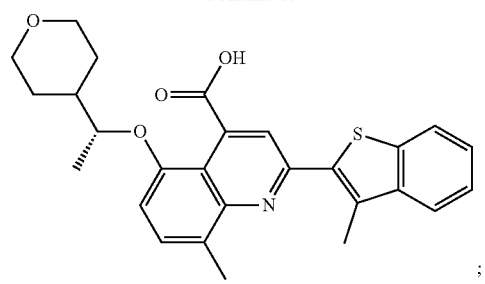
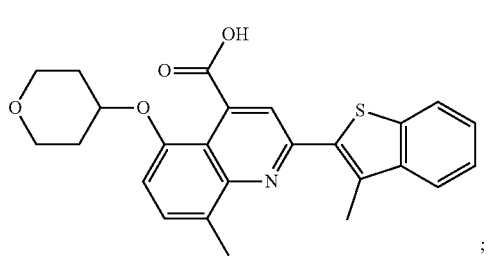
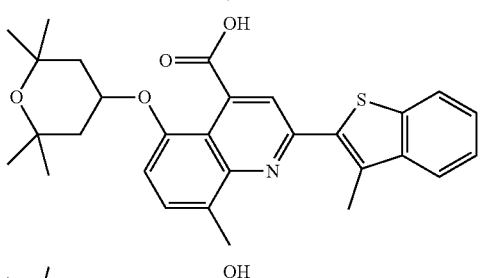
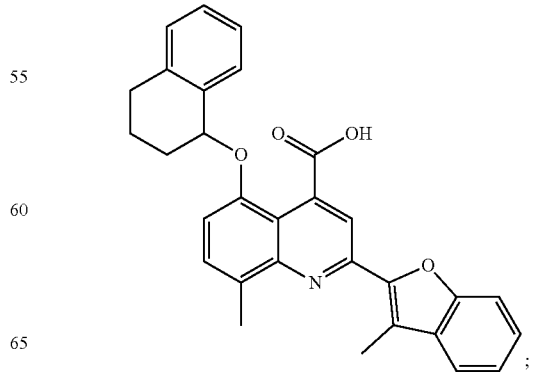

403
-continued
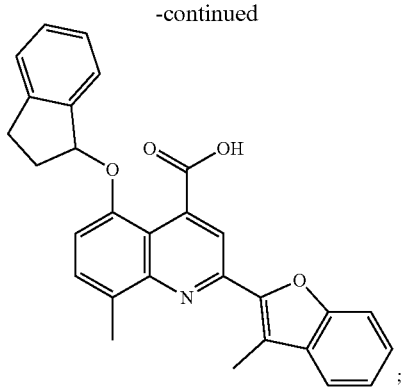
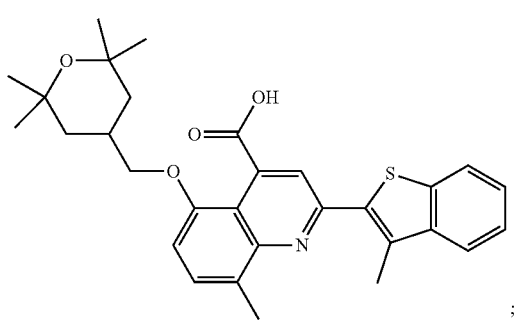
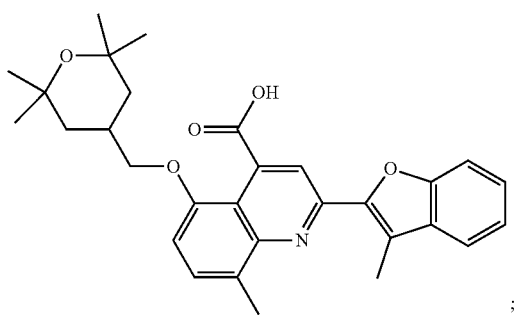
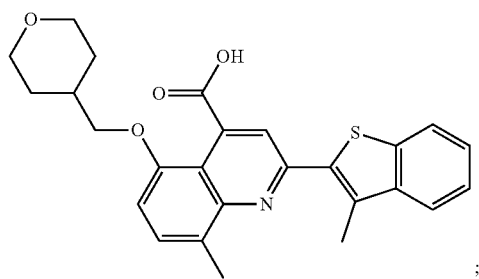
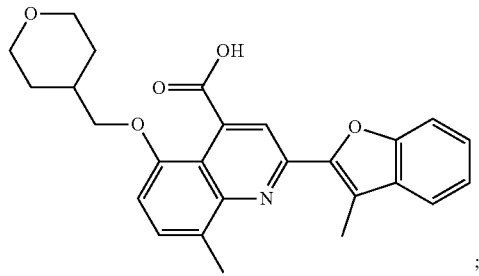
404
-continued
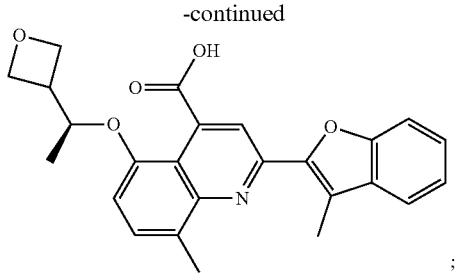
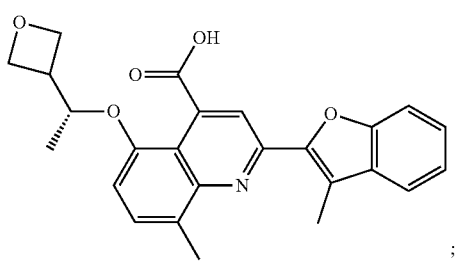
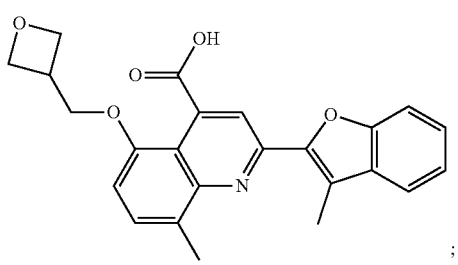
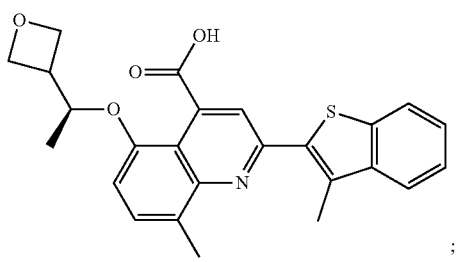
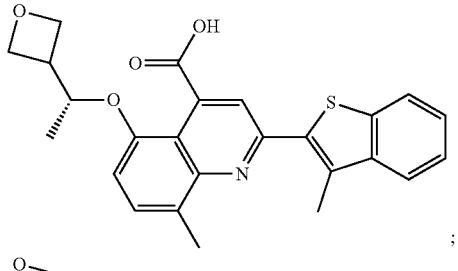
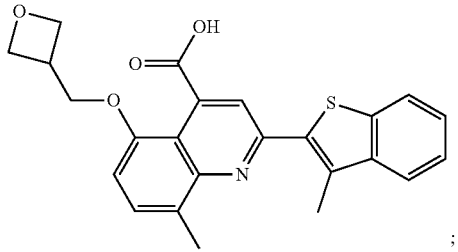

405
-continued
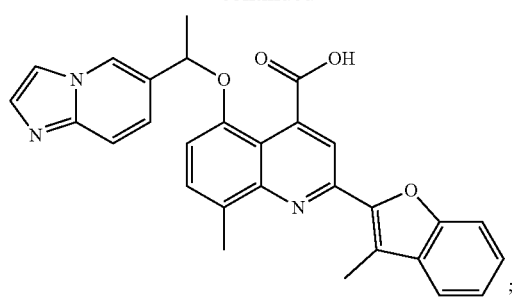
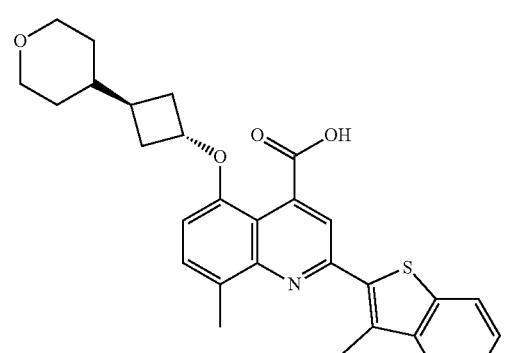
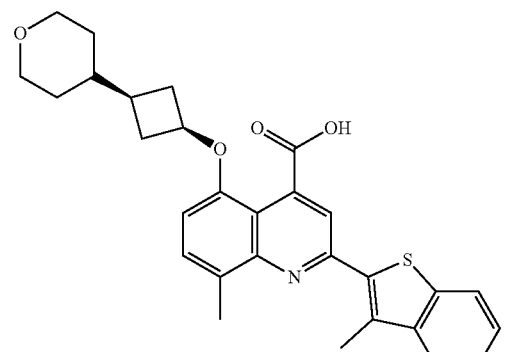
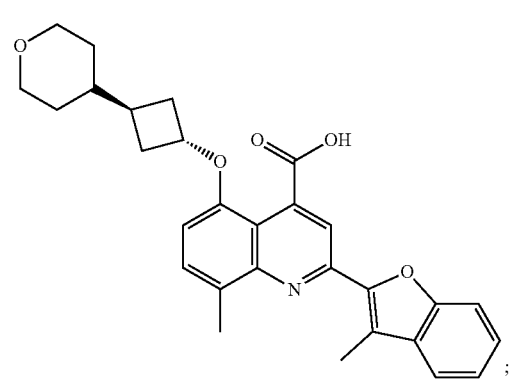
406
-continued
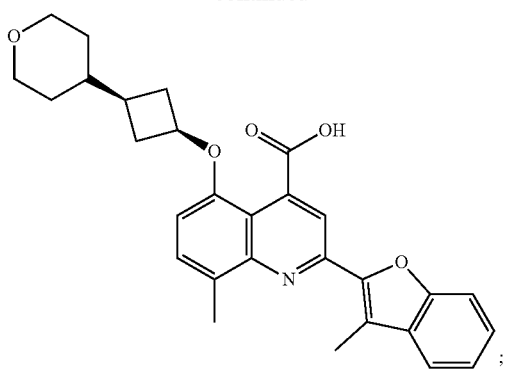
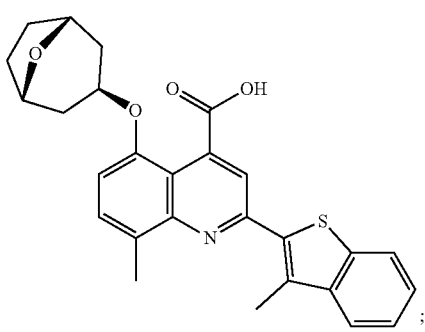
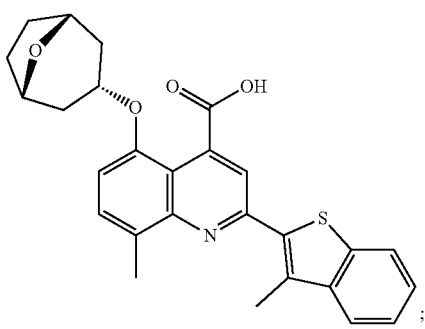
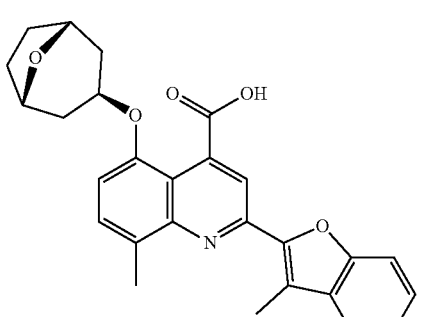
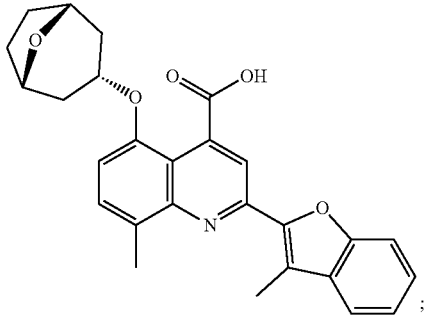

407
-continued
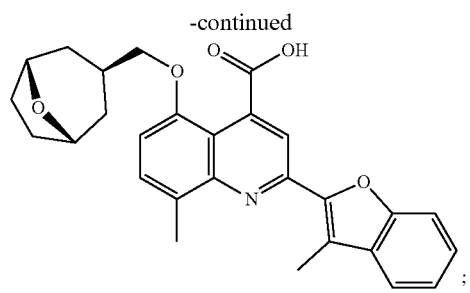
;
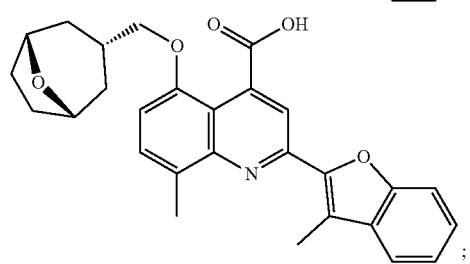
;
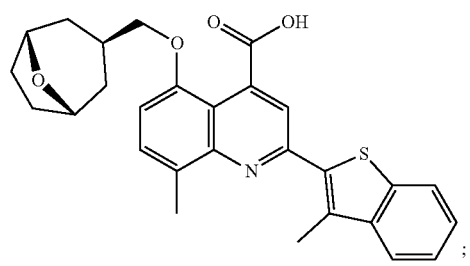
;
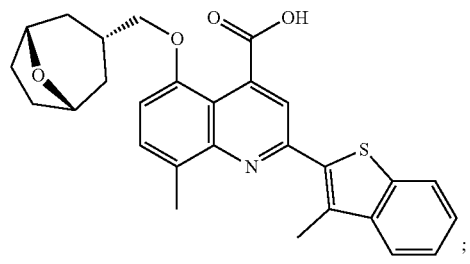
;
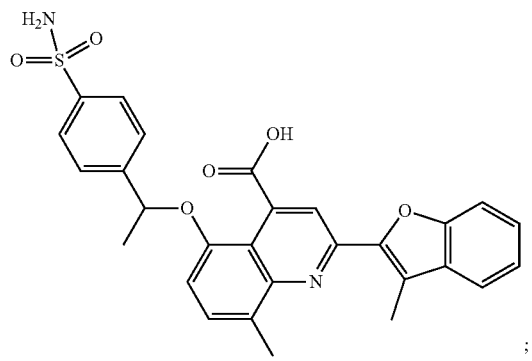
;
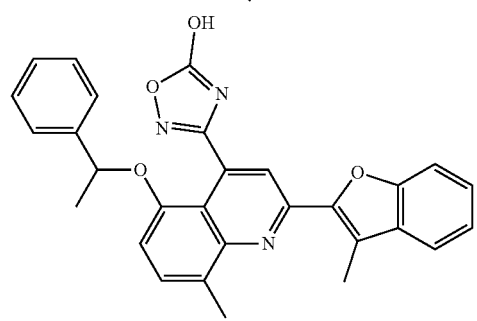
;
408
-continued
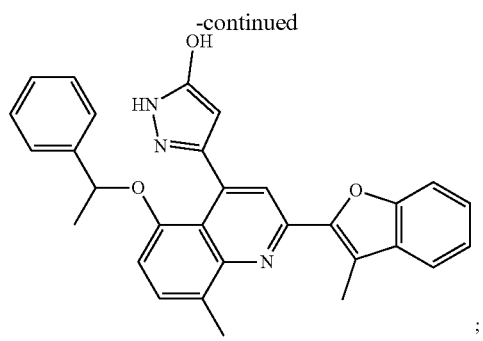
;
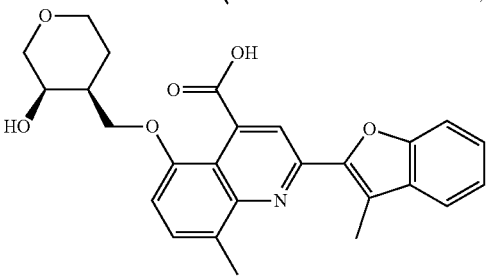
;
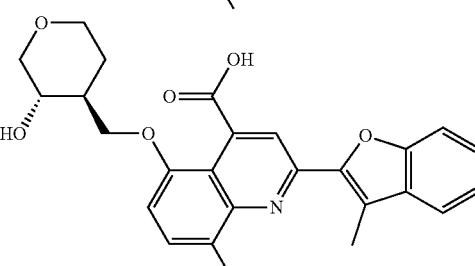
;
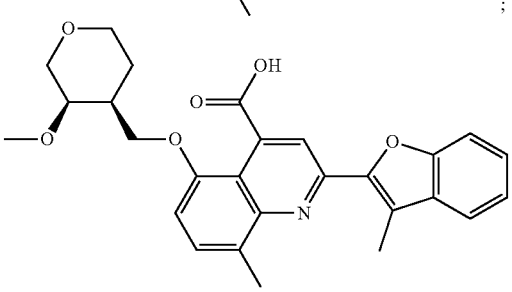
;
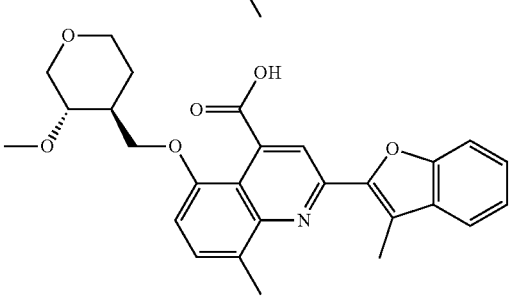
;
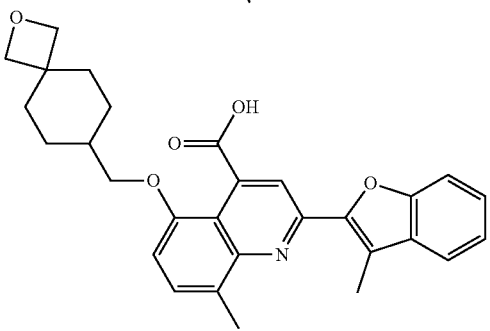
;

409
-continued
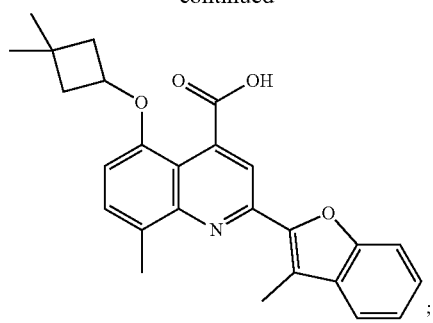
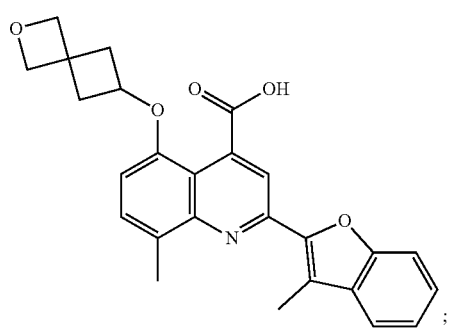
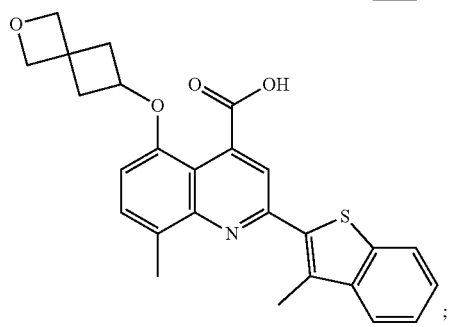
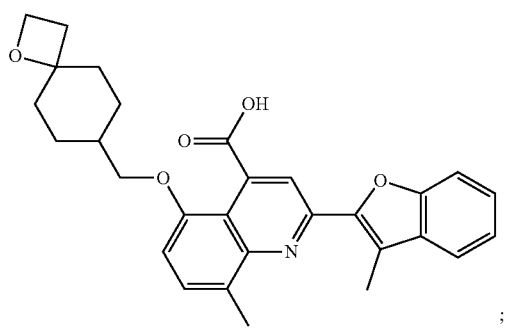
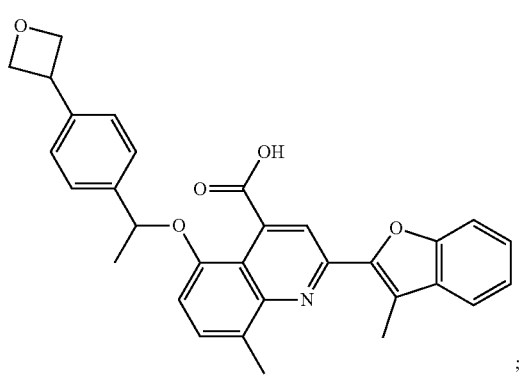
410
-continued
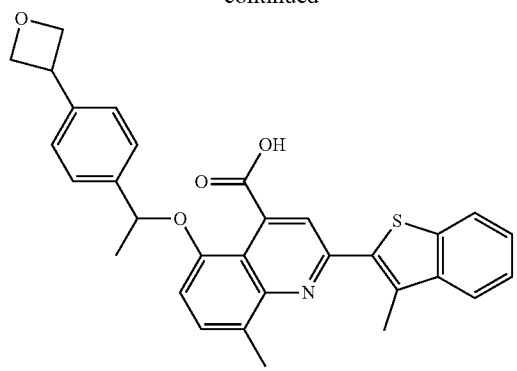
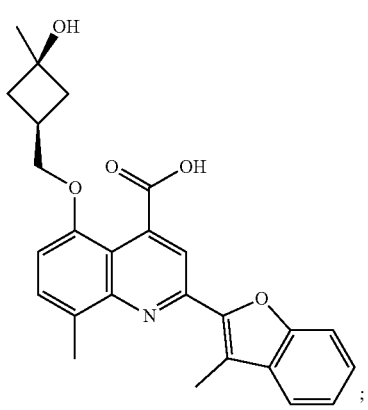
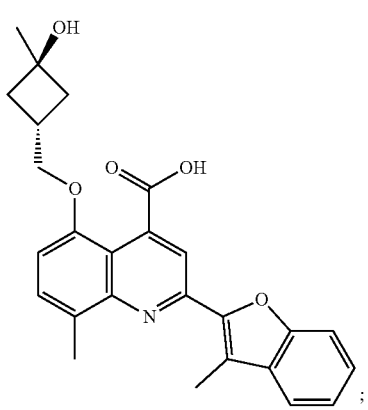
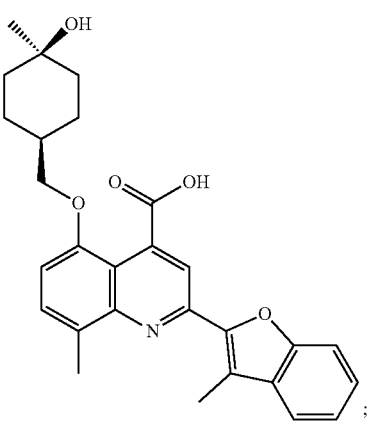

411
-continued
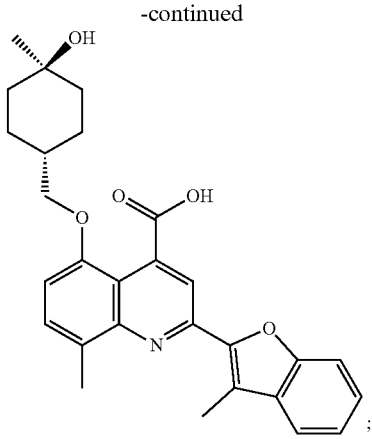
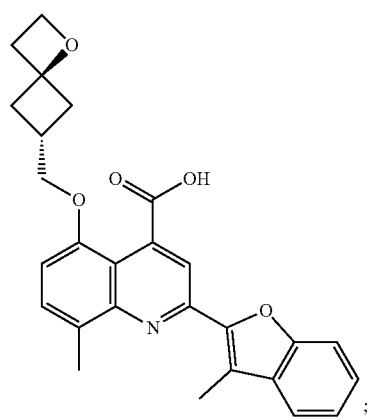
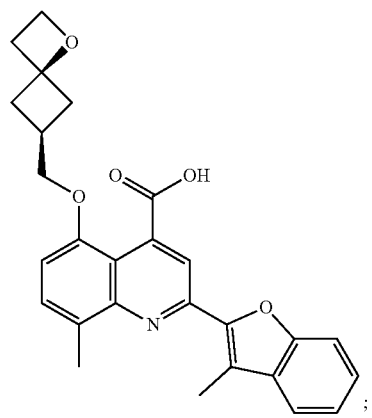
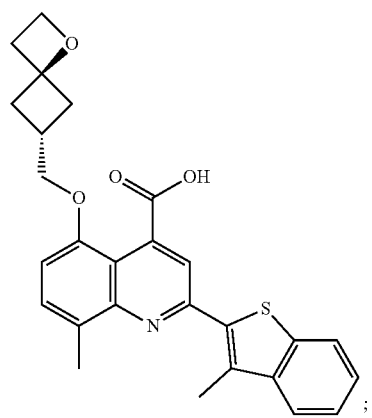
412
-continued
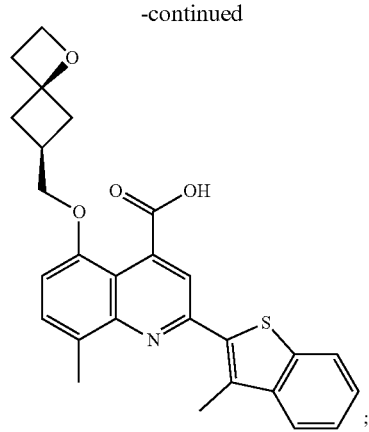
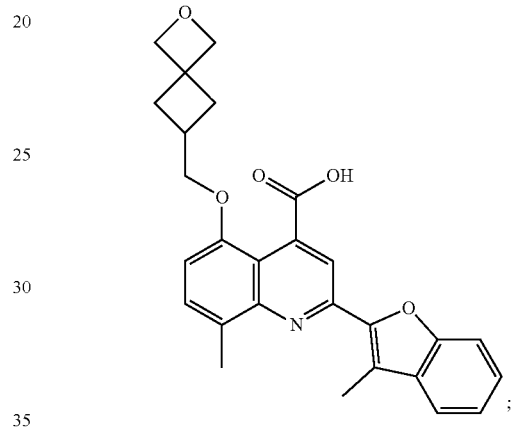
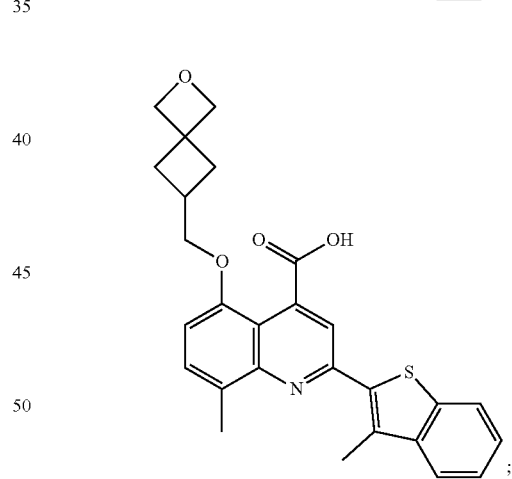
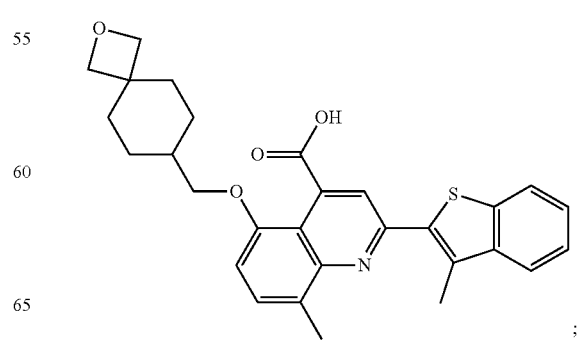

413
-continued
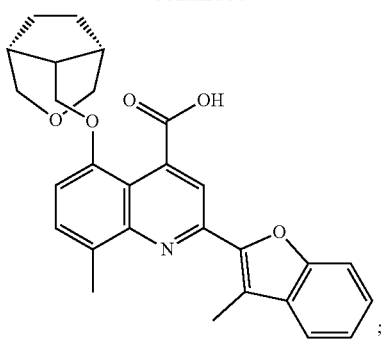
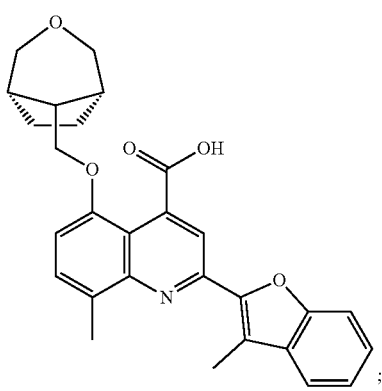
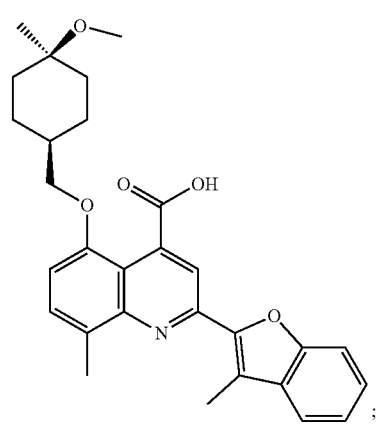
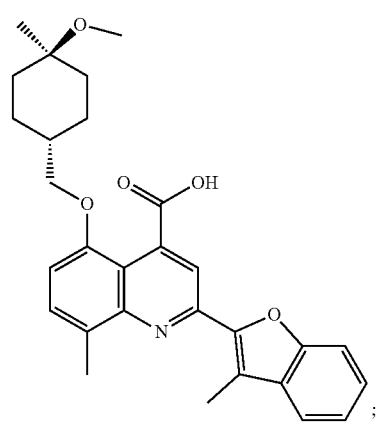
414
-continued
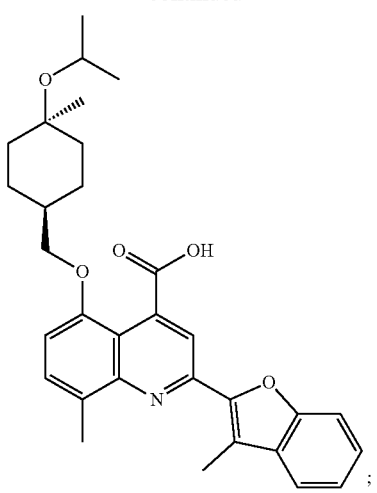
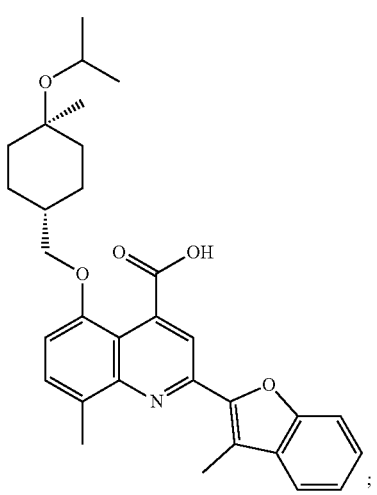
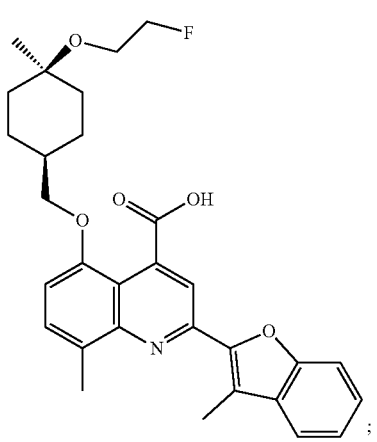

415
-continued
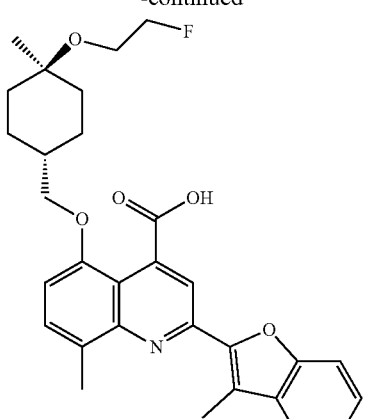
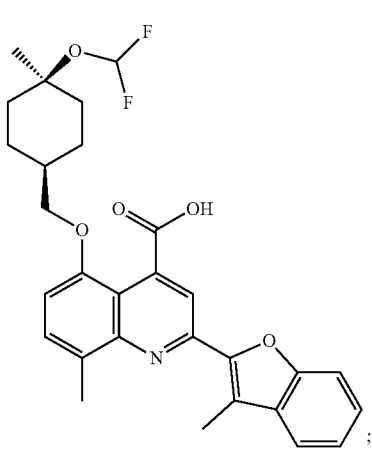
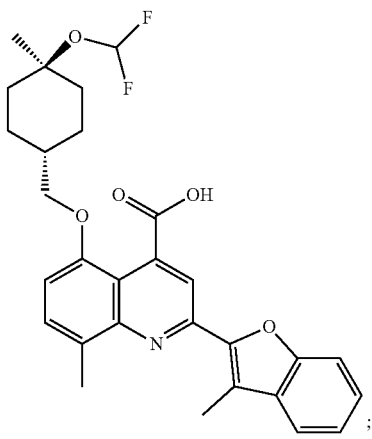
416
-continued
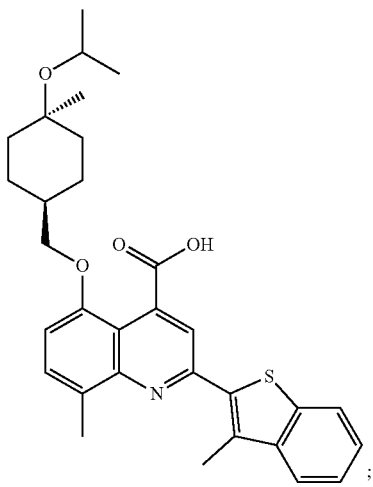
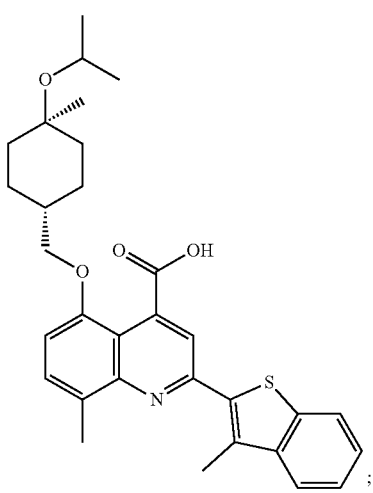
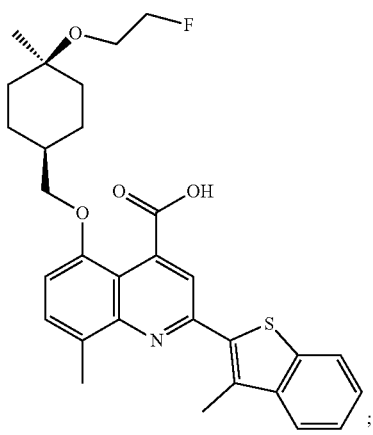

417
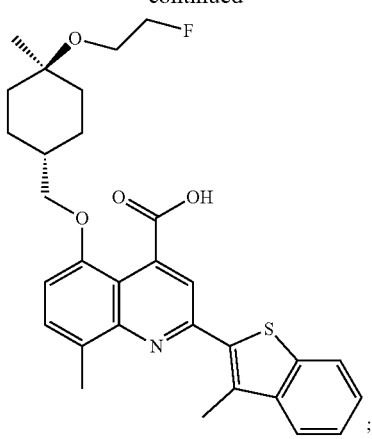
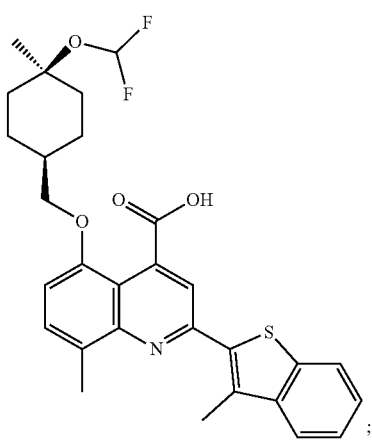
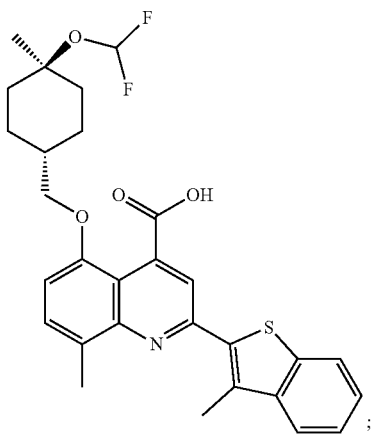
418
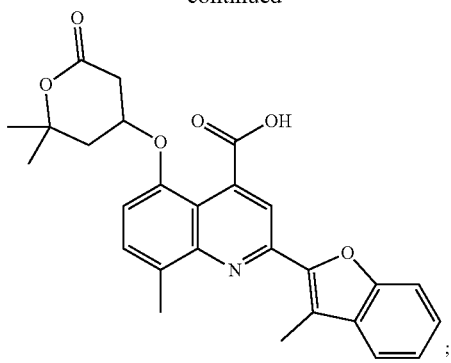
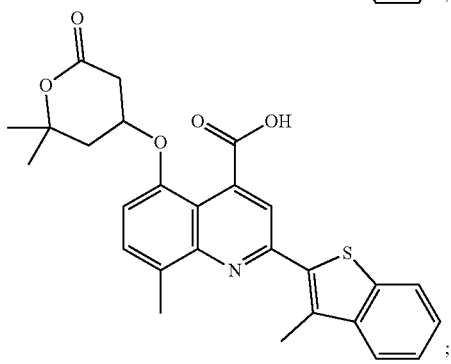
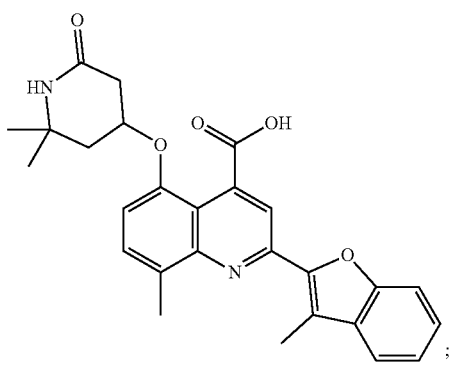

-continued

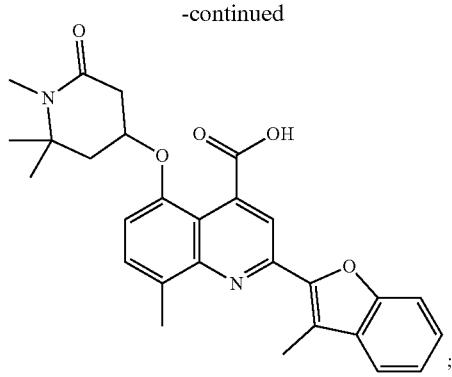

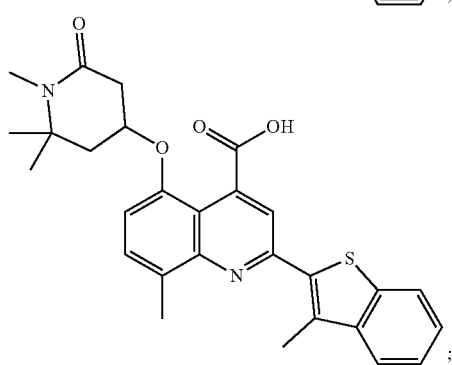

-continued

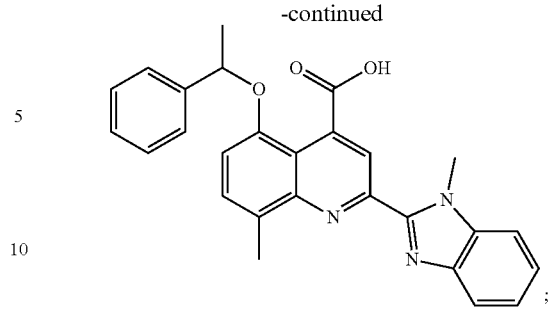

and a pharmaceutically acceptable salt or stereoisomer thereof.

10. A pharmaceutical composition comprising a compound of claim 1 and a pharmaceutically acceptable excipient.

11. The pharmaceutical composition of claim 10, wherein the composition further comprises at least one additional CFTR modulator.

12. The pharmaceutical composition of claim 11, wherein the composition further comprises two, three, four or more additional CFTR modulators.

13. A method of treating cystic fibrosis in a patient in need thereof, comprising administering to the patient an effective amount of compound of claim 1.

* * * * *